US012698341B2

(12) United States Patent
Desjarlais et al.

(10) Patent No.: US 12,698,341 B2
(45) Date of Patent: Aug. 4, 2026

(54) ANTIGEN BINDING DOMAINS THAT BIND TO MESOTHELIN (MSLN)

(71) Applicant: Xencor, Inc., Pasadena, CA (US)

(72) Inventors: John R. Desjarlais, Pasadena, CA (US); Matthew Bernett, Monrovia, CA (US); Michael Hedvat, Encino, CA (US); Veronica Gusti Zeng, Monrovia, CA (US); Matthew S. Faber, Monrovia, CA (US)

(73) Assignee: Xencor, Inc., Pasadena, CA (US)

( * ) Notice: Subject to any disclaimer, the term of this patent is extended or adjusted under 35 U.S.C. 154(b) by 0 days.

(21) Appl. No.: 18/652,669

(22) Filed: May 1, 2024

(65) Prior Publication Data

US 2024/0279356 A1     Aug. 22, 2024

Related U.S. Application Data

(63) Continuation of application No. 17/321,272, filed on May 14, 2021, now abandoned.

(60) Provisional application No. 63/025,021, filed on May 14, 2020.

(51) Int. Cl.
| | |
|---|---|
| *C07K 16/30* | (2006.01) |
| *A61K 39/00* | (2006.01) |
| *C07K 16/28* | (2006.01) |

(52) U.S. Cl.
CPC ...... *C07K 16/3069* (2013.01); *C07K 16/2809* (2013.01); *A61K 39/00* (2013.01); *C07K 2317/31* (2013.01); *C07K 2317/56* (2013.01); *C07K 2317/565* (2013.01); *C07K 2317/622* (2013.01)

(58) Field of Classification Search
CPC ........................ C07K 16/3069; C07K 2317/56
See application file for complete search history.

(56) References Cited

U.S. PATENT DOCUMENTS

| | | | |
|---|---|---|---|
| 3,773,919 | A | 11/1973 | Boswell et al. |
| 4,169,888 | A | 10/1979 | Hanka et al. |
| 4,179,337 | A | 12/1979 | Davis et al. |
| 4,256,746 | A | 3/1981 | Miyashita et al. |
| 4,294,757 | A | 10/1981 | Asai |
| 4,301,144 | A | 11/1981 | Iwashita et al. |
| 4,307,016 | A | 12/1981 | Asai et al. |
| 4,313,946 | A | 2/1982 | Powell et al. |
| 4,315,929 | A | 2/1982 | Freedman et al. |
| 4,322,348 | A | 3/1982 | Asai et al. |
| 4,331,598 | A | 5/1982 | Hasegawa et al. |
| 4,361,650 | A | 11/1982 | Asai et al. |
| 4,362,663 | A | 12/1982 | Kida et al. |
| 4,364,866 | A | 12/1982 | Asai et al. |
| 4,364,935 | A | 12/1982 | Kung et al. |
| 4,371,533 | A | 2/1983 | Akimoto et al. |
| 4,424,219 | A | 1/1984 | Hashimoto et al. |
| 4,450,254 | A | 5/1984 | Isley et al. |
| 4,496,689 | A | 1/1985 | Mitra |
| 4,640,835 | A | 2/1987 | Shimizu et al. |
| 4,670,417 | A | 6/1987 | Iwasaki et al. |
| 4,791,192 | A | 12/1988 | Nakagawa et al. |
| 4,880,935 | A | 11/1989 | Thorpe |
| 4,923,990 | A | 5/1990 | Nakano et al. |
| 4,943,533 | A | 7/1990 | Mendelsohn et al. |
| 4,970,198 | A | 11/1990 | Lee et al. |
| 5,053,394 | A | 10/1991 | Ellestad et al. |
| 5,070,092 | A | 12/1991 | Kanda et al. |
| 5,084,468 | A | 1/1992 | Saito et al. |
| 5,101,038 | A | 3/1992 | Nakano et al. |
| 5,122,368 | A | 6/1992 | Greenfield et al. |
| 5,187,186 | A | 2/1993 | Kanda et al. |
| 5,208,020 | A | 5/1993 | Chari et al. |
| 5,264,586 | A | 11/1993 | Nicolaou et al. |
| 5,384,412 | A | 1/1995 | Nicolaou et al. |
| 5,416,064 | A | 5/1995 | Chari et al. |
| 5,475,092 | A | 12/1995 | Chari et al. |
| 5,500,362 | A | 3/1996 | Robinson et al. |
| 5,530,101 | A | 6/1996 | Queen et al. |
| 5,541,087 | A | 7/1996 | Lo et al. |
| 5,550,246 | A | 8/1996 | Nicolaou et al. |
| 5,558,864 | A | 9/1996 | Bendig et al. |
| 5,585,089 | A | 12/1996 | Queen et al. |
| 5,585,097 | A | 12/1996 | Bolt et al. |
| 5,585,499 | A | 12/1996 | Chari et al. |
| 5,622,929 | A | 4/1997 | Willner et al. |
| 5,635,483 | A | 6/1997 | Pettit et al. |
| 5,641,780 | A | 6/1997 | Amishiro et al. |
| 5,663,149 | A | 9/1997 | Pettit et al. |
| 5,677,171 | A | 10/1997 | Hudziak et al. |

(Continued)

FOREIGN PATENT DOCUMENTS

| | | |
|---|---|---|
| CN | 107840891 A | 3/2018 |
| EP | 0425235 B1 | 9/1996 |

(Continued)

OTHER PUBLICATIONS

Lazar et al, Mol. Cell. Biol., 8:1247-1252, 1988 (Year: 1988).*
Burgess et al., J. Cell Biol. 111:2129-2138, 1990 (Year: 1990).*
Brown et al., J Immunol. May 1996;156(9):3285-91 (Year: 1996).*
Greenspan et al. 1999, Nature Biotechnology, 17:936-937 (Year: 1999).*
Skolnick et al., Trends Biotechnol. Jan. 2000;18(1):34-9 (Year: 2000).*
Bork, Genome Research, 2000, 10:398-400 (Year: 2000).*
Vajdos et al., J Mol Biol. Jul. 5, 2002;320(2):415-28 (Year: 2002).*
Miosge, Proc Natl Acad Sci U S A. Sep. 15, 2015;112(37):E5189-98 (Year: 2015).*

(Continued)

*Primary Examiner* — Vanessa L. Ford
*Assistant Examiner* — Danaya L Middleton
(74) *Attorney, Agent, or Firm* — Louis-Vu T. Nguyen; Christopher J. Betti; Morgan, Lewis & Bockius, LLP

(57) ABSTRACT

The present invention is directed to antibodies, including novel antigen binding domains and heterodimeric antibodies, that bind Mesothelin (MSLN).

6 Claims, 124 Drawing Sheets

Specification includes a Sequence Listing.

(56) References Cited

U.S. PATENT DOCUMENTS

| | | | |
|---|---|---|---|
| 5,693,761 | A | 12/1997 | Queen et al. |
| 5,693,762 | A | 12/1997 | Queen et al. |
| 5,703,080 | A | 12/1997 | Nakakura et al. |
| 5,712,374 | A | 1/1998 | Kuntsmann et al. |
| 5,714,586 | A | 2/1998 | Kuntsmann et al. |
| 5,726,044 | A | 3/1998 | Lo et al. |
| 5,731,168 | A | 3/1998 | Carter et al. |
| 5,736,137 | A | 4/1998 | Anderson et al. |
| 5,739,116 | A | 4/1998 | Hamann et al. |
| 5,767,237 | A | 6/1998 | Sakakibara et al. |
| 5,767,285 | A | 6/1998 | Hamann et al. |
| 5,770,701 | A | 6/1998 | McGahren et al. |
| 5,770,710 | A | 6/1998 | McGahren et al. |
| 5,773,001 | A | 6/1998 | Hamann et al. |
| 5,780,588 | A | 7/1998 | Pettit et al. |
| 5,807,706 | A | 9/1998 | Carter et al. |
| 5,821,333 | A | 10/1998 | Carter et al. |
| 5,821,337 | A | 10/1998 | Carter et al. |
| 5,824,805 | A | 10/1998 | King et al. |
| 5,846,545 | A | 12/1998 | Chari et al. |
| 5,859,205 | A | 1/1999 | Adair et al. |
| 5,877,291 | A | 3/1999 | Mezes et al. |
| 5,877,296 | A | 3/1999 | Hamann et al. |
| 5,891,996 | A | 4/1999 | Mateo de Acosta del Rio et al. |
| 5,892,020 | A | 4/1999 | Mezes et al. |
| 5,945,311 | A | 8/1999 | Lindhofer et al. |
| 5,968,509 | A | 10/1999 | Gorman et al. |
| 6,054,297 | A | 4/2000 | Carter et al. |
| 6,071,515 | A | 6/2000 | Mezes et al. |
| 6,124,431 | A | 9/2000 | Sakakibara et al. |
| 6,177,078 | B1 | 1/2001 | Lopez |
| 6,180,370 | B1 | 1/2001 | Queen et al. |
| 6,214,345 | B1 | 4/2001 | Firestone et al. |
| 6,235,883 | B1 | 5/2001 | Jakobovits et al. |
| 6,329,507 | B1 | 12/2001 | Mezes et al. |
| 6,407,213 | B1 | 6/2002 | Carter et al. |
| 6,441,163 | B1 | 8/2002 | Chari et al. |
| 6,455,677 | B1 | 9/2002 | Park et al. |
| 6,506,883 | B2 | 1/2003 | Meteo de Acosta del Rio et al. |
| 6,602,684 | B1 | 8/2003 | Umana et al. |
| 6,632,927 | B2 | 10/2003 | Adair et al. |
| 6,706,265 | B1 | 3/2004 | Bolt et al. |
| 6,716,410 | B1 | 4/2004 | Witztum |
| 6,723,538 | B2 | 4/2004 | Mack et al. |
| 6,884,869 | B2 | 4/2005 | Senter et al. |
| 6,989,452 | B2 | 1/2006 | Ng et al. |
| 7,087,600 | B2 | 8/2006 | Ng et al. |
| 7,112,324 | B1 | 9/2006 | Dorken et al. |
| 7,129,261 | B2 | 10/2006 | Ng et al. |
| 7,183,076 | B2 | 2/2007 | Arathoon et al. |
| 7,276,497 | B2 | 10/2007 | Chari et al. |
| 7,303,749 | B1 | 12/2007 | Chari |
| 7,368,565 | B2 | 5/2008 | Chari et al. |
| 7,498,302 | B2 | 3/2009 | Ng et al. |
| 7,507,420 | B2 | 3/2009 | Ng et al. |
| 7,517,903 | B2 | 4/2009 | Chen et al. |
| 7,601,354 | B2 | 10/2009 | Chari |
| 7,642,228 | B2 | 1/2010 | Carter et al. |
| 7,691,962 | B2 | 4/2010 | Boyd et al. |
| 7,695,936 | B2 | 4/2010 | Carter et al. |
| 7,696,338 | B2 | 4/2010 | Neville, Jr. et al. |
| 7,728,114 | B2 | 6/2010 | Mach et al. |
| 7,850,962 | B2 | 12/2010 | Teeling et al. |
| 8,063,187 | B2 | 11/2011 | Chu et al. |
| 8,114,967 | B2 | 2/2012 | Bhatt et al. |
| 8,216,805 | B2 | 7/2012 | Carter et al. |
| 8,236,308 | B2 | 8/2012 | Kischel et al. |
| 8,309,690 | B2 | 11/2012 | Allan et al. |
| 8,367,805 | B2 | 2/2013 | Chamberlain et al. |
| 8,409,568 | B2 | 4/2013 | Gao et al. |
| 8,592,562 | B2 | 11/2013 | Kannan et al. |
| 8,637,641 | B2 | 1/2014 | Dahiyat et al. |
| 8,946,387 | B2 | 2/2015 | Koenig et al. |
| 9,181,334 | B2 | 11/2015 | Kobayashi et al. |
| 9,650,446 | B2 | 5/2017 | Moore et al. |
| 9,822,181 | B2 | 11/2017 | Bonvini et al. |
| 9,822,186 | B2 | 11/2017 | Bernett et al. |
| 9,856,327 | B2 | 1/2018 | Bernett et al. |
| 10,131,710 | B2 | 11/2018 | Moore et al. |
| 10,227,410 | B2 | 3/2019 | Moore et al. |
| 10,258,887 | B2 | 4/2019 | Kulavik et al. |
| 10,294,300 | B2 | 5/2019 | Raum et al. |
| 10,316,088 | B2 | 6/2019 | Moore et al. |
| 10,414,815 | B2 | 9/2019 | Ellmark et al. |
| 10,428,155 | B2 | 10/2019 | Moore et al. |
| 10,526,417 | B2 | 1/2020 | Bernett et al. |
| 10,639,368 | B2 | 5/2020 | Van Dijk et al. |
| 10,738,132 | B2 | 8/2020 | Desjarlais et al. |
| 10,738,133 | B2 | 8/2020 | Moore et al. |
| 10,982,006 | B2 | 4/2021 | Desjarlais et al. |
| 11,053,316 | B2 | 7/2021 | Moore et al. |
| 11,066,483 | B2 | 7/2021 | Nezu et al. |
| 11,225,521 | B2 | 1/2022 | Moore et al. |
| 11,225,528 | B2 | 1/2022 | Bernett et al. |
| 11,472,890 | B2 | 10/2022 | Rashid et al. |
| 11,505,595 | B2 | 11/2022 | Bernett et al. |
| 11,530,274 | B2 | 12/2022 | Nolan-Stevaux |
| 11,591,401 | B2 | 2/2023 | Desjarlais et al. |
| 11,623,957 | B2 | 4/2023 | Moore et al. |
| 11,919,958 | B2 | 3/2024 | Desjarlais et al. |
| 2002/0076406 | A1 | 6/2002 | Leung |
| 2002/0103345 | A1 | 8/2002 | Zhu |
| 2002/0131968 | A1 | 9/2002 | Waldmann et al. |
| 2003/0003097 | A1 | 1/2003 | Reff et al. |
| 2003/0017979 | A1 | 1/2003 | Mack et al. |
| 2003/0091561 | A1 | 5/2003 | Van de Winekl |
| 2003/0157108 | A1 | 8/2003 | Presta |
| 2003/0223999 | A1 | 12/2003 | Lindhofer |
| 2004/0018191 | A1 | 1/2004 | Wang |
| 2004/0071696 | A1 | 4/2004 | Adams et al. |
| 2004/0162411 | A1 | 8/2004 | Lanzavecchia |
| 2004/0170626 | A1 | 9/2004 | Schuurman |
| 2004/0242851 | A1 | 12/2004 | Zhu |
| 2005/0100543 | A1 | 5/2005 | Hansen et al. |
| 2005/0114037 | A1 | 5/2005 | Desjarlais et al. |
| 2005/0136050 | A1 | 6/2005 | Kufer et al. |
| 2005/0142133 | A1 | 6/2005 | Lazar et al. |
| 2005/0176028 | A1 | 8/2005 | Hofmeiser et al. |
| 2005/0191702 | A1 | 9/2005 | Mack et al. |
| 2005/0238648 | A1 | 10/2005 | Jacobs |
| 2005/0238649 | A1 | 10/2005 | Doronina |
| 2006/0008883 | A1 | 1/2006 | Lazar |
| 2006/0018897 | A1 | 1/2006 | Lee et al. |
| 2006/0024298 | A1 | 2/2006 | Lazar et al. |
| 2006/0024317 | A1 | 2/2006 | Boyd |
| 2006/0073142 | A1 | 4/2006 | Chan et al. |
| 2006/0074008 | A1 | 4/2006 | Senter |
| 2006/0115481 | A1 | 6/2006 | Lindhofer et al. |
| 2006/0121032 | A1 | 6/2006 | Dahiyat et al. |
| 2006/0134105 | A1 | 6/2006 | Lazar et al. |
| 2006/0235208 | A1 | 10/2006 | Lazar |
| 2007/0071675 | A1 | 3/2007 | Wu et al. |
| 2007/0105199 | A1 | 5/2007 | Yan et al. |
| 2007/0123479 | A1 | 5/2007 | Kufer et al. |
| 2007/0148170 | A1 | 6/2007 | Desjarlais |
| 2007/0287170 | A1 | 12/2007 | Davis et al. |
| 2008/0044413 | A1 | 2/2008 | Hammond et al. |
| 2008/0050370 | A1 | 2/2008 | Glaser et al. |
| 2008/0138335 | A1 | 6/2008 | Takahashi et al. |
| 2008/0213273 | A1 | 9/2008 | Burge |
| 2008/0219974 | A1 | 9/2008 | Bernett et al. |
| 2008/0242845 | A1 | 10/2008 | Lazar et al. |
| 2008/0279851 | A1 | 11/2008 | Coyle et al. |
| 2009/0004195 | A1 | 1/2009 | Vranic et al. |
| 2009/0082213 | A1 | 3/2009 | Horowitz et al. |
| 2009/0163699 | A1 | 6/2009 | Chamberlain et al. |
| 2009/0214539 | A1 | 8/2009 | Grosmaire et al. |
| 2009/0252683 | A1 | 10/2009 | Kischel et al. |
| 2009/0252729 | A1 | 10/2009 | Farrington et al. |
| 2009/0274692 | A1 | 11/2009 | Tan et al. |
| 2009/0311253 | A1 | 12/2009 | Ghayur et al. |
| 2009/0317869 | A1 | 12/2009 | Alley et al. |
| 2010/0004431 | A1 | 1/2010 | Bernett et al. |
| 2010/0015133 | A1 | 1/2010 | Igawa et al. |

(56) References Cited

U.S. PATENT DOCUMENTS

| | | |
|---|---|---|
| 2010/0080814 A1 | 4/2010 | Desjarlais et al. |
| 2010/0150918 A1 | 6/2010 | Kufer et al. |
| 2010/0174053 A1 | 7/2010 | Johnson et al. |
| 2010/0178298 A1 | 7/2010 | Lindhofer |
| 2010/0183554 A1 | 7/2010 | Mach et al. |
| 2010/0226925 A1 | 9/2010 | Dillon et al. |
| 2010/0239567 A1 | 9/2010 | Esue |
| 2010/0239582 A1 | 9/2010 | Humphreys et al. |
| 2010/0256339 A1 | 10/2010 | Bossenmaier et al. |
| 2010/0256340 A1 | 10/2010 | Brinkmann et al. |
| 2010/0298542 A1 | 11/2010 | Igawa et al. |
| 2010/0322933 A1 | 12/2010 | Lindhofer et al. |
| 2010/0330089 A1 | 12/2010 | Damle et al. |
| 2010/0331527 A1 | 12/2010 | Davis et al. |
| 2011/0054151 A1 | 3/2011 | Lazar et al. |
| 2011/0076275 A1 | 3/2011 | Igawa et al. |
| 2011/0177500 A1 | 7/2011 | Winther et al. |
| 2011/0189178 A1 | 8/2011 | Desjarlais et al. |
| 2011/0189209 A1 | 8/2011 | Neville, Jr. et al. |
| 2011/0201032 A1 | 8/2011 | Zeng et al. |
| 2011/0217302 A1 | 9/2011 | Odegard et al. |
| 2011/0262439 A1 | 10/2011 | Kufer et al. |
| 2011/0275787 A1 | 11/2011 | Kufer et al. |
| 2011/0293619 A1 | 12/2011 | Kufer et al. |
| 2012/0028304 A1 | 2/2012 | Dahiyat et al. |
| 2012/0034228 A1 | 2/2012 | Kufer et al. |
| 2012/0039906 A1 | 2/2012 | Olive |
| 2012/0121597 A1 | 5/2012 | Ho et al. |
| 2012/0149876 A1 | 6/2012 | Von Kreudenstein et al. |
| 2012/0156207 A1 | 6/2012 | Chu et al. |
| 2012/0251531 A1 | 10/2012 | Baehner et al. |
| 2012/0251541 A1 | 10/2012 | Baurin et al. |
| 2013/0018174 A1 | 1/2013 | Igawa et al. |
| 2013/0089541 A1 | 4/2013 | D'Angelo et al. |
| 2013/0095097 A1 | 4/2013 | Blakenship et al. |
| 2013/0101586 A1 | 4/2013 | Riegler et al. |
| 2013/0115208 A1 | 5/2013 | Ho et al. |
| 2013/0129723 A1 | 5/2013 | Blakenship et al. |
| 2013/0142793 A1 | 6/2013 | Ledbetter et al. |
| 2013/0171095 A1 | 7/2013 | Bernett et al. |
| 2013/0195849 A1 | 8/2013 | Kreudenstein et al. |
| 2013/0209355 A1 | 8/2013 | De Weers et al. |
| 2013/0267686 A1 | 10/2013 | Brinkmann |
| 2013/0336981 A1 | 12/2013 | de Kruif et al. |
| 2014/0010814 A1 | 1/2014 | Benhar et al. |
| 2014/0024111 A1 | 1/2014 | Kannan et al. |
| 2014/0044714 A1 | 2/2014 | Ho et al. |
| 2014/0056879 A1 | 2/2014 | Lazar |
| 2014/0072581 A1 | 3/2014 | Dixit et al. |
| 2014/0086916 A1 | 3/2014 | Zha |
| 2014/0161790 A1 | 6/2014 | Desjarlais et al. |
| 2014/0199311 A1 | 7/2014 | Kobayashi et al. |
| 2014/0212435 A1 | 7/2014 | Moore et al. |
| 2014/0212436 A1 | 7/2014 | Moore et al. |
| 2014/0249297 A1 | 9/2014 | Lazar et al. |
| 2014/0288275 A1 | 9/2014 | Moore et al. |
| 2014/0294759 A1 | 10/2014 | Chu et al. |
| 2014/0294823 A1 | 10/2014 | Moore et al. |
| 2014/0294833 A1 | 10/2014 | Desjarlais et al. |
| 2014/0294835 A1 | 10/2014 | Moore et al. |
| 2014/0294836 A1 | 10/2014 | Chu et al. |
| 2014/0302035 A1 | 10/2014 | Harms et al. |
| 2014/0302064 A1 | 10/2014 | Moore |
| 2014/0322217 A1 | 10/2014 | Moore et al. |
| 2014/0356381 A1 | 12/2014 | Moore et al. |
| 2014/0363426 A1 | 12/2014 | Moore et al. |
| 2014/0370013 A1 | 12/2014 | Desjarlais et al. |
| 2014/0370020 A1 | 12/2014 | Kuramochi et al. |
| 2014/0377269 A1 | 12/2014 | Mabry et al. |
| 2014/0377270 A1 | 12/2014 | Moore et al. |
| 2015/0071948 A1 | 3/2015 | Lazar et al. |
| 2015/0119555 A1 | 4/2015 | Jung et al. |
| 2015/0307628 A1 | 10/2015 | Kim et al. |
| 2015/0307629 A1 | 10/2015 | Bernett et al. |
| 2016/0060360 A1 | 3/2016 | Moore et al. |
| 2016/0068588 A1 | 3/2016 | Bernett et al. |
| 2016/0108123 A1 | 4/2016 | Freeman et al. |
| 2016/0176969 A1 | 6/2016 | Bernett et al. |
| 2016/0215063 A1 | 7/2016 | Bernett et al. |
| 2016/0229924 A1 | 8/2016 | Bernett et al. |
| 2016/0355608 A1 | 12/2016 | Bernett et al. |
| 2017/0020963 A1 | 1/2017 | Qu et al. |
| 2017/0088618 A1 | 3/2017 | Bennett et al. |
| 2017/0107270 A1 | 4/2017 | Pons et al. |
| 2017/0320947 A1 | 11/2017 | Moore et al. |
| 2017/0355756 A1 | 12/2017 | Julien et al. |
| 2018/0118828 A1 | 5/2018 | Bernett et al. |
| 2018/0118836 A1 | 5/2018 | Bernett et al. |
| 2018/0127501 A1 | 5/2018 | Bernett et al. |
| 2018/0305465 A1 | 10/2018 | Stevens et al. |
| 2019/0106504 A1 | 4/2019 | Wu et al. |
| 2019/0263909 A1 | 8/2019 | Bernett et al. |
| 2019/0270816 A1 | 9/2019 | Bernett et al. |
| 2019/0314411 A1 | 10/2019 | Xiao et al. |
| 2019/0345252 A1 | 11/2019 | Kinsella et al. |
| 2019/0352362 A1 | 11/2019 | Bernett et al. |
| 2019/0359684 A1 | 11/2019 | Bernett et al. |
| 2019/0382495 A1 | 12/2019 | Bernett et al. |
| 2019/0389954 A1 | 12/2019 | Bernett et al. |
| 2021/0102002 A1 | 4/2021 | Bernett et al. |
| 2022/0098306 A1 | 3/2022 | Desjarlais et al. |
| 2022/0119530 A1 | 4/2022 | Desjarlais et al. |
| 2023/0257466 A1 | 8/2023 | Desjarlais et al. |
| 2023/0279071 A1 | 9/2023 | Bernett et al. |
| 2023/0331813 A1 | 10/2023 | Bernett et al. |
| 2024/0025968 A1 | 1/2024 | Bernett et al. |

FOREIGN PATENT DOCUMENTS

| | | |
|---|---|---|
| EP | 1752471 | 2/2007 |
| EP | 1829895 A1 | 9/2007 |
| EP | 2006381 A1 | 12/2008 |
| EP | 2009101 A1 | 12/2008 |
| EP | 2194066 A1 | 6/2010 |
| EP | 2202245 A1 | 6/2010 |
| EP | 2522724 A1 | 11/2012 |
| EP | 2155788 | 2/2014 |
| EP | 3199628 A1 | 8/2017 |
| EP | 3252078 | 12/2017 |
| EP | 3339326 A1 | 6/2018 |
| JP | 2003111595 A | 4/2003 |
| RU | 2014114179 A | 10/2015 |
| WO | WO8705330 | 9/1987 |
| WO | WO9211018 | 7/1992 |
| WO | WO9321232 | 10/1993 |
| WO | WO9413804 A1 | 6/1994 |
| WO | WO9520045 A1 | 7/1995 |
| WO | WO96027011 | 9/1996 |
| WO | WO9640210 A1 | 12/1996 |
| WO | WO1997024373 | 7/1997 |
| WO | WO1997044352 A1 | 11/1997 |
| WO | WO98050431 | 11/1998 |
| WO | WO199937791 A1 | 7/1999 |
| WO | WO99054440 | 10/1999 |
| WO | WO99066951 | 12/1999 |
| WO | WO200061739 A1 | 10/2000 |
| WO | WO200124763 A2 | 4/2001 |
| WO | WO200129246 A1 | 4/2001 |
| WO | WO200162931 A2 | 8/2001 |
| WO | WO200188138 A1 | 11/2001 |
| WO | WO2001083525 A2 | 11/2001 |
| WO | WO2001090192 A2 | 11/2001 |
| WO | WO200216368 | 2/2002 |
| WO | WO200230954 A1 | 4/2002 |
| WO | WO200231140 A1 | 4/2002 |
| WO | WO2002088172 A2 | 7/2002 |
| WO | WO2002062850 A2 | 8/2002 |
| WO | WO2002083180 A1 | 10/2002 |
| WO | WO2002098883 | 12/2002 |
| WO | WO2004056875 A1 | 12/2003 |
| WO | WO2004010957 A2 | 2/2004 |
| WO | WO2004043493 | 5/2004 |
| WO | WO2004103272 | 12/2004 |
| WO | WO2004106383 | 12/2004 |

(56)          References Cited

FOREIGN PATENT DOCUMENTS

| | | |
|---|---|---|
| WO | WO2005063816 | 7/2005 |
| WO | WO2005092925 A2 | 10/2005 |
| WO | WO2005103083 A2 | 11/2005 |
| WO | WO2005112919 A2 | 12/2005 |
| WO | WO2005118635 | 12/2005 |
| WO | WO2006006693 A1 | 1/2006 |
| WO | WO2006020258 | 2/2006 |
| WO | WO2006034488 | 3/2006 |
| WO | WO2006036834 | 4/2006 |
| WO | WO2006072620 | 7/2006 |
| WO | WO2006106905 A1 | 10/2006 |
| WO | WO2006110476 A2 | 10/2006 |
| WO | WO-2006124641 A2 * 11/2006 ............ C07K 16/30 |  |
| WO | WO2006131013 | 12/2006 |
| WO | WO2007005612 | 1/2007 |
| WO | WO2007018431 A2 | 2/2007 |
| WO | WO2007033230 | 3/2007 |
| WO | WO2007042261 | 4/2007 |
| WO | WO2007042309 A2 | 4/2007 |
| WO | WO2007046006 | 4/2007 |
| WO | WO2007047829 | 4/2007 |
| WO | WO2007059404 A2 | 5/2007 |
| WO | WO2007062037 | 5/2007 |
| WO | WO2007084342 | 7/2007 |
| WO | WO2007089149 A2 | 8/2007 |
| WO | WO2007093630 | 8/2007 |
| WO | WO2007098934 | 9/2007 |
| WO | WO2007110205 | 10/2007 |
| WO | WO2007113648 | 10/2007 |
| WO | WO2007145941 A2 | 12/2007 |
| WO | WO20070147901 | 12/2007 |
| WO | WO2008003103 | 1/2008 |
| WO | WO2008003115 | 1/2008 |
| WO | WO2008003116 | 1/2008 |
| WO | WO2008047242 A2 | 4/2008 |
| WO | WO2008048942 | 4/2008 |
| WO | WO2008068048 A2 | 6/2008 |
| WO | WO2008119096 | 10/2008 |
| WO | WO2008119566 | 10/2008 |
| WO | WO2008124858 | 10/2008 |
| WO | WO 2008143684 A1 | 11/2008 |
| WO | WO2008145142 | 12/2008 |
| WO | WO2008150494 | 12/2008 |
| WO | WO2008156712 A1 | 12/2008 |
| WO | WO2009000006 | 12/2008 |
| WO | WO2009017394 A1 | 2/2009 |
| WO | WO2009017823 | 2/2009 |
| WO | WO2009030734 | 3/2009 |
| WO | WO2009032782 | 3/2009 |
| WO | WO2009086320 | 7/2009 |
| WO | WO2009089004 | 7/2009 |
| WO | WO2009106096 | 9/2009 |
| WO | WO2009106321 | 9/2009 |
| WO | WO2010022737 A1 | 3/2010 |
| WO | WO2010028796 | 3/2010 |
| WO | WO2010029434 A1 | 3/2010 |
| WO | WO2010033736 | 3/2010 |
| WO | WO2010034441 | 4/2010 |
| WO | WO2010037835 | 4/2010 |
| WO | WO2010042904 | 4/2010 |
| WO | WO2010062171 A2 | 6/2010 |
| WO | WO2010085682 | 7/2010 |
| WO | WO2010106180 | 9/2010 |
| WO | WO2010115551 | 10/2010 |
| WO | WO2010115552 | 10/2010 |
| WO | WO2010115553 | 10/2010 |
| WO | WO2010115589 | 10/2010 |
| WO | WO2010119119 | 10/2010 |
| WO | WO20100112193 | 10/2010 |
| WO | WO2010136172 | 12/2010 |
| WO | WO2010151792 | 12/2010 |
| WO | WO2010151808 | 12/2010 |
| WO | WO2011005621 | 1/2011 |
| WO | WO2011028952 | 3/2011 |
| WO | WO2011036183 | 3/2011 |
| WO | WO2011051307 | 5/2011 |
| WO | WO2011063348 | 5/2011 |
| WO | WO2011066342 | 6/2011 |
| WO | WO2011066501 | 6/2011 |
| WO | WO2011078332 A1 | 6/2011 |
| WO | WO2011090762 A1 | 7/2011 |
| WO | WO 2011097603 A1 | 8/2011 |
| WO | WO2011121110 | 10/2011 |
| WO | WO2011131746 | 10/2011 |
| WO | WO2011133886 | 10/2011 |
| WO | WO2011143545 | 11/2011 |
| WO | WO2011154453 A1 | 12/2011 |
| WO | WO2011159877 | 12/2011 |
| WO | WO2012016227 | 2/2012 |
| WO | WO2012018687 | 2/2012 |
| WO | WO2012032080 | 3/2012 |
| WO | WO2012058768 | 5/2012 |
| WO | WO2012062596 | 5/2012 |
| WO | WO2012107417 | 8/2012 |
| WO | WO2012116453 | 9/2012 |
| WO | WO2012125495 | 9/2012 |
| WO | WO2012125850 | 9/2012 |
| WO | WO2012131555 | 10/2012 |
| WO | WO2012146394 | 11/2012 |
| WO | WO2012146628 | 11/2012 |
| WO | WO2012162067 | 11/2012 |
| WO | WO2013006544 | 1/2013 |
| WO | WO2013016714 | 1/2013 |
| WO | WO2013022855 | 2/2013 |
| WO | WO2013023251 | 2/2013 |
| WO | WO2013026833 | 2/2013 |
| WO | WO2013033008 | 3/2013 |
| WO | WO2013047748 | 4/2013 |
| WO | WO2013055809 | 4/2013 |
| WO | WO2013059885 A2 | 5/2013 |
| WO | WO2013063702 | 5/2013 |
| WO | WO2013070565 | 5/2013 |
| WO | WO2013096828 | 6/2013 |
| WO | WO2013101909 A1 | 7/2013 |
| WO | WO2013125667 | 8/2013 |
| WO | WO2013164694 | 11/2013 |
| WO | WO2013173820 A2 | 11/2013 |
| WO | WO2013180201 | 12/2013 |
| WO | WO2014004586 | 1/2014 |
| WO | WO2014012085 | 1/2014 |
| WO | WO2014018572 | 1/2014 |
| WO | WO2014047231 A1 | 3/2014 |
| WO | WO2014055897 A2 | 4/2014 |
| WO | WO2014056783 | 4/2014 |
| WO | WO2014079000 | 5/2014 |
| WO | WO2014089335 A2 | 6/2014 |
| WO | WO2014110601 | 7/2014 |
| WO | WO2014113510 | 7/2014 |
| WO | WO2014145806 | 9/2014 |
| WO | WO2014145907 | 9/2014 |
| WO | WO2014151910 A1 | 9/2014 |
| WO | WO2014164553 | 10/2014 |
| WO | WO2014207064 | 12/2014 |
| WO | WO2014209804 | 12/2014 |
| WO | WO2015018528 | 2/2015 |
| WO | WO2015026684 A1 | 2/2015 |
| WO | WO2015026892 | 2/2015 |
| WO | WO2015063339 | 5/2015 |
| WO | WO2015095392 | 6/2015 |
| WO | WO2015095410 | 6/2015 |
| WO | WO2015095423 | 6/2015 |
| WO | WO2015103072 | 7/2015 |
| WO | WO2015112900 A1 | 7/2015 |
| WO | WO2015130728 A1 | 9/2015 |
| WO | WO2015143079 | 9/2015 |
| WO | WO2015149077 | 10/2015 |
| WO | WO2015168379 A2 | 11/2015 |
| WO | WO2015184207 | 12/2015 |
| WO | WO2016014984 | 1/2016 |
| WO | WO2016020856 A2 | 2/2016 |
| WO | WO2016028672 | 2/2016 |
| WO | WO2016028896 | 2/2016 |
| WO | WO2016040294 A2 | 3/2016 |
| WO | WO2016071355 A1 | 5/2016 |

(56) References Cited

FOREIGN PATENT DOCUMENTS

| | | |
|---|---|---|
| WO | WO2016079050 A1 | 5/2016 |
| WO | WO2016086186 | 6/2016 |
| WO | WO2016086189 | 6/2016 |
| WO | WO2016086196 | 6/2016 |
| WO | WO2016105450 | 6/2016 |
| WO | WO2016110584 | 7/2016 |
| WO | WO2016115274 | 7/2016 |
| WO | WO2016120789 A1 | 8/2016 |
| WO | WO2016141387 | 9/2016 |
| WO | WO2016166629 A1 | 10/2016 |
| WO | WO2016182751 | 11/2016 |
| WO | WO2016210223 A1 | 12/2016 |
| WO | WO2017019846 | 2/2017 |
| WO | WO2017021356 A1 | 2/2017 |
| WO | WO2017023761 A1 | 2/2017 |
| WO | WO2017055391 A1 | 4/2017 |
| WO | WO2017072366 A1 | 5/2017 |
| WO | WO2017112775 A1 | 6/2017 |
| WO | WO2017134158 A1 | 8/2017 |
| WO | WO2017210443 | 12/2017 |
| WO | WO2017210485 | 12/2017 |
| WO | WO2017214092 | 12/2017 |
| WO | WO2017220990 A1 | 12/2017 |
| WO | WO2018005706 | 1/2018 |
| WO | WO2018017863 | 1/2018 |
| WO | WO2018041838 A1 | 3/2018 |
| WO | WO2018209304 A1 | 11/2018 |
| WO | WO2019050521 | 3/2019 |
| WO | WO2019104075 A1 | 5/2019 |
| WO | WO2019173324 A1 | 9/2019 |
| WO | WO2019190969 A1 | 10/2019 |
| WO | WO2019224718 A2 | 11/2019 |
| WO | WO 2020023553 A1 | 1/2020 |
| WO | WO 2020033702 A1 | 2/2020 |
| WO | WO2020052692 A2 | 3/2020 |
| WO | WO2020236797 A1 | 11/2020 |
| WO | WO2021026387 A2 | 2/2021 |
| WO | WO2021229507 A2 | 11/2021 |
| WO | WO2022094299 A2 | 5/2022 |
| WO | WO2023098770 A1 | 6/2023 |
| WO | WO2023201309 A1 | 10/2023 |

OTHER PUBLICATIONS

Kulmanov et al, Bioinformatics, 34(4), 2018, 660-668 (Year: 2018).*
U.S. Appl. No. 12/631,508, filed Dec. 4, 2009, Chari et al.
(No Author Name) "A method for making multispecific antibodies having heteromultimeric and common components", Expert Opinion on Therapeutic Patents, Genentech, Inc. (1999) 9(6): 785-790, pp. 785-790.
"Polythene Glycol and Derivatives for Advanced PEGylation", Catalog 2005-2006, Nektar Therapeutics.
"Xencor Provides Data Updates on XmaB Bispecific Antibody Program and Announces Presentations at Upcoming American Society of Hematology 2014 Annual Meeting", Nov. 6, 2014, XP055255549, retrieved from the internet: http://files.shareholder.com/downloads/AMDA-2B2V8N/0x0x792404/77590b72-837a-4085-bc55-78fa500638dc/XNCR_News_2014_11_6_General_Releases.pdf.
Abbott Laboratories, Strategies and Current Approaches for Improving Drug-Like-Properties During Biologics Drug Candidate Selection, AAPS Webinar—Nov. 10, 2011.
Adams, et al., Avidity-Mediated Enhancement of In vivo Tumor Targeting by Single-Chain Fv Dimers, Clin Cancer Res, 2006, vol. 12(5), pp. 1599-1605, doi:10.1158/1078-0432.CCR-05-2217.
Alberola-Ila et al., Stimulation Through the TCR/CD3 Complex Up-Regulates the CD2 Srface Expression on Human T Lymphocytes, Feb. 15, 1991.
Alibaud et al., A New Monoclonal Anti-CD3? Antibody Reactive on Paraffin Sections, Journal of Histochemistry & Cytochemistry, 2000, vol. 48, p. 1609.

An, et al., IgG2m4, an engineered antibody isotype with reduced Fc function, mAbs, 2009, vol. 1, Issue 6, pp. 572-579, www.landesbioscience.com/journals/mabs/article/10185.
Aplin et al., , Preparation, properties, and applications of carbohydrate conjugates of proteins and lipids, 1981, CRC Crit. Rev. Biochem., pp. 259-306.
Arnett, et al., Crystal structure of a human CD3-ε/δ dimer in complex with a UCHT1 single-chain antibody fragment, PNAS, 2004, vol. 101, No. 46, pp. 16268-16273.
Asano, et al., Cytotoxic enhancement of a bispecific diabody (Db) by format conversion to tandem single-chain variable fragment (taFv): The Case of the hEx3 Diabody, JBC Papers in Press, 2010, http://www.jbc.org/cgi/doi/10.1074/jbc.M110.172957.
Asano, et al., Highly Effective Recombinant Format of a Humanized IgG-like Bispecific Antibody for Cancer Immunotherapy with Retargeting of Lymphocytes to Tumor Cells, The Journal of Biological Chemistry, 2007, vol. 282, No. 38, pp. 27659-27665.
Atwell, et al., Stable Heterodimers from Remodeling the Domain Interface of a Homodimer using a Phage Display Library, J. Mol. Biol., 1997, vol. 270, pp. 26-35.
Baca et al., Antibody humanization using monovalent phage display, 1997, J. Biol. Chem. 272(16):10678-10684.
Baeuerle, et al., Response to Letter, "Correct TandAb protein," Molecular Immunology, 2007, vol. 44, p. 3084.
Baeuerle, et al., Review—Bispecific T-Cell Engaging Antibodies for Cancer Therapy, Cancer Res, 2009, vol. 69: (12), pp. 4941-4944.
Barbas, et al. In vitro evolution of a neutralizing human antibody to human immunodeficiency virus type 1 to enhance affinity and broaden strain cross-reactivity, 1994, Proc. Nat. Acad. Sci, USA 91:3809-3813.
Bargou et al., Tumor Regression in Cancer Patients by Very Low Doses of a T Cell-Engaging Antibody, Science, 2008, vol. 321, pp. 974-977.
Bernett et al., Multiple Bispecific Checkpoint Combinations Promote T cell activation., Nov. 11, 2016, retrieved from the internet: http://files.shareholder.com/downloads/AMDA-2B2V8N/0x0x916283/67AE1A8B-40E8-4316-9F79-384D06B2C395/XNCR_SITC_2016_PD1xCTLA4_Poster126_12Nov2016.pdf.
Bhatt, Sea Lane—DDD presentation, "Surrobodies™—A Novel Approach to Bispecifics . . . ," Aug. 8, 2012.
Bibollet-Ruche et al., The Quality of Chimpanzee T-Cell Activation and Simian Immunodeficiency Virus/Human Immunodeficiency Virus Susceptibility Achieved via Antibody-Mediated T-Cell Receptor/CD3 Stimulation Is a Function of the Anti-CD3 Antibody Isotype, Jul. 30, 2008.
Biochemica, Your apoptosis specialist, 1999, No. 2, pp. 34-37 (Roche Molecular Biochemicals).
Bird et al., Single-chain antigen-binding proteins, 1988, Science 242:423-426.
Bluemel, et al., Epitope distance to the target cell membrane and antigen size determine the potency of T cell-mediated lysis by BiTE antibodies specific for a large melanoma surface antigen, Cancer Immunol Immunother, 2010, vol. 59(8), pp. 1197-1209.
Borras, et al., Generic Approach for the Generation of Stable Humanized Single-chain Fv Fragments from Rabbit Monoclonal Antibodies, The Journal of Biological Chemistry, 2010, vol. 285, No. 12, pp. 9054-9066.
Bortoletto, Nicola et al., "Optimizing anti-CD3 affinity for effective T cell targeting against tumor cells.", Eur J Immunol. Nov. 2002;32(11):3102-7.
Boswell et al., Effects of Charge on Antibody Tissue Distribution and Pharmacokinetics, 2010, Bioconjugate Chem, 21(21):2153-2163.
Brandl, et al., Bispecific antibody fragments with CD20 3 CD28 specificity allow effective autologous and allogeneic T-cell activation against malignant cells in peripheral blood and bone marrow cultures from patients with B-cell lineage leukemia and lymphoma, Experimental Hematology, 1999, vol. 27, pp. 1264-1270.
Brinkmann , et al., presentation slideshow—"Roche Penzberg & Roche Glycart, Schlieren: Centers of Excellence for Recombinant Proteins".

(56)          References Cited

OTHER PUBLICATIONS

Brinkmann, et al., A recombinant immunotoxin containing a disulfide-stabilized Fv fragment, Proc. Natl. Acad. Sci. USA, 1993, vol. 90, pp. 7538-7542.

Cao, et al., Oligomerization is required for the activity of recombinant soluble LOX-1., FEBS J. Sep. 2009;276(17):4909-20. doi: 10.1111/j.1742-4658.2009.07190.x. Epub Jul. 31, 2009.

Carpenter, et al., Non-Fc Receptor-Binding Humanized Anti-CD3 Antibodies Induce Apoptosis of Activated Human T Cells, J. Immunol., 2000, vol. 165, No. 11, pp. 6205-6213.

Carter et al., Antibody-drug conjugates for cancer therapy, 2008, Cancer J. 14(3):154-169.

Carter et al., Humanization of an anti-p185HER2 antibody for human cancer therapy, 1992, Proc Natl Acad Sci USA 89:4285-9.

Castoldi, et al., Molecular characterization of novel trispecific ErbB-cMet-IGF1R antibodies and their antigen-binding properties, Protein Engineering, Design & Selection, 2012, vol. 25, No. 10, pp. 551-559.

Cemerski, et al., Suppression of mast cell degranulation through a dual-targeting tandem IgE-IgG Fc domain biologic engineered to bind with high affinity to FcγRIIb., Immunol Lett. Mar. 30, 2012;143(1):34-43. doi: 10.1016/j.imlet.2012.01.008. Epub Jan. 25, 2012.

Chames et al., Bispecific antibodies for cancer therapy—The light at the end of the tunnel?, mAbs, 2009, vol. 1, Issue 6, pp. 1-9.

Chang, et al., Monoclonal antibodies against oxidized low-density lipoprotein bind to apoptotic cells and inhibit their phagocytosis by elicited macrophages: evidence that oxidation-specific epitopes mediate macrophage recognition., Proc Natl Acad Sci U S A. May 25, 1999;96(11):6353-8.

Chari et al., Immunoconjugates containing novel maytansinoids: promising anticancer drugs, 1992, Cancer Research 52: 127-131.

Chatal, 1989, Monoclonal Antibodies in Immunoscintigraphy, CRC Press (Book Abstract).

Chelius, et al., Structural and functional characterization of the trifunctional antibody catumaxomab, mAbs, 2010, vol. 2, Issue 3, pp. 309-319.

Chichili et al., A CD3xCD123 bispecific DART for redirecting host T cells to myelogenous leukemia: preclinical activity and safety in nonhuman primates., Sci Transl Med. May 27, 2015;7(289):289ra82. doi: 10.1126/scitranslmed.aaa5693.

Chichili et al., Co-targeting of PD-1 and CTLA-4 Inhibitory Pathways with Bispecific Dart® and Trident™ Molecules., Apr. 4, 2017, retrieved from the internet: http://files.shareholder.com/downloads/AMDA-278VRP/0x0x935572/8CC86417-40BA-41C0-935D-EF1B7DB0B5BB/AACR_2017_-_Co-targeting_PD-1_and_CTLA-4_Inhibitory_Pathways_with_DART_and_TRIDENT_Molecules.pdf.

Chothia et al., Canonical structures for the hypervariable regions of immunoglobulins, 1987, J. Mol. Biol. 196:901-917.

Chothia, et al., Structural Determinants in the Sequences of Immunoglobulin Variable Domain, J. Mol. Biol., 1998, vol. 278, pp. 457-479.

Chu et al., Immunotherapy with Long-Lived Anti-CD123 x Anti-CD3 Bispecific Antibodies Stimulates Potent T Cell Mediated Killing of Human AML Cell Lines and of CD123+ Cells In Monkeys: A Potential Therapy for Acute Myelogenous Leukemia, Blood 2014, 124:2316.

Chu et al., Immunotherapy with Long-Lived Anti-CD123 x Anti-CD3 Bispecific Antibodies Stimulates Potent T Cell-Mediated Killing of Human B Cell Lines and of Circulating and Lymphoid B Cells in Monkeys: A Potential Therapy for B Cell Lymphomas and Leukemias, Blood 2014, 124:3111.

Chu et al., Inhibition of B cell receptor-mediated activation of primary human B cells by coengagement of CD19 and FcgammaRIIb with Fc-engineered antibodies., Mol Immunol. Sep. 2008;45(15):3926-33. doi: 10.1016/j.molimm.2008.06.027. Epub Aug. 8, 2008.

Chu et al., Reduction of total IgE by targeted coengagement of IgE B-cell receptor and FcγRIIb with Fc-engineered antibody., J Allergy Clin Immunol. Apr. 2012;129(4):1102-15. doi: 10.1016/j.jaci.2011.11.029. Epub Jan. 16, 2012.

Conrad, et al., TCR and CD3 Antibody Cross-Reactivity in 44 Species, Cytometry Part A, 2007, vol. 71A, pp. 925-933.

Conrath, et al., Antigen Binding and Solubility Effects upon the Veneering of a Camel VHH in Framework-2 to Mimic a VH, J. Mol. Biol. , 2005, vol. 350, pp. 112-125.

Counterman et al., "Volumes of Individual Amino Acid Residues in Gas-Phase Peptide Ions.", J. Am. Chem. Soc., 1999, 121 (16), pp. 4031-4039.

Cuesta, et al., Multivalent antibodies: when design surpasses evolution, Trends in Biotechnology, 2010, vol. 28, No. 7, pp. 355-362, doi:10.1016/j.tibtech.2010.03.007.

D'Argouges, et al., Combination of rituximab with blinatumomab (MT103/MEDI-538), a T cell-engaging CD19-/CD3-bispecific antibody, for highly efficient lysis of human B lymphoma cells, Leukemia Research, 2009, vol. 33, pp. 465-473.

Davies et al., Expression of GnTIII in recombinant anti-CD20 CHO production cell line: expression of antibodies with altered glycoforms leads to an increase in ADCC through higher affinity for FCγRIII, 2001, Biotechnol Bioeng 74:288-294.

Davila, et al., Efficacy and Toxicity Management of 19-28z CAR T Cell Therapy in B Cell Acute Lymphoblastic Leukemia, Sci. Transl. Med., 2014, vol. 6, Issue 224, pp. 1-10, 224ra25.

Davis, et al., SEEDbodies: fusion proteins based on strand-exchange engineered domain (SEED) $C_H3$ heterodimers in an Fc analogue platform for asymmetric binders or immunofusions and bispecific antibodies, Protein Engineering, Design & Selection, 2010, vol. 23, No. 4 pp. 195-202.

De Groot et al., De-Immunization Of Therapeutic Proteins By T-Cell Epitope Modification, 2005, Dev. In Biologicals, 2005, 122:171-194.

De Pascalis et al., Grafting of "abbreviated" complementarity-determining regions containing specificity-determining residues essential for ligand contact to engineer a less immunogenic humanized monoclonal antibody, 2002, J. Immunol. 169:3076-3084.

Del Nagro et al., A critical role for complement C3d and the B cell coreceptor (CD19/CD21) complex in the initiation of inflammatory arthritis., J Immunol. Oct. 15, 2005;175(8):5379-89.

Demarest et al., Antibody therapeutics, antibody engineering, and the merits of protein stability, Current Opinin in Drug Discovery & Development, 2008 11(5): 675-587, Sep. 11, 2008.

Deyev, et al., Multivalency: the hallmark of antibodies used for optimization of tumor targeting by design, BioEssays, 2008, vol. 30, pp. 904-918.

DiGiammarino et al., Ligand association rates to the inner-variable-domain of a dual-variable-domain immunoglobulin are significantly impacted by linker design, mAbs3:5, 1-8; Sep.-Oct.; 3(5):487-94, Landes Bioscience, Sep. 1, 2011.

DiGiandomenico et al., A multifunctional bispecific antibody protects against Pseudomonas aeruginosa., Sci Transl Med. Nov. 12, 2014;6(262):262ra155. doi: 10.1126/scitranslmed.3009655.

Dixon, et al., Activation of Human T Lymphocytes by Crosslinking of Anti-CD3 Monoclonal Antibodies, Journal of Leukocyte Biology, 1989, vol. 46, pp. 214-220.

Dong et al., A stable IgG-like bispecific antibody targeting the epidermal growth factor receptor and the type I insulin-like growth factor receptor demonstrates superior anti-tumor activity, mAbs 3:3, May-Jun. 2011: 273-288, May 1, 2011.

Doronina , Development of potent monoclonal antibody auristatin conjugates for cancer therapy, 2003, Nat Biotechnol 21(7):778-784.

Dreier, et al., Extremely Potent, Rapid and Costimulation-Independent Cytotoxic T-cell Response Against Lymphoma Cells Catalyzed by a Single-Chain Bispecific Antibody, Int. J. Cancer, 2002, vol. 100, pp. 690-697.

Dreier, et al., T Cell Costimulus-Independent and Very Efficacious Inhibition of Tumor Growth in Mice Bearing Subcutaneous or Leukemic Human B Cell Lymphoma Xenografts by a CD19-/CD3-Bispecific Single-Chain Antibody Construct, The Journal of Immunology, 2003, vol. 170, pp. 4397-4402.

(56)        References Cited

OTHER PUBLICATIONS

Dubowchik et al., Receptor-mediated and enzyme-dependent targeting of cytotoxic anticancer drugs, 1999, Pharm. Therapeutics 83:67-123.

Ducry et al., Antibody-drug conjugates: linking cytotoxic payloads to monoclonal antibodies, 2010, Bioconjugate Chem. 21:5-13.

Dudgeon, et al., General strategy for the generation of human antibody variable domains with increased aggregation resistance, PNAS Early Edition, 2012, pp. 10879-10884, www.pnas.org/cgi/doi/10.1073/pnas.1202866109 & Supporting Information.

Duke, et al., Measurement of apoptosis and other forms of cell death, 2004, Curr protocols immunol. 3.17.1-3.17.16.

DukSin et al., Relationship of the structure and biological activity of the natural homologues of tunicamycin, 1982, J. Biol. Chem. 257:3105.

Duval, et al., A Bispecific Antibody Composed of a Nonneutralizing Antibody to the gp41 Immunodominant Region and an Anti-CD89 Antibody Directs Broad Human Immunodeficiency Virus Destruction by Neutrophils, Journal of Virology, 2008, pp. 4671-4674, doi:10.1128/JVI.02499-07.

Edge et al., Deglycosylation of glycoproteins by trifluoromethanesulfonic acid, 1981, Anal. Biochem. 118:131.

Elliott, et al., Antiparallel Conformation of Knob and Hole Aglycosylated Half-Antibody Homodimers Is Mediated by a CH2—CH3 Hydrophobic Interaction, Journal of Molecular Biology, 2014, vol. 426, Issue 9, pp. 1947-1957.

Feldmann et al., Novel Humanized and Highly Efficient Bispecific Antibodies Mediate Killing of Prostate Stem Cell Antigen-Expressing Tumor Cells by CD8+ and CD4+ T cells, Aug. 8, 2012.

Feldmann et al., Retargeting of T Cells to Prostate Stem Cell Antigen Expressing Tumor Cells: Comparison of Different Antibody Formats, Dec. 28, 2010.

Fernandes, et al., T Cell Receptors are Structures Capable of Initiating Signaling in the Absence of Large Conformational Rearrangements, The Journal of Biological Chemistry, 2012, vol. 287, No. 16, pp. 13324-13335.

Fischer, Nicolas et al., "Bispecifc antibodies: molecules that enable novel therapeutic strategies", 2007, vol. 74, pp. 3-14.

Foreman, et al., ErbB3 Inhibitory Surrobodies Inhibit Tumor Cell Proliferation In Vitro and In Vivo, Mol Cancer Ther, 2012, vol. 11(7) , pp. 1411-1420.

Foreman, et al., PEGS poster, "ErbB3 Inhibitory Surrobodies Inhibit Tumor Cell Proliferation In Vitro and In Vivo," 2012.

Hamilton et al., Crystal structure of peptide cyclo-(D-VAL-L-PRO-L-VAL-D-PRO)$_3$, 1978, Biochem. Biophys. Res. Commun. 80(4):849-57.

Francois, et al., Construction of a Bispecific Antibody Reacting with the α- and β-Chains of the Human IL-2 Receptor, The Journal of Immunology, May 15, 1993, vol. 150, No. 10, pp. 4610-4619.

F-star Modular Antibodies Fact Sheet, Apr. 2008, "Modular Antibody Technology" (w/ reference to Ruker WO 2006/072620 A1).

F-star Modular Antibodies Press Release, Mar. 28, 2008, "Antibody Engineering Company F-Star Buys Back Royalty Obligations. TVM Capital Joins Investor Syndicate."

Fudenberg, et al., Serologic Demonstration of Dual Specificity of Rabbit Bivalent Hybrid Antibody, The Journal of Experimental Medicine, 1964, vol. 119(1), pp. 151-166.

Ganesan, et al., FcγRIIb on Liver Sinusoidal Endothelium Clears Small Immune Complexes, The Journal of Immunology, Nov. 15, 2012, vol. 189 No. 10, pp. 4981-4988.

GenBank AAA38124.1, immunoglobulin heavy-chain VJ region [Mus musculus] Protein/NCBI, ROD: Apr. 27, 1993.

GenBank AAA39180.1, immunoglobulin light-chain VJ region [Mus musculus] Protein/NCBI, ROD: Apr. 27, 1993.

Ghendler et al., One of the CD3ε Subunits within a T Cell Receptor Complex Lies in Close Proximity to the CβFG Loop, J. Exp. Med., 1998, vol. 187, No. 9. pp. 1529-1536.

Ghetie et al., Multiple roles for the major histocompatibility complex Class I-related receptor FcRn, 2000, Annu Rev Immunol 18:739-766.

Gilliland, et al., Universal bispecific antibody for targeting tumor cells for destruction by cytotoxic T cells, Proc. Natl. Acad. Sci. USA, 1988, vol. 85, pp. 7719-7723.

Gorman et al., Reshaping a therapeutic CD4 antibody, Proc. Natl. Acad. Sci. USA, May 1991, 88:4181-4185.

Grodzki & Bernstein, "Antibody Purification: Ion-Exchange Chromatography.", Methods Mol Biol 2010 ;588:27-32.

Gunasekaran et al., Enhancing Antibody Fc Heterodimer Formation through Electrostatic Steering Effects, Journal of Biological Cheminstry, vol. 285, No. 25, pp. 19637-10946, Apr. 16, 2010 & Supplementary Tables.

Haagen, et al., The Efficacy of CD3 x CD19 Bispecific Monoclonal Antibody (BsAb) in a Clonogenic Assay: The Effect of Repeated Addition of BsAb, and Interleukin-2, Blood, 1995, vol. 85, No. 11, pp. 3208-3212.

Hakimuddin et al., A chemical method for the deglycosylation of proteins, 1987, Arch. Biochem. Biophys. 259:52.

Hamel, et al., The Role of the $V_L$- and $V_H$-Segments in the Preferential Reassociation of Immunoglobulin Subunits, Molecular Immunology, 1986, vol. 23, No. 5, pp. 503-510.

Hawkins et al, Selection of phage antibodies by binding affinity mimicking affinity maturation, 1992, J. Mol. Biol. 226:889-896.

Hayden-Ledbetter, et al., CD20-Directed Small Modular Immunopharmaceutical, TRU-015, Depletes Normal and Malignant B Cells, Clin Cancer Res, 2009, vol. 15(8), pp. 2739-2746.

He et al., Humanization and pharmacokinetics of a monoclonal antibody with specificity for both E- and P-selectin, 1998, J. Immunol. 160:1029-1035.

Hedvat et al., Dual Blockade of PD-1 and CTLA-4 with Bispecific Antibodies Promotes Human T cell Activation and Proliferation., Nov. 11, 2016, retrieved from the internet: http://files.shareholder.com/downloads/AMDA-2B2V8N/0x0x916284/D8084990-61EC-4DFE-8B76-60CF58B8C06F/CPI_bispecifics.pdf.

Hennecke et al., "Non-repetitive single-chain Fv linkers selected by selectively infective phage (SIP) technology.", Protein Eng. May 1998;11(5):405-10.

Hernandez-Caselles, et al., A study of CD33 (SIGLEC-3) antigen expression and function on activated human T and NK cells: two isoforms of CD33 are generated by alternative splicing, J. Leukoc. Biol., 2006, vol. 79, pp. 46-58.

Hexham, et al., Influence of relative binding affinity on efficacy in a panel of anti-CD3 scFv immunotoxins, Molecular Immunology, 2001, vol. 38, pp. 397-408.

Hinman et al., Preparation and characterization of monoclonal antibody conjugates of the calicheamicins: a novel and potent family of antitumor antibodies, 1993 Cancer Res. 53:3336-3342.

Hoffmann, et al., Serial killing of tumor cells by cytotoxic T cells redirected with a CD19-/CD3-bispecific single-chain antibody construct, Int. J. Cancer, 2005, vol. 115, pp. 98-104.

Holliger et al., "Diabodies": Small Bivalent and bispecific antibody fragments, 1993, Proc. Natl. Acad. Sci. U.S.A. 90:6444-6448.

Holliger et al., Engineering bispecific antibodies, 1993, Current Opinion Biotechnol. 4:446-449.

Houtenbos, et al., The novel bispecific diabody αCD40/αCD28 strengthens leukaemic dendritic cell-induced T-cell reactivity, British Journal of Haematology, 2008, vol. 142, pp. 273-283.

Hu et al., Minibody: A novel engineered anti-carcinoembryonic antigen antibody fragment (single-chain Fv-$C_H$3) which exhibits rapid, high-level targeting of xenografts, 1996, Cancer Res. 56:3055-3061.

Huston et al., Protein engineering antibody binding sites: recovery of specific activity in an anti-digoxin single-chain Fv analogue produced in *Escherichia coli*, 1988, Proc. Natl. Acad. Sci. U.S.A. 85:5879-5883.

Igawa et al., Reduced elimination of IgG antibodies by engineering the variable region, 2010, PEDS. 23(5): 385-392.

Igawa, $V_H/V_L$ interface engineering to promote selective expression and inhibit conformational isomerization of thrombopoietin receptor agonist single-chain diabody, Protein Engineering, Design & Selection, 2010, vol. 23, No. 8, pp. 667-677.

Ishigaki et al., Impact of Plasma Oxidized Low-Density Lipoprotein Removal on Atherosclerosis., Circulation 118: 75-83, 2008.

(56) References Cited

OTHER PUBLICATIONS

Jackson et al., In vitro antibody maturation, 1995, J. Immunol. 154(7):3310-9.

Jäger, et al., The Trifunctional Antibody Ertumaxomab Destroys Tumor Cells That Express Low Levels of Human Epidermal Growth Factor Receptor 2, Cancer Res, 2009, vol. 69(10), pp. 4270-4276.

Jefferis et al., Interaction sites on human IgG-Fc for FcyR: current models, 2002, Immunol Lett 82:57-65.

Jespers, et al., Crystal Structure of HEL4, a Soluble, Refoldable Human $V_H$ Single Domain with a Germ-line Scaffold, J. Mol. Biol., 2004, vol. 337, pp. 893-903.

Jimenez, et al., A recombinant, fully human, bispecific antibody neutralizes the biological activities mediated by both vascular endothelial growth factor receptors 2 and 3, Mol Cancer Ther, 2005, vol. 4(3), pp. 427-434.

Jin et al. The Design and Engineering of IgG-Like Bispecific Antibodies., Chapter 9, Bispecific Antibodies, pp. 151-169, Jan. 1, 2011.

Jin, et al., MetMAb, the One-Armed 5D5 Anti-c-Met Antibody, Inhibits Orthotopic Pancreatic Tumor Growth and Improves Survival, Cancer Res 2008, vol. 68, pp. 4360-4368.

Johnson et al., Anti-tumor activity of CC49-doxorubicin immunoconguates, 1995, Anticancer Res. 15:1387-93.

Johnson, et al., Effector Cell Recruitment with Novel Fv-based Dual-affinity Re-targeting Protein Leads to Potent Tumor Cytolysis and in Vivo B-cell Depletion, J. Mol. Biol., 2010, vol. 399, pp. 436-449.

Jones et al., Replacing the complementarity-determining regions in a human antibody with those from a mouse, 1986, Nature 321:522-525.

Jordan et al., Structural understanding of stabilization patterns in engineered bispecific Ig-like antibody molecules, Proteins 2009; 77:832-841, Jun. 19, 2009.

Jung, et al., Design of interchain disulfide bonds in the framework region of the Fv fragment of the monoclonal antibody B3, Proteins, 1994, vol. 19(1), pp. 35-47.

Jung, et al., Target Cell-restricted Triggering of the CD95 (APO-1/Fas) Death Receptor with Bispecific Antibody Fragments, Cancer Research, 2001, vol. 61, pp. 1846-1848.

Jungbluth et al., A monoclonal antibody recognizing human cancers with amplification/overexpression of the human epidermal growth factor receptor, 2003, Proc Natl Acad Sci U S A. 100(2):639-44.

Kabat et al., 1991, Sequences of proteins of immunological interest, Department of Health and Human Services, Bethesda, vol. 1, $5^{th}$ Ed.

Kakutani et al., Accumulation of LOX-1 ligand in plasma and atherosclerosis lesions of Watanabe heritable hyperlipidemic rabbits: identification by a novel enzyme immunoassay., Biochem Biophys Res Commun. Mar. 23, 2001;282(1):180-5.

Kanakaraj, et al., Simultaneous targeting of TNF and Ang2 with a novel bispecific antibody enhances efficacy in an in vivo model of arthritis, mAbs, 2012, vol. 4, Issue 5, pp. 600-613, http://dx.doi.org/10.4161/mabs.21227 & Supplemental Data.

Kettleborough et al., Humanization of a mouse monoclonal antibody by CDR-grafting: the importance of framework residues on loop conformation, 1991, Protein Eng. 4(7):773-83.

Keyna, et al., Surrogate Light Chain-Dependent Selection of Ig Heavy Chain V Regions, J. Immunol., 1995, vol. 155, pp. 5536-5542.

Kharmate et al., Inhibition of tumor promoting signals by activation of SSTR2 and opioid receptors in human breast cancer cells., Cancer Cell Int. Sep. 23, 2013;13(1):93. doi: 10.1186/1475-2867-13-93.

Kiewe, et al., Phase I Trial of the Trifunctional Anti-HER2 x Anti-CD3 Antibody Ertumaxomab in Metastatic Breast Cancer, Clin Cancer Res., 2006, vol. 12(10), pp. 3085-3091.

Kim et al., "Localization of the site of murine IgG1 molecule that is involved in binding the murine intestinal Fc receptor," Eur. J. Immunol., 24:2429-2434, 1994.

Kim et al., Mutational approaches to improve the biophysical properties of human single-domain antibodies., Biochim Biophys Acta. Nov. 2014;1844(11):1983-2001. doi: 10.1016/j.bbapap.2014.07.008. Epub Jul. 24, 2014.

Kipriyanov, et al., Bispecific CD3 x CD19 Diabody for T Cell-Mediated Lysis of Malignant Human B Cells, Int. J. Cancer, 1998. vol. 77, pp. 763-772.

Kipriyanov, et al., Bispecific Tandem Diabody for Tumor Therapy with Improved Antigen Binding and Pharmacokinetics, J. Mol. Biol., 1999, vol. 293, pp. 41-56.

Kipriyanov, et al., Effect of Domain Order on the Activity of Bacterially Produced Bispecific Single-chain Fv Antibodies, J. Mol. Biol., 2003, vol. 330, pp. 99-111.

Kipriyanov, et al., Two amino acid mutations in an anti-human CD3 single chain Fv antibody fragment that affect the yield on bacterial secretion but not the affinity, Protein Engineering, 1997, vol. 10, No. 4, pp. 445-453.

Klein et al., Progression of metastatic human prostate cancer to androgen independence in immunodeficient SDIC mice, 1997, Nature Medicine 3: 402-408.

Klein, et al., Progress in overcoming the chain association issue in bispecific heterodimeric IgG antibodies, mAbs, Nov.-Dec. 2012, vol. 4, issue 6, pp. 653-663, doi: 10.4161/mabs.21379, Epub Aug. 27, 2012.

Klinger, et al., Immunopharmacologic response of patients with B-lineage acute lymphoblastic leukemia to continuous infusion of T cell-engaging CD19/CD3-bispecific BiTE antibody blinatumomab, Blood, 2012, vol. 119, No. 26, pp. 6226-6233.

Koristka, et al., Retargeting of Human Regulatory T Cells by Single-Chain Bispecific Antibodies, The Journal of Immunology, 2012, vol. 188, pp. 1551-1558, www.jimmunol.org/cgi/doi/10.4049/jimmunol.1101760.

Kostelny, et al., Formation of a Bispecific Antibody by the Use of Leucine Zippers, The Journal of Immunology 1992, vol. 148, pp. 1547-1553.

Krah et al., "Single-domain antibodies for biomedical applications.", Immunopharmacol Immunotoxicol. 2016;38(1):21-8. doi: 10.3109/08923973.2015.1102934. Epub Nov. 9, 2015.

Krauss et al., Specificity grafting of human antibody frameworks selected from a phage display library: generation of a highly stable humanized anti-CD22 single-chain Fv fragment, 2003, Protein Engineering 16(10):753-759.

Krupka, et al., CD33 target validation and sustained depletion of AML blasts in long-term cultures by the bispecific T-cell-engaging antibody AMG 330, Blood, 2014, vol. 123, No. 3, pp. 356-365, Prepublished online Dec. 3, 2013; doi: 10.1182/blood-2013-08-523548 & Data Supplement.

Kung, et al., Monoclonal Antibodies Defining Distinctive Human T Cell Surface Antigens, Science, 1979, vol. 206, pp. 347-349.

Kuppen, peter et al., The development and purification of a bispecific antibody for lymphokine-activated killer cell targeting against the rat colon carcinoma CC531., Cancer Immunol Immunother. Jun. 1993;36(6):403-8.

Labrijn, et al., Efficient generation of stable bispecific IgG1 by controlled Fab-arm exchange, Feb. 19, 2013, www.pnas.org/cgi/doi/10.1073/pnas.1220145110 & Supporting Information.

Laszlo et al., Cellular determinants for preclinical activity of a novel CD33/CD3 bispecific T-cell engager (BiTE) antibody, AMG 330, against human AML, blood 2014 123: 554-561, Dec. 5, 2013.

Lau et al., Conjugation of Doxorubicin to monoclonal anti-carcinoembryonic antigen antibody via novel thiol-directed cross-linking regents, 1995, Bioorg-Med-Chem. 3(10):1299-1304.

Lau et al., Novel doxorubicin-monoclonal anti-carcinoembryonic antigen antibody immunoconjugate activity in vitro, 1995, Bioorg-Med-Chem. 3(10):1305-12.

Declaration of G. A. Lazar, dated Dec. 27, 2010, pp. 1-4.

Lewis, et al., Generation of bispecific IgG antibodies by structure-based design of an orthogonal Fab interface, Nature Biotechnology, 2014, doi:10.1038/nbt.2797 & Supplemental Information.

Li, et al., Construction and characterization of a humanized anti-human CD3 monoclonal antibody 12F6 with effective immunoregulation functions, Immunology, 2005, vol. 116, pp. 487-498.

(56)                    References Cited

OTHER PUBLICATIONS

Lindhofer, et al., Preferential Species-Restricted Heavy/Light Chain Pairing in Rat/Mouse Quadromas: Implications for a Single-Step Purification of Bispecific Antibodies, The Journal of Immunology, 1995, vol. 155, pp. 219-225.

Ling, et al., Interspecies Scaling of Therapeutic Monoclonal Antibodies: Initial Look, J Clin Pharmacol, 2009, vol. 49, pp. 1382-1402, doi: 10.1177/0091270009337134.

Link, et al., Production and Characterization of a Bispecific IgG Capable of Inducing T-Cell-Mediated Lysis of Malignant B Cells, Blood, 1993, vol. 81, No., 12, pp. 3343-3349.

Linke, et al., Catumaxomab, Clinical development and future directions, mAbs, 2010, vol. 2, Issue 2, pp. 129-136.

Little, et al., Letter to the Editor, "Flawed TandAb production," Molecular Immunology, 2007, vol. 44, p. 3083.

Liu et al., Asymmetrical Fc Engineering Greatly Enhances Antibody-dependent Cellular Cytotoxicity (ADCC) Effector Function and Stability of the Modified Antibodies, J. Biol. Chem. 2014, 289: 3571-3590, Dec. 5, 2013.

Liu et al., Eradication of large colon tumor xenografts by targeted delivery of maytansinoids, 1996 Proc. Natl. Acad. Sci. USA 93:8618-8623.

Liu, et al., Crystallization of a Deglycosylated T Cell Receptor (TCR) Complexed with an Anti-TCR Fab Fragment, The Journal of Biological Chemistry, 1996, vol. 271, No. 52, pp. 33639-33646.

Lode et al., Targeted therapy with a novel enediyene antibiotic calicheamicins $o_1^i$ effectively suppress growth and dissemination of liver metastases in a syngeneic model of murine neuroblastoma, 1998, Cancer Res. 58:2928.

Löffler, et al., A recombinant bispecific single-chain antibody, CD19×CD3, induces rapid, and high lymphoma-directed cytotoxicity by unstimulated T lymphocytes, Blood, 2000, vol. 95, No. 6, pp. 2098-2103.

Lu, et al., A Fully Human Recombinant IgG-like Bispecific Antibody to Both the Epidermal Growth Factor Receptor and the Insulin-like Growth Factor Receptor for Enhanced Antitumor Activity, The Journal of Biological Chemistry, 2005, vol. 280, No. 20, pp. 19665-19672.

Lu, et al., Di-diabody: a novel tetravalent bispecific antibody molecule by design, Journal of Immunological Methods, 2003, vol. 279, pp. 219-232.

Lu, et al., Fab-scFv fusion protein: an efficient approach to production of bispecific antibody fragments, Journal of Immunological Methods, 2002, vol. 267, pp. 213-226.

Lu, et al., The effect of variable domain orientation and arrangement on the antigen-binding activity of a recombinant human bispecific diabody, Biochemical and Biophysical Research Communications, 2004, vol. 318, pp. 507-513.

Lum, et al., The new face of bispecific antibodies: targeting cancer and much more, Experimental Hematology, 2006, vol. 34, pp. 1-6.

Lutterbuese, et al., AACR Poster, "Conversion of Cetuximab, Panitumumab, Trastuzumab and Omalizumab into T Cell-engaging BiTE Antibodies Creates Novel Drug Candidates of High Potency," 2008.

Lutterbuese, et al., T cell-engaging BiTE antibodies specific for EGFR potently eliminate KRAS- and BRAF-mutated colorectal cancer cells, PNAS Early Edition, 2010, www.pnas.org/cgi/doi/10.1073/pnas.1000976107 & Supporting Information.

Ma, et al., Expression and Characterization of a Divalent Chimeric Anti-Human CD3 Single Chain Antibody, Scand.J.Immunol, 1996, vol. 43, pp. 134-139.

Mabry, et al., A dual-targeting PDGFRβ/VEGF-A molecule assembled from stable antibody fragments demonstrates anti-angiogenic activity in vitro and in vivo, mAbs, 2010, vol. 2, Issue 1, pp. 20-34; www.landesbioscience.com/journals/mabs/article/10498 & Supplemental Information.

Mabry, et al., Engineering of stable bispecific antibodies targeting IL-17A and IL-23, Protein Engineering, Design & Selection, 2009, vol. 23, No. 3, pp. 115-127; doi: 10.1093/protein/gzp073 & Supplementary Figures 1-8.

Mack, et al., A small bispecific antibody construct expressed as a functional single-chain molecule with high tumor cell cytotoxicity, Proc. Natl. Acad. Sci. USA, 1995, vol. 92, pp. 7021-7025.

Mack, et al., Biologic Properties of a Bispecific Single-Chain Antibody Directed Against 17-1A (EpCAM) and CD3-Tumor Cell-Dependent T Cell Stimulation and Cytotoxic Activity, The Journal of Immunology, 1997, vol. 158, pp. 3965-3970.

MacroGenics Factsheet, Dual Affinity Re-Targeting ("DART") Platform, 2010.

Mandler et al., Immunoconjugates of geldanamycin and anti-HER2 Monoclonal antibodies: antiproliferative activity on human breast carcinoma cell lines, 2000, J. Nat. Cancer Inst. 92(19):1573-1581.

Mandler et al., Modifications in synthesis strategy improve the yield and efficacy of geldanamycin-herceptin immunoconjugates, 2002, Bioconjugate Chem. 13:786-791).

Mandler et al., Synthesis and evaluation of antiproliferative activity of a geldanaymcin-herceptin™ immunoconjugates, 2000, Bioorganic & Med. Chem. Letters 10:1025-1028.

Mandy, et al., Effect of Reduction of Several Disulfide Bonds on the Properties and Recombination of Univalent Fragments of Rabbit Antibody, The Journal of Biological Chemistry, 1963, vol. 238, No. 1, pp. 206-213.

Mandy, et al., Recombination of Univalent Subunits Derived from Rabbit Antibody, The Journal of Biological Chemistry, 1961, vol. 236, No. 12, pp. 3221-3226.

Marks et al., By-passing immunization: building high affinity human antibodies by chain shuffling, 1992, Biotechnology 10:779-783.

Martin, et al., Generation of the Germline Peripheral B Cell Repertoire: VH81X-λ B Cells Are Unable to Complete All Developmental Programs, J. Immunol., 1998, vol. 160, pp. 3748-3758.

Martinez, et al., Characterization of a novel modification on IgG2 light chain: Evidence for the presence of O-linked mannosylation, J. Chromatogr. A, 2007, vol. 1156 pp. 183-187.

Marvin, Bispecific antibodies for dual-modality cancer therapy: killing two signaling cascades with one stone, Curr Opin Drug Discov Devel, 2006, vol. 9(2), pp. 184-193.

Marvin, et al., Recombinant approaches to IgG-like bispecific antibodies, Acta Pharmacologica Sinica, 2005, vol. 26 (6), pp. 649-658.

Mateo et al., Humanization of a mouse nonoclonal antibody that blocks the epidermal growth factor receptor: recovery of antagonistic activity, 1997, Immunotechnology, 3(1):71-81.

McPhee, Engineering human immunodeficiency virus 1 protease heterodimers as macromolecular inhibitors of viral maturation, Proc. Natl. Acad. Sci. USA, 1996, vol. 93, pp. 11477-11481.

Meijer, et al., Isolation of Human Antibody Repertoires with Preservation of the Natural Heavy and Light Chain Pairing, J. Mol. Biol., 2006, vol. 358, pp. 764-772.

Merchant, et al., An efficient route to human bispecific IgG, Nature Biotechnology, 1998, vol. 16, pp. 677-681.

Mertens, Nico, "Tribodies: Fab-scFv fusion proteins as a platform to create multi-functional pharmaceuticals.", SpringerLink 2011, 135-149.

Metz, et al., Bispecific antibody derivatives with restricted binding functionalities that are activated by proteolytic processing, Protein Engineering, Design & Selection, 2012, vol. 25, No. 10, pp. 571-580.

Metz, et al., Bispecific digoxigenin-binding antibodies for targeted payload delivery, PNAS, 2011, vol. 108, No. 20, pp. 8194-8199.

Michaelson et al., Anti-tumor activity of stability-engineered IgG-like bispecific antibodies targeting TRAIL-R2 and LTbetaR, [mAbs 1:2, 128-141; Mar./Apr. 2009]; Mar. 11, 2009.

Michalk et al., Characterization of a novel single-chain bispecific antibody for retargeting of T cells to tumor cells via the TCR co-receptor CD8., PLoS One. Apr. 21, 2014;9(4):e95517. doi: 10.1371/journal.pone.0095517.

Miller et al., Stability engineering of scFvs for the development of bispecific and multivalent antibodies, PEDS, 2010, vol. 23, No. 7, pp. 549-557 & Supplementary Data.

Miller, biogen idec Stability Engineering and Production of IgG-like Bispecifc Antibodies, AAPS National Biotechnology Conference, Jun. 24 to Jun. 27, 2007.

(56)          References Cited

OTHER PUBLICATIONS

Milutinovic, et al., Sanford Burnham Medical Research Institute / AACR Poster, #4318, "Development of a novel dual agonist Surrobody™ that simultaneously activates both death receptors DR4 and DR5 and induces cancer cell death with high potency" , Apr. 2013.

Mimoto et al., Engineered antibody Fc variant with selectively enhanced FcγRIIb binding over both FcγRIIa(R131) and FcγRIIa(H131)., Protein Eng Des Sel. Oct. 2013;26(10):589-98. doi: 10.1093/protein/gzt022. Epub Jun. 5, 2013.

Mimoto, et al., Novel asymmetrically engineered antibody Fc variant with superior FcγR binding affinity and specificity compared with afucosylated Fc variant, mAbs, 2013, vol. 5, Issue 2, pp. 229-236.

Modjtahedi et al., Phase I trial and tumour localization of the anti-EGFR monoclonal antibody ICR62 in head and neck or lung cancer, 1996, Br J Cancer, 73(2):228-35.

Modjtahedi et al., Targeting of cells expressing wild-type EGFR and type-III mutant EGFR (EGFRVIII) by anti-EGFR MaB ICR62: a two-pronged attack for tumor therapy, 2003, Int J Cancer, 105(2):273-80.

Modjtahedi et al., Antitumor activity of combinations of antibodies directed against different epitopes on the extracellular domain of the human EGF receptor, 1993, J. Cell Biophys. 1993, 22(1-3):129-46.

Modjtahedi et al., The human EGF receptor as a target for cancer therapy: six new rat mAbs against the receptor on the breast carcinoma MDA-MB 468, 1993, Br J Cancer. 1993, 67(2):247-53.

Mølhøj, et al., CD19-/CD3-bispecific antibody of the BiTE class is far superior to tandem diabody with respect to redirected tumor cell lysis, Molecular Immunology 2007, vol. 44 , pp. 1935-1943.

Moore et al., Tuning T Cell Affinity Improves Efficacy and Safety of Anti-CD38 x Anti-CD3 Bispecific Antibodies in Monkeys—a Potential Therapy for Multiple Myeloma., 57th ASH Annual Meeting and Exposition (Dec. 5-8, 2015), American Society of Hematology, Orlando, Florida.

Moore, et al., A novel bispecific antibody format enables simultaneous bivalent and monovalent co-engagement of distinct target antigens., MAbs. Nov.-Dec. 2011; 3(6): 546-557; Published online Nov. 1, 2011. doi: 10.4161/mabs.3.6.18123.

Moore, et al., Application of dual affinity retargeting molecules to achieve optimal redirected T-cell killing of B-cell lymphoma, Blood, 2011, vol. 117, No. 17, pp. 4542-4551.

Moretti et al., Beat® the bispecific challenge: a novel and efficient platform for the expression of bispecific IgGs. BMC Proceedings 2013 7(Suppl 6):O9.

Morrison, et al., News and Views: Two heads are better than one, Nature Biotechnology, 2007, vol. 25, No. 11, pp. 1233-1234.

Mosmann, 1983, Rapid colorimetric assay for cellular growth and survival: application to proliferation and cytotoxicity assays, J. Immunol. Methods 65:55-63.

Muda, et al., Therapeutic assessment of SEED: a new engineered antibody platform designed to generate mono and bispecific antibodies, Protein Engineering, Design & Selection, 2011, vol. 24, No. 5, pp. 447-454.

Muramatsu et al., Production and characterization of an active single-chain variable fragment antibody recognizing CD25., Cancer Lett. Jul. 28, 2005;225(2):225-36. Epub Jan. 23, 2005.

Murthy et al., Binding of an antagonistic monoclonal antibody to an intact and fragmented EGF-receptor polypeptide, 1987, Arch Biochem Biophys. 252(2):549-60.

Nagorsen, et al., Blinatumomab: A historical perspective, Pharmacology & Therapeutics, 2012, vol. 136, pp. 334-342, http://dx.doi.org/10.1016/j.pharmthera.2012.07.013.

Nelson, et al., Point of View: Antibody fragments—Hope and hype, mAbs, 2010, vol. 2, Issue 1, pp. 77-83.

Neville et al., Enhancement of immunotoxin efficacy by acid-cleavable cross-ling agents utilizing diphtheria toxin and toxin mutants, 1989, Biol. Chem. 264:14653-14661.

Nielsen, et al., Human T cells resistant to complement lysis by bivalent antibody can be efficiently lysed by dimers of monovalent antibody, Blood, 2002, vol. 100, No. 12, pp. 4067-4073.

Nisonoff, et al., Letters to the Editors: Recombination of a Mixture of Univalent Antibody Fragments of Different Specificity, Arch. Biochem. Biophys., 1961, pp. 460-462.

Nisonoff, et al., Quantitative Estimation of the Hybridization of Rabbit Antibodies, Nature, 1962, vol. 194, No. 4826, pp. 355-359.

North, et al., A New Clustering of Antibody CDR Loop Conformations, J. Mol. Biol., 2011, vol. 406, pp. 228-256, doi:10.1016/j.jmb.2010.10.030.

O'Connor et al., Humanization of an antibody against human protein C and calcium-dependence involving framework residues, 1998, Protein Eng 11:321-8.

Olafsen, et al., Covalent disulfide-linked anti-CEA diabody allows site-specific conjugation and radiolabeling for tumor targeting applications, Protein Engineering, Design & Selection, 2004, vol. 17, No. 1, pp. 21-27.

Ott et al., CTLA-4 and PD-1/PD-L1 blockade: new immunotherapeutic modalities with durable clinical benefit in melanoma patients., Clin Cancer Res. Oct. 1, 2013;19(19):5300-9. doi: 10.1158/1078-0432.CCR-13-0143.

Page et al., 1993, Intermantional. Journal of Oncology 3:473-476.

Panke, et al., Quantification of cell surface proteins with bispecific antibodies, Protein Engineering, Design & Selection, 2013, vol. 26, No. 10, pp. 645-654.

Pessano, et al., The T3/T cell receptor complex: antigenic distinction between the two 20-kd T3 (T3-δand T3-ε) subunits, The EMBO Journal, 1985, vol. 4, No. 2, pp. 337-344.

Pettit et al., Antineoplastic agents 365. Dolastatin 10 SAR probes, 1998, Anti-Cancer Drug Design 13:243-277.

Pettit et al., Dolastatins 24. Synthesis of (–)-dolastatin 10.1 X-ray molecular structure of N, N-dimethylvalyl-valyl-dolaisoleuine tert-butyl ester, 1996, J. Chem. Soc. Perkin Trans. 1 5:859-863.

Pettit et al., Specific activities of dolastatin 10 and peptide derivatives against Cryptococcus neoformans, 1998, Antimicrob. Agents Chemother. 42(11):2961-2965.

Pettit et al., Structure-activity studies with chiral isomers and with segments of the antimitotic marine peptide dolastation 10., Biochem Pharmacol . Oct. 15, 1990;40(8):1859-64. doi: 10.1016/0006-2952(90)90367-t.

Pettit, et al., The dolastatins; 18: Sterospecific synthesis of dolaproine1, 1996, Synthesis 719-725.

Pichler et al., Differences of T-Cell Activation by the Anti-CD3 Antibodies Leu4 and BMA030, Mar. 30, 1987.

Potapov et al., Protein-Protein Recognition: Juxtaposition of Domain and Interface Cores in Immunoglobulins and Other Sandwich-like Proteins, J. Mol. Biol., 2004, vol. 342, pp. 665-679.

Presta et al., Humanization of an anti-vascular endothelial growth factor monoclonal antibody for the therapy of solid tumors and other disorders, 1997, Cancer Res.57(20):4593-9.

Queen et al., A humanized antibody that binds to the interleukin 2 receptor, 1989, Proc Natl Acad Sci, USA 86:10029-33.

Rader et al., A phage display approach for rapid antibody humanization: designed combinatorial V gene libraries, 1998, Proc. Natl. Acad. Sci. USA 95: 8910-8915.

Raghavan et al., Fc receptors and their interactions with immunoglobulins, 1996, Annu Rev Cell Dev Biol 12:181-220.

Rattel, et al., AACR Poster, "Validation of Cynomolgus Monkeys as Relevant Species for Safety Assessment of a Novel Human BiTE Antibody Platform for Cancer Therapy," 2010.

Reddy et al., Elimination of Fc receptor-dependent effector functions of a modified IgG4 monoclonal antibody to human CD4., J Immunol. Feb. 15, 2000;164(4):1925-33.

Reiter et al., Disulfide stabilization of antibody Fv: computer predictions and experimental evaluation, Protein Eng., 1995, vol. 8(12), pp. 1323-1331.

Reiter et al., Engineering interchain disulfide bonds into conserved framework regions of Fv fragments: improved biochemical characteristics of recombinant immunotoxins containing disulfide-stabilized Fv, Protein Eng., 1994, vol. 7(5), pp. 697-704.

Remington's Pharmaceutical Sciences 16th edition, Osol, A. Ed. (1980) (Book Abstract).

(56) References Cited

OTHER PUBLICATIONS

Repp, et al., Combined Fc-protein- and Fc-glyco-engineering of scFv-Fc fusion proteins synergistically enhances CD16a binding but does not further enhance NK-cell mediated ADCC, Journal of Immunological Methods, 2011, vol. 373, Issues 1-2, pp. 67-78.
Ridgway, et al., 'Knobs-into-holes' engineering of antibody CH3 domains for heavy chain heterodimerization, Protein Engineering, 1996, vol. 9, No. 7, pp. 617-621.
Riechmann et al., Reshaping human antibodies for therapy, 1988, Nature 332:323-329.
Riethmüller, Symmetry breaking: bispecific antibodies, the beginnings, and 50 years on, Cancer Immunity, 2012, vol. 12, p. 12, pp. 1-7.
Rodeck et al., Interactions between growth factor receptors and corresponding monoclonal antibodies in human tumors, 1987, J Cell Biochem. 35(4):315-20.
Roguska et al., Humanization of murine monoclonal antibodies through variable domain resurfacing, 1994, Proc. Natl. Acad. Sci. USA 91:969-973.
Roosnek, et al., Triggering T Cells by Otherwise Inert Hybrid Anti-CD3/Antitumor Antibodies Requires Encounter with the Specific Target Cell, J . Exp. Med., 1989, vol. 170, pp. 297-302.
Roque et al., Antibodies and genetically engineered related molecules: production and purification, 2004, Biotechnol. Prog. 20:639-654.
Rose, et al., Mutation of Y407 in the CH3 domain dramatically alters glycosylation and structure of human IgG, mAbs, 2013, vol. 5, Issue 2, pp. 219-228.
Rose, et al., Quantitative Analysis of the Interaction Strength and Dynamics of Human IgG4 Half Molecules by Native Mass Spectrometry, Structure, 2011, vol. 19, pp. 1274-1282.
Rosok et al., A combinatorial library strategy for the rapid humanization of anticarcinoma BR 96 Fab, 1996, J. Biol. Chem. 271(37):22611-22618.
Rossi, et al., A new class of bispecific antibodies to redirect T cells for cancer immunotherapy, mAbs 2014, vol. 6, Issue 2, pp. 381-391.
Roux, et al., Structural analysis of the nurse shark (new) antigen receptor (NAR): Molecular convergence of NAR and unusual mammalian immunoglobulins, Proc. Natl. Acad. Sci. USA, 1998, vol. 95, pp. 11804-11809.
Rudnick, et al., Affinity and Avidity in Antibody-Based Tumor Targeting, Cancer Biotherapy and Radiopharmaceuticals, 2009, vol. 24, No. 2, pp. 155-161, doi: 10.1089/cbr.2009.0627.
Rothlisberger, et al., Domain Interactions in the Fab Fragment: A Comparative Evaluation of the Single-chain Fv and Fab Format Engineered with Variable Domains of Different Stability, J. Mol. Biol. , 2005, vol. 347, pp. 773-789.
Salmeron et al., A conformational epitope expressed upon association of CD3-epsilon with either CD3-delta or CD3-gamma is the main target for recognition by anti-CD3 monoclonal antibodies, Nov. 1, 1991.
Sancho et al., CD3-Surface Expression Is Required for CD4-p56ick-mediated Up-regulation of T Cell Antigen Receptor-CD3 Signaling in T Cells, Apr. 16, 1992.
Schaefer, et al., A Two-in-One Antibody against HER3 and EGFR Has Superior Inhibitory Activity Compared with Monospecific Antibodies, Cancer Cell, 2011, vol. 20, pp. 472-486 & Supplemental Information, pp. 1-21.
Schaefer, et al., Immunoglobulin domain crossover as a generic approach for the production of bispecific IgG antibodies, PNAS, 2011, vol. 108, No. 27, pp. 11187-11192.
Schlapschy, et al., Functional humanization of an anti-CD16 Fab fragment: obstacles of switching from murine λ to human λ or κ light chains, Protein Engineering, Design & Selection, 2009, vol. 22, No. 3, pp. 175-188, doi:10.1093/protein/gzn066.
Schlereth, et al., Eradication of Tumors from a Human Colon Cancer Cell Line and from Ovarian Cancer Metastases in Immunodeficient Mice by a Single-Chain Ep-CAM-/CD3-Bispecific Antibody Construct, Cancer Res 2005, vol. 65(7), pp. 2882-2889.

Schlereth, et al., T-cell activation and B-cell depletion in chimpanzees treated with a bispecific anti-CD19/anti-CD3 single-chain antibody construct, Cancer Immunol Immunother, 2006, vol. 55, pp. 503-514, doi:10.1007/s00262-005-0001-1.
Schoonjans, et al., Fab Chains As an Efficient Heterodimerization Scaffold for the Production of Recombinant Bispecific and Trispecific Antibody Derivatives, The Journal of Immunology, 2000, vol. 165, pp. 7050-7057.
Schroder et al., The Peptides, vol. pp 76-136, 1965, Academic Press.
Senter et al., Immunoconjugates comprised of drugs with impaired cellular permeability: A new approach to targeted therapy., Proceedings of the American Association for Cancer Research, 2004, vol. 45, Abstract No. 623.
Senter, Potent antibody drug conjugates for cancer therapy, 2009, Current Opin. Chem. Biol. 13:235.
Sforzini et al., Targeting of saporin to Hodgkin's lymphoma cells by anti-CD30 and anti-CD25 bispecific antibodies., Br J Haematol. Sep. 1998;102(4):1061-8.
Shalaby, et al., Development of Humanized Bispecific Antibodies Reactive with Cytotoxic Lymphocytes and Tumor Cells Overexpressing the HER2 Protooncogene, J.Exp. Med., 1992, vol. 175, pp. 217-225.
Shan, et al., Characterization of scFv-Ig Constructs Generated from the Anti-CD20 mAb 1F5 Using Linker Peptides of Varying Lengths, J Immunol, 1999, vol. 162, pp. 6589-6595.
Shearman, et al., Construction, Expression and Characterization of Humanized Antibodies Directed Against the Human α/βT Cell Receptor, The Journal of Immunology, 1991, vol. 147, No. 12, pp. 4366-4373.
Shen, et al., Catumaxomab, a rat/murine hybrid trifunctional bispecific monoclonal antibody for the treatment of cancer, Curr Opin Mol Ther, 2008, vol. 10(3), pp. 273-284.
Shen, et al., Single Variable Domain-IgG Fusion: A Novel Recombinant Approach to Fc Domain-Containing Bispecific Antibodies, The Journal of Biological Chemistry, 2006, vol. 281, No. 16, pp. 10706-10714.
Shields et al., Lack of fucose on human IgG1 N-linked oligosaccharide improves binding to human FcγRIII and antibody-dependent cellular toxicity, 2002, J Biol Chem 277:26733-26740.
Shier et al., Identification of functional and structural amino-acid residues by parsimonious mutagenesis, 1995, Gene 169:147-155.
Shinkawa et al., The absence of fucose but not the presence of galactose or bisecting N-acetylglucosamine of human IgG1 complex-type oligosaccharides shows the critical role of enhancing antibody-dependent cellular cytotoxicity, 2003, J Biol Chem 278:3466-3473.
Skehan et al., Identification of functional and structural amino-acid residues by parsimonious mutagenesis, 1990, J. Natl. Cancer Inst. 82(13):1107-12.
Smith et al., Mouse model recapitulating human Fcγ receptor structural and functional diversity., Proc Natl Acad Sci U S A. Apr. 17, 2012;109(16):6181-6. doi: 10.1073/pnas.1203954109. Epub Apr. 2, 2012.
Soumyarani et al, Oxidatively modified high density lipoprotein promotes inflammatory response in human monocytes-macrophages by enhanced production of ROS, TNF-α, MMP-9, and MMP-2., Mol Cell Biochem. Jul. 2012;366(1-2):277-85. doi: 10.1007/s11010-012-1306-y. Epub Apr. 17, 2012.
Spies et al., Alternative molecular formats and therapeutic applications for bispecific antibodies., Mol Immunol. Jan. 27, 2015. pii: S0161-5890(15)00005-X. doi: 10.1016/j.molimm.2015.01.003.
Spiess, et al., Bispecific antibodies with natural architecture produced by co-culture of bacteria expressing two distinct half-antibodies, Nature Biotechnology, 2013, doi:10.1038/nbt.2621 & Supplemental Information.
Spranger et al., Mechanism of tumor rejection with doublets of CTLA-4, PD-1/PD-L1, or IDO blockade involves restored IL-2 production and proliferation of CD8(+) T cells directly within the tumor microenvironment., J Immunother Cancer. Feb. 18, 2014;2:3. doi: 10.1186/2051-1426-2-3. eCollection 2014.
Stamova, Unexpected recombinations in single chain bispecific anti-CD3-anti-CD33 antibodies can be avoided by a novel linker module., Mol Immunol. Dec. 2011;49(3):474-82. doi: 10.1016/j.molimm.2011.09.019. Epub Oct. 19, 2011.

(56)　　　　　References Cited

OTHER PUBLICATIONS

Stanfield, et al., Maturation of Shark Single-domain (IgNAR) Antibodies: Evidence for Induced-fit Binding, J. Mol. Biol., 2007, vol. 367, pp. 358-372.

Stewart, et al., Recombinant CD36 inhibits oxLDL-induced ICAM-1-dependent monocyte adhesion., Mol Immunol. Feb. 2006;43(3):255-67.

Strop, P. et al., Generating Bispecific Human IgG1 and IgG2 Antibodies from Any Antibody Pair, J. Mol. Biol., 2012, doi:10.1016/j.jmb.2012.04.020.

Szymkowski et al., Creating the next generation of protein therapeutics through rational drug design, Current opinion in drug discovery & development, Sep. 1, 2005, p. 590, XP055354917, England.

Tabrizi et al., Biodistribution mechanisms of therapeutic monoclonal antibodies in health and disease., AAPS J. Mar. 2010;12(1):33-43. doi: 10.1208/s12248-009-9157-5. Epub Nov. 19, 2009.

Tan et al., "Superhumanized" antibodies: reduction of immunogenic potential by complementarity-determining region grafting with human germline sequences: application to an anti-CD28, 2002, J. Immunol. 169:1119-1125.

Tan, Philip, Presentation at PepTalk, Jan. 25, 2013, "Bi-specific Adaptir Molecule Targeting CD86 and Delivering Monomeric IL10 to Inhibit Antigen Presenting Cells".

Tang et al., Selection of linkers for a catalytic single-chain antibody using phage display technology., Journal of Biological Chemistry, American Society for Biochemistry and Molecular Biology, US, vol. 271, No. 26, Jan. 1, 1996, pp. 15682-15686.

Tarcsa et al., Chapter 10 Dual-Variable Domain Immunoglobulin (DVD-Ig™) Technology: A Versatile, Novel Format for the Next Generation of Dual-Targeting Biologics, Bispecific Antibodies 2011, pp. 171-185, 2011.

Teachey, et al., Cytokine release syndrome after blinatumomab treatment related to abnormal macrophage activation and ameliorated with cytokine-directed therapy, Blood, 2013, vol. 121, No. 26, pp. 5154-5157.

Tedgui, et al., Cytokines in atherosclerosis: pathogenic and regulatory pathways., Physiol Rev. Apr. 2006;86(2):515-81.

Terry M., "FDA Places Clinical Hold on AML Drug Co-Developed by Johnson & Johnson (JNJ) and Genmab A/S (Gen Co.)", Biospace 2016, Retrieved from the internet: https://www.biospace.com/article/fda-places-clinical-hold-on-aml-drug-co-developed-by-johnson-and-johnson-and-genmab-a-s-/.

Thompson, et al., An Anti-CD3 Single-chain Immunotoxin with a Truncated Diphtheria Toxin Avoids Inhibition by Pre-existing Antibodies in Human Blood, J.Biol.Chem., 1995, vol. 270, No. 47, pp. 28037-28041.

Thompson, et al., Improved binding of a bivalent single-chain immunotoxin results in increased efficacy for in vivo T-cell depletion, Protein Engineering, 2001, vol. 14, No. 12, pp. 1035-1041.

Thorne, et al., CD36 is a receptor for oxidized high density lipoprotein: implications for the development of atherosclerosis., FEBS Lett. Mar. 20, 2007;581(6):1227-32. Epub Feb. 28, 2007.

Thorpe et al., New coupling agents for the synthesis of immunotoxins containing a hindered disulfide bond with improved stability in Vivo, 1987, Cancer Res. 47:5924-5931.

Thotakura et al., Enzymatic deglycosylating of glycoproteins, 1987, Meth. Enzymol. 138:350.

Thurman et al., Detection of complement activation using monoclonal antibodies against C3d., J Clin Invest. May 2013;123(5):2218-30. doi: 10.1172/JCI65861. Epub Apr. 24, 2013.

Tomlinson et al., Methods for generating multivalent and bispecific antibody fragments, 2000, Methods Enzymol. 326:461-479.

Topp, et al., Targeted Therapy With the T-Cell-Engaging Antibody Blinatumomab of Chemotherapy-Refractory Minimal Residual Disease in B-Lineage Acute Lymphoblastic Leukemia Patients Results in High Response Rate and Prolonged Leukemia-Free Survival, Jun. 20, 2011, J Clin Oncol vol. 29, No. 18, pp. 2493-2498.

Traunecker, et al., Bispecific single chain molecules (Janusins) target cytotoxic lymphocytes on HIV infected cells, The EMBO Journal, 1991, vol. 1, No. 12, pp. 3655-3659.

Tsurushita et al., Humanization of monoclonal antibodies, 2004, Molecular Biology of B Cells 533-545.

Umaña et al., Engineered glycoforms of an antineuro-blastoma IgG1 with optimized antibody-dependent cellular cytotoxic activity, 1999, Nat Biotechnol 17:176-180.

Valliere-Douglass, et al., O-Fucosylation of an antibody light chain: Characterization of a modification occurring on an IgG1 molecule, Glycobiology, 2009, vol. 19, No. 2, pp. 144-152, doi:10.1093/glycob/cwn116.

Van Boxel, et al., Some lessons from the systematic production and structural analysis of soluble αβ T-cell receptors, Journal of Immunological Methods, 2009, vol. 350, pp. 14-21.

Van Wauwe, et al., OKT3: A Monoclonal Anti-Human T Lymphoctye Antibody with Potent Mitogenic Properties, The Journal of Immunology, 1980, vol. 124, No. 6, pp. 2708-2713.

Verdier, et al., Determination of lymphocyte subsets and cytokine levels in Cynomolgus monkeys, Toxicology, 1995, vol. 105, pp. 81-90.

Verhoeyen et al., Reshaping human antibodies: grafting an antilysozyme activity, 1988, Science, 239: 1534-1536.

Veri, et al., Therapeutic Control of B Cell Activation via Recruitment of Fcγ Receptor IIb (CD32B) Inhibitory Function With a Novel Bispecific Antibody Scaffold, Arthritis & Rheumatism, 2010, vol. 62, No. 7, pp. 1933-1943.

Vettermann, et al., Powered by pairing: The surrogate light chain amplifies immunoglobulin heavy chain signaling and pre-selects the antibody repertoire, Seminars in Immunology 18, 2006, pp. 44-55.

Von Kreudenstein, et al., Improving biophysical properties of a bispecific antibody scaffold to aid developability: Quality by molecular design, mAbs, 2013, vol. 5, Issue 5, pp. 1-9, http://dx.doi.org/10.4161/mabs.25632 & Supplemental Material.

Wang et al., Conserved amino acid networks involved in antibody variable domain interactions, Proteins, 2009, vol. 76, pp. 99-114.

Wang et al., Expression and characterization of recombinant soluble monkey CD3 molecules: mapping the FN18 polymorphic epitope, Molecular Immunology, 2004, vol. 40, pp. 1179-1188.

Wang, et al., A block in both early T lymphocyte and natural killer cell development in transgenic mice with high-copy numbers of the human CD3E gene, Proc. Natl. Acad. Sci. USA, 1994, vol. 91, pp. 9402-9406.

Ward, et al., Protein Engineering of Homodimeric Tyrosyl-tRNA Synthetase to Produce Active Heterodimers, The Journal of Biological Chemistry, 1986, vol. 261, No. 21, pp. 9576-9578.

Wawrzynczak et al., Methods for preparing immunotoxins: Effect of the linkage on activity and stability. In Immunoconjugates. 1987, Antibody Conjugates in Radio imaging and Therapy of Cancer. (C.-W. Vogel, editor). New York, Oxford University Press, pp. 28-55.

Weatherill, et al., Towards a universal disulphide stabilised single chain Fv format: importance of interchain disulphide bond location and vL-vH orientation, Protein Engineering, Design & Selection, 2012, vol. 25, No. 7, pp. 321-329.

Weiner, et al., The Role of T Cell Activation Bispecific Antibody Therapy in Anti-CD3 X Antitumor, Journal of Immunology, 1994, vol. 152, pp. 2385-2392.

Wesolowski, et al., Single domain antibodies: promising experimental and therapeutic tools in infection and immunity, Med Microbiol Immunol, 2009, vol. 198, pp. 157-174.

Whitlow, et al., An improved linker for single-chain Fv with reduced aggregation and enhanced proteolytic stability, Protein Engineering, 1993, vol. 6 , No. 8, pp. 989-995.

Wigginton et al., An immunoglobulin E-reactive chimeric human immunoglobulin G1 anti-idiotype inhibits basophil degranulation through cross-linking of FcεRI with FcγRIIb., Jan. 11, 2007, Clinical & Experimental Allergy, 38: 313-319.

Wong, et al., The Mechanism of Anti-CD3 Monoclonal Antibodies, Transplantation, 1990, vol. 50, No. 4, pp. 683-689.

Woods, et al., LC-MS characterization and purity assessment of a prototype bispecific antibody, mAbs, 2013, vol. 5, Issue 5, pp. 711-722, http://dx.doi.org/10.4161/mabs.25488.

(56)          References Cited

OTHER PUBLICATIONS

Woyke et al., In vitro activities and postantifungal effects of the potent dolastation 10 derivative auristatin PHE, 2001, Antimicrob. Agents and Chemother. 45(12):3580-3584.

Wu et al., Molecular construction and optimization of anti-human IL-11α/β dual variable domain immunoglobulin (DVD-Ig™) molecules, [mAbs 1:4, 339-347; Jul./Aug. 2009]; Landes Bioscience, Apr. 10, 2009.

Wu et al., Simultaneous targeting of multiple disease mediators by a dual-variable-domain immunoglobulin, Nature Biotechnology vol. 25, pp. 1290-1297 (2007).

Wu et al., Humanization of a murine monoclonal antibody by simultaneous optimization of framework and CDR residues, 1999, J. Mol. Biol. 294:151-162.

Wu, et al., Multimerization of a chimeric anti-CD20 single-chain Fv-Fc fusion protein is mediated through variable domain exchange, Protein Engineering, 2001, vol. 14, No. 12, pp. 1025-1033.

Wu et al., Fab-based bispecific antibody formats with robust biophysical properties and biological activity., MAbs. 2015;7(3):470-82. doi: 10.1080/19420862.2015.1022694.

Wucherpfennig, et al., Structural Biology of the T-cell Receptor: Insights into Receptor Assembly, Ligand Recognition, and Initiation of Signaling, Cold Spring Harb Perspect Biol 2010;2:a005140.

Xie, et al., A new format of bispecific antibody: highly efficient heterodimerization, expression and tumor cell lysis, Journal of Immunological Methods, 2005, vol. 296 , pp. 95-101, doi:10.1016/j.jim.2004.11.005.

Xu, et al., Combinatorial surrobody libraries, PNAS, 2008, vol. 105, No. 31, pp. 10756-10761.

Xu, et al., Rapid optimization and prototyping for therapeutic antibody-like molecules, mAbs, 2013, vol. 5, Issue 2, pp. 237-254.

Xu, et al., Surrobodies with Functional Tails, J. Mol. Biol., 2010, vol. 397, pp. 352-360.

Yang et al., Differential in vitro activation of CD8-CD4+ and CD4-CD8+ T lymphocytes by combinations of anti-CD2 and anti-CD3 antibodies, Apr. 1, 1988.

Yelton et al., Affinity maturation of the BR96 anti-carcinoma antibody by codon-based mutagenesis, 1995, J. Immunol. 155:1994-2004.

Yeung, et al., Engineering human IgG1 affinity to human neonatal Fc receptor: impact of affinity improvement on pharmacokinetics in primates, J Immunol. Jun. 15, 2009;182(12):7663-71. doi: 10.4049/jimmunol.0804182.

Yoshino et al., Upgrading of flow cytometric analysis for absolute counts, cytokines and other antigenic molecules of cynomolgus monkeys (Macaca fascicularis) by using anti-human cross-reactive antibodies, Exp. Anim., 2000, vol. 49(2), pp. 97-100.

Yu et al., The biosynthetic gene cluster of the maytansinoids antitumor agent ansamitocin from actinosynnema pretiosum, 2002, PNAS 99:7968-7973.

Zalevsky et al. "Enhanced antibody half-life improves in vivo activity." Nature Biotechnology, vol. 28, No. 2, Feb. 1, 2010, pp. 157-159.

Zamyatnin AA., Amino acid, peptide, and protein volume in solution., Annu Rev Biophys Bioeng. 1984;13:145-65.

Zeidler, et al., The Fc-region of a new class of intact bispecific antibody mediates activation of accessory cells and NK cells and induces direct phagocytosis of tumour cells, Br J Cancer, 2000, vol. 83(2), pp. 261-266.

Zhu, et al., Identification of Heavy Chain Residues in a Humanized Anti-CD3 Antibody Important for Efficient Antigen Binding and T Cell Activation, The Journal of Immunology, 1995, vol. 155, pp. 1903-1910.

Zhu, et al., Remodeling domain interfaces to enhance heterodimer formation, Protein Science, 1997, vol. 6, pp. 781-788.

Zeibig et al., Effect of the oxLDL Binding Protein Fc-CD68 on Plaque Extension and Vulnerability in Atherosclerosis., Circulation Research 108: 695-703, 2011.

Zuo, et al., An efficient route to the production of an IgG-like bispecific antibody, Protein Engineering, 2000, vol. 13, No. 5, pp. 361-367.

Sun et al., Anti-CD20/CD3 T cell-dependent bispecific antibody for the treatment of B cell malignancies., Science Translational Medicine May 13, 2015: vol. 7, Issue 287, pp. 287ra70 DOI: 10.1126/scitranslmed.aaa480.

Capizzi et al., Curative chemotherapy for acute myeloid leukemia: the development of high-dose ara-C from the laboratory to bedside., Invest New Drugs. 1996;14(3):249-56.

Giles et al., Intravenous corticosteroids to reduce gemtuzumab ozogamicin infusion reactions. Ann Pharmacother. Sep. 2003;37(9):1182-5.

Duong et al., Targeted treatment of acute myeloid leukemia in older adults: role of gemtuzumab ozogamicin., Clin Interv Aging. 2009;4:197-205. Epub May 14, 2009.

Sun et al. , Preclinical Characterization of Combinability and Potential Synergy of Anti-CD20/CD3 T-Cell Dependent Bispecific Antibody with Chemotherapy and PD-1/PD-L1 Blockade., Blood 2016 128:4168.

Gantke et al., Trispecific antibodies for CD16A-directed NK cell engagement and dual-targeting of tumor cells., Protein Eng Des Sel. Sep. 1, 2017;30(9):673-684. doi: 10.1093/protein/gzx043.

Zhang et al., The development of bispecific antibodies and their applications in tumor immune escape., May 2, 2017, Experimental Hematology & Oncology20176:12.

Krupka et al., Blockade of the PD-1/PD-L1 axis augments lysis of AML cells by the CD33/CD3 BiTE antibody construct AMG 330: reversing a T-cell-induced immune escape mechanism., Leukemia. Feb. 2016;30(2):484-91. doi: 10.1038/leu.2015.214. Epub Aug. 4, 2015.

Osada et al., CEA/CD3-bispecific T cell-engaging (BiTE) antibody-mediated T lymphocyte cytotoxicity maximized by inhibition of both PD1 and PD-L1., Cancer Immunol Immunother. Jun. 2015;64(6):677-88. doi: 10.1007/s00262-015-1671-y. Epub Mar. 6, 2015.

Masarova et al., Immune Checkpoint Approaches in AML and MDS: A Next Frontier?, The Journal of Targeted Therapies in Cancer, Mar. 6, 2017 (Mar. 6, 2017), XP002784099.

Scott et al., Antibody therapy of cancer., Nat Rev Cancer. Mar. 22, 2012;12(4):278-87. doi: 10.1038/nrc3236.

Clynes et al., Redirected T Cell Cytotoxicity in Cancer Therapy., Annu Rev Med. Jan. 27, 2019;70:437-450. doi: 10.1146/annurev-med-062617-035821. Epub Oct. 31, 2018.

Merchant et al., Monovalent antibody design and mechanism of action of onartuzumab, a MET antagonist with anti-tumor activity as a therapeutic agent., Proc Natl Acad Sci U S A. Aug. 6, 2013;110(32):E2987-96. doi: 10.1073/pnas.1302725110. Epub Jul. 23, 2013.

Fos et al., ICOS ligation recruits the p50alpha PI3K regulatory subunit to the immunological synapse., J Immunol. Aug. 1, 2008;181(3):1969-77.

Sanmamed et al., Agonists of Co-stimulation in Cancer Immunotherapy Directed Against CD137, OX40, GITR, CD27, CD28, and ICOS., Semin Oncol. Aug. 2015;42(4):640-55. doi: 10.1053/j.seminoncol.2015.05.014. Epub Jun. 11, 2015.

Vieira et al., ICOS-mediated signaling regulates cytokine production by human T cells and provides a unique signal to selectively control the clonal expansion of Th2 helper cells., Eur J Immunol. May 2004;34(5):1282-90.

Madrenas et al., Conversion of CTLA-4 from inhibitor to activator of T cells with a bispecific tandem single-chain Fv ligand., J Immunol. May 15, 2004;172(10):5948-56.

Yokosuka et al., Spatiotemporal basis of CTLA-4 costimulatory molecule-mediated negative regulation of T cell activation., Immunity. Sep. 24, 2010;33(3):326-39. doi: 10.1016/j.immuni.2010.09.006.

Carpenter et al., Activation of human B cells by the agonist CD40 antibody CP-870,893 and augmentation with simultaneous toll-like receptor 9 stimulation., J Transl Med. Nov. 11, 2009;7:93. doi: 10.1186/1479-5876-7-93.

(56)　　　　　References Cited

OTHER PUBLICATIONS

Fan et al., Engagement of the ICOS pathway markedly enhances efficacy of CTLA-4 blockade in cancer immunotherapy., J Exp Med. Apr. 7, 2014;211(4): 715-25. doi: 10.1084/jem.20130590. Epub Mar. 31, 2014.

Gilboa et al., Use of oligonucleotide aptamer ligands to modulate the function of immune receptors., Clin Cancer Res. Mar. 1, 2013;19(5):1054-62. doi: 10.1158/1078-0432.CCR-Dec. 2067.

Uy et al., Preliminary Results of a Phase 1 Study of Flotetuzumab, a CD123 x CD3 Bispecific Dart® Protein, in Patients with Relapsed/Refractory Acute Myeloid Leukemia and Myelodysplastic Syndrome., Blood 2017 130:637.

Vey et al., Interim Results from a Phase 1 First-in-Human study of flotetuzumab, a CD123 x CD3 bispecific DART molecule, in AML/MDS., Annals of Oncology (2017) 28 (suppl_5): v355-v371. 10.1093/annonc/mdx373.

Ravandi et al., Complete Responses in Relapsed/Refractory Acute Myeloid Leukemia (AML) Patients on a Weekly Dosing Schedule of XmAb14045, a CD123 x CD3 T Cell-Engaging Bispecific Antibody: Initial Results of a Phase 1 Study., Blood 2018 132:763; doi: https://doi.org/10.1182/blood-2018-99-119786.

Bacac et al., A Novel Carcinoembryonic Antigen T-Cell Bispecific Antibody (CEA TCB) for the Treatment of Solid Tumors., Clin Cancer Res. Jul. 1, 2016;22(13):3286-97.

Schuster et al., Immunotherapy with the trifunctional anti-CD20 x anti-CD3 antibody FBTA05 (Lymphomun) in paediatric high-risk patients with recurrent CD20-positive B cell malignancies., Br J Haematol. Apr. 2015;169(1):90-102. doi: 10.1111/bjh.13242. Epub Dec. 11, 2014.

Shields et al; "High Resolution Mapping of the Binding Site on Human IgG 1 for FcγRI, FcγRII, FcγRIII, and FcRn and Design of IgG1 Variants with Improved Binding to the FcγR*", The Journal of Biological Chemistry, 2001, 276(2):6591-6604.

Szymkowski et al.; " Anti-CD38—anti-CD3 bispecific antibody in multiple myeloma", Xencor, pp. 1-15. Mar. 28, 2014.

Julg, B. et al."Enhanced Anti-HIV Functional Activity Associated with Gag-Specific CD8 T-Cell Responses." Journal of Virology 84.11 (2010): 5540-5549. Mar. 24, 2010.

Tutt et al., Trispecific F(ab')3 derivatives that use cooperative signaling via the TCR/CD3 complex and CD2 to activate and redirect resting cytotoxic T cells., The Journal of Immunology Jul. 1, 1991, 147 (1) 60-69.

Armour et al., Recombinant human IgG molecules lacking FcγY receptor I binding and monocyte triggering activities., Eur. J. Immunol. 1999. 29: 2613-2624.

Bogolyubova et al. , Cancer immunotherapy based on the blockade of immune checkpoints, Oct. 2015, Medical Immunology (Russia) 17(5):395.

Schanzer et al., "A Novel Glycoengineered Bispecific Antibody Format for Targeted Inhibition of Epidermal Growth Factor Receptor (EGFR) and Insulin-like Growth Factor Receptor Type I (IGF-1 R) Demonstrating Unique Molecular Properties", Journal of Biological Chemistry, vol. 289, No. 27, May 19, 2014 (May 19, 2014), pp. 18693-18706.

Volker Baum et al., "Antitumor activities of PSMA x CD3 diabodies by redirected T-cell lysis of prostate cancer cells", Immunotherapy, vol. 5, No. 1, pp. 27-38, Jan. 31, 2013.

Stewart et al., "The role of Fc gamma receptors in the activity of immunomodulatory antibodies for cancer", Journal for Immunotherapy of Cancer, Biomed Central, London, UK, vol. 2, No. 1, Aug. 19, 2014 (Aug. 19, 2014), p. 29.

Moore et al., A robust heterodimeric Fc platform engineered for efficient development of bispecific antibodies of multiple formats., Methods. Feb. 1, 2019;154:38-50. doi: 10.1016/j.ymeth.2018.10. 006. Epub Oct. 23, 2018.

Celine Monnet et al: "Selection of IgG variants with increased FcRn binding using random and directed mutagenesis: impact on effector functions", Frontiers in Immunology, vol. 6, No. 39, Feb. 4, 2015 (Feb. 4, 2015), pp. 1-14, XP055238838, DOI: 10.3389/fimmu.2015. 00039.

Sondermann Peter et al: "Harnessing Fc receptor biology in the design of therapeutic antibodies", Current Opinion in Immunology, Elsevier, Oxford, GB, vol. 40, Mar. 30, 2016 (Mar. 30, 2016), pp. 78-87, XP029551351, ISSN: 0952-7915, DOI: 10.1016/J.COI.2016. 03.005.

Deckert et al., "A Novel Humanized CD38-Targeting Antibody, Demonstrates Potent Antitumor Activity in Models of Multiple Myeloma and Other CD38+ Hematologic Malignancies", Clinical Cancer Research, vol. 20, No. 17, pp. 4574-4583 (Sep. 2014).

De Weers et al., "Daratumumab, a Novel Therapeutic Human CD38 Monoclonal Antibody, Induces Killing of Multiple Myeloma and Other Hematological Tumors", The Journal of Immunology, vol. 186, No. 3, pp. 1840-1848 (Dec. 2010).

Wang et al., Comparison of Biologic Activity of Two Anti-PSA/Anti-CD3 Bispecific Singlechain Antibodies, National Journal of Androloqy, vol. 13(1), pp. 8-12 (2007).

Wu et al., Fab-based bispecific antibody formats with robust biophysical properties and biological activity. mAbs, 7:3, 470-482, Published online: May 1, 2015.

Holliger et al., Engineered antibody fragments and the rise of single domains., Nature Biotechnology, vol. 23, pp. 1126-1136 (2005).

Reusch et al., Anti-CD3 x anti-epidermal growth factor receptor (EGFR) bispecific antibody redirects T-cell cytolytic activity to EGFRpositive cancers in vitro and in an animal model, Clinical Cancer Research, the American Association for Cancer Research, US, vol. 12, No. 1, Jan. 1, 2006 (Jan. 1, 2006), pp. 183-190.

Kontermann Roland : "Dual targeting strategies with bispecific antibodies", mAbs, vol. 4, No. 2, Mar. 1, 2012 (Mar. 1, 2012), pp. 182-197, XP055566203.

Kontermann Rolande: "Recombinant bispecific antibodies for cancer therapy", Acta Pharmacologica Sinica, vol. 26, No. 1, Jan. 1, 2005 (Jan. 1, 2005), pp. 1-9, XP002426874.

Dickopf et al, "Format and geometries matter: Structure-based design defines the functionality of bispecific antibodies", Computational and Structural Biotechnology Journal, vol. 18, May 14, 2020 (May 14, 2020), p. 1221-1227.

Roda-Navarro Pedro et al, "Understanding the Spatial Topology of Artificial Immunological Synapses Assembled in T Cell-Redirecting Strategies: A Major Issue in Cancer Immunotherapy", Frontiers in Cell and Developmental Biology, vol. 7, Jan. 10, 2020 (Jan. 10, 2020).

Suurs Frans V et al, "A review of bispecific antibodies and antibody constructs in oncology and clinical challenges", Apr. 24, 2019 (Apr. 24, 2019), vol. 201, p. 103-119.

Chen Shixue et al, "Immunoglobulin Gamma-Like Therapeutic Bispecific Antibody Formats for Tumor Therapy", US Feb. 11, 2019 (Feb. 11, 2019), vol. 2019, p. 1-13.

Van Blarcom et al, "Productive common light chain libraries yield diverse panels of high affinity bispecific antibodies", MABS, vol. 10, No. 2, Dec. 14, 2017 (Dec. 14, 2017), p. 256-268.

Hedvat Michael et al, "697—Tumor-targeted CD28 costimulatory bispecific antibodies enhance T cell activation in solid tumors", Journal for Immunotherapy of Cancer, vol. 8, No. Suppl 3, Nov. 1, 2020 (Nov. 1, 2020), p. A739-A739.

Correnti Colin E et al: "Simultaneous multiple interaction T-cell engaging (SMITE) bispecific antibodies overcome bispecific T-cell engager (BiTE) resistance via CD28 co-stimulation", Leukemia, Nature Publishing Group UK, London, vol. 32, No. 5, Jan. 31, 2018 (Jan. 31, 2018), pp. 1239-1243.

Correnti, Colin E. et al: Supplemental Methods Simultaneous multiple interaction T-cell engaging (SMITE) bispecific antibodies overcome bispecific T-cell engager (BiTE) resistance via CD28 co-stimulation, Leukemia, Jan. 31, 2018 (Jan. 31, 2018), pp. 1-7, XP055656259, DOI: 10.1038/s41375-018-0014-3 Retrieved from the Internet: URL:doi: 10.1038/s41375-018-0014-3 [retrieved on Jan. 9, 2020].

Brinkmann et al: The making of bispecific antibodies, MABS, vol. 9, No. 2, Jan. 10, 2017 (Jan. 10, 2017), pp. 182-212.

Moore Gregory L et al: "Abstract 1880:PDL1-targeted CD28 costimulatory bispecific antibodies enhance T cell activation in solid tumors", Cancer Research, Jul. 1, 2021 (Jul. 1, 2021), XP05588152.

Tolcher Anthony W. et al: "A phase 1 study of anti-TGF[beta] receptor type-II monoclonal antibody LY3022859 in patients with

(56)          References Cited

OTHER PUBLICATIONS advanced solid tumors", Cancer Chemotherapy and Pharmacology, Springer Verlag, Berlin, DE, vol. 79, No. 4, Mar. 9, 2017 (Mar. 9, 2017), pp. 673-680, XP036196406.

Moore Gregory et al: "Abstract #714 "PD1 x TGF[beta]R2 bispecifics selectively block TGF[beta]R2 on PDI-positive T cells, promote T cell activation, and elicit an anti-tumor response in solid tumors", Journal for immunotherapy of cancer, Nov. 9, 2020 (Nov. 9, 2020), pp. A756-A756, XP055884418, London DOI: 10.1136/jitc-2020-SITC2020.0714 Retrieved from the Internet: URL:https://investors.xencor.com/static-files/abballc4-fe9a-4152a209-88c0d55c3906 [retrieved on Jan. 27, 2022].

Brinkmann et al., Cloning and expression of the recombinant FAb fragment of monoclonal antibody K1 that reacts with mesothelin present on mesotheliomas and ovarian cancers., Int J Cancer. May 16, 1997;71(4):638-44.

Stadler et al., Elimination of large tumors in mice by mRNA-encoded bispecific antibodies., Nat Med. Jul. 2017;23(7):815-817. doi: 10.1038/nm.4356. Epub Jun. 12, 2017.

Zhu et al., Targeting CLDN18.2 by CD3 Bispecific and ADC Modalities for the Treatments of Gastric and Pancreatic Cancer., Scientific Reports vol. 9, Article No. 8420 (2019).

Bonifant, Chall ice L., et al. "CD123-engager T cells as a novel immunotherapeutic for AML." Blood 124.21 (2014): 3762.

A Pizzitola, I., et al. "Chimeric antigen receptors against CD33/ CD123 antigens efficiently target primary acute myeloid leukemia cells in vivo." Leukemia 28.8 (2014): 1596-1605.

Lloyd et al. Modelling the human immune response: performance of a 10" human antibody repertoire against a broad panel of therapeutically relevant antigens, Protein Eng Des Sel. Mar. 2009;22(3):159-68. doi: 10.1093/protein/gzn058. Epub Oct. 29, 2008.

Edwards et al., The remarkable flexibility of the human antibody repertoire; isolation of over one thousand different antibodies to a single protein, BLyS., J Mol Biol. Nov. 14, 2003;334(1):103-18. doi: 10.1016/j.jmb.2003.09.054.

Al Qaraghuli et al., Antibody-protein binding and conformational changes: identifying allosteric signalling pathways to engineer a better effector response., Sci Rep. Aug. 13, 2020;10(1):13696. doi: 10.1038/s41598-020-70680-0.

Iwahashi et al., CDR substitutions of a humanized monoclonal antibody (CC49): contributions of individual CDRs to antigen binding and immunogenicity., Mol Immunol. Oct.-Nov. 1999;36(15-16):1079-91. doi: 10.1016/s0161-5890(99)00094-2.

Pescovitz, M.D., Rituximab, an anti-cd20 monoclonal antibody: history and mechanism of action., Am J Transplant May 2006;6(5 Pt 1):859-66. doi: 10.1111/j.1600-6143.2006.01288.x.

Leeansyah, E. et al., " Activation, exhaustion, and persistent decline of the antimicrobial MR1-restricted MAIT-cell population in chronic HIV-1 infection" Blood, 121(7), pp. 1124-1135, Feb. 14, 2013 (Feb. 14, 2013).

Poirier et al., "CD28-Specific Immunomodulating Antibodies: What Can Be Learned From Experimental Models ?: CD28-Specific Immunomodulating Antibodies", American Journal of Transplantation, vol. 12, No. 7, Jul. 1, 2012 (Jul. 1, 2012), pp. 1682-1690.

Bilsen et al., "The neonatal Fc receptor is expressed by human lymphocytes", Journal of Translational Medicine, Biomed Central, vol. 8, No. Suppl 1, Nov. 25, 2010 (Nov. 25, 2010), p. P1.

Marsh et al., "Monocyte IL-8 release is induced by two independent Fc gamma R-mediated pathways", The Journal of Immunology, vol. 157, No. 6, Sep. 15, 1996 (Sep. 15, 1996), pp. 2632-2637.

Ishiguro et al., An anti-glypican 3/CD3 bispecific T cell-redirecting antibody for treatment of solid tumors., Sci Transl Med. Oct. 4, 2017;9(410):eaal4291. doi: 10.1126/scitranslmed.aal4291.

Fortmüller et al., Effective targeting of prostate cancer by lymphocytes redirected by a PSMA x CD3 bispecific single-chain diabody. Prostate. May 2011;71(6):588-96. doi: 10.1002/pros.21274. Epub Oct. 13, 2010.

Fang, M., Jiang, X., Yang, Z et al. Effects of interlinker sequences on the biological properties of bispecific single-chain antibodies. Chin.Sci.Bull. 48, 2277-2283 (2003). https://doi.org/10.1360/03wc0168.

Zhao Xiao, Study on the Bispecific Antibody based Rapid Diagnosis of Tropical Diseases., Chinese Master's Thesis Full text Database (Electronic Journal) Medicine and Health Sciences / Jan. 1, 2018.

Le Gall et al., Immunosuppressive properties of anti-CD3 single-chain Fv and diabody., Journal of Immunological Methods, 2004, 285: 111-127.

Mariuzza et al., The structural basis of antigen-antibody recognition., Annu. Rev. Biophys. Biophys. Chem., 16: 139-159, 1987.

McCarthy et al., Altering the fine specificity of an anti-Legionella single chain antibody by a single amino acid insertion., J. Immunol. Methods, 251(1-2): 137-149, 2001.

Lin et al., Improved affinity of a chicken single-chain antibody to avian infectious bronchitis virus by site-directed mutagenesis of complementarity-determining region H3., African Journal of Biotechnology, 10(79): 18294-18302, 2011.

English translation of WO2006006693A1.

Chiu et al., Antibody Structure and Function: The Basis for Engineering Therapeutics., Antibodies (Basel). Dec. 3, 2019;8(4):55. doi: 10.3390/antib8040055.

Sela-Culang et al., The structural basis of antibody-antigen recognition., Front Immunol. Oct. 8, 2013:4:302. doi: 10.3389/fimmu.2013.00302.

Burgess et al., Possible dissociation of the heparin-binding and mitogenic activities of heparin-binding (acidic fibroblast) growth factor-1 from its receptor-binding activities by site-directed mutagenesis of a single lysine residue., J Cell Biol. Nov. 1990;111(5 Pt 1):2129-38. doi: 10.1083/jcb.111.5.2129.

Bowie et al., Deciphering the message in protein sequences: tolerance to amino acid substitutions., Science. Mar. 16, 1990;247(4948):1306-10. doi: 10.1126/science.2315699.

Greenspan et al., Defining epitopes: It's not as easy as it seems., Nat Biotechnol. Oct. 1999;17(10):936-7. doi: 10.1038/13590.

Bork, P., Powers and pitfalls in sequence analysis: the 70% hurdle., Genome Res. Apr. 2000;10(4):398-400. doi: 10.1101/gr.10.4.398.

Lazar et al., Transforming growth factor alpha: mutation of aspartic acid 47 and leucine 48 results in different biological activities., Mol Cell Biol. Mar. 1988;8(3):1247-52. doi: 10.1128/mcb.8.3.1247-1252.1988.

Bardia et al., Efficacy and Safety of Anti-Trop-2 Antibody Drug Conjugate Sacituzumab Govitecan (IMMU-132) in Heavily Pretreated Patients With Metastatic Triple-Negative Breast Cancer.

Socinski et al., Atezolizumab for First-Line Treatment of Metastatic Nonsquamous Nsclc., N Engl J Med. Jun. 14, 2018;378(24):2288-2301. doi: 10.1056/NEJMoa1716948. Epub Jun. 4, 2018.

Wu et al: "Basic Study on the Therapeutic Function of Trispecific Antibodies Targeting CD3-TROP2-PDL1 in Triple-negative Breast Cancer", Jan. 16, 2022 (Jan. 16, 2022), Master's Thesis, China Medical University, China, pp. 1-43, XP009556737.

Bashour et al., CD28 and CD3 have complementary roles in T-cell traction forces., Proc Natl Acad Sci USA. Feb. 11, 2014;111(6):2241-6. doi: 10.1073/pnas.1315606111. Epub Jan. 27, 2014.

Rabia et al., Understanding and overcoming trade-offs between antibody affinity, specificity, stability and solubility., Biochem Eng J. Sep. 15, 2018:137:365-374.

Tiller et al., Arginine mutations in antibody complementarity-determining regions display context-dependent affinity/specificity trade-offs., J Biol Chem. Oct. 6, 2017;292(40):16638-16652.

Tsjui et al., Somatic Hypermutation and Framework Mutations of Variable Region Contribute to Anti-Zika Virus-Specific Monoclonal Antibody Binding and Function., J Virol. Jun. 8, 2022;96(11):e0007122.

Brown et al., Tolerance of single, but not multiple, amino acid replacements in antibody VH CDR 2: a means of minimizing B cell wastage from somatic hypermutation?, J Immunol. May 1, 1996;156(9):3285-91.

Skolnick et al., From genes to protein structure and function: novel applications of computational approaches in the genomic era., Trends Biotechnol. Jan. 2000;18(1):34-9.

(56)　　　　　　References Cited

OTHER PUBLICATIONS

Vajdos et al., Comprehensive functional maps of the antigen-binding site of an anti-ErbB2 antibody obtained with shotgun scanning mutagenesis., J Mol Biol. Jul. 5, 2002;320(2):415-28.

Miosge et al., Comparison of predicted and actual consequences of missense mutations., Proc Natl Acad Sci U S A. Sep. 15, 2015;112(37):E5189-98.

Kulmanov et al., DeepGO: predicting protein functions from sequence and interactions using a deep ontology-aware classifier., Bioinformatics. Feb. 15, 2018;34(4):660-668.

Bedouelle et al., Diversity and junction residues as hotspots of binding energy in an antibody neutralizing the dengue virus., FEBS J. Jan. 2006;273(1):34-46).

P.M. Colman, Effects of amino acid sequence changes on antibody-antigen interactions., Res Immunol. Jan. 1994;145(1):33-6.

Rudikoff et al., Single amino acid substitution altering antigen-binding specificity., Proc Natl Acad Sci U S A. Mar. 1982;79(6):1979-83.

Krishnamurthy et al., Bispecific antibodies for cancer therapy: A review., Pharmacol Ther. May 2018:185:122-134. doi: 10.1016/j.pharmthera.2017.12.002. Epub Dec. 18, 2017.

Morris et al.: "The molecular details of cytokine signaling via the JAK/STAT pathway: Cytokine Signaling via the JAK/STATPathway", Protein Science, vol. 27, No. 12, Dec. 1, 2018 (Dec. 1, 2018), pp. 1984-2009, XP055809868.

Almagro et al., Progress and Challenges in the Design and Clinical Development of Antibodies for Cancer Therapy., Front Immunol. Jan. 4, 2018:8:1751. doi: 10.3389/fimmu.2017.01751. eCollection 2017.

Marvin et al., Redesigning an antibody fragment for faster association with its antigen., Biochemistry. Jun. 17, 2003;42(23):7077-83. doi: 10.1021/bi026947q.

Okazaki et al., PD-1 and PD-1 ligands: from discovery to clinical application., Int Immunol. Jul. 2007;19(7):813-24. doi: 10.1093/intimm/dxm057. Epub Jul. 2, 2007.

Sunshine et al., PD-1/PD-L1 inhibitors., Curr Opin Pharmacol. Aug. 2015:23:32-8. doi: 10.1016/j.coph.2015.05.011. Epub Jun. 2, 2015.

* cited by examiner

Figure 1A

| Monomer 1 | Monomer 2 |
|---|---|
| F405A | T394F |
| S364D | Y349K |
| S364E | L368K |
| S364E | Y349K |
| S364F | K370G |
| S364H | Y349K |
| S364H | Y349T |
| S364Y | K370G |
| T411K | K370E |
| V397S/F405A | T394F |
| K370R/T411K | K370E/T411E |
| L351E/S364D | Y349K/L351K |
| L351E/S364E | Y349K/L351K |
| L351E/T366D | L351K/T366K |
| P395T/V397S/F405A | T394F |
| S364D/K370G | S364Y/K370R |
| S364D/T394F | Y349K/F405A |
| S364E/F405A | Y349K/T394F |
| S364E/F405S | Y349K/T394Y |
| S364E/T411E | Y349K/D401K |
| S364H/D401K | Y349T/T411E |
| S364H/F405A | Y349T/T394F |
| S364H/T394F | Y349T/F405A |
| Y349C/S364E | Y349K/S354C |
| L351E/S364D/F405A | Y349K/L351K/T394F |
| L351K/S364H/D401K | Y349T/L351E/T411E |
| S364E/T411E/F405A | Y349K/T394F/D401K |
| S364H/D401K/F405A | Y349T/T394F/T411E |
| S364H/F405A/T411E | Y349T/T394F/D401K |

Figure 1B

| Monomer 1 | Monomer 2 |
|---|---|
| K370E/T411D | T411K |
| L368E/K409E | L368K |
| Y349T/T394F/S354C | S364H/F405A/Y349C |
| T411E | D401K |
| T411E | D401R/T411R |
| Q347E/K360E | Q347R |
| L368E | S364K |
| L368E/K370S | S364K |
| L368E/K370T | S364K |
| L368E/D401R | S364K |
| L368E/D401N | S364K |
| L368E | E357S/S364K |
| L368E | S364K/K409E |
| L368E | S364K/K409V |
| L368D | S364K |
| L368D/K370S | S364K |
| L368D/K370S | S364K/E357L |
| L368D/K370S | S364K/E357Q |
| T411E/K360E/Q362E | D401K |
| K370S | S364K |
| L368E/K370S | S364K/E357Q |
| K370S | S364K/E357Q |
| T411E/K360D | D401K |
| T411E/K360E | D401K |
| T411E/Q362E | D401K |
| T411E/N390D | D401K |
| T411E | D401K/Q347K |
| T411E | D401K/Q347R |
| T411E/K360D/Q362E | D401K |

Figure 1C

| Monomer 1 | Monomer 2 |
|---|---|
| T411E/K360E/N390D | D401K |
| T411E/Q362E/N390D | D401K |
| T411E/Q347R | D401K/K360D |
| T411E/Q347R | D401K/K360E |
| T411E/K360 | D401K/Q347K |
| T411E/K360D | D401K/Q347R |
| T411E/K360E | D401K/Q347K |
| T411E/K360E | D401K/Q347R |
| T411E/S364K | D401K/K370S |
| T411E/K370S | D401K/S364K |
| Q347E | E357Q |
| Q347E | E357Q/Q362K |
| K360D/Q362E | Q347R |
| K360D/Q362E | D401K |
| K360D/Q362E | Q347R/D401K |
| K360E/Q362E | Q347R |
| K360E/Q362E | D401K |
| K360E/Q362E | Q347R/D401K |
| Q362E/N390D | D401K |
| Q347E/K360D | D401N |
| K360D | Q347R/N390K |
| K360D | N390K/D401N |
| K360E | Y349H |
| K370S/Q347E | S364K |
| K370S/E357L | S364K |
| K370S/E357Q | S364K |
| K370S/Q347E/E357L | S364K |
| K370S/Q347E/E357Q | S364K |

Figure 1D

| Monomer 1 | Monomer 2 |
|---|---|
| L368D/K370S/Q347E | S364K |
| L368D/K370S/E357L | S364K |
| L368D/K370S/E357Q | S364K |
| L368D/K370S/Q347E/E357L | S364K |
| L368D/K370S/Q347E/E357Q | S364K |
| L368E/K370S/Q347E | S364K |
| L368E/K370S/E357L | S364K |
| L368E/K370S/E357Q | S364K |
| L368E/K370S/Q347E/E357L | S364K |
| L368E/K370S/Q347E/E357Q | S364K |
| L368D/K370T/Q347E | S364K |
| L368D/K370T/E357L | S364K |
| L368D/K370T/E357Q | S364K |
| L368D/K370T/Q347E/E357L | S364K |
| L368D/K370T/Q347E/E357Q | S364K |
| L368E/K370T/Q347E | S364K |
| L368E/K370T/E357L | S364K |
| L368E/K370T/E357Q | S364K |
| L368E/K370T/Q347E/E357L | S364K |
| L368E/K370T/Q347E/E357Q | S364K |
| T411E/Q362E | D401K/T411K |
| T411E/N390D | D401K/T411K |
| T411E/Q362E | D401R/T411R |
| T411E/N390D | D401R/T411R |
| Y407T | T366Y |
| F405A | T394W |
| T366Y/F405A | T394W/Y407T |
| Y407A | T366W |
| T366S/L368A/Y407V | T366W |
| T366S/L368A/Y407V/Y349C | T366W/S354C |

Figure 1E

| Monomer 1 | Monomer 2 |
|---|---|
| K392D/K409D | E356K/D399K |
| K370D/K392D/K409D | E356K/E357K/D399K |
| I199T/N203D/K247Q/R355Q/N384S/K392N/V397M/Q419E/K447_ | Q196K/I199T/P217R/P228R/N276K |
| I199T/N203D/K247Q/R355Q/N384S/K392N/V397M/Q419E/K447_ | Q196K/I199T/N276K |
| N384S/K392N/V397M/Q419E | N276K |
| D221E/P228E/L368E | D221R/P228R/K409R |
| C220E/P228E/L368E | C220R/E224R/P228R/K409R |
| F405L | K409R |
| T366I/K392M/T394W | F405A/Y407V |
| T366V/K409F | L351Y/Y407A |
| T366A/K392E/K409F/T411E | D399R/S400R/Y407A |
| L351K | L351E |
| I199T/N203D/K247Q/R355Q/Q419E/K447_ | Q196K/I199T/P217R/P228R/N276K |
| I199T/N203D/K247Q/R355Q/Q419E/K447_ | Q196K/I199T/N276K |
| I199T/N203D/K274Q/R355Q/N384S/K392N/V397M/Q419E/K447_ | |
| N208D/Q295E/N384D/Q418E/N421D | |
| N208D/Q295E/Q418E/N421D | |
| Q196K/I199T/P217R/P228R/N276K | |
| Q196K/I199T/N276K | |
| E269Q/E272Q/E283Q/E357Q | |
| E269Q/E272Q/E283Q | |
| E269Q/E272Q | |
| E269Q/E283Q | |
| E272Q/E283Q | |
| E269Q | |

Figure 2

| Variant constant region | Substitutions |
|---|---|
| pI-ISO(-) | I199T/N203D/K274Q/R355Q/N384S/K392N/N397M/Q419E/K447_ |
| pI_ISO(-)-Fc only | K274Q/R355Q/N384S/K392N/V397M/Q419E/K447_ |
| pI_(-)_isosteric_A | N208D/Q295E/N384D/Q418E/N421D |
| pI_(-)_isosteric A-Fc only | Q295E/N384D/Q418E/N421D |
| pI_(-)_isosteric_B | N208D/Q295E/Q418E/N421D |
| pI_(-)_isosteric_B-Fc only | Q295E/Q418E/N421D |
| pI_ISO(+RR) | Q196K/I199T/P217R/P228R/N276K |
| pI_ISO(+RR)-Fc only | P217R/P228R/N276K |
| pI_ISO(+) | Q196K/I199T/N276K |
| pI_ISO(+)-Fc only | N276K |
| pI_(+)_isosteric_A | E269Q/E272Q/E283Q/E357Q |
| pI_(+)_isosteric_B | E269Q/E272Q/E283Q |
| pI_(+)_isosteric_E269Q/E272Q | E269Q/E272Q |
| pI_(+)_isosteric_E269Q/E283Q | E269Q/E283Q |
| pI_(+)_isosteric_E272Q/E283Q | E272Q/E283Q |
| pI_(+)_isosteric_E269Q | E269Q |

Figure 3

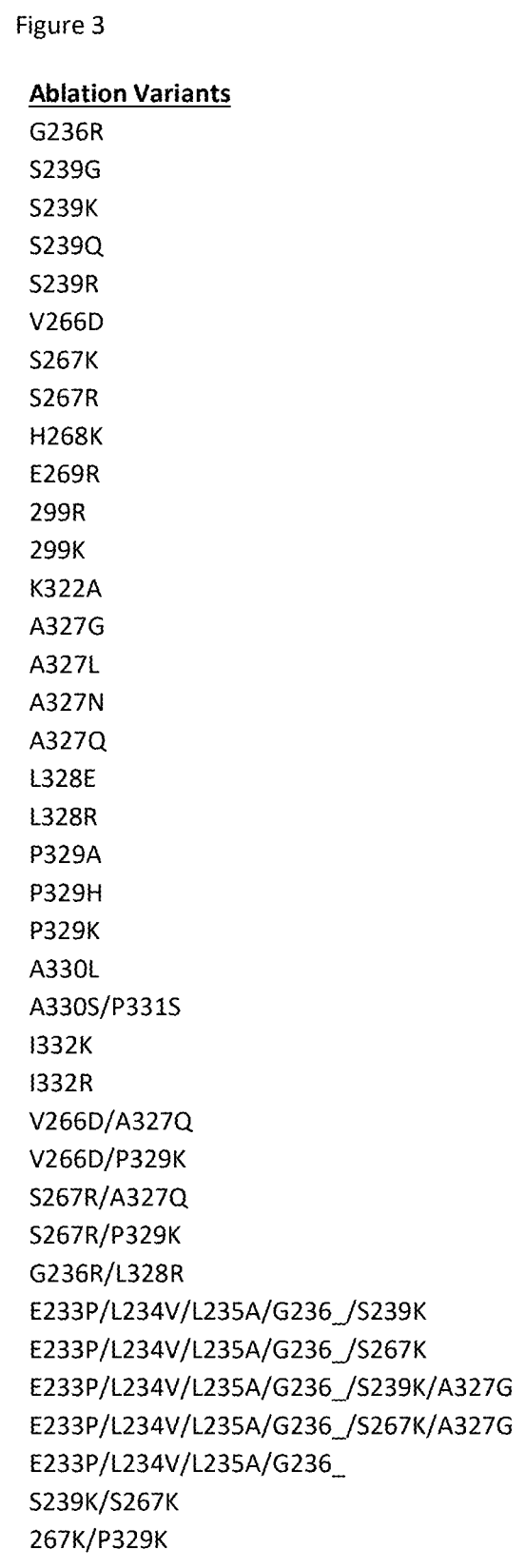

Ablation Variants
G236R
S239G
S239K
S239Q
S239R
V266D
S267K
S267R
H268K
E269R
299R
299K
K322A
A327G
A327L
A327N
A327Q
L328E
L328R
P329A
P329H
P329K
A330L
A330S/P331S
I332K
I332R
V266D/A327Q
V266D/P329K
S267R/A327Q
S267R/P329K
G236R/L328R
E233P/L234V/L235A/G236_/S239K
E233P/L234V/L235A/G236_/S267K
E233P/L234V/L235A/G236_/S239K/A327G
E233P/L234V/L235A/G236_/S267K/A327G
E233P/L234V/L235A/G236_
S239K/S267K
267K/P329K

Figure 4

| Heavy Chain 1 (-) e.g. Fab-Fc | Heavy Chain 2 (+) e.g. scFv-Fc or Fab-scFv-Fc |
|---|---|
|  | C220S |
| Heterodimer pI variants L368D/K370S | Heterodimer pI variants S364K/E357Q |
| Isosteric pI substitutions N208D/Q295E/N384D/Q418E/N421D |  |
| FcKO E233P/L234V/L235A/G236_/S267K | FcKO E233P/L234V/L235A/G236_/S267K |
| ±M428L/N434S | ±M428L/N434S |

Figure 5

Positive Charged scFv Linkers

| Name | Sequence | Length | Charge | SEQ ID NO: |
|---|---|---|---|---|
| Gly-Ser 15 | GGGGSGGGGSGGGGS | 15 | 0 | 5 |
| Whitlow linker | GSTSGSGKPGSGEGSTKG | 18 | +1 | 6 |
| 6paxA_1 (+A) | IRPRAIGGSKPRVA | 14 | +4 | 7 |
| +B | GKGGSGKGGSGKGGS | 15 | +3 | 8 |
| +C | GGKGSGGKGSGGKGS | 15 | +3 | 9 |
| +D | GGGKSGGGKSGGGKS | 15 | +3 | 10 |
| +E | GKGKSGKGKSGKGKS | 15 | +6 | 11 |
| +F | GGGKSGGKGSGKGGS | 15 | +3 | 12 |
| +G | GKPGSGKPGSGKPGS | 15 | +3 | 13 |
| +H | GKPGSGKPGSGKPGSGKPGS | 20 | +4 | 1 |
| +I | GKGKSGKGKSGKGKSGKGKS | 20 | +8 | 14 |

Negative Charged scFv Linkers

| Name | Sequence | Length | Charge | SEQ ID NO: |
|---|---|---|---|---|
| Gly-Ser 20 | GGGGSGGGGSGGGGSGGGGS | 20 | 0 | 15 |
| 3hsc_2 (-A) | STAGDTHLGGEDFD | 14 | -4 | 16 |
| -B | GEGGSGEGGSGEGGS | 15 | -3 | 17 |
| -C | GGEGSGGEGSGGEGS | 15 | -3 | 18 |
| -D | GGGESGGGESGGGES | 15 | -3 | 19 |
| -E | GEGESGEGESGEGES | 15 | -6 | 20 |
| -F | GGGESGGEGSGEGGS | 15 | -3 | 21 |
| -G | GEGESGEGESGEGESGEGES | 20 | -8 | 22 |

Additional scFv Linkers

| | |
|---|---|
| GGGGSGGGGSGGGGS | SEQ ID NO:5 |
| GGGGSGGGGSGGGGSGGGGS | SEQ ID NO:15 |
| GSTSGSGKPGSGEGSTKG | SEQ ID NO:6 |
| PRGASKSGSASQTGSAPGS | SEQ ID NO:23 |
| GTAAAGAGAAGGAAAGAAG | SEQ ID NO:24 |
| GTSGSSGSGSGGSGSGGGG | SEQ ID NO:25 |
| GKPGSGKPGSGKPGSGKPGS | SEQ ID NO:1 |

Figure 6

Useful domain linkers

| Name | Sequence | SEQ ID NO: |
|---|---|---|
| (GGGGS)$_1$ or GGGGS | GGGGS | 2 |
| (GGGGS)$_2$ | GGGGSGGGGS | 26 |
| (GGGGS)$_3$ | GGGGSGGGGSGGGGS | 5 |
| (GGGGS)$_4$ | GGGGSGGGGSGGGGSGGGGS | 15 |
| (GGGGS)$_5$ | GGGGSGGGGSGGGGSGGGGSGGGGS | 27 |
| (GGGGS)$_6$ | GGGGSGGGGSGGGGSGGGGSGGGGSGGGGS | 28 |
| (GGGGS)$_7$ | GGGGSGGGGSGGGGSGGGGSGGGGSGGGGSGGGGS | 29 |
| (GGGGA)$_1$ or GGGGA | GGGGA | 30 |
| (GGGGA)$_2$ | GGGGAGGGGA | 31 |
| (GGGGA)$_3$ | GGGGAGGGGAGGGGA | 32 |
| (GGGGA)$_4$ | GGGGAGGGGAGGGGAGGGGA | 33 |
| (GGGGA)$_5$ | GGGGAGGGGAGGGGAGGGGAGGGGA | 34 |
| (GGGGA)$_6$ | GGGGAGGGGAGGGGAGGGGAGGGGAGGGGA | 35 |
| (GGGGA)$_7$ | GGGGAGGGGAGGGGAGGGGAGGGGAGGGGAGGGGA | 36 |
| 30AA-linker | DPALVHQRPAPPGGGGSGGGGSGGGGSGGG | 37 |
| (GKPGS)$_1$ or GKPGS | GKPGS | 38 |
| (GKPGS)$_5$ | GKPGSGKPGSGKPGSGKPGSGKPGS | 39 |
| (GKPGS)$_6$ | GKPGSGKPGSGKPGSGKPGSGKPGSGKPGS | 40 |
| (GGGES)$_1$ or GGGES | GGGES | 41 |
| "half hinge" | KTHTCPPCP | 42 |
| "full hinge C220S variant" | EPKSSDKTHTCPPCP | 43 |
| "flex half hinge" | GGGGSGGGGSKTHTCPPCP | 44 |
| "charged half hinge1" | GKPGSGKPGSKTHTCPPCP | 45 |
| "charged half hinge2" | GKPGSKTHTCPPCP | 46 |

Figure 7A

1 + 1 Fab-scFv-Fc Backbone 1

>Fab-Fc Side (SEQ ID NO: 47)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYNSTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRWEQGDVFSCS
VMHEALHNHYTQKSLSLSPGK

>scFv-Fc Side (SEQ ID NO: 48)
EPKSSDKTHTCPPCPAPPVAGPSVFLFPPKPKDTLMISRTPEVTCVVVDVKHEDPEVKFNWYVDGVEVHNAKTKPRE
EQYNSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK

1 + 1 Fab-scFv-Fc Backbone 2

>Fab-Fc Side (SEQ ID NO: 49)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYNSTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRWEQGDVFSCS
VMHEALHNHYTQKSLSLSPGK

>scFv-Fc Side (SEQ ID NO: 50)
EPKSSDKTHTCPPCPAPPVAGPSVFLFPPKPKDTLMISRTPEVTCVVVDVKHEDPEVKFNWYVDGVEVHNAKTKPRE
EQYNSTYRVVSVLTVLHQDWLNGKEYKCKVSNKALPAPIEKTISKAKGQPREPQVYTLPPSREEMTKNQVKLTCLVK
GFYPSDIAVEWESNGQPENNYKTTPPVLDSDGSFFLYSKLTVDKSRWQQGNVFSCSVMHEALHNHYTQKSLSLSPGK

1 + 1 Fab-scFv-Fc Backbone 3

>Fab-Fc Side (SEQ ID NO: 51)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYNSTYRVVSVLTVLHQDWLNGKEYKCKVSNKALPAPIEKTISKAKGQPREPQVY
TLPPSREEMTKNQVSLTCEVSGFYPSDIAVEWESDGQPENNYKTTPPVLDSDGSFFLYSKLTVDKSRWEQGDVFSCS
VMHEALHNHYTQKSLSLSPGK

>scFv-Fc Side (SEQ ID NO: 52)
EPKSSDKTHTCPPCPAPPVAGPSVFLFPPKPKDTLMISRTPEVTCVVVDVKHEDPEVKFNWYVDGVEVHNAKTKPRE
EQYNSTYRVVSVLTVLHQDWLNGKEYKCKVSNKALPAPIEKTISKAKGQPREPQVYTLPPSREEMTKNQVKLTCLVK
GFYPSDIAVEWESNGQPENNYKTTPPVLDSDGSFFLYSKLTVDKSRWQQGNVFSCSVMHEALHNHYTQKSLSLSPGK

Figure 7B

1 + 1 Fab-scFv-Fc Backbone 4

>Fab-Fc Side (SEQ ID NO: 53)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYNSTYRVVSVLTVLHQDWLNGKEYKCKVSNKALPAPIEKTISKAKGQPREPQVY
TLPPSREEMTENEVSLTCLVKGFYPSDIAVEWESDGQPENNYKTTPPVLDSDGSFFLYSKLEVDKSRWEQGDVFSCS
VMHEALHNHYTQKSLSLSPGK

>scFv-Fc Side (SEQ ID NO: 54)
EPKSSDKTHTCPPCPAPPVAGPSVFLFPPKPKDTLMISRTPEVTCVVVDVKHEDPEVKFNWYVDGVEVHNAKTKPRE
EQYNSTYRVVSVLTVLHQDWLNGKEYKCKVSNKALPAPIEKTISKAKGQPREPQVYTLPPSREEMTKNQVSLTCLVK
GFYPSDIAVEWESNGQPENNYKTTPPVLDSKGSFFLYSKLTVDKSRWQQGNVFSCSVMHEALHNHYTQKSLSLSPGK

1 + 1 Fab-scFv-Fc Backbone 5

>Fab-Fc Side (SEQ ID NO: 55)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYNSTYRVVSVLTVLHQDWLNGKEYKCKVSNKALPAPIEKTISKAKGQPREPQVY
TLPPSRDELTKNQVSLTCDVSGFYPSDIAVEWESDGQPENNYKTTPPVLDSDGSFFLYSKLTVDKSRWEQGDVFSCS
VMHEALHNHYTQKSLSLSPGK

>scFv-Fc Side (SEQ ID NO: 56)
EPKSSDKTHTCPPCPAPPVAGPSVFLFPPKPKDTLMISRTPEVTCVVVDVKHEDPEVKFNWYVDGVEVHNAKTKPRE
EQYNSTYRVVSVLTVLHQDWLNGKEYKCKVSNKALPAPIEKTISKAKGQPREPQVYTLPPSRDQLTKNQVKLTCLVK
GFYPSDIAVEWESNGQPENNYKTTPPVLDSDGSFFLYSKLTVDKSRWQQGNVFSCSVMHEALHNHYTQKSLSLSPGK

1 + 1 Fab-scFv-Fc Backbone 6

>Fab-Fc Side (SEQ ID NO: 57)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYASTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRWEQGDVFSCS
VMHEALHNHYTQKSLSLSPGK

>scFv-Fc Side (SEQ ID NO: 58)
EPKSSDKTHTCPPCPAPPVAGPSVFLFPPKPKDTLMISRTPEVTCVVVDVKHEDPEVKFNWYVDGVEVHNAKTKPRE
EQYASTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK

Figure 7C

1 + 1 Fab-scFv-Fc Backbone 7

>Fab-Fc Side (SEQ ID NO: 59)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYSSTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRWEQGDVFSCS
VMHEALHNHYTQKSLSLSPGK

>scFv-Fc Side (SEQ ID NO: 60)
EPKSSDKTHTCPPCPAPPVAGPSVFLFPPKPKDTLMISRTPEVTCVVVDVKHEDPEVKFNWYVDGVEVHNAKTKPRE
EQYSSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK

1 + 1 Fab-scFv-Fc Backbone 8

>Fab-Fc Side (SEQ ID NO: 61)
ASTKGPSVFPLAPCSRSTSESTAALGCLVKDYFPEPVTVSWNSGALTSGVHTFPAVLQSSGLYSLSSVVTVPSSSLG
TKTYTCNVDHKPSDTKVDKRVESKYGPPCPPCPAPEFLGGPSVFLFPPKPKDTLMISRTPEVTCVVVDVSQEDPEVQ
FNWYVDGVEVHNAKTKPREEEFNSTYRVVSVLTVLHQDWLNGKEYKCKVSNKGLPSSIEKTISKAKGQPREPQVYTL
PPSQEEMTKNQVSLTCDVSGFYPSDIAVEWESDGQPENNYKTTPPVLDSDGSFFLYSRLTVDKSRWEEGDVFSCSVM
HEALHNHYTQKSLSLSLGK

>scFv-Fc Side (SEQ ID NO: 62)
ESKYGPPCPPCPAPEFLGGPSVFLFPPKPKDTLMISRTPEVTCVVVDVSQEDPEVQFNWYVDGVEVHNAKTKPREEQ
FNSTYRVVSVLTVLHQDWLNGKEYKCKVSNKGLPSSIEKTISKAKGQPREPQVYTLPPSQEQMTKNQVKLTCLVKGF
YPSDIAVEWESNGQPENNYKTTPPVLDSDGSFFLYSRLTVDKSRWQEGNVFSCSVMHEALHNHYTQKSLSLSLGK

1 + 1 Fab-scFv-Fc Backbone 9

>Fab-Fc Side (SEQ ID NO: 63)
ASTKGPSVFPLAPCSRSTSESTAALGCLVKDYFPEPVTVSWNSGALTSGVHTFPAVLQSSGLYSLSSVVTVPSSNFG
TQTYTCNVDHKPSDTKVDKTVERKCCVECPPCPAPPVAGPSVFLFPPKPKDTLMISRTPEVTCVVVDVSHEDPEVQF
NWYVDGVEVHNAKTKPREEEFNSTFRVVSVLTVVHQDWLNGKEYKCKVSNKGLPAPIEKTISKTKGQPREPQVYTLP
PSREEMTKNQVSLTCDVSGFYPSDIAVEWESDGQPENNYKTTPPMLDSDGSFFLYSKLTVDKSRWEQGDVFSCSVMH
EALHNHYTQKSLSLSPGK

>scFv-Fc Side (SEQ ID NO: 64)
ERKCCVECPPCPAPPVAGPSVFLFPPKPKDTLMISRTPEVTCVVVDVSHEDPEVQFNWYVDGVEVHNAKTKPREEQF
NSTFRVVSVLTVVHQDWLNGKEYKCKVSNKGLPAPIEKTISKTKGQPREPQVYTLPPSREQMTKNQVKLTCLVKGFY
PSDIAVEWESNGQPENNYKTTPPMLDSDGSFFLYSKLTVDKSRWQQGNVFSCSVMHEALHNHYTQKSLSLSPGK

Figure 7D

1 + 1 Fab-scFv-Fc Backbone 10

>Fab-Fc Side (SEQ ID NO: 65)
ASTKGPSVFPLAPCSRSTSESTAALGCLVKDYFPEPVTVSWNSGALTSGVHTFPAVLQSSGLYSLSSVVTVPSSNFG
TQTYTCNVDHKPSDTKVDKTVERKCCVECPPCPAPPVAGPSVFLFPPKPKDTLMISRTPEVTCVVVDVKHEDPEVQF
NWYVDGVEVHNAKTKPREEEFNSTFRVVSVLTVVHQDWLNGKEYKCKVSNKGLPAPIEKTISKTKGQPREPQVYTLP
PSREEMTKNQVSLTCDVSGFYPSDIAVEWESDGQPENNYKTTPPMLDSDGSFFLYSKLTVDKSRWEQGDVFSCSVMH
EALHNHYTQKSLSLSPGK

>scFv-Fc Side (SEQ ID NO: 66)
ERKCCVECPPCPAPPVAGPSVFLFPPKPKDTLMISRTPEVTCVVVDVKHEDPEVQFNWYVDGVEVHNAKTKPREEQF
NSTFRVVSVLTVVHQDWLNGKEYKCKVSNKGLPAPIEKTISKTKGQPREPQVYTLPPSREQMTKNQVKLTCLVKGFY
PSDIAVEWESNGQPENNYKTTPPMLDSDGSFFLYSKLTVDKSRWQQGNVFSCSVMHEALHNHYTQKSLSLSPGK

1 + 1 Fab-scFv-Fc Backbone 11

>Fab-Fc Side (SEQ ID NO: 67)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYNSTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRWEQGDVFSCS
VLHEALHSHYTQKSLSLSPGK

>scFv-Fc Side (SEQ ID NO: 68)
EPKSSDKTHTCPPCPAPPVAGPSVFLFPPKPKDTLMISRTPEVTCVVVDVKHEDPEVKFNWYVDGVEVHNAKTKPRE
EQYNSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVLHEALHSHYTQKSLSLSPGK

1 + 1 Fab-scFv-Fc Backbone 12

>Fab-Fc Side (SEQ ID NO: 69)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREEMTKNQVSLTCDVAGFYPSDIAVEWESNGQPENNYKTTPPVLDSDGSFFLYSKLTVDKSRWQQGNVFSCS
VMHEALHNHYTQKSLSLSPGK

>scFv-Fc Side (SEQ ID NO: 70)
ERKSSDKTHTCPPRPAPPVAGPSVFLFPPKPKDTLMISRTPEVTCVVVDVKHEDPEVKFKWYVDGVEVHNAKTKPRE
EQYNSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK

Figure 8A

2 + 1 Fab2-scFv-Fc Backbone 1

>Fab-Fc Side (SEQ ID NO: 71)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYNSTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRWEQGDVFSCS
VMHEALHNHYTQKSLSLSPGK

>Fab-scFv-Fc Side (SEQ ID NO: 72)
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREQMTKNQVKLTCLVKGFYPSDIAVEWESNG
QPENNYKTTPPVLDSDGSFFLYSKLTVDKSRWQQGNVFSCSVMHEALHNHYTQKSLSLSPGK

2 + 1 Fab2-scFv-Fc Backbone 2

>Fab-Fc Side (SEQ ID NO: 73)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYNSTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRWEQGDVFSCS
VMHEALHNHYTQKSLSLSPGK

>Fab-scFv-Fc Side (SEQ ID NO: 74)
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVKLTCLVKGFYPSDIAVEWESNG
QPENNYKTTPPVLDSDGSFFLYSKLTVDKSRWQQGNVFSCSVMHEALHNHYTQKSLSLSPGK

2 + 1 Fab2-scFv-Fc Backbone 3

>Fab-Fc Side (SEQ ID NO: 75)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYNSTYRVVSVLTVLHQDWLNGKEYKCKVSNKALPAPIEKTISKAKGQPREPQVY
TLPPSREEMTKNQVSLTCEVSGFYPSDIAVEWESDGQPENNYKTTPPVLDSDGSFFLYSKLTVDKSRWEQGDVFSCS
VMHEALHNHYTQKSLSLSPGK

>Fab-scFv-Fc Side (SEQ ID NO: 76)
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVKLTCLVKGFYPSDIAVEWESNG
QPENNYKTTPPVLDSDGSFFLYSKLTVDKSRWQQGNVFSCSVMHEALHNHYTQKSLSLSPGK

Figure 8B

2 + 1 Fab2-scFv-Fc Backbone 4

>Fab-Fc Side (SEQ ID NO: 77)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYNSTYRVVSVLTVLHQDWLNGKEYKCKVSNKALPAPIEKTISKAKGQPREPQVY
TLPPSREEMTENEVSLTCLVKGFYPSDIAVEWESDGQPENNYKTTPPVLDSDGSFFLYSKLEVDKSRWEQGDVFSCS
VMHEALHNHYTQKSLSLSPGK

>Fab-scFv-Fc Side (SEQ ID NO: 78)
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREEMTKNQVSLTCLVKGFYPSDIAVEWESNG
QPENNYKTTPPVLDSKGSFFLYSKLTVDKSRWQQGNVFSCSVMHEALHNHYTQKSLSLSPGK

2 + 1 Fab2-scFv-Fc Backbone 5

>Fab-Fc Side (SEQ ID NO: 79)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYNSTYRVVSVLTVLHQDWLNGKEYKCKVSNKALPAPIEKTISKAKGQPREPQVY
TLPPSRDELTKNQVSLTCDVSGFYPSDIAVEWESDGQPENNYKTTPPVLDSDGSFFLYSKLTVDKSRWEQGDVFSCS
VMHEALHNHYTQKSLSLSPGK

>Fab-scFv-Fc Side (SEQ ID NO: 80)
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSRDQLTKNQVKLTCLVKGFYPSDIAVEWESNG
QPENNYKTTPPVLDSDGSFFLYSKLTVDKSRWQQGNVFSCSVMHEALHNHYTQKSLSLSPGK

2 + 1 Fab2-scFv-Fc Backbone 6

>Fab-Fc Side (SEQ ID NO: 81)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYASTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRWEQGDVFSCS
VMHEALHNHYTQKSLSLSPGK

>Fab-scFv-Fc Side (SEQ ID NO: 82)
APPVAGPSVFLFPPKPKDTLMISRTPEVTCVVVDVKHEDPEVKFNWYVDGVEVHNAKTKPREEQYASTYRVVSVLTV
LHQDWLNGKEYKCKVSNKALPAPIEKTISKAKGQPREPQVYTLPPSREQMTKNQVKLTCLVKGFYPSDIAVEWESNG
QPENNYKTTPPVLDSDGSFFLYSKLTVDKSRWQQGNVFSCSVMHEALHNHYTQKSLSLSPGK

Figure 8C

2 + 1 Fab2-scFv-Fc Backbone 7

>Fab-Fc Side (SEQ ID NO: 83)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYSSTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRWEQGDVFSCS
VMHEALHNHYTQKSLSLSPGK

>Fab-scFv-Fc Side (SEQ ID NO: 84)
APPVAGPSVFLFPPKPKDTLMISRTPEVTCVVVDVKHEDPEVKFNWYVDGVEVHNAKTKPREEQYSSTYRVVSVLTV
LHQDWLNGKEYKCKVSNKALPAPIEKTISKAKGQPREPQVYTLPPSREQMTKNQVKLTCLVKGFYPSDIAVEWESNG
QPENNYKTTPPVLDSDGSFFLYSKLTVDKSRWQQGNVFSCSVMHEALHNHYTQKSLSLSPGK

2 + 1 Fab2-scFv-Fc Backbone 8

>Fab-Fc Side (SEQ ID NO: 85)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSDTKVDKKVEPKSCDKTHTCPPCPAPPVAGPSVFLFPPKPKDTLMISRTPEVTCVVVDVKHEDPE
VKFNWYVDGVEVHNAKTKPREEEYNSTYRVVSVLTVLHQDWLNGKEYKCKVSNKALPAPIEKTISKAKGQPREPQVY
TLPPSREEMTKNQVSLTCDVSGFYPSDIAVEWESDGQPENNYKTTPPVLDSDGSFFLYSKLTVDKSRWEQGDVFSCS
VLHEALHSHYTQKSLSLSPGK

>Fab-scFv-Fc Side (SEQ ID NO: 86)
APPVAGPSVFLFPPKPKDTLMISRTPEVTCVVVDVKHEDPEVKFNWYVDGVEVHNAKTKPREEQYNSTYRVVSVLTV
LHQDWLNGKEYKCKVSNKALPAPIEKTISKAKGQPREPQVYTLPPSREQMTKNQVKLTCLVKGFYPSDIAVEWESNG
QPENNYKTTPPVLDSDGSFFLYSKLTVDKSRWQQGNVFSCSVLHEALHSHYTQKSLSLSPGK

2 + 1 Fab2-scFv-Fc Backbone 9

>Fab-Fc Side (SEQ ID NO: 87)
ASTKGPSVFPLAPSSKSTSGGTAALGCLVKDYFPEPVTVSWNSGALTSGVHTFPAVLQSSGLYSLSSVVTVPSSSLG
TQTYICNVNHKPSNTKVDKKVEPKSCDKTHTCPPCPAPPVAGPSVFLFPPKPKDTLMISRTPEVTCVVVDVKHEDPE
VKFNWYVDGVEVHNAKTKPREEQYNSTYRVVSVLTVLHQDWLNGKEYKCKVSNKALPAPIEKTISKAKGQPREPQVY
TLPPSREEMTKNQVSLTCDVAGFYPSDIAVEWESNGQPENNYKTTPPVLDSDGSFFLYSKLTVDKSRWQQGNVFSCS
VMHEALHNHYTQKSLSLSPGK

>Fab-scFv-Fc Side (SEQ ID NO: 88)
APPVAGPSVFLFPPKPKDTLMISRTPEVTCVVVDVKHEDPEVKFKWYVDGVEVHNAKTKPREEQYNSTYRVVSVLTV
LHQDWLNGKEYKCKVSNKALPAPIEKTISKAKGQPREPQVYTLPPSREQMTKNQVKLTCLVKGFYPSDIAVEWESNG
QPENNYKTTPPVLDSDGSFFLYSKLTVDKSRWQQGNVFSCSVMHEALHNHYTQKSLSLSPGK

Figure 9

Constant Light Domain – Kappa (SEQ ID NO: 89)

RTVAAPSVFIFPPSDEQLKSGTASVVCLLNNFYPREAKVQWKVDNALQSGNSQESVTEQDSKDSTYSLSSTLTLSKADYEKHKVYACEVTHQG
LSSPVTKSFNRGEC

Constant Light Domain – Lambda (SEQ ID NO: 90)

GQPKAAPSVTLFPPSSEELQANKATLVCLISDFYPGAVTVAWKADSSPVKAGVETTTPSKQSNNKYAASSYLSLTPE
QWKSHRSYSCQVTHEGSTVEKTVAPTECS

Figure 10A

CD3 High – [anti-CD3]_H1.30_L1.47_scFv

| | Sequence | SEQ ID NO: |
|---|---|---|
| scFv | EVQLVESGGGLVQPGGSLRLSCAASGFTFSTYAMNWVRQAPGKGLEWVGRIRSK YNNYATYYADSVKGRFTISRDDSKNTLYLQMNSLRAEDTAVYYCVRHGNFGDSY VSWFAYWGQGTLVTVSS/GKPGSGKPGSGKPGSGKPGS/QAVVTQEPSLTVSPG GTVTLTCGSSTGAVTTSNYANWVQQKPGKSPRGLIGGTNKRAPGVPARFSGSLL GGKAALTISGAQPEDEADYYCALWYSNHWVFGGGTKLTVL | 91 |
| Variable Heavy (vh) Domain | EVQLVESGGGLVQPGGSLRLSCAASGFTFSTYAMNWVRQAPGKGLEWVGRIRSK YNNYATYYADSVKGRFTISRDDSKNTLYLQMNSLRAEDTAVYYCVRHGNFGDSY VSWFAYWGQGTLVTVSS | 92 |
| vhCDR1 | TYAMN | 93 |
| vhCDR2 | RIRSKYNNYATYYADSVKG | 94 |
| vhCDR3 | HGNFGDSYVSWFAY | 95 |
| Variable Light (vl) Domain | QAVVTQEPSLTVSPGGTVTLTCGSSTGAVTTSNYANWVQQKPGKSPRGLIGGTN KRAPGVPARFSGSLLGGKAALTISGAQPEDEADYYCALWYSNHWVFGGGTKLTV L | 96 |
| vlCDR1 | GSSTGAVTTSNYAN | 97 |
| vlCDR2 | GTNKRAP | 98 |
| vlCDR3 | ALWYSNHWV | 99 |
| Linker | GKPGSGKPGSGKPGSGKPGS | 100 |

CD3 High-Int #1 – [anti-CD3]_H1.32_L1.47_scFv

| | Sequence | SEQ ID NO: |
|---|---|---|
| scFv | EVQLVESGGGLVQPGGSLRLSCAASGFTFSTYAMNWVRQAPGKGLEWVGRIRSK ANNYATYYADSVKGRFTISRDDSKNTLYLQMNSLRAEDTAVYYCVRHGNFGDSY VSWFAYWGQGTLVTVSS/GKPGSGKPGSGKPGSGKPGS/QAVVTQEPSLTVSPG GTVTLTCGSSTGAVTTSNYANWVQQKPGKSPRGLIGGTNKRAPGVPARFSGSLL GGKAALTISGAQPEDEADYYCALWYSNHWVFGGGTKLTVL | 101 |
| Variable Heavy (vh) Domain | EVQLVESGGGLVQPGGSLRLSCAASGFTFSTYAMNWVRQAPGKGLEWVGRIRSK ANNYATYYADSVKGRFTISRDDSKNTLYLQMNSLRAEDTAVYYCVRHGNFGDSY VSWFAYWGQGTLVTVSS | 102 |
| vhCDR1 | TYAMN | 103 |
| vhCDR2 | RIRSKANNYATYYADSVKG | 104 |
| vhCDR3 | HGNFGDSYVSWFAY | 105 |
| Variable Light (vl) Domain | QAVVTQEPSLTVSPGGTVTLTCGSSTGAVTTSNYANWVQQKPGKSPRGLIGGTN KRAPGVPARFSGSLLGGKAALTISGAQPEDEADYYCALWYSNHWVFGGGTKLTV L | 106 |
| vlCDR1 | GSSTGAVTTSNYAN | 107 |
| vlCDR2 | GTNKRAP | 108 |
| vlCDR3 | ALWYSNHWV | 109 |
| Linker | GKPGSGKPGSGKPGSGKPGS | 110 |

Figure 10B

CD3 High-Int #2 – [anti-CD3]_H1.89_L1.47_scFv

|  | Sequence | SEQ ID NO: |
|---|---|---|
| scFv | EVQLVESGGGLVQPGGSLRLSCAASGFTFSTYAMNWVRQAPGKGLEWVGRIRSK YNNYATYYADSVKGRFTISRDDSKNTLYLQMNSLRAEDTAVYYCVRHGNFGDEY VSWFAYWGQGTLVTVSS/GKPGSGKPGSGKPGSGKPGS/QAVVTQEPSLTVSPG GTVTLTCGSSTGAVTTSNYANWVQQKPGKSPRGLIGGTNKRAPGVPARFSGSLL GGKAALTISGAQPEDEADYYCALWYSNHWVFGGGTKLTVL | 111 |
| Variable Heavy (vh) Domain | EVQLVESGGGLVQPGGSLRLSCAASGFTFSTYAMNWVRQAPGKGLEWVGRIRSK YNNYATYYADSVKGRFTISRDDSKNTLYLQMNSLRAEDTAVYYCVRHGNFGDEY VSWFAYWGQGTLVTVSS | 112 |
| vhCDR1 | TYAMN | 113 |
| vhCDR2 | RIRSKYNNYATYYADSVKG | 114 |
| vhCDR3 | HGNFGDEYVSWFAY | 115 |
| Variable Light (vl) Domain | QAVVTQEPSLTVSPGGTVTLTCGSSTGAVTTSNYANWVQQKPGKSPRGLIGGTN KRAPGVPARFSGSLLGGKAALTISGAQPEDEADYYCALWYSNHWVFGGGTKLTV L | 116 |
| vlCDR1 | GSSTGAVTTSNYAN | 117 |
| vlCDR2 | GTNKRAP | 118 |
| vlCDR3 | ALWYSNHWV | 119 |
| Linker | GKPGSGKPGSGKPGSGKPGS | 120 |

CD3 High-Int – [anti-CD3]_H1.90_L1.47_scFv

|  | Sequence | SEQ ID NO: |
|---|---|---|
| scFv | EVQLVESGGGLVQPGGSLRLSCAASGFTFSTYAMNWVRQAPGKGLEWVGRIRSK YNNYATYYADSVKGRFTISRDDSKNTLYLQMNSLRAEDTAVYYCVRHGNFGDPY VSWFAYWGQGTLVTVSS/GKPGSGKPGSGKPGSGKPGS/QAVVTQEPSLTVSPG GTVTLTCGSSTGAVTTSNYANWVQQKPGKSPRGLIGGTNKRAPGVPARFSGSLL GGKAALTISGAQPEDEADYYCALWYSNHWVFGGGTKLTVL | 121 |
| Variable Heavy (vh) Domain | EVQLVESGGGLVQPGGSLRLSCAASGFTFSTYAMNWVRQAPGKGLEWVGRIRSK YNNYATYYADSVKGRFTISRDDSKNTLYLQMNSLRAEDTAVYYCVRHGNFGDPY VSWFAYWGQGTLVTVSS | 122 |
| vhCDR1 | TYAMN | 123 |
| vhCDR2 | RIRSKYNNYATYYADSVKG | 124 |
| vhCDR3 | HGNFGDPYVSWFAY | 125 |
| Variable Light (vl) Domain | QAVVTQEPSLTVSPGGTVTLTCGSSTGAVTTSNYANWVQQKPGKSPRGLIGGTN KRAPGVPARFSGSLLGGKAALTISGAQPEDEADYYCALWYSNHWVFGGGTKLTV L | 126 |
| vlCDR1 | GSSTGAVTTSNYAN | 127 |
| vlCDR2 | GTNKRAP | 128 |
| vlCDR3 | ALWYSNHWV | 129 |
| Linker | GKPGSGKPGSGKPGSGKPGS | 130 |

Figure 10C

Anti-CD3-Intermediate – [anti-CD3]_H1.33_L1.47_scFv

| | Sequence | SEQ ID NO: |
|---|---|---|
| scFv | EVQLVESGGGLVQPGGSLRLSCAASGFTFSTYAMNWVRQAPGKGLEWVGRIRSK YNNYATYYADSVKGRFTISRDDSKNTLYLQMNSLRAEDTAVYYCVRHGNFGDSY VSWFDYWGQGTLVTVSS/GKPGSGKPGSGKPGSGKPGS/QAVVTQEPSLTVSPG GTVTLTCGSSTGAVTTSNYANWVQQKPGKSPRGLIGGTNKRAPGVPARFSGSLL GGKAALTISGAQPEDEADYYCALWYSNHWVFGGGTKLTVL | 131 |
| Variable Heavy (vh) Domain | EVQLVESGGGLVQPGGSLRLSCAASGFTFSTYAMNWVRQAPGKGLEWVGRIRSK YNNYATYYADSVKGRFTISRDDSKNTLYLQMNSLRAEDTAVYYCVRHGNFGDSY VSWFDYWGQGTLVTVSS | 132 |
| vhCDR1 | TYAMN | 133 |
| vhCDR2 | RIRSKYNNYATYYADSVKG | 134 |
| vhCDR3 | HGNFGDSYVSWFDY | 135 |
| Variable Light (vl) Domain | QAVVTQEPSLTVSPGGTVTLTCGSSTGAVTTSNYANWVQQKPGKSPRGLIGGTN KRAPGVPARFSGSLLGGKAALTISGAQPEDEADYYCALWYSNHWVFGGGTKLTV L | 136 |
| vlCDR1 | GSSTGAVTTSNYAN | 137 |
| vlCDR2 | GTNKRAP | 138 |
| vlCDR3 | ALWYSNHWV | 139 |
| Linker | GKPGSGKPGSGKPGSGKPGS | 140 |

CD3 High-Int – [anti-CD3]_H1.31_L1.47_scFv

| | Sequence | SEQ ID NO: |
|---|---|---|
| scFv | EVQLVESGGGLVQPGGSLRLSCAASGFTFSTYAMSWVRQAPGKGLEWVGRIRSK YNNYATYYADSVKGRFTISRDDSKNTLYLQMNSLRAEDTAVYYCVRHGNFGDSY VSWFAYWGQGTLVTVSS/GKPGSGKPGSGKPGSGKPGS/QAVVTQEPSLTVSPG GTVTLTCGSSTGAVTTSNYANWVQQKPGKSPRGLIGGTNKRAPGVPARFSGSLL GGKAALTISGAQPEDEADYYCALWYSNHWVFGGGTKLTVL | 141 |
| Variable Heavy (vh) Domain | EVQLVESGGGLVQPGGSLRLSCAASGFTFSTYAMSWVRQAPGKGLEWVGRIRSK YNNYATYYADSVKGRFTISRDDSKNTLYLQMNSLRAEDTAVYYCVRHGNFGDSY VSWFAYWGQGTLVTVSS | 142 |
| vhCDR1 | TYAMS | 143 |
| vhCDR2 | RIRSKYNNYATYYADSVKG | 144 |
| vhCDR3 | HGNFGDSYVSWFAY | 145 |
| Variable Light (vl) Domain | QAVVTQEPSLTVSPGGTVTLTCGSSTGAVTTSNYANWVQQKPGKSPRGLIGGTN KRAPGVPARFSGSLLGGKAALTISGAQPEDEADYYCALWYSNHWVFGGGTKLTV L | 146 |
| vlCDR1 | GSSTGAVTTSNYAN | 147 |
| vlCDR2 | GTNKRAP | 148 |
| vlCDR3 | ALWYSNHWV | 149 |
| Linker | GKPGSGKPGSGKPGSGKPGS | 150 |

Figure 10D

CD3 High[VL-VH] – [anti-CD3]_L1.47_H1.30_scFv

|  | Sequence | SEQ ID NO: |
|---|---|---|
| scFv | QAVVTQEPSLTVSPGGTVTLTCGSSTGAVTTSNYANWVQQKPGKSPRGLIGGTN KRAPGVPARFSGSLLGGKAALTISGAQPEDEADYYCALWYSNHWVFGGGTKLTV L/GKPGSGKPGSGKPGSGKPGS/EVQLVESGGGLVQPGGSLRLSCAASGFTFST YAMNWVRQAPGKGLEWVGRIRSKYNNYATYYADSVKGRFTISRDDSKNTLYLQM NSLRAEDTAVYYCVRHGNFGDSYVSWFAYWGQGTLVTVSS | 151 |
| Variable Light (vl) Domain | QAVVTQEPSLTVSPGGTVTLTCGSSTGAVTTSNYANWVQQKPGKSPRGLIGGTN KRAPGVPARFSGSLLGGKAALTISGAQPEDEADYYCALWYSNHWVFGGGTKLTV L | 152 |
| vlCDR1 | GSSTGAVTTSNYAN | 153 |
| vlCDR2 | GTNKRAP | 154 |
| vlCDR3 | ALWYSNHWV | 155 |
| Variable Heavy (vh) Domain | EVQLVESGGGLVQPGGSLRLSCAASGFTFSTYAMNWVRQAPGKGLEWVGRIRSK YNNYATYYADSVKGRFTISRDDSKNTLYLQMNSLRAEDTAVYYCVRHGNFGDSY VSWFAYWGQGTLVTVSS | 156 |
| vhCDR1 | TYAMN | 157 |
| vhCDR2 | RIRSKYNNYATYYADSVKG | 158 |
| vhCDR3 | HGNFGDSYVSWFAY | 159 |
| Linker | GKPGSGKPGSGKPGSGKPGS | 160 |

CD3 High-Int #1[VL-VH] – [anti-CD3]_L1.47_H1.32_scFv

|  | Sequence | SEQ ID NO: |
|---|---|---|
| scFv | QAVVTQEPSLTVSPGGTVTLTCGSSTGAVTTSNYANWVQQKPGKSPRGLIGGTN KRAPGVPARFSGSLLGGKAALTISGAQPEDEADYYCALWYSNHWVFGGGTKLTV L/GKPGSGKPGSGKPGSGKPGS/EVQLVESGGGLVQPGGSLRLSCAASGFTFST YAMNWVRQAPGKGLEWVGRIRSKANNYATYYADSVKGRFTISRDDSKNTLYLQM NSLRAEDTAVYYCVRHGNFGDSYVSWFAYWGQGTLVTVSS | 161 |
| Variable Light (vl) Domain | QAVVTQEPSLTVSPGGTVTLTCGSSTGAVTTSNYANWVQQKPGKSPRGLIGGTN KRAPGVPARFSGSLLGGKAALTISGAQPEDEADYYCALWYSNHWVFGGGTKLTV L | 162 |
| vlCDR1 | GSSTGAVTTSNYAN | 163 |
| vlCDR2 | GTNKRAP | 164 |
| vlCDR3 | ALWYSNHWV | 165 |
| Variable Heavy (vh) Domain | EVQLVESGGGLVQPGGSLRLSCAASGFTFSTYAMNWVRQAPGKGLEWVGRIRSK ANNYATYYADSVKGRFTISRDDSKNTLYLQMNSLRAEDTAVYYCVRHGNFGDSY VSWFAYWGQGTLVTVSS | 166 |
| vhCDR1 | TYAMN | 167 |
| vhCDR2 | RIRSKANNYATYYADSVKG | 168 |
| vhCDR3 | HGNFGDSYVSWFAY | 169 |
| Linker | GKPGSGKPGSGKPGSGKPGS | 170 |

Figure 10E

CD3 High-Int #2[VL-VH] – [anti-CD3]_L1.47_H1.89_scFv

|  | Sequence | SEQ ID NO: |
|---|---|---|
| scFv | QAVVTQEPSLTVSPGGTVTLTCGSSTGAVTTSNYANWVQQKPGKSPRGLIGGTN KRAPGVPARFSGSLLGGKAALTISGAQPEDEADYYCALWYSNHWVFGGGTKLTV L/GKPGSGKPGSGKPGSGKPGS/EVQLVESGGGLVQPGGSLRLSCAASGFTFST YAMNWVRQAPGKGLEWVGRIRSKYNNYATYYADSVKGRFTISRDDSKNTLYLQM NSLRAEDTAVYYCVRHGNFGDEYVSWFAYWGQGTLVTVSS | 171 |
| Variable Light (vl) Domain | QAVVTQEPSLTVSPGGTVTLTCGSSTGAVTTSNYANWVQQKPGKSPRGLIGGTN KRAPGVPARFSGSLLGGKAALTISGAQPEDEADYYCALWYSNHWVFGGGTKLTV L | 172 |
| vlCDR1 | GSSTGAVTTSNYAN | 173 |
| vlCDR2 | GTNKRAP | 174 |
| vlCDR3 | ALWYSNHWV | 175 |
| Variable Heavy (vh) Domain | EVQLVESGGGLVQPGGSLRLSCAASGFTFSTYAMNWVRQAPGKGLEWVGRIRSK YNNYATYYADSVKGRFTISRDDSKNTLYLQMNSLRAEDTAVYYCVRHGNFGDEY VSWFAYWGQGTLVTVSS | 176 |
| vhCDR1 | TYAMN | 177 |
| vhCDR2 | RIRSKYNNYATYYADSVKG | 178 |
| vhCDR3 | HGNFGDEYVSWFAY | 179 |
| Linker | GKPGSGKPGSGKPGSGKPGS | 180 |

CD3 High-Int[VL-VH] – [anti-CD3]_L1.47_H1.90_scFv

|  | Sequence | SEQ ID NO: |
|---|---|---|
| scFv | QAVVTQEPSLTVSPGGTVTLTCGSSTGAVTTSNYANWVQQKPGKSPRGLIGGTN KRAPGVPARFSGSLLGGKAALTISGAQPEDEADYYCALWYSNHWVFGGGTKLTV L/GKPGSGKPGSGKPGSGKPGS/EVQLVESGGGLVQPGGSLRLSCAASGFTFST YAMNWVRQAPGKGLEWVGRIRSKYNNYATYYADSVKGRFTISRDDSKNTLYLQM NSLRAEDTAVYYCVRHGNFGDPYVSWFAYWGQGTLVTVSS | 181 |
| Variable Light (vl) Domain | QAVVTQEPSLTVSPGGTVTLTCGSSTGAVTTSNYANWVQQKPGKSPRGLIGGTN KRAPGVPARFSGSLLGGKAALTISGAQPEDEADYYCALWYSNHWVFGGGTKLTV L | 182 |
| vlCDR1 | GSSTGAVTTSNYAN | 183 |
| vlCDR2 | GTNKRAP | 184 |
| vlCDR3 | ALWYSNHWV | 185 |
| Variable Heavy (vh) Domain | EVQLVESGGGLVQPGGSLRLSCAASGFTFSTYAMNWVRQAPGKGLEWVGRIRSK YNNYATYYADSVKGRFTISRDDSKNTLYLQMNSLRAEDTAVYYCVRHGNFGDPY VSWFAYWGQGTLVTVSS | 186 |
| vhCDR1 | TYAMN | 187 |
| vhCDR2 | RIRSKYNNYATYYADSVKG | 188 |
| vhCDR3 | HGNFGDPYVSWFAY | 189 |
| Linker | GKPGSGKPGSGKPGSGKPGS | 190 |

Figure 10F

Anti-CD3-Intermediate[VL-VH] – [anti-CD3]_L1.47__H1.33_scFv

| | Sequence | SEQ ID NO: |
|---|---|---|
| scFv | QAVVTQEPSLTVSPGGTVTLTCGSSTGAVTTSNYANWVQQKPGKSPRGLIGGTN KRAPGVPARFSGSLLGGKAALTISGAQPEDEADYYCALWYSNHWVFGGGTKLTV L/GKPGSGKPGSGKPGSGKPGS/EVQLVESGGGLVQPGGSLRLSCAASGFTFST YAMNWVRQAPGKGLEWVGRIRSKYNNYATYYADSVKGRFTISRDDSKNTLYLQM NSLRAEDTAVYYCVRHGNFGDSYVSWFDYWGQGTLVTVSS | 191 |
| Variable Light (vl) Domain | QAVVTQEPSLTVSPGGTVTLTCGSSTGAVTTSNYANWVQQKPGKSPRGLIGGTN KRAPGVPARFSGSLLGGKAALTISGAQPEDEADYYCALWYSNHWVFGGGTKLTV L | 192 |
| vlCDR1 | GSSTGAVTTSNYAN | 193 |
| vlCDR2 | GTNKRAP | 194 |
| vlCDR3 | ALWYSNHWV | 195 |
| Variable Heavy (vh) Domain | EVQLVESGGGLVQPGGSLRLSCAASGFTFSTYAMNWVRQAPGKGLEWVGRIRSK YNNYATYYADSVKGRFTISRDDSKNTLYLQMNSLRAEDTAVYYCVRHGNFGDSY VSWFDYWGQGTLVTVSS | 196 |
| vhCDR1 | TYAMN | 197 |
| vhCDR2 | RIRSKYNNYATYYADSVKG | 198 |
| vhCDR3 | HGNFGDSYVSWFDY | 199 |
| Linker | GKPGSGKPGSGKPGSGKPGS | 200 |

CD3 High-Int[VL-VH] – [anti-CD3]_L1.47__H1.31_scFv

| | Sequence | SEQ ID NO: |
|---|---|---|
| scFv | QAVVTQEPSLTVSPGGTVTLTCGSSTGAVTTSNYANWVQQKPGKSPRGLIGGTN KRAPGVPARFSGSLLGGKAALTISGAQPEDEADYYCALWYSNHWVFGGGTKLTV L/GKPGSGKPGSGKPGSGKPGS/EVQLVESGGGLVQPGGSLRLSCAASGFTFST YAMSWVRQAPGKGLEWVGRIRSKYNNYATYYADSVKGRFTISRDDSKNTLYLQM NSLRAEDTAVYYCVRHGNFGDSYVSWFAYWGQGTLVTVSS | 201 |
| Variable Light (vl) Domain | QAVVTQEPSLTVSPGGTVTLTCGSSTGAVTTSNYANWVQQKPGKSPRGLIGGTN KRAPGVPARFSGSLLGGKAALTISGAQPEDEADYYCALWYSNHWVFGGGTKLTV L | 202 |
| vlCDR1 | GSSTGAVTTSNYAN | 203 |
| vlCDR2 | GTNKRAP | 204 |
| vlCDR3 | ALWYSNHWV | 205 |
| Variable Heavy (vh) Domain | EVQLVESGGGLVQPGGSLRLSCAASGFTFSTYAMSWVRQAPGKGLEWVGRIRSK YNNYATYYADSVKGRFTISRDDSKNTLYLQMNSLRAEDTAVYYCVRHGNFGDSY VSWFAYWGQGTLVTVSS | 206 |
| vhCDR1 | TYAMS | 207 |
| vhCDR2 | RIRSKYNNYATYYADSVKG | 208 |
| vhCDR3 | HGNFGDSYVSWFAY | 209 |
| Linker | GKPGSGKPGSGKPGSGKPGS | 210 |

Figure 12

| | | PREVALENCE | | |
| | | Score 3 | Score 2 | Score 1 |
| | (n) | % (n) | % (n) | % (n) |
| SEROUS ADENOCARCINOMA (MAJORITY OF THE SEGMENT) | 154 | 52% (80) | 29% (45) | 19% (29) |
| MUCINOUS ADENOCARCINOMA (MINORITY OF THE SEGMENT) | 33 | 12% (4) | 18% (6) | 70% (23) |
| ADENOCARCINOMA | 4 | 25% (1) | 50% (2) | 25% (1) |
| TOTAL CORES | 191 | | | |

Figure 13

| | | IHC | | | FACS |
|---|---|---|---|---|---|
| Represent Cancer With High and Medium Expression Score by IHC | OVCAR8 | | SCORE 3 | ~89.8K Surface MSLN | ISOTYPE |
| | ASPC1 | | SCORE 2 | ~36.7K Surface MSLN | |
| Represents Normal Tissue | SKOV3 | | | ~8.9K Surface MSLN | |
| | HT29 | | | ~6.5K Surface MSLN | |
| | MCF7 | | | ~1.8K Surface MSLN | |
| | A549 | | | ~1.1K Surface MSLN | |
| | Huh7 | | | Low Surface MSLN | |

Figure 14A

Human MSLN sequence

>sp|O14638

MESTLTLATEQPVKKNTLKKYKIACIVLLALLVIMSLGLGLGLGLRKLEKQGSCRKKCFDASFRGLENCRCDVACKD
RGDCCWDFEDTCVESTRIWMCNKFRCGETRLEASLCSCSDDCLQRKDCCADYKSVCQGETSWLEENCDTAQQSQCPE
GFDLPPVILFSMDGFRAEYLYTWDTLMPNINKLKTCGIHSKYMRAMYPTKTFPNHYTIVTGLYPESHGIIDNNMYDV
NLNKNFSLSSKEQNNPAWWHGQPMWLTAMYQGLKAATYFWPGSEVAINGSFPSIYMPYNGSVPFEERISTLLKWLDL
PKAERPRFYTMYFEEPDSSGHAGGPVSARVIKALQVVDHAFGMLMEGLKQRNLHNCVNIILLADHGMDQTYCNKMEY
MTDYFPRINFFYMYEGPAPRIRAHNIPHDFFSFNSEEIVRNLSCRKPDQHFKPYLTPDLPKRLHYAKNVRIDKVHLF
VDQQWLAVRSKSNTNCGGGNHGYNNEFRSMEAIFLAHGPSFKEKTEVEPFENIEVYNLMCDLLRIQPAPNNGTHGSL
NHLLKVPFYEPSHAEEVSKFSVCGFANPLPTESLDCFCPHLQNSTQLEQVNQMLNLTQEEITATVKVNLPFGRPRVL
QKNVDHCLLYHREYVSGFGKAMRMPMWSSYTVPQLGDTSPLPPTVPDCLRADVRVPPSESQKCSFYLADKNITHGFL
YPPPASNRTSDSQYDALITSNLVPMYEEFRKMWDYFHSVLLIKHATERNGVNVVSGPIFDYNYDGHFDAPDEITKHLA
NTDVPIPTHYFVVLTSCKNKSHTPENCPGWLDVLPFIIPHRPTNVESCPEGKPEALWVEERFTAHIARVRDVELLTG
LDFYQDKVQPVSEILQLKTYLPTFETTI (SEQ ID NO: 211)

Human MSLN sequence, extracellular domain

>sp|O14638|31-875

LLVIMSLGLGLGLGLRKLEKQGSCRKKCFDASFRGLENCRCDVACKDRGDCCWDFEDTCVESTRIWMCNKFRCGETR
LEASLCSCSDDCLQRKDCCADYKSVCQGETSWLEENCDTAQQSQCPEGFDLPPVILFSMDGFRAEYLYTWDTLMPNI
NKLKTCGIHSKYMRAMYPTKTFPNHYTIVTGLYPESHGIIDNNMYDVNLNKNFSLSSKEQNNPAWWHGQPMWLTAMY
QGLKAATYFWPGSEVAINGSFPSIYMPYNGSVPFEERISTLLKWLDLPKAERPRFYTMYFEEPDSSGHAGGPVSARV
IKALQVVDHAFGMLMEGLKQRNLHNCVNIILLADHGMDQTYCNKMEYMTDYFPRINFFYMYEGPAPRIRAHNIPHDF
FSFNSEEIVRNLSCRKPDQHFKPYLTPDLPKRLHYAKNVRIDKVHLFVDQQWLAVRSKSNTNCGGGNHGYNNEFRSM
EAIFLAHGPSFKEKTEVEPFENIEVYNLMCDLLRIQPAPNNGTHGSLNHLLKVPFYEPSHAEEVSKFSVCGFANPLP
TESLDCFCPHLQNSTQLEQVNQMLNLTQEEITATVKVNLPFGRPRVLQKNVDHCLLYHREYVSGFGKAMRMPMWSSY
TVPQLGDTSPLPPTVPDCLRADVRVPPSESQKCSFYLADKNITHGFLYPPASNRTSDSQYDALITSNLVPMYEEFRK
MWDYFHSVLLIKHATERNGVNVVSGPIFDYNYDGHFDAPDEITKHLANTDVPIPTHYFVVLTSCKNKSHTPENCPGW
LDVLPFIIPHRPTNVESCPEGKPEALWVEERFTAHIARVRDVELLTGLDFYQDKVQPVSEILQLKTYLPTFETTI
(SEQ ID NO: 212)

Mouse MSLN sequence

>sp|Q6DYE8

MDSRLALATEEPIKKDSLKKYKILCVVLLALLVIVSLGLGLGLGLRKPEEQGSCRKKCFDSSHRGLEGCRCDSGCTG
RGDCCWDFEDTCVKSTQIWTCNLFRCGENRLETALCSCADDCLQRKDCCADYKTVCQGESPWVTEACASSQEPQCPP
GFDLPPVILFSMDGFRAEYLQTWSTLLPNINKLKTCGIHSKYMRAMYPTKTFPNHYTIVTGLYPESHGIIDNNMYDV
HLNKNFSLSSVEKSNPAWWSGQPIWLTAMYQGLKAACYYWPGSDVAVNGSFPTIYRNYSNSVPYERRITTLLQWLDL
PKADRPSFYTIYVEEPDSAGHSSGPVSAGVIKALQSVDNAFGMLMEGLKQRNLHNCVNIIVLADHGMDQTSCDRVEY
MTDYFPKINFYMYQGPAPRIRTRNIPQDFFTFNSEEIVRNLSCRKPDQHFKPYLTPDLPKRLHYAKNVRIDKAHLMV
DRQWLAFRSKGSSNCGGGTHGYNNEFKSMEAIFLAHGPSFIEKTVIEPFENIEVYNLLCDLLHIEPAPNNGTHGSLN
HLLKTPFYKPSHAGELSTPADCGFTTPLPTDPLDCSCPALQNTPGLEEQANQRLNLSEGEVAATVKANLPFGRPRVM
QKNGDHCLLYHRDYISGYGKAMKMPMWSSYTVLKPGDTSSLPPTVPDCLRADVRVAPSESQKCSFYLADKNITHGFL
YPAIKGTNESRYDALITSNLVPMYEFKKMWDYFHEVLLIKYAIERNGLNVVSGPIFDYNYDGHFDAPDEITQYVAG
TDVPIPTHYFVVLTSCKDQTHTPDSCPGWLDVLPFIVPHRPTNIESCSENKTEDLWVEERFQAHAARVRDVELLTGL
DFYQEKAQPVSQILQLKTYLPTFETII (SEQ ID NO: 213)

Figure 14B

Mouse MSLN sequence, extracellular domain

>sp|Q6DYE8|31-874

LLVIVSLGLGLGLGLRKPEEQGSCRKKCFDSSHRGLEGCRCDSGCTGRGDCCWDFEDTCVKSTQIWTCNLFRCGENR
LETALCSCADDCLQRKDCCADYKTVCQGESPWVTEACASSQEPQCPPGFDLPPVILFSMDGFRAEYLQTWSTLLPNI
NKLKTCGIHSKYMRAMYPTKTFPNHYTIVTGLYPESHGIIDNNMYDVHLNKNFSLSSVEKSNPAWWSGQPIWLTAMY
QGLKAACYYWPGSDVAVNGSFPTIYRNYSNSVPYERRITTLLQWLDLPKADRPSFYTIYVEEPDSAGHSSGPVSAGV
IKALQSVDNAFGMLMEGLKQRNLHNCVNIIVLADHGMDQTSCDRVEYMTDYFPKINFYMYQGPAPRIRTRNIPQDFF
TFNSEEIVRNLSCRKPDQHFKPYLTPDLPKRLHYAKNVRIDKAHLMVDRQWLAFRSKGSSNCGGGTHGYNNEFKSME
AIFLAHGPSFIEKTVIEPFENIEVYNLLCDLLHIEPAPNNGTHGSLNHLLKTPFYKPSHAGELSTPADCGFTTPLPT
DPLDCSCPALQNTPGLEEQANQRLNLSEGEVAATVKANLPFGRPRVMQKNGDHCLLYHRDYISGYGKAMKMPMWSSY
TVLKPGDTSSLPPTVPDCLRADVRVAPSESQKCSFYLADKNITHGFLYPAIKGTNESRYDALITSNLVPMYKEFKKM
WDYFHEVLLIKYAIERNGLNVVSGPIFDYNYDGHFDAPDEITQYVAGTDVPIPTHYFVVLTSCKDQTHTPDSCPGWL
DVLPFIVPHRPTNIESCSENKTEDLWVEERFQAHAARVRDVELLTGLDFYQEKAQPVSQILQLKTYLPTFETII
(SEQ ID NO: 214)

Macaca fascicularis MSLN sequence

>tr|A0A2K5TKP4

MESMLTLATEQPVKKNTLKKYKIACIVLLALLVIMSLGLGLGLGLRKLEKQGSCRKKCFDASFRGLENCRCDVACED
RGDCCWDFEDTCVESTRIWTCNKFRCGETRLEASLCSCSDDCLQRKDCCADYKSVCQGETSWLEENCDTAQQSQCPE
GFDLPPVILFSMDGFRAEYLYTWDTLMPNINKLKTCGIHSKYMRAMYPTKTFPNHYTIVTGLYPESHGIIDNNMYDV
NLNKNFSLSSEEQNNPAWWHGQPMWLTAMYQGLKAATYFWPGSEVAINGSFPSIYMPYNRSVPYEERISTLLKWLDL
PKAERPSFYTMYFEEPDSSGHAGGPVSARVIKALQVVDHAFGMLMEGLKQRNLHNCVNIILLADHGMDQTYCNKMEY
MTDYFPRINFYMYEGPAPRIRALNVPHDFFSCKYEDTYMKKRCRKPDQHFKPYLTPDLPKRLHYAKNVRIDKVHLFV
DRQWLAVGSKSNTNCGGGNHGYNNEFRSMEAIFLAHGPSFKEKTEVEPFENIEVYNLMCDLLRIQPAPNNGTRGSLN
HLLKVPFYEPSHAEEVSKFSVCGFANPLPTNNLSCLCPHLQNSIQLEQVNQMLNLTQEEITATVKVNLPFGRPRVLQ
KNVDNCLLYHREYVSGFGKAMRMPMWSSYTVPQLGDTSPLPPTVPDCLRADVRVPPSESQKCSFYLADENITHGFLY
PPAINRTSDSQYDALIMSNLVPMYEEFRKMWDYFHSVLLIKHATERNGVNVVSGPIFDYNYDGHFDAPEEITKHIAN
TDIPIPTHYFVVLTSCKNKSHTPENCPGWLDVLPFIIPHRPTNVESCPEGKPEALWVEERFTAHIARVRDVELLTGL
DFYQDKAQPVSEILQLKTYLPTFETTI (SEQ ID NO: 215)

Macaca fascicularis PD-1 sequence, extracellular domain (predicted)

>tr|A0A2K5TKP4|31-874

LLVIMSLGLGLGLGLRKLEKQGSCRKKCFDASFRGLENCRCDVACEDRGDCCWDFEDTCVESTRIWTCNKFRCGETR
LEASLCSCSDDCLQRKDCCADYKSVCQGETSWLEENCDTAQQSQCPEGFDLPPVILFSMDGFRAEYLYTWDTLMPNI
NKLKTCGIHSKYMRAMYPTKTFPNHYTIVTGLYPESHGIIDNNMYDVNLNKNFSLSSEEQNNPAWWHGQPMWLTAMY
QGLKAATYFWPGSEVAINGSFPSIYMPYNRSVPYEERISTLLKWLDLPKAERPSFYTMYFEEPDSSGHAGGPVSARV
IKALQVVDHAFGMLMEGLKQRNLHNCVNIILLADHGMDQTYCNKMEYMTDYFPRINFYMYEGPAPRIRALNVPHDFF
SCKYEDTYMKKRCRKPDQHFKPYLTPDLPKRLHYAKNVRIDKVHLFVDRQWLAVGSKSNTNCGGGNHGYNNEFRSME
AIFLAHGPSFKEKTEVEPFENIEVYNLMCDLLRIQPAPNNGTRGSLNHLLKVPFYEPSHAEEVSKFSVCGFANPLPT
NNLSCLCPHLQNSIQLEQVNQMLNLTQEEITATVKVNLPFGRPRVLQKNVDNCLLYHREYVSGFGKAMRMPMWSSYT
VPQLGDTSPLPPTVPDCLRADVRVPPSESQKCSFYLADENITHGFLYPPAINRTSDSQYDALIMSNLVPMYEEFRKM
WDYFHSVLLIKHATERNGVNVVSGPIFDYNYDGHFDAPEEITKHIANTDIPIPTHYFVVLTSCKNKSHTPENCPGWL
DVLPFIIPHRPTNVESCPEGKPEALWVEERFTAHIARVRDVELLTGLDFYQDKAQPVSEILQLKTYLPTFETTI
(SEQ ID NO: 216)

Figure 15A

MESO-A[MSLN]_H1.1_L1

| | sequence | SEQ ID NO: |
|---|---|---|
| Variable heavy (vh) domain | EVQLVESGGGLVQPGGSLKLSCAASGFDFSRYWMSWVRQAPGKGLEW VSEINPDSSTIVYTPSVKGRFTISRDNAKNSLYLQMNSLRAEDTAVY YCARRGSHYYGYRTGYFDVWGAGTTVTVSS | 217 |
| vhCDR1 | RYWMS | 218 |
| vhCDR2 | EINPDSSTIVYTPSVKG | 219 |
| vhCDR3 | RGSHYYGYRTGYFDV | 220 |
| Variable light (vl) domain | DVVLTQSPATLSLSPGERATLSCRASSSVSYMYWHQQKPDQSPKLLI YDTSNLASGVPVRFSGSGSGTDYTLTISSLEPEDFAVYYCQQWSSYP PTFGGGTKLEIK | 221 |
| vlCDR1 | RASSSVSYMY | 222 |
| vlCDR2 | DTSNLAS | 223 |
| vlCDR3 | QQWSSYPPT | 224 |

>XENP16249 MESO-A[MSLN]_H1.1_L1_IgG1

Chain 1 - MESO-A[MSLN]_H1.1_IgG1 Heavy Chain
EVQLVESGGGLVQPGGSLKLSCAASGFDFSRYWMSWVRQAPGKGLEWVSEINPDSSTIVYTPSVKGRFTISRDNAKN
SLYLQMNSLRAEDTAVYYCARRGSHYYGYRTGYFDVWGAGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKKVEPKSCDKT
HTCPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSLTCLVKGFYPSDI
AVEWESNGQPENNYKTTPPVLDSDGSFFLYSKLTVDKSRWQQGNVFSCSVMHEALHNHYTQKSLSLSPGK (SEQ
ID NO: 225)

Chain 2 - MESO-A[MSLN]_L1 Light Chain
DVVLTQSPATLSLSPGERATLSCRASSSVSYMYWHQQKPDQSPKLLIYDTSNLASGVPVRFSGSGSGTDYTLTISSL
EPEDFAVYYCQQWSSYPPTFGGGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC (SEQ ID NO: 226)

>XENP16250 MESO-A[MSLN]_H1.1_L1_IgG1_PVA_/S267K

Chain 1 - MESO-A[MSLN]_H1.1_IgG1_PVA_/S267K Heavy Chain
EVQLVESGGGLVQPGGSLKLSCAASGFDFSRYWMSWVRQAPGKGLEWVSEINPDSSTIVYTPSVKGRFTISRDNAKN
SLYLQMNSLRAEDTAVYYCARRGSHYYGYRTGYFDVWGAGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKKVEPKSCDKT
HTCPPCPAPPVAGPSVFLFPPKPKDTLMISRTPEVTCVVVDVKHEDPEVKFNWYVDGVEVHNAKTKPREEQYNSTYR
VVSVLTVLHQDWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSPGK (SEQ ID
NO: 227)

Chain 2 - MESO-A[MSLN]_L1 Light Chain
DVVLTQSPATLSLSPGERATLSCRASSSVSYMYWHQQKPDQSPKLLIYDTSNLASGVPVRFSGSGSGTDYTLTISSL
EPEDFAVYYCQQWSSYPPTFGGGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC (SEQ ID NO: 228)

Figure 15B

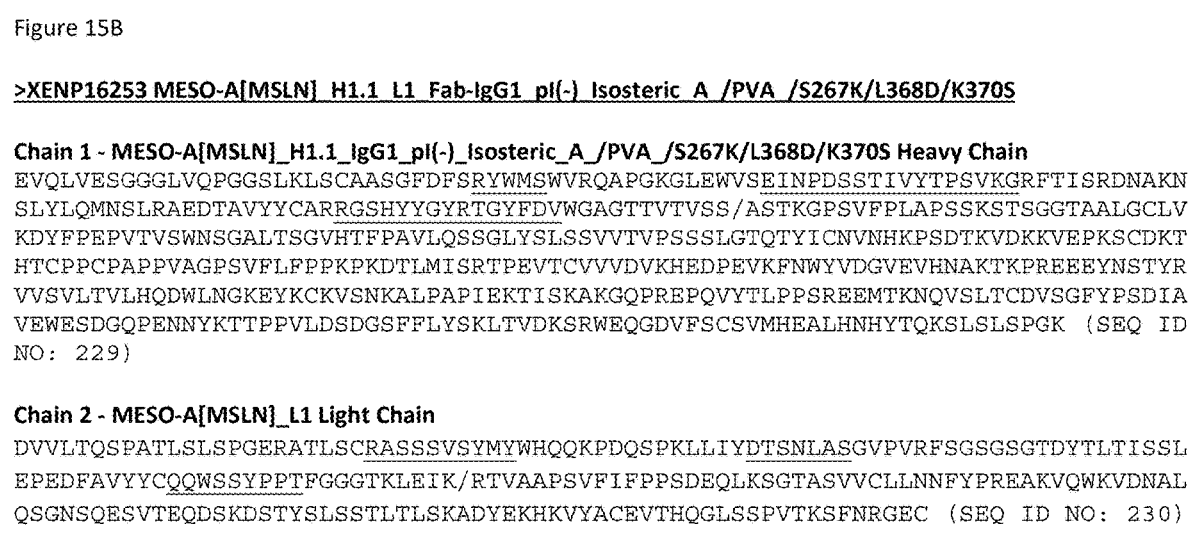

>XENP16253 MESO-A[MSLN]_H1.1_L1_Fab-IgG1_pI(-)_Isosteric_A_/PVA_/S267K/L368D/K370S Chain 1 - MESO-A[MSLN]_H1.1_IgG1_pI(-)_Isosteric_A_/PVA_/S267K/L368D/K370S Heavy Chain EVQLVESGGGLVQPGGSLKLSCAASGFDFSRYWMSWVRQAPGKGLEWVSEINPDSSTIVYTPSVKGRFTISRDNAKN
SLYLQMNSLRAEDTAVYYCARRGSHYYGYRTGYFDVWGAGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSDTKVDKKVEPKSCDKT
HTCPPCPAPPVAGPSVFLFPPKPKDTLMISRTPEVTCVVVDVKHEDPEVKFNWYVDGVEVHNAKTKPREEEYNSTYR
VVSVLTVLHQDWLNGKEYKCKVSNKALPAPIEKTISKAKGQPREPQVYTLPPSREEMTKNQVSLTCDVSGFYPSDIA
VEWESDGQPENNYKTTPPVLDSDGSFFLYSKLTVDKSRWEQGDVFSCSVMHEALHNHYTQKSLSLSPGK (SEQ ID
NO: 229)

Chain 2 - MESO-A[MSLN]_L1 Light Chain

DVVLTQSPATLSLSPGERATLSCRASSSVSYMYWHQQKPDQSPKLLIYDTSNLASGVPVRFSGSGSGTDYTLTISSL
EPEDFAVYYCQQWSSYPPTFGGGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC (SEQ ID NO: 230)

Figure 16

MESO-B[MSLN]_H0L0

|  | sequence | SEQ ID NO: |
|---|---|---|
| Variable heavy (vh) domain | QVQLQQSGPGLVTPSQTLSLTCAISGDSVSSNSATWNWIRQSPSRGL EWLGRTYYRSKWYNDYAVSVKSRMSINPDTSKNQFSLQLNSVTPEDT AVYYCARGMMTYYYGMDVWGQGTTVTVSS | 231 |
| vhCDR1 | SNSATWN | 232 |
| vhCDR2 | RTYYRSKWYNDYAVSVKS | 233 |
| vhCDR3 | GMMTYYYGMDV | 234 |
| Variable light (vl) domain | QPVLTQSSSLSASPGASASLTCTLRSGINVGPYRIYWYQQKPGSPPQ YLLNYKSDSDKQQGSGVPSRFSGSKDASANAGVLLISGLRSEDEADY YCMIWHSSAAVFGGGTQLTVL | 235 |
| vlCDR1 | TLRSGINVGPYRIY | 236 |
| vlCDR2 | SDKQQGS | 237 |
| vlCDR3 | MIWHSSAAV | 238 |

>XENP16827 MESO-B[MSLN]_H0L0_IgG1

Chain 1 - MESO-B[MSLN]_H0_IgG1 Heavy Chain
QVQLQQSGPGLVTPSQTLSLTCAISGDSVSSNSATWNWIRQSPSRGLEWLGRTYYRSKWYNDYAVSVKSRMSINPDT
SKNQFSLQLNSVTPEDTAVYYCARGMMTYYYGMDVWGQGTTVTVSS/ASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEMTKNQVSLTCLVKGFYPSDIA
VEWESNGQPENNYKTTPPVLDSDGSFFLYSKLTVDKSRWQQGNVFSCSVMHEALHNHYTQKSLSLSPGK (SEQ ID
NO: 239)

Chain 2 - MESO-B[MSLN]_L0 Light Chain
QPVLTQSSSLSASPGASASLTCTLRSGINVGPYRIYWYQQKPGSPPQYLLNYKSDSDKQQGSGVPSRFSGSKDASAN
AGVLLISGLRSEDEADYYCMIWHSSAAVFGGGTQLTVL/GQPKAAPSVTLFPPSSEELQANKATLVCLISDFYPGAV
TVAWKADSSPVKAGVETTTPSKQSNNKYAASSYLSLTPEQWKSHRSYSCQVTHEGSTVEKTVAPTECS (SEQ ID
NO: 240)

Figure 17

MESO-C[MSLN]_H1L1

|  | sequence | SEQ ID NO: |
|---|---|---|
| Variable heavy (vh) domain | QVQLVQSGAEVKKPGASVKVSCKASGYTFTSYWMHWVRQAPGQGLEW MGMIHPNSDNTIYYEKFQGRVTMTVDKSISTAYMELSRLRSDDTAVY YCAIIITPVVPKFDYWGQGTLVTVSS | 241 |
| vhCDR1 | SYWMH | 242 |
| vhCDR2 | MIHPNSDNTIYYEKFQG | 243 |
| vhCDR3 | IIITPVVPKFDY | 244 |
| Variable light (vl) domain | DIVMTQSPDSLAVSLGERATINCKASHDVGTSVAWYQQKPGQSPKLL IYWASTRHTGVPDRFTGSGSGTDFTLTISSLQAEDVAVYFCQQYSSY PLTFGAGTKLEIK | 245 |
| vlCDR1 | KASHDVGTSVA | 246 |
| vlCDR2 | WASTRHT | 247 |
| vlCDR3 | QQYSSYPLT | 248 |

>XENP31693 MESO-C[MSLN]_H1L1_IgG1_PVA_/S267K

Chain 1 - MESO-C[MSLN]_H1_IgG1_PVA_/S267K Heavy Chain
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHTCP
PCPAPPVAGPSVFLFPPKPKDTLMISRTPEVTCVVVDVKHEDPEVKFNWYVDGVEVHNAKTKPREEQYNSTYRVVSV
LTVLHQDWLNGKEYKCKVSNKALPAPIEKTISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHEALHNHYTQKSLSLSPGK (SEQ ID NO: 249)

Chain 2 - MESO-C[MSLN]_L1 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO: 250)

Figure 18

>*MESO-C[MSLN]_H1.1 Variable Heavy*
QVQLVQSGAEVKKPGASVKVSCKASGYTFTGYWMHWVRQAPGQGLEWMGMIHPNSDNTIYYEKFQGRVTMTVDKSIS
TAYMELSRLRSDDTAVYYCAIIITPVVPKFDYWGQGTLVTVSS (SEQ ID NO: 251)
>*MESO-C[MSLN]_H1.2 Variable Heavy*
QVQLVQSGAEVKKPGASVKVSCKASGYTFTSYYMHWVRQAPGQGLEWMGMIHPNSDNTIYYEKFQGRVTMTVDKSIS
TAYMELSRLRSDDTAVYYCAIIITPVVPKFDYWGQGTLVTVSS (SEQ ID NO: 252)
>*MESO-C[MSLN]_H1.3 Variable Heavy*
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS (SEQ ID NO: 253)
>*MESO-C[MSLN]_H1.4 Variable Heavy*
QVQLVQSGAEVKKPGASVKVSCKASGYTFTSYWMHWVRQAPGQGLEWMGMINPNSDNTIYYEKFQGRVTMTVDKSIS
TAYMELSRLRSDDTAVYYCAIIITPVVPKFDYWGQGTLVTVSS (SEQ ID NO: 254)
>*MESO-C[MSLN]_H1.5 Variable Heavy*
QVQLVQSGAEVKKPGASVKVSCKASGYTFTSYWMHWVRQAPGQGLEWMGMIHPQSDNTIYYEKFQGRVTMTVDKSIS
TAYMELSRLRSDDTAVYYCAIIITPVVPKFDYWGQGTLVTVSS (SEQ ID NO: 255)
>*MESO-C[MSLN]_H1.6 Variable Heavy*
QVQLVQSGAEVKKPGASVKVSCKASGYTFTSYWMHWVRQAPGQGLEWMGMIHPNSGNTIYYEKFQGRVTMTVDKSIS
TAYMELSRLRSDDTAVYYCAIIITPVVPKFDYWGQGTLVTVSS (SEQ ID NO: 256)
>*MESO-C[MSLN]_H1.7 Variable Heavy*
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCARIITPVVPKFDYWGQGTLVTVSS (SEQ ID NO: 257)
>*MESO-C[MSLN]_H1.8 Variable Heavy*
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIISPVVPKFDYWGQGTLVTVSS (SEQ ID NO: 258)
>*MESO-C[MSLN]_H1.9 Variable Heavy*
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPRFDYWGQGTLVTVSS (SEQ ID NO: 259)
>*MESO-C[MSLN]_H1.12 Variable Heavy*
QVQLVQSGAEVKKPGASVKVSCKASGYTFTSYWMHWVRQAPGQGLEWMGMIHPNSDNTIYYQKFQGRVTMTVDKSIS
TAYMELSRLRSDDTAVYYCAIIITPVVPKFDYWGQGTLVTVSS (SEQ ID NO: 260)
>*MESO-C[MSLN]_H1.13 Variable Heavy*
QVQLVQSGAEVKKPGASVKVSCKASGYTFTSYWMHWVRQAPGQGLEWMGMIHPNSDNTIYYYKFQGRVTMTVDKSIS
TAYMELSRLRSDDTAVYYCAIIITPVVPKFDYWGQGTLVTVSS (SEQ ID NO: 261)

Figure 19A

>*MESO-C[MSLN]_L1.1 Variable Light*
DIVMTQSPDSLAVSLGERATINCKSSHDVGTSVAWYQQKPGQSPKLLIYWASTRHTGVPDRFTGSGSGTDFTLTISS
LQAEDVAVYFCQQYSSYPLTFGAGTKLEIK (SEQ ID NO: 262)
>*MESO-C[MSLN]_L1.2 Variable Light*
DIVMTQSPDSLAVSLGERATINCKASQDVGTSVAWYQQKPGQSPKLLIYWASTRHTGVPDRFTGSGSGTDFTLTISS
LQAEDVAVYFCQQYSSYPLTFGAGTKLEIK (SEQ ID NO: 263)
>*MESO-C[MSLN]_L1.3 Variable Light*
DIVMTQSPDSLAVSLGERATINCKASHSVGTSVAWYQQKPGQSPKLLIYWASTRHTGVPDRFTGSGSGTDFTLTISS
LQAEDVAVYFCQQYSSYPLTFGAGTKLEIK (SEQ ID NO: 264)
>*MESO-C[MSLN]_L1.4 Variable Light*
DIVMTQSPDSLAVSLGERATINCKASHDVLTSVAWYQQKPGQSPKLLIYWASTRHTGVPDRFTGSGSGTDFTLTISS
LQAEDVAVYFCQQYSSYPLTFGAGTKLEIK (SEQ ID NO: 265)
>*MESO-C[MSLN]_L1.5 Variable Light*
DIVMTQSPDSLAVSLGERATINCKASHDVGTYVAWYQQKPGQSPKLLIYWASTRHTGVPDRFTGSGSGTDFTLTISS
LQAEDVAVYFCQQYSSYPLTFGAGTKLEIK (SEQ ID NO: 266)
>*MESO-C[MSLN]_L1.6 Variable Light*
DIVMTQSPDSLAVSLGERATINCKASHDVGTSLAWYQQKPGQSPKLLIYWASTRHTGVPDRFTGSGSGTDFTLTISS
LQAEDVAVYFCQQYSSYPLTFGAGTKLEIK (SEQ ID NO: 267)
>*MESO-C[MSLN]_L1.7 Variable Light*
DIVMTQSPDSLAVSLGERATINCKASHDVGTSVAWYQQKPGQSPKLLIYWASTRETGVPDRFTGSGSGTDFTLTISS
LQAEDVAVYFCQQYSSYPLTFGAGTKLEIK (SEQ ID NO: 268)
>*MESO-C[MSLN]_L1.8 Variable Light*
DIVMTQSPDSLAVSLGERATINCKASHDVGTSVAWYQQKPGQSPKLLIYWASTRHSGVPDRFTGSGSGTDFTLTISS
LQAEDVAVYFCQQYSSYPLTFGAGTKLEIK (SEQ ID NO: 269)
>*MESO-C[MSLN]_L1.9 Variable Light*
DIVMTQSPDSLAVSLGERATINCKASHDVGTSVAWYQQKPGQSPKLLIYWASTRHTGVPDRFTGSGSGTDFTLTISS
LQAEDVAVYFCQQYYSYPLTFGAGTKLEIK (SEQ ID NO: 270)
>*MESO-C[MSLN]_L1.10 Variable Light*
DIVMTQSPDSLAVSLGERATINCKASHDVGTSVAWYQQKPGQSPKLLIYWASTRHTGVPDRFTGSGSGTDFTLTISS
LQAEDVAVYFCQQYSSTPLTFGAGTKLEIK (SEQ ID NO: 271)
>*MESO-C[MSLN]_L1.13 Variable Light*
DIVMTQSPDSLAVSLGERATINCKASHDVGQSVAWYQQKPGQSPKLLIYWASTRHTGVPDRFTGSGSGTDFTLTISS
LQAEDVAVYFCQQYSSYPLTFGAGTKLEIK (SEQ ID NO: 272)
>*MESO-C[MSLN]_L1.14 Variable Light*
DIVMTQSPDSLAVSLGERATINCKASHDVGTSVAWYQQKPGQSPKLLIYWASTRHTGVPDRFTGSGSGTDFTLTISS
LQAEDVAVYFCQQYSSFPLTFGAGTKLEIK (SEQ ID NO: 273)
>*MESO-C[MSLN]_L1.15 Variable Light*
DIVMTQSPDSLAVSLGERATINCKASHDVGTSVAWYQQKPGQSPKLLIYWASTRHTGVPDRFTGSGSGTDFTLTISS
LQAEDVAVYFCQQYSSLPLTFGAGTKLEIK (SEQ ID NO: 274)
>*MESO-C[MSLN]_L1.16 Variable Light*
DIVMTQSPDSLAVSLGERATINCKASHDVGTSVAWYQQKPGQSPKLLIYWASTRHTGVPDRFTGSGSGTDFTLTISS
LQAEDVAVYFCQQYSSVPLTFGAGTKLEIK (SEQ ID NO: 275)
>*MESO-C[MSLN]_L1.17 Variable Light*
DIVMTQSPDSLAVSLGERATINCKASHDVGTSVAWYQQKPGQSPKLLIYWASTRHTGVPDRFTGSGSGTDFTLTISS
LQAEDVAVYFCQQYSSIPLTFGAGTKLEIK (SEQ ID NO: 276)
>*MESO-C[MSLN]_L1.18 Variable Light*
DIVMTQSPDSLAVSLGERATINCKASHDVGTSVAWYQQKPGQSPKLLIYWASTRHTGVPDRFTGSGSGTDFTLTISS
LQAEDVAVYFCQQYSSHPLTFGAGTKLEIK (SEQ ID NO: 277)
>*MESO-C[MSLN]_L1.19 Variable Light*
DIVMTQSPDSLAVSLGERATINCKASHDVGTYVAWYQQKPGQSPKLLIYWASTRHTGVPDRFTGSGSGTDFTLTISS
LQAEDVAVYFCQQYYSYPLTFGAGTKLEIK (SEQ ID NO: 278)

Figure 19B

>MESO-C[MSLN]_L1.20 Variable Light
DIVMTQSPDSLAVSLGERATINCKASHDVGTSVAWYQQKPGQSPKLLIYWASTRHTGVPDRFTGSGSGTDFTLTISS
LQAEDVAVYFCQQYYSFPLTFGAGTKLEIK (SEQ ID NO: 279)
>MESO-C[MSLN]_L1.21 Variable Light
DIVMTQSPDSLAVSLGERATINCKASHDVGTSVAWYQQKPGQSPKLLIYWASTRHTGVPDRFTGSGSGTDFTLTISS
LQAEDVAVYFCQQYYSVPLTFGAGTKLEIK (SEQ ID NO: 280)
>MESO-C[MSLN]_L1.22 Variable Light
DIVMTQSPDSLAVSLGERATINCKASHDVGTSVAWYQQKPGQSPKLLIYWASTRHTGVPDRFTGSGSGTDFTLTISS
LQAEDVAVYFCQQYYSIPLTFGAGTKLEIK (SEQ ID NO: 281)

Figure 20

| | MESO-C Variant | VH Variant | VL Variant | human MSLN | | | | cyno MSLN | | | |
|---|---|---|---|---|---|---|---|---|---|---|---|
| XENP | | | | Response | $K_D$ (M) | $k_a$(1/Ms) | $k_d$(1/s) | Response | $K_D$ (M) | $k_a$(1/Ms) | $k_d$(1/s) |
| 31701 | H1_L1 | WT | WT | 0.8598 | 8.05E-11 | 5.83E+05 | 4.69E-05 | 0.7372 | 9.38E-11 | 6.12E+05 | 5.74E-05 |
| 32550 | H1.1_L1 | S31G | WT | 1.0243 | 6.01E-10 | 5.22E+05 | 3.14E-04 | 0.8907 | 2.54E-10 | 5.76E+05 | 1.46E-04 |
| 32551 | H1.2_L1 | W32Y | WT | 1.1872 | 1.60E-09 | 4.83E+05 | 7.73E-04 | 1.0999 | 1.66E-09 | 4.95E+05 | 8.22E-04 |
| 32552 | H1.3_L1 | M50W | WT | 0.915 | 3.00E-08 | 4.91E+05 | 1.47E-02 | 0.8268 | 3.21E-08 | 4.59E+05 | 1.48E-02 |
| 32553 | H1.4_L1 | H52N | WT | 1.1642 | 6.87E-10 | 5.39E+05 | 3.70E-04 | 1.0566 | 5.85E-10 | 5.75E+05 | 3.37E-04 |
| 32554 | H1.5_L1 | N53Q | WT | 1.1336 | 4.83E-10 | 5.55E+05 | 2.68E-04 | 1.0288 | 4.14E-10 | 5.55E+05 | 2.30E-04 |
| 32555 | H1.6_L1 | D55G | WT | 1.2313 | 6.84E-10 | 5.49E+05 | 3.75E-04 | 1.1106 | 6.03E-10 | 5.66E+05 | 3.42E-04 |
| 32556 | H1.7_L1 | I94R | WT | 1.1815 | 4.69E-10 | 4.25E+05 | 1.99E-04 | 1.0735 | 3.95E-10 | 3.99E+05 | 1.57E-04 |
| 32557 | H1.8_L1 | T97S | WT | 1.1509 | 7.21E-10 | 5.19E+05 | 3.74E-04 | 1.0862 | 6.20E-10 | 5.18E+05 | 3.21E-04 |
| 32558 | H1.9_L1 | K100bR | WT | 1.1729 | 7.95E-10 | 2.49E+05 | 1.98E-04 | 1.1144 | 7.00E-10 | 2.38E+05 | 1.66E-04 |
| 32559 | H1_L1.1 | WT | A25S | 1.1102 | 2.83E-10 | 5.69E+05 | 1.61E-04 | 1.0438 | 2.23E-10 | 5.75E+05 | 1.28E-04 |
| 32560 | H1_L1.2 | WT | H27Q | 1.0302 | 6.33E-10 | 6.05E+05 | 3.83E-04 | 0.9475 | 1.20E-09 | 6.34E+05 | 7.62E-04 |
| 32561 | H1_L1.3 | WT | D28S | 1.0766 | 3.55E-10 | 6.06E+05 | 2.15E-04 | 0.9758 | 4.13E-10 | 6.00E+05 | 2.48E-04 |
| 32562 | H1_L1.4 | WT | G30L | 1.0099 | 6.28E-10 | 6.51E+05 | 4.09E-04 | 0.9005 | 8.87E-10 | 6.69E+05 | 5.94E-04 |
| 32563 | H1_L1.5 | WT | S32Y | 0.8985 | 1.28E-08 | 5.27E+05 | 6.72E-03 | 0.8174 | 1.31E-08 | 5.43E+05 | 7.13E-03 |
| 32564 | H1_L1.6 | WT | V33L | 0.9522 | 8.61E-11 | 6.60E+05 | 5.68E-05 | 0.8489 | 2.97E-11 | 6.76E+05 | 2.01E-05 |
| 32565 | H1_L1.7 | WT | H55E | 1.1139 | 2.86E-10 | 5.90E+05 | 1.69E-04 | 1.0026 | 2.55E-10 | 5.92E+05 | 1.51E-04 |
| 32566 | H1_L1.8 | WT | T56S | 1.0481 | 1.80E-10 | 6.27E+05 | 1.13E-04 | 0.9412 | 1.63E-10 | 6.16E+05 | 1.00E-04 |
| 32567 | H1_L1.9 | WT | S92Y | 0.9532 | 1.53E-08 | 5.78E+05 | 8.87E-03 | 0.8223 | 2.15E-08 | 6.08E+05 | 1.30E-02 |
| 32568 | H1_L1.10 | WT | Y94T | 0.1072 | | | | 0.0728 | | | |
| 32569 | H1.5_L1.3 | N53Q | D28S | 0.978 | 1.35E-10 | 6.93E+05 | 9.35E-05 | 0.8666 | 1.89E-10 | 6.60E+05 | 1.25E-04 |
| 32570 | H1.6_L1.3 | D55G | D28S | 0.9808 | 1.03E-10 | 7.17E+05 | 7.35E-05 | 0.9504 | 1.55E-10 | 6.76E+05 | 1.05E-04 |

Figure 21

| XENP | MESO-C Variant | VH Variant | VL Variant | human MSLN | | | |
|---|---|---|---|---|---|---|---|
| | | | | Response | $K_D$ (M) | $k_a$(1/Ms) | $k_d$(1/s) |
| 32937 | H1.12_L1.9 | E61Q | S92Y | 0.1835 | 1.02E-08 | 8.03E+05 | 8.22E-03 |
| 32938 | H1.13_L1.9 | E61Y | S92Y | 0.1689 | 1.62E-08 | 6.35E+05 | 1.03E-02 |
| 32939 | H1.3_L1.13 | M50W | T37Q | 0.2021 | 9.04E-08 | 4.24E+05 | 3.83E-02 |
| 32940 | H1.3_L1.14 | M50W | Y100F | 0.1359 | 2.46E-07 | 3.32E+05 | 8.16E-02 |
| 32941 | H1.3_L1.15 | M50W | Y94L | 0.0251 | N/A | N/A | N/A |
| 32942 | H1.3_L1.16 | M50W | Y94V | 0.0356 | N/A | N/A | N/A |
| 32943 | H1.3_L1.17 | M50W | Y94I | 0.0022 | N/A | N/A | N/A |
| 32944 | H1.3_L1.18 | M50W | Y94H | 0.0218 | N/A | N/A | N/A |
| 32945 | H1.3_L1.9 | M50W | S92Y | 0.0668 | N/A | N/A | N/A |
| 32946 | H1.3_L1.5 | M50W | S32Y | 0.0448 | N/A | N/A | N/A |

| XENP | MESO-C Variant | VH Variant | VL Variant | human MSLN (M) | cyno MSLN (M) |
|---|---|---|---|---|---|
| 31697 | H1L1 | WT | WT | 2.8E-10 | |
| 32552 | H1.3_L1 | M50W | WT | 9.2E-09 | 1.0E-08 |
| 32561 | H1_L1.3 | WT | D28S | 4.5E-10 | |
| 32562 | H1_L1.4 | WT | G30L | 7.4E-10 | |
| 32567 | H1_L1.9 | WT | S92Y | 3.9E-09 | 6.7E-09 |

1 + 1 Fab-scFv-Fc

2 + 1 Fab$_2$-scFv-Fc

Figure 23A

>XENP16248 MESO-A[MSLN]_H1.1_L1_Fab-[CD3]_H1.30_L1.47_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-A[MSLN]_H1.1_IgG1_pI(-)_Isosteric_A_/PVA_/S267K/L368D/K370S
EVQLVESGGGLVQPGGSLKLSCAASGFDFSRYWMSWVRQAPGKGLEWVSEINPDSSTIVYTPSVKGRFTISRDNAKN
SLYLQMNSLRAEDTAVYYCARRGSHYYGYRTGYFDVWGAGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSDTKVDKKVEPKSCDKT
HTCPPCPAPPVAGPSVFLFPPPKPKDTLMISRTPEVTCVVVDVKHEDPEVKFNWYVDGVEVHNAKTKPREEEYNSTYR
VVSVLTVLHQDWLNGKEYKCKVSNKALPAPIEKTISKAKGQPREPQVYTLPPSREEMTKNQVSLTCDVSGFYPSDIA
VEWESDGQPENNYKTTPPVLDSDGSFFLYSKLTVDKSRWEQGDVFSCSVMHEALHNHYTQKSLSLSPGK (SEQ ID
NO: 282)

Chain 2 - [CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDS
KNTLYLQMNSLRAEDTAVYYCVRHGNFGDSYVSWFAYWGQGTLVTVSS/GKPGSGKPGSGKPGSGKPGS/QAVVTQE
PSLTVSPGGTVTLTCGSSTGAVTTSNYANWVQQKPGKSPRGLIGGTNKRAPGVPARFSGSLLGGKAALTISGAQPED
EADYYCALWYSNHWVFGGGTKLTVL/EPKSSDKTHTCPPCPAPPVAGPSVFLFPPPKPKDTLMISRTPEVTCVVVDVK
HEDPEVKFNWYVDGVEVHNAKTKPREEQYNSTYRVVSVLTVLHQDWLNGKEYKCKVSNKALPAPIEKTISKAKGQPR
EPQVYTLPPSREQMTKNQVKLTCLVKGFYPSDIAVEWESNGQPENNYKTTPPVLDSDGSFFLYSKLTVDKSRWQQGN
VFSCSVMHEALHNHYTQKSLSLSPGK (SEQ ID NO: 283)

Chain 3 - MESO-A[MSLN]_L1 Light Chain
DVVLTQSPATLSLSPGERATLSCRASSSVSYMYWHQQKPDQSPKLLIYDTSNLASGVPVRFSGSGSGTDYTLTISSL
EPEDFAVYYCQQWSSYPPTFGGGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC (SEQ ID NO: 284)

>XENP16833 MESO-B[MSLN]_H0L0_Fab-[CD3]_H1.30_L1.47_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-B[MSLN]_H0L0_Fab_IgG1_pI(-)_Isosteric_A_/PVA_/S267K/L368D/K370S
QVQLQQSGPGLVTPSQTLSLTCAISGDSVSSNSATWNWIRQSPSRGLEWLGRTYYRSKWYNDYAVSVKSRMSINPDT
SKNQFSLQLNSVTPEDTAVYYCARGMMTYYYGMDVWGQGTTVTVSS/ASTKGPSVFPLAPSSKSTSGGTAALGCLVK
DYFPEPVTVSWNSGALTSGVHTFPAVLQSSGLYSLSSVVTVPSSSLGTQTYICNVNHKPSDTKVDKKVEPKSCDKTH
TCPPCPAPPVAGPSVFLFPPPKPKDTLMISRTPEVTCVVVDVKHEDPEVKFNWYVDGVEVHNAKTKPREEEYNSTYRV
VSVLTVLHQDWLNGKEYKCKVSNKALPAPIEKTISKAKGQPREPQVYTLPPSREEMTKNQVSLTCDVSGFYPSDIAV
EWESDGQPENNYKTTPPVLDSDGSFFLYSKLTVDKSRWEQGDVFSCSVMHEALHNHYTQKSLSLSPGK (SEQ ID
NO: 285)

Chain 2 - [CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDS
KNTLYLQMNSLRAEDTAVYYCVRHGNFGDSYVSWFAYWGQGTLVTVSS/GKPGSGKPGSGKPGSGKPGS/QAVVTQE
PSLTVSPGGTVTLTCGSSTGAVTTSNYANWVQQKPGKSPRGLIGGTNKRAPGVPARFSGSLLGGKAALTISGAQPED
EADYYCALWYSNHWVFGGGTKLTVL/EPKSSDKTHTCPPCPAPPVAGPSVFLFPPPKPKDTLMISRTPEVTCVVVDVK
HEDPEVKFNWYVDGVEVHNAKTKPREEQYNSTYRVVSVLTVLHQDWLNGKEYKCKVSNKALPAPIEKTISKAKGQPR
EPQVYTLPPSREQMTKNQVKLTCLVKGFYPSDIAVEWESNGQPENNYKTTPPVLDSDGSFFLYSKLTVDKSRWQQGN
VFSCSVMHEALHNHYTQKSLSLSPGK (SEQ ID NO: 286)

Chain 3 - MESO-B[MSLN]_L0 Light Chain
QPVLTQSSSLSASPGASASLTCTLRSGINVGPYRIYWYQQKPGSPPQYLLNYKSDSDKQQGSGVPSRFSGSKDASAN
AGVLLISGLRSEDEADYYCMIWHSSAAVFGGGTQLTVL/GQPKAAPSVTLFPPSSEELQANKATLVCLISDFYPGAV
TVAWKADSSPVKAGVETTTPSKQSNNKYAASSYLSLTPEQWKSHRSYSCQVTHEGSTVEKTVAPTECS (SEQ ID
NO: 287)

Figure 23B

>XENP31697 MESO-C[MSLN]_H1L1_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
288)

Chain 2 - [CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDS
KNTLYLQMNSLRAEDTAVYYCVRHGNFGDSYVSWFAYWGQGTLVTVSS/GKPGSGKPGSGKPGSGKPGS/QAVVTQE
PSLTVSPGGTVTLTCGSSTGAVTTSNYANWVQQKPGKSPRGLIGGTNKRAPGVPARFSGSLLGGKAALTISGAQPED
EADYYCALWYSNHWVFGGGTKLTVL/EPKSSDKTHTCPPCPAPPVAGPSVFLFPPKPKDTLMISRTPEVTCVVVDVK
HEDPEVKFNWYVDGVEVHNAKTKPREEQYNSTYRVVSVLTVLHQDWLNGKEYKCKVSNKALPAPIEKTISKAKGQPR
EPQVYTLPPSREQMTKNQVKLTCLVKGFYPSDIAVEWESNGQPENNYKTTPPVLDSDGSFFLYSKLTVDKSRWQQGN
VFSCSVMHEALHNHYTQKSLSLSPGK (SEQ ID NO: 289)

Chain 3 - MESO-C[MSLN]_L1 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
290)

>XENP32550 MESO-C[MSLN]_H1.1_L1_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1.1_IgG1_pI(-)_Isosteric_A_/PVA_/S267K/L368D/K370S
QVQLVQSGAEVKKPGASVKVSCKASGYTFTGYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
291)

Chain 2 - MESO-C[MSLN]_H1.1_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDS
KNTLYLQMNSLRAEDTAVYYCVRHGNFGDSYVSWFAYWGQGTLVTVSS/GKPGSGKPGSGKPGSGKPGS/QAVVTQE
PSLTVSPGGTVTLTCGSSTGAVTTSNYANWVQQKPGKSPRGLIGGTNKRAPGVPARFSGSLLGGKAALTISGAQPED
EADYYCALWYSNHWVFGGGTKLTVL/EPKSSDKTHTCPPCPAPPVAGPSVFLFPPKPKDTLMISRTPEVTCVVVDVK
HEDPEVKFNWYVDGVEVHNAKTKPREEQYNSTYRVVSVLTVLHQDWLNGKEYKCKVSNKALPAPIEKTISKAKGQPR
EPQVYTLPPSREQMTKNQVKLTCLVKGFYPSDIAVEWESNGQPENNYKTTPPVLDSDGSFFLYSKLTVDKSRWQQGN
VFSCSVMHEALHNHYTQKSLSLSPGK (SEQ ID NO: 292)

Chain 3 - MESO-C[MSLN]_L1 Light Chain
DIVMTQSPDSLAVSLGERATINCKASHDVGTSVAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 293)

Figure 23C

>XENP32551 MESO-C[MSLN]_H1.2_L1_Fab-[CD3]_H1.30_L1.47_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1.2_IgG1_pI(-)_Isosteric_A_/PVA_/S267K/L368D/K370S
QVQLVQSGAEVKKPGASVKVSCKASGYTFTSYYMHWVRQAPGQGLEWMGMIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 294)

Chain 2 - MESO-C[MSLN]_H1.2_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 295)

Chain 3 - MESO-C[MSLN]_L1 Light Chain
DIVMTQSPDSLAVSLGERATINCKASHDVGTSVAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 296)

>XENP32552 MESO-C[MSLN]_H1.3_L1_Fab-[CD3]_H1.30_L1.47_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1.3_IgG1_pI(-)_Isosteric_A_/PVA_/S267K/L368D/K370S
QVQLVQSGAEVKKPGASVKVSCKASGYTFTSYWMHWVRQAPGQGLEWMGWIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 297)

Chain 2 - MESO-C[MSLN]_H1.3_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 298)

Chain 3 - MESO-C[MSLN]_L1 Light Chain
DIVMTQSPDSLAVSLGERATINCKASHDVGTSVAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 299)

Figure 23D

>XENP32553 MESO-C[MSLN]_H1.4_L1_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1.4_IgG1_pI(-)_Isosteric_A_/PVA_/S267K/L368D/K370S
QVQLVQSGAEVKKPGASVKVSCKASGYTFTSYWMHWVRQAPGQGLEWMGMINPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 300)

Chain 2 - MESO-C[MSLN]_H1.4_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 301)

Chain 3 - MESO-C[MSLN]_L1 Light Chain
DIVMTQSPDSLAVSLGERATINCKASHDVGTSVAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 302)

>XENP32554 MESO-C[MSLN]_H1.5_L1_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1.5_IgG1_pI(-)_Isosteric_A_/PVA_/S267K/L368D/K370S
QVQLVQSGAEVKKPGASVKVSCKASGYTFTSYWMHWVRQAPGQGLEWMGMIRPQSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 303)

Chain 2 - MESO-C[MSLN]_H1.5_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 304)

Chain 3 - MESO-C[MSLN]_L1 Light Chain
DIVMTQSPDSLAVSLGERATINCKASHDVGTSVAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 305)

Figure 23E

>XENP32555 MESO-C[MSLN]_H1.6_L1_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1.6_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSGNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 306)

Chain 2 - MESO-C[MSLN]_H1.6_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 307)

Chain 3 - MESO-C[MSLN]_L1 Light Chain
DIVMTQSPDSLAVSLGERATINCKASHDVGTSVAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 308)

>XENP32556 MESO-C[MSLN]_H1.7_L1_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1.7_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSISTAYME
LSRLRSDDTAVYYCARIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 309)

Chain 2 - MESO-C[MSLN]_H1.7_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 310)

Chain 3 - MESO-C[MSLN]_L1 Light Chain
DIVMTQSPDSLAVSLGERATINCKASHDVGTSVAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 311)

Figure 23F

>XENP32557 MESO-C[MSLN]_H1.8_L1_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1.8_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSISTAYME
LSRLRSDDTAVYYCAIIISPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 312)

Chain 2 - MESO-C[MSLN]_H1.8_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 313)

Chain 3 - MESO-C[MSLN]_L1 Light Chain
DIVMTQSPDSLAVSLGERATINCKASHDVGTSVAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 314)

>XENP32558 MESO-C[MSLN]_H1.9_L1_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1.9_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSISTAYME
LSRLRSDDTAVYYCAIIITPVVPRFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 315)

Chain 2 - MESO-C[MSLN]_H1.9_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 316)

Chain 3 - MESO-C[MSLN]_L1 Light Chain
DIVMTQSPDSLAVSLGERATINCKASHDVGTSVAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 317)

Figure 23G

>XENP32559 MESO-C[MSLN]_H1_L1.1_Fab-[CD3]_H1.30_L1.47_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 318)

Chain 2 - MESO-C[MSLN]_H1_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 319)

Chain 3 - MESO-C[MSLN]_L1.1 Light Chain
DIVMTQSPDSLAVSLGERATINCKSSSHDVGTSVAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 320)

>XENP32560 MESO-C[MSLN]_H1_L1.2_Fab-[CD3]_H1.30_L1.47_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 321)

Chain 2 - MESO-C[MSLN]_H1_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 322)

Chain 3 - MESO-C[MSLN]_L1.2 Light Chain
DIVMTQSPDSLAVSLGERATINCKASQDVGTSVAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 323)

Figure 23H

>XENP32561 MESO-C[MSLN]_H1_L1.3_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 324)

Chain 2 - MESO-C[MSLN]_H1_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 325)

Chain 3 - MESO-C[MSLN]_L1.3 Light Chain
DIVMTQSPDSLAVSLGERATINCKASHSVGTSVAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 326)

>XENP32562 MESO-C[MSLN]_H1_L1.4_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 327)

Chain 2 - MESO-C[MSLN]_H1_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 328)

Chain 3 - MESO-C[MSLN]_L1.4 Light Chain
DIVMTQSPDSLAVSLGERATINCKASHDVLTSVAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 329)

Figure 23I

>XENP32563 MESO-C[MSLN]_H1_L1.5_Fab-[CD3]_H1.30_L1.47_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 330)

Chain 2 - MESO-C[MSLN]_H1_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 331)

Chain 3 - MESO-C[MSLN]_L1.5 Light Chain
DIVMTQSPDSLAVSLGERATINCKASHDVGTYVAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 332)

>XENP32564 MESO-C[MSLN]_H1_L1.6_Fab-[CD3]_H1.30_L1.47_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 333)

Chain 2 - MESO-C[MSLN]_H1_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 334)

Chain 3 - MESO-C[MSLN]_L1.6 Light Chain
DIVMTQSPDSLAVSLGERATINCKASHDVGTSLAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 335)

Figure 23J

>XENP32565 MESO-C[MSLN]_H1_L1.7_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 336)

Chain 2 - MESO-C[MSLN]_H1_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 337)

Chain 3 - MESO-C[MSLN]_L1.7 Light Chain
DIVMTQSPDSLAVSLGERATINCKASHDVGTSVAWYQQKPGQSPKLLIYWASTRETGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 338)

>XENP32566 MESO-C[MSLN]_H1_L1.8_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 339)

Chain 2 - MESO-C[MSLN]_H1_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 340)

Chain 3 - MESO-C[MSLN]_L1.8 Light Chain
DIVMTQSPDSLAVSLGERATINCKASHDVGTSVAWYQQKPGQSPKLLIYWASTRHSGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 341)

Figure 23K

>XENP32567 MESO-C[MSLN]_H1_L1.9_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 342)

Chain 2 - MESO-C[MSLN]_H1_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 343)

Chain 3 - MESO-C[MSLN]_L1.9 Light Chain
DIVMTQSPDSLAVSLGERATINCKASHDVGTSVAWYQQKPGQSPKLLIYWASTRHTGVPDRFTGSGSGTDFTLTISSLQAED
VAVYFCQQYYSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 344)

>XENP32568 MESO-C[MSLN]_H1_L1.10_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 345)

Chain 2 - MESO-C[MSLN]_H1_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 346)

Chain 3 - MESO-C[MSLN]_L1.10 Light Chain
DIVMTQSPDSLAVSLGERATINCKASHDVGTSVAWYQQKPGQSPKLLIYWASTRHTGVPDRFTGSGSGTDFTLTISSLQAED
VAVYFCQQYSSTPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 347)

Figure 23L

>XENP32569 MESO-C[MSLN]_H1.5_L1.3_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1.5_IgG1_pI(-)_Isosteric_A_/PVA_/S267K/L368D/K370S
QVQLVQSGAEVKKPGASVKVSCKASGYTFTSYWMHWVRQAPGQGLEWMGMIHPQSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 348)

Chain 2 - MESO-C[MSLN]_H1.5_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 349)

Chain 3 - MESO-C[MSLN]_L1.3 Light Chain
DIVMTQSPDSLAVSLGERATINCKASHSVGTSVAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 350)

>XENP32570 MESO-C[MSLN]_H1.6_L1.3_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1.6_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSGNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 351)

Chain 2 - MESO-C[MSLN]_H1.6_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 352)

Chain 3 - MESO-C[MSLN]_L1.3 Light Chain
DIVMTQSPDSLAVSLGERATINCKASHSVGTSVAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 353)

Figure 23M

>XENP32937 MESO-C[MSLN]_H1.12_L1.9_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1.12_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYQKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 354)

Chain 2 - MESO-C[MSLN]_H1.12_[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 355)

Chain 3 - MESO-C[MSLN]_L1.9 Light Chain
DIVMTQSPDSLAVSLGERATINCKASHDVGTSVAWYQQKPGQSPKLLIYWASTRHTGVPDRFTGSGSGTDFTLTISSLQAED
VAVYFCQQYYSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 356)

>XENP32938 MESO-C[MSLN]_H1.13_L1.9_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1.13_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYYKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 357)

Chain 2 - MESO-C[MSLN]_H1.13_[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 358)

Chain 3 - MESO-C[MSLN]_L1.9 Light Chain
DIVMTQSPDSLAVSLGERATINCKASHDVGTSVAWYQQKPGQSPKLLIYWASTRHTGVPDRFTGSGSGTDFTLTISSLQAED
VAVYFCQQYYSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 359)

Figure 23N

>XENP32939 MESO-C[MSLN]_H1.3_L1.13_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1.3_IgG1_pI(-)_Isosteric_A_/PVA_/S267K/L368D/K370S
QVQLVQSGAEVKKPGASVKVSCKASGYTFTSYWMHWVRQAPGQGLEWMGWIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 360)

Chain 2 - MESO-C[MSLN]_H1.3_[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 361)

Chain 3 - MESO-C[MSLN]_L1.13 Light Chain
DIVMTQSPDSLAVSLGERATINCKASHDVGQSVAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 362)

>XENP32940 MESO-C[MSLN]_H1.3_L1.14_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1.3_IgG1_pI(-)_Isosteric_A_/PVA_/S267K/L368D/K370S
QVQLVQSGAEVKKPGASVKVSCKASGYTFTSYWMHWVRQAPGQGLEWMGWIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 363)

Chain 2 - MESO-C[MSLN]_H1.3_[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 364)

Chain 3 - MESO-C[MSLN]_L1.14 Light Chain
DIVMTQSPDSLAVSLGERATINCKASHDVGTSVAWYQQKPGQSPKLLIYWASTRHTGVPDRFTGSGSGTDFTLTISSLQAED
VAVYFCQQYSSFPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 365)

Figure 23O

>XENP32941 MESO-C[MSLN]_H1.3_L1.15_Fab-[CD3]_H1.30_L1.47_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1.3_IgG1_pI(-)_Isosteric_A_/PVA_/S267K/L368D/K370S
QVQLVQSGAEVKKPGASVKVSCKASGYTFTSYWMHWVRQAPGQGLEWMGWIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 366)

Chain 2 - MESO-C[MSLN]_H1.3_[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 367)

Chain 3 - MESO-C[MSLN]_L1.15 Light Chain
DIVMTQSPDSLAVSLGERATINCKASHDVGTSVAWYQQKPGQSPKLLIYWASTRHTGVPDRFTGSGSGTDFTLTISSLQAED
VAVYFCQQYSSLPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 368)

>XENP32942 MESO-C[MSLN]_H1.3_L1.16_Fab-[CD3]_H1.30_L1.47_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1.3_IgG1_pI(-)_Isosteric_A_/PVA_/S267K/L368D/K370S
QVQLVQSGAEVKKPGASVKVSCKASGYTFTSYWMHWVRQAPGQGLEWMGWIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 369)

Chain 2 - MESO-C[MSLN]_H1.3_[CD3]_H1.30_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 370)

Chain 3 - MESO-C[MSLN]_L1.16 Light Chain
DIVMTQSPDSLAVSLGERATINCKASHDVGTSVAWYQQKPGQSPKLLIYWASTRHTGVPDRFTGSGSGTDFTLTISSLQAED
VAVYFCQQYSSVPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 371)

Figure 23P

>XENP32943 MESO-C[MSLN]_H1.3_L1.17_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1.3_IgG1_pI(-)_Isosteric_A_/PVA_/S267K/L368D/K370S
QVQLVQSGAEVKKPGASVKVSCKASGYTFTSYWMHWVRQAPGQGLEWMGWIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 372)

Chain 2 - MESO-C[MSLN]_H1.3_[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 373)

Chain 3 - MESO-C[MSLN]_L1.17 Light Chain
DIVMTQSPDSLAVSLGERATINCKASHDVGTSVAWYQQKPGQSPKLLIYWASTRHTGVPDRFTGSGSGTDFTLTISSLQAED
VAVYFCQQYSSIPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 374)

>XENP32944 MESO-C[MSLN]_H1.3_L1.18_Fab-[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1.3_IgG1_pI(-)_Isosteric_A_/PVA_/S267K/L368D/K370S
QVQLVQSGAEVKKPGASVKVSCKASGYTFTSYWMHWVRQAPGQGLEWMGWIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 375)

Chain 2 - MESO-C[MSLN]_H1.3_[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 376)

Chain 3 - MESO-C[MSLN]_L1.18 Light Chain
DIVMTQSPDSLAVSLGERATINCKASHDVGTSVAWYQQKPGQSPKLLIYWASTRHTGVPDRFTGSGSGTDFTLTISSLQAED
VAVYFCQQYSSHPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 377)

Figure 23Q

>XENP32945 MESO-C[MSLN]_H1.3_L1.9_Fab-[CD3]_H1.30_L1.47_scFv(GKPGS)4-IgG1_pI(-
)_Isosteric_A_/PVA_/S267K/L368D/K370S-Fc(216)_IgG1_C220S/PVA_/S267K/S364K/E357Q Chain 1 - MESO-C[MSLN]_H1.3_IgG1_pI(-)_Isosteric_A_/PVA_/S267K/L368D/K370S
QVQLVQSGAEVKKPGASVKVSCKASGYTFTSYWMHWVRQAPGQGLEWMGWIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 378)

Chain 2 - MESO-C[MSLN]_H1.3_[CD3]_H1.30_L1.47_scFv(GKPGS)4-IgG1_pI(-)_Isosteric_A_/PVA_/S267K/L368D/K370S-
Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 379)

Chain 3 - MESO-C[MSLN]_L1.9 Light Chain
DIVMTQSPDSLAVSLGERATINCKASHDVGTSVAWYQQKPGQSPKLLIYWASTRHTGVPDRFTGSGSGTDFTLTISSLQAED
VAVYFCQQYYSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 380)

>XENP32946 MESO-C[MSLN]_H1.3_L1.5_Fab-[CD3]_H1.30_L1.47_scFv(GKPGS)4-IgG1_pI(-
)_Isosteric_A_/PVA_/S267K/L368D/K370S-Fc(216)_IgG1_C220S/PVA_/S267K/S364K/E357Q Chain 1 - MESO-C[MSLN]_H1.3_IgG1_pI(-)_Isosteric_A_/PVA_/S267K/L368D/K370S
QVQLVQSGAEVKKPGASVKVSCKASGYTFTSYWMHWVRQAPGQGLEWMGWIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 381)

Chain 2 - MESO-C[MSLN]_H1.3_[CD3]_H1.30_L1.47_scFv(GKPGS)4-IgG1_pI(-)_Isosteric_A_/PVA_/S267K/L368D/K370S-
Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDSKNTLY
LQMNSLRAEDTAVYYCVRHGNFGDSYVSWFAYWGQGTLVTVSS/GKPGSGKPGSGKPGSGKPGS/QAVVTQEPSLTVSPGGT
VTLTCGSSTGAVTTSNYANWVQQKPGKSPRGLIGGTNKRAPGVPARFSGSLLGGKAALTISGAQPEDEADYYCALWYSNHWV
FGGGTKLTVL/EPKSSDKTHTCPPCPAPPVAGPSVFLFPPKPKDTLMISRTPEVTCVVVDVKHEDPEVKFNWYVDGVEVHNA
KTKPREEQYNSTYRVVSVLTVLHQDWLNGKEYKCKVSNKALPAPIEKTISKAKGQPREPQVYTLPPSREQMTKNQVKLTCLV
KGFYPSDIAVEWESNGQPENNYKTTPPVLDSDGSFFLYSKLTVDKSRWQQGNVFSCSVMHEALHNHYTQKSLSLSPGK
(SEQ ID NO: 382)

Chain 3 - MESO-C[MSLN]_L1.5 Light Chain
DIVMTQSPDSLAVSLGERATINCKASHDVGTYVAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 383)

Figure 23R

>XENP33888 MESO-C[MSLN]_H1_L1.20_Fab-[CD3]_H1.30_L1.47_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
EVQLVESGGGLVQPGGSLRLSCAASGFTFSTYAMNWVRQAPGKGLEWVGRIRSKYNNYATYYADSVKGRFTISRDDS
KNTLYLQMNSLRAEDTAVYYCVRHGNFGDSYVSWFAYWGQGTLVTVSS/GKPGSGKPGSGKPGSGKPGS/QAVVTQE
PSLTVSPGGTVTLTCGSSTGAVTTSNYANWVQQKPGKSPRGLIGGTNKRAPGVPARFSGSLLGGKAALTISGAQPED
EADYYCALWYSNHWVFGGGTKLTVL/EPKSSDKTHTCPPCPAPPVAGPSVFLFPPKPKDTLMISRTPEVTCVVVDVK
HEDPEVKFNWYVDGVEVHNAKTKPREEQYNSTYRVVSVLTVLHQDWLNGKEYKCKVSNKALPAPIEKTISKAKGQPR
EPQVYTLPPSREQMTKNQVKLTCLVKGFYPSDIAVEWESNGQPENNYKTTPPVLDSDGSFFLYSKLTVDKSRWQQGN
VFSCSVMHEALHNHYTQKSLSLSPGK (SEQ ID NO: 384)

Chain 2 - [CD3]_H1.30_L1.47_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
385)

Chain 3 - MESO-C[MSLN]_L1.20 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYYSFPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
386)

>XENP33889 MESO-C[MSLN]_H1.12_L1.20_Fab-[CD3]_H1.30_L1.47_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1.12_IgG1_pI(-)_Isosteric_A_/PVA_/S267K/L368D/K370S
EVQLVESGGGLVQPGGSLRLSCAASGFTFSTYAMNWVRQAPGKGLEWVGRIRSKYNNYATYYADSVKGRFTISRDDS
KNTLYLQMNSLRAEDTAVYYCVRHGNFGDSYVSWFAYWGQGTLVTVSS/GKPGSGKPGSGKPGSGKPGS/QAVVTQE
PSLTVSPGGTVTLTCGSSTGAVTTSNYANWVQQKPGKSPRGLIGGTNKRAPGVPARFSGSLLGGKAALTISGAQPED
EADYYCALWYSNHWVFGGGTKLTVL/EPKSSDKTHTCPPCPAPPVAGPSVFLFPPKPKDTLMISRTPEVTCVVVDVK
HEDPEVKFNWYVDGVEVHNAKTKPREEQYNSTYRVVSVLTVLHQDWLNGKEYKCKVSNKALPAPIEKTISKAKGQPR
EPQVYTLPPSREQMTKNQVKLTCLVKGFYPSDIAVEWESNGQPENNYKTTPPVLDSDGSFFLYSKLTVDKSRWQQGN
VFSCSVMHEALHNHYTQKSLSLSPGK (SEQ ID NO: 387)

Chain 2 - [CD3]_H1.30_L1.47_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGMIHPNSDNTIYYQKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
388)

Chain 3 - MESO-C[MSLN]_L1.20 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYYSFPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
389)

Figure 24A

>XENP30764 MESO-A[MSLN]_H1.1_L1_Fab-[CD3]_H1.32_L1.47_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-A[MSLN]_H1.1_L1_Fab_IgG1_pI(-)_Isosteric_A_/PVA_/S267K/L368D/K370S
EVQLVESGGGLVQPGGSLKLSCAASGFDFSRYWMSWVRQAPGKGLEWVSEINPDSSTIVYTPSVKGRFTISRDNAKN
SLYLQMNSLRAEDTAVYYCARRGSHYYGYRTGYFDVWGAGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSDTKVDKKVEPKSCDKT
HTCPPCPAPPVAGPSVFLFPPKPKDTLMISRTPEVTCVVVDVKHEDPEVKFNWYVDGVEVHNAKTKPREEEYNSTYR
VVSVLTVLHQDWLNGKEYKCKVSNKALPAPIEKTISKAKGQPREPQVYTLPPSREEMTKNQVSLTCDVSGFYPSDIA
VEWESDGQPENNYKTTPPVLDSDGSFFLYSKLTVDKSRWEQGDVFSCSVMHEALHNHYTQKSLSLSPGK (SEQ ID
NO: 390)

Chain 2 - [CD3]_H1.32_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKANNYATYYADSVKGRFTISRDDS
KNTLYLQMNSLRAEDTAVYYCVRHGNFGDSYVSWFAYWGQGTLVTVSS/GKPGSGKPGSGKPGSGKPGS/QAVVTQE
PSLTVSPGGTVTLTCGSSTGAVTTSNYANWVQQKPGKSPRGLIGGTNKRAPGVPARFSGSLLGGKAALTISGAQPED
EADYYCALWYSNHWVFGGGTKLTVL/EPKSSDKTHTCPPCPAPPVAGPSVFLFPPKPKDTLMISRTPEVTCVVVDVK
HEDPEVKFNWYVDGVEVHNAKTKPREEQYNSTYRVVSVLTVLHQDWLNGKEYKCKVSNKALPAPIEKTISKAKGQPR
EPQVYTLPPSREQMTKNQVKLTCLVKGFYPSDIAVEWESNGQPENNYKTTPPVLDSDGSFFLYSKLTVDKSRWQQGN
VFSCSVMHEALHNHYTQKSLSLSPGK (SEQ ID NO: 391)

Chain 3 - MESO-A[MSLN]_L1 Light Chain
DVVLTQSPATLSLSPGERATLSCRASSSVSYMYWHQQKPDQSPKLLIYDTSNLASGVPVRFSGSGSGTDYTLTISSL
EPEDFAVYYCQQWSSYPPTFGGGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC (SEQ ID NO: 392)

>XENP30765 MESO-B[MSLN]_H0L0_Fab-[CD3]_H1.32_L1.47_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-B[MSLN]_H0L0_Fab_IgG1_pI(-)_Isosteric_A_/PVA_/S267K/L368D/K370S
QVQLQQSGPGLVTPSQTLSLTCAISGDSVSSNSATWNWIRQSPSRGLEWLGRTYYRSKWYNDYAVSVKSRMSINPDT
SKNQFSLQLNSVTPEDTAVYYCARGMMTYYYGMDVWGQGTTVTVSS/ASTKGPSVFPLAPSSKSTSGGTAALGCLVK
DYFPEPVTVSWNSGALTSGVHTFPAVLQSSGLYSLSSVVTVPSSSLGTQTYICNVNHKPSDTKVDKKVEPKSCDKTH
TCPPCPAPPVAGPSVFLFPPKPKDTLMISRTPEVTCVVVDVKHEDPEVKFNWYVDGVEVHNAKTKPREEEYNSTYRV
VSVLTVLHQDWLNGKEYKCKVSNKALPAPIEKTISKAKGQPREPQVYTLPPSREEMTKNQVSLTCDVSGFYPSDIAV
EWESDGQPENNYKTTPPVLDSDGSFFLYSKLTVDKSRWEQGDVFSCSVMHEALHNHYTQKSLSLSPGK (SEQ ID
NO: 393)

Chain 2 - [CD3]_H1.32_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKANNYATYYADSVKGRFTISRDDS
KNTLYLQMNSLRAEDTAVYYCVRHGNFGDSYVSWFAYWGQGTLVTVSS/GKPGSGKPGSGKPGSGKPGS/QAVVTQE
PSLTVSPGGTVTLTCGSSTGAVTTSNYANWVQQKPGKSPRGLIGGTNKRAPGVPARFSGSLLGGKAALTISGAQPED
EADYYCALWYSNHWVFGGGTKLTVL/EPKSSDKTHTCPPCPAPPVAGPSVFLFPPKPKDTLMISRTPEVTCVVVDVK
HEDPEVKFNWYVDGVEVHNAKTKPREEQYNSTYRVVSVLTVLHQDWLNGKEYKCKVSNKALPAPIEKTISKAKGQPR
EPQVYTLPPSREQMTKNQVKLTCLVKGFYPSDIAVEWESNGQPENNYKTTPPVLDSDGSFFLYSKLTVDKSRWQQGN
VFSCSVMHEALHNHYTQKSLSLSPGK (SEQ ID NO: 394)

Chain 3 - MESO-B[MSLN]_L0 Light Chain
QPVLTQSSSLSASPGASASLTCTLRSGINVGPYRIYWYQQKPGSPPQYLLNYKSDSDKQQGSGVPSRFSGSKDASAN
AGVLLISGLRSEDEADYYCMIWHSSAAVFGGGTQLTVL/GQPKAAPSVTLFPPSSEELQANKATLVCLISDFYPGAV
TVAWKADSSPVKAGVETTTPSKQSNNKYAASSYLSLTPEQWKSHRSYSCQVTHEGSTVEKTVAPTECS (SEQ ID
NO: 395)

Figure 24B

>XENP31701 MESO-C[MSLN]_H1L1_Fab-[CD3]_H1.32_L1.47_scFv{GKPGS}4-IgG1_pI(-
)_Isosteric_A_/PVA_/S267K/L368D/K370S-Fc(216)_IgG1_C220S/PVA_/S267K/S364K/E357Q Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
396)

Chain 2 - [CD3]_H1.32_L1.47_scFv{GKPGS}4_Fc(216)_IgG1_C220S/PVA_/S267K/S364K/E357Q
EVQLVESGGGLVQPGGSLRLSCAASGFTFSTYAMNWVRQAPGKGLEWVGRIRSKANNYATYYADSVKGRFTISRDDS
KNTLYLQMNSLRAEDTAVYYCVRHGNFGDSYVSWFAYWGQGTLVTVSS/GKPGSGKPGSGKPGSGKPGS/QAVVTQE
PSLTVSPGGTVTLTCGSSTGAVTTSNYANWVQQKPGKSPRGLIGGTNKRAPGVPARFSGSLLGGKAALTISGAQPED
EADYYCALWYSNHWVFGGGTKLTVL/EPKSSDKTHTCPPCPAPPVAGPSVFLFPPKPKDTLMISRTPEVTCVVVDVK
HEDPEVKFNWYVDGVEVHNAKTKPREEQYNSTYRVVSVLTVLHQDWLNGKEYKCKVSNKALPAPIEKTISKAKGQPR
EPQVYTLPPSREQMTKNQVKLTCLVKGFYPSDIAVEWESNGQPENNYKTTPPVLDSDGSFFLYSKLTVDKSRWQQGN
VFSCSVMHEALHNHYTQKSLSLSPGK (SEQ ID NO: 397)

Chain 3 - MESO-C[MSLN]_L1 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
398)

Figure 25A

>XENP33969 MESO-C[MSLN]_H1.14_L1.14_Fab-[CD3]_L1.47_H1.32_scFv(GKPGS)4-IgG1_pI(-
)_Isosteric_A_PVA_/S267K/L368D/K370S-Fc(216)_IgG1_C220S/PVA_/S267K/S364K/E357Q

Chain 1 - MESO-C[MSLN]_H1.14_IgG1_pI(-)_Isosteric_A_PVA_/S267K/L368D/K370S
QVQLVQSGAEVKKPGASVKVSCKASGYTFTSYWMHWVRQAPGQGLEWMGWIHPQSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
399)

Chain 2 - [CD3]_L1.47_H1.32_scFv(GKPGS)4_Fc(216)_IgG1_C220S/PVA_/S267K/S364K/E357Q
QAVVTQEPSLTVSPGGTVTLTCGSSTGAVTTSNYANWVQQKPGKSPRGLIGGTNKRAPGVPARFSGSLLGGKAALTI
SGAQPEDEADYYCALWYSNHWVFGGGTKLTVL/GKPGSGKPGSGKPGSGKPGS/EVQLVESGGGLVQPGGSLRLSCA
ASGFTFSTYAMNWVRQAPGKGLEWVGRIRSKANNYATYYADSVKGRFTISRDDSKNTLYLQMNSLRAEDTAVYYCVR
HGNFGDSYVSWFAYWGQGTLVTVSS/EPKSSDKTHTCPPCPAPPVAGPSVFLFPPKPKDTLMISRTPEVTCVVVDVK
HEDPEVKFNWYVDGVEVHNAKTKPREEQYNSTYRVVSVLTVLHQDWLNGKEYKCKVSNKALPAPIEKTISKAKGQPR
EPQVYTLPPSREQMTKNQVKLTCLVKGFYPSDIAVEWESNGQPENNYKTTPPVLDSDGSFFLYSKLTVDKSRWQQGN
VFSCSVMHEALHNHYTQKSLSLSPGK (SEQ ID NO: 400)

Chain 3 - MESO-C[MSLN]_L1.14 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSSFPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
401)

>XENP33971 MESO-C[MSLN]_H1.15_L1.14_Fab-[CD3]_L1.47_H1.32_scFv(GKPGS)4-IgG1_pI(-
)_Isosteric_A_PVA_/S267K/L368D/K370S-Fc(216)_IgG1_C220S/PVA_/S267K/S364K/E357Q

Chain 1 - MESO-C[MSLN]_H1.15_IgG1_pI(-)_Isosteric_A_PVA_/S267K/L368D/K370S
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCARIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
402)

Chain 2 - [CD3]_L1.47_H1.32_scFv(GKPGS)4_Fc(216)_IgG1_C220S/PVA_/S267K/S364K/E357Q
QAVVTQEPSLTVSPGGTVTLTCGSSTGAVTTSNYANWVQQKPGKSPRGLIGGTNKRAPGVPARFSGSLLGGKAALTI
SGAQPEDEADYYCALWYSNHWVFGGGTKLTVL/GKPGSGKPGSGKPGSGKPGS/EVQLVESGGGLVQPGGSLRLSCA
ASGFTFSTYAMNWVRQAPGKGLEWVGRIRSKANNYATYYADSVKGRFTISRDDSKNTLYLQMNSLRAEDTAVYYCVR
HGNFGDSYVSWFAYWGQGTLVTVSS/EPKSSDKTHTCPPCPAPPVAGPSVFLFPPKPKDTLMISRTPEVTCVVVDVK
HEDPEVKFNWYVDGVEVHNAKTKPREEQYNSTYRVVSVLTVLHQDWLNGKEYKCKVSNKALPAPIEKTISKAKGQPR
EPQVYTLPPSREQMTKNQVKLTCLVKGFYPSDIAVEWESNGQPENNYKTTPPVLDSDGSFFLYSKLTVDKSRWQQGN
VFSCSVMHEALHNHYTQKSLSLSPGK (SEQ ID NO: 403)

Chain 3 - MESO-C[MSLN]_L1.14 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSSFPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
404)

Figure 25B

>XENP33973 MESO-C[MSLN]_H1.16_L1.14_Fab-[CD3]_L1.47_H1.32_scFv(GKPGS)4-IgG1_pI(-)_Isosteric_A_PVA_/S267K/L368D/K370S-Fc(216)_IgG1_C220S/PVA_/S267K/S364K/E357Q

Chain 1 - MESO-C[MSLN]_H1.16_IgG1_pI(-)_Isosteric_A_PVA_/S267K/L368D/K370S
QVQLVQSGAEVKKPGASVKVSCKASGYTFTSYWMHWVRQAPGQGLEWMGWIHPQSDNTIYYEKFQGRVTMTVDKSIS
TAYMELSRLRSDDTAVYYCARIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
405)

Chain 2 - [CD3]_L1.47_H1.32_scFv(GKPGS)4_Fc(216)_IgG1_C220S/PVA_/S267K/S364K/E357Q
QAVVTQEPSLTVSPGGTVTLTCGSSTGAVTTSNYANWVQQKPGKSPRGLIGGTNKRAPGVPARFSGSLLGGKAALTI
SGAQPEDEADYYCALWYSNHWVFGGGTKLTVL/GKPGSGKPGSGKPGSGKPGS/EVQLVESGGGLVQPGGSLRLSCA
ASGFTFSTYAMNWVRQAPGKGLEWVGRIRSKANNYATYYADSVKGRFTISRDDSKNTLYLQMNSLRAEDTAVYYCVR
HGNFGDSYVSWFAYWGQGTLVTVSS/EPKSSDKTHTCPPCPAPPVAGPSVFLFPPKPKDTLMISRTPEVTCVVVDVK
HEDPEVKFNWYVDGVEVHNAKTKPREEQYNSTYRVVSVLTVLHQDWLNGKEYKCKVSNKALPAPIEKTISKAKGQPR
EPQVYTLPPSREQMTKNQVKLTCLVKGFYPSDIAVEWESNGQPENNYKTTPPVLDSDGSFFLYSKLTVDKSRWQQGN
VFSCSVMHEALHNHYTQKSLSLSPGK (SEQ ID NO: 406)

Chain 3 - MESO-C[MSLN]_L1.14 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSSFPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
407)

Figure 26

>XENP16251 MESO-A[MSLN]_H1.1_L1_Fab-[CD3]_H1.33_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-A[MSLN]_H1.1_L1_Fab_IgG1_pI(-)_Isosteric_A_/PVA_/S267K/L368D/K370S
EVQLVESGGGLVQPGGSLKLSCAASGFDFSRYWMSWVRQAPGKGLEWVSEINPDSSTIVYTPSVKGRFTISRDNAKN
SLYLQMNSLRAEDTAVYYCARRGSHYYGYRTGYFDVWGAGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSDTKVDKKVEPKSCDKT
HTCPPCPAPPVAGPSVFLFPPKPKDTLMISRTPEVTCVVVDVKHEDPEVKFNWYVDGVEVHNAKTKPREEEYNSTYR
VVSVLTVLHQDWLNGKEYKCKVSNKALPAPIEKTISKAKGQPREPQVYTLPPSREEMTKNQVSLTCDVSGFYPSDIA
VEWESDGQPENNYKTTPPVLDSDGSFFLYSKLTVDKSRWEQGDVFSCSVMHEALHNHYTQKSLSLSPGK (SEQ ID
NO: 408)

Chain 2 - [CD3]_H1.33_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDS
KNTLYLQMNSLRAEDTAVYYCVRHGNFGDSYVSWFDYWGQGTLVTVSS/GKPGSGKPGSGKPGSGKPGS/QAVVTQE
PSLTVSPGGTVTLTCGSSTGAVTTSNYANWVQQKPGKSPRGLIGGTNKRAPGVPARFSGSLLGGKAALTISGAQPED
EADYYCALWYSNHWVFGGGTKLTVL/EPKSSDKTHTCPPCPAPPVAGPSVFLFPPKPKDTLMISRTPEVTCVVVDVK
HEDPEVKFNWYVDGVEVHNAKTKPREEQYNSTYRVVSVLTVLHQDWLNGKEYKCKVSNKALPAPIEKTISKAKGQPR
EPQVYTLPPSREQMTKNQVKLTCLVKGFYPSDIAVEWESNGQPENNYKTTPPVLDSDGSFFLYSKLTVDKSRWQQGN
VFSCSVMHEALHNHYTQKSLSLSPGK (SEQ ID NO: 409)

Chain 3 - MESO-A[MSLN]_L1 Light Chain
DVVLTQSPATLSLSPGERATLSCRASSSVSYMYWHQQKPDQSPKLLIYDTSNLASGVPVRFSGSGSGTDYTLTISSL
EPEDFAVYYCQQWSSYPPTFGGGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC (SEQ ID NO: 410)

>XENP16834 MESO-B[MSLN]_H0L0_Fab-[CD3]_H1.33_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-B[MSLN]_H0L0_Fab_IgG1_pI(-)_Isosteric_A_/PVA_/S267K/L368D/K370S
QVQLQQSGPGLVTPSQTLSLTCAISGDSVSSNSATWNWIRQSPSRGLEWLGRTYYRSKWYNDYAVSVKSRMSINPDT
SKNQFSLQLNSVTPEDTAVYYCARGMMTYYYGMDVWGQGTTVTVSS/ASTKGPSVFPLAPSSKSTSGGTAALGCLVK
DYFPEPVTVSWNSGALTSGVHTFPAVLQSSGLYSLSSVVTVPSSSLGTQTYICNVNHKPSDTKVDKKVEPKSCDKTH
TCPPCPAPPVAGPSVFLFPPKPKDTLMISRTPEVTCVVVDVKHEDPEVKFNWYVDGVEVHNAKTKPREEEYNSTYRV
VSVLTVLHQDWLNGKEYKCKVSNKALPAPIEKTISKAKGQPREPQVYTLPPSREEMTKNQVSLTCDVSGFYPSDIAV
EWESDGQPENNYKTTPPVLDSDGSFFLYSKLTVDKSRWEQGDVFSCSVMHEALHNHYTQKSLSLSPGK (SEQ ID
NO: 411)

Chain 2 - [CD3]_H1.33_L1.47_scFv(GKPGS)4_Fc(216)_IgG1_C220S/PVA_/S267K/S364K/E357Q
EVQLVESGGGLVQPGGSLRLSCAASGFTFSTYAMNWVRQAPGKGLEWVGRIRSKYNNYATYYADSVKGRFTISRDDS
KNTLYLQMNSLRAEDTAVYYCVRHGNFGDSYVSWFDYWGQGTLVTVSS/GKPGSGKPGSGKPGSGKPGS/QAVVTQE
PSLTVSPGGTVTLTCGSSTGAVTTSNYANWVQQKPGKSPRGLIGGTNKRAPGVPARFSGSLLGGKAALTISGAQPED
EADYYCALWYSNHWVFGGGTKLTVL/EPKSSDKTHTCPPCPAPPVAGPSVFLFPPKPKDTLMISRTPEVTCVVVDVK
HEDPEVKFNWYVDGVEVHNAKTKPREEQYNSTYRVVSVLTVLHQDWLNGKEYKCKVSNKALPAPIEKTISKAKGQPR
EPQVYTLPPSREQMTKNQVKLTCLVKGFYPSDIAVEWESNGQPENNYKTTPPVLDSDGSFFLYSKLTVDKSRWQQGN
VFSCSVMHEALHNHYTQKSLSLSPGK (SEQ ID NO: 412)

Chain 3 - MESO-B[MSLN]_L0 Light Chain
QPVLTQSSSLSASPGASASLTCTLRSGINVGPYRIYWYQQKPGSPPQYLLNYKSDSDKQQGSGVPSRFSGSKDASAN
AGVLLISGLRSEDEADYYCMIWHSSAAVFGGGTQLTVL/GQPKAAPSVTLFPPSSEELQANKATLVCLISDFYPGAV
TVAWKADSSPVKAGVETTTPSKQSNNKYAASSYLSLTPEQWKSHRSYSCQVTHEGSTVEKTVAPTECS (SEQ ID
NO: 413)

Figure 27

>XENP16252 MESO-A[MSLN]_H1.1_L1_Fab-[CD3]_H1.31_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-A[MSLN]_H1.1_L1_Fab_IgG1_pI(-)_Isosteric_A_/PVA_/S267K/L368D/K370S

EVQLVESGGGLVQPGGSLKLSCAASGFDFSRYWMSWVRQAPGKGLEWVSEINPDSSTIVYTPSVKGRFTISRDNAKN
SLYLQMNSLRAEDTAVYYCARRGSHYYGYRTGYFDVWGAGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSDTKVDKKVEPKSCDKT
HTCPPCPAPPVAGPSVFLFPPKPKDTLMISRTPEVTCVVVDVKHEDPEVKFNWYVDGVEVHNAKTKPREEEYNSTYR
VVSVLTVLHQDWLNGKEYKCKVSNKALPAPIEKTISKAKGQPREPQVYTLPPSREEMTKNQVSLTCDVSGFYPSDIA
VEWESDGQPENNYKTTPPVLDSDGSFFLYSKLTVDKSRWEQGDVFSCSVMHEALHNHYTQKSLSLSPGK (SEQ ID
NO: 414)

Chain 2 - [CD3]_H1.31_L1.47_scFv(GKPGS)4_Fc(216)_IgG1_C220S/PVA_/S267K/S364K/E357Q

EVQLVESGGGLVQPGGSLRLSCAASGFTFSTYAMSWVRQAPGKGLEWVGRIRSKYNNYATYYADSVKGRFTISRDDS
KNTLYLQMNSLRAEDTAVYYCVRHGNFGDSYVSWFAYWGQGTLVTVSS/GKPGSGKPGSGKPGSGKPGS/QAVVTQE
PSLTVSPGGTVTLTCGSSTGAVTTSNYANWVQQKPGKSPRGLIGGTNKRAPGVPARFSGSLLGGKAALTISGAQPED
EADYYCALWYSNHWVFGGGTKLTVL/EPKSSDKTHTCPPCPAPPVAGPSVFLFPPKPKDTLMISRTPEVTCVVVDVK
HEDPEVKFNWYVDGVEVHNAKTKPREEQYNSTYRVVSVLTVLHQDWLNGKEYKCKVSNKALPAPIEKTISKAKGQPR
EPQVYTLPPSREQMTKNQVKLTCLVKGFYPSDIAVEWESNGQPENNYKTTPPVLDSDGSFFLYSKLTVDKSRWQQGN
VFSCSVMHEALHNHYTQKSLSLSPGK (SEQ ID NO: 415)

Chain 3 - MESO-A[MSLN]_L1 Light Chain

DVVLTQSPATLSLSPGERATLSCRASSSVSYMYWHQQKPDQSPKLLIYDTSNLASGVPVRFSGSGSGTDYTLTISSL
EPEDFAVYYCQQWSSYPPTFGGGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC (SEQ ID NO: 416)

>XENP16835 MESO-B[MSLN]_H0L0_Fab-[CD3]_H1.31_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-B[MSLN]_H0L0_Fab_IgG1_pI(-)_Isosteric_A_/PVA_/S267K/L368D/K370S

QVQLQQSGPGLVTPSQTLSLTCAISGDSVSSNSATWNWIRQSPSRGLEWLGRTYYRSKWYNDYAVSVKSRMSINPDT
SKNQFSLQLNSVTPEDTAVYYCARGMMTYYYGMDVWGQGTTVTVSS/ASTKGPSVFPLAPSSKSTSGGTAALGCLVK
DYFPEPVTVSWNSGALTSGVHTFPAVLQSSGLYSLSSVVTVPSSSLGTQTYICNVNHKPSDTKVDKKVEPKSCDKTH
TCPPCPAPPVAGPSVFLFPPKPKDTLMISRTPEVTCVVVDVKHEDPEVKFNWYVDGVEVHNAKTKPREEEYNSTYRV
VSVLTVLHQDWLNGKEYKCKVSNKALPAPIEKTISKAKGQPREPQVYTLPPSREEMTKNQVSLTCDVSGFYPSDIAV
EWESDGQPENNYKTTPPVLDSDGSFFLYSKLTVDKSRWEQGDVFSCSVMHEALHNHYTQKSLSLSPGK (SEQ ID
NO: 417)

Chain 2 - [CD3]_H1.31_L1.47_scFv(GKPGS)4_Fc(216)_IgG1_C220S/PVA_/S267K/S364K/E357Q

EVQLVESGGGLVQPGGSLRLSCAASGFTFSTYAMSWVRQAPGKGLEWVGRIRSKYNNYATYYADSVKGRFTISRDDS
KNTLYLQMNSLRAEDTAVYYCVRHGNFGDSYVSWFAYWGQGTLVTVSS/GKPGSGKPGSGKPGSGKPGS/QAVVTQE
PSLTVSPGGTVTLTCGSSTGAVTTSNYANWVQQKPGKSPRGLIGGTNKRAPGVPARFSGSLLGGKAALTISGAQPED
EADYYCALWYSNHWVFGGGTKLTVL/EPKSSDKTHTCPPCPAPPVAGPSVFLFPPKPKDTLMISRTPEVTCVVVDVK
HEDPEVKFNWYVDGVEVHNAKTKPREEQYNSTYRVVSVLTVLHQDWLNGKEYKCKVSNKALPAPIEKTISKAKGQPR
EPQVYTLPPSREQMTKNQVKLTCLVKGFYPSDIAVEWESNGQPENNYKTTPPVLDSDGSFFLYSKLTVDKSRWQQGN
VFSCSVMHEALHNHYTQKSLSLSPGK (SEQ ID NO: 418)

Chain 3 - MESO-B[MSLN]_L0 Light Chain

QPVLTQSSSLSASPGASASLTCTLRSGINVGPYRIYWYQQKPGSPPQYLLNYKSDSDKQQGSGVPSRFSGSKDASAN
AGVLLISGLRSEDEADYYCMIWHSSAAVFGGGTQLTVL/GQPKAAPSVTLFPPSSEELQANKATLVCLISDFYPGAV
TVAWKADSSPVKAGVETTTPSKQSNNKYAASSYLSLTPEQWKSHRSYSCQVTHEGSTVEKTVAPTECS (SEQ ID
NO: 419)

Figure 28A

>XENP31063 MESO-A[MSLN]_H1.1_L1_Fab-MESO-A[MSLN]_H1.1_L1_Fab_[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-A[MSLN]_H1.1_IgG1_pI(-)_Isosteric_A_/PVA_/S267K/L368D/K370S
EVQLVESGGGLVQPGGSLKLSCAASGFDFSRYWMSWVRQAPGKGLEWVSEINPDSSTIVYTPSVKGRFTISRDNAKNSLYLQ
MNSLRAEDTAVYYCARRGSHYYGYRTGYFDVWGAGTTVTVSS/ASTKGPSVFPLAPSSKSTSGGTAALGCLVKDYFPEPVTV
SWNSGALTSGVHTFPAVLQSSGLYSLSSVVTVPSSSLGTQTYICNVNHKPSDTKVDKKVEPKSCDKTHTCPPCPAPPVAGPS
VFLFPPKPKDTLMISRTPEVTCVVVDVKHEDPEVKFNWYVDGVEVHNAKTKPREEEYNSTYRVVSVLTVLHQDWLNGKEYKC
KVSNKALPAPIEKTISKAKGQPREPQVYTLPPSREEMTKNQVSLTCDVSGFYPSDIAVEWESDGQPENNYKTTPPVLDSDGS
FFLYSKLTVDKSRWEQGDVFSCSVMHEALHNHYTQKSLSLSPGK (SEQ ID NO: 420)

Chain 2 - MESO-A[MSLN]_H1.1_[CD3]_H1.30_L1.47_scFv(GKPGS)4_Fc(216)_IgG1_C220S/PVA_/S267K/S364K/E357Q
EVQLVESGGGLVQPGGSLKLSCAASGFDFSRYWMSWVRQAPGKGLEWVSEINPDSSTIVYTPSVKGRFTISRDNAKNSLYLQ
MNSLRAEDTAVYYCARRGSHYYGYRTGYFDVWGAGTTVTVSS/ASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKKVEPKSC/GGGGSGGGGS/EVQLVE
SGGGLVQPGGSLRLSCAASGFTFSTYAMNWVRQAPGKGLEWVGRIRSKYNNYATYYADSVKGRFTISRDDSKNTLYLQMNSL
RAEDTAVYYCVRHGNFGDSYVSWFAYWGQGTLVTVSS/GKPGSGKPGSGKPGSGKPGS/QAVVTQEPSLTVSPGGTVTLTCG
SSTGAVTTSNYANWVQQKPGKSPRGLIGGTNKRAPGVPARFSGSLLGGKAALTISGAQPEDEADYYCALWYSNHWVFGGGTK
LTVL/GGGGSGGGGS/KTHTCPPCPAPPVAGPSVFLFPPKPKDTLMISRTPEVTCVVVDVKHEDPEVKFNWYVDGVEVHNAK
TKPREEQYNSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK (SEQ
ID NO: 421)

Chain 3 - MESO-A[MSLN]_L1 Light Chain
DVVLTQSPATLSLSPGERATLSCRASSSVSYMYWHQQKPDQSPKLLIYDTSNLASGVPVRFSGSGSGTDYTLTISSLEPEDF
AVYYCQQWSSYPPTFGGGTKLEIK/RTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC (SEQ ID NO: 422)

>XENP31067 MESO-B[MSLN]_H0L0_Fab-MESO-B[MSLN]_H0L0_Fab_[CD3]_H1.30_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-B[MSLN]_H0_IgG1_pI(-)_Isosteric_A_/PVA_/S267K/L368D/K370S
QVQLQQSGPGLVTPSQTLSLTCAISGDSVSSNSATWNWIRQSPSRGLEWLGRTYYRSKWYNDYAVSVKSRMSINPDTSKNQF
SLQLNSVTPEDTAVYYCARGMMTYYYGMDVWGQGTTVTVSS/ASTKGPSVFPLAPSSKSTSGGTAALGCLVKDYFPEPVTVS
WNSGALTSGVHTFPAVLQSSGLYSLSSVVTVPSSSLGTQTYICNVNHKPSDTKVDKKVEPKSCDKTHTCPPCPAPPVAGPSV
FLFPPKPKDTLMISRTPEVTCVVVDVKHEDPEVKFNWYVDGVEVHNAKTKPREEEYNSTYRVVSVLTVLHQDWLNGKEYKCK
VSNKALPAPIEKTISKAKGQPREPQVYTLPPSREEMTKNQVSLTCDVSGFYPSDIAVEWESDGQPENNYKTTPPVLDSDGSF
FLYSKLTVDKSRWEQGDVFSCSVMHEALHNHYTQKSLSLSPGK (SEQ ID NO: 423)

Chain 2 - MESO-B[MSLN]_H0_[CD3]_H1.30_L1.47_scFv(GKPGS)4_Fc(216)_IgG1_C220S/PVA_/S267K/S364K/E357Q
QVQLQQSGPGLVTPSQTLSLTCAISGDSVSSNSATWNWIRQSPSRGLEWLGRTYYRSKWYNDYAVSVKSRMSINPDTSKNQF
SLQLNSVTPEDTAVYYCARGMMTYYYGMDVWGQGTTVTVSS/ASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKKVEPKSC/GGGGSGGGGS/EVQLVES
GGGLVQPGGSLRLSCAASGFTFSTYAMNWVRQAPGKGLEWVGRIRSKYNNYATYYADSVKGRFTISRDDSKNTLYLQMNSLR
AEDTAVYYCVRHGNFGDSYVSWFAYWGQGTLVTVSS/GKPGSGKPGSGKPGSGKPGS/QAVVTQEPSLTVSPGGTVTLTCGS
STGAVTTSNYANWVQQKPGKSPRGLIGGTNKRAPGVPARFSGSLLGGKAALTISGAQPEDEADYYCALWYSNHWVFGGGTKL
TVL/GGGGSGGGGS/KTHTCPPCPAPPVAGPSVFLFPPKPKDTLMISRTPEVTCVVVDVKHEDPEVKFNWYVDGVEVHNAKT
KPREEQYNSTYRVVSVLTVLHQDWLNGKEYKCKVSNKALPAPIEKTISKAKGQPREPQVYTLPPSREQMTKNQVKLTCLVKG
FYPSDIAVEWESNGQPENNYKTTPPVLDSDGSFFLYSKLTVDKSRWQQGNVFSCSVMHEALHNHYTQKSLSLSPGK (SEQ
ID NO: 424)

Figure 28B

Chain 3 - MESO-B[MSLN]_L0 Light Chain
QPVLTQSSSLSASPGASASLTCTLRSGINVGPYRIYWYQQKPGSPPQYLLNYKSDSDKQQGSGVPSRFSGSKDASAN
AGVLLISGLRSEDEADYYCMIWHSSAAVFGGGTQLTVL/GQPKAAPSVTLFPPSSEELQANKATLVCLISDFYPGAV
TVAWKADSSPVKAGVETTTPSKQSNNKYAASSYLSLTPEQWKSHRSYSCQVTHEGSTVEKTVAPTECS (SEQ ID
NO: 425)

>XENP31705 MESO-C[MSLN]_H1L1_Fab-MESO-C[MSLN]_H1L1_Fab_(G4S)2_[CD3]_H1.30_L1.47_scFv(GKPGS)4-
IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
426)

Chain 2 - MESO-
C[MSLN]_H1_[CD3]_H1.30_L1.47_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/EVQLVESGGGLVQPGGSLRLSCAASGFTFSTYAMNWVRQAPGKGLEWVGRIRSKYNNYATYYADSVKGRFTI
SRDDSKNTLYLQMNSLRAEDTAVYYCVRHGNFGDSYVSWFAYWGQGTLVTVSS/GKPGSGKPGSGKPGSGKPGS/QA
VVTQEPSLTVSPGGTVTLTCGSSTGAVTTSNYANWVQQKPGKSPRGLIGGTNKRAPGVPARFSGSLLGGKAALTISG
AQPEDEADYYCALWYSNHWVFGGGTKLTVL/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 427)

Chain 3 - MESO-C[MSLN]_L1 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
428)

Figure 29A

>XENP31451 MESO-A[MSLN]_H1.1_L1_Fab-MESO-
A[MSLN]_H1.1_L1_Fab_(G4S)2_[CD3]_L1.47_H1.30_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-A[MSLN]_H1.1_IgG1_pI(-)_Isosteric_A_/PVA_/S267K/L368D/K370S
EVQLVESGGGLVQPGGSLKLSCAASGFDFSRYWMSWVRQAPGKGLEWVSEINPDSSTIVYTPSVKGRFTISRDNAKN
SLYLQMNSLRAEDTAVYYCARRGSHYYGYRTGYFDVWGAGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSDTKVDKKVEPKSCDKT
HTCPPCPAPPVAGPSVFLFPPKPKDTLMISRTPEVTCVVVDVKHEDPEVKFNWYVDGVEVHNAKTKPREEEYNSTYR
VVSVLTVLHQDWLNGKEYKCKVSNKALPAPIEKTISKAKGQPREPQVYTLPPSREEMTKNQVSLTCDVSGFYPSDIA
VEWESDGQPENNYKTTPPVLDSDGSFFLYSKLTVDKSRWEQGDVFSCSVMHEALHNHYTQKSLSLSPGK (SEQ ID
NO: 429)

**Chain 2 - MESO-
A[MSLN]_H1.1_(G4S)2_[CD3]_L1.47_H1.30_scFv(GKPGS)4_Fc(216)_IgG1_C220S/PVA_/S267K/S364K/E357Q**
EVQLVESGGGLVQPGGSLKLSCAASGFDFSRYWMSWVRQAPGKGLEWVSEINPDSSTIVYTPSVKGRFTISRDNAKN
SLYLQMNSLRAEDTAVYYCARRGSHYYGYRTGYFDVWGAGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKKVEPKSC/GG
GGSGGGGS/QAVVTQEPSLTVSPGGTVTLTCGSSTGAVTTSNYANWVQQKPGKSPRGLIGGTNKRAPGVPARFSGSL
LGGKAALTISGAQPEDEADYYCALWYSNHWVFGGGTKLTVL/GKPGSGKPGSGKPGSGKPGS/EVQLVESGGGLVQP
GGSLRLSCAASGFTFSTYAMNWVRQAPGKGLEWVGRIRSKYNNYATYYADSVKGRFTISRDDSKNTLYLQMNSLRAE
DTAVYYCVRHGNFGDSYVSWFAYWGQGTLVTVSS/GGGGSGGGGS/KTHTCPPCPAPPVAGPSVFLFPPKPKDTLMI
SRTPEVTCVVVDVKHEDPEVKFNWYVDGVEVHNAKTKPREEQYNSTYRVVSVLTVLHQDWLNGKEYKCKVSNKALPA
PIEKTISKAKGQPREPQVYTLPPSREQMTKNQVKLTCLVKGFYPSDIAVEWESNGQPENNYKTTPPVLDSDGSFFLY
SKLTVDKSRWQQGNVFSCSVMHEALHNHYTQKSLSLSPGK (SEQ ID NO: 430)

Chain 3 - MESO-A[MSLN]_L1 Light Chain
DVVLTQSPATLSLSPGERATLSCRASSSVSYMYWHQQKPDQSPKLLIYDTSNLASGVPVRFSGSGSGTDYTLTISSL
EPEDFAVYYCQQWSSYPPTFGGGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC (SEQ ID NO: 431)

>XENP31452 MESO-B[MSLN]_H0L0_Fab-MESO-B[MSLN]_H0L0_Fab_(G4S)2_[CD3]_L1.47_H1.30_scFv(GKPGS)4-
IgG1_pI(-)_Isosteric_A_/PVA_/S267K/L368D/K370S-Fc(216)_IgG1_C220S/PVA_/S267K/S364K/E357Q

Chain 1 - MESO-B[MSLN]_H0_IgG1_pI(-)_Isosteric_A_/PVA_/S267K/L368D/K370S
QVQLQQSGPGLVTPSQTLSLTCAISGDSVSSNSATWNWIRQSPSRGLEWLGRTYYRSKWYNDYAVSVKSRMSINPDT
SKNQFSLQLNSVTPEDTAVYYCARGMMTYYYGMDVWGQGTTVTVSS/ASTKGPSVFPLAPSSKSTSGGTAALGCLVK
DYFPEPVTVSWNSGALTSGVHTFPAVLQSSGLYSLSSVVTVPSSSLGTQTYICNVNHKPSDTKVDKKVEPKSCDKTH
TCPPCPAPPVAGPSVFLFPPKPKDTLMISRTPEVTCVVVDVKHEDPEVKFNWYVDGVEVHNAKTKPREEEYNSTYRV
VSVLTVLHQDWLNGKEYKCKVSNKALPAPIEKTISKAKGQPREPQVYTLPPSREEMTKNQVSLTCDVSGFYPSDIAV
EWESDGQPENNYKTTPPVLDSDGSFFLYSKLTVDKSRWEQGDVFSCSVMHEALHNHYTQKSLSLSPGK (SEQ ID
NO: 432)

Figure 29B

Chain 2 - MESO-B[MSLN]_H0_(G4S)2_[CD3]_L1.47_H1.30_scFv(GKPGS)4_Fc(216)_IgG1_C220S/PVA_/S267K/S364K/E357Q

QVQLQQSGPGLVTPSQTLSLTCAISGDSVSSNSATWNWIRQSPSRGLEWLGRTYYRSKWYNDYAVSVKSRMSINPDT
SKNQFSLQLNSVTPEDTAVYYCARGMMTYYYGMDVWGQGTTVTVSS/ASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSC/GGG
GSGGGGS/QAVVTQEPSLTVSPGGTVTLTCGSSTGAVTTSNYANWVQQKPGKSPRGLIGGTNKRAPGVPARFSGSLL
GGKAALTISGAQPEDEADYYCALWYSNHWVFGGGTKLTVL/GKPGSGKPGSGKPGSGKPGS/EVQLVESGGGLVQPG
GSLRLSCAASGFTFSTYAMNWVRQAPGKGLEWVGRIRSKYNNYATYYADSVKGRFTISRDDSKNTLYLQMNSLRAED
TAVYYCVRHGNFGDSYVSWFAYWGQGTLVTVSS/GGGGSGGGGS/KTHTCPPCPAPPVAGPSVFLFPPKPKDTLMIS
RTPEVTCVVVDVKHEDPEVKFNWYVDGVEVHNAKTKPREEQYNSTYRVVSVLTVLHQDWLNGKEYKCKVSNKALPAP
IEKTISKAKGQPREPQVYTLPPSREQMTKNQVKLTCLVKGFYPSDIAVEWESNGQPENNYKTTPPVLDSDGSFFLYS
KLTVDKSRWQQGNVFSCSVMHEALHNHYTQKSLSLSPGK (SEQ ID NO: 433)

Chain 3 - MESO-B[MSLN]_L0 Light Chain

QPVLTQSSSLSASPGASASLTCTLRSGINVGPYRIYWYQQKPGSPPQYLLNYKSDSDKQQGSGVPSRFSGSKDASAN
AGVLLISGLRSEDEADYYCMIWHSSAAVFGGGTQLTVL/GQPKAAPSVTLFPPSSEELQANKATLVCLISDFYPGAV
TVAWKADSSPVKAGVETTTPSKQSNNKYAASSYLSLTPEQWKSHRSYSCQVTHEGSTVEKTVAPTECS (SEQ ID
NO: 434)

>XENP31713 MESO-C[MSLN]_H1L1_Fab-MESO-C[MSLN]_H1L1_Fab_(G4S)2_[CD3]_L1.47_H1.30_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S

QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
435)

Chain 2 - MESO-C[MSLN]_H1_[CD3]_L1.47_H1.30_scFv(GKPGS)4_Fc(216)_IgG1_C220S/PVA_/S267K/S364K/E357Q

QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKYNNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 436)

Chain 3 - MESO-C[MSLN]_L1 Light Chain

DIVMTQSPDSLAVSLGERATINCKASHDVGTSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
437)

Figure 30A

>XENP31064 MESO-A[MSLN]_H1.1_L1_Fab-MESO-A[MSLN]_H1.1_L1_Fab_[CD3]_H1.32_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-A[MSLN]_H1.1_IgG1_pI(-)_Isosteric_A_/PVA_/S267K/L368D/K370S
EVQLVESGGGLVQPGGSLKLSCAASGFDFSRYWMSWVRQAPGKGLEWVSEINPDSSTIVYTPSVKGRFTISRDNAKNSLYLQ
MNSLRAEDTAVYYCARRGSHYYGYRTGYFDVWGAGTTVTVSS/ASTKGPSVFPLAPSSKSTSGGTAALGCLVKDYFPEPVTV
SWNSGALTSGVHTFPAVLQSSGLYSLSSVVTVPSSSLGTQTYICNVNHKPSDTKVDKKVEPKSCDKTHTCPPCPAPPVAGPS
VFLFPPKPKDTLMISRTPEVTCVVVDVKHEDPEVKFNWYVDGVEVHNAKTKPREEEYNSTYRVVSVLTVLHQDWLNGKEYKC
KVSNKALPAPIEKTISKAKGQPREPQVYTLPPSREEMTKNQVSLTCDVSGFYPSDIAVEWESDGQPENNYKTTPPVLDSDGS
FFLYSKLTVDKSRWEQGDVFSCSVMHEALHNHYTQKSLSLSPGK (SEQ ID NO: 438)

Chain 2 - MESO-A[MSLN]_H1.1_[CD3]_H1.32_L1.47_scFv(GKPGS)4_Fc(216)_IgG1_C220S/PVA_/S267K/S364K/E357Q
EVQLVESGGGLVQPGGSLKLSCAASGFDFSRYWMSWVRQAPGKGLEWVSEINPDSSTIVYTPSVKGRFTISRDNAKNSLYLQ
MNSLRAEDTAVYYCARRGSHYYGYRTGYFDVWGAGTTVTVSS/ASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKKVEPKSC/GGGGSGGGGS/EVQLVE
SGGGLVQPGGSLRLSCAASGFTFSTYAMNWVRQAPGKGLEWVGRIRSKANNYATYYADSVKGRFTISRDDSKNTLYLQMNSL
RAEDTAVYYCVRHGNFGDSYVSWFAYWGQGTLVTVSS/GKPGSGKPGSGKPGSGKPGS/QAVVTQEPSLTVSPGGTVTLTCG
SSTGAVTTSNYANWVQQKPGKSPRGLIGGTNKRAPGVPARFSGSLLGGKAALTISGAQPEDEADYYCALWYSNHWVFGGGTK
LTVL/GGGGSGGGGS/KTHTCPPCPAPPVAGPSVFLFPPKPKDTLMISRTPEVTCVVVDVKHEDPEVKFNWYVDGVEVHNAK
TKPREEQYNSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK (SEQ
ID NO: 439)

Chain 3 - MESO-A[MSLN]_L1 Light Chain
DVVLTQSPATLSLSPGERATLSCRASSSVSYMYWHQQKPDQSPKLLIYDTSNLASGVPVRFSGSGSGTDYTLTISSLEPEDF
AVYYCQQWSSYPPTFGGGTKLEIK/RTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC (SEQ ID NO: 440)

>XENP31068 MESO-B[MSLN]_H0L0_Fab-MESO-B[MSLN]_H0L0_Fab_[CD3]_H1.32_L1.47_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-B[MSLN]_H0_IgG1_pI(-)_Isosteric_A_/PVA_/S267K/L368D/K370S
QVQLQQSGPGLVTPSQTLSLTCAISGDSVSSNSATWNWIRQSPSRGLEWLGRTYYRSKWYNDYAVSVKSRMSINPDTSKNQF
SLQLNSVTPEDTAVYYCARGMMTYYYGMDVWGQGTTVTVSS/ASTKGPSVFPLAPSSKSTSGGTAALGCLVKDYFPEPVTVS
WNSGALTSGVHTFPAVLQSSGLYSLSSVVTVPSSSLGTQTYICNVNHKPSDTKVDKKVEPKSCDKTHTCPPCPAPPVAGPSV
FLFPPKPKDTLMISRTPEVTCVVVDVKHEDPEVKFNWYVDGVEVHNAKTKPREEEYNSTYRVVSVLTVLHQDWLNGKEYKCK
VSNKALPAPIEKTISKAKGQPREPQVYTLPPSREEMTKNQVSLTCDVSGFYPSDIAVEWESDGQPENNYKTTPPVLDSDGSF
FLYSKLTVDKSRWEQGDVFSCSVMHEALHNHYTQKSLSLSPGK (SEQ ID NO: 441)

Chain 2 - MESO-B[MSLN]_H0_[CD3]_H1.32_L1.47_scFv(GKPGS)4_Fc(216)_IgG1_C220S/PVA_/S267K/S364K/E357Q
QVQLQQSGPGLVTPSQTLSLTCAISGDSVSSNSATWNWIRQSPSRGLEWLGRTYYRSKWYNDYAVSVKSRMSINPDTSKNQF
SLQLNSVTPEDTAVYYCARGMMTYYYGMDVWGQGTTVTVSS/ASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKKVEPKSC/GGGGSGGGGS/EVQLVES
GGGLVQPGGSLRLSCAASGFTFSTYAMNWVRQAPGKGLEWVGRIRSKANNYATYYADSVKGRFTISRDDSKNTLYLQMNSLR
AEDTAVYYCVRHGNFGDSYVSWFAYWGQGTLVTVSS/GKPGSGKPGSGKPGSGKPGS/QAVVTQEPSLTVSPGGTVTLTCGS
STGAVTTSNYANWVQQKPGKSPRGLIGGTNKRAPGVPARFSGSLLGGKAALTISGAQPEDEADYYCALWYSNHWVFGGGTKL
TVL/GGGGSGGGGS/KTHTCPPCPAPPVAGPSVFLFPPKPKDTLMISRTPEVTCVVVDVKHEDPEVKFNWYVDGVEVHNAKT
KPREEQYNSTYRVVSVLTVLHQDWLNGKEYKCKVSNKALPAPIEKTISKAKGQPREPQVYTLPPSREQMTKNQVKLTCLVKG
FYPSDIAVEWESNGQPENNYKTTPPVLDSDGSFFLYSKLTVDKSRWQQGNVFSCSVMHEALHNHYTQKSLSLSPGK (SEQ
ID NO: 442)

Figure 30B

Chain 3 - MESO-B[MSLN]_L0 Light Chain
QPVLTQSSSLSASPGASASLTCTLRSGINVGPYRIYWYQQKPGSPPQYLLNYKSDSDKQQGSGVPSRFSGSKDASAN
AGVLLISGLRSEDEADYYCMIWHSSAAVFGGGTQLTVL/GQPKAAPSVTLFPPSSEELQANKATLVCLISDFYPGAV
TVAWKADSSPVKAGVETTTPSKQSNNKYAASSYLSLTPEQWKSHRSYSCQVTHEGSTVEKTVAPTECS (SEQ ID
NO: 443)

**>XENP31709 MESO-C[MSLN]_H1L1_Fab-MESO-C[MSLN]_H1L1_Fab_(G4S)2_[CD3]_H1.32_L1.47_scFv(GKPGS)4-
IgG1_pI(-)_Isosteric_A_/PVA_/S267K/L368D/K370S-Fc(216)_IgG1_C220S/PVA_/S267K/S364K/E357Q**

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
444)

**Chain 2 - MESO-
C[MSLN]_H1_[CD3]_H1.32_L1.47_scFv(GKPGS)4_Fc(216)_IgG1_C220S/PVA_/S267K/S364K/E357Q**
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/EVQLVESGGGLVQPGGSLRLSCAASGFTFSTYAMNWVRQAPGKGLEWVGRIRSKANNYATYYADSVKGRFTI
SRDDSKNTLYLQMNSLRAEDTAVYYCVRHGNFGDSYVSWFAYWGQGTLVTVSS/GKPGSGKPGSGKPGSGKPGS/QA
VVTQEPSLTVSPGGTVTLTCGSSTGAVTTSNYANWVQQKPGKSPRGLIGGTNKRAPGVPARFSGSLLGGKAALTISG
AQPEDEADYYCALWYSNHWVFGGGTKLTVL/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 445)

Chain 3 - MESO-C[MSLN]_L1 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
446)

**>XENP32744 MESO-C[MSLN]_H1_L1.3_Fab-MESO-
C[MSLN]_H1_L1.3_Fab_(G4S)2_[CD3]_H1.32_L1.47_scFv(GKPGS)4-IgG1_pI(-
)_Isosteric_A_/PVA_/S267K/L368D/K370S-Fc(216)_IgG1_C220S/PVA_/S267K/S364K/E357Q**

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
447)

Figure 30C

Chain 2 - MESO-
C[MSLN]_H1_(G4S)2_[CD3]_H1.32_L1.47_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGMIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKKVEPKSC/GGGGSGGGGS/EVQLVESGGG
LVQPGGSLRLSCAASGFTFSTYAMNWVRQAPGKGLEWVGRIRSKANNYATYYADSVKGRFTISRDDSKNTLYLQMNSLRAED
TAVYYCVRHGNFGDSYVSWFAYWGQGTLVTVSS/GKPGSGKPGSGKPGSGKPGS/QAVVTQEPSLTVSPGGTVTLTCGSSTG
AVTTSNYANWVQQKPGKSPRGLIGGTNKRAPGVPARFSGSLLGGKAALTISGAQPEDEADYYCALWYSNHWVFGGGTKLTVL
/GGGGSGGGGS/KTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK (SEQ ID
NO: 448)

Chain 3 - MESO-C[MSLN]_L1.3 Light Chain
DIVMTQSPDSLAVSLGERATINCKASHSVGTSVAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 449)

>XENP32747 MESO-C[MSLN]_H1_L1.4_Fab-MESO-C[MSLN]_H1_L1.4_Fab_(G4S)2_[CD3]_H1.32_L1.47_scFv(GKPGS)4-
IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 450)

Chain 2 - MESO-
C[MSLN]_H1_(G4S)2_[CD3]_H1.32_L1.47_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGMIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKKVEPKSC/GGGGSGGGGS/EVQLVESGGG
LVQPGGSLRLSCAASGFTFSTYAMNWVRQAPGKGLEWVGRIRSKANNYATYYADSVKGRFTISRDDSKNTLYLQMNSLRAED
TAVYYCVRHGNFGDSYVSWFAYWGQGTLVTVSS/GKPGSGKPGSGKPGSGKPGS/QAVVTQEPSLTVSPGGTVTLTCGSSTG
AVTTSNYANWVQQKPGKSPRGLIGGTNKRAPGVPARFSGSLLGGKAALTISGAQPEDEADYYCALWYSNHWVFGGGTKLTVL
/GGGGSGGGGS/KTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK (SEQ ID
NO: 451)

Chain 3 - MESO-C[MSLN]_L1.4 Light Chain
DIVMTQSPDSLAVSLGERATINCKASHDVLTSVAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 452)

>XENP32750 MESO-C[MSLN]_H1_L1.5_Fab-MESO-C[MSLN]_H1_L1.5_Fab_(G4S)2_[CD3]_H1.32_L1.47_scFv(GKPGS)4-
IgG1_pI(-)_Isosteric_A_/PVA_/S267K/L368D/K370S-Fc(216)_IgG1_C220S/PVA_/S267K/S364K/E357Q

Figure 30D

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 453)

Chain 2 - MESO-
C[MSLN]_H1_(G4S)2_[CD3]_H1.32_L1.47_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGMIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKKVEPKSC/GGGGSGGGGS/EVQLVESGGG
LVQPGGSLRLSCAASGFTFSTYAMNWVRQAPGKGLEWVGRIRSKANNYATYYADSVKGRFTISRDDSKNTLYLQMNSLRAED
TAVYYCVRHGNFGDSYVSWFAYWGQGTLVTVSS/GKPGSGKPGSGKPGSGKPGS/QAVVTQEPSLTVSPGGTVTLTCGSSTG
AVTTSNYANWVQQKPGKSPRGLIGGTNKRAPGVPARFSGSLLGGKAALTISGAQPEDEADYYCALWYSNHWVFGGGTKLTVL
/GGGGSGGGGS/KTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK (SEQ ID
NO: 454)

Chain 3 - MESO-C[MSLN]_L1.5 Light Chain
DIVMTQSPDSLAVSLGERATINCKASHDVGTYVAWYQQKPGQSPKLLIYWASTRHTGVPDRFTGSGSGTDFTLTISSLQAED
VAVYFCQQYSSYPLTFGAGTKLEIK/RTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC (SEQ ID NO: 455)

>XENP32851 MESO-C[MSLN]_H1_L1.9_Fab-MESO-C[MSLN]_H1_L1.9_Fab_(G4S)2_[CD3]_H1.32_L1.47_scFv(GKPGS)4-
IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSDTKVDKKVEPKSCDKTHTCPPCPAPPVAGPSVFLF
PPKPKDTLMISRTPEVTCVVVDVKHEDPEVKFNWYVDGVEVHNAKTKPREEEYNSTYRVVSVLTVLHQDWLNGKEYKCKVSN
KALPAPIEKTISKAKGQPREPQVYTLPPSREEMTKNQVSLTCDVSGFYPSDIAVEWESDGQPENNYKTTPPVLDSDGSFFLY
SKLTVDKSRWEQGDVFSCSVMHEALHNHYTQKSLSLSPGK (SEQ ID NO: 456)

Chain 2 - MESO-
C[MSLN]_H1_(G4S)2_[CD3]_H1.32_L1.47_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGMIHPNSDNTIYYEKFQGRVTMTVDKSISTAYME
LSRLRSDDTAVYYCAIIITPVVPKFDYWGQGTLVTVSS/ASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKKVEPKSC/GGGGSGGGGS/EVQLVESGGG
LVQPGGSLRLSCAASGFTFSTYAMNWVRQAPGKGLEWVGRIRSKANNYATYYADSVKGRFTISRDDSKNTLYLQMNSLRAED
TAVYYCVRHGNFGDSYVSWFAYWGQGTLVTVSS/GKPGSGKPGSGKPGSGKPGS/QAVVTQEPSLTVSPGGTVTLTCGSSTG
AVTTSNYANWVQQKPGKSPRGLIGGTNKRAPGVPARFSGSLLGGKAALTISGAQPEDEADYYCALWYSNHWVFGGGTKLTVL
/GGGGSGGGGS/KTHTCPPCPAPPVAGPSVFLFPPKPKDTLMISRTPEVTCVVVDVKHEDPEVKFNWYVDGVEVHNAKTKPR
EEQYNSTYRVVSVLTVLHQDWLNGKEYKCKVSNKALPAPIEKTISKAKGQPREPQVYTLPPSREQMTKNQVKLTCLVKGFYP
SDIAVEWESNGQPENNYKTTPPVLDSDGSFFLYSKLTVDKSRWQQGNVFSCSVMHEALHNHYTQKSLSLSPGK (SEQ ID
NO: 457)

Figure 30E

Chain 3 - MESO-C[MSLN]_L1.9 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYYSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
458)

Figure 31A

>XENP31453 MESO-A[MSLN]_H1.1_L1_Fab-MESO-
A[MSLN]_H1.1_L1_Fab_(G4S)2_[CD3]_L1.47_H1.32_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-A[MSLN]_H1.1_IgG1_pI(-)_Isosteric_A_/PVA_/S267K/L368D/K370S
EVQLVESGGGLVQPGGSLKLSCAASGFDFSRYWMSWVRQAPGKGLEWVSEINPDSSTIVYTPSVKGRFTISRDNAKN
SLYLQMNSLRAEDTAVYYCARRGSHYYGYRTGYFDVWGAGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSDTKVDKKVEPKSCDKT
HTCPPCPAPPVAGPSVFLFPPKPKDTLMISRTPEVTCVVVDVKHEDPEVKFNWYVDGVEVHNAKTKPREEEYNSTYR
VVSVLTVLHQDWLNGKEYKCKVSNKALPAPIEKTISKAKGQPREPQVYTLPPSREEMTKNQVSLTCDVSGFYPSDIA
VEWESDGQPENNYKTTPPVLDSDGSFFLYSKLTVDKSRWEQGDVFSCSVMHEALHNHYTQKSLSLSPGK (SEQ ID
NO: 459)

**Chain 2 - MESO-
A[MSLN]_H1.1_(G4S)2_[CD3]_L1.47_H1.32_scFv(GKPGS)4_Fc(216)_IgG1_C220S/PVA_/S267K/S364K/E357Q**
EVQLVESGGGLVQPGGSLKLSCAASGFDFSRYWMSWVRQAPGKGLEWVSEINPDSSTIVYTPSVKGRFTISRDNAKN
SLYLQMNSLRAEDTAVYYCARRGSHYYGYRTGYFDVWGAGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKKVEPKSC/GG
GGSGGGGS/QAVVTQEPSLTVSPGGTVTLTCGSSTGAVTTSNYANWVQQKPGKSPRGLIGGTNKRAPGVPARFSGSL
LGGKAALTISGAQPEDEADYYCALWYSNHWVFGGGTKLTVL/GKPGSGKPGSGKPGSGKPGS/EVQLVESGGGLVQP
GGSLRLSCAASGFTFSTYAMNWVRQAPGKGLEWVGRIRSKANNYATYYADSVKGRFTISRDDSKNTLYLQMNSLRAE
DTAVYYCVRHGNFGDSYVSWFAYWGQGTLVTVSS/GGGGSGGGGS/KTHTCPPCPAPPVAGPSVFLFPPKPKDTLMI
SRTPEVTCVVVDVKHEDPEVKFNWYVDGVEVHNAKTKPREEQYNSTYRVVSVLTVLHQDWLNGKEYKCKVSNKALPA
PIEKTISKAKGQPREPQVYTLPPSREQMTKNQVKLTCLVKGFYPSDIAVEWESNGQPENNYKTTPPVLDSDGSFFLY
SKLTVDKSRWQQGNVFSCSVMHEALHNHYTQKSLSLSPGK (SEQ ID NO: 460)

Chain 3 - MESO-A[MSLN]_L1 Light Chain
DVVLTQSPATLSLSPGERATLSCRASSSVSYMYWHQQKPDQSPKLLIYDTSNLASGVPVRFSGSGSGTDYTLTISSL
EPEDFAVYYCQQWSSYPPTFGGGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC (SEQ ID NO: 461)

>XENP31454 MESO-B[MSLN]_H0L0_Fab-MESO-B[MSLN]_H0L0_Fab_(G4S)2_[CD3]_L1.47_H1.32_scFv(GKPGS)4-
IgG1_pI(-)_Isosteric_A_/PVA_/S267K/L368D/K370S-Fc(216)_IgG1_C220S/PVA_/S267K/S364K/E357Q

Chain 1 - MESO-B[MSLN]_H0_IgG1_pI(-)_Isosteric_A_/PVA_/S267K/L368D/K370S
QVQLQQSGPGLVTPSQTLSLTCAISGDSVSSNSATWNWIRQSPSRGLEWLGRTYYRSKWYNDYAVSVKSRMSINPDT
SKNQFSLQLNSVTPEDTAVYYCARGMMTYYYGMDVWGQGTTVTVSS/ASTKGPSVFPLAPSSKSTSGGTAALGCLVK
DYFPEPVTVSWNSGALTSGVHTFPAVLQSSGLYSLSSVVTVPSSSLGTQTYICNVNHKPSDTKVDKKVEPKSCDKTH
TCPPCPAPPVAGPSVFLFPPKPKDTLMISRTPEVTCVVVDVKHEDPEVKFNWYVDGVEVHNAKTKPREEEYNSTYRV
VSVLTVLHQDWLNGKEYKCKVSNKALPAPIEKTISKAKGQPREPQVYTLPPSREEMTKNQVSLTCDVSGFYPSDIAV
EWESDGQPENNYKTTPPVLDSDGSFFLYSKLTVDKSRWEQGDVFSCSVMHEALHNHYTQKSLSLSPGK (SEQ ID
NO: 462)

Figure 31B

Chain 2 - MESO-
B[MSLN]_H0_(G4S)2_[CD3]_L1.47_H1.32_scFv(GKPGS)4_Fc(216)_IgG1_C220S/PVA_/S267K/S364K/E357Q
QVQLQQSGPGLVTPSQTLSLTCAISGDSVSSNSATWNWIRQSPSRGLEWLGRTYYRSKWYNDYAVSVKSRMSINPDT
SKNQFSLQLNSVTPEDTAVYYCARGMMTYYYGMDVWGQGTTVTVSS/ASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSC/GGG
GSGGGGS/QAVVTQEPSLTVSPGGTVTLTCGSSTGAVTTSNYANWVQQKPGKSPRGLIGGTNKRAPGVPARFSGSLL
GGKAALTISGAQPEDEADYYCALWYSNHWVFGGGTKLTVL/GKPGSGKPGSGKPGSGKPGS/EVQLVESGGGLVQPG
GSLRLSCAASGFTFSTYAMNWVRQAPGKGLEWVGRIRSKANNYATYYADSVKGRFTISRDDSKNTLYLQMNSLRAED
TAVYYCVRHGNFGDSYVSWFAYWGQGTLVTVSS/GGGGSGGGGS/KTHTCPPCPAPPVAGPSVFLFPPKPKDTLMIS
RTPEVTCVVVDVKHEDPEVKFNWYVDGVEVHNAKTKPREEQYNSTYRVVSVLTVLHQDWLNGKEYKCKVSNKALPAP
IEKTISKAKGQPREPQVYTLPPSREQMTKNQVKLTCLVKGFYPSDIAVEWESNGQPENNYKTTPPVLDSDGSFFLYS
KLTVDKSRWQQGNVFSCSVMHEALHNHYTQKSLSLSPGK (SEQ ID NO: 463)

Chain 3 - MESO-B[MSLN]_L0 Light Chain
QPVLTQSSSLSASPGASASLTCTLRSGINVGPYRIYWYQQKPGSPPQYLLNYKSDSDKQQGSGVPSRFSGSKDASAN
AGVLLISGLRSEDEADYYCMIWHSSAAVFGGGTQLTVL/GQPKAAPSVTLFPPSSEELQANKATLVCLISDFYPGAV
TVAWKADSSPVKAGVETTTPSKQSNNKYAASSYLSLTPEQWKSHRSYSCQVTHEGSTVEKTVAPTECS (SEQ ID
NO: 464)

>XENP31717 MESO-C[MSLN]_H1L1_Fab-MESO-C[MSLN]_H1L1_Fab_(G4S)2_[CD3]_L1.47_H1.32_scFv(GKPGS)4-
IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
465)

Chain 2 - MESO-
C[MSLN]_H1_[CD3]_L1.47_H1.32_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 466)

Chain 3 - MESO-C[MSLN]_L1 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
467)

Figure 31C

>XENP32745 MESO-C[MSLN]_H1_L1.3_Fab-MESO-
C[MSLN]_H1_L1.3_Fab_(G4S)2_[CD3]_L1.47_H1.32_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
468)

**Chain 2 - MESO-
C[MSLN]_H1_(G4S)2_[CD3]_L1.47_H1.32_scFv(GKPGS)4_Fc(216)_IgG1_C220S/PVA_/S267K/S364K/E357Q**
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 469)

Chain 3 - MESO-C[MSLN]_L1.3 Light Chain
DIVMTQSPDSLAVSLGERATINCKASHSVGTSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
470)

>XENP32748 MESO-C[MSLN]_H1_L1.4_Fab-MESO-
C[MSLN]_H1_L1.4_Fab_(G4S)2_[CD3]_L1.47_H1.32_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
471)

Figure 31D

Chain 2 - MESO-C[MSLN]_H1_(G4S)2_[CD3]_L1.47_H1.32_scFv(GKPGS)4_Fc(216)_IgG1_C220S/PVA_/S267K/S364K/E357Q

QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 472)

Chain 3 - MESO-C[MSLN]_L1.4 Light Chain

DIVMTQSPDSLAVSLGERATINCKASHDVLTSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
473)

>XENP32751 MESO-C[MSLN]_H1_L1.5_Fab-MESO-C[MSLN]_H1_L1.5_Fab_(G4S)2_[CD3]_L1.47_H1.32_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S

QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
474)

Chain 2 - MESO-C[MSLN]_H1_(G4S)2_[CD3]_L1.47_H1.32_scFv(GKPGS)4_Fc(216)_IgG1_C220S/PVA_/S267K/S364K/E357Q

QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 475)

Chain 3 - MESO-C[MSLN]_L1.5 Light Chain

DIVMTQSPDSLAVSLGERATINCKASHDVGTYVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGE (SEQ ID NO: 476)

Figure 31E

>XENP32852 MESO-C[MSLN]_H1_L1.9_Fab-MESO-
C[MSLN]_H1_L1.9_Fab_(G4S)2_[CD3]_L1.47_H1.32_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
477)

**Chain 2 - MESO-
C[MSLN]_H1_(G4S)2_[CD3]_L1.47_H1.32_scFv(GKPGS)4_Fc(216)_IgG1_C220S/PVA_/S267K/S364K/E357Q**
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 478)

Chain 3 - MESO-C[MSLN]_L1.9 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYYSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
479)

>XENP32947 MESO-C[MSLN]_H1.3_L1_Fab-MESO-
C[MSLN]_H1.3_L1_Fab_(G4S)2_[CD3]_L1.47_H1.32_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1.3_IgG1_pI(-)_Isosteric_A_/PVA_/S267K/L368D/K370S
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
480)

Figure 31F

Chain 2 - MESO-
C[MSLN]_H1.3_(G4S)2_[CD3]_L1.47_H1.32_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 481)

Chain 3 - MESO-C[MSLN]_L1 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
482)

>XENP32948 MESO-C[MSLN]_H1.12_L1.9_Fab-MESO-
C[MSLN]_H1.12_L1.9_Fab_(G4S)2_[CD3]_L1.47_H1.32_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1.12_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYQKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
483)

Chain 2 - MESO-
C[MSLN]_H1.12_(G4S)2_[CD3]_L1.47_H1.32_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGMIHPNSDNTIYYQKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 484)

Chain 3 - MESO-C[MSLN]_L1.9 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYYSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
485)

Figure 31G

>XENP32949 MESO-C[MSLN]_H1.13_L1.9_Fab-MESO-
C[MSLN]_H1.13_L1.9_Fab_(G4S)2_[CD3]_L1.47_H1.32_scFv(GKPGS)4-IgG1_pI(-
)_Isosteric_A_/PVA_/S267K/L368D/K370S-Fc(216)_IgG1_C220S/PVA_/S267K/S364K/E357Q Chain 1 - MESO-C[MSLN]_H1.13_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYYKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
486)

Chain 2 - MESO-
C[MSLN]_H1.13_(G4S)2_[CD3]_L1.47_H1.32_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGMIHPNSDNTIYYYKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 487)

Chain 3 - MESO-C[MSLN]_L1.9 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYYSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
488)

>XENP32950 MESO-C[MSLN]_H1.3_L1.9_Fab-MESO-
C[MSLN]_H1.3_L1.9_Fab_(G4S)2_[CD3]_L1.47_H1.32_scFv(GKPGS)4-IgG1_pI(-
)_Isosteric_A_/PVA_/S267K/L368D/K370S-Fc(216)_IgG1_C220S/PVA_/S267K/S364K/E357Q Chain 1 - MESO-C[MSLN]_H1.3_IgG1_pI(-)_Isosteric_A_/PVA_/S267K/L368D/K370S
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
489)

Figure 31H

Chain 2 - MESO-
C[MSLN]_H1.3_(G4S)2_[CD3]_L1.47_H1.32_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 490)

Chain 3 - MESO-C[MSLN]_L1.9 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYYSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
491)

>XENP32951 MESO-C[MSLN]_H1.3_L1.5_Fab-MESO-
C[MSLN]_H1.3_L1.5_Fab_(G4S)2_[CD3]_L1.47_H1.32_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1.3_IgG1_pI(-)_Isosteric_A_/PVA_/S267K/L368D/K370S
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
492)

Chain 2 - MESO-
C[MSLN]_H1.3_(G4S)2_[CD3]_L1.47_H1.32_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 493)

Chain 3 - MESO-C[MSLN]_L1.5 Light Chain
DIVMTQSPDSLAVSLGERATINCKASHDVGTYVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
494)

Figure 31I

**>XENP33366 MESO-C[MSLN]_H1.3_L1.13_Fab-MESO-
C[MSLN]_H1.3_L1.13_Fab_(G4S)2_[CD3]_L1.47_H1.32_scFv(GKPGS)4-IgG1_pI(-
)_Isosteric_A_/PVA_/S267K/L368D/K370S-Fc(216)_IgG1_C220S/PVA_/S267K/S364K/E357Q**

Chain 1 - MESO-C[MSLN]_H1.3_IgG1_pI(-)_Isosteric_A_/PVA_/S267K/L368D/K370S
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
495)

**Chain 2 - MESO-
C[MSLN]_H1.3_(G4S)2_[CD3]_L1.47_H1.32_scFv(GKPGS)4_Fc(216)_IgG1_C220S/PVA_/S267K/S364K/E357Q**
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 496)

Chain 3 - MESO-C[MSLN]_L1.13 Light Chain
DIVMTQSPDSLAVSLGERATINCKASHDVGQSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
497)

**>XENP33367 MESO-C[MSLN]_H1.3_L1.14_Fab-MESO-
C[MSLN]_H1.3_L1.14_Fab_(G4S)2_[CD3]_L1.47_H1.32_scFv(GKPGS)4-IgG1_pI(-
)_Isosteric_A_/PVA_/S267K/L368D/K370S-Fc(216)_IgG1_C220S/PVA_/S267K/S364K/E357Q**

Chain 1 - MESO-C[MSLN]_H1.3_IgG1_pI(-)_Isosteric_A_/PVA_/S267K/L368D/K370S
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
498)

Figure 31J

Chain 2 - MESO-C[MSLN]_H1.3_(G4S)2_[CD3]_L1.47_H1.32_scFv(GKPGS)4_Fc(216)_IgG1_C220S/PVA_/S267K/S364K/E357Q

QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 499)

Chain 3 - MESO-C[MSLN]_L1.14 Light Chain

DIVMTQSPDSLAVSLGERATINCKASHDVGTSVAWYQQKPGQSPKLLIYWASTRHTGVPDRFTGSGSGTDFTLTISS
LQAEDVAVYFCQQYSSFPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
500)

>XENP33460 MESO-C[MSLN]_H1_L1.19_Fab-MESO-C[MSLN]_H1_L1.19_Fab_(G4S)2_[CD3]_L1.47_H1.32_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S

QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
501)

Chain 2 - MESO-C[MSLN]_H1_(G4S)2_[CD3]_L1.47_H1.32_scFv(GKPGS)4_Fc(216)_IgG1_C220S/PVA_/S267K/S364K/E357Q

QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 502)

Chain 3 - MESO-C[MSLN]_L1.19 Light Chain

DIVMTQSPDSLAVSLGERATINCKASHDVGTYVAWYQQKPGQSPKLLIYWASTRHTGVPDRFTGSGSGTDFTLTISS
LQAEDVAVYFCQQYYSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
503)

Figure 31K

>XENP33461 MESO-C[MSLN]_H1_L1.20_Fab-MESO-
C[MSLN]_H1_L1.20_Fab_(G4S)2_[CD3]_L1.47_H1.32_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S

QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
504)

**Chain 2 - MESO-
C[MSLN]_H1_(G4S)2_[CD3]_L1.47_H1.32_scFv(GKPGS)4_Fc(216)_IgG1_C220S/PVA_/S267K/S364K/E357Q**

QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 505)

Chain 3 - MESO-C[MSLN]_L1.20 Light Chain

DIVMTQSPDSLAVSLGERATINCKASHDVGTSVAWYQQKPGQSPKLLIYWASTRHTGVPDRFTGSGSGTDFTLTISS
LQAEDVAVYFCQQYYSFPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
506)

>XENP33462 MESO-C[MSLN]_H1_L1.21_Fab-MESO-
C[MSLN]_H1_L1.21_Fab_(G4S)2_[CD3]_L1.47_H1.32_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
507)

Figure 31L

Chain 2 - MESO-
C[MSLN]_H1_(G4S)2_[CD3]_L1.47_H1.32_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 508)

Chain 3 - MESO-C[MSLN]_L1.21 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYYSVPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
509)

>XENP33463 MESO-C[MSLN]_H1_L1.22_Fab-MESO-
C[MSLN]_H1_L1.22_Fab_(G4S)2_[CD3]_L1.47_H1.32_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
510)

Chain 2 - MESO-
C[MSLN]_H1_(G4S)2_[CD3]_L1.47_H1.32_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 511)

Chain 3 - MESO-C[MSLN]_L1.22 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYYSIPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
512)

Figure 31M

>XENP33464 MESO-C[MSLN]_H1.12_L1.19_Fab-MESO-C[MSLN]_H1.12_L1.19_Fab_(G4S)2_[CD3]_L1.47_H1.32_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1.12_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYQKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
513)

Chain 2 - MESO-C[MSLN]_H1.12_(G4S)2_[CD3]_L1.47_H1.32_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGMIHPNSDNTIYYQKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEEYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 514)

Chain 3 - MESO-C[MSLN]_L1.19 Light Chain
DIVMTQSPDSLAVSLGERATINCKASHDVGTYVAWYQQKPGQSPKLLIYWASTRHTGVPDRFTGSGSGTDFTLTISS
LQAEDVAVYFCQQYYSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
515)

>XENP33465 MESO-C[MSLN]_H1.12_L1.20_Fab-MESO-C[MSLN]_H1.12_L1.20_Fab_(G4S)2_[CD3]_L1.47_H1.32_scFv(GKPGS)4-IgG1_pI(-)_Isosteric_A_/PVA_/S267K/L368D/K370S-Fc(216)_IgG1_C220S/PVA_/S267K/S364K/E357Q

Chain 1 - MESO-C[MSLN]_H1.12_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYQKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
516)

Figure 31N

Chain 2 - MESO-
C[MSLN]_H1.12_(G4S)2_[CD3]_L1.47_H1.32_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGMIHPNSDNTIYYQKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 517)

Chain 3 - MESO-C[MSLN]_L1.20 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYYSFPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
518)

>XENP33466 MESO-C[MSLN]_H1.12_L1.21_Fab-MESO-
C[MSLN]_H1.12_L1.21_Fab_(G4S)2_[CD3]_L1.47_H1.32_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1.12_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYQKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
519)

Chain 2 - MESO-
C[MSLN]_H1.12_(G4S)2_[CD3]_L1.47_H1.32_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGMIHPNSDNTIYYQKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 520)

Chain 3 - MESO-C[MSLN]_L1.21 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYYSVPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
521)

Figure 31O

>XENP33467 MESO-C[MSLN]_H1.12_L1.22_Fab-MESO-
C[MSLN]_H1.12_L1.22_Fab_(G4S)2_[CD3]_L1.47_H1.32_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1.12_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYQKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
522)

**Chain 2 - MESO-
C[MSLN]_H1.12_(G4S)2_[CD3]_L1.47_H1.32_scFv(GKPGS)4_Fc(216)_IgG1_C220S/PVA_/S267K/S364K/E357Q**
QVQLVQSGAEVKKPGASVKVSCKASGYTFTSYWMHWVRQAPGQGLEWMGMIHPNSDNTIYYQKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 523)

Chain 3 - MESO-C[MSLN]_L1.22 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYYSIPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
524)

>XENP33968 MESO-C[MSLN]_H1.14_L1.14_Fab-MESO-
C[MSLN]_H1.14_L1.14_Fab_(G4S)2_[CD3]_L1.47_H1.32_scFv(GKPGS)4-IgG1_pI(-
)_Isosteric_A_PVA_/S267K/L368D/K370S-(G4S)2_IgG1_PVA_/S267K/S364K/E357Q

**Chain 1 - MESO-C[MSLN]_H1.14_IgG1_pI(-)_Isosteric_A_PVA_/S267K/L368D/K370S-
(G4S)2_IgG1_PVA_/S267K/S364K/E357Q**
QVQLVQSGAEVKKPGASVKVSCKASGYTFTSYWMHWVRQAPGQGLEWMGWIHPQSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
525)

Figure 31P

Chain 2 - MESO-C[MSLN]_H1.14_(G4S)2_[CD3]_(G4S)2_IgG1_PVA_/S267K/S364K/E357Q
QVQLVQSGAEVKKPGASVKVSCKASGYTFTSYWMHWVRQAPGQGLEWMGWIHPQSDNTIYYEKFQGRVTMTVDKSIS
TAYMELSRLRSDDTAVYYCAIIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 526)

Chain 3 - MESO-C[MSLN]_L1.14 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSSFPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
527)
>XENP33970 MESO-C[MSLN]_H1.15_L1.14_Fab-MESO-
C[MSLN]_H1.15_L1.14_Fab_(G4S)2_[CD3]_L1.47_H1.32_scFv(GKPGS)4-IgG1_pI(-
)_Isosteric_A_PVA_/S267K/L368D/K370S-(G4S)2_IgG1_PVA_/S267K/S364K/E357Q

**Chain 1 - MESO-C[MSLN]_H1.15_IgG1_pI(-)_Isosteric_A_PVA_/S267K/L368D/K370S-
(G4S)2_IgG1_PVA_/S267K/S364K/E357Q**
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCARIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
528)

Chain 2 - MESO-C[MSLN]_H1.15_(G4S)2_[CD3]_(G4S)2_IgG1_PVA_/S267K/S364K/E357Q
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCARIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 529)

Chain 3 - MESO-C[MSLN]_L1.14 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSSFPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
530)

Figure 31Q

>XENP33972 MESO-C[MSLN]_H1.16_L1.14_Fab-MESO-
C[MSLN]_H1.16_L1.14_Fab_(G4S)2_[CD3]_L1.47_H1.32_scFv(GKPGS)4-IgG1_pI(-
)_Isosteric_A_PVA_/S267K/L368D/K370S-(G4S)2_IgG1_PVA_/S267K/S364K/E357Q Chain 1 - MESO-C[MSLN]_H1.16_IgG1_pI(-)_Isosteric_A_PVA_/S267K/L368D/K370S-
(G4S)2_IgG1_PVA_/S267K/S364K/E357Q
QVQLVQSGAEVKKPGASVKVSCKASGYTFTSYWMHWVRQAPGQGLEWMGWIHPQSDNTIYYEKFQGRVTMTVDKSIS
TAYMELSRLRSDDTAVYYCARIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
531)

Chain 2 - MESO-C[MSLN]_H1.16_(G4S)2_[CD3]_(G4S)2_IgG1_PVA_/S267K/S364K/E357Q
QVQLVQSGAEVKKPGASVKVSCKASGYTFTSYWMHWVRQAPGQGLEWMGWIHPQSDNTIYYEKFQGRVTMTVDKSIS
TAYMELSRLRSDDTAVYYCARIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 532)

Chain 3 - MESO-C[MSLN]_L1.14 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSSFPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
533)

>XENP34155 MESO-C[MSLN]_H1.3_L1.14_Fab-MESO-
C[MSLN]_H1.3_L1.14_Fab_(G4S)2_[CD3]_L1.47_H1.32_scFv(GKPGS)4-IgG1_pI(-
)_Isosteric_A_/PVA_/S267K/L368D/K370S/M248L/N434S-
Fc(216)_IgG1_C220S/PVA_/S267K/S364K/E357Q/M248L/N434S Chain 1 - MESO-C[MSLN]_H1.3_IgG1_pI(-)_Isosteric_A_/PVA_/S267K/L368D/K370S/M248L/N434S
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVLHEALHSHYTQKSLSLSPGK (SEQ ID NO:
534)

Figure 31R

Chain 2 - MESO-C[MSLN]_H1.3_(G4S)2_[CD3]_L1.47_H1.32_scFv(GKPGS)4_Fc(216)_IgG1_C220S/PVA_/S267K/S364K/E357Q/M248L/N434S

QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVLHEALHSHYTQKSLSLSPGK (SEQ ID NO: 535)

Chain 3 - MESO-C[MSLN]_L1.14 Light Chain

DIVMTQSPDSLAVSLGERATINCKASHDVGTSVAWYQQKPGQSPKLLIYWASTRHTGVPDRFTGSGSGTDFTLTISS
LQAEDVAVYFCQQYSSFPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
536)

>XENP34156 MESO-C[MSLN]_H1.3_L1.13_Fab-MESO-C[MSLN]_H1.3_L1.13_Fab_(G4S)2_[CD3]_L1.47_H1.32_scFv(GKPGS)4-IgG1_pI(-)_Isosteric_A_/PVA_/S267K/L368D/K370S/M248L/N434S-Fc(216)_IgG1_C220S/PVA_/S267K/S364K/E357Q/M248L/N434S

Chain 1 - MESO-C[MSLN]_H1.3_IgG1_pI(-)_Isosteric_A_/PVA_/S267K/L368D/K370S/M248L/N434S

QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVLHEALHSHYTQKSLSLSPGK (SEQ ID NO:
537)

Chain 2 - MESO-C[MSLN]_H1.3_(G4S)2_[CD3]_L1.47_H1.32_scFv(GKPGS)4_Fc(216)_IgG1_C220S/PVA_/S267K/S364K/E357Q/M248L/N434S

QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVLHEALHSHYTQKSLSLSPGK (SEQ ID NO: 538)

Chain 3 - MESO-C[MSLN]_L1.13 Light Chain

DIVMTQSPDSLAVSLGERATINCKASHDVGQSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
539)

Figure 31S

>XENP34157 MESO-C[MSLN]_H1.3_L1_Fab-MESO-
C[MSLN]_H1.3_L1_Fab_(G4S)2_[CD3]_L1.47_H1.32_scFv(GKPGS)4-IgG1_pI(-
)_Isosteric_A_/PVA_/S267K/L368D/K370S/M248L/N434S-
Fc(216)_IgG1_C220S/PVA_/S267K/S364K/E357Q/M248L/N434S

Chain 1 - MESO-C[MSLN]_H1.3_IgG1_pI(-)_Isosteric_A_/PVA_/S267K/L368D/K370S/M248L/N434S
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVLHEALHSHYTQKSLSLSPGK (SEQ ID NO:
540)

**Chain 2 - MESO-
C[MSLN]_H1.3_(G4S)2_[CD3]_L1.47_H1.32_scFv(GKPGS)4_Fc(216)_IgG1_C220S/PVA_/S267K/S364K/E357Q/M2
48L/N434S**
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKANNYATYYADSVKGRFTISRDDSKNTLYLQMNSLRAEDTAV
YYCVRHGNFGDSYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVLHEALHSHYTQKSLSLSPGK (SEQ ID NO: 541)

Chain 3 - MESO-C[MSLN]_L1 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
542)

>XENP34158 MESO-C[MSLN]_H1.12_L1.9_Fab-MESO-
C[MSLN]_H1.12_L1.9_Fab_(G4S)2_[CD3]_L1.47_H1.32_scFv(GKPGS)4-IgG1_pI(-
)_Isosteric_A_/PVA_/S267K/L368D/K370S/M248L/N434S-
Fc(216)_IgG1_C220S/PVA_/S267K/S364K/E357Q/M248L/N434S

Chain 1 - MESO-C[MSLN]_H1.12_IgG1_pI(-)_Isosteric_A_/PVA_/S267K/L368D/K370S/M248L/N434S
QVQLVQSGAEVKKPGASVKVSCKASGYTFTSYWMHWVRQAPGQGLEWMGMIHPNSDNTIYYQKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVLHEALHSHYTQKSLSLSPGK (SEQ ID NO:
543)

Figure 31T

Chain 2 - MESO-C[MSLN]_H1.12_(G4S)2_[CD3]_L1.47_H1.32_scFv(GKPGS)4_Fc(216)_IgG1_C220S/PVA_/S267K/S364K/E357Q/M248L/N434S

QVQLVQSGAEVKKPGASVKVSCKASGYTFT<u>SYWMH</u>WVRQAPGQGLEWMGM<u>IHPNSDNTIYY</u>QKFQGRVTMTVDKSIS
TAYMELSRLRSDDTAVYYCAI<u>IITPVVPKFDY</u>WGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/<u>GGGGSG</u>
<u>GGGS</u>/QAVVTQEPSLTVSPGGTVTLTC<u>GSSTGAVTTSNYAN</u>WVQQKPGKSPRGLI<u>GGTNKRAP</u>GVPARFSGSLLGGK
AALTISGAQPEDEADYYC<u>ALWYSNHWV</u>FGGGTKLTVL/<u>GKPGSGKPGSGKPGSGKPGS</u>/EVQLVESGGGLVQPGGSL
RLSCAASGFTFS<u>TYAMN</u>WVRQAPGKGLEWVG<u>RIRSKANNYATYYADSVKG</u>RFTISRDDSKNTLYLQMNSLRAEDTAV
YYCVR<u>HGNFGDSYVSWFAY</u>WGQGTLVTVSS/<u>GGGGSGGGGS</u>/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVLHEALHSHYTQKSLSLSPGK (SEQ ID NO: 544)

Chain 3 - MESO-C[MSLN]_L1.9 Light Chain

DIVMTQSPDSLAVSLGERATINC<u>KASHDVGTSVA</u>WYQQKPGQSPKLLIY<u>WASTRHT</u>GVPDRFTGSGSGTDFTLTISS
LQAEDVAVYFC<u>QQYYSYPLT</u>FGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
545)

Figure 32A

>XENP31455 MESO-A[MSLN]_H1.1_L1_Fab-MESO-A[MSLN]_H1.1_L1_Fab_(G4S)2_[CD3]_L1.47_H1.89_scFv(GKPGS)4-
IgG1_pI(-)_Isosteric_A_/PVA_/S267K/L368D/K370S-Fc(216)_(G4S)2_IgG1_C220S/PVA_/S267K/S364K/E357Q

Chain 1 - MESO-A[MSLN]_H1.1_IgG1_pI(-)_Isosteric_A_/PVA_/S267K/L368D/K370S
EVQLVESGGGLVQPGGSLKLSCAASGFDFSRYWMSWVRQAPGKGLEWVSEINPDSSTIVYTPSVKGRFTISRDNAKNSLYLQ
MNSLRAEDTAVYYCARRGSHYYGYRTGYFDVWGAGTTVTVSS/ASTKGPSVFPLAPSSKSTSGGTAALGCLVKDYFPEPVTV
SWNSGALTSGVHTFPAVLQSSGLYSLSSVVTVPSSSLGTQTYICNVNHKPSDTKVDKKVEPKSCDKTHTCPPCPAPPVAGPS
VFLFPPKPKDTLMISRTPEVTCVVVDVKHEDPEVKFNWYVDGVEVHNAKTKPREEEYNSTYRVVSVLTVLHQDWLNGKEYKC
KVSNKALPAPIEKTISKAKGQPREPQVYTLPPSREEMTKNQVSLTCDVSGFYPSDIAVEWESDGQPENNYKTTPPVLDSDGS
FFLYSKLTVDKSRWEQGDVFSCSVMHEALHNHYTQKSLSLSPGK (SEQ ID NO: 546)

Chain 2 - MESO-A[MSLN]_H1.1_(G4S)2_[CD3]_(G4S)2_IgG1_C220S/PVA_/S267K/S364K/E357Q
EVQLVESGGGLVQPGGSLKLSCAASGFDFSRYWMSWVRQAPGKGLEWVSEINPDSSTIVYTPSVKGRFTISRDNAKNSLYLQ
MNSLRAEDTAVYYCARRGSHYYGYRTGYFDVWGAGTTVTVSS/ASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKKVEPKSC/GGGGSGGGGS/QAVVTQ
EPSLTVSPGGTVTLTCGSSTGAVTTSNYANWVQQKPGKSPRGLIGGTNKRAPGVPARFSGSLLGGKAALTISGAQPEDEADY
YCALWYSNHWVFGGGTKLTVL/GKPGSGKPGSGKPGSGKPGS/EVQLVESGGGLVQPGGSLRLSCAASGFTFSTYAMNWVRQ
APGKGLEWVGRIRSKYNNYATYYADSVKGRFTISRDDSKNTLYLQMNSLRAEDTAVYYCVRHGNFGDEYVSWFAYWGQGTLV
TVSS/GGGGSGGGGS/KTHTCPPCPAPPVAGPSVFLFPPKPKDTLMISRTPEVTCVVVDVKHEDPEVKFNWYVDGVEVHNAK
TKPREEQYNSTYRVVSVLTVLHQDWLNGKEYKCKVSNKALPAPIEKTISKAKGQPREPQVYTLPPSREQMTKNQVKLTCLVK
GFYPSDIAVEWESNGQPENNYKTTPPVLDSDGSFFLYSKLTVDKSRWQQGNVFSCSVMHEALHNHYTQKSLSLSPGK (SEQ
ID NO: 547)

Chain 3 - MESO-A[MSLN]_L1 Light Chain
DVVLTQSPATLSLSPGERATLSCRASSSVSYMYWHQQKPDQSPKLLIYDTSNLASGVPVRFSGSGSGTDYTLTISSLEPEDF
AVYYCQQWSSYPPTFGGGTKLEIK/RTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC (SEQ ID NO: 548)

>XENP31456 MESO-B[MSLN]_H0L0_Fab-MESO-B[MSLN]_H0L0_Fab_(G4S)2_[CD3]_L1.47_H1.89_scFv(GKPGS)4-
IgG1_pI(-)_Isosteric_A_/PVA_/S267K/L368D/K370S-Fc(216)_(G4S)2_IgG1_C220S/PVA_/S267K/S364K/E357Q

Chain 1 - MESO-B[MSLN]_H0_IgG1_pI(-)_Isosteric_A_/PVA_/S267K/L368D/K370S
QVQLQQSGPGLVTPSQTLSLTCAISGDSVSSNSATWNWIRQSPSRGLEWLGRTYYRSKWYNDYAVSVKSRMSINPDTSKNQF
SLQLNSVTPEDTAVYYCARGMMTYYYGMDVWGQGTTVTVSS/ASTKGPSVFPLAPSSKSTSGGTAALGCLVKDYFPEPVTVS
WNSGALTSGVHTFPAVLQSSGLYSLSSVVTVPSSSLGTQTYICNVNHKPSDTKVDKKVEPKSCDKTHTCPPCPAPPVAGPSV
FLFPPKPKDTLMISRTPEVTCVVVDVKHEDPEVKFNWYVDGVEVHNAKTKPREEEYNSTYRVVSVLTVLHQDWLNGKEYKCK
VSNKALPAPIEKTISKAKGQPREPQVYTLPPSREEMTKNQVSLTCDVSGFYPSDIAVEWESDGQPENNYKTTPPVLDSDGSF
FLYSKLTVDKSRWEQGDVFSCSVMHEALHNHYTQKSLSLSPGK (SEQ ID NO: 549)

Chain 2 - MESO-B[MSLN]_H0_(G4S)2_[CD3]_(G4S)2_IgG1_C220S/PVA_/S267K/S364K/E357Q
QVQLQQSGPGLVTPSQTLSLTCAISGDSVSSNSATWNWIRQSPSRGLEWLGRTYYRSKWYNDYAVSVKSRMSINPDTSKNQF
SLQLNSVTPEDTAVYYCARGMMTYYYGMDVWGQGTTVTVSS/ASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKKVEPKSC/GGGGSGGGGS/QAVVTQE
PSLTVSPGGTVTLTCGSSTGAVTTSNYANWVQQKPGKSPRGLIGGTNKRAPGVPARFSGSLLGGKAALTISGAQPEDEADYY
CALWYSNHWVFGGGTKLTVL/GKPGSGKPGSGKPGSGKPGS/EVQLVESGGGLVQPGGSLRLSCAASGFTFSTYAMNWVRQA
PGKGLEWVGRIRSKYNNYATYYADSVKGRFTISRDDSKNTLYLQMNSLRAEDTAVYYCVRHGNFGDEYVSWFAYWGQGTLVT
VSS/GGGGSGGGGS/KTHTCPPCPAPPVAGPSVFLFPPKPKDTLMISRTPEVTCVVVDVKHEDPEVKFNWYVDGVEVHNAKT
KPREEQYNSTYRVVSVLTVLHQDWLNGKEYKCKVSNKALPAPIEKTISKAKGQPREPQVYTLPPSREQMTKNQVKLTCLVKG
FYPSDIAVEWESNGQPENNYKTTPPVLDSDGSFFLYSKLTVDKSRWQQGNVFSCSVMHEALHNHYTQKSLSLSPGK (SEQ
ID NO: 550)

Figure 32B

Chain 3 - MESO-B[MSLN]_L0 Light Chain

QPVLTQSSSLSASPGASASLTCTLRSGINVGPYRIYWYQQKPGSPPQYLLNYKSDSDKQQGSGVPSRFSGSKDASAN
AGVLLISGLRSEDEADYYCMIWHSSAAVFGGGTQLTVL/GQPKAAPSVTLFPPSSEELQANKATLVCLISDFYPGAV
TVAWKADSSPVKAGVETTTPSKQSNNKYAASSYLSLTPEQWKSHRSYSCQVTHEGSTVEKTVAPTECS (SEQ ID
NO: 551)

**>XENP32249 MESO-A[MSLN]_H1.1_L1_Fab-MESO-
A[MSLN]_H1.1_L1_Fab_(G4S)2_[CD3]_L1.47_H1.89_scFv(GKPGS)4-IgG1_pI(-
)_Isosteric_A_/PVA_/S267K/L368D/K370S-Fc(216)_IgG1_C220S/PVA_/S267K/S364K/E357Q**

Chain 1 - MESO-A[MSLN]_H1.1_IgG1_pI(-)_Isosteric_A_/PVA_/S267K/L368D/K370S

EVQLVESGGGLVQPGGSLKLSCAASGFDFSRYWMSWVRQAPGKGLEWVSEINPDSSTIVYTPSVKGRFTISRDNAKN
SLYLQMNSLRAEDTAVYYCARRGSHYYGYRTGYFDVWGAGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSDTKVDKKVEPKSCDKT
HTCPPCPAPPVAGPSVFLFPPKPKDTLMISRTPEVTCVVVDVKHEDPEVKFNWYVDGVEVHNAKTKPREEEYNSTYR
VVSVLTVLHQDWLNGKEYKCKVSNKALPAPIEKTISKAKGQPREPQVYTLPPSREEMTKNQVSLTCDVSGFYPSDIA
VEWESDGQPENNYKTTPPVLDSDGSFFLYSKLTVDKSRWEQGDVFSCSVMHEALHNHYTQKSLSLSPGK (SEQ ID
NO: 552)

**Chain 2 - MESO-
A[MSLN]_H1.1_(G4S)2_[CD3]_L1.47_H1.89_scFv(GKPGS)4_Fc(216)_IgG1_C220S/PVA_/S267K/S364K/E357Q**

EVQLVESGGGLVQPGGSLKLSCAASGFDFSRYWMSWVRQAPGKGLEWVSEINPDSSTIVYTPSVKGRFTISRDNAKN
SLYLQMNSLRAEDTAVYYCARRGSHYYGYRTGYFDVWGAGTTVTVSS/ASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKKVEPKSC/GG
GGSGGGGS/QAVVTQEPSLTVSPGGTVTLTCGSSTGAVTTSNYANWVQQKPGKSPRGLIGGTNKRAPGVPARFSGSL
LGGKAALTISGAQPEDEADYYCALWYSNHWVFGGGTKLTVL/GKPGSGKPGSGKPGSGKPGS/EVQLVESGGGLVQP
GGSLRLSCAASGFTFSTYAMNWVRQAPGKGLEWVGRIRSKYNNYATYYADSVKGRFTISRDDSKNTLYLQMNSLRAE
DTAVYYCVRHGNFGDEYVSWFAYWGQGTLVTVSS/EPKSSDKTHTCPPCPAPPVAGPSVFLFPPKPKDTLMISRTPE
VTCVVVDVKHEDPEVKFNWYVDGVEVHNAKTKPREEQYNSTYRVVSVLTVLHQDWLNGKEYKCKVSNKALPAPIEKT
ISKAKGQPREPQVYTLPPSREQMTKNQVKLTCLVKGFYPSDIAVEWESNGQPENNYKTTPPVLDSDGSFFLYSKLTV
DKSRWQQGNVFSCSVMHEALHNHYTQKSLSLSPGK (SEQ ID NO: 553)

Chain 3 - MESO-A[MSLN]_L1 Light Chain

DVVLTQSPATLSLSPGERATLSCRASSSVSYMYWHQQKPDQSPKLLIYDTSNLASGVPVRFSGSGSGTDYTLTISSL
EPEDFAVYYCQQWSSYPPTFGGGTKLEIK/RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC (SEQ ID NO: 554)

**>XENP32250 MESO-B[MSLN]_H0L0_Fab-MESO-B[MSLN]_H0L0_Fab_(G4S)2_[CD3]_L1.47_H1.89_scFv(GKPGS)4-
IgG1_pI(-)_Isosteric_A_/PVA_/S267K/L368D/K370S-Fc(216)_IgG1_C220S/PVA_/S267K/S364K/E357Q**

Chain 1 - MESO-B[MSLN]_H0_IgG1_pI(-)_Isosteric_A_/PVA_/S267K/L368D/K370S

QVQLQQSGPGLVTPSQTLSLTCAISGDSVSSNSATWNWIRQSPSRGLEWLGRTYYRSKWYNDYAVSVKSRMSINPDT
SKNQFSLQLNSVTPEDTAVYYCARGMMTYYYGMDVWGQGTTVTVSS/ASTKGPSVFPLAPSSKSTSGGTAALGCLVK
DYFPEPVTVSWNSGALTSGVHTFPAVLQSSGLYSLSSVVTVPSSSLGTQTYICNVNHKPSDTKVDKKVEPKSCDKTH
TCPPCPAPPVAGPSVFLFPPKPKDTLMISRTPEVTCVVVDVKHEDPEVKFNWYVDGVEVHNAKTKPREEEYNSTYRV
VSVLTVLHQDWLNGKEYKCKVSNKALPAPIEKTISKAKGQPREPQVYTLPPSREEMTKNQVSLTCDVSGFYPSDIAV
EWESDGQPENNYKTTPPVLDSDGSFFLYSKLTVDKSRWEQGDVFSCSVMHEALHNHYTQKSLSLSPGK (SEQ ID
NO: 555)

Figure 32C

**Chain 2 - MESO-
B[MSLN]_H0_(G4S)2_[CD3]_L1.47_H1.89_scFv(GKPGS)4_Fc(216)_IgG1_C220S/PVA_/S267K/S364K/E357Q**
QVQLQQSGPGLVTPSQTLSLTCAISGDSVSSNSATWNWIRQSPSRGLEWLGRTYYRSKWYNDYAVSVKSRMSINPDT
SKNQFSLQLNSVTPEDTAVYYCARGMMTYYYGMDVWGQGTTVTVSS/ASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSC/GGG
GSGGGGS/QAVVTQEPSLTVSPGGTVTLTCGSSTGAVTTSNYANWVQQKPGKSPRGLIGGTNKRAPGVPARFSGSLL
GGKAALTISGAQPEDEADYYCALWYSNHWVFGGGTKLTVL/GKPGSGKPGSGKPGSGKPGS/EVQLVESGGGLVQPG
GSLRLSCAASGFTFSTYAMNWVRQAPGKGLEWVGRIRSKYNNYATYYADSVKGRFTISRDDSKNTLYLQMNSLRAED
TAVYYCVRHGNFGDEYVSWFAYWGQGTLVTVSS/EPKSSDKTHTCPPCPAPPVAGPSVFLFPPKPKDTLMISRTPEV
TCVVVDVKHEDPEVKFNWYVDGVEVHNAKTKPREEQYNSTYRVVSVLTVLHQDWLNGKEYKCKVSNKALPAPIEKTI
SKAKGQPREPQVYTLPPSREQMTKNQVKLTCLVKGFYPSDIAVEWESNGQPENNYKTTPPVLDSDGSFFLYSKLTVD
KSRWQQGNVFSCSVMHEALHNHYTQKSLSLSPGK (SEQ ID NO: 556)

Chain 3 - MESO-B[MSLN]_L0 Light Chain
QPVLTQSSSLSASPGASASLTCTLRSGINVGPYRIYWYQQKPGSPPQYLLNYKSDSDKQQGSGVPSRFSGSKDASAN
AGVLLISGLRSEDEADYYCMIWHSSAAVFGGGTQLTVL/GQPKAAPSVTLFPPSSEELQANKATLVCLISDFYPGAV
TVAWKADSSPVKAGVETTTPSKQSNNKYAASSYLSLTPEQWKSHRSYSCQVTHEGSTVEKTVAPTECS (SEQ ID
NO: 557)

**>XENP32251 MESO-C[MSLN]_H1L1_Fab-MESO-C[MSLN]_H1L1_Fab_(G4S)2_[CD3]_L1.47_H1.89_scFv(GKPGS)4-
IgG1_pI(-)_Isosteric_A_/PVA_/S267K/L368D/K370S-Fc(216)_IgG1_C220S/PVA_/S267K/S364K/E357Q**

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
558)

**Chain 2 - MESO-
C[MSLN]_H1_[CD3]_L1.47_H1.89_scFv(GKPGS)4_Fc(216)_IgG1_C220S/PVA_/S267K/S364K/E357Q**
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKYNNYATYYADSVKGRFTISRDDSKNTLYLQMNSLRAEDTAV
YYCVRHGNFGDEYVSWFAYWGQGTLVTVSS/EPKSSDKTHTCPPCPAPPVAGPSVFLFPPKPKDTLMISRTPEVTCV
VVDVKHEDPEVKFNWYVDGVEVHNAKTKPREEQYNSTYRVVSVLTVLHQDWLNGKEYKCKVSNKALPAPIEKTISKA
KGQPREPQVYTLPPSREQMTKNQVKLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 559)

Chain 3 - MESO-C[MSLN]_L1 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
560)

Figure 32D

>XENP32746 MESO-C[MSLN]_H1_L1.3_Fab-MESO-
C[MSLN]_H1_L1.3_Fab_(G4S)2_[CD3]_L1.47_H1.89_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
561)

Chain 2 - MESO-
C[MSLN]_H1_(G4S)2_[CD3]_L1.47_H1.89_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKYNNYATYYADSVKGRFTISRDDSKNTLYLQMNSLRAEDTAV
YYCVRHGNFGDEYVSWFAYWGQGTLVTVSS/EPKSSDKTHTCPPCPAPPVAGPSVFLFPPKPKDTLMISRTPEVTCV
VVDVKHEDPEVKFNWYVDGVEVHNAKTKPREEQYNSTYRVVSVLTVLHQDWLNGKEYKCKVSNKALPAPIEKTISKA
KGQPREPQVYTLPPSREQMTKNQVKLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 562)

Chain 3 - MESO-C[MSLN]_L1.3 Light Chain
DIVMTQSPDSLAVSLGERATINCKASHSVGTSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
563)

>XENP32749 MESO-C[MSLN]_H1_L1.4_Fab-MESO-
C[MSLN]_H1_L1.4_Fab_(G4S)2_[CD3]_L1.47_H1.89_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
564)

Figure 32E

Chain 2 – MESO
C[MSLN]_H1_(G4S)2_[CD3]_L1.47_H1.89_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKYNNYATYYADSVKGRFTISRDDSKNTLYLQMNSLRAEDTAV
YYCVRHGNFGDEYVSWFAYWGQGTLVTVSS/EPKSSDKTHTCPPCPAPPVAGPSVFLFPPKPKDTLMISRTPEVTCV
VVDVKHEDPEVKFNWYVDGVEVHNAKTKPREEQYNSTYRVVSVLTVLHQDWLNGKEYKCKVSNKALPAPIEKTISKA
KGQPREPQVYTLPPSREQMTKNQVKLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 565)

Chain 3 - MESO-C[MSLN]_L1.4 Light Chain
DIVMTQSPDSLAVSLGERATINCKASHDVLTSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
566)
>XENP32752 MESO-C[MSLN]_H1_L1.5_Fab-MESO-
C[MSLN]_H1_L1.5_Fab_(G4S)2_[CD3]_L1.47_H1.89_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
567)

Chain 2 - MESO-
C[MSLN]_H1_(G4S)2_[CD3]_L1.47_H1.89_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKYNNYATYYADSVKGRFTISRDDSKNTLYLQMNSLRAEDTAV
YYCVRHGNFGDEYVSWFAYWGQGTLVTVSS/EPKSSDKTHTCPPCPAPPVAGPSVFLFPPKPKDTLMISRTPEVTCV
VVDVKHEDPEVKFNWYVDGVEVHNAKTKPREEQYNSTYRVVSVLTVLHQDWLNGKEYKCKVSNKALPAPIEKTISKA
KGQPREPQVYTLPPSREQMTKNQVKLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 568)

Chain 3 - MESO-C[MSLN]_L1.5 Light Chain
DIVMTQSPDSLAVSLGERATINCKASHDVGTYVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
569)

Figure 32F

>XENP32853 MESO-C[MSLN]_H1_L1.9_Fab-MESO-
C[MSLN]_H1_L1.9_Fab_(G4S)2_[CD3]_L1.47_H1.89_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1_IgG1_pI(-)_Isosteric_A_/PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
570)

Chain 2 - MESO-
C[MSLN]_H1_(G4S)2_[CD3]_L1.47_H1.89_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKYNNYATYYADSVKGRFTISRDDSKNTLYLQMNSLRAEDTAV
YYCVRHGNFGDEYVSWFAYWGQGTLVTVSS/EPKSSDKTHTCPPCPAPPVAGPSVFLFPPKPKDTLMISRTPEVTCV
VVDVKHEDPEVKFNWYVDGVEVHNAKTKPREEQYNSTYRVVSVLTVLHQDWLNGKEYKCKVSNKALPAPIEKTISKA
KGQPREPQVYTLPPSREQMTKNQVKLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 571)

Chain 3 - MESO-C[MSLN]_L1.9 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYYSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
572)

>XENP33974 MESO-C[MSLN]_H1.3_L1.14_Fab-MESO-
C[MSLN]_H1.3_L1.14_Fab_(G4S)2_[CD3]_L1.47_H1.89_scFv(GKPGS)4-IgG1_pI(-
)_Isosteric_A_PVA_/S267K/L368D/K370S-Fc(216)_IgG1_PVA_/S267K/S364K/E357Q

Chain 1 - MESO-C[MSLN]_H1.3_IgG1_pI(-)_Isosteric_A_PVA_/S267K/L368D/K370S
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKYNNYATYYADSVKGRFTISRDDSKNTLYLQMNSLRAEDTAV
YYCVRHGNFGDEYVSWFAYWGQGTLVTVSS/EPKSSDKTHTCPPCPAPPVAGPSVFLFPPKPKDTLMISRTPEVTCV
VVDVKHEDPEVKFNWYVDGVEVHNAKTKPREEQYNSTYRVVSVLTVLHQDWLNGKEYKCKVSNKALPAPIEKTISKA
KGQPREPQVYTLPPSREQMTKNQVKLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 573)

Figure 32G

Chain 2 - MESO-
C[MSLN]_H1.3_(G4S)2_[CD3]_L1.47_H1.89_scFv(GKPGS)4_Fc(216)_IgG1_PVA_/S267K/S364K/E357Q
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
574)

Chain 3 - MESO-C[MSLN]_L1.14 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSSFPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
575)

>XENP33975 MESO-C[MSLN]_H1_L1.20_Fab-MESO-
C[MSLN]_H1_L1.20_Fab_(G4S)2_[CD3]_L1.47_H1.89_scFv(GKPGS)4-IgG1_pl(-
)_Isosteric_A_PVA_/S267K/L368D/K370S-Fc(216)_IgG1_PVA_/S267K/S364K/E357Q

Chain 1 - MESO-C[MSLN]_H1_IgG1_pl(-)_Isosteric_A_PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKYNNYATYYADSVKGRFTISRDDSKNTLYLQMNSLRAEDTAV
YYCVRHGNFGDEYVSWFAYWGQGTLVTVSS/EPKSSDKTHTCPPCPAPPVAGPSVFLFPPKPKDTLMISRTPEVTCV
VVDVKHEDPEVKFNWYVDGVEVHNAKTKPREEQYNSTYRVVSVLTVLHQDWLNGKEYKCKVSNKALPAPIEKTISKA
KGQPREPQVYTLPPSREQMTKNQVKLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 576)

Chain 2 - MESO-
C[MSLN]_H1_(G4S)2_[CD3]_L1.47_H1.89_scFv(GKPGS)4_Fc(216)_IgG1_PVA_/S267K/S364K/E357Q
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
577)

Chain 3 - MESO-C[MSLN]_L1.20 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSFPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
578)

Figure 32H

>XENP33976 MESO-C[MSLN]_H1.12_L1.20_Fab-MESO-
C[MSLN]_H1.12_L1.20_Fab_(G4S)2_[CD3]_L1.47_H1.89_scFv(GKPGS)4-IgG1_pI(-
)_Isosteric_A_PVA_/S267K/L368D/K370S-Fc(216)_IgG1_PVA_/S267K/S364K/E357Q

Chain 1 - MESO-C[MSLN]_H1.12_IgG1_pI(-)_Isosteric_A_PVA_/S267K/L368D/K370S
QVQLVQSGAEVKKPGASVKVSCKASGYTFTSYWMHWVRQAPGQGLEWMGMIHPNSDNTIYYQKFQGRVTMTVDKSIS
TAYMELSRLRSDDTAVYYCAIIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKYNNYATYYADSVKGRFTISRDDSKNTLYLQMNSLRAEDTAV
YYCVRHGNFGDEYVSWFAYWGQGTLVTVSS/EPKSSDKTHTCPPCPAPPVAGPSVFLFPPKPKDTLMISRTPEVTCV
VVDVKHEDPEVKFNWYVDGVEVHNAKTKPREEQYNSTYRVVSVLTVLHQDWLNGKEYKCKVSNKALPAPIEKTISKA
KGQPREPQVYTLPPSREQMTKNQVKLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 579)

**Chain 2 - MESO-
C[MSLN]_H1.12_(G4S)2_[CD3]_L1.47_H1.89_scFv(GKPGS)4_Fc(216)_IgG1_PVA_/S267K/S364K/E357Q**
QVQLVQSGAEVKKPGASVKVSCKASGYTFTSYWMHWVRQAPGQGLEWMGMIHPNSDNTIYYQKFQGRVTMTVDKSIS
TAYMELSRLRSDDTAVYYCAIIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
580)

Chain 3 - MESO-C[MSLN]_L1.20 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYYSFPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
581)

>XENP33977 MESO-C[MSLN]_H1.3_L1.13_Fab-MESO-
C[MSLN]_H1.3_L1.13_Fab_(G4S)2_[CD3]_L1.47_H1.89_scFv(GKPGS)4-IgG1_pI(-
)_Isosteric_A_PVA_/S267K/L368D/K370S-Fc(216)_IgG1_PVA_/S267K/S364K/E357Q

Chain 1 - MESO-C[MSLN]_H1.3_IgG1_pI(-)_Isosteric_A_PVA_/S267K/L368D/K370S
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKYNNYATYYADSVKGRFTISRDDSKNTLYLQMNSLRAEDTAV
YYCVRHGNFGDEYVSWFAYWGQGTLVTVSS/EPKSSDKTHTCPPCPAPPVAGPSVFLFPPKPKDTLMISRTPEVTCV
VVDVKHEDPEVKFNWYVDGVEVHNAKTKPREEQYNSTYRVVSVLTVLHQDWLNGKEYKCKVSNKALPAPIEKTISKA
KGQPREPQVYTLPPSREQMTKNQVKLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 582)

Figure 32I

Chain 2 - MESO-
C[MSLN]_H1.3_(G4S)2_[CD3]_L1.47_H1.89_scFv(GKPGS)4_Fc(216)_IgG1_PVA_/S267K/S364K/E357Q
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
583)

Chain 3 - MESO-C[MSLN]_L1.13 Light Chain
DIVMTQSPDSLAVSLGERATINCKASHDVGQSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
584)

>XENP33978 MESO-C[MSLN]_H1.3_L1_Fab-MESO-
C[MSLN]_H1.3_L1_Fab_(G4S)2_[CD3]_L1.47_H1.89_scFv(GKPGS)4-IgG1_pI(-
)_Isosteric_A_PVA_/S267K/L368D/K370S-Fc(216)_IgG1_PVA_/S267K/S364K/E357Q

Chain 1 - MESO-C[MSLN]_H1.3_IgG1_pI(-)_Isosteric_A_PVA_/S267K/L368D/K370S
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKYNNYATYYADSVKGRFTISRDDSKNTLYLQMNSLRAEDTAV
YYCVRHGNFGDEYVSWFAYWGQGTLVTVSS/EPKSSDKTHTCPPCPAPPVAGPSVFLFPPKPKDTLMISRTPEVTCV
VVDVKHEDPEVKFNWYVDGVEVHNAKTKPREEQYNSTYRVVSVLTVLHQDWLNGKEYKCKVSNKALPAPIEKTISKA
KGQPREPQVYTLPPSREQMTKNQVKLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 585)

Chain 2 - MESO-
C[MSLN]_H1.3_(G4S)2_[CD3]_L1.47_H1.89_scFv(GKPGS)4_Fc(216)_IgG1_PVA_/S267K/S364K/E357Q
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
586)

Chain 3 - MESO-C[MSLN]_L1 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
587)

Figure 32J

>XENP33979 MESO-C[MSLN]_H1_L1.9_Fab-MESO-
C[MSLN]_H1_L1.9_Fab_(G4S)2_[CD3]_L1.47_H1.89_scFv(GKPGS)4-IgG1_pI(-
)_Isosteric_A_PVA_/S267K/L368D/K370S-Fc(216)_IgG1_PVA_/S267K/S364K/E357Q

Chain 1 - MESO-C[MSLN]_H1_IgG1_pI(-)_Isosteric_A_PVA_/S267K/L368D/K370S
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKYNNYATYYADSVKGRFTISRDDSKNTLYLQMNSLRAEDTAV
YYCVRHGNFGDEYVSWFAYWGQGTLVTVSS/EPKSSDKTHTCPPCPAPPVAGPSVFLFPPKPKDTLMISRTPEVTCV
VVDVKHEDPEVKFNWYVDGVEVHNAKTKPREEQYNSTYRVVSVLTVLHQDWLNGKEYKCKVSNKALPAPIEKTISKA
KGQPREPQVYTLPPSREQMTKNQVKLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 588)

**Chain 2 - MESO-
C[MSLN]_H1_(G4S)2_[CD3]_L1.47_H1.89_scFv(GKPGS)4_Fc(216)_IgG1_PVA_/S267K/S364K/E357Q**
QVQLVQSGAEVKKPGASVKVSCKASGYTFTSYWMHWVRQAPGQGLEWMGMIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
589)

Chain 3 - MESO-C[MSLN]_L1.9 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYYSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
590)

>XENP33980 MESO-C[MSLN]_H1.12_L1.9_Fab-MESO-
C[MSLN]_H1.12_L1.9_Fab_(G4S)2_[CD3]_L1.47_H1.89_scFv(GKPGS)4-IgG1_pI(-
)_Isosteric_A_PVA_/S267K/L368D/K370S-Fc(216)_IgG1_PVA_/S267K/S364K/E357Q

Chain 1 - MESO-C[MSLN]_H1.12_IgG1_pI(-)_Isosteric_A_PVA_/S267K/L368D/K370S
QVQLVQSGAEVKKPGASVKVSCKASGYTFTSYWMHWVRQAPGQGLEWMGMIHPNSDNTIYYQKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKYNNYATYYADSVKGRFTISRDDSKNTLYLQMNSLRAEDTAV
YYCVRHGNFGDEYVSWFAYWGQGTLVTVSS/EPKSSDKTHTCPPCPAPPVAGPSVFLFPPKPKDTLMISRTPEVTCV
VVDVKHEDPEVKFNWYVDGVEVHNAKTKPREEQYNSTYRVVSVLTVLHQDWLNGKEYKCKVSNKALPAPIEKTISKA
KGQPREPQVYTLPPSREQMTKNQVKLTCLVKGFYPSDIAVEWESNGQPENNYKTTPPVLDSDGSFFLYSKLTVDKSR
WQQGNVFSCSVMHEALHNHYTQKSLSLSPGK (SEQ ID NO: 591)

Figure 32K

Chain 2 - MESO-
C[MSLN]_H1.12_(G4S)2_[CD3]_L1.47_H1.89_scFv(GKPGS)4_Fc(216)_IgG1_PVA_/S267K/S364K/E357Q
QVQLVQSGAEVKKPGASVKVSCKASGYTFTSYWMHWVRQAPGQGLEWMGMIHPNSDNTIYYQKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
592)

Chain 3 - MESO-C[MSLN]_L1.9 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYYSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
593)

>XENP34151 MESO-C[MSLN]_H1.3_L1.14_Fab-MESO-
C[MSLN]_H1.3_L1.14_Fab_(G4S)2_[CD3]_L1.47_H1.89_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1.3_IgG1_pI(-)_Isosteric_A_/PVA_/S267K/L368D/K370S
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
594)

Chain 2 - MESO-
C[MSLN]_H1.3_(G4S)2_[CD3]_L1.47_H1.89_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKYNNYATYYADSVKGRFTISRDDSKNTLYLQMNSLRAEDTAV
YYCVRHGNFGDEYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEEYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 595)

Chain 3 - MESO-C[MSLN]_L1.14 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSSFPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
596)

Figure 32L

>XENP34152 MESO-C[MSLN]_H1.3_L1.13_Fab-MESO-
C[MSLN]_H1.3_L1.13_Fab_(G4S)2_[CD3]_L1.47_H1.89_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1.3_IgG1_pI(-)_Isosteric_A_/PVA_/S267K/L368D/K370S
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
597)

Chain 2 - MESO-
C[MSLN]_H1.3_(G4S)2_[CD3]_L1.47_H1.89_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKYNNYATYYADSVKGRFTISRDDSKNTLYLQMNSLRAEDTAV
YYCVRHGNFGDEYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 598)

Chain 3 - MESO-C[MSLN]_L1.13 Light Chain
DIVMTQSPDSLAVSLGERATINCKASHDVGQSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
599)

>XENP34153 MESO-C[MSLN]_H1.3_L1_Fab-MESO-
C[MSLN]_H1.3_L1_Fab_(G4S)2_[CD3]_L1.47_H1.89_scFv(GKPGS)4-IgG1_pI(-
)_Isosteric_A_/PVA_/S267K/L368D/K370S-Fc(216)_IgG1_C220S/PVA_/S267K/S364K/E357Q

Chain 1 - MESO-C[MSLN]_H1.3_IgG1_pI(-)_Isosteric_A_/PVA_/S267K/L368D/K370S
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
600)

Figure 32M

Chain 2 - MESO-
C[MSLN]_H1.3_(G4S)2_[CD3]_L1.47_H1.89_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKYNNYATYYADSVKGRFTISRDDSKNTLYLQMNSLRAEDTAV
YYCVRHGNFGDEYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 601)

Chain 3 - MESO-C[MSLN]_L1 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
602)

>XENP34154 MESO-C[MSLN]_H1.12_L1.9_Fab-MESO-
C[MSLN]_H1.12_L1.9_Fab_(G4S)2_[CD3]_L1.47_H1.89_scFv(GKPGS)4-IgG1_pl(-
)_Isosteric_A_/PVA_/S267K/L368D/K370S-Fc(216)_IgG1_C220S/PVA_/S267K/S364K/E357Q

Chain 1 - MESO-C[MSLN]_H1.12_IgG1_pl(-)_Isosteric_A_/PVA_/S267K/L368D/K370S
QVQLVQSGAEVKKPGASVKVSCKASGYTFTSYWMHWVRQAPGQGLEWMGMIHPNSDNTIYYQKFQGRVTMTVDKSIS
TAYMELSRLRSDDTAVYYCAIIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVMHEALHNHYTQKSLSLSPGK (SEQ ID NO:
603)

Chain 2 - MESO-
C[MSLN]_H1.12_(G4S)2_[CD3]_L1.47_H1.89_scFv(GKPGS)4_Fc(216)_IgG1_C220S/PVA_/S267K/S364K/E357Q
QVQLVQSGAEVKKPGASVKVSCKASGYTFTSYWMHWVRQAPGQGLEWMGMIHPNSDNTIYYQKFQGRVTMTVDKSIS
TAYMELSRLRSDDTAVYYCAIIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKYNNYATYYADSVKGRFTISRDDSKNTLYLQMNSLRAEDTAV
YYCVRHGNFGDEYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVMHEALHNHYTQKSLSLSPGK (SEQ ID NO: 604)

Chain 3 - MESO-C[MSLN]_L1.9 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYYSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
605)

Figure 32N

>XENP34159 MESO-C[MSLN]_H1.3_L1.14_Fab-MESO-
C[MSLN]_H1.3_L1.14_Fab_(G4S)2_[CD3]_L1.47_H1.89_scFv(GKPGS)4-IgG1_pI(-
)_Isosteric_A_/PVA_/S267K/L368D/K370S/M248L/N434S-
Fc(216)_IgG1_C220S/PVA_/S267K/S364K/E357Q/M248L/N434S Chain 1 - MESO-C[MSLN]_H1.3_IgG1_pI(-)_Isosteric_A_/PVA_/S267K/L368D/K370S/M248L/N434S
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVLHEALHSHYTQKSLSLSPGK (SEQ ID NO:
606)

Chain 2 - MESO-
C[MSLN]_H1.3_(G4S)2_[CD3]_L1.47_H1.89_scFv(GKPGS)4_Fc(216)_IgG1_C220S/PVA_/S267K/S364K/E357Q/M2
48L/N434S
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKYNNYATYYADSVKGRFTISRDDSKNTLYLQMNSLRAEDTAV
YYCVRHGNFGDEYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVLHEALHSHYTQKSLSLSPGK (SEQ ID NO: 607)

Chain 3 - MESO-C[MSLN]_L1.14 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSSFPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
608)

>XENP34160 MESO-C[MSLN]_H1.3_L1.13_Fab-MESO-
C[MSLN]_H1.3_L1.13_Fab_(G4S)2_[CD3]_L1.47_H1.89_scFv(GKPGS)4-IgG1_pI(-
)_Isosteric_A_/PVA_/S267K/L368D/K370S/M248L/N434S-
Fc(216)_IgG1_C220S/PVA_/S267K/S364K/E357Q/M248L/N434S Chain 1 - MESO-C[MSLN]_H1.3_IgG1_pI(-)_Isosteric_A_/PVA_/S267K/L368D/K370S/M248L/N434S
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVLHEALHSHYTQKSLSLSPGK (SEQ ID NO:
609)

Figure 32O

Chain 2 - MESO-
C[MSLN]_H1.3_(G4S)2_[CD3]_L1.47_H1.89_scFv(GKPGS)4_Fc(216)_IgG1_C220S/PVA_/S267K/S364K/E357Q/M2
48L/N434S
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKYNNYATYYADSVKGRFTISRDDSKNTLYLQMNSLRAEDTAV
YYCVRHGNFGDEYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVLHEALHSHYTQKSLSLSPGK (SEQ ID NO: 610)

Chain 3 - MESO-C[MSLN]_L1.13 Light Chain
DIVMTQSPDSLAVSLGERATINCKASHDVGQSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
611)

>XENP34161 MESO-C[MSLN]_H1.3_L1_Fab-MESO-
C[MSLN]_H1.3_L1_Fab_(G4S)2_[CD3]_L1.47_H1.89_scFv(GKPGS)4-IgG1_pI(-
)_Isosteric_A_/PVA_/S267K/L368D/K370S/M248L/N434S-
Fc(216)_IgG1_C220S/PVA_/S267K/S364K/E357Q/M248L/N434S

Chain 1 - MESO-C[MSLN]_H1.3_IgG1_pI(-)_Isosteric_A_/PVA_/S267K/L368D/K370S/M248L/N434S
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVLHEALHSHYTQKSLSLSPGK (SEQ ID NO:
612)

Chain 2 - MESO-
C[MSLN]_H1.3_(G4S)2_[CD3]_L1.47_H1.89_scFv(GKPGS)4_Fc(216)_IgG1_C220S/PVA_/S267K/S364K/E357Q/M2
48L/N434S
QVQLVQSGAEVKKPGASVKVSCKASGYTFTSYWMHWVRQAPGQGLEWMGWIHPNSDNTIYYEKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKYNNYATYYADSVKGRFTISRDDSKNTLYLQMNSLRAEDTAV
YYCVRHGNFGDEYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVLHEALHSHYTQKSLSLSPGK (SEQ ID NO: 613)

Chain 3 - MESO-C[MSLN]_L1 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYSSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
614)

Figure 32P

>XENP34162 MESO-C[MSLN]_H1.12_L1.9_Fab-MESO-
C[MSLN]_H1.12_L1.9_Fab_(G4S)2_[CD3]_L1.47_H1.89_scFv(GKPGS)4-IgG1_pI(-
)_Isosteric_A_/PVA_/S267K/L368D/K370S/M248L/N434S-
Fc(216)_IgG1_C220S/PVA_/S267K/S364K/E357Q/M248L/N434S

Chain 1 - MESO-C[MSLN]_H1.12_IgG1_pI(-)_Isosteric_A_/PVA_/S267K/L368D/K370S/M248L/N434S
QVQLVQSGAEVKKPGASVKVSCKASGYTFTSYWMHWVRQAPGQGLEWMGMIHPNSDNTIYYQKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSDTKVDKKVEPKSCDKTHTCP
PCPAPPVAGPSVFLFPPKPKDTLMISRTPEVTCVVVDVKHEDPEVKFNWYVDGVEVHNAKTKPREEEYNSTYRVVSV
LTVLHQDWLNGKEYKCKVSNKALPAPIEKTISKAKGQPREPQVYTLPPSREEMTKNQVSLTCDVSGFYPSDIAVEWE
SDGQPENNYKTTPPVLDSDGSFFLYSKLTVDKSRWEQGDVFSCSVLHEALHSHYTQKSLSLSPGK (SEQ ID NO:
615)

Chain 2 - MESO-C[MSLN]_H1.12_(G4S)2_[CD3]_L1.47_H1.89_scFv(GKPGS)4_Fc(216)_IgG1_C220S/PVA_/S267K/S364K/E357Q/M248L/N434S
QVQLVQSGAEVKKPGASVKVSCKASGYTFTSYWMHWVRQAPGQGLEWMGMIHPNSDNTIYYQKFQGRVTMTVDKSIS
TAYMELSRLRSDDTAVYYCAIIITPVVPKFDYWGQGTLVTVSS/ASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSC/GGGGSG
GGGS/QAVVTQEPSLTVSPGGTVTLTCGSSTGAVTTSNYANWVQQKPGKSPRGLIGGTNKRAPGVPARFSGSLLGGK
AALTISGAQPEDEADYYCALWYSNHWVFGGGTKLTVL/GKPGSGKPGSGKPGSGKPGS/EVQLVESGGGLVQPGGSL
RLSCAASGFTFSTYAMNWVRQAPGKGLEWVGRIRSKYNNYATYYADSVKGRFTISRDDSKNTLYLQMNSLRAEDTAV
YYCVRHGNFGDEYVSWFAYWGQGTLVTVSS/GGGGSGGGGS/KTHTCPPCPAPPVAGPSVFLFPPKPKDTLMISRTP
EVTCVVVDVKHEDPEVKFNWYVDGVEVHNAKTKPREEQYNSTYRVVSVLTVLHQDWLNGKEYKCKVSNKALPAPIEK
TISKAKGQPREPQVYTLPPSREQMTKNQVKLTCLVKGFYPSDIAVEWESNGQPENNYKTTPPVLDSDGSFFLYSKLT
VDKSRWQQGNVFSCSVLHEALHSHYTQKSLSLSPGK (SEQ ID NO: 616)

Chain 3 - MESO-C[MSLN]_L1.9 Light Chain
DIVMTQSPDSLAVSLGERATINCKASHDVGTSVAWYQQKPGQSPKLLIYWASTRHTGVPDRFTGSGSGTDFTLTISS
LQAEDVAVYFCQQYYSYPLTFGAGTKLEIK/RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC (SEQ ID NO:
617)

Figure 33
A)
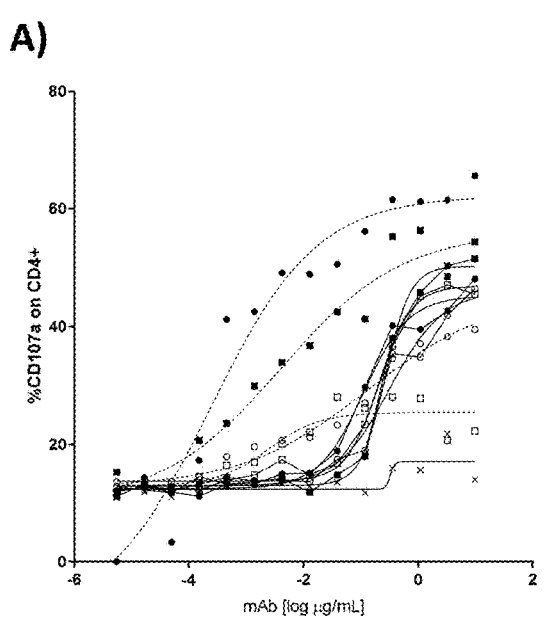
B)
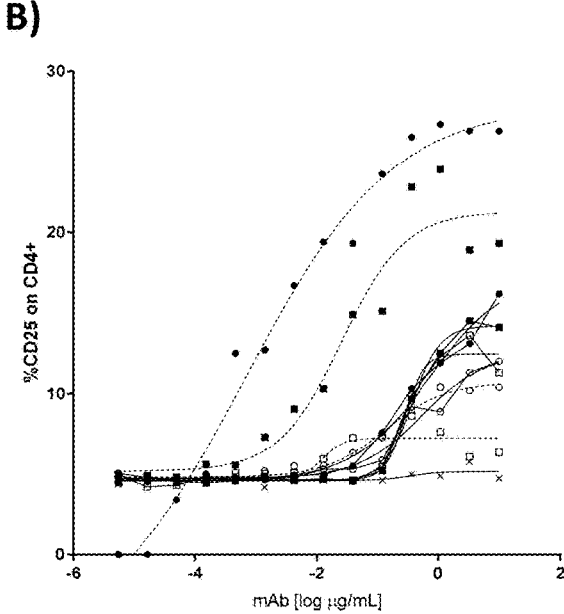
C)
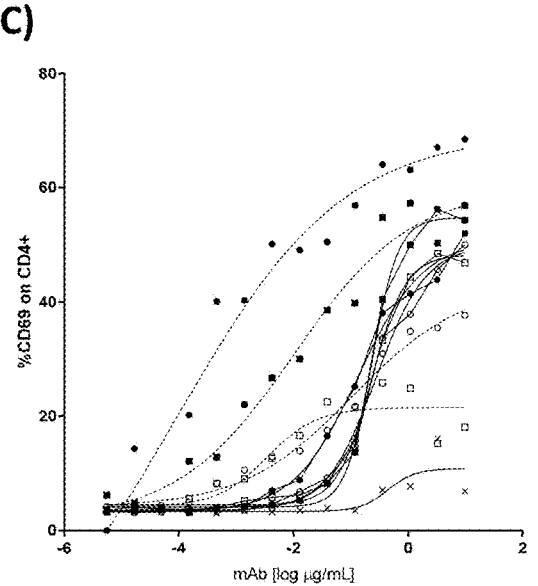
XENP15074 anti-RSV mAb
XENP16248 MESO-A 1+1 CD3 High[VHVL]
XENP31063 MESO-A 2+1 CD3 High[VHVL]
XENP30764 MESO-A 1+1 CD3 High-Int#1[VHVL]
XENP31064 MESO-A 2+1 CD3 High-Int#1[VHVL]
XENP16833 MESO-B 1+1 CD3 High[VHVL]
XENP31067 MESO-B 2+1 CD3 High[VHVL]
XENP30765 MESO-B 1+1 CD3 High-Int#1[VHVL]
XENP31066 MESO-B 2+1 CD3 High-Int#1[VHVL]

Figure 34
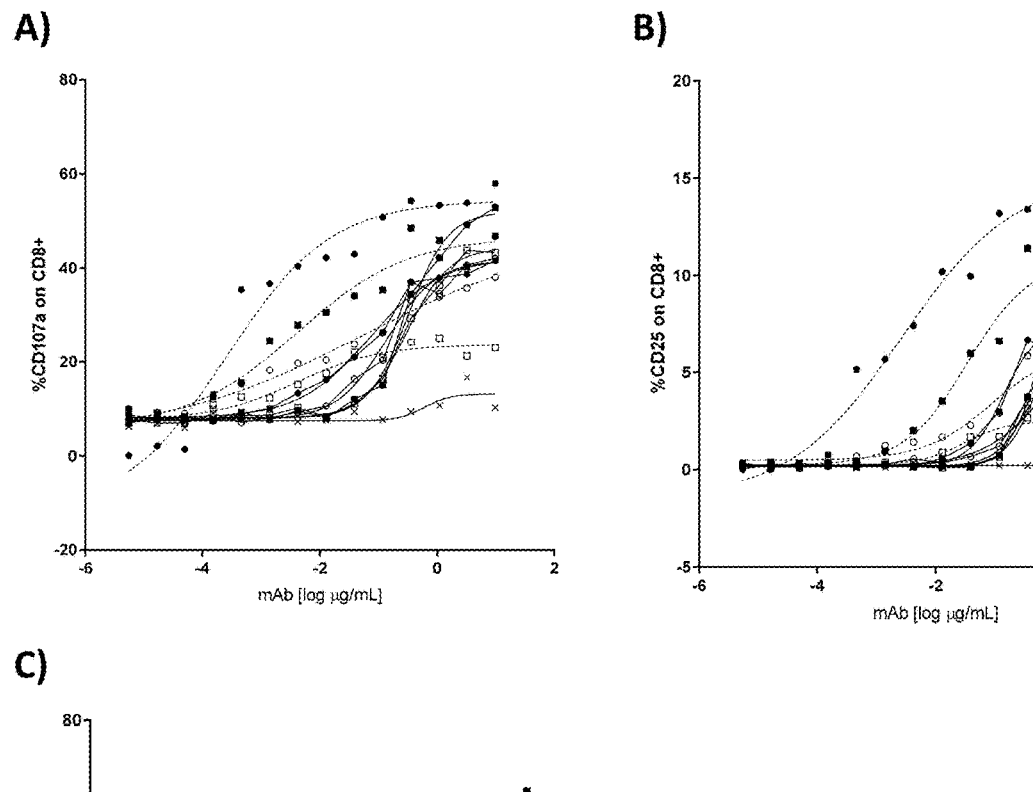
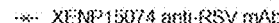

Figure 35A
A)
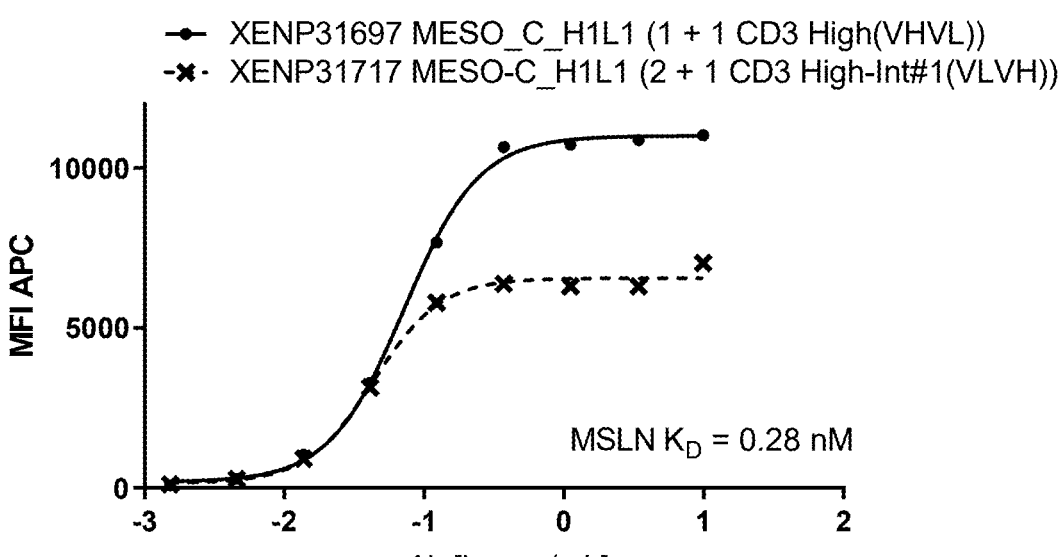
B)
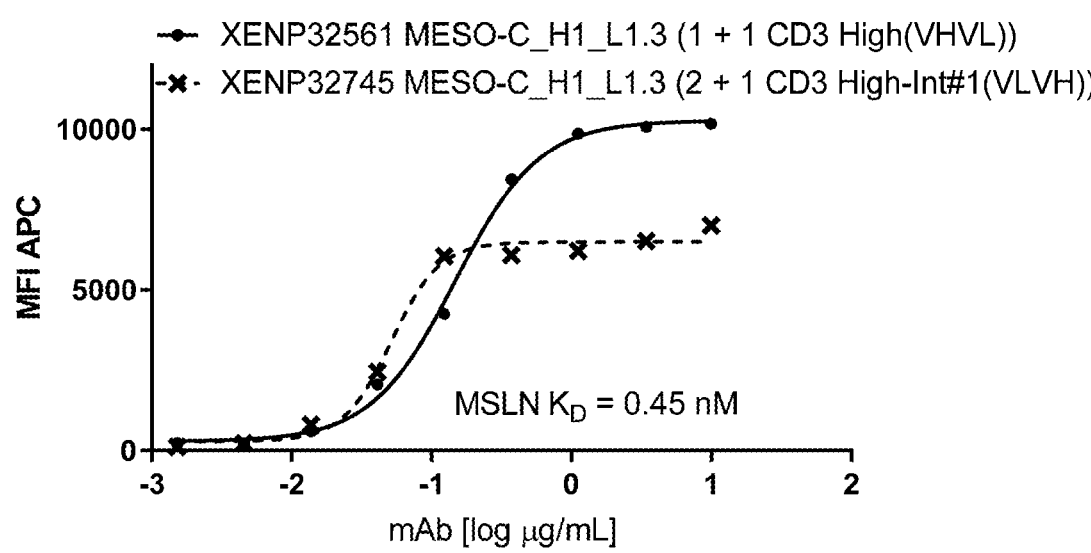

Figure 35B
C)
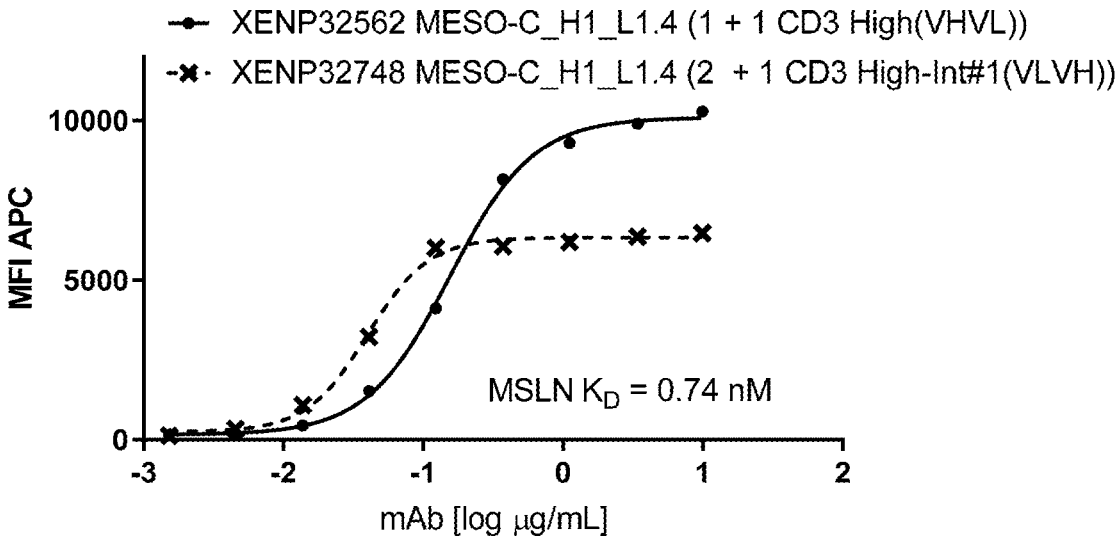
D)
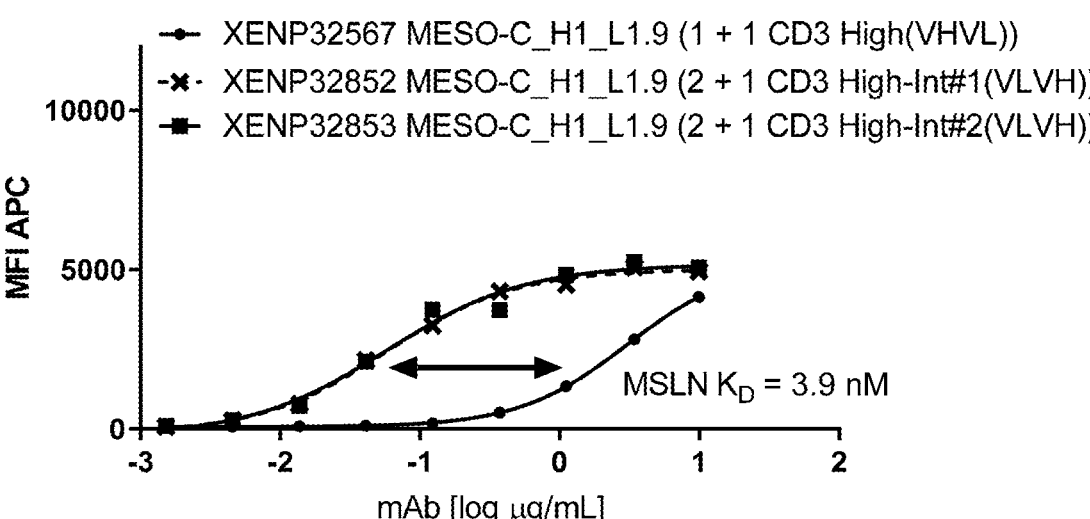

Figure 35C
E)
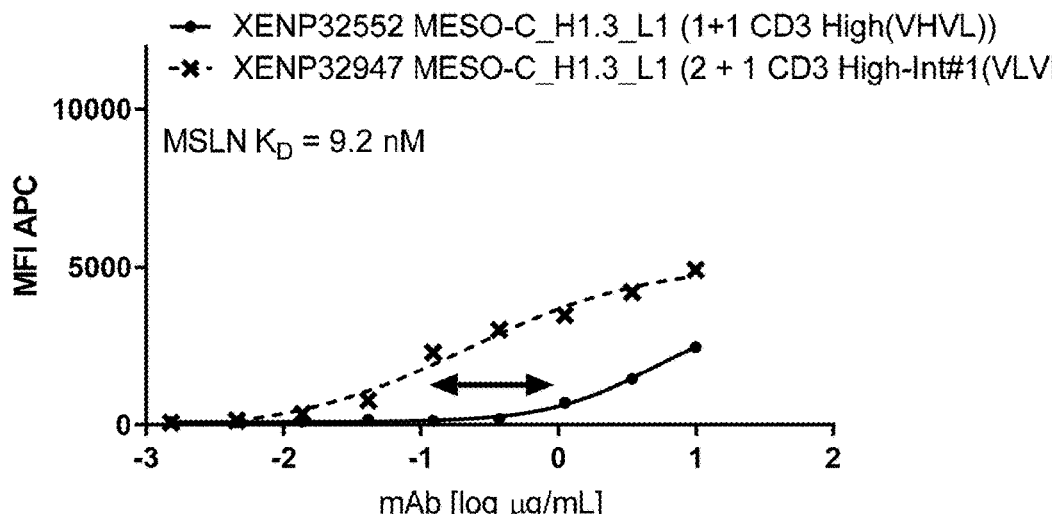
F)
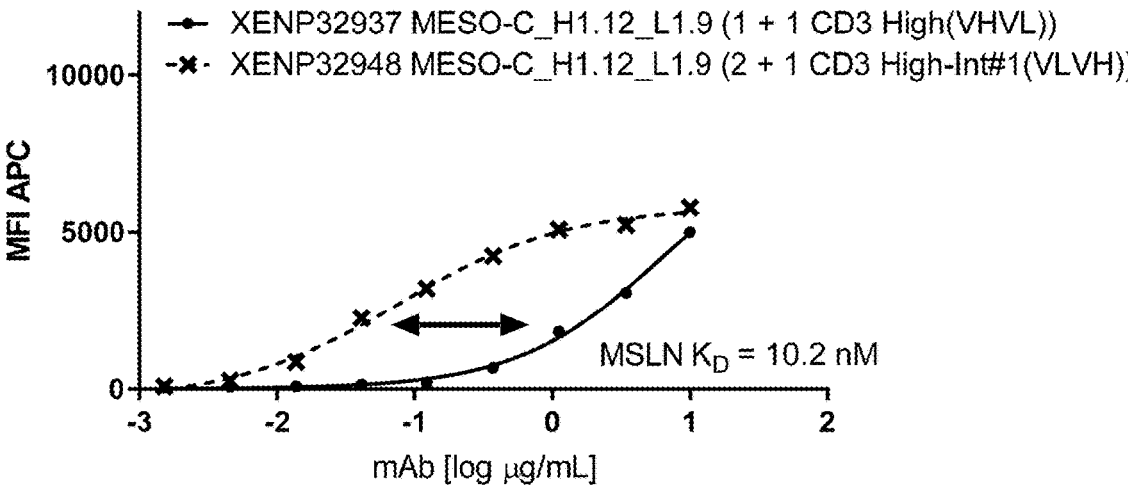

G)

IHC Score 3 (Target)

- ◆ OVCAR8 (~89.8K MSLN Density)

IHC Score 1 and Score 0

- ✶ SKOV3 (~8.9K MSLN Density)
- ● HT29 (~6.5K MSLN Density)
- ■ A549 (~1.1K MSLN Density)
- ▲ MCF7 (~5.8K MSLN Density)

Figure 37
A)
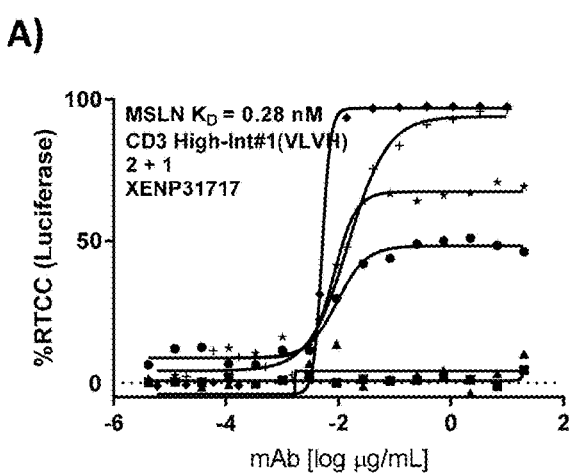
B)
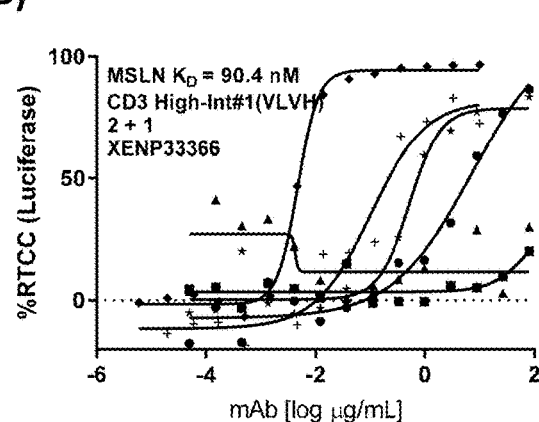
C)
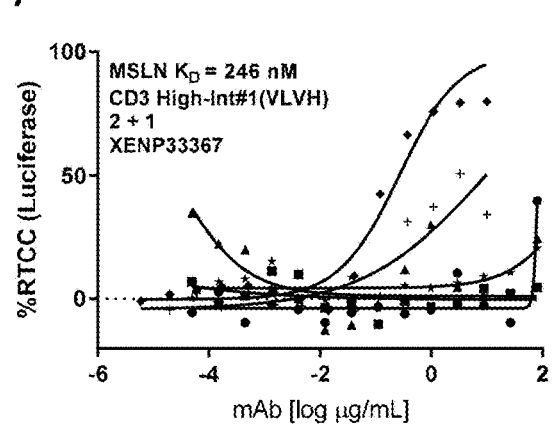
IHC Score 3 and Score 2 (Target)
- ◆ OVCAR8 (~89.8K MSLN Density)
- ✦ OVCAR3
IHC Score 1 and Score 0
- ★ SKOV3 (~8.9K MSLN Density)
- ● HT29 (~6.5K MSLN Density)
- ✱ A549 (~1.1K MSLN Density)
- ▲ MCF7 (~5.8K MSLN Density)

Figure 38
A)
B)
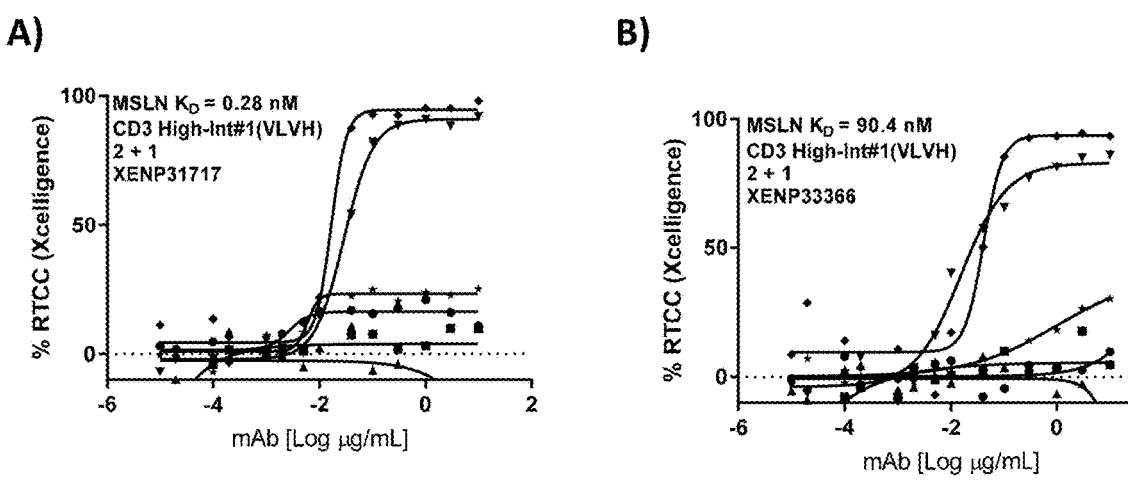
C)
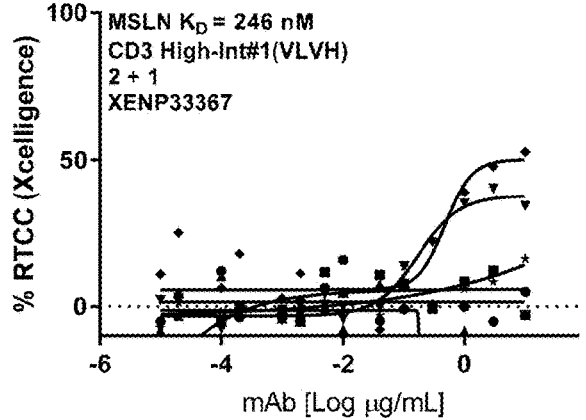
IHC Score 3 and Score 2 (Target)
- ◆ OVCAR8 (~89.8K MSLN Density)
- ▼ ASPC1 (~36.7K MSLN Density)
IHC Score 1 and Score 0
- ★ SKOV3 (~8.9K MSLN Density)
- ● HT29 (~6.5K MSLN Density)
- ✻ A549 (~1.1K MSLN Density)
- ▲ MCF7 (~5.8K MSLN Density)

Figure 39
A)
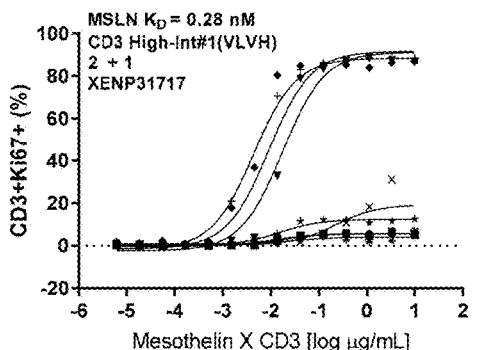
B)
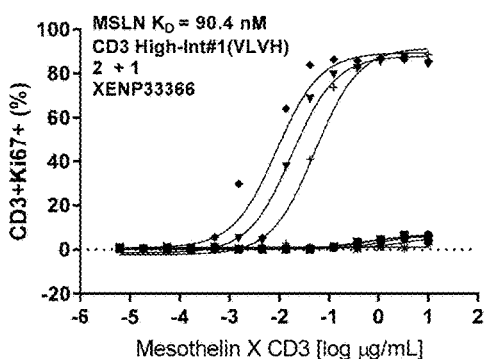
C)
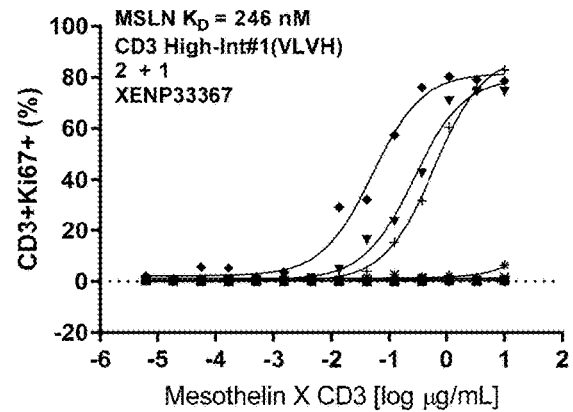
IHC Score 3 and Score 2 (Target)
* ◆ OVCAR8 (~89.8K MSLN Density)
* + OVCAR3
* ▼ ASPC1 (~36.7K MSLN Density)
IHC Score 1 and Score 0
* ✳ SKOV3 (~8.9K MSLN Density)
* ● HT29 (~6.5K MSLN Density)
* ■ A549 (~1.1K MSLN Density)
* ✶ Huh7 (Low MSLN Density)
* × 22RV1 (Low MSLN Density)

Figure 40
A)
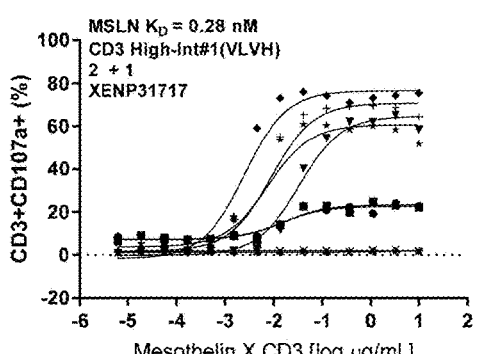
B)
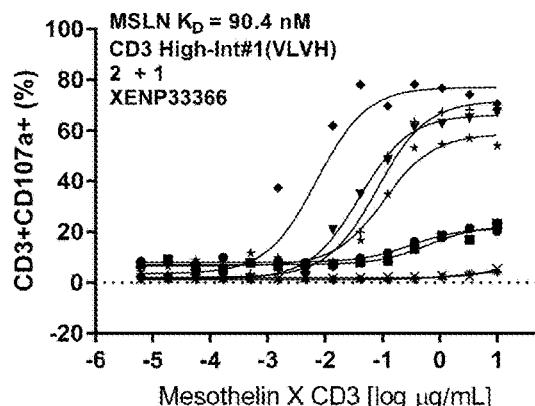
C)
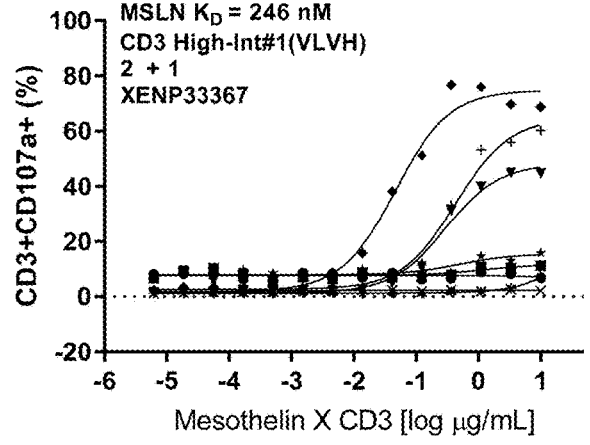
IHC Score 3 and Score 2  (Target)
- ◆  OVCAR8 (~89.8K MSLN Density)
- +   OVCAR3
- ▼  ASPC1 (~36.7K MSLN Density)
IHC Score 1 and Score 0
- ✶  SKOV3 (~8.9K MSLN Density)
- ■  HT29 (~6.5K MSLN Density)
- ✳  A549 (~1.1K MSLN Density)
- ✻  Huh7 (Low MSLN Density)
- ×  22RV1 (Low MSLN Density)

Figure 41
A)
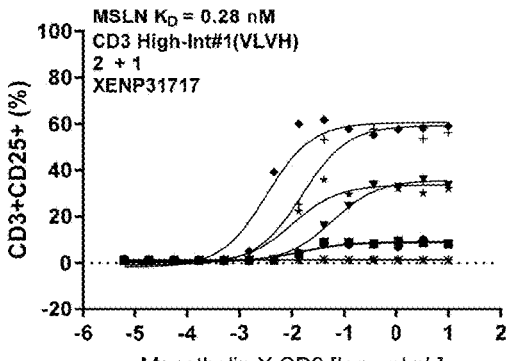
B)
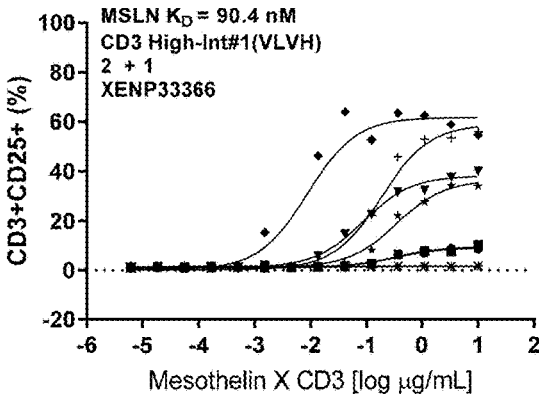
C)
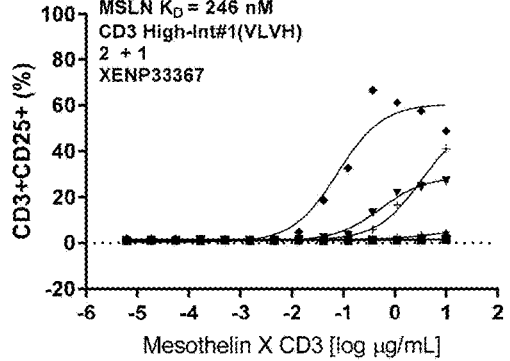
IHC Score 3 and Score 2 (Target)
- ◆ OVCAR8 (~89.8K MSLN Density)
- ✧ OVCAR3
- ▼ ASPC1 (~36.7K MSLN Density)
IHC Score 1 and Score 0
- ★ SKOV3 (~8.9K MSLN Density)
- ● HT29 (~6.5K MSLN Density)
- ▪ A549 (~1.1K MSLN Density)
- ✳ Huh7 (Low MSLN Density)
- ✕ 22RV1 (Low MSLN Density)

Figure 42
A)
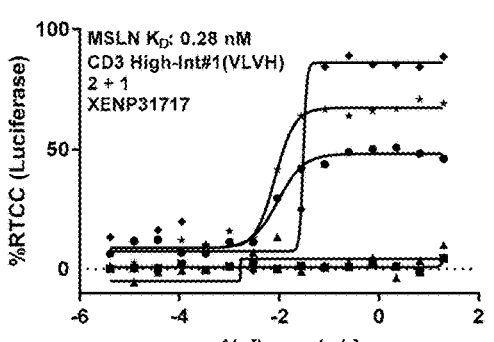
B)
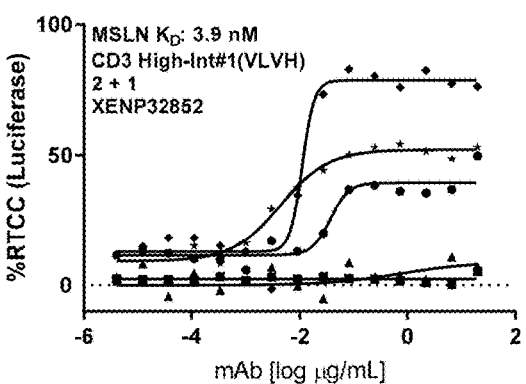
C)
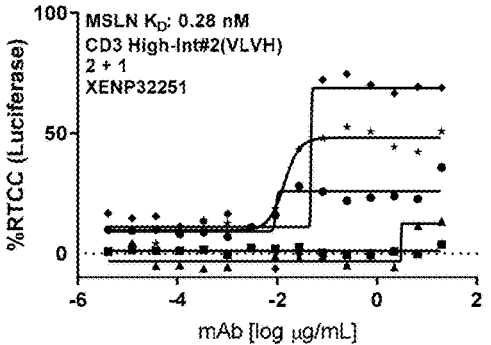
D)
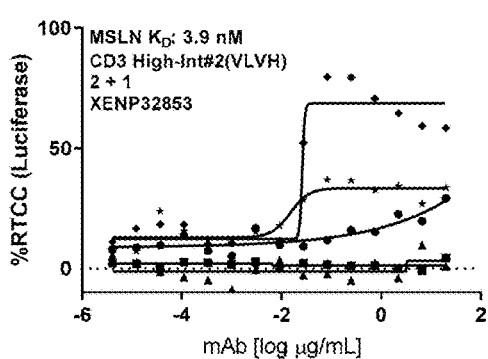

Figure 43A
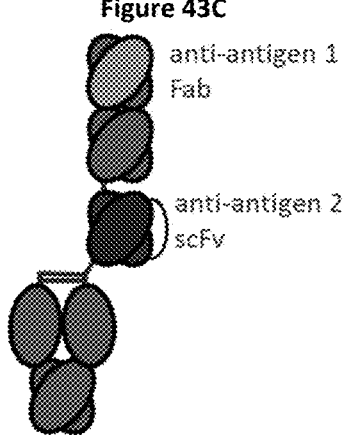
**Bottle Opener or
1+1 Fab-scFv-Fc**
Figure 43B
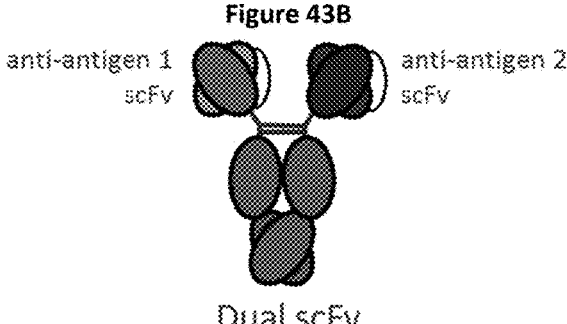
Dual scFv
Figure 43C
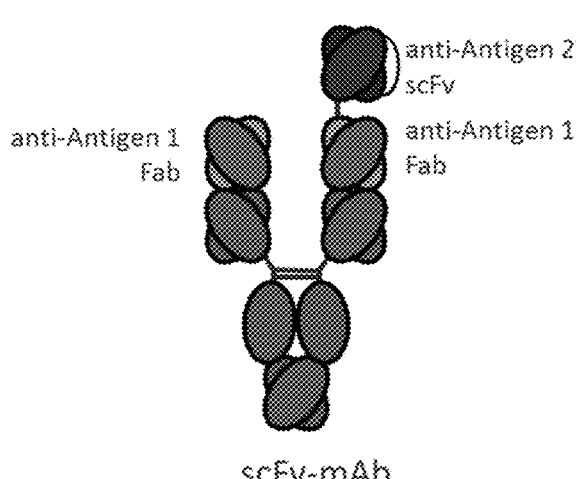
One-arm central-scFv
Figure 43D
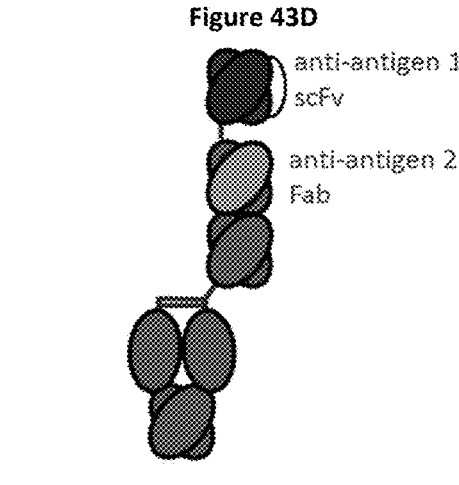
Figu One-arm scFv-mAb
Figure 43E
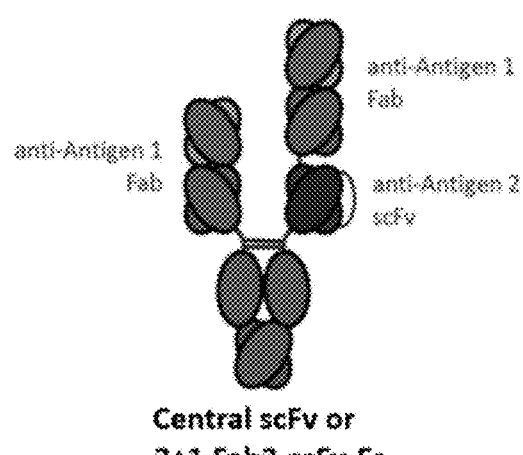
scFv-mAb
Figure 43F
**Central scFv or
2+1 Fab2-scFv-Fc** anti-Antigen 1 Fab anti-Antigen 1 Fab anti-Antigen 2 scFv mAb-Fv anti-Antigen 1 Fab anti-Antigen 1 Fab anti-Antigen 2 scFv mAb-scFv anti-Antigen 1 Fab anti-Antigen 1 Fab anti-Antigen 2 scFv central-Fv anti-Antigen 1 Fv anti-Antigen 2 Fv Bispecific mAb anti-Antigen 1
Fv anti-Antigen 1
Fv anti-Antigen 2
Fab Trident

ANTIGEN BINDING DOMAINS THAT BIND TO MESOTHELIN (MSLN)

PRIORITY

This application is a continuation of U.S. patent application Ser. No. 17/321,272, filed May 14, 2021, which claims priority to U.S. Provisional Patent Application No. 63/025,021, filed May 14, 2020, which is hereby incorporated by reference in its entirety.

SEQUENCE LISTING INCORPORATION PARAGRAPH

The instant application contains a Sequence Listing which has been submitted electronically in XML format and is hereby incorporated by reference in its entirety. Said XML file, created on May 1, 2024, is named 067461-5268-US01.xml and is 1,210,988 bytes in size.

BACKGROUND

Antibody-based therapeutics have been used successfully to treat a variety of diseases, including cancer. An increasingly prevalent avenue being explored is the engineering of single immunoglobulin molecules that co-engage two different antigens. Such alternate antibody formats that engage two different antigens are often referred to as bispecific antibodies. Because the considerable diversity of the antibody variable region (Fv) makes it possible to produce an Fv that recognizes virtually any molecule, the typical approach to bispecific antibody generation is the introduction of new variable regions into the antibody.

A particularly useful approach for bispecific antibodies is to engineer a first binding domain which engages CD3 and a second binding domain which engages an antigen associated with or upregulated on cancer cells so that the bispecific antibody redirects CD3⁺ T cells to destroy the cancer cells. Mesothelin (MSLN) has previously been reported to be highly expressed in ovarian tumors. Current treatment options for ovarian cancer have only modest efficacy and there remains a large unmet need for new targeted therapies. The present invention provides novel bispecific antibodies to CD3 and MSLN that are capable of localizing CD3⁺ effector T cells to MSLN expressing tumors such as in ovarian cancer.

BRIEF SUMMARY

Accordingly, provided herein are MSLN antigen binding domains and anti-MSLN antibodies (e.g., bispecific antibodies).

In one aspect, provided herein is a composition that includes a Mesothelin (MSLN) binding domain that includes the variable heavy complementary determining regions 1-3 (vhCDR1-3) and the variable light complementary determining regions (vlCDR1-3) of any of the following MSLN binding domains: MESO-A[MSLN]_H1.1_L1, MESO-B[MSLN]_H0L0, MESO-C[MSLN]_H1L1, MESO-C[MSLN]_H1.1_L1, MESO-C[MSLN]_H1.2L1, MESO-C[MSLN]_H1.3_L1, MESO-C[MSLN]_H1.4_L1, MESO-C[MSLN]_H1.5_L1, MESO-C[MSLN]_H1.6_L1, MESO-C[MSLN]_H1.7_L1, MESO-C[MSLN]_H1.8_L1, MESO-C[MSLN]_H1.9_L1, MESO-C[MSLN]_H1_L1.1, MESO-C[MSLN]_H1_L1.2, MESO-C[MSLN]_H1_L1.3, MESO-C[MSLN]_H1_L1.4, MESO-C[MSLN]_H1_L1.5, MESO-C[MSLN]_H1_L1.6, MESO-C[MSLN]_H1_L1.7, MESO-C[MSLN]_H1_L1.8, MESO-C[MSLN]_H1_L1.9, MESO-C[MSLN]_H1_L1.10, MESO-C[MSLN]_H1.5_L1.3, MESO-C[MSLN]_H1.6_L1.3, MESO-C[MSLN]_H1.12_L1.9, MESO-C[MSLN]_H1.13_L1.9, MESO-C[MSLN]_H1.3_L1.13, MESO-C[MSLN]_H1.3_L1.14, MESO-C[MSLN]_H1.3_L1.15, MESO-C[MSLN]_H1.3_L1.16, MESO-C[MSLN]_H1.3_L1.17, MESO-C[MSLN]_H1.3_L1.18, MESO-C[MSLN]_H1.3_L1.9, MESO-C[MSLN]_H1.3_L1.5, MESO-C[MSLN]_H1_L1.20, MESO-C[MSLN]_H1.12_L1.20, MESO-C[MSLN]_H1.14_L1.14, MESO-C[MSLN]_H1.15_L1.14, MESO-C[MSLN]_H1.16_L1.14, MESO-C[MSLN]_H1_L1.19_, MESO-C[MSLN]_H1_L1.21, MESO-C[MSLN]_H1_L1.22, MESO-C[MSLN]_H1.12_L1.19, MESO-C[MSLN]_H1.12_L1.21, MESO-C[MSLN]_H1.12_L1.22, and MESO-C[MSLN]_H1.12_L1.9 (FIGS. 15-21).

In another aspect, provided herein is a composition that includes a Mesothelin (MSLN) binding domain that includes a variable heavy domain and a variable light domain of any of the following MSLN binding domains: MESO-A[MSLN]_H1.1_L1, MESO-B[MSLN]_H0L0, MESO-C[MSLN]_H1L1, MESO-C[MSLN]_H1.1_L1, MESO-C[MSLN]_H1.2L1, MESO-C[MSLN]_H1.3_L1, MESO-C[MSLN]_H1.4_L1, MESO-C[MSLN]_H1.5_L1, MESO-C[MSLN]_H1.6_L1, MESO-C[MSLN]_H1.7_L1, MESO-C[MSLN]_H1.8_L1, MESO-C[MSLN]_H1.9_L1, MESO-C[MSLN]_H1_L1.1, MESO-C[MSLN]_H1_L1.2, MESO-C[MSLN]_H1_L1.3, MESO-C[MSLN]_H1_L1.4, MESO-C[MSLN]_H1_L1.5, MESO-C[MSLN]_H1_L1.6, MESO-C[MSLN]_H1_L1.7, MESO-C[MSLN]_H1_L1.8, MESO-C[MSLN]_H1_L1.9, MESO-C[MSLN]_H1_L1.10, MESO-C[MSLN]_H1.5_L1.3, MESO-C[MSLN]_H1.6_L1.3, MESO-C[MSLN]_H1.12_L1.9, MESO-C[MSLN]_H1.13_L1.9, MESO-C[MSLN]_H1.3_L1.13, MESO-C[MSLN]_H1.3_L1.14, MESO-C[MSLN]_H1.3_L1.15, MESO-C[MSLN]_H1.3_L1.16, MESO-C[MSLN]_H1.3_L1.17, MESO-C[MSLN]_H1.3_L1.18, MESO-C[MSLN]_H1.3_L1.9, MESO-C[MSLN]_H1.3_L1.5, MESO-C[MSLN]_H1_L1.20, MESO-C[MSLN]_H1.12_L1.20, MESO-C[MSLN]_H1.14_L1.14, MESO-C[MSLN]_H1.15_L1.14, MESO-C[MSLN]_H1.16_L1.14, MESO-C[MSLN]_H1_L1.19_, MESO-C[MSLN]_H1_L1.21, MESO-C[MSLN]_H1_L1.22, MESO-C[MSLN]_H1.12_L1.19, MESO-C[MSLN]_H1.12_L1.21, MESO-C[MSLN]_H1.12_L1.22, and MESO-C[MSLN]_H1.12_L1.9 (FIGS. 15-21).

In another aspect, the present invention provides a composition that includes a Mesothelin (MSLN) binding domain selected from the following MSLN binding domains: MESO-A[MSLN]_H1.1_L1, MESO-B[MSLN]_H0L0, MESO-C[MSLN]_H1L1, MESO-C[MSLN]_H1.1_L1, MESO-C[MSLN]_H1.2L1, MESO-C[MSLN]_H1.3_L1, MESO-C[MSLN]_H1.4_L1, MESO-C[MSLN]_H1.5_L1, MESO-C[MSLN]_H1.6_L1, MESO-C[MSLN]_H1.7_L1, MESO-C[MSLN]_H1.8_L1, MESO-C[MSLN]_H1.9_L1, MESO-C[MSLN]_H1_L1.1, MESO-C[MSLN]_H1_L1.2, MESO-C[MSLN]_H1_L1.3, MESO-C[MSLN]_H1_L1.4, MESO-C[MSLN]_H1_L1.5, MESO-C[MSLN]_H1_L1.6, MESO-C[MSLN]_H1_L1.7, MESO-C[MSLN]_H1_L1.8, MESO-C[MSLN]_H1_L1.9, MESO-C[MSLN]_H1_L1.10, MESO-C[MSLN]_H1.5_L1.3, MESO-C[MSLN]_H1.6_L1.3, MESO-C[MSLN]_H1.12_L1.9, MESO-C[MSLN]_H1.13_L1.9, MESO-C[MSLN]_H1.3_L1.13, MESO-C[MSLN]_H1.3_L1.14, MESO-C[MSLN]_H1.3_L1.15, MESO-C[MSLN]_H1.3_L1.16, MESO-C[MSLN]_H1.3_L1.17, MESO-C[MSLN]_H1.3_L1.18, MESO-C[MSLN]_H1.3_L1.9, MESO-C[MSLN]_H1.3_L1.5, MESO-C[MSLN]_H1_L1.20, MESO-C[MSLN]_H1.12_L1.20, MESO-C[MSLN]_H1.14_L1.14, MESO-C[MSLN]_H1.15_L1.14, MESO-C[MSLN]_H1.16_L1.14, MESO-C[MSLN]_H1_L1.19, MESO-C[MSLN]_H1_L1.21, MESO-C[MSLN]_H1_L1.22, MESO-C[MSLN]_H1.12_L1.19, MESO-C[MSLN]_H1.12_L1.21, MESO-C[MSLN]_H1.12_L1.22, and MESO-C[MSLN]_H1.12_L1.9 (FIGS. 15-21).

In another aspect, the present invention provides a nucleic acid composition that includes: a) a first nucleic acid encoding a variable heavy domain that includes the variable heavy complementary determining regions 1-3 (vhCDR1-3) of a MSLN binding domain; and b) a second nucleic acid encoding a variable light domain that includes the variable light complementary determining regions 1-3 (vlCDR1-3) of the MSLN binding domain, wherein the MSLN binding domain is one of the following MSLN binding domains: MESO-A[MSLN]_H1.1_L1, MESO-B[MSLN]_H0L0, MESO-C[MSLN]_H1L1, MESO-C[MSLN]_H1.1_L1, MESO-C[MSLN]_H1.2L1, MESO-C[MSLN]_H1.3_L1, MESO-C[MSLN]_H1.4_L1, MESO-C[MSLN]_H1.5_L1, MESO-C[MSLN]_H1.6_L1, MESO-C[MSLN]_H1.7_L1, MESO-C[MSLN]_H1.8_L1, MESO-C[MSLN]_H1.9_L1, MESO-C[MSLN]_H1_L1.1, MESO-C[MSLN]_H1_L1.2, MESO-C[MSLN]_H1_L1.3, MESO-C[MSLN]_H1_L1.4, MESO-C[MSLN]_H1_L1.5, MESO-C[MSLN]_H1_L1.6, MESO-C[MSLN]_H1_L1.7, MESO-C[MSLN]_H1_L1.8, MESO-C[MSLN]_H1_L1.9, MESO-C[MSLN]_H1_L1.10, MESO-C[MSLN]_H1.5_L1.3, MESO-C[MSLN]_H1.6_L1.3, MESO-C[MSLN]_H1.12_L1.9, MESO-C[MSLN]_H1.13_L1.9, MESO-C[MSLN]_H1.3_L1.13, MESO-C[MSLN]_H1.3_L1.14, MESO-C[MSLN]_H1.3_L1.15, MESO-C[MSLN]_H1.3_L1.16, MESO-C[MSLN]_H1.3_L1.17, MESO-C[MSLN]_H1.3_L1.18, MESO-C[MSLN]_H1.3_L1.9, MESO-C[MSLN]_H1.3_L1.5, MESO-C[MSLN]_H1_L1.20, MESO-C[MSLN]_H1.12_L1.20, MESO-C[MSLN]_H1.14_L1.14, MESO-C[MSLN]_H1.15_L1.14, MESO-C[MSLN]_H1.16_L1.14, MESO-C[MSLN]_H1_L1.19, MESO-C[MSLN]_H1_L1.21, MESO-C[MSLN]_H1_L1.22, MESO-C[MSLN]_H1.12_L1.19, MESO-C[MSLN]_H1.12_L1.21, MESO-C[MSLN]_H1.12_L1.22, and MESO-C[MSLN]_H1.12_L1.9 (FIGS. 15-21).

In another aspect, the present invention provides a nucleic acid composition that includes: a) a first nucleic acid encoding a variable heavy domain that includes the variable heavy domain of a MSLN binding domain; and b) a second nucleic acid encoding a variable light domain that includes the variable light domain of the MSLN binding domain, wherein the MSLN binding domain is any one of the following MSLN binding domains: MESO-A[MSLN]_H1.1_L1, MESO-B[MSLN]_H0L0, MESO-C[MSLN]_H1L1, MESO-C[MSLN]_H1.1_L1, MESO-C[MSLN]_H1.2L1, MESO-C[MSLN]_H1.3_L1, MESO-C[MSLN]_H1.4_L1, MESO-C[MSLN]_H1.5_L1, MESO-C[MSLN]_H1.6_L1, MESO-C[MSLN]_H1.7_L1, MESO-C[MSLN]_H1.8_L1, MESO-C[MSLN]_H1.9_L1, MESO-C[MSLN]_H1_L1.1, MESO-C[MSLN]_H1_L1.2, MESO-C[MSLN]_H1_L1.3, MESO-C[MSLN]_H1_L1.4, MESO-C[MSLN]_H1_L1.5, MESO-C[MSLN]_H1_L1.6, MESO-C[MSLN]_H1_L1.7, MESO-C[MSLN]_H1_L1.8, MESO-C[MSLN]_H1_L1.9, MESO-C[MSLN]_H1_L1.10, MESO-C[MSLN]_H1.5_L1.3, MESO-C[MSLN]_H1.6_L1.3, MESO-C[MSLN]_H1.12_L1.9, MESO-C[MSLN]_H1.13_L1.9, MESO-C[MSLN]_H1.3_L1.13, MESO-C[MSLN]_H1.3_L1.14, MESO-C[MSLN]_H1.3_L1.15, MESO-C[MSLN]_H1.3_L1.16, MESO-C[MSLN]_H1.3_L1.17, MESO-C[MSLN]_H1.3_L1.18, MESO-C[MSLN]_H1.3_L1.9, MESO-C[MSLN]_H1.3_L1.5, MESO-C[MSLN]_H1_L1.20, MESO-C[MSLN]_H1.12_L1.20, MESO-C[MSLN]_H1.14_L1.14, MESO-C[MSLN]_H1.15_L1.14, MESO-C[MSLN]_H1.16_L1.14, MESO-C[MSLN]_H1_L1.19, MESO-C[MSLN]_H1_L1.21, MESO-C[MSLN]_H1_L1.22, MESO-C[MSLN]_H1.12_L1.19, MESO-C[MSLN]_H1.12_L1.21, MESO-C[MSLN]_H1.12_L1.22, and MESO-C[MSLN]_H1.12_L1.9 (FIGS. 15-21).

In some embodiments, the present invention provides an expression vector composition that includes: a) a first expression vector that includes the first nucleic acid b) a second expression vector that includes a second nucleic acid. In further embodiments, the present invention provides a host cell that includes the expression vector composition.

In some embodiments, the present invention provides a method of making a Mesothelin (MSLN) binding domain that includes culturing the host cell under conditions wherein the MSLN binding domain is expressed, and recovering the MSLN binding domain.

In another aspect, the present invention provides an anti-MSLN antibody that includes an Mesothelin (MSLN) binding domain, the MSLN binding domain includes the variable heavy complementary determining regions 1-3 (vhCDR1-3) and the variable light complementary determining regions (vlCDR1-3) of any of the following MSLN binding domains: MESO-A[MSLN]_H1.1_L1, MESO-B[MSLN]_H0L0, MESO-C[MSLN]_H1L1, MESO-C[MSLN]_H1.1_L1, MESO-C[MSLN]_H1.2L1, MESO-C[MSLN]_H1.3_L1, MESO-C[MSLN]_H1.4_L1, MESO-C[MSLN]_H1.5_L1, MESO-C[MSLN]_H1.6_L1, MESO-C[MSLN]_H1.7_L1, MESO-C[MSLN]_H1.8_L1, MESO-C[MSLN]_H1.9_L1, MESO-C[MSLN]_H1_L1.1, MESO-C[MSLN]_H1_L1.2, MESO-C[MSLN]_H1_L1.3, MESO-C[MSLN]_H1_L1.4, MESO-C[MSLN]_H1_L1.5, MESO-C[MSLN]_H1_L1.6, MESO-C[MSLN]_H1_L1.7, MESO-C[MSLN]_H1_L1.8, MESO-C[MSLN]_H1_L1.9, MESO-C[MSLN]_H1_L1.10, MESO-C[MSLN]_H1.5_L1.3, MESO-C[MSLN]_H1.6_L1.3, MESO-C[MSLN]_H1.12_L1.9, MESO-C[MSLN]_H1.13_L1.9, MESO-C[MSLN]_H1.3_L1.13, MESO-C[MSLN]_H1.3_L1.14, MESO-C[MSLN]_H1.3_L1.15, MESO-C[MSLN]_H1.3_L1.16, MESO-C[MSLN]_H1.3_L1.17, MESO-C[MSLN]_H1.3_L1.18, MESO-C[MSLN]_H1.3_L1.9, MESO-C[MSLN]_H1.3_L1.5, MESO-C[MSLN]_H1_L1.20, MESO-C[MSLN]_H1.12_L1.20, MESO-C[MSLN]_H1.14_L1.14, MESO-C[MSLN]_H1.15_L1.14, MESO-C[MSLN]_H1.16_L1.14, MESO-C[MSLN]_H1_L1.19_, MESO-C[MSLN]_H1_L1.21, MESO-C[MSLN]_H1_L1.22, MESO-C[MSLN]_H1.12_L1.19, MESO-C[MSLN]_H1.12_L1.21, MESO-C[MSLN]_H1.12_L1.22, and MESO-C[MSLN]_H1.12_L1.9 (FIGS. 15-21).

In some embodiments, the vhCDR1-3 and vlCDR1-3 are selected from the vhCDR1-3 and vlCDR1-3 of any of the following MSLN binding domains in FIGS. 15-21.

In another aspect, the present invention provides an anti-MSLN antibody that includes an Mesothelin (MSLN) binding domain, the MSLN binding domain includes a variable heavy domain and a variable light domain of any of the following MSLN binding domains: MESO-A[MSLN]_H1.1_L1, MESO-B[MSLN]_H0L0, MESO-C[MSLN]_H1L1, MESO-C[MSLN]_H1.1_L1, MESO-C[MSLN]_H1.2L1, MESO-C[MSLN]_H1.3_L1, MESO-C[MSLN]_

US 12,698,341 B2

5

H1.4_L1, MESO-C[MSLN]_H1.5_L1, MESO-C[MSLN]_
H1.6_L1, MESO-C[MSLN]_H1.7_L1, MESO-C[MSLN]_
H1.8_L1, MESO-C[MSLN]_H1.9_L1, MESO-C[MSLN]_
H1_L1.1, MESO-C[MSLN]_H1_L1.2, MESO-C[MSLN]_
H1_L1.3, MESO-C[MSLN]_H1_L1.4, MESO-C[MSLN]_
H1_L1.5, MESO-C[MSLN]_H1_L1.6, MESO-C[MSLN]_
H1_L1.7, MESO-C[MSLN]_H1_L1.8, MESO-C[MSLN]_
H1_L1.9, MESO-C[MSLN]_H1_L1.10, MESO-C
[MSLN]_ H1.5_L1.3, MESO-C[MSLN]_H1.6_L1.3,
MESO-C[MSLN]_H1.12_L1.9, MESO-C[MSLN]_
H1.13_L1.9, MESO-C[MSLN]_H1.3_L1.13, MESO-C
[MSLN]_ H1.3_L1.14, MESO-C[MSLN]_H1.3_L1.15,
MESO-C[MSLN]_H1.3_L1.16, MESO-C[MSLN]_
H1.3_L1.17, MESO-C[MSLN]_H1.3_L1.18, MESO-C
[MSLN]_ H1.3_L1.9, MESO-C[MSLN]_H1.3_L1.5,
MESO-C[MSLN]_H1_L1.20, MESO-C[MSLN]_
H1.12_L1.20, MESO-C[MSLN]_H1.14_L1.14, MESO-C
[MSLN]_ H1.15_L1.14, MESO-C[MSLN]_H1.16_L1.14,
MESO-C[MSLN]_H1_L1.19_, MESO-C[MSLN]_
H1_L1.21, MESO-C[MSLN]_H1_L1.22, MESO-C
[MSLN]_ H1.12_L1.19, MESO-C[MSLN]_H1.12_L1.21,
MESO-C[MSLN]_H1.12_L1.22, and MESO-C[MSLN]_
H1.12_L1.9 (FIGS. 15-21).

In another aspect, provided herein is an anti-MSLN
antibody that includes an Mesothelin (MSLN) binding
domain selected from any one of the following MSLN
binding domains: MESO-A[MSLN]_H1.1_L1, MESO-B
[MSLN]_H0L0, MESO-C[MSLN]_H1L1, MESO-C
[MSLN]_H1.1_L1, MESO-C[MSLN]_H1.2L1, MESO-C
[MSLN]_H1.3_L1, MESO-C[MSLN]_H1.4_L1, MESO-C
[MSLN]_H1.5_L1, MESO-C[MSLN]_H1.6_L1, MESO-C
[MSLN]_H1.7_L1, MESO-C[MSLN]_H1.8_L1, MESO-C
[MSLN]_H1.9_L1, MESO-C[MSLN]_H1_L1.1, MESO-C
[MSLN]_H1_L1.2, MESO-C[MSLN]_H1_L1.3, MESO-C
[MSLN]_H1_L1.4, MESO-C[MSLN]_H1_L1.5, MESO-C
[MSLN]_H1_L1.6, MESO-C[MSLN]_H1_L1.7, MESO-C
[MSLN]_H1_L1.8, MESO-C[MSLN]_H1_L1.9, MESO-C
[MSLN]_H1_L1.10, MESO-C[MSLN]_H1.5_L1.3,
MESO-C[MSLN]_H1.6_L1.3, MESO-C[MSLN]_
H1.12_L1.9, MESO-C[MSLN]_H1.13_L1.9, MESO-C
[MSLN]_H1.3_L1.13, MESO-C[MSLN]_H1.3_L1.14,
MESO-C[MSLN]_H1.3_L1.15, MESO-C[MSLN]_
H1.3_L1.16, MESO-C[MSLN]_H1.3_L1.17, MESO-C
[MSLN]_H1.3_L1.18, MESO-C[MSLN]_H1.3_L1.9,
MESO-C[MSLN]_H1.3_L1.5, MESO-C[MSLN]_
H1_L1.20, MESO-C[MSLN]_H1.12_L1.20, MESO-C
[MSLN]_H1.14_L1.14, MESO-C[MSLN]_H1.15_L1.14,
MESO-C[MSLN]_H1.16_L1.14, MESO-C[MSLN]_
H1_L1.19_, MESO-C[MSLN]_H1_L1.21, MESO-C
[MSLN]_H1_L1.22, MESO-C[MSLN]_H1.12_L1.19,
MESO-C[MSLN]_H1.12_L1.21, MESO-C[MSLN]_
H1.12_L1.22, and MESO-C[MSLN]_H1.12_L1.9 (FIGS.
15-21). In some embodiments, the antibody includes: a) a
first monomer that includes a first antigen binding domain
and a first constant domain; and b) a second monomer that
includes a second antigen binding domain and a second
constant domain, wherein either of the first antigen binding
domain or second antigen binding domain is the MSLN
binding domain. In further embodiments, first antigen bind-
ing domain and the second antigen binding domain bind
different antigens. In further embodiments, the first antigen
binding domain is the MSLN binding domain and the
second antigen binding domain is a CD3 binding domain. In
further embodiments, the CD3 binding domain includes the
vhCDR1-3, and vlCDR1-3 of any of the following CD3
binding domains: H1.30_L1.47, H1.32_L1.47,
H1.89_L1.47, H1.90_L1.47, H1.33_L1.47, H1.31_L1.47,

6

L1.47_H1.30, L1.47_H1.30, L1.47_H1.32, L1.47_H1.89,
L1.47_H1.90, L1.47_H1.33, and L1.47_H1.31 (FIGS. 10A-
10F). In further embodiments, the vhCDR1-3 and vlCDR1-3
of the CD3 binding domain are selected from the vhCDR1-3
and vlCDR1-3 in FIGS. 10A-10F.

In some embodiments, the CD3 binding domain includes
the variable heavy domain and variable light domain of any
of the following CD3 binding domains: H1.30_L1.47,
H1.32_L1.47, H1.89_L1.47, H1.90_L1.47, H1.33_L1.47,
H1.31_L1.47, L1.47_H1.30, L1.47_H1.30, L1.47_H1.32,
L1.47_H1.89, L1.47_H1.90, L1.47_H1.33, and
L1.47_H1.31 (FIGS. 10A-10F).

In some embodiments, the CD3 binding domain is an
anti-CD3 scFv.

In some embodiments, wherein the first and second con-
stant domains each includes CH2-CH3.

In some embodiments, the first and second constant
domains each includes CH1-hinge-CH2-CH3.

In some embodiments, the first and second constant
domains each are a variant constant domain.

In some embodiments, the first and second monomers
include a set of heterodimerization variants are any one of
the variants depicted in FIGS. 1A-1E. In some embodi-
ments, the set of heterodimerization variants includes one of
the follow set of variants: S364K/E357Q: L368D/K370S;
S364K: L368D/K370S; S364K: L368E/K370S; D401K:
T411E/K360E/Q362E; and T366W: T366S/L368A/Y407V.

In some embodiments, the first and second monomers
each further include an ablation variant. In further embodi-
ments, the ablation variant is E233P/L234V/L235A/
G236del/S267K.

In some embodiments, the at least one of the first or
second monomer further includes a pI variant. In further
embodiments, the pI variant is N208D/Q295E/N384D/
Q418E/N421D. In some embodiments, the scFv includes a
charged scFv linker.

In some embodiments, the present invention provides a
nucleic acid composition including nucleic acids encoding
the anti-MSLN. In some embodiments, the composition
including nucleic acids encoding first and second mono-
mers. In some embodiments, the present invention provides
expression vectors that include the nucleic acids. In some
embodiments, the present invention provides a host cell
transformed with the expression vector.

In some embodiments, the present invention provides a
method of making an anti-MSLN antibody according to any
one of claims B1 to B21. The method includes culturing the
host cell according to claim B25 under conditions wherein
the anti-MSLN antibody is expressed, and recovering the
anti-MSLN antibody. In some embodiments, the present
invention provides a method of treating a cancer that
includes administering to a patient in need thereof the
antibody.

In another aspect, the present invention provides a het-
erodimeric antibody that includes: a) a first monomer that
includes: i) an anti-CD3 scFv that includes a first variable
light domain, an scFv linker and a first variable heavy
domain; and ii) a first Fc domain, wherein the scFv is
covalently attached to the N-terminus of the first Fc domain
using a domain linker; b) a second monomer that includes a
VH2-CH1-hinge-CH2-CH3 monomer, wherein VH is a sec-
ond variable heavy domain and CH2-CH3 is a second Fc
domain; and c) a light chain that includes a second variable
light domain, wherein the second variable heavy domain and
the second variable light domain form a MSLN binding
domain.

In some embodiments, the MSLN binding domain
includes the vhCDR1-3 and vlCDR1-3 of any of the following MSLN binding domains: MESO-A[MSLN]_
H1.1_L1, MESO-B[MSLN]_H0L0, MESO-C[MSLN]_
H1L1, MESO-C[MSLN]_H1.1_L1, MESO-C[MSLN]_
H1.2L1, MESO-C[MSLN]_H1.3_L1, MESO-C[MSLN]_
H1.4_L1, MESO-C[MSLN]_H1.5_L1, MESO-C[MSLN]_
H1.6_L1, MESO-C[MSLN]_H1.7_L1, MESO-C[MSLN]_
H1.8_L1, MESO-C[MSLN]_H1.9_L1, MESO-C[MSLN]_
H1_L1.1, MESO-C[MSLN]_H1_L1.2, MESO-C[MSLN]_
H1_L1.3, MESO-C[MSLN]_H1_L1.4, MESO-C[MSLN]_
H1_L1.5, MESO-C[MSLN]_H1_L1.6, MESO-C[MSLN]_
H1_L1.7, MESO-C[MSLN]_H1_L1.8, MESO-C[MSLN]_
H1_L1.9, MESO-C[MSLN]_H1_L1.10, MESO-C
[MSLN]_ H1.5_L1.3, MESO-C[MSLN]_H1.6_L1.3,
MESO-C[MSLN]_H1.12_L1.9, MESO-C[MSLN]_
H1.13_L1.9, MESO-C[MSLN]_H1.3_L1.13, MESO-C
[MSLN]_ H1.3_L1.14, MESO-C[MSLN]_H1.3_L1.15,
MESO-C[MSLN]_H1.3_L1.16, MESO-C[MSLN]_
H1.3_L1.17, MESO-C[MSLN]_H1.3_L1.18, MESO-C
[MSLN]_ H1.3_L1.9, MESO-C[MSLN]_H1.3_L1.5,
MESO-C[MSLN]_H1_L1.20, MESO-C[MSLN]_
H1.12_L1.20, MESO-C[MSLN]_H1.14_L1.14, MESO-C
[MSLN]_ H1.15_L1.14, MESO-C[MSLN]_H1.16_L1.14,
MESO-C[MSLN]_H1_L1.19, MESO-C[MSLN]_
H1_L1.21, MESO-C[MSLN]_H1_L1.22, MESO-C
[MSLN]_ H1.12_L1.19, MESO-C[MSLN]_H1.12_L1.21,
MESO-C[MSLN]_H1.12_L1.22, and MESO-C[MSLN]_
H1.12_L1.9 (FIGS. 15-21).

In some embodiments, the vhCDR1-3 and vlCDR1-3 of
the MSLN binding domain are selected from the vhCDR1-3
and vlCDR1-3 sequences of the MSLN binding domains
provided in FIGS. 15-21.

In some embodiments, the second heavy variable domain
includes a heavy variable domain and the second light
variable domain includes a variable light domain of any of
the following MSLN binding domains: MESO-A[MSLN]_
H1.1_L1, MESO-B[MSLN]_H0L0, MESO-C[MSLN]_
H1L1, MESO-C[MSLN]_H1.1_L1, MESO-C[MSLN]_
H1.2L1, MESO-C[MSLN]_H1.3_L1, MESO-C[MSLN]_
H1.4_L1, MESO-C[MSLN]_H1.5_L1, MESO-C[MSLN]_
H1.6_L1, MESO-C[MSLN]_H1.7_L1, MESO-C[MSLN]_
H1.8_L1, MESO-C[MSLN]_H1.9_L1, MESO-C[MSLN]_
H1_L1.1, MESO-C[MSLN]_H1_L1.2, MESO-C[MSLN]_
H1_L1.3, MESO-C[MSLN]_H1_L1.4, MESO-C[MSLN]_
H1_L1.5, MESO-C[MSLN]_H1_L1.6, MESO-C[MSLN]_
H1_L1.7, MESO-C[MSLN]_H1_L1.8, MESO-C[MSLN]_
H1_L1.9, MESO-C[MSLN]_H1_L1.10, MESO-C
[MSLN]_ H1.5_L1.3, MESO-C[MSLN]_H1.6_L1.3,
MESO-C[MSLN]_H1.12_L1.9, MESO-C[MSLN]_
H1.13_L1.9, MESO-C[MSLN]_H1.3_L1.13, MESO-C
[MSLN]_ H1.3_L1.14, MESO-C[MSLN]_H1.3_L1.15,
MESO-C[MSLN]_H1.3_L1.16, MESO-C[MSLN]_
H1.3_L1.17, MESO-C[MSLN]_H1.3_L1.18, MESO-C
[MSLN]_ H1.3_L1.9, MESO-C[MSLN]_H1.3_L1.5,
MESO-C[MSLN]_H1_L1.20, MESO-C[MSLN]_
H1.12_L1.20, MESO-C[MSLN]_H1.14_L1.14, MESO-C
[MSLN]_ H1.15_L1.14, MESO-C[MSLN]_H1.16_L1.14,
MESO-C[MSLN]_H1_L1.19_, MESO-C[MSLN]_
H1_L1.21, MESO-C[MSLN]_H1_L1.22, MESO-C
[MSLN]_ H1.12_L1.19, MESO-C[MSLN]_H1.12_L1.21,
MESO-C[MSLN]_H1.12_L1.22, and MESO-C[MSLN]_
H1.12_L1.9 (FIGS. 15-21).

In some embodiments, the anti-CD3 scFv includes the
vhCDR1-3 and the vlCDR1-3 of any of the following CD3
binding domains: H1.30_L1.47, H1.32_L1.47,
H1.89_L1.47, H1.90_L1.47, H1.33_L1.47, H1.31_L1.47, L1.47_H1.30, L1.47_H1.30, L1.47_H1.32, L1.47_H1.89,
L1.47_H1.90, L1.47_H1.33, and L1.47_H1.31 (FIGS. 10A-
10F).

In some embodiments, the vhCDR1-3 and vlCDR1-3 of
the anti-CD3 scFv are selected from the vhCDR1-3 and
vlCDR1-3 in FIGS. 10A-10F.

In some embodiments, the anti-CD3 scFv includes the
variable heavy domain and variable light domain of any of
the following CD3 binding domains: H1.30_L1.47,
H1.32_L1.47, H1.89_L1.47, H1.90_L1.47, H1.33_L1.47,
H1.31_L1.47, L1.47_H1.30, L1.47_H1.30, L1.47_H1.32,
L1.47_H1.89, L1.47_H1.90, L1.47_H1.33, and
L1.47_H1.31 (FIGS. 10A-10F).

In some embodiments, the first variable light domain is
covalently attached to the N-terminus of the first Fc domain
using a domain linker.

In some embodiments, the first variable heavy domain is
covalently attached to the N-terminus of the first Fc domain
using a domain linker.

In some embodiments, the scFv linker is a charged scFv
linker.

In some embodiments, the first and second Fc domains are
variant Fc domains.

In some embodiments, the first and second monomers
includes a set of heterodimerization variants selected from
any of the heterodimerization variants in FIGS. 1A-1E. In
some embodiments, the set of heterodimerization variants
selected is from following: S364K/E357Q: L368D/K370S;
S364K: L368D/K370S; S364K: L368E/K370S; D401K:
T411E/K360E/Q362E; and T366W: T366S/L368A/Y407V,
wherein numbering is according to EU numbering.

In some embodiments, the first and second monomers
further includes an ablation variant. In some embodiments,
the ablation variant is E233P/L234V/L235A/G236del/
S267K, wherein numbering is according to EU numbering.

In some embodiments, one of the first or second monomer
includes a pI variant.

In some embodiments, the pI variant is N208D/Q295E/
N384D/Q418E/N421D, wherein numbering is according to
EU numbering.

In some embodiments, the first monomer includes amino
acid variants S364K/E357Q/E233P/L234V/L235A/
G236del/S267K, wherein the second monomer includes
amino acid variants
L368D/K370S/N208D/Q295E/N384D/Q418E/N421D/
E233P/L234V/L235A/G236del/S267 K, and wherein num-
bering is according to EU numbering.

In some embodiments, the scFv linker is a charged scFv
linker having the amino acid sequence (GKPGS)$_4$ (SEQ ID
NO: 1).

In some embodiments, the first and second monomers
each further include amino acid variants 428/434S.

In some embodiments, the heterodimeric antibody
includes the following heterodimeric antibodies:
XENP16248, XENP16833, XENP31697, XENP32550,
XENP32551, XENP32552, XENP32553, XENP32554,
XENP32555, XENP32556, XENP32557, XENP32558,
XENP32559, XENP32560, XENP32561, XENP32562,
XENP32563, XENP32564, XENP32565, XENP32566,
XENP32567, XENP32568, XENP32569, XENP32570,
XENP32937, XENP32938, XENP32939, XENP32940,
XENP32941, XENP32942, XENP32943, XENP32944,
XENP32945, XENP32946, XENP33888, XENP33889,
XENP30764, XENP30765, XENP31701, XENP33969,
XENP33971, XENP33973, XENP16251, XENP16834,
XENP16252, and XENP16835 (FIGS. 23-27).

In another aspect, the present invention provides a heterodimeric antibody that includes: a) a first monomer that includes from N-terminus to C-terminus, a scFv-linker-CH2-CH3, wherein scFv is an anti-CD3 scFV and CH2-CH3 is a first Fc domain; b) a second monomer that includes from N-terminus to C-terminus a VH-CH1-hinge-CH2-CH3, wherein CH2-CH3 is a second Fc domain; and c) a light chain that includes a VL-CL; wherein the first variant Fc domain includes amino acid variants S364K/E357Q, wherein the second variant Fc domain includes amino acid variants L368D/K370S, wherein the first and second variant Fc domains each include amino acid variants E233P/L234V/L235A/G236del/S267K, wherein the hinge-CH2-CH3 of the second monomer includes amino acid variants N208D/Q295E/N384D/Q418E/N421D, wherein the VH and VL form a MSLN binding domain that includes the variable heavy domain and the variable light domain, respectively, of a MSLN binding domain selected from: MESO-A[MSLN]_H1.1_L1, MESO-B[MSLN]_H0L0, MESO-C[MSLN]_H1L1, MESO-C[MSLN]_H1.1_L1, MESO-C[MSLN]_H1.2L1, MESO-C[MSLN]_H1.3_L1, MESO-C[MSLN]_H1.4_L1, MESO-C[MSLN]_H1.5_L1, MESO-C[MSLN]_H1.6_L1, MESO-C[MSLN]_H1.7_L1, MESO-C[MSLN]_H1.8_L1, MESO-C[MSLN]_H1.9_L1, MESO-C[MSLN]_H1_L1.1, MESO-C[MSLN]_H1_L1.2, MESO-C[MSLN]_H1_L1.3, MESO-C[MSLN]_H1_L1.4, MESO-C[MSLN]_H1_L1.5, MESO-C[MSLN]_H1_L1.6, MESO-C[MSLN]_H1_L1.7, MESO-C[MSLN]_H1_L1.8, MESO-C[MSLN]_H1_L1.9, MESO-C[MSLN]_H1_L1.10, MESO-C[MSLN]_H1.5_L1.3, MESO-C[MSLN]_H1.6_L1.3, MESO-C[MSLN]_H1.12_L1.9, MESO-C[MSLN]_H1.13_L1.9, MESO-C[MSLN]_H1.3_L1.13, MESO-C[MSLN]_H1.3_L1.14, MESO-C[MSLN]_H1.3_L1.15, MESO-C[MSLN]_H1.3_L1.16, MESO-C[MSLN]_H1.3_L1.17, MESO-C[MSLN]_H1.3_L1.18, MESO-C[MSLN]_H1.3_L1.9, MESO-C[MSLN]_H1.3_L1.5, MESO-C[MSLN]_H1_L1.20, MESO-C[MSLN]_H1.12_L1.20, MESO-C[MSLN]_H1.14_L1.14, MESO-C[MSLN]_H1.15_L1.14, MESO-C[MSLN]_H1.16_L1.14, MESO-C[MSLN]_H1_L1.19, MESO-C[MSLN]_H1_L1.21, MESO-C[MSLN]_H1_L1.22, MESO-C[MSLN]_H1.12_L1.19, MESO-C[MSLN]_H1.12_L1.21, MESO-C[MSLN]_H1.12_L1.22, and MESO-C[MSLN]_H1.12_L1.9 (FIGS. 15-21), wherein the anti-CD3 scFv includes the variable heavy domain and the variable light domain of a CD3 binding domain selected from H1.30_L1.47, H1.32_L1.47, H1.89_L1.47, H1.90_L1.47, H1.33_L1.47, H1.31_L1.47, L1.47_H1.30, L1.47_H1.30, L1.47_H1.32, L1.47_H1.89, L1.47_H1.90, L1.47_H1.33, and L1.47_H1.31 (FIGS. 10A-10F), and wherein numbering is according to EU numbering.

In some embodiments, the scFv includes a charged scFv linker having the amino acid sequence (GKPGS)$_4$ (SEQ ID NO: 1).

In some embodiments, the first and second variant Fc domains each further include amino acid variants 428/434S, wherein numbering is according to EU numbering.

In some embodiments, the present invention provides a nucleic acid composition that includes nucleic acids encoding the first and second monomers and the light chain of the antibody.

In some embodiments, the present invention provides an expression vector that includes the nucleic acids. In some embodiments, the present invention provides a host cell transformed with the expression vector.

In some embodiments, the present invention provides a method of treating a MSLN associated cancer that includes administering to a patient in need thereof any one of the antibodies provided herein.

In another aspect, the present invention provides a heterodimeric antibody that includes: a) a first monomer that includes from N-terminus to C-terminus, a VH1-CH1-linker 1-scFv-linker 2-CH2-CH3, wherein VH1 is a first variable heavy domain, scFv is an anti-CD3 scFV, linker 1 and linker 2 are a first domain linker and second domain linker, respectively, and CH2-CH3 is a first Fc domain; b) a second monomer that includes from N-terminus to C-terminus a VH2-CH1-hinge-CH2-CH3, wherein VH2 is a second variable heavy domain and CH2-CH3 is a second Fc domain; and c) a common light chain that includes a variable light domain; wherein the first variable heavy domain and the variable light domain form a first MSLN binding domain, and the second variable heavy domain and the variable light domain form a second MSLN binding domain.

In some embodiments, the first and second MSLN binding domains each includes the vhCDR1-3 and vlCDR1-3 of any of the following MSLN binding domains: MESO-A[MSLN]_H1.1_L1, MESO-B[MSLN]_H0L0, MESO-C[MSLN]_H1L1, MESO-C[MSLN]_H1.1_L1, MESO-C[MSLN]_H1.2L1, MESO-C[MSLN]_H1.3_L1, MESO-C[MSLN]_H1.4_L1, MESO-C[MSLN]_H1.5_L1, MESO-C[MSLN]_H1.6_L1, MESO-C[MSLN]_H1.7_L1, MESO-C[MSLN]_H1.8_L1, MESO-C[MSLN]_H1.9_L1, MESO-C[MSLN]_H1_L1.1, MESO-C[MSLN]_H1_L1.2, MESO-C[MSLN]_H1_L1.3, MESO-C[MSLN]_H1_L1.4, MESO-C[MSLN]_H1_L1.5, MESO-C[MSLN]_H1_L1.6, MESO-C[MSLN]_H1_L1.7, MESO-C[MSLN]_H1_L1.8, MESO-C[MSLN]_H1_L1.9, MESO-C[MSLN]_H1_L1.10, MESO-C[MSLN]_H1.5_L1.3, MESO-C[MSLN]_H1.6_L1.3, MESO-C[MSLN]_H1.12_L1.9, MESO-C[MSLN]_H1.13_L1.9, MESO-C[MSLN]_H1.3_L1.13, MESO-C[MSLN]_H1.3_L1.14, MESO-C[MSLN]_H1.3_L1.15, MESO-C[MSLN]_H1.3_L1.16, MESO-C[MSLN]_H1.3_L1.17, MESO-C[MSLN]_H1.3_L1.18, MESO-C[MSLN]_H1.3_L1.9, MESO-C[MSLN]_H1.3_L1.5, MESO-C[MSLN]_H1_L1.20, MESO-C[MSLN]_H1.12_L1.20, MESO-C[MSLN]_H1.14_L1.14, MESO-C[MSLN]_H1.15_L1.14, MESO-C[MSLN]_H1.16_L1.14, MESO-C[MSLN]_H1_L1.19_, MESO-C[MSLN]_H1_L1.21, MESO-C[MSLN]_H1_L1.22, MESO-C[MSLN]_H1.12_L1.19, MESO-C[MSLN]_H1.12_L1.21, MESO-C[MSLN]_H1.12_L1.22, and MESO-C[MSLN]_H1.12_L1.9 (FIGS. 15-21).

In some embodiments, the vhCDR1-3 and vlCDR1-3 of the first and second MSLN binding domains are selected from the vhCDR1-3 and vlCDR1-3 provided in FIGS. 15-21.

In some embodiments, the first and second variable heavy domain each include a variable heavy domain of a MSLN binding domain, and the first and second variable light domain each include a variable light domain of the MSLN binding domain, wherein the MSLN binding domain is any of the following MSLN binding domains: MESO-A[MSLN]_H1.1_L1, MESO-B[MSLN]_H0L0, MESO-C[MSLN]_H1L1, MESO-C[MSLN]_H1.1_L1, MESO-C[MSLN]_H1.2L1, MESO-C[MSLN]_H1.3_L1, MESO-C[MSLN]_H1.4_L1, MESO-C[MSLN]_H1.5_L1, MESO-C[MSLN]_H1.6_L1, MESO-C[MSLN]_H1.7_L1, MESO-C[MSLN]_H1.8_L1, MESO-C[MSLN]_H1.9_L1, MESO-C[MSLN]_H1_L1.1, MESO-C[MSLN]_H1_L1.2, MESO-C[MSLN]_H1_L1.3, MESO-C[MSLN]_H1_L1.4, MESO-C[MSLN]_H1_L1.5, MESO-C[MSLN]_H1_L1.6, MESO-C

[MSLN]_H1_L1.7, MESO-C[MSLN]_H1_L1.8, MESO-C[MSLN]_H1_L1.9, MESO-C[MSLN]_H1_L1.10, MESO-C[MSLN]_H1.5_L1.3, MESO-C[MSLN]_H1.6_L1.3, MESO-C[MSLN]_H1.12_L1.9, MESO-C[MSLN]_H1.13_L1.9, MESO-C[MSLN]_H1.3_L1.13, MESO-C[MSLN]_H1.3_L1.14, MESO-C[MSLN]_H1.3_L1.15, MESO-C[MSLN]_H1.3_L1.16, MESO-C[MSLN]_H1.3_L1.17, MESO-C[MSLN]_H1.3_L1.18, MESO-C[MSLN]_H1.3_L1.9, MESO-C[MSLN]_H1.3_L1.5, MESO-C[MSLN]_H1_L1.20, MESO-C[MSLN]_H1.12_L1.20, MESO-C[MSLN]_H1.14_L1.14, MESO-C[MSLN]_H1.15_L1.14, MESO-C[MSLN]_H1.16_L1.14, MESO-C[MSLN]_H1_L1.19, MESO-C[MSLN]_H1_L1.21, MESO-C[MSLN]_H1_L1.22, MESO-C[MSLN]_H1.12_L1.19, MESO-C[MSLN]_H1.12_L1.21, MESO-C[MSLN]_H1.12_L1.22, and MESO-C[MSLN]_H1.12_L1.9 (FIGS. 15-21).

In some embodiments, the scFv includes the vhCDR1-3 and the vlCDR1-3 of any of the following CD3 binding domains: H1.30_L1.47, H1.32_L1.47, H1.89_L1.47, H1.90_L1.47, H1.33_L1.47, H1.31_L1.47, L1.47_H1.30, L1.47_H1.30, L1.47_H1.32, L1.47_H1.89, L1.47_H1.90, L1.47_H1.33, and L1.47_H1.31 (FIGS. 10A-10F).

In some embodiments, the vhCDR1-3 and vlCDR1-3 of the scFv are selected from the vhCDR1-3 and vlCDR1-3 in FIGS. 10A-10F.

In some embodiments, the scFv includes the variable heavy domain and variable light domain of any of the following CD3 binding domains: H1.30_L1.47, H1.32_L1.47, H1.89_L1.47, H1.90_L1.47, H1.33_L1.47, H1.31_L1.47, L1.47_H1.30, L1.47_H1.30, L1.47_H1.32, L1.47_H1.89, L1.47_H1.90, L1.47_H1.33, and L1.47_H1.31 (FIGS. 10A-10F).

In some embodiments, the scFv includes an scFv variable heavy domain, an scFv variable light domain and an scFv linker that connects the scFv variable heavy domain and the scFv variable light domain.

In some embodiments, the scFv variable heavy domain is attached to the C-terminus of the CH1 of the first monomer using the first domain linker and the scFv variable light domain is covalently attached to the N-terminus of the first Fc domain using the second domain linker.

In some embodiments, the scFv variable light domain is attached to the C-terminus of the CH1 of the first monomer using the first domain linker and the scFv variable heavy domain is covalently attached to the N-terminus of the first Fc domain using the second domain linker.

In some embodiments, the scFv linker is a charged scFv linker.

In some embodiments, the first and second Fc domains are variant Fc domains.

In some embodiments, the first and second monomers includes a set of heterodimerization variants selected from those depicted in FIGS. 1A-1E.

In some embodiments, the set of heterodimerization variants selected is from the following: S364K/E357Q: L368D/K370S; S364K: L368D/K370S; S364K: L368E/K370S; D401K: T411E/K360E/Q362E; and T366W: T366S/L368A/Y407V, wherein numbering is according to EU numbering.

In some embodiments, the first and second monomers further include an ablation variant.

In some embodiments, the ablation variant is E233P/L234V/L235A/G236del/S267K, wherein numbering is according to EU numbering.

In some embodiments, one of the first or second monomer further includes a pI variant.

In some embodiments, the pI variant is N208D/Q295E/N384D/Q418E/N421D, wherein numbering is according to EU numbering.

In some embodiments, first variant Fc domain includes amino acid variants S364K/E357Q/E233P/L234V/L235A/G236del/S267K, wherein the second variant Fc domain includes amino acid variants L368D/K370S/N208D/Q295E/N384D/Q418E/N421D/E233P/L234V/L235A/G236del/S267 K, and wherein numbering is according to EU numbering.

In some embodiments, the scFv linker is a charged scFv linker having the amino acid sequence (GKPGS)$_4$ (SEQ ID NO: 1).

In some embodiments, the first and second variant Fc domains each further include amino acid variants 428/434S, wherein numbering is according to EU numbering.

In some embodiments, the heterodimeric antibody includes the following heterodimeric antibodies: XENP31063, XENP31067, XENP31705, XENP31451, XENP31452, XENP31713, XENP31064, XENP31068, XENP31709, ENP32744, XENP32747, XENP32750, XENP32851, XENP31453, XENP31454, XENP31717, XENP32745, XENP32748, XENP32751, XENP32852, XENP32947, XENP32948, XENP32949, XENP32950, XENP32951, XENP33366, XENP33367, XENP33460, XENP33461, XENP33462, XENP33463, XENP33464, XENP33465, XENP33466, XENP33467, XENP33968, XENP33970, XENP33972, XENP34155, XENP34156, XENP34157, XENP34158, XENP31455, XENP31456, XENP32249, XENP32250, XENP32251, XENP32746, XENP32749, XENP32752, XENP32853, XENP33974, XENP33975, XENP33976, XENP33977, XENP33978, XENP33979, XENP33980, XENP34151, XENP34152, XENP34153, XENP34154, XENP34159, XENP34160, XENP34161, and XENP34162 (FIGS. 28-32).

In another aspect, the heterodimeric antibody includes: a) a first monomer that includes from N-terminus to C-terminus, a VH1-CH1-linker 1-scFv-linker 2-CH2-CH3, wherein scFv is an anti-CD3 scFV and CH2-CH3 is a first Fc domain; b) a second monomer that includes from N-terminus to C-terminus a VH1-CH1-hinge-CH2-CH3, wherein CH2-CH3 is a second Fc domain; and c) a common light chain that includes VL-CL; wherein the first variant Fc domain includes amino acid variants S364K/E357Q, wherein the second variant Fc domain includes amino acid variants L368D/K370S, wherein the first and second variant Fc domains each include amino acid variants E233P/L234V/L235A/G236del/S267K, wherein the hinge-CH2-CH3 of the second monomer includes amino acid variants N208D/Q295E/N384D/Q418E/N421D, wherein said VH and VL include the variable heavy domain and the variable light domain of a MSLN binding domain selected from: MESO-A[MSLN]_H1.1_L1, MESO-B[MSLN]_H0L0, MESO-C[MSLN]_H1L1, MESO-C[MSLN]_H1.1_L1, MESO-C[MSLN]_H1.2L1, MESO-C[MSLN]_H1.3_L1, MESO-C[MSLN]_H1.4_L1, MESO-C[MSLN]_H1.5_L1, MESO-C[MSLN]_H1.6_L1, MESO-C[MSLN]_H1.7_L1, MESO-C[MSLN]_H1.8_L1, MESO-C[MSLN]_H1.9_L1, MESO-C[MSLN]_H1_L1.1, MESO-C[MSLN]_H1_L1.2, MESO-C[MSLN]_H1_L1.3, MESO-C[MSLN]_H1_L1.4, MESO-C[MSLN]_H1_L1.5, MESO-C[MSLN]_H1_L1.6, MESO-C[MSLN]_H1_L1.7, MESO-C[MSLN]_H1_L1.8, MESO-C[MSLN]_H1_L1.9, MESO-C[MSLN]_H1_L1.10, MESO-C[MSLN]_H1.5_L1.3, MESO-C[MSLN]_H1.6_L1.3, MESO-C[MSLN]_H1.12_L1.9, MESO-C[MSLN]_H1.13_L1.9, MESO-C[MSLN]_H1.3_L1.13, MESO-C[MSLN]_H1.3_L1.14, MESO-C[MSLN]_H1.3_L1.15, MESO-C[MSLN]_H1.3_L1.16, MESO-C[MSLN]_H1.3_L1.17, MESO-C[MSLN]_H1.3_L1.18, MESO-C[MSLN]_H1.3_L1.9, MESO-C[MSLN]_H1.3_L1.5, MESO-C[MSLN]_H1_L1.20, MESO-C[MSLN]_H1.12_L1.20, MESO-C[MSLN]_H1.14_L1.14, MESO-C[MSLN]_H1.15_L1.14, MESO-C[MSLN]_H1.16_L1.14, MESO-C[MSLN]_H1_L1.19, MESO-C[MSLN]_H1_L1.21, MESO-C[MSLN]_H1_L1.22, MESO-C[MSLN]_H1.12_L1.19, MESO-C[MSLN]_H1.12_L1.21, MESO-C[MSLN]_H1.12_L1.22, and MESO-C[MSLN]_H1.12_L1.9 (FIGS. 15-21), wherein the anti-CD3 scFv includes the variable heavy domain and the variable light domain of a CD3 binding domain selected from H1.30_L1.47, H1.32_L1.47, H1.89_L1.47, H1.90_L1.47, H1.33_L1.47, H1.31_L1.47, L1.47_H1.30, L1.47_H1.30, L1.47_H1.32, L1.47_H1.89, L1.47_H1.90, L1.47_H1.33, and L1.47_H1.31 (FIGS. 10A-10F), and wherein numbering is according to EU numbering.

In some embodiments, the scFv includes a charged scFv linker having the amino acid sequence (GKPGS)$_4$ (SEQ ID NO: 1).

In some embodiments, the first and second variant Fc domains each further include amino acid variants 428/434S.

In some embodiments, the first and second monomers and the common light chain of the antibody XENP34156. In some embodiments, the present invention provides an expression vector that includes the nucleic acids. In some embodiments, the present invention provides a host cell transformed with the expression vector. In some embodiments, the present invention provides treating a MSLN associated cancer includes administering to a patient in need thereof the antibody.

In another aspect, the present invention provides a heterodimeric antibody including the following heterodimeric antibodies: XENP16248, XENP16833, XENP31697, XENP32550, XENP32551, XENP32552, XENP32553, XENP32554, XENP32555, XENP32556, XENP32557, XENP32558, XENP32559, XENP32560, XENP32561, XENP32562, XENP32563, XENP32564, XENP32565, XENP32566, XENP32567, XENP32568, XENP32569, XENP32570, XENP32937, XENP32938, XENP32939, XENP32940, XENP32941, XENP32942, XENP32943, XENP32944, XENP32945, XENP32946, XENP33888, XENP33889, XENP30764, XENP30765, XENP31701, XENP33969, XENP33971, XENP33973, XENP16251, XENP16834, XENP16252, and XENP16835 (FIGS. 23-27).

In another aspect, the present invention provides a heterodimeric antibody including the following heterodimeric antibodies: XENP31063, XENP31067, XENP31705, XENP31451, XENP31452, XENP31713, XENP31064, XENP31068, XENP31709, ENP32744, XENP32747, XENP32750, XENP32851, XENP31453, XENP31454, XENP31717, XENP32745, XENP32748, XENP32751, XENP32852, XENP32947, XENP32948, XENP32949, XENP32950, XENP32951, XENP33366, XENP33367, XENP33460, XENP33461, XENP33462, XENP33463, XENP33464, XENP33465, XENP33466, XENP33467, XENP33968, XENP33970, XENP33972, XENP34155, XENP34156, XENP34157, XENP34158, XENP31455, XENP31456, XENP32249, XENP32250, XENP32251, XENP32746, XENP32749, XENP32752, XENP32853, XENP33974, XENP33975, XENP33976, XENP33977, XENP33978, XENP33979, XENP33980, XENP34151, XENP34152, XENP34153, XENP34154, XENP34159, XENP34160, XENP34161, and XENP34162 (FIGS. 28-32).

In some embodiments, the present invention provides nucleic acid composition that includes the nucleic acids encoding the heterodimeric antibody. In some embodiments, the present invention provides an expression vector includes the nucleic acids. In some embodiments, the present invention provides a host cell transformed with the expression vector.

In some embodiments, the present method provides a method of treating a MSLN related cancer that includes administering to a patient in need thereof any one of the heterodimeric antibodies provided herein.

BRIEF DESCRIPTION OF THE DRAWINGS

FIG. 1A-1E depict useful pairs of Fc heterodimerization variant sets (including skew and pI variants). There are variants for which there are no corresponding "monomer 2" variants; these are pI variants which can be used alone on either monomer.

FIG. 2 depicts a list of isosteric variant antibody constant regions and their respective substitutions. pI_(−) indicates lower pI variants, while pI_(+) indicates higher pI variants. These can be optionally and independently combined with other heterodimerization variants of the inventions (and other variant types as well, as outlined herein.)

FIG. 3 depicts useful ablation variants that ablate FcγR binding (sometimes referred to as "knock outs" or "KO" variants). Generally, ablation variants are found on both monomers, although in some cases they may be on only one monomer.

FIG. 4 depicts particularly useful embodiments of "non-Fv" components of the antibodies described herein.

FIG. 5 depicts a number of charged scFv linkers that find use in increasing or decreasing the pI of the subject heterodimeric bsAbs that utilize one or more scFv as a component, as described herein. The (+H) positive linker finds particular use herein, particularly with anti-CD3 VL and VH sequences shown herein. A single prior art scFv linker with a single charge is referenced as "Whitlow", from Whitlow et al., Protein Engineering 6 (8): 989-995 (1993). It should be noted that this linker was used for reducing aggregation and enhancing proteolytic stability in scFvs. Such charged scFv linkers can be used in any of the subject antibody formats disclosed herein that include scFvs (e.g., 1+1 Fab-scFv-Fc and 2+1 Fab₂-scFv-Fc formats).

FIG. 6 depicts a number of exemplary domain linkers. In some embodiments, these linkers find use linking a single-chain Fv to an Fc chain. In some embodiments, these linkers may be combined. For example, a GGGGS linker (SEQ ID NO: 2) may be combined with a "half hinge" linker.

FIGS. 7A-7D depict the sequences of several useful 1+1 Fab-scFv-Fc bispecific antibody format heavy chain backbones based on human IgG1, without the Fv sequences (e.g. the scFv and the VH for the Fab side). Backbone 1 is based on human IgG1 (356E/358M allotype), and includes the S364K/E357Q: L368D/K370S skew variants, C220S on the chain with the S364K/E357Q skew variants, the N208D/Q295E/N384D/Q418E/N421D pI variants on the chain with L368D/K370S skew variants and the E233P/L234V/L235A/G236del/S267K ablation variants on both chains. Backbone 2 is based on human IgG1 (356E/358M allotype), and includes S364K: L368D/K370S skew variants, C220S on the chain with the S364K skew variant, the N208D/Q295E/N384D/Q418E/N421D pI variants on the chain with L368D/K370S skew variants, and the E233P/L234V/L235A/G236del/S267K ablation variants on both chains. Backbone 3 is based on human IgG1 (356E/358M allotype), and includes S364K: L368E/K370S skew variants, C220S on the chain with the S364K skew variant, the N208D/Q295E/

Figure 11:
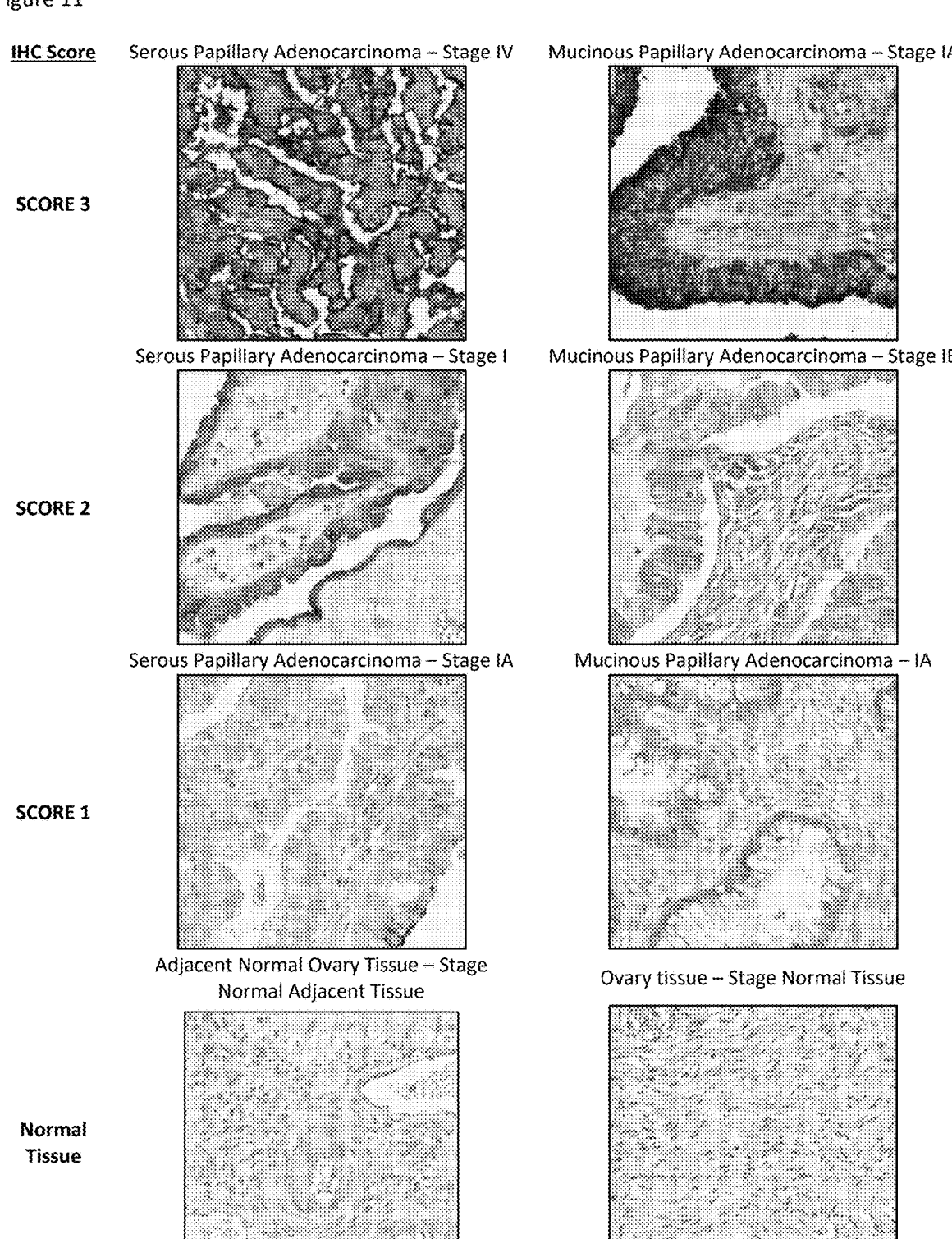

N384D/Q418E/N421D pI variants on the chain with L368E/ K370S skew variants and the E233P/L234V/L235A/ G236del/S267K ablation variants on both chains. Backbone 4 is based on human IgG1 (356E/358M allotype), and includes D401K: K360E/Q362E/T411E skew variants, C220S on the chain with the D401K skew variant, the N208D/Q295E/N384D/Q418E/N421D pI variants on the chain with K360E/Q362E/T411E skew variants and the E233P/L234V/L235A/G236del/S267K ablation variants on both chains. Backbone 5 is based on human IgG1 (356D/ 358L allotype), and includes S364K/E357Q: L368D/K370S skew variants, C220S on the chain with the S364K/E357Q skew variants, the N208D/Q295E/N384D/Q418E/N421D pI variants on the chain with L368D/K370S skew variants and the E233P/L234V/L235A/G236del/S267K ablation variants on both chains. Backbone 6 is based on human IgG1 (356E/358M allotype), and includes S364K/E357Q: L368D/ K370S skew variants, C220S on the chain with the S364K/ E357Q skew variants, N208D/Q295E/N384D/Q418E/ N421D pI variants on the chain with L368D/K370S skew variants and the E233P/L234V/L235A/G236del/S267K ablation variants on both chains, as well as an N297A variant on both chains. Backbone 7 is identical to 6 except the mutation is N297S. Backbone 8 is based on human IgG4, and includes the S364K/E357Q: L368D/K370S skew variants, the N208D/Q295E/N384D/Q418E/N421D pI variants on the chain with L368D/K370S skew variants, as well as a S228P (EU numbering, this is S241P in Kabat) variant on both chains that ablates Fab arm exchange as is known in the art. Backbone 9 is based on human IgG2, and includes the S364K/E357Q: L368D/K370S skew variants, the N208D/ Q295E/N384D/Q418E/N421D pI variants on the chain with L368D/K370S skew variants. Backbone 10 is based on human IgG2, and includes the S364K/E357Q: L368D/ K370S skew variants, the N208D/Q295E/N384D/Q418E/ N421D pI variants on the chain with L368D/K370S skew variants as well as a S267K variant on both chains. Backbone 11 is identical to backbone 1, except it includes M428L/N434S Xtend™ mutations. Backbone 12 is based on human IgG1 (356E/358M allotype), and includes S364K/ E357Q: L368D/K370S skew variants, C220S and the P217R/P229R/N276K pI variants on the chain with S364K/ E357Q skew variants and the E233P/L234V/L235A/ G236del/S267K ablation variants on both chains. Included within each of these backbones are sequences that are 90, 95, 98 and 99% identical (as defined herein) to the recited sequences, and/or contain from 1, 2, 3, 4, 5, 6, 7, 8, 9 or 10 additional amino acid substitutions (as compared to the "parent" of the Figure, which, as will be appreciated by those in the art, already contain a number of amino acid modifications as compared to the parental human IgG1 (or IgG2 or IgG4, depending on the backbone). That is, the recited backbones may contain additional amino acid modifications (generally amino acid substitutions) in addition to the skew, pI and ablation variants contained within the backbones of this figure.

FIGS. 8A-8C depicts the sequences of several useful 2+1 Fab₂-scFv-Fc bispecific antibody format heavy chain backbones based on human IgG1, without the Fv sequences (e.g. the scFv and the VH for the Fab side). Backbone 1 is based on human IgG1 (356E/358M allotype), and includes the S364K/E357Q: L368D/K370S skew variants, the N208D/ Q295E/N384D/Q418E/N421D pI variants on the chain with L368D/K370S skew variants and the E233P/L234V/L235A/ G236del/S267K ablation variants on both chains. Backbone 2 is based on human IgG1 (356E/358M allotype), and includes S364K: L368D/K370S skew variants, the N208D/

Q295E/N384D/Q418E/N421D pI variants on the chain with L368D/K370S skew variants, and the E233P/L234V/ L235A/G236del/S267K ablation variants on both chains. Backbone 3 is based on human IgG1 (356E/358M allotype), and includes S364K: L368E/K370S skew variants, the N208D/Q295E/N384D/Q418E/N421D pI variants on the chain with L368E/K370S skew variants and the E233P/ L234V/L235A/G236del/S267K ablation variants on both chains. Backbone 4 is based on human IgG1 (356E/358M allotype), and includes D401K: K360E/Q362E/T411E skew variants, the N208D/Q295E/N384D/Q418E/N421D pI variants on the chain with K360E/Q362E/T411E skew variants and the E233P/L234V/L235A/G236del/S267K ablation variants on both chains. Backbone 5 is based on human IgG1 (356D/358L allotype), and includes S364K/E357Q: L368D/ K370S skew variants, the N208D/Q295E/N384D/Q418E/ N421D pI variants on the chain with L368D/K370S skew variants and the E233P/L234V/L235A/G236del/S267K ablation variants on both chains. Backbone 6 is based on human IgG1 (356E/358M allotype), and includes S364K/ E357Q: L368D/K370S skew variants, N208D/Q295E/ N384D/Q418E/N421D pI variants on the chain with L368D/ K370S skew variants and the E233P/L234V/L235A/ G236del/S267K ablation variants on both chains, as well as an N297A variant on both chains. Backbone 7 is identical to 6 except the mutation is N297S. Backbone 8 is identical to backbone 1, except it includes M428L/N434S Xtend™ mutations. Backbone 9 is based on human IgG1 (356E/ 358M allotype), and includes S364K/E357Q: L368D/ K370S skew variants, the P217R/P229R/N276K pI variants on the chain with S364K/E357Q skew variants and the E233P/L234V/L235A/G236del/S267K ablation variants on both chains. Included within each of these backbones are sequences that are 90, 95, 98 and 99% identical (as defined herein) to the recited sequences, and/or contain from 1, 2, 3, 4, 5, 6, 7, 8, 9 or 10 additional amino acid substitutions (as compared to the "parent" of the Figure, which, as will be appreciated by those in the art, already contain a number of amino acid modifications as compared to the parental human IgG1 (or IgG2 or IgG4, depending on the backbone). That is, the recited backbones may contain additional amino acid modifications (generally amino acid substitutions) in addition to the skew, pI and ablation variants contained within the backbones of this figure.

FIG. 9 depicts the sequences of several useful constant light domain backbones based on human IgG1, without the Fv sequences (e.g. the scFv or the Fab). Included herein are constant light backbone sequences that are 90, 95, 98 and 99% identical (as defined herein) to the recited sequences, and/or contain from 1, 2, 3, 4, 5, 6, 7, 8, 9 or 10 additional amino acid modifications.

FIGS. 10A-10F depicts sequences for exemplary anti-CD3 scFvs suitable for use in the bispecific antibodies of the invention. The CDRs are underlined, the scFv linker is double underlined (in the sequences, the scFv linker is a positively charged scFv (GKPGS)₄ linker (SEQ ID NO: 1), although as will be appreciated by those in the art, this linker can be replaced by other linkers, including uncharged or negatively charged linkers, some of which are depicted in FIG. 5), and the slashes indicate the border(s) of the variable domains. In addition, the naming convention illustrates the orientation of the scFv from N- to C-terminus. As noted herein and is true for every sequence herein containing CDRs, the exact identification of the CDR locations may be slightly different depending on the numbering used as is shown in Table 2, and thus included herein are not only the CDRs that are underlined but also CDRs included within the VH and VL domains using other numbering systems. Furthermore, as for all the sequences in the Figures, these VH and VL sequences can be used either in a scFv format or in a Fab format.

FIG. 11 depicts illustrative IHC of ovarian cancer biopsy cores and adjacent normal tissue showing mesothelin expression.

FIG. 12 depicts breakdown of IHC scores of 191 ovarian cancer biopsy cores showing mesothelin expression.

FIG. 13 depicts endogenous mesothelin expression on cancer cell lines as determined by IHC and flow.

FIGS. 14A-14B depict the antigen sequences for a number of antigens of use in the antibodies described herein, including both human and cyno, to facilitate the development of antigen binding domains that bind to both for ease of clinical development.

FIGS. 15A-15B depict the variable heavy and variable light chain sequences for an exemplary MSLN binding domain referred to herein as MESO-A, as well as the sequences for XENP16249, XENP16250, and XENP16253, anti-MSLN mAbs based on MESO-A and IgG1 backbone. CDRs are underlined and slashes indicate the border(s) between the variable regions and constant domain. As noted herein and is true for every sequence herein containing CDRs, the exact identification of the CDR locations may be slightly different depending on the numbering used as is shown in Table 2, and thus included herein are not only the CDRs that are underlined but also CDRs included within the VH and VL domains using other numbering systems. Furthermore, as for all the sequences in the Figures, these VH and VL sequences can be used either in a scFv format or in a Fab format.

FIG. 16 depicts the variable heavy and variable light chain sequences for an exemplary MSLN binding domain referred to herein as MESO-B, as well as the sequences for XENP16827, an anti-MSLN mAb based on MESO-B and IgG1 backbone. CDRs are underlined and slashes indicate the border(s) between the variable regions and constant domain. As noted herein and is true for every sequence herein containing CDRs, the exact identification of the CDR locations may be slightly different depending on the numbering used as is shown in Table 2, and thus included herein are not only the CDRs that are underlined but also CDRs included within the VH and VL domains using other numbering systems. Furthermore, as for all the sequences in the Figures, these VH and VL sequences can be used either in a scFv format or in a Fab format.

FIG. 17 depicts the variable heavy and variable light chain sequences for an exemplary MSLN binding domain referred to herein as MESO-C, as well as the sequences for XENP31693, an anti-MSLN mAb based on MESO-C and IgG1 backbone. CDRs are underlined and slashes indicate the border(s) between the variable regions and constant domain. As noted herein and is true for every sequence herein containing CDRs, the exact identification of the CDR locations may be slightly different depending on the numbering used as is shown in Table 2, and thus included herein are not only the CDRs that are underlined but also CDRs included within the VH and VL domains using other numbering systems. Furthermore, as for all the sequences in the Figures, these VH and VL sequences can be used either in a scFv format or in a Fab format.

FIG. 18 depicts the variable heavy chain sequences for MESO-C variants engineered with the aim to tune binding affinity for human MSLN. CDRs are underlined and slashes indicate the border(s) between the variable regions and constant domain. As noted herein and is true for every sequence herein containing CDRs, the exact identification of the CDR locations may be slightly different depending on the numbering used as is shown in Table 2, and thus included herein are not only the CDRs that are underlined but also CDRs included within VH domains using other numbering systems. Further, as for all the sequences in the Figures, these VL sequences can be used either in a scFv format or in a Fab format. Each of the variable heavy domains depicted herein can be paired with any other αMSLN variable light domain.

FIGS. 19A-19B depict the variable light chain sequences for MESO-C variants engineered with the aim to tune binding affinity for human MSLN. CDRs are underlined and slashes indicate the border(s) between the variable regions and constant domain. As noted herein and is true for every sequence herein containing CDRs, the exact identification of the CDR locations may be slightly different depending on the numbering used as is shown in Table 2, and thus included herein are not only the CDRs that are underlined but also CDRs included within $V_L$ domains using other numbering systems. Further, as for all the sequences in the Figures, these $V_L$ sequences can be used either in a scFv format or in a Fab format. Each of the variable light domains depicted herein can be paired with any other αMSLN variable heavy domain.

FIG. 20 depicts BLI-response, dissociation constant ($K_D$), association rate ($k_a$), and dissociation rate ($k_d$) of affinity-engineered MESO-C variants (in the context of 1+1 Fab-scFv-Fc anti-MSLN×anti-CD3 bispecific antibodies) for human and cynomolgus MSLN as determined by Octet®. Substitutions in variable regions are based on Kabat numbering. It should be noted that for Kabat numbering, some positions are numbered using letters as well; for example, in Kabat numbering, there is one amino acid at position 100b (K100b) but a different amino acid at position 100a (P100a); that is, the inclusion of the small letters denotes a position, not a particular amino acid in that position.

FIG. 21 depicts BLI-response, dissociation constant ($K_D$), association rate ($k_a$), and dissociation rate ($k_d$) of affinity-engineered MESO-C variants (in the context of 1+1 Fab-scFv-Fc anti-MSLN×anti-CD3 bispecific antibodies) for human MSLN as determined by Octet® (multiple concentration Octet® run). Substitutions in variable regions are based on Kabat numbering.

Figure 22A:
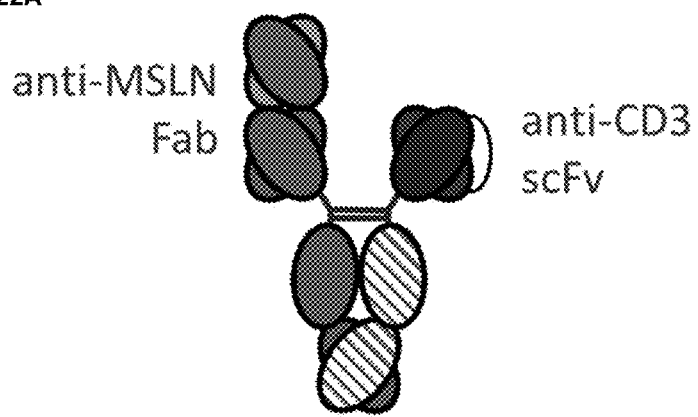
Figure 22B:
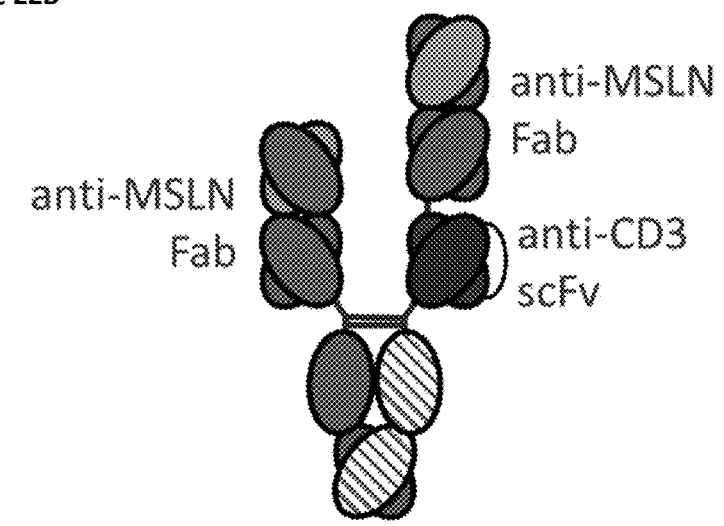
Figure 35D:
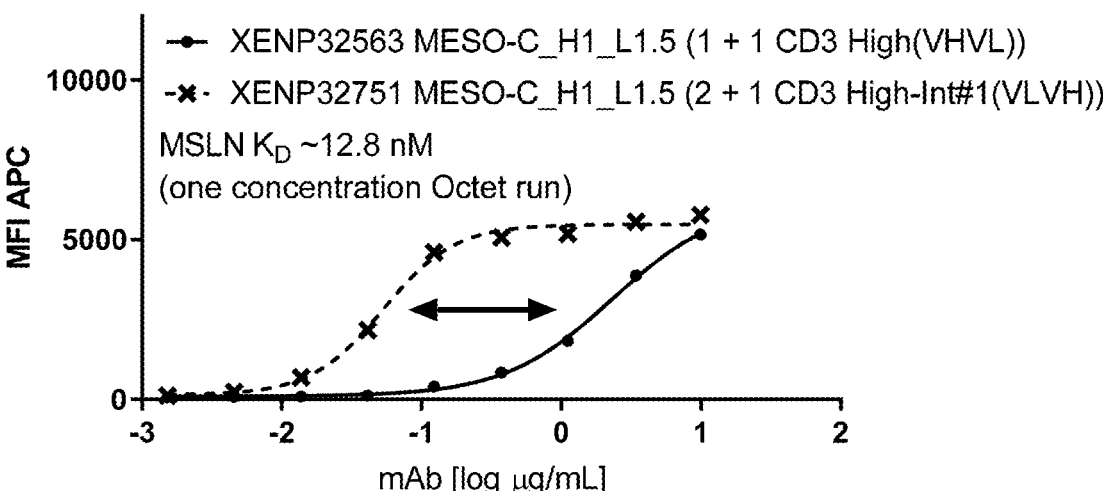

FIGS. 22A-22B depict a couple of formats of the present invention. FIG. 22A depicts the "1+1 Fab-scFv-Fc" format, with a first Fab arm binding MSLN and a second scFv arm binding CD3. FIG. 22B depicts the "2+1 Fab₂-scFv-Fc" format, with a first Fab arm binding MSLN and a second Fab-scFv arm, wherein the Fab binds MSLN and the scFv binds CD3.

FIGS. 23A-23R depict the sequences for illustrative αMSLN×αCD3 bsAbs in the 1+1 Fab-scFv-Fc format and comprising a H1.30_L1.47 anti-CD3 scFv (a.k.a. CD3 High [VHVL]). CDRs are underlined and slashes indicate the border(s) between the variable regions and other chain components (e.g. constant region and domain linkers). It should be noted that the αMSLN×αCD3 bsAbs can utilize variable region, Fc region, and constant domain sequences that are 90, 95, 98 and 99% identical (as defined herein), and/or contain from 1, 2, 3, 4, 5, 6, 7, 8, 9 or 10 amino acid substitutions. In addition, each sequence outlined herein can include or exclude the M428L/N434S variants in one or preferably both Fc domains, which results in longer half-life in serum.

FIGS. 24A-24B depict the sequences for illustrative αMSLN×αCD3 bsAbs in the 1+1 Fab-scFv-Fc format and comprising a H1.32_L1.47 anti-CD3 scFv (a.k.a. CD3 High-Int #1 [VHVL]). CDRs are underlined and slashes indicate the border(s) between the variable regions and other chain components (e.g. constant region and domain linkers). It should be noted that the αMSLNxαCD3 bsAbs can utilize variable region, Fc region, and constant domain sequences that are 90, 95, 98 and 99% identical (as defined herein), and/or contain from 1, 2, 3, 4, 5, 6, 7, 8, 9 or 10 amino acid substitutions. In addition, each sequence outlined herein can include or exclude the M428L/N434S variants in one or preferably both Fc domains, which results in longer half-life in serum.

FIGS. 25A-25B depict the sequences for illustrative αMSLNxαCD3 bsAbs in the 1+1 Fab-scFv-Fc format and comprising a L1.47_H1.32 anti-CD3 scFv (a.k.a. CD3 High-Int #1 [VLVH]). CDRs are underlined and slashes indicate the border(s) between the variable regions and other chain components (e.g. constant region and domain linkers). It should be noted that the αMSLNxαCD3 bsAbs can utilize variable region, Fc region, and constant domain sequences that are 90, 95, 98 and 99% identical (as defined herein), and/or contain from 1, 2, 3, 4, 5, 6, 7, 8, 9 or 10 amino acid substitutions. In addition, each sequence outlined herein can include or exclude the M428L/N434S variants in one or preferably both Fc domains, which results in longer half-life in serum.

FIG. 26 depict the sequences for illustrative αMSLNx αCD3 bsAbs in the 1+1 Fab-scFv-Fc format and comprising a H1.33_L1.47 anti-CD3 scFv (a.k.a. CD3 Intermediate [VHVL]). CDRs are underlined and slashes indicate the border(s) between the variable regions and other chain components (e.g. constant region and domain linkers). It should be noted that the αMSLNxαCD3 bsAbs can utilize variable region, Fc region, and constant domain sequences that are 90, 95, 98 and 99% identical (as defined herein), and/or contain from 1, 2, 3, 4, 5, 6, 7, 8, 9 or 10 amino acid substitutions. In addition, each sequence outlined herein can include or exclude the M428L/N434S variants in one or preferably both Fc domains, which results in longer half-life in serum.

FIG. 27 depicts the sequences for illustrative αMSLNx αCD3 bsAbs in the 1+1 Fab-scFv-Fc format and comprising a H1.31_L1.47 anti-CD3 scFv (a.k.a. CD3 Low [VHVL]). CDRs are underlined and slashes indicate the border(s) between the variable regions and other chain components (e.g. constant region and domain linkers). It should be noted that the αMSLNxαCD3 bsAbs can utilize variable region, Fc region, and constant domain sequences that are 90, 95, 98 and 99% identical (as defined herein), and/or contain from 1, 2, 3, 4, 5, 6, 7, 8, 9 or 10 amino acid substitutions. In addition, each sequence outlined herein can include or exclude the M428L/N434S variants in one or preferably both Fc domains, which results in longer half-life in serum.

FIGS. 28A-28B depict the sequences for illustrative αMSLNxαCD3 bsAbs in the 2+1 Fab₂-scFv-Fc format and comprising a H1.30_L1.47 anti-CD3 scFv (a.k.a. CD3 High [VHVL]). CDRs are underlined and slashes indicate the border(s) between the variable regions and other chain components (e.g. constant region and domain linkers). It should be noted that the αMSLNxαCD3 bsAbs can utilize variable region, Fc region, and constant domain sequences that are 90, 95, 98 and 99% identical (as defined herein), and/or contain from 1, 2, 3, 4, 5, 6, 7, 8, 9 or 10 amino acid substitutions. In addition, each sequence outlined herein can include or exclude the M428L/N434S variants in one or preferably both Fc domains, which results in longer half-life in serum.

FIGS. 29A-29B depict the sequences for illustrative αMSLNxαCD3 bsAbs in the 2+1 Fab₂-scFv-Fc format and comprising a L1.47_H1.30 anti-CD3 scFv (a.k.a. CD3 High [VLVH]). CDRs are underlined and slashes indicate the border(s) between the variable regions and other chain components (e.g. constant region and domain linkers). It should be noted that the αMSLNxαCD3 bsAbs can utilize variable region, Fc region, and constant domain sequences that are 90, 95, 98 and 99% identical (as defined herein), and/or contain from 1, 2, 3, 4, 5, 6, 7, 8, 9 or 10 amino acid substitutions. In addition, each sequence outlined herein can include or exclude the M428L/N434S variants in one or preferably both Fc domains, which results in longer half-life in serum.

FIGS. 30A-30E depict the sequences for illustrative αMSLNxαCD3 bsAbs in the 2+1 Fab₂-scFv-Fc format and comprising a H1.32_L1.47 anti-CD3 scFv (a.k.a. CD3 High-Int #1 [VHVL]). CDRs are underlined and slashes indicate the border(s) between the variable regions and other chain components (e.g. constant region and domain linkers). It should be noted that the αMSLNxαCD3 bsAbs can utilize variable region, Fc region, and constant domain sequences that are 90, 95, 98 and 99% identical (as defined herein), and/or contain from 1, 2, 3, 4, 5, 6, 7, 8, 9 or 10 amino acid substitutions. In addition, each sequence outlined herein can include or exclude the M428L/N434S variants in one or preferably both Fc domains, which results in longer half-life in serum.

FIGS. 31A-31T depict the sequences for illustrative αMSLNxαCD3 bsAbs in the 2+1 Fab₂-scFv-Fc format and comprising a L1.47_H1.32 anti-CD3 scFv (a.k.a. CD3 High-Int #1 [VLVH]). CDRs are underlined and slashes indicate the border(s) between the variable regions and other chain components (e.g. constant region and domain linkers). It should be noted that the @MSLNxαCD3 bsAbs can utilize variable region, Fc region, and constant domain sequences that are 90, 95, 98 and 99% identical (as defined herein), and/or contain from 1, 2, 3, 4, 5, 6, 7, 8, 9 or 10 amino acid substitutions. In addition, each sequence outlined herein can include or exclude the M428L/N434S variants in one or preferably both Fc domains, which results in longer half-life in serum.

FIGS. 32A-32P depict the sequences for illustrative αMSLNxαCD3 bsAbs in the 2+1 Fab₂-scFv-Fc format and comprising a L1.47_H1.89 anti-CD3 scFv (a.k.a. CD3 High-Int #2 [VLVH]). CDRs are underlined and slashes indicate the border(s) between the variable regions and other chain components (e.g. constant region and domain linkers). It should be noted that the αMSLNxαCD3 bsAbs can utilize variable region, Fc region, and constant domain sequences that are 90, 95, 98 and 99% identical (as defined herein), and/or contain from 1, 2, 3, 4, 5, 6, 7, 8, 9 or 10 amino acid substitutions. In addition, each sequence outlined herein can include or exclude the M428L/N434S variants in one or preferably both Fc domains, which results in longer half-life in serum.

FIG. 33 depicts activation of CD4⁺ T cells, as indicated by A) CD107a degranulation, B) CD25 expression, and C) CD69 expression following incubation of T cells with Kuramochi cells and the indicated test articles. The data show that anti-MSLNxanti-CD3 bsAbs in the 2+1 Fab2-scFv-Fc format (XENP31063, XENP31064, XENP31067, and XENP31068) promoted activity of CD4⁺ T cells more potently than corresponding 1+1 Fab-scFv-Fc bsAbs (XENP16248, XENP30764, XENP16833, and XENP30765).

FIG. 34 depicts activation of CD8$^+$ T cells, as indicated by A) CD107a degranulation, B) CD25 expression, and C) CD69 expression following incubation of T cells with Kuramochi cells and the indicated test articles. The data show that anti-MSLN×anti-CD3 bsAbs in the 2+1 Fab2-scFv-Fc format (XENP31063, XENP31064, XENP31067, and XENP31068) promoted activity of CD8$^+$ T cells more potently than corresponding 1+1 Fab-scFv-Fc bsAbs (XENP16248, XENP30764, XENP16833, and XENP30765).

FIGS. 35A-35D depict the binding to OVCAR8 cells by A) XENP31697 vs. XENP31717 (both having 0.28 nM MSLN $K_D$), B) XENP32561 vs. XENP32745 (both having 0.45 nM MSLN $K_D$), C) XENP32562 vs. XENP32748 (both having 0.74 nM MSLN $K_D$), D) XENP32567 vs. XENP32852 vs. XENP32853 (each having 3.9 nM MSLN $K_D$), E) XENP32552 vs. XENP32947 (both having 9.2 nM MSLN $K_D$), F) XENP32937 vs. XENP32948 (both having 10.2 nM MSLN $K_D$), and G) XENP32751 vs. XENP32563 (both having ~12.8 nM MSLN $K_D$). The data show that as the MSLN binding affinity is decreased, the 2+1 Fab$_2$-scFv-Fc format provides more potent binding to OVCAR8 cells than the 1+1 Fab-scFv-Fc format. Further, XENP32852 and XENP32853 which differ only in CD3 binding affinity have identical binding to OVCAR8 cells confirming that avid binding is due to the MSLN binding domain.

Figure 36:
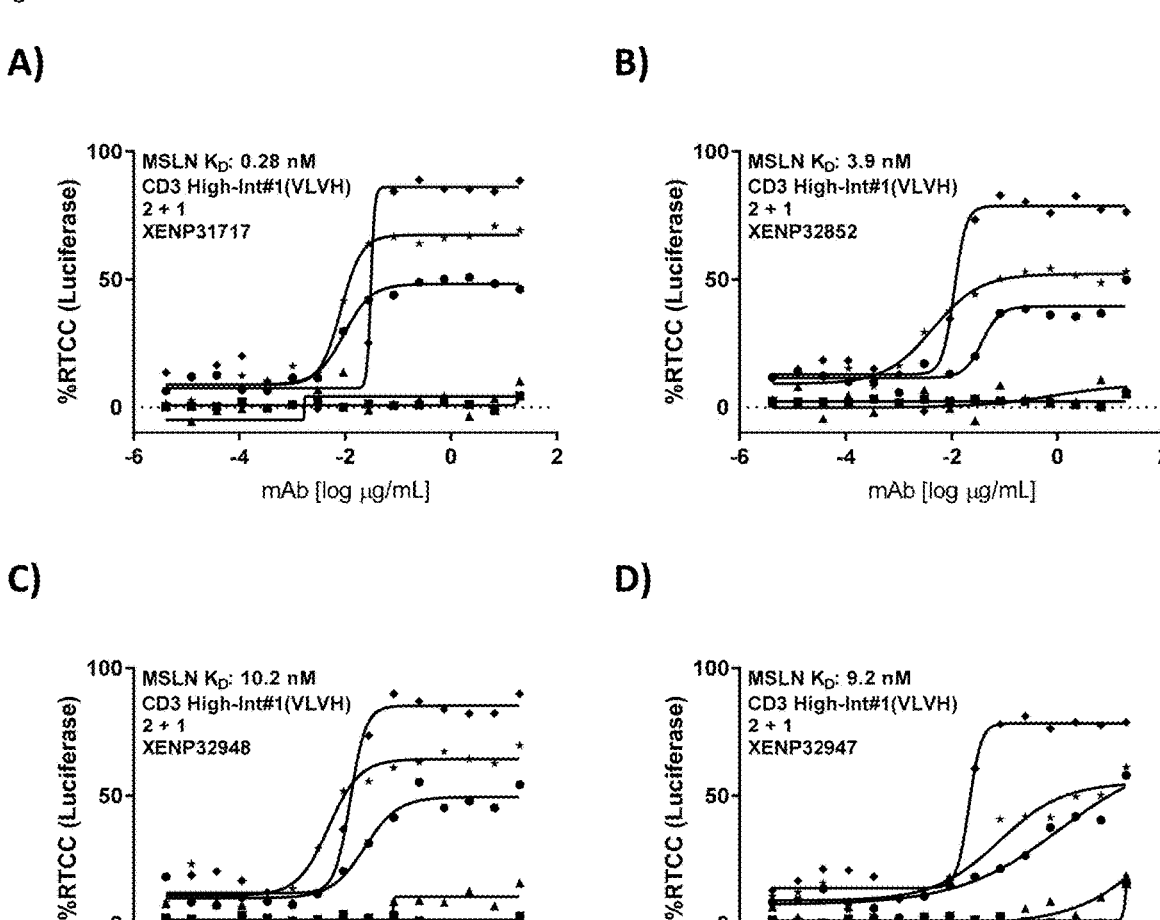
Figures 43G, 43H, 43I, 43J:
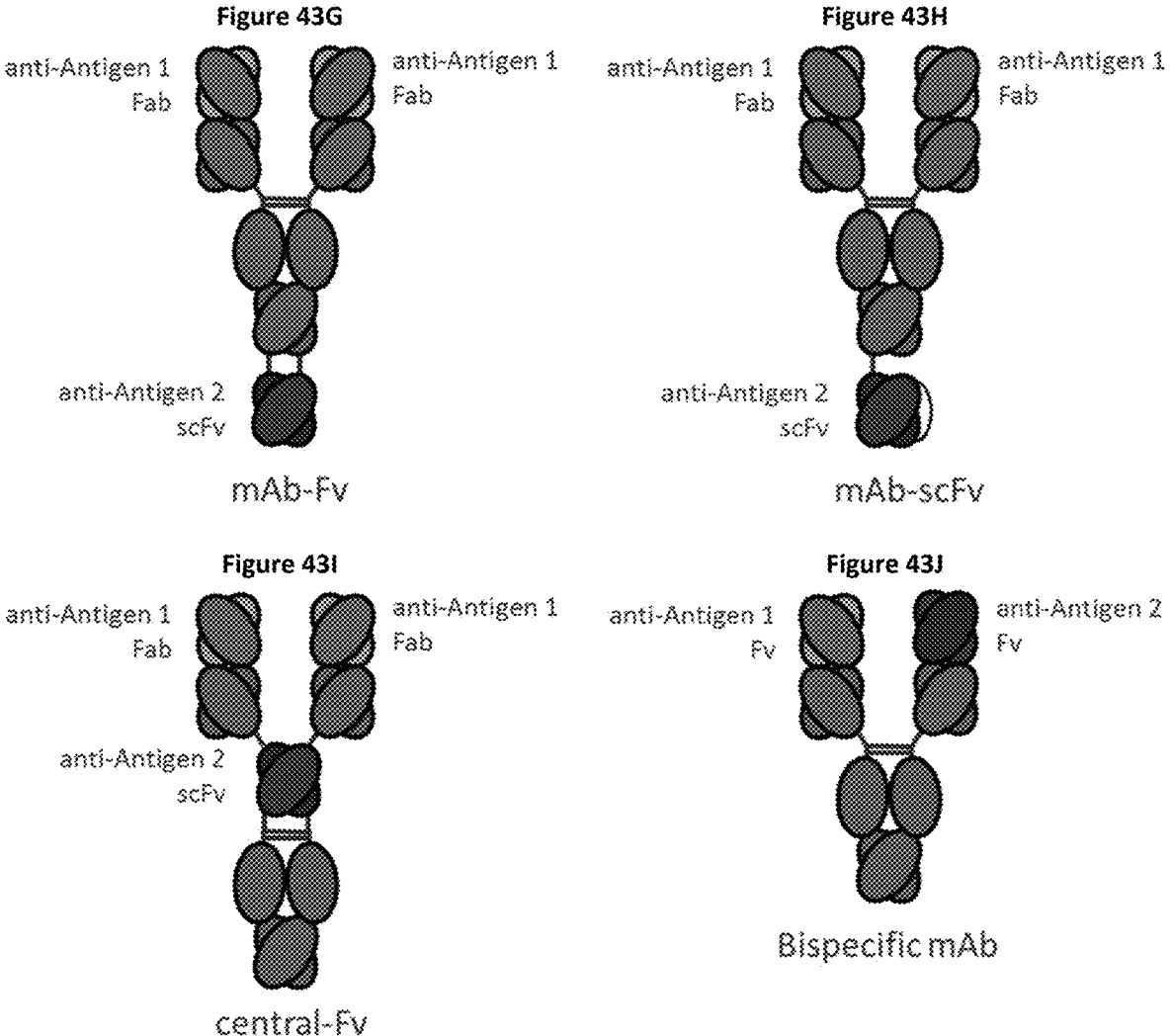
Figure 43K:
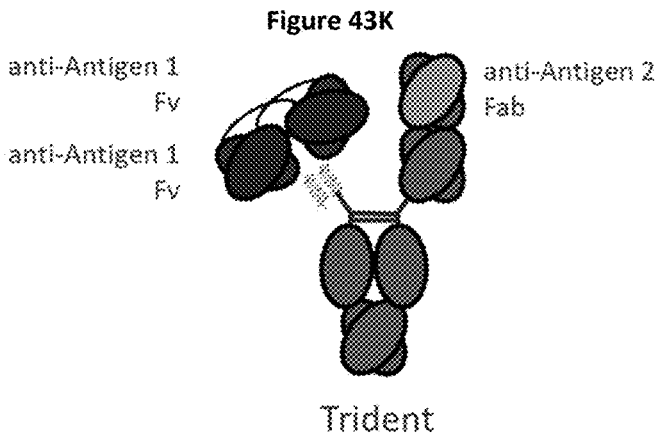

FIG. 36 depicts the RTCC on A549, HT29, MCF7, OVCAR8, and SKOV3 cells by A) XENP31717 (having 0.28 nM MSLN $K_D$), B) XENP32852 (having 3.9 nM MSLN $K_D$), C) XENP32948 (having 10.2 nM MSLN $K_D$), and D) XENP32947 (having 9.2 nM MSLN $K_D$). The data show that at high MSLN binding affinity, the 2+1 bsAbs induced potent RTCC on MSLN$^{high}$ OVCAR8 cell lines as well as MSLN$^{low}$ SKOV3 and HT29 cell lines. As MSLN binding affinity is reduced, the RTCC potency of the 2+1 bsAbs on the MSLN$^{low}$ cell lines is reduced.

FIG. 37 depicts induction of RTCC on luciferase-transfected cell lines with varying surface MSLN densities by A) XENP31717, B) XENP33366, and C) XENP33367. XENP33366 having 90.4 nM MSLN binding affinity enabled improved selectivity for MSLN$^{high}$ OVCAR8, as indicated by reduced potency in killing of SKOV3 cells and more potent killing of OVCAR8. XENP33367 having 246 nM MSLN binding affinity demonstrated little to no RTCC activity on MSLN$^{low}$ cells, but was also less potent on OVCAR8 than XENP33366.

FIG. 38 depicts induction of RTCC (as determined by xCELLigence® Real Time Cell Analysis instrument) on cell lines with varying surface MSLN densities by A) XENP31717, B) XENP33366, and C) XENP33367. XENP33366 having 90.4 nM MSLN binding affinity enabled improved selectivity for MSLN$^{high}$ OVCAR8, as indicated by reduced potency in killing of SKOV3 cells and more potent killing of OVCAR8. XENP33367 having 246 nM MSLN binding affinity demonstrated little to no RTCC activity on MSLN$^{low}$ cells, but was also less potent on OVCAR8 than XENP33366. RTCC activity on ASPC-1, a cancer cell line with ~36K surface MSLN expression and a lower cancer IHC score, was similar to RTCC activity on OVCAR8 cell.

FIG. 39 depicts induction of T cell proliferation (as indicated by percentage T cells expressing Ki67) by A) XENP31717, B) XENP33366, and C) XENP33367 in the presence of cell lines with varying surface MSLN densities. Each of the three bispecific antibodies enabled proliferation in the presence of Score 3 and Score 2 cell lines, but not in the presence of Score 1 cell lines.

FIG. 40 depicts induction of T cell proliferation (as indicated by percentage T cells expressing Ki67) by A) XENP31717, B) XENP33366, and C) XENP33367 in the presence of cell lines with varying surface MSLN densities. Reduction in MSLN binding affinity reduced T cell degranulation in the presence of Score 1 cell lines.

FIG. 41 depicts induction of T cell proliferation (as indicated by percentage T cells expressing Ki67) by A) XENP31717, B) XENP33366, and C) XENP33367 in the presence of cell lines with varying surface MSLN densities. Reduction in MSLN binding affinity reduced T cell activation in the presence of Score 1 cell lines.

FIG. 42 induction of RTCC on luciferase-transfected cell lines with varying surface MSLN densities by A) XENP31717, B) XENP32852, C) XENP32251, and D) XENP32853. The data show that bsAbs with lower CD3 binding affinity (e.g. CD3 High-Int #2) enabled enhanced selectivity for OVCAR8 (MSLN$^{high}$) over bsAbs with higher CD3 binding affinity (e.g. CD3 High-Int #1).

FIGS. 43A-43K depict several formats for use in the anti-MSLN×anti-CD3 bispecific antibodies disclosed herein. The first is the "1+1 Fab-scFv-Fc" format (also referred to as the "bottle opener" or "Triple F" format), with a first antigen binding domain that is a Fab domain and a second anti-antigen binding domain that is an scFv domain. Additionally, "mAb-Fv," "mAb-scFv," "2+1 Fab2-scFv-Fc" (also referred to as the "central scFv" or "central-scFv" format"), "central-Fv," "one armed central-scFv," "one scFv-mAb," "scFv-mAb," "dual scFv," "trident," and non-heterodimeric bispecific formats are all shown. The scFv domains can be either, from N- to C-terminus orientation: variable heavy-(optional linker)-variable light, or variable light-(optional linker)-variable heavy. In addition, for the one armed scFv-mAb, the scFv can be attached either to the N-terminus of a heavy chain monomer or to the N-terminus of the light chain. In certain embodiments, "Anti-antigen 1" in FIGS. 43A-43K refers to a MSLN binding domain. In certain embodiments, "Anti-antigen 1" in FIGS. 43A-43K refers to a CD3 binding domain. In certain embodiments, "Anti-antigen 2" in FIGS. 43A-43K refers to a MSLN binding domain. In certain embodiments "Anti-antigen 2" in FIGS. 43A-43K refers to a CD3 binding domain. In some embodiments, "Anti-antigen 1" in FIGS. 43A-43K refers to a MSLN binding domain and "Anti-antigen 2" in FIGS. 43A-43K refers to a CD3 binding domain. In some embodiments, "Anti-antigen 1" in FIGS. 43A-43K refers to a CD3 binding domain and "Anti-antigen 2" in FIGS. 43A-43K refers to a MSLN binding domain. Any of the MSLN binding domains and CD3 binding domains disclosed can be included in the bispecific formats of FIGS. 43A-43K.

DETAILED DESCRIPTION OF THE INVENTION

I. Overview

Anti-bispecific antibodies that co-engage CD3 and a tumor antigen target are used to redirect T cells to attack and lyse targeted tumor cells. Examples include the BiTE® and DART® antibody formats, which monovalently engage CD3 and a tumor antigen. While the CD3-targeting approach has shown considerable promise, a common side effect of such therapies is the associated production of cytokines, often leading to toxic cytokine release syndrome. Because the anti-CD3 binding domain of the bispecific antibody engages all T cells, the high cytokine-producing CD4 T cell subset is recruited. Moreover, the CD4 T cell subset includes regulatory T cells, whose recruitment and expansion can potentially lead to immune suppression and have a negative impact on long-term tumor suppression. In addition, these formats do not contain Fc domains and show very short serum half-lives in patients.

Provided herein are novel anti-CD3×anti-MSLN (also referred to as anti-MSLN×anti-CD3, αCD3×αMSLN, or αMSLN×αCD3) heterodimeric bispecific antibodies and methods of using such antibodies for the treatment of cancers. In particular, provided herein are anti-CD3, anti-MSLN bispecific antibodies in a variety of formats such as those depicted in FIGS. 22A, 22B and 43A-43K. These bispecific antibodies are useful for the treatment of cancers, particularly those with increased MSLN expression such as ovarian cancer, colon cancer, breast cancer, hepatocellular carcinoma, lung cancer, mesothelioma, pancreatic cancer, non-small cell lung cancer (such as lung adenocarcinoma) and endometrial cancer. Such antibodies are used to direct CD3+ effector T cells to MSLN+ tumors, thereby allowing the CD3+ effector T cells to attack and lyse the MSLN+ tumors.

Additionally, in some embodiments, the disclosure provides bispecific antibodies that have different binding affinities to human CD3 that can alter or reduce the potential side effects of anti-CD3 therapy. That is, in some embodiments the antibodies described herein provide antibody constructs comprising anti-CD3 antigen binding domains that are "strong" or "high affinity" binders to CD3 (e.g. one example are heavy and light variable domains depicted as H1.30_L1.47 (optionally including a charged linker as appropriate)) and also bind to MSLN. In other embodiments, the antibodies described herein provide antibody constructs comprising anti-CD3 antigen binding domains that are "lite" or "lower affinity" binders to CD3. Additional embodiments provides antibody constructs comprising anti-CD3 antigen binding domains that have intermediate or "medium" affinity to CD3 that also bind to MSLN. While a very large number of anti-CD3 antigen binding domains (ABDs) can be used, particularly useful embodiments use 6 different anti-CD3 ABDs, although they can be used in two scFv orientations as discussed herein. Affinity is generally measured using a Biacore™ assay.

It should be appreciated that the "high, medium, low" anti-CD3 sequences provided herein can be used in a variety of heterodimerization formats as depicted in FIGS. 22A, 22B, and 43A-43K. In general, due to the potential side effects of T cell recruitment, exemplary embodiments utilize formats that only bind CD3 monovalently, such as depicted in FIGS. 22A and 22B, and in the formats depicted herein, it is the CD3 ABD that is a scFv as more fully described herein. In contrast, the subject bispecific antibodies can bind MSLN either monovalently (e.g. FIG. 22A) or bivalently (e.g. FIG. 22B).

Provided herein are compositions that include MSLN binding domains, including antibodies with such MSLN binding domains (e.g., MSLN×CD3 bispecific antibodies). Subject antibodies that include such MSLN binding domains advantageously elicit a range of different immune responses, depending on the particular MSLN binding domain used. For example, the subject antibodies exhibit differences in selectivity for cells with different MSLN expression, potencies for MSLN expressing cells, ability to elicit cytokine release, and sensitivity to soluble MSLN. Such MSLN binding domains and related antibodies find use, for example, in the treatment of MSLN associated cancers.

Accordingly, in one aspect, provided herein are heterodimeric antibodies that bind to two different antigens, e.g. the antibodies are "bispecific", in that they bind two different target antigens, generally MSLN and CD3 as described herein. These heterodimeric antibodies can bind these target antigens either monovalently (e.g. there is a single antigen binding domain such as a variable heavy and variable light domain pair) or bivalently (there are two antigen binding domains that each independently bind the antigen). In some embodiments, the heterodimeric antibody provided herein includes one CD3 binding domain and one MSLN binding domain (e.g., heterodimeric antibodies in the "1+1 Fab-scFv-Fc" format described herein). In other embodiments, the heterodimeric antibody provided herein includes one CD3 binding domain and two MSLN binding domains (e.g., heterodimeric antibodies in the "2+1 Fab2-scFv-Fc" formats described herein). The heterodimeric antibodies provided herein are based on the use different monomers which contain amino acid substitutions that "skew" formation of heterodimers over homodimers, as is more fully outlined below, coupled with "pI variants" that allow simple purification of the heterodimers away from the homodimers, as is similarly outlined below. The heterodimeric bispecific antibodies provided generally rely on the use of engineered or variant Fc domains that can self-assemble in production cells to produce heterodimeric proteins, and methods to generate and purify such heterodimeric proteins.

II. Nomenclature

The antibodies provided herein are listed in several different formats. In some instances, each monomer of a particular antibody is given a unique "XENP" number, although as will be appreciated in the art, a longer sequence might contain a shorter one. For example, a "scFv-Fc" monomer of a 1+1 Fab-scFv-Fc format antibody may have a first XENP number, while the scFv domain itself will have a different XENP number. Some molecules have three polypeptides, so the XENP number, with the components, is used as a name. Thus, the molecule XENP31063, which is in 2+1 Fab₂-scFv-Fc format, comprises three sequences (see FIG. 28A) a "Fab-Fc Heavy Chain" monomer; 2) a "Fab-scFv-Fc Heavy Chain" monomer; and 3) a "Light Chain" monomer or equivalents, although one of skill in the art would be able to identify these easily through sequence alignment. These XENP numbers are in the sequence listing as well as identifiers, and used in the Figures. In addition, one molecule, comprising the three components, gives rise to multiple sequence identifiers. For example, the listing of the Fab includes, the full heavy chain sequence, the variable heavy domain sequence and the three CDRs of the variable heavy domain sequence, the full light chain sequence, a variable light domain sequence and the three CDRs of the variable light domain sequence. A Fab-scFv-Fc monomer includes a full length sequence, a variable heavy domain sequence, 3 heavy CDR sequences, and an scFv sequence (include scFv variable heavy domain sequence, scFv variable light domain sequence and scFv linker). Note that some molecules herein with a scFv domain use a single charged scFv linker (+H), although others can be used. In addition, the naming nomenclature of particular antigen binding domains (e.g., MSLN and CD3 binding domains) use a "Hx.xx_Ly.yy" type of format, with the numbers being unique identifiers to particular variable chain sequences. Thus, the variable domain of the Fab side of MSLN binding domain MESO-C[MSLN]_H1L1 (e.g., FIG. 17) is "H1 L1", which indicates that the variable heavy domain, H1, was combined with the light domain L1. In the case that these sequences are used as scFvs, the designation "H1 L1", indicates that the variable heavy domain, H1 is combined with the light domain, L1, and is in VH-linker-VL orientation, from N- to C-terminus. This molecule with the identical sequences of the heavy and light variable domains but in the reverse order (VL-linker-VH orientation, from N- to C-terminus) would be designated "L1_H1.1". Similarly, different constructs may "mix and match" the heavy and light chains as will be evident from the sequence listing and the figures.

III. Definitions

In order that the application may be more completely understood, several definitions are set forth below. Such definitions are meant to encompass grammatical equivalents.

By "MSLN" or "Mesothelin" or "MESO" (e.g., FIG. 14A-14B) herein is meant a protein belonging to a series of ectoenzymes that are involved in hydrolysis of extracellular nucleotides. MSLN sequences are depicted, for example, in FIGS. 14A and 14B. MSLN is expressed in particular cancers, including ovarian cancer, colon cancer, breast cancer, hepatocellular carcinoma, lung cancer, mesothelioma, pancreatic cancer, non-small cell lung cancer (such as lung adenocarcinoma) and endometrial cancer.

By "ablation" herein is meant a decrease or removal of activity. Thus for example, "ablating FcγR binding" means the Fc region amino acid variant has less than 50% starting binding as compared to an Fc region not containing the specific variant, with more than 70-80-90-95-98% loss of activity being preferred, and in general, with the activity being below the level of detectable binding in a Biacore™, SPR or BLI assay. Of particular use in the ablation of FcγR binding are those shown in FIG. 5, which generally are added to both monomers.

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell. ADCC is correlated with binding to FcγRIIIa; increased binding to FcγRIIIa leads to an increase in ADCC activity.

By "ADCP" or antibody dependent cell-mediated phagocytosis as used herein is meant the cell-mediated reaction wherein nonspecific phagocytic cells that express FcγRs recognize bound antibody on a target cell and subsequently cause phagocytosis of the target cell.

As used herein, term "antibody" is used generally. Antibodies described herein can take on a number of formats as described herein, including traditional antibodies as well as antibody derivatives, fragments and mimetics, described herein.

Traditional immunoglobulin (Ig) antibodies are "Y" shaped tetramers. Each tetramer is typically composed of two identical pairs of polypeptide chains, each pair having one "light chain" monomer (typically having a molecular weight of about 25 kDa) and one "heavy chain" monomer (typically having a molecular weight of about 50-70 kDa).

Other useful antibody formats include, but are not limited to, the 1+1 Fab-scFv-Fc format and 2+1 Fab-scFv-Fc antibody formats described herein, as well as "mAb-Fv," "mAb-scFv," "central-Fv", "one armed scFv-mAb," "scFv-mAb," "dual scFv," and "trident" format antibodies, as shown in FIG. 43A-43K.

Antibody heavy chains typically include a variable heavy (VH) domain, which includes vhCDR1-3, and an Fc domain, which includes a CH2-CH3 monomer. In some embodiments, antibody heavy chains include a hinge and CH1 domain. Traditional antibody heavy chains are monomers that are organized, from N- to C-terminus: VH-CH1-hinge-CH2-CH3. The CH1-hinge-CH2-CH3 is collectively referred to as the heavy chain "constant domain" or "constant region" of the antibody, of which there are five different categories or "isotypes": IgA, IgD, IgG, IgE and IgM. Thus, "isotype" as used herein is meant any of the subclasses of immunoglobulins defined by the chemical and antigenic characteristics of their constant regions. It should be understood that therapeutic antibodies can also comprise hybrids of isotypes and/or subclasses. For example, as shown in US Publication 2009/0163699, incorporated by reference, the antibodies described herein include the use of human IgG1/G2 hybrids.

In some embodiments, the antibodies provided herein include IgG isotype constant domains, which has several subclasses, including, but not limited to IgG1, IgG2, IgG3, and IgG4. In the IgG subclass of immunoglobulins, there are several immunoglobulin domains in the heavy chain. By "immunoglobulin (Ig) domain" herein is meant a region of an immunoglobulin having a distinct tertiary structure. Of interest in the antibodies described herein are the heavy chain domains, including, the constant heavy (CH) domains and the hinge domains. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat. As shown herein and described below, the pI variants can be in one or more of the CH regions, as well as the hinge region, discussed below.

It should be noted that IgG1 has different allotypes with polymorphisms at 356 (D or E) and 358 (L or M). The sequences depicted herein use the 356D/358M allotype, however the other allotype is included herein. That is, any sequence inclusive of an IgG1 Fc domain included herein can have 356E/358L replacing the 356D/358M allotype. It should be understood that therapeutic antibodies can also comprise hybrids of isotypes and/or subclasses. For example, as shown in US Publication 2009/0163699, incorporated by reference, the present antibodies, in some embodiments, include IgG1/IgG2 hybrids.

By "Fc" or "Fc region" or "Fc domain" as used herein is meant the polypeptide comprising the constant region of an antibody, in some instances, excluding all of the first constant region immunoglobulin domain (e.g., CH1) or a portion thereof, and in some cases, optionally including all or part of the hinge. For IgG, the Fc domain comprises immunoglobulin domains CH2 and CH3 (Cγ2 and Cγ3), and optionally all or a portion of the hinge region between CH1 (Cγ1) and CH2 (Cγ2). Thus, in some cases, the Fc domain includes, from N- to C-terminal, CH2-CH3 and hinge-CH2-CH3. In some embodiments, the Fc domain is that from IgG1, IgG2, IgG3 or IgG4, with IgG1 hinge-CH2-CH3 and IgG4 hinge-CH2-CH3 finding particular use in many embodiments. Additionally, in the case of human IgG1 Fc domains, frequently the hinge includes a C220S amino acid substitution. Furthermore, in the case of human IgG4 Fc domains, frequently the hinge includes a S228P amino acid substitution. Although the boundaries of the Fc region may vary, the human IgG heavy chain Fc region is usually defined to include residues E216, C226, or A231 to its carboxyl-terminal, wherein the numbering is according to the EU index as in Kabat. In some embodiments, as is more fully described below, amino acid modifications are made to the Fc region, for example to alter binding to one or more FcγR or to the FcRn.

By "heavy chain constant region" herein is meant the CH1-hinge-CH2-CH3 portion of an antibody (or fragments thereof), excluding the variable heavy domain; in EU numbering of human IgG1 this is amino acids 118-447. By "heavy chain constant region fragment" herein is meant a heavy chain constant region that contains fewer amino acids from either or both of the N- and C-termini but still retains the ability to form a dimer with another heavy chain constant region.

Another type of Ig domain of the heavy chain is the hinge region. By "hinge" or "hinge region" or "antibody hinge region" or "hinge domain" herein is meant the flexible polypeptide comprising the amino acids between the first and second constant domains of an antibody. Structurally, the IgG CH1 domain ends at EU position 215, and the IgG CH2 domain begins at residue EU position 231. Thus for IgG the antibody hinge is herein defined to include positions 216 (E216 in IgG1) to 230 (p230 in IgG1), wherein the numbering is according to the EU index as in Kabat. In some cases, a "hinge fragment" is used, which contains fewer amino acids at either or both of the N- and C-termini of the hinge domain. As noted herein, pI variants can be made in the hinge region as well. Many of the antibodies herein have at least one the cysteines at position 220 according to EU numbering (hinge region) replaced by a serine. Generally, this modification is on the "scFv monomer" side for most of the sequences depicted herein, although it can also be on the "Fab monomer" side, or both, to reduce disulfide formation. Specifically included within the sequences herein are one or both of these cysteines replaced (C220S).

As will be appreciated by those in the art, the exact numbering and placement of the heavy constant region domains can be different among different numbering systems. A useful comparison of heavy constant region numbering according to EU and Kabat is as below, see Edelman et al., 1969, Proc Natl Acad Sci USA 63:78-85 and Kabat et al., 1991, Sequences of Proteins of Immunological Interest, 5th Ed., United States Public Health Service, National Institutes of Health, Bethesda, entirely incorporated by reference.

TABLE 1

|  | EU Numbering | Kabat Numbering |
|---|---|---|
| CH1 | 118-215 | 114-223 |
| Hinge | 216-230 | 226-243 |
| CH2 | 231-340 | 244-360 |
| CH3 | 341-447 | 361-478 |

The antibody light chain generally comprises two domains: the variable light domain (VL), which includes light chain CDRs vlCDR1-3, and a constant light chain region (often referred to as CL or CK). The antibody light chain is typically organized from N- to C-terminus: VL-CL.

By "antigen binding domain" or "ABD" herein is meant a set of six Complementary Determining Regions (CDRs) that, when present as part of a polypeptide sequence, specifically binds a target antigen (e.g., MSLN or CD3) as discussed herein. As is known in the art, these CDRs are generally present as a first set of variable heavy CDRs (vhCDRs or VHCDRs) and a second set of variable light CDRs (vlCDRs or VLCDRs), each comprising three CDRs: vhCDR1, vhCDR2, vhCDR3 variable heavy CDRs and vlCDR1, vlCDR2 and vlCDR3 vhCDR3 variable light CDRs. The CDRs are present in the variable heavy domain (vhCDR1-3) and variable light domain (vlCDR1-3). The variable heavy domain and variable light domain from an Fv region.

The antibodies described herein provide a large number of different CDR sets. In this case, a "full CDR set" comprises the three variable light and three variable heavy CDRs, e.g., a vlCDR1, vlCDR2, vlCDR3, vhCDR1, vhCDR2 and vhCDR3. These can be part of a larger variable light or variable heavy domain, respectfully. In addition, as more fully outlined herein, the variable heavy and variable light domains can be on separate polypeptide chains, when a heavy and light chain is used (for example when Fabs are used), or on a single polypeptide chain in the case of scFv sequences.

As will be appreciated by those in the art, the exact numbering and placement of the CDRs can be different among different numbering systems. However, it should be understood that the disclosure of a variable heavy and/or variable light sequence includes the disclosure of the associated (inherent) CDRs. Accordingly, the disclosure of each variable heavy region is a disclosure of the vhCDRs (e.g., vhCDR1, vhCDR2 and vhCDR3) and the disclosure of each variable light region is a disclosure of the vlCDRs (e.g., vlCDR1, vlCDR2 and vlCDR3). A useful comparison of CDR numbering is as below, see Lafranc et al., Dev. Comp. Immunol. 27 (1): 55-77 (2003):

TABLE 2

|  | Kabat + Chothia | IMGT | Rabat | AbM | Chothia | Contact | Xencor |
|---|---|---|---|---|---|---|---|
| vhCDR1 | 26-35 | 27-38 | 31-35 | 26-35 | 26-32 | 30-35 | 27-35 |
| vhCDR2 | 50-65 | 56-65 | 50-65 | 50-58 | 52-56 | 47-58 | 54-61 |
| vhCDR3 | 95-102 | 105-117 | 95-102 | 95-102 | 95-102 | 93-101 | 103-116 |
| vlCDR1 | 24-34 | 27-38 | 24-34 | 24-34 | 24-34 | 30-36 | 27-38 |
| vlCDR2 | 50-56 | 56-65 | 50-56 | 50-56 | 50-56 | 46-55 | 56-62 |
| vlCDR3 | 89-97 | 105-117 | 89-97 | 89-97 | 89-97 | 89-96 | 97-105 |

Throughout the present specification, the Kabat numbering system is generally used when referring to a residue in the variable domain (approximately, residues 1-107 of the light chain variable region and residues 1-113 of the heavy chain variable region) and the EU numbering system for Fc regions (e.g., Kabat et al., supra (1991)).

The CDRs contribute to the formation of the antigen-binding, or more specifically, epitope binding site of the antigen binding domains and antibodies. "Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope.

The epitope may comprise amino acid residues directly involved in the binding (also called immunodominant component of the epitope) and other amino acid residues, which are not directly involved in the binding, such as amino acid residues which are effectively blocked by the specifically antigen binding peptide; in other words, the amino acid residue is within the footprint of the specifically antigen binding peptide.

Epitopes may be either conformational or linear. A conformational epitope is produced by spatially juxtaposed amino acids from different segments of the linear polypeptide chain. A linear epitope is one produced by adjacent amino acid residues in a polypeptide chain. Conformational and nonconformational epitopes may be distinguished in that the binding to the former but not the latter is lost in the presence of denaturing solvents.

An epitope typically includes at least 3, and more usually, at least 5 or 8-10 amino acids in a unique spatial conformation. Antibodies that recognize the same epitope can be verified in a simple immunoassay showing the ability of one antibody to block the binding of another antibody to a target antigen, for example "binning." As outlined below, the disclosure not only includes the enumerated antigen binding domains and antibodies herein, but those that compete for binding with the epitopes bound by the enumerated antigen binding domains.

In some embodiments, the six CDRs of the antigen binding domain are contributed by a variable heavy and a variable light domain. In a "Fab" format, the set of 6 CDRs are contributed by two different polypeptide sequences, the variable heavy domain (vh or VH; containing the vhCDR1, vhCDR2 and vhCDR3) and the variable light domain (vl or VL; containing the vlCDR1, vlCDR2 and vlCDR3), with the C-terminus of the vh domain being attached to the N-terminus of the CH1 domain of the heavy chain and the C-terminus of the vl domain being attached to the N-terminus of the constant light domain (and thus forming the light chain). In a scFv format, the vh and vl domains are covalently attached, generally through the use of a linker (a "scFv linker") as outlined herein, into a single polypeptide sequence, which can be either (starting from the N-terminus) vh-linker-vl or vl-linker-vh, with the former being generally preferred (including optional domain linkers on each side, depending on the format used (e.g., from FIG. 1). In general, the C-terminus of the scFv domain is attached to the N-terminus of the hinge in the second monomer.

By "variable region" or "variable domain" as used herein is meant the region of an immunoglobulin that comprises one or more Ig domains substantially encoded by any of the VK, VA, and/or VH genes that make up the kappa, lambda, and heavy chain immunoglobulin genetic loci respectively, and contains the CDRs that confer antigen specificity. Thus, a "variable heavy domain" pairs with a "variable light domain" to form an antigen binding domain ("ABD"). In addition, each variable domain comprises three hypervariable regions ("complementary determining regions," "CDRs") (VHCDR1, VHCDR2 and VHCDR3 for the variable heavy domain and VLCDR1, VLCDR2 and VLCDR3 for the variable light domain) and four framework (FR) regions, arranged from amino-terminus to carboxy-terminus in the following order: FR1-CDR1-FR2-CDR2-FR3-CDR3-FR4. The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917. Specific CDRs of the invention are described in Table 2.

By "Fab" or "Fab region" as used herein is meant the polypeptide that comprises the VH, CH1, VL, and CL immunoglobulin domains, generally on two different polypeptide chains (e.g. VH-CH1 on one chain and VL-CL on the other). Fab may refer to this region in isolation, or this region in the context of a bispecific antibody described herein. In the context of a Fab, the Fab comprises an Fv region in addition to the CH1 and CL domains.

By "Fv" or "Fv fragment" or "Fv region" as used herein is meant a polypeptide that comprises the VL and VH domains of an ABD. Fv regions can be formatted as both Fabs (as discussed above, generally two different polypeptides that also include the constant regions as outlined above) and scFvs, where the VL and VH domains are combined (generally with a linker as discussed herein) to form an scFv.

By "single chain Fv" or "scFv" herein is meant a variable heavy domain covalently attached to a variable light domain, generally using a scFv linker as discussed herein, to form a scFv or scFv domain. A scFv domain can be in either orientation from N-to C-terminus (VH-linker-VL or VL-linker-VH). In the sequences depicted in the sequence listing and in the figures, the order of the VH and VL domain is indicated in the name, e.g. H.X_L.Y means N-to C-terminal is VH-linker-VL, and L.Y_H.X is VL-linker-VH.

Some embodiments of the subject antibodies provided herein comprise at least one scFv domain, which, while not naturally occurring, generally includes a variable heavy domain and a variable light domain, linked together by a scFv linker. As outlined herein, while the scFv domain is generally from N- to C-terminus oriented as VH-scFv linker-VL, this can be reversed for any of the scFv domains (or those constructed using vh and vl sequences from Fabs), to VL-scFv linker-VH, with optional linkers at one or both ends depending on the format.

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g. the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution E272Y refers to a variant polypeptide, in this case an Fc variant, in which the glutamic acid at position 272 is replaced with tyrosine. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "amino acid insertion" or "insertion" as used herein is meant the addition of an amino acid sequence at a particular position in a parent polypeptide sequence. For example, −233E or 233E designates an insertion of glutamic acid after position 233 and before position 234. Additionally, −233ADE or A233ADE designates an insertion of AlaAsp-Glu after position 233 and before position 234.

By "amino acid deletion" or "deletion" as used herein is meant the removal of an amino acid sequence at a particular position in a parent polypeptide sequence. For example, E233− or E233 #, E233( ) or E233del designates a deletion of glutamic acid at position 233. Additionally, EDA233− or EDA233 #designates a deletion of the sequence GluAspAla that begins at position 233.

By "variant protein" or "protein variant", or "variant" as used herein is meant a protein that differs from that of a parent protein by virtue of at least one amino acid modification. The protein variant has at least one amino acid modification compared to the parent protein, yet not so many that the variant protein will not align with the parental protein using an alignment program such as that described below. In general, variant proteins (such as variant Fc domains, etc., outlined herein, are generally at least 75, 80, 85, 90, 91, 92, 93, 94, 95, 96, 97, 98 or 99% identical to the parent protein, using the alignment programs described below, such as BLAST® sequence alignment search tool. "Variant" as used herein also refers to particular amino acid modifications that confer particular function (e.g., a "het-erodimerization variant," "pI variant," "ablation variant," etc.).

As described below, in some embodiments the parent polypeptide, for example an Fc parent polypeptide, is a human wild type sequence, such as the heavy constant domain or Fc region from IgG1, IgG2, IgG3 or IgG4, although human sequences with variants can also serve as "parent polypeptides", for example the IgG1/2 hybrid of US Publication 2006/0134105 can be included. The protein variant sequence herein will preferably possess at least about 80% identity with a parent protein sequence, and most preferably at least about 90% identity, more preferably at least about 95-98-99% identity. Accordingly, by "antibody variant" or "variant antibody" as used herein is meant an antibody that differs from a parent antibody by virtue of at least one amino acid modification, "IgG variant" or "variant IgG" as used herein is meant an antibody that differs from a parent IgG (again, in many cases, from a human IgG sequence) by virtue of at least one amino acid modification, and "immunoglobulin variant" or "variant immunoglobulin" as used herein is meant an immunoglobulin sequence that differs from that of a parent immunoglobulin sequence by virtue of at least one amino acid modification. "Fc variant" or "variant Fc" as used herein is meant a protein comprising an amino acid modification in an Fc domain as compared to an Fc domain of human IgG1, IgG2 or IgG4.

"Fc variant" or "variant Fc" as used herein is meant a protein comprising an amino acid modification in an Fc domain. The modification can be an addition, deletion, or substitution. The Fc variants are defined according to the amino acid modifications that compose them. Thus, for example, N434S or 434S is an Fc variant with the substitution for serine at position 434 relative to the parent Fc polypeptide, wherein the numbering is according to the EU index. Likewise, M428L/N434S defines an Fc variant with the substitutions M428L and N434S relative to the parent Fc polypeptide. The identity of the WT amino acid may be unspecified, in which case the aforementioned variant is referred to as 428L/434S. It is noted that the order in which substitutions are provided is arbitrary, that is to say that, for example, 428L/434S is the same Fc variant as 434S/428L, and so on. For all positions discussed herein that relate to antibodies or derivatives and fragments thereof (e.g., Fc domains), unless otherwise noted, amino acid position num-bering is according to the EU index. The "EU index" or "EU index as in Kabat" or "EU numbering" scheme refers to the numbering of the EU antibody (Edelman et al., 1969, Proc Natl Acad Sci USA 63:78-85, hereby entirely incorporated by reference).

In general, variant Fc domains have at least about 80, 85, 90, 95, 97, 98 or 99 percent identity to the corresponding parental human IgG Fc domain (using the identity algo-rithms discussed below, with one embodiment utilizing the BLAST® sequence alignment search tool algorithm as is known in the art, using default parameters). Alternatively, the variant Fc domains can have from 1, 2, 3, 4, 5, 6, 7, 8, 9, 10, 11, 12, 13, 14, 15, 16, 11, 12, 13, 14, 15, 16, 17, 18, 19 or 20 amino acid modifications as compared to the parental Fc domain. Alternatively, the variant Fc domains can have up to 1, 2, 3, 4, 5, 6, 7, 8, 9, 10, 11, 12, 13, 14, 15, 16, 11, 12, 13, 14, 15, 16, 17, 18, 19 or 20 amino acid modifications as compared to the parental Fc domain. Addi-tionally, as discussed herein, the variant Fc domains described herein still retain the ability to form a dimer with another Fc domain as measured using known techniques as described herein, such as non-denaturing gel electrophore-sis.

By "protein" herein is meant at least two covalently attached amino acids, which includes proteins, polypeptides, oligopeptides and peptides. In addition, polypeptides that make up the antibodies described herein may include syn-thetic derivatization of one or more side chains or termini, glycosylation, PEGylation, circular permutation, cycliza-tion, linkers to other molecules, fusion to proteins or protein domains, and addition of peptide tags or labels.

By "residue" as used herein is meant a position in a protein and its associated amino acid identity. For example, Asparagine 297 (also referred to as Asn297 or N297) is a residue at position 297 in the human antibody IgG1.

By "IgG subclass modification" or "isotype modification" as used herein is meant an amino acid modification that converts one amino acid of one IgG isotype to the corre-sponding amino acid in a different, aligned IgG isotype. For example, because IgG1 comprises a tyrosine and IgG2 a phenylalanine at EU position 296, a F296Y substitution in IgG2 is considered an IgG subclass modification.

By "non-naturally occurring modification" as used herein is meant an amino acid modification that is not isotypic. For example, because none of the human IgGs comprise a serine at position 434, the substitution 434S in IgG1, IgG2, IgG3, or IgG4 (or hybrids thereof) is considered a non-naturally occurring modification.

By "amino acid" and "amino acid identity" as used herein is meant one of the 20 naturally occurring amino acids that are coded for by DNA and RNA.

By "effector function" as used herein is meant a biochemi-cal event that results from the interaction of an antibody Fc region with an Fc receptor or ligand. Effector functions include but are not limited to ADCC, ADCP, and CDC.

By "IgG Fc ligand" as used herein is meant a molecule, preferably a polypeptide, from any organism that binds to the Fc region of an IgG antibody to form an Fc/Fc ligand complex. Fc ligands include but are not limited to FcγRIs, FcγRIIs, FcγRIIIs, FcRn, C1q, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis et al., 2002, Immunological Reviews 190:123-136, entirely incorporated by reference). Fc ligands may include undiscovered molecules that bind Fc. Particular IgG Fc ligands are FcRn and Fc gamma receptors. By "Fc ligand" as used herein is meant a molecule, preferably a polypeptide, from any organism that binds to the Fc region of an antibody to form an Fc/Fc ligand complex.

By "Fc gamma receptor", "FcγR" or "FcgammaR" as used herein is meant any member of the family of proteins that bind the IgG antibody Fc region and is encoded by an FcγR gene. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIb-NA1 and FcγRIIb-NA2) (Jefferis et al., 2002, Immunol Lett 82:57-65, entirely incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes.

By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin. A variety of FcRn variants used to increase binding to the FcRn receptor, and in some cases, to increase serum half-life. An "FcRn variant" is one that increases binding to the FcRn receptor, and suitable FcRn variants are shown below.

By "parent polypeptide" as used herein is meant a starting polypeptide that is subsequently modified to generate a variant. The parent polypeptide may be a naturally occurring polypeptide, or a variant or engineered version of a naturally occurring polypeptide. Accordingly, by "parent immunoglobulin" as used herein is meant an unmodified immunoglobulin polypeptide that is modified to generate a variant, and by "parent antibody" as used herein is meant an unmodified antibody that is modified to generate a variant antibody. It should be noted that "parent antibody" includes known commercial, recombinantly produced antibodies as outlined below. In this context, a "parent Fc domain" will be relative to the recited variant; thus, a "variant human IgG1 Fc domain" is compared to the parent Fc domain of human IgG1, a "variant human IgG4 Fc domain" is compared to the parent Fc domain human IgG4, etc.

By "position" as used herein is meant a location in the sequence of a protein. Positions may be numbered sequentially, or according to an established format, for example the EU index for antibody numbering.

By "target antigen" as used herein is meant the molecule that is bound specifically by the antigen binding domain comprising the variable regions of a given antibody.

By "strandedness" in the context of the monomers of the heterodimeric antibodies described herein is meant that, similar to the two strands of DNA that "match", heterodimerization variants are incorporated into each monomer so as to preserve the ability to "match" to form heterodimers. For example, if some pI variants are engineered into monomer A (e.g. making the pI higher) then steric variants that are "charge pairs" that can be utilized as well do not interfere with the pI variants, e.g. the charge variants that make a pI higher are put on the same "strand" or "monomer" to preserve both functionalities. Similarly, for "skew" variants that come in pairs of a set as more fully outlined below, the skilled artisan will consider pI in deciding into which strand or monomer one set of the pair will go, such that pI separation is maximized using the pI of the skews as well.

By "target cell" as used herein is meant a cell that expresses a target antigen.

By "host cell" in the context of producing a bispecific antibody according to the antibodies described herein is meant a cell that contains the exogeneous nucleic acids encoding the components of the bispecific antibody and is capable of expressing the bispecific antibody under suitable conditions. Suitable host cells are discussed below.

By "wild type or WT" herein is meant an amino acid sequence or a nucleotide sequence that is found in nature, including allelic variations. A WT protein has an amino acid sequence or a nucleotide sequence that has not been intentionally modified.

Provided herein are a number of antibody domains that have sequence identity to human antibody domains. Sequence identity between two similar sequences (e.g., antibody variable domains) can be measured by algorithms such as that of Smith, T.F. & Waterman, M. S. (1981) "Comparison Of Biosequences," Adv. Appl. Math. 2:482 [local homology algorithm]; Needleman, S.B. & Wunsch, CD. (1970) "A General Method Applicable To The Search For Similarities In The Amino Acid Sequence Of Two Proteins," J. Mol. Biol. 48:443 [homology alignment algorithm], Pearson, W.R. & Lipman, D.J. (1988) "Improved Tools For Biological Sequence Comparison," Proc. Natl. Acad. Sci. (U.S.A.) 85:2444 [search for similarity method]; or Altschul, S. F. et al, (1990) "Basic Local Alignment Search Tool," J. Mol. Biol. 215:403-10, the BLAST® sequence alignment search tool algorithm, see blast.ncbi.nlm.nih.gov. When using any of the aforementioned algorithms, the default parameters (for Window length, gap penalty, etc) are used. In one embodiment, sequence identity is done using the BLAST® sequence alignment search tool algorithm, using default parameters The antibodies described herein are generally isolated or recombinant. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic specificities. "Recombinant" means the antibodies are generated using recombinant nucleic acid techniques in exogeneous host cells, and they can be isolated as well.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a $K_D$ for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$ M, alternatively at least about 10-10 M, at least about 10-11 M, at least about 10-12 M, or greater, where $K_D$ refers to a dissociation rate of a particular antibody-antigen interaction. Typically, an antibody that specifically binds an antigen will have a $K_D$ that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction. Binding affinity is generally measured using a Biacore™, SPR or BLI assay.

IV. MSLN Binding Domains

In one aspect, provided herein are MSLN antigen binding domains (ABDs) and compositions that include such MSLN antigen binding domains (ABDs), including anti-MSLN antibodies. Subject antibodies that include such MSLN antigen binding domains (e.g., anti-MSLN×anti-CD3 bispecific antibodies) advantageously elicit a range of different immune responses. Such MSLN binding domains and related antibodies find use, for example, in the treatment of MSLN associated cancers.

As will be appreciated by those in the art, suitable MSLN binding domains can comprise a set of 6 CDRs as depicted in the sequence listing and FIGS. 15-21, either as the CDRs are underlined or, in the case where a different numbering scheme is used as described herein and as shown in Table 2, as the CDRs that are identified using other alignments within the variable heavy (VH) domain and variable light domain (VL) sequences of those depicted in FIGS. 15-21 and the Sequence Listing (see Table 2). Suitable MSLN ABDs can also include the entire VH and VL sequences as depicted in these sequences and figures, used as scFvs or as Fab domains.

In one embodiment, the MSLN antigen binding domain includes the 6 CDRs (i.e., vhCDR1-3 and vlCDR1-3) of a MSLN ABD described herein, including the figures and sequence listing. In exemplary embodiments, the MSLN ABD is one of the following MSLN ABDs: MESO-A [MSLN]_H1.1_L1, MESO-B[MSLN]_H0L0, MESO-C [MSLN]_H1L1, MESO-C[MSLN]_H1.1_L1, MESO-C [MSLN]_H1.2L1, MESO-C[MSLN]_H1.3_L1, MESO-C [MSLN]_H1.4_L1, MESO-C[MSLN]_H1.5_L1, MESO-C [MSLN]_H1.6_L1, MESO-C[MSLN]_H1.7_L1, MESO-C [MSLN]_H1.8_L1, MESO-C[MSLN]_H1.9_L1, MESO-C

[MSLN]_H1_L1.1, MESO-C[MSLN]_H1_L1.2, MESO-C [MSLN]_H1_L1.3, MESO-C[MSLN]_H1_L1.4, MESO-C [MSLN]_H1_L1.5, MESO-C[MSLN]_H1_L1.6, MESO-C [MSLN]_H1_L1.7, MESO-C[MSLN]_H1_L1.8, MESO-C [MSLN]_H1_L1.9, MESO-C[MSLN]_H1_L1.10, MESO-C[MSLN]_H1.5_L1.3, MESO-C[MSLN]_H1.6_L1.3, MESO-C[MSLN]_H1.12_L1.9, MESO-C[MSLN]_ H1.13_L1.9, MESO-C[MSLN]_H1.3_L1.13, MESO-C [MSLN]_H1.3_L1.14, MESO-C[MSLN]_H1.3_L1.15, MESO-C[MSLN]_H1.3_L1.16, MESO-C[MSLN]_ H1.3_L1.17, MESO-C[MSLN]_H1.3_L1.18, MESO-C [MSLN]_H1.3_L1.9, MESO-C[MSLN]_H1.3_L1.5, MESO-C[MSLN]_H1_L1.20, MESO-C[MSLN]_ H1.12_L1.20, MESO-C[MSLN]_H1.14_L1.14, MESO-C [MSLN]_H1.15_L1.14, MESO-C[MSLN]_H1.16_L1.14, MESO-C[MSLN]_H1_L1.19_, MESO-C[MSLN]_ H1_L1.21, MESO-C[MSLN]_H1_L1.22, MESO-C [MSLN]_H1.12_L1.19, MESO-C[MSLN]_H1.12_L1.21, MESO-C[MSLN]_H1.12_L1.22, and MESO-C[MSLN]_ H1.12_L1.9 (FIGS. 15-21). In addition to the parental CDR sets disclosed in the figures and sequence listing that form an ABD to MSLN, provided herein are variant MSLN ABDs having CDRs that include at least one modification of the MSLN ABD CDRs disclosed herein. In one embodiment, the MSLN ABD includes a set of 6 CDRs with 1, 2, 3, 4, 5, 6, 7, 8, 9, 10 amino acid modifications as compared to the 6 CDRs of a MSLN ABD described herein, including the figures and sequence listing. In exemplary embodiments, the MSLN ABD includes a set of 6 CDRs with 1, 2, 3, 4, 5, 6, 7, 8, 9, 10 amino acid modifications as compared to the 6 CDRs of one of the following MSLN ABDs: MESO-A [MSLN]_H1.1_L1, MESO-B[MSLN]_H0L0, MESO-C [MSLN]_H1L1, MESO-C[MSLN]_H1.1_L1, MESO-C [MSLN]_H1.2L1, MESO-C[MSLN]_H1.3_L1, MESO-C [MSLN]_H1.4_L1, MESO-C[MSLN]_H1.5_L1, MESO-C [MSLN]_H1.6_L1, MESO-C[MSLN]_H1.7_L1, MESO-C [MSLN]_H1.8_L1, MESO-C[MSLN]_H1.9_L1, MESO-C [MSLN]_H1_L1.1, MESO-C[MSLN]_H1_L1.2, MESO-C [MSLN]_H1_L1.3, MESO-C[MSLN]_H1_L1.4, MESO-C [MSLN]_H1_L1.5, MESO-C[MSLN]_H1_L1.6, MESO-C [MSLN]_H1_L1.7, MESO-C[MSLN]_H1_L1.8, MESO-C [MSLN]_H1_L1.9, MESO-C[MSLN]_H1_L1.10, MESO-C[MSLN]_H1.5_L1.3, MESO-C[MSLN]_H1.6_L1.3, MESO-C[MSLN]_H1.12_L1.9, MESO-C[MSLN]_ H1.13_L1.9, MESO-C[MSLN]_H1.3_L1.13, MESO-C [MSLN]_H1.3_L1.14, MESO-C[MSLN]_H1.3_L1.15, MESO-C[MSLN]_H1.3_L1.16, MESO-C[MSLN]_ H1.3_L1.17, MESO-C[MSLN]_H1.3_L1.18, MESO-C [MSLN]_H1.3_L1.9, MESO-C[MSLN]_H1.3_L1.5, MESO-C[MSLN]_H1_L1.20, MESO-C[MSLN]_ H1.12_L1.20, MESO-C[MSLN]_H1.14_L1.14, MESO-C [MSLN]_H1.15_L1.14, MESO-C[MSLN]_H1.16_L1.14, MESO-C[MSLN]_H1_L1.19, MESO-C[MSLN]_ H1_L1.21, MESO-C[MSLN]_H1_L1.22, MESO-C [MSLN]_H1.12_L1.19, MESO-C[MSLN]_H1.12_L1.21, MESO-C[MSLN]_H1.12_L1.22, and MESO-C[MSLN]_ H1.12_L1.9 (FIGS. 15-21).

In certain embodiments, the variant MSLN ABD is capable of binding MSLN antigen, as measured by at least one of a Biacore™, surface plasmon resonance (SPR) and/or BLI (biolayer interferometry, e.g., Octet® assay) assay, with the latter finding particular use in many embodiments. In particular embodiments, the MSLN ABD is capable of binding human MSLN antigen.

In one embodiment, the MSLN ABD includes 6 CDRs that are at least 90, 95, 97, 98 or 99% identical to the 6 CDRs of a MSLN ABD as described herein, including the figures and sequence listing. In exemplary embodiments, the MSLN ABD includes 6 CDRs that are at least 90, 95, 97, 98 or 99% identical to the 6 CDRs of one of the following MSLN ABDs: MESO-A[MSLN]_H1.1_L1, MESO-B[MSLN]_ H0L0, MESO-C[MSLN]_H1L1, MESO-C[MSLN]_ H1.1_L1, MESO-C[MSLN]_H1.2L1, MESO-C[MSLN]_ H1.3_L1, MESO-C[MSLN]_H1.4_L1, MESO-C[MSLN]_ H1.5_L1, MESO-C[MSLN]_H1.6_L1, MESO-C[MSLN]_ H1.7_L1, MESO-C[MSLN]_H1.8_L1, MESO-C[MSLN]_ H1.9_L1, MESO-C[MSLN]_H1_L1.1, MESO-C[MSLN]_ H1_L1.2, MESO-C[MSLN]_H1_L1.3, MESO-C[MSLN]_ H1_L1.4, MESO-C[MSLN]_H1_L1.5, MESO-C[MSLN]_ H1_L1.6, MESO-C[MSLN]_H1_L1.7, MESO-C[MSLN]_ H1_L1.8, MESO-C[MSLN]_H1_L1.9, MESO-C[MSLN]_ H1_L1.10, MESO-C[MSLN]_H1.5_L1.3, MESO-C [MSLN]_H1.6_L1.3, MESO-C[MSLN]_H1.12_L1.9, MESO-C[MSLN]_H1.13_L1.9, MESO-C[MSLN]_ H1.3_L1.13, MESO-C[MSLN]_H1.3_L1.14, MESO-C [MSLN]_H1.3_L1.15, MESO-C[MSLN]_H1.3_L1.16, MESO-C[MSLN]_H1.3_L1.17, MESO-C[MSLN]_ H1.3_L1.18, MESO-C[MSLN]_H1.3_L1.9, MESO-C [MSLN]_H1.3_L1.5, MESO-C[MSLN]_H1_L1.20, MESO-C[MSLN]_H1.12_L1.20, MESO-C[MSLN]_ H1.14_L1.14, MESO-C[MSLN]_H1.15_L1.14, MESO-C [MSLN]_H1.16_L1.14, MESO-C[MSLN]_H1_L1.19_, MESO-C[MSLN]_H1_L1.21, MESO-C[MSLN]_ H1_L1.22, MESO-C[MSLN]_H1.12_L1.19, MESO-C [MSLN]_H1.12_L1.21, MESO-C[MSLN]_H1.12_L1.22, and MESO-C[MSLN]_H1.12_L1.9 (FIGS. 15-21). In certain embodiments, the MSLN ABD is capable of binding to MSLN antigen, as measured by at least one of a Biacore™, surface plasmon resonance (SPR) and/or BLI (biolayer interferometry, e.g., Octet® assay) assay, with the latter finding particular use in many embodiments. In particular embodiments, the MSLN ABD is capable of binding human MSLN antigen (see FIG. 14A).

In another exemplary embodiment, the MSLN ABD include the variable heavy (VH) domain and variable light (VL) domain of any one of the MSLN ABDs described herein, including the figures and sequence listing (e.g., FIGS. 15-21). In exemplary embodiments, the MSLN ABD is one of the following MSLN ABDs: MESO-A[MSLN]_ H1.1_L1, MESO-B[MSLN]_H0L0, MESO-C[MSLN]_ H1L1, MESO-C[MSLN]_H1.1_L1, MESO-C[MSLN]_ H1.2L1, MESO-C[MSLN]_H1.3_L1, MESO-C[MSLN]_ H1.4_L1, MESO-C[MSLN]_H1.5_L1, MESO-C[MSLN]_ H1.6_L1, MESO-C[MSLN]_H1.7_L1, MESO-C[MSLN]_ H1.8_L1, MESO-C[MSLN]_H1.9_L1, MESO-C[MSLN]_ H1_L1.1, MESO-C[MSLN]_H1_L1.2, MESO-C[MSLN]_ H1_L1.3, MESO-C[MSLN]_H1_L1.4, MESO-C[MSLN]_ H1_L1.5, MESO-C[MSLN]_H1_L1.6, MESO-C[MSLN]_ H1_L1.7, MESO-C[MSLN]_H1_L1.8, MESO-C[MSLN]_ H1_L1.9, MESO-C[MSLN]_H1_L1.10, MESO-C [MSLN]_ H1.5_L1.3, MESO-C[MSLN]_H1.6_L1.3, MESO-C[MSLN]_H1.12_L1.9, MESO-C[MSLN]_ H1.13_L1.9, MESO-C[MSLN]_H1.3_L1.13, MESO-C [MSLN]_ H1.3_L1.14, MESO-C[MSLN]_H1.3_L1.15, MESO-C[MSLN]_H1.3_L1.16, MESO-C[MSLN]_ H1.3_L1.17, MESO-C[MSLN]_H1.3_L1.18, MESO-C [MSLN]_ H1.3_L1.9, MESO-C[MSLN]_H1.3_L1.5, MESO-C[MSLN]_H1_L1.20, MESO-C[MSLN]_ H1.12_L1.20, MESO-C[MSLN]_H1.14_L1.14, MESO-C [MSLN]_ H1.15_L1.14, MESO-C[MSLN]_H1.16_L1.14, MESO-C[MSLN]_H1_L1.19, MESO-C[MSLN]_ H1_L1.21, MESO-C[MSLN]_H1_L1.22, MESO-C

[MSLN]_H1.12_L1.19, MESO-C[MSLN]_H1.12_L1.21, MESO-C[MSLN]_H1.12_L1.22, and MESO-C[MSLN]_ H1.12_L1.9 (FIGS. 15-21).

In addition to the parental MSLN variable heavy and variable light domains disclosed herein, provided herein are MSLN ABDs that include a variable heavy domain and/or a variable light domain that are variants of a MSLN ABD VH and VL domain disclosed herein. In one embodiment, the variant VH domain and/or VL domain has from 1, 2, 3, 4, 5, 6, 7, 8, 9 or 10 amino acid changes from a VH and/or VL domain of a MSLN ABD described herein, including the figures and sequence listing. In exemplary embodiments, the variant VH domain and/or VL domain has from 1, 2, 3, 4, 5, 6, 7, 8, 9 or 10 amino acid changes from a VH and/or VL domain of one of the following MSLN ABDs: MESO-A [MSLN]_H1.1_L1, MESO-B[MSLN]_H0L0, MESO-C [MSLN]_H1L1, MESO-C[MSLN]_H1.1_L1, MESO-C [MSLN]_H1.2L1, MESO-C[MSLN]_H1.3_L1, MESO-C [MSLN]_H1.4_L1, MESO-C[MSLN]_H1.5_L1, MESO-C [MSLN]_H1.6_L1, MESO-C[MSLN]_H1.7_L1, MESO-C [MSLN]_H1.8_L1, MESO-C[MSLN]_H1.9_L1, MESO-C [MSLN]_H1_L1.1, MESO-C[MSLN]_H1_L1.2, MESO-C [MSLN]_H1_L1.3, MESO-C[MSLN]_H1_L1.4, MESO-C [MSLN]_H1_L1.5, MESO-C[MSLN]_H1_L1.6, MESO-C [MSLN]_H1_L1.7, MESO-C[MSLN]_H1_L1.8, MESO-C [MSLN]_H1_L1.9, MESO-C[MSLN]_H1_L1.10, MESO-C[MSLN]_H1.5_L1.3, MESO-C[MSLN]_H1.6_L1.3, MESO-C[MSLN]_H1.12_L1.9, MESO-C[MSLN]_ H1.13_L1.9, MESO-C[MSLN]_H1.3_L1.13, MESO-C [MSLN]_H1.3_L1.14, MESO-C[MSLN]_H1.3_L1.15, MESO-C[MSLN]_H1.3_L1.16, MESO-C[MSLN]_ H1.3_L1.17, MESO-C[MSLN]_H1.3_L1.18, MESO-C [MSLN]_H1.3_L1.9, MESO-C[MSLN]_H1.3_L1.5, MESO-C[MSLN]_H1_L1.20, MESO-C[MSLN]_ H1.12_L1.20, MESO-C[MSLN]_H1.14_L1.14, MESO-C [MSLN]_H1.15_L1.14, MESO-C[MSLN]_H1.16_L1.14, MESO-C[MSLN]_H1_L1.19, MESO-C[MSLN]_ H1_L1.21, MESO-C[MSLN]_H1_L1.22, MESO-C [MSLN]_H1.12_L1.19, MESO-C[MSLN]_H1.12_L1.21, MESO-C[MSLN]_H1.12_L1.22, and MESO-C[MSLN]_ H1.12_L1.9 (FIGS. 15-21). In certain embodiments, the MSLN ABD is capable of binding to MSLN, as measured at least one of a Biacore™, surface plasmon resonance (SPR) and/or BLI (biolayer interferometry, e.g., Octet® assay) assay, with the latter finding particular use in many embodiments. In particular embodiments, the MSLN ABD is capable of binding human MSLN antigen.

In one embodiment, the variant VH and/or VL domain is at least 90, 95, 97, 98 or 99% identical to the VH and/or VL of a MSLN ABD as described herein, including the figures and sequence listing. In exemplary embodiments, the variant VH and/or VL domain is at least 90, 95, 97, 98 or 99% identical to the VH and/or VL of one of the following MSLN ABDs: MESO-A[MSLN]_H1.1_L1, MESO-B[MSLN]_ H0L0, MESO-C[MSLN]_H1L1, MESO-C[MSLN]_ H1.1_L1, MESO-C[MSLN]_H1.2L1, MESO-C[MSLN]_ H1.3_L1, MESO-C[MSLN]_H1.4_L1, MESO-C[MSLN]_ H1.5_L1, MESO-C[MSLN]_H1.6_L1, MESO-C[MSLN]_ H1.7_L1, MESO-C[MSLN]_H1.8_L1, MESO-C[MSLN]_ H1.9_L1, MESO-C[MSLN]_H1_L1.1, MESO-C[MSLN]_ H1_L1.2, MESO-C[MSLN]_H1_L1.3, MESO-C[MSLN]_ H1_L1.4, MESO-C[MSLN]_H1_L1.5, MESO-C[MSLN]_ H1_L1.6, MESO-C[MSLN]_H1_L1.7, MESO-C[MSLN]_ H1_L1.8, MESO-C[MSLN]_H1_L1.9, MESO-C[MSLN]_ H1_L1.10, MESO-C[MSLN]_H1.5_L1.3, MESO-C [MSLN]_H1.6_L1.3, MESO-C[MSLN]_H1.12_L1.9, MESO-C[MSLN]_H1.13_L1.9, MESO-C[MSLN]_H1.3_L1.13, MESO-C[MSLN]_H1.3_L1.14, MESO-C[MSLN]_H1.3_L1.15, MESO-C[MSLN]_H1.3_L1.16, MESO-C[MSLN]_H1.3_L1.17, MESO-C[MSLN]_H1.3_L1.18, MESO-C[MSLN]_H1.3_L1.9, MESO-C[MSLN]_H1.3_L1.5, MESO-C[MSLN]_H1_L1.20, MESO-C[MSLN]_H1.12_L1.20, MESO-C[MSLN]_H1.14_L1.14, MESO-C[MSLN]_H1.15_L1.14, MESO-C[MSLN]_H1.16_L1.14, MESO-C[MSLN]_H1_L1.19_, MESO-C[MSLN]_H1_L1.21, MESO-C[MSLN]_H1_L1.22, MESO-C[MSLN]_H1.12_L1.19, MESO-C[MSLN]_H1.12_L1.21, MESO-C[MSLN]_H1.12_L1.22, and MESO-C[MSLN]_H1.12_L1.9 (FIGS. 15-21). In certain embodiments, the MSLN ABD is capable of binding to the MSLN, as measured by at least one of a Biacore™, surface plasmon resonance (SPR) and/or BLI (biolayer interferometry, e.g., Octet® assay) assay, with the latter finding particular use in many embodiments. In particular embodiments, the MSLN ABD is capable of binding human MSLN antigen.

V. Antibodies

In one aspect, provided herein are antibodies that bind to MSLN (e.g., anti-MSLN antibodies). In certain embodiments, the antibody binds to human MSLN (FIG. 14A). Subject anti-MSLN antibodies include monospecific MSLN antibodies, as well as multi-specific (e.g., bispecific) anti-MSLN antibodies. In certain embodiments, the anti-MSLN antibody has a format according to any one of the antibody formats depicted in FIGS. 22A, 22B, and 43A-43K.

In some embodiments, the subject compositions include a MSLN binding domain. In some embodiments, the composition includes an antibody having a MSLN binding domain. Antibodies provided herein include one, two, three, four, and five or more MSLN binding domains. In certain embodiments, the MSLN binding domain includes any one of the vhCDR1, vhCDR2, vhCDR3, vlCDR1, vlCDR2 and vlCDR3 sequences of a MSLN binding domain selected from those depicted in FIGS. 15-21. In some embodiments, the MSLN binding domain includes the underlined vhCDR1, vhCDR2, vhCDR3, vlCDR1, vlCDR2 and vlCDR3 sequences of a MSLN binding domain selected from those depicted in FIGS. 15-21. In some embodiments, the MSLN binding domain includes the variable heavy domain and variable light domain of a MSLN binding domain selected from those depicted in FIGS. 15-21. MSLN binding domains depicted in FIGS. 15-21 include: MESO-A[MSLN]_H1.1_L1, MESO-B[MSLN]_H0L0, MESO-C[MSLN]_H1L1, MESO-C[MSLN]_H1.1_L1, MESO-C[MSLN]_H1.2L1, MESO-C[MSLN]_H1.3_L1, MESO-C[MSLN]_H1.4_L1, MESO-C[MSLN]_H1.5_L1, MESO-C[MSLN]_H1.6_L1, MESO-C[MSLN]_H1.7_L1, MESO-C[MSLN]_H1.8_L1, MESO-C[MSLN]_H1.9_L1, MESO-C[MSLN]_H1_L1.1, MESO-C[MSLN]_H1_L1.2, MESO-C[MSLN]_H1_L1.3, MESO-C[MSLN]_H1_L1.4, MESO-C[MSLN]_H1_L1.5, MESO-C[MSLN]_H1_L1.6, MESO-C[MSLN]_H1_L1.7, MESO-C[MSLN]_H1_L1.8, MESO-C[MSLN]_H1_L1.9, MESO-C[MSLN]_H1_L1.10, MESO-C[MSLN]_H1.5_L1.3, MESO-C[MSLN]_H1.6_L1.3, MESO-C[MSLN]_H1.12_L1.9, MESO-C[MSLN]_H1.13_L1.9, MESO-C[MSLN]_H1.3_L1.13, MESO-C[MSLN]_H1.3_L1.14, MESO-C[MSLN]_H1.3_L1.15, MESO-C[MSLN]_H1.3_L1.16, MESO-C[MSLN]_H1.3_L1.17, MESO-C[MSLN]_H1.3_L1.18, MESO-C[MSLN]_H1.3_L1.9, MESO-C[MSLN]_H1.3_L1.5, MESO-C[MSLN]_H1_L1.20, MESO-C[MSLN]_H1.12_L1.20, MESO-C[MSLN]_H1.14_L1.14, MESO-C[MSLN]_H1.15_L1.14, MESO-C[MSLN]_H1.16_L1.14, MESO-C[MSLN]_H1_L1.19_, MESO-C[MSLN]_H1_L1.21, MESO-C[MSLN]_H1_L1.22, MESO-C[MSLN]_H1.12_L1.19, MESO-C[MSLN]_H1.12_L1.21, MESO-C[MSLN]_H1.12_L1.22, and MESO-C[MSLN]_H1.12_L1.9 (FIGS. 15-21).

In one aspect, provided herein are bispecific antibodies that bind to MSLN and CD3, in various formats as outlined below, and generally depicted in FIGS. 22A-22B, and 43A-43K. These bispecific, heterodimeric antibodies include a MSLN binding domain. In certain embodiments, the MSLN binding domain includes the VHCDR1, VHCDR2, VHCDR3, VLCDR1, VLCDR2 and VLCDR3 sequences of a MSLN binding domain selected from the group consisting of those depicted in FIGS. 15-21. In some embodiments, the MSLN binding domain includes the underlined VHCDR1, VHCDR2, VHCDR3, VLCDR1, VLCDR2 and VLCDR3 sequences of a MSLN binding domain selected from those depicted in FIGS. 15-21.

These bispecific heterodimeric antibodies bind MSLN and CD3. Such antibodies include a CD3 binding domain and at least one MSLN binding domain. Any suitable MSLN binding domain can be included in the anti-MSLN×anti-CD3 bispecific antibody. In some embodiments, the anti-MSLN×anti-CD3 bispecific antibody includes one, two, three, four or more MSLN binding domains, including but not limited to those depicted in FIGS. 15-21. In certain embodiments, the anti-MSLN×anti-CD3 antibody includes a MSLN binding domain that includes the VHCDR1, VHCDR2, VHCDR3, VLCDR1, VLCDR2 and VLCDR3 sequences of a MSLN binding domain selected from the group consisting of those depicted in FIGS. 15-21. In some embodiments, the anti-MSLN×anti-CD3 antibody includes a MSLN binding domain that includes the underlined VHCDR1, VHCDR2, VHCDR3, VLCDR1, VLCDR2 and VLCDR3 sequences of a MSLN binding domain selected from the group consisting of those depicted in FIGS. 15-21. In some embodiments, the anti-MSLN×anti-CD3 antibody includes a MSLN binding domain that includes the variable heavy domain and variable light domain of a MSLN binding domain selected from the group consisting of those depicted in FIGS. 15-21. In an exemplary embodiment, the anti-MSLN×anti-CD3 antibody includes an anti-MSLN MESO-C[MSLN]_H1L1 binding domain.

The anti-MSLN×anti-CD3 antibody provided herein can include any suitable CD3 binding domain. In certain embodiments, the anti-MSLN×anti-CD3 antibody includes a CD3 binding domain that includes the VHCDR1, VHCDR2, VHCDR3, VLCDR1, VLCDR2 and VLCDR3 sequences of a CD3 binding domain selected from the group consisting of those depicted in FIGS. 10A-F. In some embodiments, the anti-MSLN×anti-CD3 antibody includes a CD3 binding domain that includes the underlined VHCDR1, VHCDR2, VHCDR3, VLCDR1, VLCDR2 and VLCDR3 sequences of a CD3 binding domain selected from the group consisting of those depicted in FIGS. 10A-10F. In some embodiments, the anti-MSLN×anti-CD3 antibody includes a CD3 binding domain that includes the variable heavy domain and variable light domain of a CD3 binding domain selected from the group consisting of those depicted in FIG. 10A-10F. In some embodiments, the CD3 binding domain is selected from anti-CD3 H1.30_L1.47, anti-CD3 H1.32_L1.47; anti-CD3 H1.89_L1.48; anti-CD3 H1.90_L1.47; Anti-CD3 H1.33_L1.47; and anti-CD3 H1.31_L1.47. As outlined herein, these anti-CD3 antigen binding domains (CD3-ABDs) can be used in scFv formats in either orientation (e.g. from N- to C-terminal, VH-scFv linker-VL or VL-scFv linker-VH).

The antibodies provided herein include different antibody domains. As described herein and known in the art, the antibodies described herein include different domains within the heavy and light chains, which can be overlapping as well. These domains include, but are not limited to, the Fc domain, the CH1 domain, the CH2 domain, the CH3 domain, the hinge domain, the heavy constant domain (CH1-hinge-Fc domain or CH1-hinge-CH2-CH3), the variable heavy domain, the variable light domain, the light constant domain, Fab domains and scFv domains.

As shown herein, there are a number of suitable linkers (for use as either domain linkers or scFv linkers) that can be used to covalently attach the recited domains (e.g., scFvs, Fabs, Fc domains, etc.), including traditional peptide bonds, generated by recombinant techniques. Exemplary linkers to attach domains of the subject antibody to each other are depicted in FIG. 6. In some embodiments, the linker peptide may predominantly include the following amino acid residues: Gly, Ser, Ala, or Thr. The linker peptide should have a length that is adequate to link two molecules in such a way that they assume the correct conformation relative to one another so that they retain the desired activity. In one embodiment, the linker is from about 1 to 50 amino acids in length, preferably about 1 to 30 amino acids in length. In one embodiment, linkers of 1 to 20 amino acids in length may be used, with from about 5 to about 10 amino acids finding use in some embodiments. Useful linkers include glycine-serine polymers, including for example (GS)n, (GSGGS)n (SEQ ID NO: 3), (GGGGS)n (SEQ ID NO: 618), and (GGGS)n (SEQ ID NO: 4), where n is an integer of at least one (and generally from 3 to 4), glycine-alanine polymers, alanine-serine polymers, and other flexible linkers, some of which are shown in FIG. 5 and FIG. 6. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers.

Other linker sequences may include any sequence of any length of CL/CH1 domain but not all residues of CL/CH1 domain; for example the first 5-12 amino acid residues of the CL/CH1 domains. Linkers can be derived from immunoglobulin light chain, for example Cκ or Cλ. Linkers can be derived from immunoglobulin heavy chains of any isotype, including for example Cγ1, Cγ2, Cγ3, Cγ4, Cα1, Cα2, Cδ, Cε, and Cμ. Linker sequences may also be derived from other proteins such as Ig-like proteins (e.g. TCR, FcR, KIR), hinge region-derived sequences, and other natural sequences from other proteins.

In some embodiments, the linker is a "domain linker", used to link any two domains as outlined herein together. For example, in FIG. 22B, there may be a domain linker that attaches the C-terminus of the CH1 domain of the Fab to the N-terminus of the scFv, with another optional domain linker attaching the C-terminus of the scFv to the CH2 domain (although in many embodiments the hinge is used as this domain linker). While any suitable linker can be used, many embodiments utilize a glycine-serine polymer as the domain linker, including for example (GS)n, (GSGGS)n (SEQ ID NO: 3), (GGGGS)n (SEQ ID NO: 618), and (GGGS)n (SEQ ID NO: 4), where n is an integer of at least one (and generally from 3 to 4 to 5) as well as any peptide sequence that allows for recombinant attachment of the two domains with sufficient length and flexibility to allow each domain to retain its biological function. In some cases, and with attention being paid to "strandedness", as outlined below, charged domain linkers, as used in some embodiments of scFv linkers can be used. Exemplary useful domain linkers are depicted in FIG. 6.

With particular reference to the domain linker used to attach the scFv domain to the Fc domain in the "2+1" format, there are several domain linkers that find particular use, including "full hinge C220S variant," "flex half hinge," "charged half hinge 1," and "charged half hinge 2" as shown in FIG. 6.

In some embodiments, the linker is a "scFv linker", used to covalently attach the VH and VL domains as discussed herein. In many cases, the scFv linker is a charged scFv linker, a number of which are shown in FIG. 5. Accordingly, in some embodiments, the antibodies described herein further provide charged scFv linkers, to facilitate the separation in pI between a first and a second monomer. That is, by incorporating a charged scFv linker, either positive or negative (or both, in the case of scaffolds that use scFvs on different monomers), this allows the monomer comprising the charged linker to alter the pI without making further changes in the Fc domains. These charged linkers can be substituted into any scFv containing standard linkers. Again, as will be appreciated by those in the art, charged scFv linkers are used on the correct "strand" or monomer, according to the desired changes in pI. For example, as discussed herein, to make 1+1 Fab-scFv-Fc format heterodimeric antibody, the original pI of the Fv region for each of the desired antigen binding domains are calculated, and one is chosen to make an scFv, and depending on the pI, either positive or negative linkers are chosen.

Charged domain linkers can also be used to increase the pI separation of the monomers of the antibodies described herein as well, and thus those included in FIG. 5 can be used in any embodiment herein where a linker is utilized.

In particular, the formats depicted in FIGS. 22A and 22B are antibodies, usually referred to as "heterodimeric antibodies", meaning that the protein has at least two associated Fc sequences self-assembled into a heterodimeric Fc domain and at least two Fv regions, whether as Fabs or as scFvs.

The MSLN binding domains provided can be included in any useful antibody format including, for example, canonical immunoglobulin, as well as the 1+1 Fab-scFv-Fc and 2+1 Fab2-scFv-Fv formats provided herein. Other useful antibody formats include, but are not limited to, "mAb-Fv," "mAb-scFv," "central-Fv", "one armed scFv-mAb," "scFv-mAb," "dual scFv," and "trident" format antibodies, as disclosed in FIGS. 43A-43K.

In some embodiments, the subject antibody includes one or more of the MSLN ABDs provided herein. In some embodiments, the antibody includes one MSLN ABD. In other embodiments, the antibody includes two MSLN ABDs. In exemplary embodiments, the MSLN ABD includes the variable heavy domain and variable light domain of one of the following MSLN ABDs: MESO-A [MSLN]_H1.1_L1, MESO-B[MSLN]_H0L0, MESO-C [MSLN]_H1L1, MESO-C[MSLN]_H1.1_L1, MESO-C [MSLN]_H1.2L1, MESO-C[MSLN]_H1.3_L1, MESO-C [MSLN]_H1.4_L1, MESO-C[MSLN]_H1.5_L1, MESO-C [MSLN]_H1.6_L1, MESO-C[MSLN]_H1.7_L1, MESO-C [MSLN]_H1.8_L1, MESO-C[MSLN]_H1.9_L1, MESO-C [MSLN]_H1_L1.1, MESO-C[MSLN]_H1_L1.2, MESO-C [MSLN]_H1_L1.3, MESO-C[MSLN]_H1_L1.4, MESO-C [MSLN]_H1_L1.5, MESO-C[MSLN]_H1_L1.6, MESO-C [MSLN]_H1_L1.7, MESO-C[MSLN]_H1_L1.8, MESO-C [MSLN]_H1_L1.9, MESO-C[MSLN]_H1_L1.10, MESO-C[MSLN]_H1.5_L1.3, MESO-C[MSLN]_H1.6_L1.3, MESO-C[MSLN]_H1.12_L1.9, MESO-C[MSLN]_H1.13_L1.9, MESO-C[MSLN]_H1.3_L1.13, MESO-C[MSLN]_H1.3_L1.14, MESO-C[MSLN]_H1.3_L1.15, MESO-C[MSLN]_H1.3_L1.16, MESO-C[MSLN]_H1.3_L1.17, MESO-C[MSLN]_H1.3_L1.18, MESO-C[MSLN]_H1.3_L1.9, MESO-C[MSLN]_H1.3_L1.5, MESO-C[MSLN]_H1_L1.20, MESO-C[MSLN]_H1.12_L1.20, MESO-C[MSLN]_H1.14_L1.14, MESO-C[MSLN]_H1.15_L1.14, MESO-C[MSLN]_H1.16_L1.14, MESO-C[MSLN]_H1_L1.19, MESO-C[MSLN]_H1_L1.21, MESO-C[MSLN]_H1_L1.22, MESO-C[MSLN]_H1.12_L1.19, MESO-C[MSLN]_H1.12_L1.21, MESO-C[MSLN]_H1.12_L1.22, and MESO-C[MSLN]_H1.12_L1.9 (FIGS. 15-21).

In an exemplary embodiment, the antibody is a bispecific antibody that includes one or two MSLN ABDs, including any of the MSLN ABDs provided herein. Bispecific antibody that include such MSLN ABDs include, for example, 1+1 Fab-scFv-Fc and 2+1 Fab₂-scFv-Fc bispecifics format antibodies. In exemplary embodiments, the MSLN ABD is one of the following MSLN ABDs: MESO-A[MSLN]_H1.1_L1, MESO-B[MSLN]_H0L0, MESO-C[MSLN]_H1L1, MESO-C[MSLN]_H1.1_L1, MESO-C[MSLN]_H1.2L1, MESO-C[MSLN]_H1.3_L1, MESO-C[MSLN]_H1.4_L1, MESO-C[MSLN]_H1.5_L1, MESO-C[MSLN]_H1.6_L1, MESO-C[MSLN]_H1.7_L1, MESO-C[MSLN]_H1.8_L1, MESO-C[MSLN]_H1.9_L1, MESO-C[MSLN]_H1_L1.1, MESO-C[MSLN]_H1_L1.2, MESO-C[MSLN]_H1_L1.3, MESO-C[MSLN]_H1_L1.4, MESO-C[MSLN]_H1_L1.5, MESO-C[MSLN]_H1_L1.6, MESO-C[MSLN]_H1_L1.7, MESO-C[MSLN]_H1_L1.8, MESO-C[MSLN]_H1_L1.9, MESO-C[MSLN]_H1_L1.10, MESO-C[MSLN]_H1.5_L1.3, MESO-C[MSLN]_H1.6_L1.3, MESO-C[MSLN]_H1.12_L1.9, MESO-C[MSLN]_H1.13_L1.9, MESO-C[MSLN]_H1.3_L1.13, MESO-C[MSLN]_H1.3_L1.14, MESO-C[MSLN]_H1.3_L1.15, MESO-C[MSLN]_H1.3_L1.16, MESO-C[MSLN]_H1.3_L1.17, MESO-C[MSLN]_H1.3_L1.18, MESO-C[MSLN]_H1.3_L1.9, MESO-C[MSLN]_H1.3_L1.5, MESO-C[MSLN]_H1_L1.20, MESO-C[MSLN]_H1.12_L1.20, MESO-C[MSLN]_H1.14_L1.14, MESO-C[MSLN]_H1.15_L1.14, MESO-C[MSLN]_H1.16_L1.14, MESO-C[MSLN]_H1_L1.19, MESO-C[MSLN]_H1_L1.21, MESO-C[MSLN]_H1_L1.22, MESO-C[MSLN]_H1.12_L1.19, MESO-C[MSLN]_H1.12_L1.21, MESO-C[MSLN]_H1.12_L1.22, and MESO-C[MSLN]_H1.12_L1.9 (FIGS. 15-21). In exemplary embodiments, the MSLN binding domains is a Fab. In some embodiments, such bispecific antibodies are heterodimeric bispecific antibodies that include any of the heterodimerization skew variants, pI variants and/or ablation variants described herein.

A. Chimeric and Humanized Antibodies

In certain embodiments, the antibodies described herein comprise a heavy chain variable region from a particular germline heavy chain immunoglobulin gene and/or a light chain variable region from a particular germline light chain immunoglobulin gene. For example, such antibodies may comprise or consist of a human antibody comprising heavy or light chain variable regions that are "the product of" or "derived from" a particular germline sequence. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody (using the methods outlined herein). A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a humanized antibody typically is at least 90% identical in amino acids sequence to an amino acid sequence encoded by a human germline immunoglobulin gene and contains amino acid residues that identify the antibody as being derived from human sequences when compared to the germline immunoglobulin amino acid sequences of other species (e.g., murine germline sequences). In certain cases, a humanized antibody may be at least 95, 96, 97, 98 or 99%, or even at least 96%, 97%, 98%, or 99% identical in amino acid sequence to the amino acid sequence encoded by the germline immunoglobulin gene. Typically, a humanized antibody derived from a particular human germline sequence will display no more than 10-20 amino acid differences from the amino acid sequence encoded by the human germline immunoglobulin gene (prior to the introduction of any skew, pI and ablation variants herein; that is, the number of variants is generally low, prior to the introduction of the variants described herein). In certain cases, the humanized antibody may display no more than 5, or even no more than 4, 3, 2, or 1 amino acid difference from the amino acid sequence encoded by the germline immunoglobulin gene (again, prior to the introduction of any skew, pI and ablation variants herein; that is, the number of variants is generally low, prior to the introduction of the variants described herein).

In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272 (16): 10678-10684; Rosok et al., 1996, J. Biol. Chem. 271 (37): 22611-22618; Rader et al., 1998, Proc. Natl. Acad. Sci. USA 95:8910-8915; Krauss et al., 2003, Protein Engineering 16 (10): 753-759, all entirely incorporated by reference. Other humanization methods may involve the grafting of only parts of the CDRs, including but not limited to methods described in U.S. Ser. No. 09/810,510; Tan et al., 2002, J. Immunol. 169:1119-1125; De Pascalis et al., 2002, J. Immunol. 169:3076-3084, all entirely incorporated by reference.

B. Heterodimeric Antibodies

In exemplary embodiments, the bispecific antibodies provided herein are heterodimeric bispecific antibodies that include two variant Fc domain sequences. Such variant Fc domains include amino acid modifications to facilitate the self-assembly and/or purification of the heterodimeric antibodies.

An ongoing problem in antibody technologies is the desire for "bispecific" antibodies that bind to two different antigens simultaneously, in general thus allowing the different antigens to be brought into proximity and resulting in new functionalities and new therapies. In general, these antibodies are made by including genes for each heavy and light chain into the host cells. This generally results in the formation of the desired heterodimer (A-B), as well as the two homodimers (A-A and B-B (not including the light chain heterodimeric issues)). However, a major obstacle in the formation of bispecific antibodies is the difficulty in biasing the formation of the desired heterodimeric antibody over the formation of the homodimers and/or purifying the heterodimeric antibody away from the homodimers.

There are a number of mechanisms that can be used to generate the subject heterodimeric antibodies. In addition, as will be appreciated by those in the art, these different mechanisms can be combined to ensure high heterodimerization. Amino acid modifications that facilitate the production and purification of heterodimers are collectively referred to generally as "heterodimerization variants." As discussed below, heterodimerization variants include "skew" variants (e.g., the "knobs and holes" and the "charge pairs" variants described below) as well as "pI variants," which allow purification of heterodimers from homodimers. As is generally described in U.S. Pat. No. 9,605,084, hereby incorporated by reference in its entirety and specifically as below for the discussion of heterodimerization variants, useful mechanisms for heterodimerization include "knobs and holes" ("KIH") as described in U.S. Pat. No. 9,605,084, "electrostatic steering" or "charge pairs" as described in U.S. Pat. No. 9,605,084, pI variants as described in U.S. Pat. No. 9,605,084, and general additional Fc variants as outlined in U.S. Pat. No. 9,605,084 and below.

Heterodimerization variants that are useful for the formation and purification of the subject heterodimeric antibody (e.g., bispecific antibodies) are further discussed in detailed below.

1. Skew Variants

In some embodiments, the heterodimeric antibody includes skew variants which are one or more amino acid modifications in a first Fc domain (A) and/or a second Fc domain (B) that favor the formation of Fc heterodimers (Fc dimers that include the first and the second Fc domain; (A-B) over Fc homodimers (Fc dimers that include two of the first Fc domain or two of the second Fc domain; A-A or B-B). Suitable skew variants are included in the FIG. 29 of US Publ. App. No. 2016/0355608, hereby incorporated by reference in its entirety and specifically for its disclosure of skew variants, as well as in FIGS. 1A-1E and FIG. 4.

One mechanism is generally referred to in the art as "knobs and holes", referring to amino acid engineering that creates steric influences to favor heterodimeric formation and disfavor homodimeric formation can also optionally be used; this is sometimes referred to as "knobs and holes", as described in U.S. Ser. No. 61/596,846, Ridgway et al., Protein Engineering 9(7):617 (1996); Atwell et al., J. Mol. Biol. 1997 270:26; U.S. Pat. No. 8,216,805, all of which are hereby incorporated by reference in their entirety. The Figures identify a number of "monomer A-monomer B" pairs that rely on "knobs and holes". In addition, as described in Merchant et al., Nature Biotech. 16:677 (1998), these "knobs and hole" mutations can be combined with disulfide bonds to skew formation to heterodimerization.

An additional mechanism that finds use in the generation of heterodimers is sometimes referred to as "electrostatic steering" as described in Gunasekaran et al., J. Biol. Chem. 285(25):19637 (2010), hereby incorporated by reference in its entirety. This is sometimes referred to herein as "charge pairs". In this embodiment, electrostatics are used to skew the formation towards heterodimerization. As those in the art will appreciate, these may also have an effect on pI, and thus on purification, and thus could in some cases also be considered pI variants. However, as these were generated to force heterodimerization and were not used as purification tools, they are classified as "steric variants". These include, but are not limited to, D221E/P228E/L368E paired with D221R/P228R/K409R (e.g. these are "monomer corresponding sets) and C220E/P228E/368E paired with C220R/E224R/P228R/K409R.

In some embodiments, the skew variants advantageously and simultaneously favor heterodimerization based on both the "knobs and holes" mechanism as well as the "electrostatic steering" mechanism. In some embodiments, the heterodimeric antibody includes one or more sets of such heterodimerization skew variants. These variants come in "pairs" of "sets". That is, one set of the pair is incorporated into the first monomer and the other set of the pair is incorporated into the second monomer. It should be noted that these sets do not necessarily behave as "knobs in holes" variants, with a one-to-one correspondence between a residue on one monomer and a residue on the other. That is, these pairs of sets may instead form an interface between the two monomers that encourages heterodimer formation and discourages homodimer formation, allowing the percentage of heterodimers that spontaneously form under biological conditions to be over 90%, rather than the expected 50% (25% homodimer A/A: 50% heterodimer A/B: 25% homodimer B/B). Exemplary heterodimerization "skew" variants are depicted in FIG. 4. In exemplary embodiments, the heterodimeric antibody includes a S364K/E357Q: L368D/K370S; L368D/K370S: S364K; L368E/K370S: S364K; T411T/E360E/Q362E: D401K; L368D/K370S: S364K/E357L; K370S: S364K/E357Q; or a T366S/L368A/Y407V: T366W (optionally including a bridging disulfide, T366S/L368A/Y407V/Y349C: T366W/S354C) "skew" variant amino acid substitution set. In an exemplary embodiment, the heterodimeric antibody includes a "S364K/E357Q: L368D/K370S" amino acid substitution set. In terms of nomenclature, the pair "S364K/E357Q: L368D/K370S" means that one of the monomers includes an Fc domain that includes the amino acid substitutions S364K and E357Q and the other monomer includes an Fc domain that includes the amino acid substitutions L368D and K370S; as above, the "strandedness" of these pairs depends on the starting pI.

In some embodiments, the skew variants provided herein can be optionally and independently incorporated with any other modifications, including, but not limited to, other skew variants (see, e.g., in FIG. 37 of US Publ. App. No. 2012/0149876, herein incorporated by reference, particularly for its disclosure of skew variants), pI variants, isotypic variants, FcRn variants, ablation variants, etc. into one or both of the first and second Fc domains of the heterodimeric antibody. Further, individual modifications can also independently and optionally be included or excluded from the subject the heterodimeric antibody.

Additional monomer A and monomer B variants that can be combined with other variants, optionally and independently in any amount, such as pI variants outlined herein or other steric variants that are shown in FIG. 37 of US 2012/0149876, the figure and legend and SEQ ID NOs of which are incorporated expressly by reference herein.

In some embodiments, the steric variants outlined herein can be optionally and independently incorporated with any pI variant (or other variants such as Fc variants, FcRn variants, etc.) into one or both monomers, and can be independently and optionally included or excluded from the proteins of the antibodies described herein.

A list of suitable skew variants is found in FIGS. 1A-1E, with FIG. 4 showing some pairs of particular utility in many embodiments. Of particular use in many embodiments are the pairs of sets including, but not limited to, S364K/E357Q: L368D/K370S; L368D/K370S: S364K; L368E/K370S: S364K; T411T/E360E/Q362E: D401K; L368D/K370S:

S364K/E357L and K370S: S364K/E357Q. In terms of nomenclature, the pair "S364K/E357Q: L368D/K370S" means that one of the monomers has the double variant set S364K/E357Q and the other has the double variant set L368D/K370S.

2. pI (Isoelectric point) Variants for Heterodimers

In some embodiments, the heterodimeric antibody includes purification variants that advantageously allow for the separation of heterodimeric antibody (e.g., anti-MSLNx anti-CD3 bispecific antibody) from homodimeric proteins.

There are several basic mechanisms that can lead to ease of purifying heterodimeric antibodies. For example, modifications to one or both of the antibody heavy chain monomers A and B such that each monomer has a different pI allows for the isoelectric purification of heterodimeric A-B antibody from monomeric A-A and B-B proteins. Alternatively, some scaffold formats, such as the "1+1 Fab-scFv-Fc" format and the "2+1 Fab₂-scFv-Fc" format, also allows separation on the basis of size. As described above, it is also possible to "skew" the formation of heterodimers over homodimers using skew variants. Thus, a combination of heterodimerization skew variants and pI variants find particular use in the heterodimeric antibodies provided herein.

Additionally, as more fully outlined below, depending on the format of the heterodimeric antibody, pI variants either contained within the constant region and/or Fc domains of a monomer, and/or domain linkers can be used. In some embodiments, the heterodimeric antibody includes additional modifications for alternative functionalities that can also create pI changes, such as Fc, FcRn and KO variants.

In some embodiments, the subject heterodimeric antibodies provided herein include at least one monomer with one or more modifications that alter the pI of the monomer (i.e., a "pI variant"). In general, as will be appreciated by those in the art, there are two general categories of pI variants: those that increase the pI of the protein (basic changes) and those that decrease the pI of the protein (acidic changes). As described herein, all combinations of these variants can be done: one monomer may be wild type, or a variant that does not display a significantly different pI from wild-type, and the other can be either more basic or more acidic. Alternatively, each monomer is changed, one to more basic and one to more acidic.

Depending on the format of the heterodimer antibody, pI variants can be either contained within the constant and/or Fc domains of a monomer, or charged linkers, either domain linkers or scFv linkers, can be used. That is, antibody formats that utilize scFv(s) such as "1+1 Fab-scFv-Fc", format can include charged scFv linkers (either positive or negative), that give a further pI boost for purification purposes. As will be appreciated by those in the art, some 1+1 Fab-scFv-Fc formats are useful with just charged scFv linkers and no additional pI adjustments, although the antibodies described herein do provide pI variants that are on one or both of the monomers, and/or charged domain linkers as well. In addition, additional amino acid engineering for alternative functionalities may also confer pI changes, such as Fc, FcRn and KO variants.

In subject heterodimeric antibodies that utilizes pI as a separation mechanism to allow the purification of heterodimeric proteins, amino acid variants are introduced into one or both of the monomer polypeptides. That is, the pI of one of the monomers (referred to herein for simplicity as "monomer A") can be engineered away from monomer B, or both monomer A and B change be changed, with the pI of monomer A increasing and the pI of monomer B decreasing. As is outlined more fully below, the pI changes of either or both monomers can be done by removing or adding a charged residue (e.g., a neutral amino acid is replaced by a positively or negatively charged amino acid residue, e.g., glycine to glutamic acid), changing a charged residue from positive or negative to the opposite charge (aspartic acid to lysine) or changing a charged residue to a neutral residue (e.g., loss of a charge; lysine to serine.). A number of these variants are shown in the FIGS. 3 and 4.

Thus, in some embodiments, the subject heterodimeric antibody includes amino acid modifications in the constant regions that alter the isoelectric point (pI) of at least one, if not both, of the monomers of a dimeric protein to form "pI antibodies") by incorporating amino acid substitutions ("pI variants" or "pI substitutions") into one or both of the monomers. As shown herein, the separation of the heterodimers from the two homodimers can be accomplished if the pIs of the two monomers differ by as little as 0.1 pH unit, with 0.2, 0.3, 0.4 and 0.5 or greater all finding use in the antibodies described herein.

As will be appreciated by those in the art, the number of pI variants to be included on each or both monomer(s) to get good separation will depend in part on the starting pI of the components, for example in the 1+1 Fab-scFv-Fc and 2+1 Fab₂-scFv-Fc formats, the starting pI of the scFv and Fab(s) of interest. That is, to determine which monomer to engineer or in which "direction" (e.g., more positive or more negative), the Fv sequences of the two target antigens are calculated and a decision is made from there. As is known in the art, different Fvs will have different starting pIs which are exploited in the antibodies described herein. In general, as outlined herein, the pIs are engineered to result in a total pI difference of each monomer of at least about 0.1 logs, with 0.2 to 0.5 being preferred as outlined herein.

In the case where pI variants are used to achieve heterodimerization, by using the constant region(s) of the heavy chain(s), a more modular approach to designing and purifying bispecific proteins, including antibodies, is provided. Thus, in some embodiments, heterodimerization variants (including skew and pI heterodimerization variants) are not included in the variable regions, such that each individual antibody must be engineered. In addition, in some embodiments, the possibility of immunogenicity resulting from the pI variants is significantly reduced by importing pI variants from different IgG isotypes such that pI is changed without introducing significant immunogenicity. Thus, an additional problem to be solved is the elucidation of low pI constant domains with high human sequence content, e.g., the minimization or avoidance of non-human residues at any particular position. Alternatively or in addition to isotypic substitutions, the possibility of immunogenicity resulting from the pI variants is significantly reduced by utilizing isosteric substitutions (e.g. Asn to Asp; and Gln to Glu).

As discussed below, a side benefit that can occur with this pI engineering is also the extension of serum half-life and increased FcRn binding. That is, as described in US Publ. App. No. US 2012/0028304 (incorporated by reference in its entirety), lowering the pI of antibody constant domains (including those found in antibodies and Fc fusions) can lead to longer serum retention in vivo. These pI variants for increased serum half-life also facilitate pI changes for purification.

In addition, it should be noted that the pI variants give an additional benefit for the analytics and quality control process of bispecific antibodies, as the ability to either eliminate, minimize and distinguish when homodimers are present is significant. Similarly, the ability to reliably test the reproducibility of the heterodimeric antibody production is important.

In general, embodiments of particular use rely on sets of variants that include skew variants, which encourage heterodimerization formation over homodimerization formation, coupled with pI variants, which increase the pI difference between the two monomers to facilitate purification of heterodimers away from homodimers.

Exemplary combinations of pI variants are shown in FIGS. 4 and 5, and FIG. 30 of US Publ. App. No. 2016/0355608, all of which are herein incorporated by reference in its entirety and specifically for the disclosure of pI variants. Preferred combinations of pI variants are shown in FIGS. 1 and 2. As outlined herein and shown in the figures, these changes are shown relative to IgG1, but all isotypes can be altered this way, as well as isotype hybrids. In the case where the heavy chain constant domain is from IgG2-4, R133E and R133Q can also be used.

In one embodiment, a preferred combination of pI variants has one monomer (the negative Fab side) comprising 208D/295E/384D/418E/421D variants (N208D/Q295E/N384D/Q418E/N421D when relative to human IgG1) and a second monomer (the positive scFv side) comprising a positively charged scFv linker, including (GKPGS)$_4$ (SEQ ID NO: 1). However, as will be appreciated by those in the art, the first monomer includes a CH1 domain, including position 208. Accordingly, in constructs that do not include a CH1 domain (for example for antibodies that do not utilize a CH1 domain on one of the domains), a preferred negative pI variant Fc set includes 295E/384D/418E/421D variants (Q295E/N384D/Q418E/N421D when relative to human IgG1).

Accordingly, in some embodiments, one monomer has a set of substitutions from FIG. 2 and the other monomer has a charged linker (either in the form of a charged scFv linker because that monomer comprises an scFv or a charged domain linker, as the format dictates, which can be selected from those depicted in FIG. 5).

In some embodiments, modifications are made in the hinge of the Fc domain, including positions 216, 217, 218, 219, 220, 221, 222, 223, 224, 225, 226, 227, 228, 229, and 230 based on EU numbering. Thus, pI mutations and particularly substitutions can be made in one or more of positions 216-230, with 1, 2, 3, 4 or 5 mutations finding use. Again, all possible combinations are contemplated, alone or with other pI variants in other domains.

Specific substitutions that find use in lowering the pI of hinge domains include, but are not limited to, a deletion at position 221, a non-native valine or threonine at position 222, a deletion at position 223, a non-native glutamic acid at position 224, a deletion at position 225, a deletion at position 235 and a deletion or a non-native alanine at position 236. In some cases, only pI substitutions are done in the hinge domain, and in others, these substitution(s) are added to other pI variants in other domains in any combination.

In some embodiments, mutations can be made in the CH2 region, including positions 233, 234, 235, 236, 274, 296, 300, 309, 320, 322, 326, 327, 334 and 339, based on EU numbering. It should be noted that changes in 233-236 can be made to increase effector function (along with 327A) in the IgG2 backbone. Again, all possible combinations of these 14 positions can be made; e.g., =may include a variant Fc domain with 1, 2, 3, 4, 5, 6, 7, 8, 9 or 10 CH2 pI substitutions.

Specific substitutions that find use in lowering the pI of CH2 domains include, but are not limited to, a non-native glutamine or glutamic acid at position 274, a non-native phenylalanine at position 296, a non-native phenylalanine at position 300, a non-native valine at position 309, a non-native glutamic acid at position 320, a non-native glutamic acid at position 322, a non-native glutamic acid at position 326, a non-native glycine at position 327, a non-native glutamic acid at position 334, a non-native threonine at position 339, and all possible combinations within CH2 and with other domains.

In this embodiment, the modifications can be independently and optionally selected from position 355, 359, 362, 384, 389,392, 397, 418, 419, 444 and 447 (EU numbering) of the CH3 region. Specific substitutions that find use in lowering the pI of CH3 domains include, but are not limited to, a non-native glutamine or glutamic acid at position 355, a non-native serine at position 384, a non-native asparagine or glutamic acid at position 392, a non-native methionine at position 397, a non-native glutamic acid at position 419, a non-native glutamic acid at position 359, a non-native glutamic acid at position 362, a non-native glutamic acid at position 389, a non-native glutamic acid at position 418, a non-native glutamic acid at position 444, and a deletion or non-native aspartic acid at position 447.

In general, as will be appreciated by those in the art, there are two general categories of pI variants: those that increase the pI of the protein (basic changes) and those that decrease the pI of the protein (acidic changes). As described herein, all combinations of these variants can be done: one monomer may be wild type, or a variant that does not display a significantly different pI from wild-type, and the other can be either more basic or more acidic. Alternatively, each monomer is changed, one to more basic and one to more acidic.

Preferred combinations of pI variants are shown in FIG. 4. As outlined herein and shown in the figures, these changes are shown relative to IgG1, but all isotypes can be altered this way, as well as isotype hybrids. In the case where the heavy chain constant domain is from IgG2-4, R133E and R133Q can also be used.

In one embodiment, for example in the FIGS. 22A and 22B formats, a preferred combination of pI variants has one monomer (the negative Fab side) comprising 208D/295E/384D/418E/421D variants (N208D/Q295E/N384D/Q418E/N421D when relative to human IgG1) and a second monomer (the positive scFv side) comprising a positively charged scFv linker, including (GKPGS)$_4$ (SEQ ID NO: 1). However, as will be appreciated by those in the art, the first monomer includes a CH1 domain, including position 208. Accordingly, in constructs that do not include a CH1 domain (for example for antibodies that do not utilize a CH1 domain on one of the domains, for example in a dual scFv format or a "one armed" format such as those depicted in FIG. 43B, 43C, or 43D), a preferred negative pI variant Fc set includes 295E/384D/418E/421D variants (Q295E/N384D/Q418E/N421D when relative to human IgG1).

Accordingly, in some embodiments, one monomer has a set of substitutions from FIG. 4 and the other monomer has a charged linker (either in the form of a charged scFv linker because that monomer comprises an scFv or a charged domain linker, as the format dictates, which can be selected from those depicted in FIG. 5).

3. Isotypic Variants

In addition, many embodiments of the antibodies described herein rely on the "importation" of pI amino acids at particular positions from one IgG isotype into another, thus reducing or eliminating the possibility of unwanted immunogenicity being introduced into the variants. A number of these are shown in FIG. 21 of US Publ. 2014/0370013, hereby incorporated by reference. That is, IgG1 is a common isotype for therapeutic antibodies for a variety of reasons, including high effector function. However, the heavy constant region of IgG1 has a higher pI than that of IgG2 (8.10 versus 7.31). By introducing IgG2 residues at particular positions into the IgG1 backbone, the pI of the resulting monomer is lowered (or increased) and additionally exhibits longer serum half-life. For example, IgG1 has a glycine (pI 5.97) at position 137, and IgG2 has a glutamic acid (pI 3.22); importing the glutamic acid will affect the pI of the resulting protein. As is described below, a number of amino acid substitutions are generally required to significant affect the pI of the variant antibody. However, it should be noted as discussed below that even changes in IgG2 molecules allow for increased serum half-life.

In other embodiments, non-isotypic amino acid changes are made, either to reduce the overall charge state of the resulting protein (e.g. by changing a higher pI amino acid to a lower pI amino acid), or to allow accommodations in structure for stability, etc. as is more further described below.

In addition, by pI engineering both the heavy and light constant domains, significant changes in each monomer of the heterodimer can be seen. As discussed herein, having the pIs of the two monomers differ by at least 0.5 can allow separation by ion exchange chromatography or isoelectric focusing, or other methods sensitive to isoelectric point.

4. Calculating pI

The pI of each monomer can depend on the pI of the variant heavy chain constant domain and the pI of the total monomer, including the variant heavy chain constant domain and the fusion partner. Thus, in some embodiments, the change in pI is calculated on the basis of the variant heavy chain constant domain, using the chart in the FIG. 19 of US Pub. 2014/0370013. As discussed herein, which monomer to engineer is generally decided by the inherent pI of the Fv and scaffold regions. Alternatively, the pI of each monomer can be compared.

5. pI Variants that Also Confer Better FcRn In Vivo Binding

In the case where the pI variant decreases the pI of the monomer, they can have the added benefit of improving serum retention in vivo.

Although still under examination, Fc regions are believed to have longer half-lives in vivo, because binding to FcRn at pH 6 in an endosome sequesters the Fc (Ghetie and Ward, 1997 Immunol Today. 18(12): 592-598, entirely incorporated by reference). The endosomal compartment then recycles the Fc to the cell surface. Once the compartment opens to the extracellular space, the higher pH, ~7.4, induces the release of Fc back into the blood. In mice, Dall'Acqua et al. showed that Fc mutants with increased FcRn binding at pH 6 and pH 7.4 actually had reduced serum concentrations and the same half life as wild-type Fc (Dall'Acqua et al. 2002, J. Immunol. 169:5171-5180, entirely incorporated by reference). The increased affinity of Fc for FcRn at pH 7.4 is thought to forbid the release of the Fc back into the blood. Therefore, the Fc mutations that will increase Fc's half-life in vivo will ideally increase FcRn binding at the lower pH while still allowing release of Fc at higher pH. The amino acid histidine changes its charge state in the pH range of 6.0 to 7.4. Therefore, it is not surprising to find His residues at important positions in the Fc/FcRn complex.

Recently it has been suggested that antibodies with variable regions that have lower isoelectric points may also have longer serum half-lives (Igawa et al., 2010 PEDS. 23(5): 385-392, entirely incorporated by reference). However, the mechanism of this is still poorly understood. Moreover, variable regions differ from antibody to antibody. Constant region variants with reduced pI and extended half-life would provide a more modular approach to improving the pharmacokinetic properties of antibodies, as described herein.

C. Additional Fc Variants for Additional Functionality

In addition to the heterodimerization variants discussed above, there are a number of useful Fc amino acid modification that can be made for a variety of reasons, including, but not limited to, altering binding to one or more FcγR receptors, altered binding to FcRn receptors, etc, as discussed below.

Accordingly, the antibodies provided herein (heterodimeric, as well as homodimeric) can include such amino acid modifications with or without the heterodimerization variants outlined herein (e.g., the pI variants and steric variants). Each set of variants can be independently and optionally included or excluded from any particular heterodimeric protein.

1. FcγR Variants

Accordingly, there are a number of useful Fc substitutions that can be made to alter binding to one or more of the FcγR receptors. In certain embodiments, the subject antibody includes modifications that alter the binding to one or more FcγR receptors (i.e., "FcγR variants"). Substitutions that result in increased binding as well as decreased binding can be useful. For example, it is known that increased binding to FcγRIIIa generally results in increased ADCC (antibody dependent cell-mediated cytotoxicity; the cell-mediated reaction wherein nonspecific cytotoxic cells that express FcγRs recognize bound antibody on a target cell and subsequently cause lysis of the target cell). Similarly, decreased binding to FcγRIIb (an inhibitory receptor) can be beneficial as well in some circumstances. Amino acid substitutions that find use in the antibodies described herein include those listed in U.S. Pat. No. 8,188,321 (particularly FIGS. 41) and U.S. Pat. No. 8,084,582, and US Publ. application Nos. 20060235208 and 20070148170, all of which are expressly incorporated herein by reference in their entirety and specifically for the variants disclosed therein. Particular variants that find use include, but are not limited to, 236A, 239D, 239E, 332E, 332D, 239D/332E, 267D, 267E, 328F, 267E/328F, 236A/332E, 239D/332E/330Y, 239D/332E/330L, 243A, 243L, 264A, 264V and 299T.

In addition, there are additional Fc substitutions that find use in increased binding to the FcRn receptor and increased serum half-life, as specifically disclosed in U.S. Ser. No. 12/341,769, hereby incorporated by reference in its entirety, including, but not limited to, 434S, 434A, 428L, 308F, 259I, 428L/434S, 259I/308F, 436I/428L, 436I or V/434S, 436V/428L and 259I/308F/428L. Such modification may be included in one or both Fc domains of the subject antibody.

2. Ablation Variants

Similarly, another category of functional variants are "FcγR ablation variants" or "Fc knock out (FcKO or KO)" variants. In these embodiments, for some therapeutic applications, it is desirable to reduce or remove the normal binding of the Fc domain to one or more or all of the Fcγ receptors (e.g. FcγR1, FcγRIIa, FcγRIIb, FcγRIIIa, etc.) to avoid additional mechanisms of action. That is, for example, in many embodiments, particularly in the use of bispecific antibodies that bind CD3 monovalently it is generally desirable to ablate FcγRIIIa binding to eliminate or significantly reduce ADCC activity, wherein one of the Fc domains comprises one or more Fcγ receptor ablation variants. These ablation variants are depicted in FIG. 14, and each can be independently and optionally included or excluded, with preferred aspects utilizing ablation variants selected from the group consisting of G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G and E233P/L234V/L235A/G236del. It should be noted that the ablation variants referenced herein ablate FcγR binding but generally not FcRn binding.

As is known in the art, the Fc domain of human IgG1 has the highest binding to the Fcγ receptors, and thus ablation variants can be used when the constant domain (or Fc domain) in the backbone of the heterodimeric antibody is IgG1. Alternatively, or in addition to ablation variants in an IgG1 background, mutations at the glycosylation position 297 (generally to A or S) can significantly ablate binding to FcγRIIIa, for example. Human IgG2 and IgG4 have naturally reduced binding to the Fcγ receptors, and thus those backbones can be used with or without the ablation variants.

D. Combination of Heterodimeric and Fc Variants

As will be appreciated by those in the art, all of the recited heterodimerization variants (including skew and/or pI variants) can be optionally and independently combined in any way, as long as they retain their "strandedness" or "monomer partition". In some embodiments, the heterodimeric antibodies provided herein include the combination of heterodimerizaition skew variants, isosteric pI substitutions and FcKO variants as depicted in FIG. 4. In addition, all of these variants can be combined into any of the heterodimerization formats.

In the case of pI variants, while embodiments finding particular use are shown in the Figures, other combinations can be generated, following the basic rule of altering the pI difference between two monomers to facilitate purification.

In addition, any of the heterodimerization variants, skew and pI, are also independently and optionally combined with Fc ablation variants, Fc variants, FcRn variants, as generally outlined herein.

Exemplary combination of variants that are included in some embodiments of the heterodimeric 1+1 Fab-scFv-Fc and 2+1 Fab₂-scFv-Fc format antibodies are included in FIG. 4. In certain embodiments, the antibody is a heterodimeric 1+1 Fab-scFv-Fc or 2+1 Fab₂-scFv-Fc format antibody as shown in FIGS. 15A and 15B.

E. Anti-MSLN×Anti-CD3 Bispecific Antibodies

In another aspect, provided herein are anti-MSLN×anti-CD3 (also referred to herein as "αMSLN×αCD3") bispecific antibodies. Such antibodies include at least one MSLN binding domain and at least one CD3 binding domain. In some embodiments, bispecific αMSLN×αCD3 provided herein immune responses selectively in tumor sites that express MSLN.

Note that unless specified herein, the order of the antigen list in the name does not confer structure; that is a MSLN×CD3 1+1 Fab-scFv-Fc antibody can have the scFv bind to MSLN or CD3, although in some cases, the order specifies structure as indicated.

As is more fully outlined herein, these combinations of ABDs can be in a variety of formats, as outlined below, generally in combinations where one ABD is in a Fab format and the other is in an scFv format. Exemplary formats that are used in the bispecific antibodies provided herein include the 1+1 Fab-scFv-Fc and 2+1 Fab2-scFv-Fv formats (see, e.g., FIGS. 22A and 22B). Other useful antibody formats include, but are not limited to, "mAb-Fv," "mAb-scFv," "central-Fv", "one armed scFv-mAb," "scFv-mAb," "dual scFv," and "trident" format antibodies, as disclosed in FIG. 43A-43K.

In addition, in general, one of the ABDs comprises a scFv as outlined herein, in an orientation from N- to C-terminus of VH-scFv linker-VL or VL-scFv linker-VH. One or both of the other ABDs, according to the format, generally is a Fab, comprising a VH domain on one protein chain (generally as a component of a heavy chain) and a VL on another protein chain (generally as a component of a light chain).

As will be appreciated by those in the art, any set of 6 CDRs or VH and VL domains can be in the scFv format or in the Fab format, which is then added to the heavy and light constant domains, where the heavy constant domains comprise variants (including within the CH1 domain as well as the Fc domain). The scFv sequences contained in the sequence listing utilize a particular charged linker, but as outlined herein, uncharged or other charged linkers can be used, including those depicted in FIG. 5 and FIG. 6.

In addition, as discussed above, the numbering used in the Sequence Listing for the identification of the CDRs is Kabat, however, different numbering can be used, which will change the amino acid sequences of the CDRs as shown in Table 2.

For all of the variable heavy and light domains listed herein, further variants can be made. As outlined herein, in some embodiments the set of 6 CDRs can have from 0, 1, 2, 3, 4 or 5 amino acid modifications (with amino acid substitutions finding particular use), as well as changes in the framework regions of the variable heavy and light domains, as long as the frameworks (excluding the CDRs) retain at least about 80, 85 or 90% identity to a human germline sequence selected from those listed in FIG. 1 of U.S. Pat. No. 7,657,380, which Figure and Legend is incorporated by reference in its entirety herein. Thus, for example, the identical CDRs as described herein can be combined with different framework sequences from human germline sequences, as long as the framework regions retain at least 80, 85 or 90% identity to a human germline sequence selected from those listed in FIG. 1 of U.S. Pat. No. 7,657,380. Alternatively, the CDRs can have amino acid modifications (e.g., from 1, 2, 3, 4 or 5 amino acid modifications in the set of CDRs (that is, the CDRs can be modified as long as the total number of changes in the set of 6 CDRs is less than 6 amino acid modifications, with any combination of CDRs being changed; e.g., there may be one change in vlCDR1, two in vhCDR2, none in vhCDR3, etc.)), as well as having framework region changes, as long as the framework regions retain at least 80, 85 or 90% identity to a human germline sequence selected from those listed in FIG. 1 of U.S. Pat. No. 7,657,380.

The anti-MSLN×anti-CD3 bispecific antibody can include any suitable CD3 ABD, including those described herein (see, e.g., FIGS. 10A-10F). In some embodiments, the CD3 ABD of the anti-MSLN×anti-CD3 bispecific antibody includes the variable heavy domain and variable light domain of a CD3 ABD provided herein, including those described in FIGS. 10A-10F and the sequence listing. In some embodiments, the CD3 ABD includes the variable heavy domain and variable light domain of one of the following CD3 ABDs: H1.30_L1.47, H1.32_L1.47, H1.89_L1.47, H1.90_L1.47, H1.33_L1.47, H1.31_L1.47, L1.47_H1.30, L1.47_H1.30, L1.47_H1.32, L1.47_H1.89, L1.47_H1.90, L1.47_H1.33, and L1.47_H1.31 (FIGS. 10A-10F). In exemplary embodiments, the CD3 ABD is one of the following CD3 ABDs: H1.30_L1.47, H1.32_L1.47, H1.89_L1.47, H1.90_L1.47, H1.33_L1.47, H1.31_L1.47, L1.47_H1.30, L1.47_H1.30, L1.47_H1.32, L1.47_H1.89, L1.47_H1.90, L1.47_H1.33, and L1.47_H1.31 (FIGS. 10A-10F) or a variant thereof.

The anti-MSLN×anti-CD3 bispecific antibody can include any suitable MSLN ABD, including those described herein (see, e.g., FIGS. 15-21). In some embodiments, the MSLN ABD of the anti-MSLN×anti-CD3 bispecific antibody includes the variable heavy domain and variable light domain of a MSLN ABD provided herein, including those described in FIGS. 15-21 and the sequence listing. In some embodiments, the MSLN ABD includes the variable heavy domain and variable light domain of one of the following MSLN ABDs: MESO-A[MSLN]_H1.1_L1, MESO-B [MSLN]_H0L0, MESO-C[MSLN]_H1L1, MESO-C [MSLN]_H1.1_L1, MESO-C[MSLN]_H1.2L1, MESO-C [MSLN]_H1.3_L1, MESO-C[MSLN]_H1.4_L1, MESO-C [MSLN]_H1.5_L1, MESO-C[MSLN]_H1.6_L1, MESO-C [MSLN]_H1.7_L1, MESO-C[MSLN]_H1.8_L1, MESO-C [MSLN]_H1.9_L1, MESO-C[MSLN]_H1_L1.1, MESO-C [MSLN]_H1_L1.2, MESO-C[MSLN]_H1_L1.3, MESO-C [MSLN]_H1_L1.4, MESO-C[MSLN]_H1_L1.5, MESO-C [MSLN]_H1_L1.6, MESO-C[MSLN]_H1_L1.7, MESO-C [MSLN]_H1_L1.8, MESO-C[MSLN]_H1_L1.9, MESO-C [MSLN]_H1_L1.10, MESO-C[MSLN]_H1.5_L1.3, MESO-C[MSLN]_H1.6_L1.3, MESO-C[MSLN]_ H1.12_L1.9, MESO-C[MSLN]_H1.13_L1.9, MESO-C [MSLN]_H1.3_L1.13, MESO-C[MSLN]_H1.3_L1.14, MESO-C[MSLN]_H1.3_L1.15, MESO-C[MSLN]_ H1.3_L1.16, MESO-C[MSLN]_H1.3_L1.17, MESO-C [MSLN]_H1.3_L1.18, MESO-C[MSLN]_H1.3_L1.9, MESO-C[MSLN]_H1.3_L1.5, MESO-C[MSLN]_ H1_L1.20, MESO-C[MSLN]_H1.12_L1.20, MESO-C [MSLN]_H1.14_L1.14, MESO-C[MSLN]_H1.15_L1.14, MESO-C[MSLN]_H1.16_L1.14, MESO-C[MSLN]_ H1_L1.19_, MESO-C[MSLN]_H1_L1.21, MESO-C [MSLN]_H1_L1.22, MESO-C[MSLN]_H1.12_L1.19, MESO-C[MSLN]_H1.12_L1.21, MESO-C[MSLN]_ H1.12_L1.22, and MESO-C[MSLN]_H1.12_L1.9 (FIGS. 15-21).

In exemplary embodiments, the MSLN ABD is one of the following MSLN ABDs: MESO-A[MSLN]_H1.1_L1, MESO-B[MSLN]_H0L0, MESO-C[MSLN]_H1L1, MESO-C[MSLN]_H1.1_L1, MESO-C[MSLN]_H1.2L1, MESO-C[MSLN]_H1.3_L1, MESO-C[MSLN]_H1.4_L1, MESO-C[MSLN]_H1.5_L1, MESO-C[MSLN]_H1.6_L1, MESO-C[MSLN]_H1.7_L1, MESO-C[MSLN]_H1.8_L1, MESO-C[MSLN]_H1.9_L1, MESO-C[MSLN]_H1_L1.1, MESO-C[MSLN]_H1_L1.2, MESO-C[MSLN]_H1_L1.3, MESO-C[MSLN]_H1_L1.4, MESO-C[MSLN]_H1_L1.5, MESO-C[MSLN]_H1_L1.6, MESO-C[MSLN]_H1_L1.7, MESO-C[MSLN]_H1_L1.8, MESO-C[MSLN]_H1_L1.9, MESO-C[MSLN]_H1_L1.10, MESO-C[MSLN]_ H1.5_L1.3, MESO-C[MSLN]_H1.6_L1.3, MESO-C [MSLN]_H1.12_L1.9, MESO-C[MSLN]_H1.13_L1.9, MESO-C[MSLN]_H1.3_L1.13, MESO-C[MSLN]_ H1.3_L1.14, MESO-C[MSLN]_H1.3_L1.15, MESO-C [MSLN]_H1.3_L1.16, MESO-C[MSLN]_H1.3_L1.17, MESO-C[MSLN]_H1.3_L1.18, MESO-C[MSLN]_ H1.3_L1.9, MESO-C[MSLN]_H1.3_L1.5, MESO-C [MSLN]_H1_L1.20, MESO-C[MSLN]_H1.12_L1.20, MESO-C[MSLN]_H1.14_L1.14, MESO-C[MSLN]_ H1.15_L1.14, MESO-C[MSLN]_H1.16_L1.14, MESO-C [MSLN]_H1_L1.19_, MESO-C[MSLN]_H1_L1.21, MESO-C[MSLN]_H1_L1.22, MESO-C[MSLN]_ H1.12_L1.19, MESO-C[MSLN]_H1.12_L1.21, MESO-C [MSLN]_H1.12_L1.22, and MESO-C[MSLN]_H1.12_L1.9 (FIGS. 15-21) or variants thereof.

In some embodiments, the anti-MSLN×anti-CD3 bispecific antibody includes a MSLN binding domain variable heavy domain selected from any of FIGS. 15-18 and 20-21.

In some embodiments, the MSLN binding domain includes a MSLN binding domain variable light domain selected from any of FIGS. 15-17 and 19-21. In some embodiments, the MSLN binding domain includes a combination of any of the MSLN binding domain variable heavy domains and variable light domains in FIGS. 15-21.

F. Useful Formats of the Invention

As will be appreciated by those in the art and discussed more fully below, the heterodimeric bispecific antibodies provided herein can take on a wide variety of configurations, as are generally depicted in FIG. 1. Some figures depict "single ended" configurations, where there is one type of specificity on one "arm" of the molecule and a different specificity on the other "arm". Other figures depict "dual ended" configurations, where there is at least one type of specificity at the "top" of the molecule and one or more different specificities at the "bottom" of the molecule. Thus, in some embodiments, the antibodies described herein are directed to novel immunoglobulin compositions that co-engage a different first and a second antigen.

As will be appreciated by those in the art, the heterodimeric formats of the antibodies described herein can have different valencies as well as be bispecific. That is, heterodimeric antibodies of the antibodies described herein can be bivalent and bispecific, wherein one target tumor antigen (e.g. CD3) is bound by one binding domain and the other target tumor antigen (e.g. MSLN) is bound by a second binding domain. The heterodimeric antibodies can also be trivalent and bispecific, wherein the first antigen is bound by two binding domains and the second antigen by a second binding domain. As is outlined herein, when CD3 is one of the target antigens, it is preferable that the CD3 is bound only monovalently, to reduce potential side effects.

The antibodies described herein utilize anti-CD3 antigen binding domains in combination with anti-MSLN binding domains. As will be appreciated by those in the art, any collection of anti-CD3 CDRs, anti-CD3 variable light and variable heavy domains, Fabs and scFvs as depicted in any of the Figures can be used. Similarly, any of the anti-MSLN antigen binding domains can be used, whether CDRs, variable light and variable heavy domains, Fabs and scFvs as depicted in any of the Figures (e.g., FIGS. 15-21) can be used, optionally and independently combined in any combination.

1. 1+1 Fab-scFv-Fc Format

One heterodimeric scaffold that finds particular use in the antibodies described herein is the "1+1 Fab-scFv-Fc" or "bottle-opener" format as shown in FIG. 15A with an exemplary combination of a CD3 binding domain and a tumor target antigen (MSLN) binding domain. In this embodiment, one heavy chain monomer of the antibody contains a single chain Fv ("scFv", as defined below) and an Fc domain. The scFv includes a variable heavy domain (VH1) and a variable light domain (VL1), wherein the VH1 is attached to the VL1 using an scFv linker that can be charged (see, e.g., FIG. 5). The scFv is attached to the heavy chain using a domain linker (see, e.g., FIG. 6). The other heavy chain monomer is a "regular" heavy chain (VH-CH1-hinge-CH2-CH3). The 1+1 Fab-scFv-Fc also includes a light chain that interacts with the VH-CH1 to form a Fab. This structure is sometimes referred to herein as the "bottle-opener" format, due to a rough visual similarity to a bottle-opener. The two heavy chain monomers are brought together by the use of amino acid variants (e.g., heterodimerization variants, discussed above) in the constant regions (e.g., the Fc domain, the CH1 domain and/or the hinge region) that promote the formation of heterodimeric antibodies as is described more fully below.

There are several distinct advantages to the present "1+1 Fab-scFv-Fc" format. As is known in the art, antibody analogs relying on two scFv constructs often have stability and aggregation problems, which can be alleviated in the antibodies described herein by the addition of a "regular" heavy and light chain pairing. In addition, as opposed to formats that rely on two heavy chains and two light chains, there is no issue with the incorrect pairing of heavy and light chains (e.g. heavy 1 pairing with light 2, etc.).

Many of the embodiments outlined herein rely in general on the 1+1 Fab-scFv-Fc or "bottle opener" format antibody that comprises a first monomer comprising an scFv, comprising a variable heavy and a variable light domain, covalently attached using an scFv linker (charged, in many but not all instances), where the scFv is covalently attached to the N-terminus of a first Fc domain usually through a domain linker The domain linker can be either charged or uncharged and exogenous or endogenous (e.g., all or part of the native hinge domain). Any suitable linker can be used to attach the scFv to the N-terminus of the first Fc domain. In some embodiments, the domain linker is chosen from the domain linkers in FIG. 6. The second monomer of the 1+1 Fab-scFv-Fc format or "bottle opener" format is a heavy chain, and the composition further comprises a light chain.

In general, in many preferred embodiments, the scFv is the domain that binds to the CD3, and the Fab forms a MSLN binding domain. An exemplary anti-MSLN×anti-CD3 bispecific antibody in the 1+1 Fab-scFv-Fc format is depicted in FIG. 22A. Exemplary anti-MSLN×anti-CD3 bispecific antibody in the 1+1 Fab-scFv-Fc format is depicted in FIGS. 23A-23R, FIGS. 24A-24B, FIGS. 25A-25B, FIG. 26, and FIG. 27.

In addition, the Fc domains of the antibodies described herein generally include skew variants (e.g. a set of amino acid substitutions as shown in FIGS. 1 and 4, with particularly useful skew variants being selected from the group consisting of S364K/E357Q: L368D/K370S; L368D/K370S: S364K; L368E/K370S: S364K; T411T/E360E/Q362E: D401K; L368D/K370S: S364K/E357L; K370S: S364K/E357Q; T366S/L368A/Y407V: T366W and T366S/L368A/Y407V/Y349C: T366W/S354C), optionally ablation variants (including those shown in FIG. 3), optionally charged scFv linkers (including those shown in FIG. 5) and the heavy chain comprises pI variants (including those shown in FIG. 4).

In certain embodiments, the 1+1 Fab-scFv-Fc scaffold format includes a first monomer that includes a scFv-domain linker-CH2-CH3 monomer, a second monomer that includes a first variable heavy domain-CH1-hinge-CH2-CH3 monomer and a third monomer that includes a first variable light domain. In some embodiments, the CH2-CH3 of the first monomer is a first variant Fc domain and the CH2-CH3 of the second monomer is a second variant Fc domain. In some embodiments, the scFv includes a scFv variable heavy domain and a scFv variable light domain that form a CD3 binding moiety. In certain embodiments, the scFv variable heavy domain and scFv variable light domain are covalently attached using an scFv linker (charged, in many but not all instances. See, e.g., FIG. 5). In some embodiments, the first variable heavy domain and first variable light domain form a MSLN binding domain. In some embodiments, the 1+1 Fab-scFv-Fc format includes skew variants, pI variants, and ablation variants. Accordingly, some embodiments include 1+1 Fab-scFv-Fc formats that comprise: a) a first monomer (the "scFv monomer") that comprises a charged scFv linker (with the +H sequence of FIG. 5 being preferred in some embodiments), the skew variants S364K/E357Q, the ablation variants E233P/L234V/L235A/G236del/S267K, and an scFv that binds to CD3 as outlined herein; b) a second monomer (the "Fab monomer") that comprises the skew variants L368D/K370S, the pI variants N208D/Q295E/N384D/Q418E/N421D, the ablation variants E233P/L234V/L235A/G236del/S267K, and a variable heavy domain; and c) a light chain that includes a variable light domain light domain (VL) and a constant light domain (CL), wherein numbering is according to EU numbering. The variable heavy domain and variable light domain make up a MSLN binding moiety. CD3 binding domain sequences finding particular use in these embodiments include, but are not limited to, H1.30_L1.47, H1.32_L1.47, H1.89_L1.47, H1.90_L1.47, H1.33_L1.47, H1.31_L1.47, L1.47_H1.30, L1.47_H1.30, L1.47_H1.32, L1.47_H1.89, L1.47_H1.90, L1.47_H1.33, and L1.47_H1.31 as well as those depicted in FIGS. 10A-10F. In some embodiments, the MSLN binding domains include the variable heavy and variable light domain of any one of the MSLN binding domains disclosed in FIGS. 15-21. MSLN binding domain sequences that are of particular use in these embodiments include, but are not limited to: MESO-A[MSLN]_H1.1_L1, MESO-B[MSLN]_ H0L0, MESO-C[MSLN]_H1L1, MESO-C[MSLN]_ H1.1_L1, MESO-C[MSLN]_H1.2L1, MESO-C[MSLN]_ H1.3_L1, MESO-C[MSLN]_H1.4_L1, MESO-C[MSLN]_ H1.5_L1, MESO-C[MSLN]_H1.6_L1, MESO-C[MSLN]_ H1.7_L1, MESO-C[MSLN]_H1.8_L1, MESO-C[MSLN]_ H1.9_L1, MESO-C[MSLN]_H1_L1.1, MESO-C[MSLN]_ H1_L1.2, MESO-C[MSLN]_H1_L1.3, MESO-C[MSLN]_ H1_L1.4, MESO-C[MSLN]_H1_L1.5, MESO-C[MSLN]_ H1_L1.6, MESO-C[MSLN]_H1_L1.7, MESO-C[MSLN]_ H1_L1.8, MESO-C[MSLN]_H1_L1.9, MESO-C[MSLN]_ H1_L1.10, MESO-C[MSLN]_H1.5_L1.3, MESO-C [MSLN]_H1.6_L1.3, MESO-C[MSLN]_H1.12_L1.9, MESO-C[MSLN]_H1.13_L1.9, MESO-C[MSLN]_ H1.3_L1.13, MESO-C[MSLN]_H1.3_L1.14, MESO-C [MSLN]_H1.3_L1.15, MESO-C[MSLN]_H1.3_L1.16, MESO-C[MSLN]_H1.3_L1.17, MESO-C[MSLN]_ H1.3_L1.18, MESO-C[MSLN]_H1.3_L1.9, MESO-C [MSLN]_H1.3_L1.5, MESO-C[MSLN]_H1_L1.20, MESO-C[MSLN]_H1.12_L1.20, MESO-C[MSLN]_ H1.14_L1.14, MESO-C[MSLN]_H1.15_L1.14, MESO-C [MSLN]_H1.16_L1.14, MESO-C[MSLN]_H1_L1.19, MESO-C[MSLN]_H1_L1.21, MESO-C[MSLN]_ H1_L1.22, MESO-C[MSLN]_H1.12_L1.19, MESO-C [MSLN]_H1.12_L1.21, MESO-C[MSLN]_H1.12_L1.22, and MESO-C[MSLN]_H1.12_L1.9 (FIGS. 15-21).

Particularly useful MSLN and CD3 sequence combinations for use with the 1+1 Fab₂-scFv-Fc format antibody include, for example, MESO-A[MSLN]_H1.1_L1×CD3 H1.30 L1.47, MESO-B[MSLN]_H0L0×CD3 H1.30 L1.47, MESO-C[MSLN]_H1L1_×CD3 H1.30 L1.47, MESO-C [MSLN]_H1.1_L1×CD3 H1.30 L1.47, MESO-C[MSLN]_ H1.2_L1×CD3 H1.30 L1.47, MESO-C[MSLN]_ H1.3_L1_×CD3 H1.30 L1.47, MESO-C[MSLN]_ H1.4_L1×CD3 H1.30 L1.47, MESO-C[MSLN]_ H1.5_L1× CD3 H1.30 L1.47, MESO-C[MSLN]_ H1.6_L1×CD3 H1.30 L1.47, MESO-C[MSLN]_ H1.7_L1×CD3 H1.30 L1.47, MESO-C[MSLN]_ H1.8_L1×CD3 H1.30 L1.47, MESO-C[MSLN]_ H1.9_L1×CD3 H1.30 L1.47, MESO-C [MSLN]_ H1_L1.1×CD3 H1.30 L1.47, MESO-C[MSLN]_ H1_L1.2×CD3 H1.30 L1.47, MESO-C[MSLN]_ H1_L1.3× CD3 H1.30 L1.47, MESO-C[MSLN]_H1_L1.4_×CD3 H.130 L1.47, MESO-C[MSLN]_H1_L1.5×CD3 H1.30

L1.47, MESO-C[MSLN]_H1_L1.6_×CD3 H1.30 L1.47, MESO-C[MSLN]_H1_L1.7×CD3 H1.30 L1.47, MESO-C[MSLN]_H1_L1.8×CD3 H1.30 L1.47, MESO-C[MSLN]_H1_L1.9×CD3 H1.30 L1.47, MESO-C[MSLN]_H1_L1.10×CD3 H1.30 L1.47, MESO-C[MSLN]_H1.5_L1.3×CD3 H1.30 L1.47, MESO-C[MSLN]_H1.6_L1.3×CD3 H.130 L1.47, MESO-C[MSLN]_H1.12_L1.9×CD3 H1.30 L1.47, MESO-C[MSLN]_H1.13_L1.9×CD3 H1.30 L1.47, MESO-C[MSLN]_H1.3_L1.13×CD3 H1.30 L1.47, MESO-C[MSLN]_H1.3_L1.14×CD3 H1.30 L1.47, MESO-C[MSLN]_H1.3_L1.15×CD3 H1.30 L1.47, MESO-C[MSLN]_H1.3_L1.16×CD3 H1.30 L1.47, MESO-C[MSLN]_H1.3_L1.17×CD3 H1.30 L1.47, MESO-C[MSLN]_H1.3_L1.18×CD3 H1.30 L1.47, MESO-C[MSLN]_H1.3_L1.9×CD3 H1.30 L1.47, MESO-C[MSLN]_H1.3_L1.5×CD3 H1.30 L1.47, MESO-C[MSLN]_H1_L1.20×CD3 H1.30 L1.47, MESO-C[MSLN]_H1.12_L1.20×CD3 H1.30 L1.47, MESO-A[MSLN]_H1.1_L1×CD3 H1.32 L1.47, MESO-B[MSLN]_H0L0×CD3 H1.32 L1.47, MESO-C[MSLN]_H1L1×CD3 H1.32 L1.47, MESO-C[MSLN]_H1.14_L1.14×CD3 L1.47 H1.32, MESO-C[MSLN]_H1.15_L1.14×CD3 L1.47 H1.32, MESO-C[MSLN]_H1.16_L1.14×CD3 L1.47 H1.32, MESO-A[MSLN]_H1.1_L1×CD3 H1.33 L1.47, MESO-B[MSLN]_H0L0×CD3 H1.33 L1.47, MESO-A[MSLN]_H1.1_L1×CD3 H1.31 L1.47, and MESO-B[MSLN]_H0L0×CD3 H1.31 L1.47 (FIGS. 23A-27).

Exemplary variable heavy and light domains of the scFv that binds to CD3 are included in FIG. 10A-10F. Exemplary variable heavy and light domains of the Fv that binds to MSLN are included in FIGS. 15-21. In some embodiments, the MSLN binding domains include the variable heavy and variable light domain of any one of the MSLN binding domains disclosed in FIGS. 15-21. In an exemplary embodiment, the MSLN binding domain of the 1+1 Fab-scFv-Fc MSLN×CD3 bispecific antibody includes the VH and VL of one of the following MSLN binding domains: MESO-A[MSLN]_H1.1_L1, MESO-B[MSLN]_H0L0, MESO-C[MSLN]_H1L1, MESO-C[MSLN]_H1.1_L1, MESO-C[MSLN]_H1.2L1, MESO-C[MSLN]_H1.3_L1, MESO-C[MSLN]_H1.4_L1, MESO-C[MSLN]_H1.5_L1, MESO-C[MSLN]_H1.6_L1, MESO-C[MSLN]_H1.7_L1, MESO-C[MSLN]_H1.8_L1, MESO-C[MSLN]_H1.9_L1, MESO-C[MSLN]_H1_L1.1, MESO-C[MSLN]_H1_L1.2, MESO-C[MSLN]_H1_L1.3, MESO-C[MSLN]_H1_L1.4, MESO-C[MSLN]_H1_L1.5, MESO-C[MSLN]_H1_L1.6, MESO-C[MSLN]_H1_L1.7, MESO-C[MSLN]_H1_L1.8, MESO-C[MSLN]_H1_L1.9, MESO-C[MSLN]_H1_L1.10, MESO-C[MSLN]_H1.5_L1.3, MESO-C[MSLN]_H1.6_L1.3, MESO-C[MSLN]_H1.12_L1.9, MESO-C[MSLN]_H1.13_L1.9, MESO-C[MSLN]_H1.3_L1.13, MESO-C[MSLN]_H1.3_L1.14, MESO-C[MSLN]_H1.3_L1.15, MESO-C[MSLN]_H1.3_L1.16, MESO-C[MSLN]_H1.3_L1.17, MESO-C[MSLN]_H1.3_L1.18, MESO-C[MSLN]_H1.3_L1.9, MESO-C[MSLN]_H1.3_L1.5, MESO-C[MSLN]_H1_L1.20, MESO-C[MSLN]_H1.12_L1.20, MESO-C[MSLN]_H1.14_L1.14, MESO-C[MSLN]_H1.15_L1.14, MESO-C[MSLN]_H1.16_L1.14, MESO-C[MSLN]_H1_L1.19, MESO-C[MSLN]_H1_L1.21, MESO-C[MSLN]_H1_L1.22, MESO-C[MSLN]_H1.12_L1.19, MESO-C[MSLN]_H1.12_L1.21, MESO-C[MSLN]_H1.12_L1.22, and MESO-C[MSLN]_H1.12_L1.9 (FIGS. 15-21). In one embodiment, the CD3 binding domain of the 1+1 Fab-scFv-Fc MSLN×CD3 bispecific antibody includes the VH and VL of one of the following CD3 binding domains: H1.30_L1.47, H1.32_L1.47, H1.89_L1.47, H1.90_L1.47, H1.33_L1.47, H1.31_L1.47, L1.47_H1.30, L1.47_H1.30, L1.47_H1.32, L1.47_H1.89, L1.47_H1.90, L1.47_H1.33, and L1.47_H1.31 (FIGS. 10A-10F). Particularly useful MSLN and CD3 combinations for use in the 1+1 Fab-scFv-Fc MSLN×CD3 bispecific antibody format are disclosed in FIGS. 23A-27 and include: MESO-A[MSLN]_H1.1_L1×CD3 H1.30 L1.47, MESO-B[MSLN]_H0L0×CD3 H1.30 L1.47, MESO-C[MSLN]_H1L1_×CD3 H1.30 L1.47, MESO-C[MSLN]_H1.1_L1×CD3 H1.30 L1.47, MESO-C[MSLN]_H1.2_L1×CD3 H1.30 L1.47, MESO-C[MSLN]_H1.3_L1_×CD3 H1.30 L1.47, MESO-C[MSLN]_H1.4_L1×CD3 H1.30 L1.47, MESO-C[MSLN]_H1.5_L1×CD3 H1.30 L1.47, MESO-C[MSLN]_H1.6_L1×CD3 H1.30 L1.47, MESO-C[MSLN]_H1.7_L1×CD3 H1.30 L1.47, MESO-C[MSLN]_H1.8_L1×CD3 H1.30 L1.47, MESO-C[MSLN]_H1.9_L1×CD3 H1.30 L1.47, MESO-C[MSLN]_H1_L1.1×CD3 H1.30 L1.47, MESO-C[MSLN]_H1_L1.2×CD3 H1.30 L1.47, MESO-C[MSLN]_H1_L1.3×CD3 H1.30 L1.47, MESO-C[MSLN]_H1_L1.4_×CD3 H.130 L1.47, MESO-C[MSLN]_H1_L1.5×CD3 H1.30 L1.47, MESO-C[MSLN]_H1_L1.6_×CD3 H1.30 L1.47, MESO-C[MSLN]_H1_L1.7×CD3 H1.30 L1.47, MESO-C[MSLN]_H1_L1.8×CD3 H1.30 L1.47, MESO-C[MSLN]_H1_L1.9×CD3 H1.30 L1.47, MESO-C[MSLN]_H1_L1.10×CD3 H1.30 L1.47, MESO-C[MSLN]_H1.5_L1.3×CD3 H1.30 L1.47, MESO-C[MSLN]_H1.6_L1.3×CD3 H.130 L1.47, MESO-C[MSLN]_H1.12_L1.9×CD3 H1.30 L1.47, MESO-C[MSLN]_H1.13_L1.9×CD3 H1.30 L1.47, MESO-C[MSLN]_H1.3_L1.13×CD3 H1.30 L1.47, MESO-C[MSLN]_H1.3_L1.14×CD3 H1.30 L1.47, MESO-C[MSLN]_H1.3_L1.15×CD3 H1.30 L1.47, MESO-C[MSLN]_H1.3_L1.16×CD3 H1.30 L1.47, MESO-C[MSLN]_H1.3_L1.17×CD3 H1.30 L1.47, MESO-C[MSLN]_H1.3_L1.18×CD3 H1.30 L1.47, MESO-C[MSLN]_H1.3_L1.9×CD3 H1.30 L1.47, MESO-C[MSLN]_H1.3_L1.5×CD3 H1.30 L1.47, MESO-C[MSLN]_H1_L1.20×CD3 H1.30 L1.47, MESO-C[MSLN]_H1.12_L1.20×CD3 H1.30 L1.47, MESO-A[MSLN]_H1.1_L1×CD3 H1.32 L1.47, MESO-B[MSLN]_H0L0×CD3 H1.32 L1.47, MESO-C[MSLN]_H1L1×CD3 H1.32 L1.47, MESO-C[MSLN]_H1.14_L1.14×CD3 L1.47 H1.32, MESO-C[MSLN]_H1.15_L1.14×CD3 L1.47 H1.32, MESO-C[MSLN]_H1.16_L1.14×CD3 L1.47 H1.32, MESO-A[MSLN]_H1.1_L1×CD3 H1.33 L1.47, MESO-B[MSLN]_H0L0×CD3 H1.33 L1.47, MESO-A[MSLN]_H1.1_L1×CD3 H1.31 L1.47, and MESO-B[MSLN]_H0L0×CD3 H1.31 L1.47.

In some embodiments, the 1+1 Fab-scFv-Fc format includes skew variants, pI variants, ablation variants and FcRn variants. Accordingly, some embodiments include 1+1 Fab-scFv-Fc formats that comprise: a) a first monomer (the "scFv monomer") that comprises a charged scFv linker (with the +H sequence of FIG. 6 being preferred in some embodiments), the skew variants S364K/E357Q, the ablation variants E233P/L234V/L235A/G236del/S267K, the FcRn variants M428L/N434S and an scFv that binds to CD3 as outlined herein; b) a second monomer (the "Fab monomer") that comprises the skew variants L368D/K370S, the pI variants N208D/Q295E/N384D/Q418E/N421D, the ablation variants E233P/L234V/L235A/G236del/S267K, the FcRn variants M428L/N434S, and a variable heavy domain; and c) a light chain that includes a variable light domain (VL) and a constant light domain (CL), wherein numbering is according to EU numbering. The variable heavy domain and variable light domain make up a MSLN binding domain. CD3 binding domain sequences finding particular use in these embodiments include, but are not limited to, H1.30_L1.47, H1.32_L1.47, H1.89_L1.47, H1.90_L1.47, H1.33_L1.47, H1.31_L1.47, L1.47_H1.30, L1.47_H1.30, L1.47_H1.32, L1.47_H1.89, L1.47_H1.90, L1.47_H1.33, and L1.47_H1.31 as well as those depicted in FIGS. 10A-10F. MSLN binding domain sequences that are of particular use in these embodiments include, but are not limited to: MESO-A[MSLN]_H1.1_L1, MESO-B[MSLN]_H0L0, MESO-C[MSLN]_H1L1, MESO-C[MSLN]_H1.1_L1, MESO-C[MSLN]_H1.2L1, MESO-C[MSLN]_H1.3_L1, MESO-C[MSLN]_H1.4_L1, MESO-C[MSLN]_H1.5_L1, MESO-C[MSLN]_H1.6_L1, MESO-C[MSLN]_H1.7_L1, MESO-C[MSLN]_H1.8_L1, MESO-C[MSLN]_H1.9_L1, MESO-C[MSLN]_H1_L1.1, MESO-C[MSLN]_H1_L1.2, MESO-C[MSLN]_H1_L1.3, MESO-C[MSLN]_H1_L1.4, MESO-C[MSLN]_H1_L1.5, MESO-C[MSLN]_H1_L1.6, MESO-C[MSLN]_H1_L1.7, MESO-C[MSLN]_H1_L1.8, MESO-C[MSLN]_H1_L1.9, MESO-C[MSLN]_H1_L1.10, MESO-C[MSLN]_H1.5_L1.3, MESO-C[MSLN]_H1.6_L1.3, MESO-C[MSLN]_H1.12_L1.9, MESO-C[MSLN]_H1.13_L1.9, MESO-C[MSLN]_H1.3_L1.13, MESO-C[MSLN]_H1.3_L1.14, MESO-C[MSLN]_H1.3_L1.15, MESO-C[MSLN]_H1.3_L1.16, MESO-C[MSLN]_H1.3_L1.17, MESO-C[MSLN]_H1.3_L1.18, MESO-C[MSLN]_H1.3_L1.9, MESO-C[MSLN]_H1.3_L1.5, MESO-C[MSLN]_H1_L1.20, MESO-C[MSLN]_H1.12_L1.20, MESO-C[MSLN]_H1.14_L1.14, MESO-C[MSLN]_H1.15_L1.14, MESO-C[MSLN]_H1.16_L1.14, MESO-C[MSLN]_H1_L1.19_, MESO-C[MSLN]_H1_L1.21, MESO-C[MSLN]_H1_L1.22, MESO-C[MSLN]_H1.12_L1.19, MESO-C[MSLN]_H1.12_L1.21, MESO-C[MSLN]_H1.12_L1.22, and MESO-C[MSLN]_H1.12_L1.9 (FIGS. 15-21).

Particularly useful MSLN and CD3 sequence combinations for use with the 1+1 Fab₂-scFv-Fc format antibody include, for example, are disclosed in FIGS. 23-27 and include: MESO-A[MSLN]_H1.1_L1×CD3 H1.30 L1.47, MESO-B[MSLN]_H0L0×CD3 H1.30 L1.47, MESO-C[MSLN]_H1L1_×CD3 H1.30 L1.47, MESO-C[MSLN]_H1.1_L1×CD3 H1.30 L1.47, MESO-C[MSLN]_H1.2_L1×CD3 H1.30 L1.47, MESO-C[MSLN]_H1.3_L1_×CD3 H1.30 L1.47, MESO-C[MSLN]_H1.4_L1×CD3 H1.30 L1.47, MESO-C[MSLN]_H1.5_L1×CD3 H1.30 L1.47, MESO-C[MSLN]_H1.6_L1×CD3 H1.30 L1.47, MESO-C[MSLN]_H1.7_L1×CD3 H1.30 L1.47, MESO-C[MSLN]_H1.8_L1×CD3 H1.30 L1.47, MESO-C[MSLN]_H1.9_L1×CD3 H1.30 L1.47, MESO-C[MSLN]_H1_L1.1×CD3 H1.30 L1.47, MESO-C[MSLN]_H1_L1.2×CD3 H1.30 L1.47, MESO-C[MSLN]_H1_L1.3×CD3 H1.30 L1.47, MESO-C[MSLN]_H1_L1.4_×CD3 H.130 L1.47, MESO-C[MSLN]_H1_L1.5×CD3 H1.30 L1.47, MESO-C[MSLN]_H1_L1.6_×CD3 H1.30 L1.47, MESO-C[MSLN]_H1_L1.7×CD3 H1.30 L1.47, MESO-C[MSLN]_H1_L1.8×CD3 H1.30 L1.47, MESO-C[MSLN]_H1_L1.9×CD3 H1.30 L1.47, MESO-C[MSLN]_H1_L1.10×CD3 H1.30 L1.47, MESO-C[MSLN]_H1.5_L1.3×CD3 H1.30 L1.47, MESO-C[MSLN]_H1.6_L1.3×CD3 H.130 L1.47, MESO-C[MSLN]_H1.12_L1.9×CD3 H1.30 L1.47, MESO-C[MSLN]_H1.13_L1.9×CD3 H1.30 L1.47, MESO-C[MSLN]_H1.3_L1.13×CD3 H1.30 L1.47, MESO-C[MSLN]_H1.3_L1.14×CD3 H1.30 L1.47, MESO-C[MSLN]_H1.3_L1.15×CD3 H1.30 L1.47, MESO-C[MSLN]_H1.3_L1.16×CD3 H1.30 L1.47, MESO-C[MSLN]_H1.3_L1.17×CD3 H1.30 L1.47, MESO-C[MSLN]_H1.3_L1.18×CD3 H1.30 L1.47, MESO-C[MSLN]_H1.3_L1.9×CD3 H1.30 L1.47, MESO-C[MSLN]_H1.3_L1.5×CD3 H1.30 L1.47, MESO-C[MSLN]_H1_L1.20×CD3 H1.30 L1.47, MESO-C[MSLN]_H1.12_L1.20×CD3 H1.30 L1.47, MESO-A[MSLN]_H1.1_L1×CD3 H1.32 L1.47, MESO-B[MSLN]_H0L0×CD3 H1.32 L1.47, MESO-C[MSLN]_H1L1×CD3 H1.32 L1.47, MESO-C[MSLN]_H1.14_L1.14×CD3 L1.47 H1.32, MESO-C[MSLN]_H1.15_L1.14×CD3 L1.47 H1.32, MESO-C[MSLN]_H1.16_L1.14×CD3 L1.47 H1.32, MESO-A[MSLN]_H1.1_L1×CD3 H1.33 L1.47, MESO-B[MSLN]_H0L0×CD3 H1.33 L1.47, MESO-A[MSLN]_H1.1_L1×CD3 H1.31 L1.47, and MESO-B[MSLN]_H0L0×CD3 H1.31 L1.47.

FIGS. 7A-7D show some exemplary Fc domain sequences that are useful in the 1+1 Fab-scFv-Fc format antibodies. The "monomer 1" sequences depicted in FIGS. 7A-7D typically refer to the Fc domain of the "Fab-Fc heavy chain" and the "monomer 2" sequences refer to the Fc domain of the "scFv-Fc heavy chain." Further, FIG. 9 provides useful CL sequences that can be used with this format.

In some embodiments, any of the VH and VL sequences depicted herein (including all VH and VL sequences depicted in the Figures and Sequence Listings, including those directed to MSLN) can be added to the bottle opener backbone formats of FIG. 7A-7D as the "Fab side", using any of the anti-CD3 scFv sequences shown in the Figures and Sequence Listings.

For bottle opener backbone 1 from FIG. 7A, (optionally including the 428L/434S variants), CD3 binding domain sequences finding particular use in these embodiments include, but are not limited to, CD3 binding domain anti-CD3 H1.30_L1.47, anti-CD3 H1.32_L1.47, anti-CD3 H1.89_L1.47, anti-CD3 H1.90_L1.47, anti-CD3 H1.33 L1.47 and anti-CD3 H1.31_L1.47, as well as those depicted in FIG. 10A-10F, attached as the scFv side of the backbones shown in FIGS. 7A-7D.

Particularly useful MSLN and CD3 sequence combinations for use (optionally including the 428L/434S variants), are disclosed in FIGS. 23-27.

In some embodiments, the 1+1 Fab-scFv-Fc format includes sequences selected from: XENP16249, XENP16250, XENP16253, XENP16827, XENP31693.

In some embodiments, the 1+1 Fab-scFv-Fc format comprises sequences selected from: XENP16248, XENP16833, XENP31697, XENP32550, XENP32551, XENP32552, XENP32553, XENP32554, XENP32555, XENP32556, XENP32557, XENP32558, XENP32559, XENP32560, XENP32561, XENP32562, XENP32563, XENP32564, XENP32565, XENP32566, XENP32567, XENP32568, XENP32569, XENP32570, XENP32937, XENP32938, XENP32939, XENP32940, XENP32941, XENP32942, XENP32943, XENP32944, XENP32945, XENP32946, XENP33888, XENP33889, XENP30764, XENP30765, XENP31701, XENP33969, XENP33971, XENP33973, XENP16251, XENP16834, XENP16252, and XENP16835 (FIGS. 23-27). In some embodiments, the 1+1 Fab-scFv-Fc format comprises a variable heavy chain MSLN sequence comprising one or more of the following mutations: S31G, W32Y, M50W, H52N, N53Q, D55G, 194R, T97S, E61Q, E61Y, and/or K100bR.

In some embodiments, the 1+1 Fab-scFv-Fc format comprises a variable light chain MSLN sequence comprising one or more of the following mutations: A25S, H27Q, D28S, G30L, S32Y, V33L, T37Q, H55E, T56S, S92Y, Y94T, Y94L, Y94V, Y94I, Y94H, D28S and Y100F.

In some embodiments, the 1+1 Fab-scFv-Fc format includes a MSLN binding domain that includes a MSLN binding domain variable heavy domain selected from any of FIGS. 15-18 and 20-21. In some embodiments, the 1+1 Fab-scFv-Fc format includes a MSLN binding domain that includes a MSLN binding domain variable light domain selected from any of FIGS. 15-17 and 19-21. In some embodiments, the 1+1 Fab-scFv-Fc format includes a MSLN binding domain that includes a combination of any of the MSLN binding domain variable heavy domains and variable light domains in FIGS. 15-21.

2. mAb-Fv

One heterodimeric scaffold that finds particular use in the antibodies described herein is the mAb-Fv format. In this embodiment, the format relies on the use of a C-terminal attachment of an "extra" variable heavy domain to one monomer and the C-terminal attachment of an "extra" variable light domain to the other monomer, thus forming a third antigen binding domain, wherein the Fab portions of the two monomers bind a MSLN and the "extra" scFv domain binds CD3.

In this embodiment, the first monomer comprises a first heavy chain, comprising a first variable heavy domain and a first constant heavy domain comprising a first Fc domain, with a first variable light domain covalently attached to the C-terminus of the first Fc domain using a domain linker (VH1-CH1-hinge-CH2-CH3-[optional linker]-VL2). The second monomer comprises a second variable heavy domain of the second constant heavy domain comprising a second Fc domain, and a third variable heavy domain covalently attached to the C-terminus of the second Fc domain using a domain linker (vh1-CH1-hinge-CH2-CH3-[optional linker]-VH2. The two C-terminally attached variable domains make up a Fv that binds CD3 (as it is less preferred to have bivalent CD3 binding). This embodiment further utilizes a common light chain comprising a variable light domain and a constant light domain that associates with the heavy chains to form two identical Fabs that bind a MSLN. As for many of the embodiments herein, these constructs include skew variants, pI variants, ablation variants, additional Fc variants, etc. as desired and described herein.

The antibodies described herein provide mAb-Fv formats where the CD3 binding domain sequences are as shown in FIG. 10A-10F. The antibodies described herein provide mAb-Fv formats wherein the MSLN binding domain sequences are as shown in FIGS. 15-21.

In addition, the Fc domains of the mAb-Fv format comprise skew variants (e.g. a set of amino acid substitutions as shown in FIGS. 1 and 4, with particularly useful skew variants being selected from the group consisting of S364K/ E357Q: L368D/K370S; L368D/K370S: S364K; L368E/ K370S: S364K; T411T/E360E/Q362E: D401K; L368D/ K370S: S364K/E357L, K370S: S364K/E357Q, T366S/ L368A/Y407V: T366W and T366S/L368A/Y407V/Y349C: T366W/S354C), optionally ablation variants (including those shown in FIG. 3), optionally charged scFv linkers (including those shown in FIG. 5) and the heavy chain comprises pI variants (including those shown in FIG. 2).

In some embodiments, the mAb-Fv format includes skew variants, pI variants, and ablation variants. Accordingly, some embodiments include mAb-Fv formats that comprise: a) a first monomer that comprises the skew variants S364K/ E357Q, the ablation variants E233P/L234V/L235A/ G236del/S267K, and a first variable heavy domain that, with the first variable light domain of the light chain, makes up an Fv that binds to MSLN, and a second variable heavy domain; b) a second monomer that comprises the skew variants L368D/K370S, the pI variants N208D/Q295E/ N384D/Q418E/N421D, the ablation variants E233P/L234V/ L235A/G236del/S267K, and a first variable heavy domain that, with the first variable light domain, makes up the Fv that binds to MSLN as outlined herein, and a second variable light chain, that together with the second variable heavy domain forms an Fv (ABD) that binds to CD3; and c) a light chain comprising a first variable light domain and a constant light domain.

In some embodiments, the mAb-Fv format includes skew variants, pI variants, ablation variants and FcRn variants. Accordingly, some embodiments include mAb-Fv formats that comprise: a) a first monomer that comprises the skew variants S364K/E357Q, the ablation variants E233P/L234V/ L235A/G236del/S267K, the FcRn variants M428L/N434S and a first variable heavy domain that, with the first variable light domain of the light chain, makes up an Fv that binds to MSLN, and a second variable heavy domain; b) a second monomer that comprises the skew variants L368D/K370S, the pI variants N208D/Q295E/N384D/Q418E/N421D, the ablation variants E233P/L234V/L235A/G236del/S267K, the FcRn variants M428L/N434S and a first variable heavy domain that, with the first variable light domain, makes up the Fv that binds to MSLN as outlined herein, and a second variable light chain, that together with the second variable heavy domain of the first monomer forms an Fv (ABD) that binds CD3; and c) a light chain comprising a first variable light domain and a constant light domain.

In some embodiments, the MSLN binding domains include the variable heavy and variable light domain of any one of the MSLN binding domains disclosed in FIGS. 15-21.

3. mAb-scFv

One heterodimeric scaffold that finds particular use in the antibodies described herein is the mAb-scFv format. In this embodiment, the format relies on the use of a C-terminal attachment of a scFv to one of the monomers, thus forming a third antigen binding domain, wherein the Fab portions of the two monomers bind MSLN and the "extra" scFv domain binds CD3. Thus, the first monomer comprises a first heavy chain (comprising a variable heavy domain and a constant domain), with a C-terminally covalently attached scFv comprising a scFv variable light domain, an scFv linker and a scFv variable heavy domain in either orientation (VH1- CH1-hinge-CH2-CH3-[optional linker]-VH2-scFv linker- VL2 or VH1-CH1-hinge-CH2-CH3-[optional linker]-VL2- scFv linker-VH2). This embodiment further utilizes a common light chain comprising a variable light domain and a constant light domain that associates with the heavy chains to form two identical Fabs that bind MSLN. As for many of the embodiments herein, these constructs include skew variants, pI variants, ablation variants, additional Fc variants, etc. as desired and described herein.

The antibodies described herein provide mAb-scFv formats where the CD binding domain sequences are as shown in FIG. 10A-10F and the MSLN binding domain sequences are as shown in FIGS. 15-21.

In addition, the Fc domains of the mAb-scFv format comprise skew variants (e.g. a set of amino acid substitutions as shown in FIGS. 1 and 4, with particularly useful skew variants being selected from the group consisting of S364K/E357Q: L368D/K370S; L368D/K370S: S364K; L368E/K370S: S364K; T411T/E360E/Q362E: D401K; L368D/K370S: S364K/E357L, K370S: S364K/E357Q, T366S/L368A/Y407V: T366W and T366S/L368A/Y407V/ Y349C: T366W/S354C), optionally ablation variants (including those shown in FIG. 3), optionally charged scFv linkers (including those shown in FIG. 5) and the heavy chain comprises pI variants (including those shown in FIG. 2).

In some embodiments, the mAb-scFv format includes skew variants, pI variants, and ablation variants. Accordingly, some embodiments include mAb-scFv formats that comprise: a) a first monomer that comprises the skew variants S364K/E357Q, the ablation variants E233P/L234V/ L235A/G236del/S267K, and a variable heavy domain that, with the variable light domain of the common light chain, makes up an Fv that binds to MSLN as outlined herein, and a scFv domain that binds to CD3; b) a second monomer that comprises the skew variants L368D/K370S, the pI variants N208D/Q295E/N384D/Q418E/N421D, the ablation variants E233P/L234V/L235A/G236del/S267K, and a variable heavy domain that, with the variable light domain of the common light chain, makes up an Fv that binds to MSLN as outlined herein; and c) a common light chain comprising a variable light domain and a constant light domain.

In some embodiments, the mAb-scFv format includes skew variants, pI variants, ablation variants and FcRn variants. Accordingly, some embodiments include mAb-scFv formats that comprise: a) a first monomer that comprises the skew variants S364K/E357Q, the ablation variants E233P/ L234V/L235A/G236del/S267K, the FcRn variants M428L/ N434S and a variable heavy domain that, with the variable light domain of the common light chain, makes up an Fv that binds to MSLN as outlined herein, and a scFv domain that binds to CD3; b) a second monomer that comprises the skew variants L368D/K370S, the pI variants N208D/Q295E/ N384D/Q418E/N421D, the ablation variants E233P/L234V/ L235A/G236del/S267K, the FcRn variants M428L/N434S and a variable heavy domain that, with the variable light domain of the common light chain, makes up an Fv that binds to MSLN as outlined herein; and c) a common light chain comprising a variable light domain and a constant light domain.

In some embodiments, the MSLN binding domains include the variable heavy and variable light domain of any one of the MSLN binding domains disclosed in FIGS. 15-21.

4. 2+1 Fab$_2$-scFv-Fc Format

One heterodimeric scaffold that finds particular use in the antibodies described herein is the "2+1 Fab$_2$-scFv-Fc" format (also referred to in previous related filings as "Central-scFv format") shown in FIG. 22B with an exemplary combination of a CD3 binding domain and two tumor target antigen (MSLN) binding domains. In this embodiment, the format relies on the use of an inserted scFv domain thus forming a third antigen binding domain, wherein the Fab portions of the two monomers bind MSLN and the "extra" scFv domain binds CD3. The scFv domain is inserted between the Fc domain and the CH1-Fv region of one of the monomers, thus providing a third antigen binding domain. As described, MSLN×CD3 bispecific antibodies having the 2+1 Fab$_2$-scFv-Fc format are potent in inducing redirected T cell cytotoxicity in cellular environments that express low levels of MSLN. Moreover, as shown in the examples, MSLN×CD3 bispecific antibodies having the 2+1 Fab$_2$-scFv-Fc format allow for the "fine tuning" of immune responses as such antibodies exhibit a wide variety of different properties, depending on the MSLN and/or CD3 binding domains used. For example, such antibodies exhibit differences in selectivity for cells with different MSLN expression, potencies for MSLN expressing cells, ability to elicit cytokine release, and sensitivity to soluble MSLN. These MSLN antibodies find use, for example, in the treatment of MSLN associated cancers.

In this embodiment, one monomer comprises a first heavy chain comprising a first variable heavy domain, a CH1 domain (and optional hinge) and Fc domain, with a scFv comprising a scFv variable light domain, an scFv linker and a scFv variable heavy domain. The scFv is covalently attached between the C-terminus of the CH1 domain of the heavy constant domain and the N-terminus of the first Fc domain using optional domain linkers (VH1-CH1-[optional linker]-VH2-scFv linker-VL2-[optional linker including the hinge]-CH2-CH3, or the opposite orientation for the scFv, VH1-CH1-[optional linker]-VL2-scFv linker-VH2-[optional linker including the hinge]-CH2-CH3). The optional linkers can be any suitable peptide linkers, including, for example, the domain linkers included in FIG. 6. In some embodiments, the optional linker is a hinge or a fragment thereof. The other monomer is a standard Fab side (i.e., VH1-CH1-hinge-CH2-CH3). This embodiment further utilizes a common light chain comprising a variable light domain and a constant light domain, that associates with the heavy chains to form two identical Fabs that bind MSLN. As for many of the embodiments herein, these constructs include skew variants, pI variants, ablation variants, additional Fc variants, etc. as desired and described herein.

In one embodiment, the 2+1 Fab$_2$-scFv-Fc format antibody includes an scFv with the VH and VL of a CD3 binding domain sequence depicted in FIG. 10A-10F or the Sequence Listing. In one embodiment, the 2+1 Fab$_2$-scFv-Fc format antibody includes two Fabs having the VH and VL of a MSLN binding domain as shown in FIGS. 15-21 and the Sequence Listing. In an exemplary embodiment, the MSLN binding domain of the 2+1 Fab$_2$-scFv-Fc MSLN×CD3 bispecific antibody includes the VH and VL of one of the following MSLN binding domains: MESO-A[MSLN]_ H1.1_L1, MESO-B[MSLN]_H0L0, MESO-C[MSLN]_ H1L1, MESO-C[MSLN]_H1.1_L1, MESO-C[MSLN]_ H1.2L1, MESO-C[MSLN]_H1.3_L1, MESO-C[MSLN]_ H1.4_L1, MESO-C[MSLN]_H1.5_L1, MESO-C[MSLN]_ H1.6_L1, MESO-C[MSLN]_H1.7_L1, MESO-C[MSLN]_ H1.8_L1, MESO-C[MSLN]_H1.9_L1, MESO-C[MSLN]_ H1_L1.1, MESO-C[MSLN]_H1_L1.2, MESO-C[MSLN]_ H1_L1.3, MESO-C[MSLN]_H1_L1.4, MESO-C[MSLN]_ H1_L1.5, MESO-C[MSLN]_H1_L1.6, MESO-C[MSLN]_ H1_L1.7, MESO-C[MSLN]_H1_L1.8, MESO-C[MSLN]_ H1_L1.9, MESO-C[MSLN]_H1_L1.10, MESO-C [MSLN]_ H1.5_L1.3, MESO-C[MSLN]_H1.6_L1.3, MESO-C[MSLN]_H1.12_L1.9, MESO-C[MSLN]_ H1.13_L1.9, MESO-C[MSLN]_H1.3_L1.13, MESO-C [MSLN]_H1.3_L1.14, MESO-C[MSLN]_H1.3_L1.15, MESO-C[MSLN]_H1.3_L1.16, MESO-C[MSLN]_ H1.3_L1.17, MESO-C[MSLN]_H1.3_L1.18, MESO-C [MSLN]_H1.3_L1.9, MESO-C[MSLN]_H1.3_L1.5, MESO-C[MSLN]_H1_L1.20, MESO-C[MSLN]_ H1.12_L1.20, MESO-C[MSLN]_H1.14_L1.14, MESO-C [MSLN]_H1.15_L1.14, MESO-C[MSLN]_H1.16_L1.14, MESO-C[MSLN]_H1_L1.19, MESO-C[MSLN]_ H1_L1.21, MESO-C[MSLN]_H1_L1.22, MESO-C [MSLN]_H1.12_L1.19, MESO-C[MSLN]_H1.12_L1.21, MESO-C[MSLN]_H1.12_L1.22, and MESO-C[MSLN]_ H1.12_L1.9 (FIGS. 15-21). In one embodiment, the CD3 binding domain of the 2+1 Fab2-scFv-Fc format antibody includes the VH and VL of one of the following CD3 binding domains: H1.30_L1.47, H1.32_L1.47, H1.89_L1.47, H1.90_L1.47, H1.33_L1.47, H1.31_L1.47, L1.47_H1.30, L1.47_H1.30, L1.47_H1.32, L1.47_H1.89, L1.47_H1.90, L1.47_H1.33, and L1.47_H1.31 (FIGS. 10A-10F). Particularly useful MSLN and CD3 combinations for use in the 2+1 Fab2-scFv-Fc format antibody format are disclosed in FIGS. 28-32 and include: MESO-A[MSLN]_H1.1_L1×CD3 H1.30 L1.47, MESO-B[MSLN]_H0L0×CD3 H1.30 L1.47, MESO-C[MSLN]_H1L1×CD3 H1.30 L1.47, MESO-A[MSLN]_H1.1_L1×CD3 L1.47 H1.30, MESO-B[MSLN]_H0L0×CD3 L1.47 H1.30, MESO-C[MSLN]_H1L1×CD3 L1.47 H1.30, MESO-A[MSLN]_H1.1_L1×CD3 H1.32 L1.47, MESO-B[MSLN]_H0L0×CD3 H1.32 L1.47, MESO-C[MSLN]_H1L1×CD3 H1.32 L1.47, MESO-C[MSLN]_H1 L1.3×CD3 H1.32 L1.47, MESO-C[MSLN]_H1 L1.4×CD3 H1.32 L1.47, MESO-C[MSLN]_H1 L1.5×CD3 H1.32 L1.47, MESO-C[MSLN]_H1 L1.9×CD3 H1.32 L1.47, MESO-A[MSLN]_H1.1 L1×CD3 L1.47 H1.32, MESO-B[MSLN]_H0L0×CD3 L1.47 H1.32, MESO-C[MSLN]_H1L1×CD3 L1.47 H1.32, MESO-C[MSLN]_H1 L1.3×CD3 L1.47 H1.32, MESO-C[MSLN]_H1 L1.4×CD3 L1.47 H1.32, MESO-C[MSLN]_H1 L1.5×CD3 L1.47 H1.32, MESO-C[MSLN]_H1 L1.9×CD3 L1.47 H1.32, MESO-C[MSLN]_H1.3 L1×CD3 L1.47 H1.32, MESO-C[MSLN]_H1.12 L1.9×CD3 L1.47 H1.32, MESO-C[MSLN]_H1.13 L1.9×CD3 L1.47 H1.32, MESO-C[MSLN]_H1.3 L1.9×CD3 L1.47 H1.32, MESO-C[MSLN]_ H1.3 L1.5×CD3 L1.47 H1.32, MESO-C[MSLN]_H1.3 L1.13×CD3 L1.47 H1.32, MESO-C[MSLN]_H1.3 L1.14×CD3 L1.47 H1.32, MESO-C[MSLN]_H1 L1.19×CD3 L1.47 H1.32, MESO-C[MSLN]_H1 L1.20×CD3 L1.47 H1.32, MESO-C[MSLN]_H1 L1.21×CD3 L1.47 H1.32, MESO-C[MSLN]_H1 L1.22×CD3 L1.47 H1.32, MESO-C[MSLN]_H1.12 L1.19×CD3 L1.47 H1.32, MESO-C[MSLN]_H1.12 L1.20×CD3 L1.47 H1.32, MESO-C[MSLN]_H1.12 L1.21×CD3 L1.47 H1.32, MESO-C[MSLN]_H1.12 L1.22×CD3 L1.47 H1.32, MESO-C[MSLN]_H1.14 L1.14×CD3 L1.47 H1.32, MESO-C[MSLN]_H1.15 L1.14×CD3 L1.47 H1.32, MESO-C[MSLN]_H1.12 L1.19×CD3 L1.47 H1.32, MESO-C[MSLN]_H1.3 L1.14×CD3 L1.47 H1.32, MESO-C[MSLN]_ H1.3 L1.13×CD3 L1.47 H1.32, MESO-C[MSLN]_H1.3 L1×CD3 L1.47 H1.32, MESO-C[MSLN]_H1.12 L1.9×CD3 L1.47 H1.32, MESO-A[MSLN]_H1.1 L1×CD3 L1.47 H1.89, MESO-B[MSLN]_H0L0×CD3 L1.47 H1.89, MESO-C[MSLN]_H1L1×CD3 L1.47 H1.89, MESO-C[MSLN]_H1 L1.3×CD3 L1.47 H1.89, MESO-C[MSLN]_H1 L1.4×CD3 L1.47 H1.89, MESO-C[MSLN]_H1 L1.5×CD3 L1.47 H1.89, MESO-C[MSLN]_H1 L1.9×CD3 L1.47 H1.89, MESO-C[MSLN]_H1.3 L1.14×CD3 L1.47 H1.89, MESO-C[MSLN]_H1 L1.20×CD3 L1.47 H1.89, MESO-C[MSLN]_H1.12 L1.20×CD3 L1.47 H1.89, MESO-C[MSLN]_H1.3 L1.13×CD3 L1.47 H1.89, MESO-C[MSLN]_H1.3 L1×CD3 L1.47 H1.89, MESO-C[MSLN]_H1 L1.9×CD3 L1.47 H1.89, MESO-C[MSLN]_H1.12 L1.9×CD3 L1.47 H1.89, MESO-C[MSLN]_H1.3 L1.14×CD3 L1.47 H1.89, MESO-C[MSLN]_H1.3 L1.13×CD3 L1.47 H1.89, MESO-C[MSLN]_H1.3 L1×CD3 L1.47 H1.89, MESO-C[MSLN]_H1.12 L1.9×CD3 L1.47 H1.89, MESO-C[MSLN]_H1.3 L1.14×CD3 L1.47 H1.89, MESO-C[MSLN]_H1.3 L1.13×CD3 L1.47 H1.89, MESO-C[MSLN]_H1.3 L1×CD3 L1.47 H1.89, and MESO-C[MSLN]_H1.12 L1.9×CD3 L1.47 H1.89.

In addition, the Fc domains of the 2+1 Fab₂-scFv-Fc format comprise skew variants (e.g. a set of amino acid substitutions as shown in FIGS. 1 and 4, with particularly useful skew variants being selected from the group consisting of S364K/E357Q: L368D/K370S; L368D/K370S: S364K; L368E/K370S: S364K; T411T/E360E/Q362E:

D401K; L368D/K370S: S364K/E357L, K370S: S364K/E357Q, T366S/L368A/Y407V: T366W and T366S/L368A/Y407V/Y349C: T366W/S354C), optionally ablation variants (including those shown in FIG. 3), optionally charged scFv linkers (including those shown in FIG. 5) and the heavy chain comprises pI variants (including those shown in FIG. 2).

In some embodiments, the 2+1 Fab₂-scFv-Fc format antibody includes skew variants, pI variants, and ablation variants. Accordingly, some embodiments include 2+1 Fab₂-scFv-Fc formats that comprise: a) a first monomer (the Fab-scFv-Fc side) that comprises the skew variants S364K/E357Q, the ablation variants E233P/L234V/L235A/G236del/S267K, and a variable heavy domain that, with the variable light domain of the common light chain, makes up an Fv that binds to MSLN as outlined herein, and an scFv domain that binds to CD3; b) a second monomer (the Fab-Fc side) that comprises the skew variants L368D/K370S, the pI variants N208D/Q295E/N384D/Q418E/N421D, the ablation variants E233P/L234V/L235A/G236del/S267K, and a variable heavy domain that, with variable light domain of the common light chain, makes up an Fv that binds to MSLN as outlined herein; and c) a common light chain comprising the variable light domain and a constant light domain, where numbering is according to EU numbering. In some embodiments, the common light chain and variable heavy domains on each monomer for MSLN binding domains. CD3 binding domain sequences finding particular use in these embodiments include, but are not limited to, H1.30_L1.47, H1.32_L1.47, H1.89_L1.47, H1.90_L1.47, H1.33_L1.47, H1.31_L1.47, L1.47_H1.30, L1.47_H1.30, L1.47_H1.32, L1.47_H1.89, L1.47_H1.90, L1.47_H1.33, and L1.47 H1.31 as well as those depicted in FIGS. 10A-10F. MSLN binding domain sequences that are of particular use in these embodiments include, but are not limited to MESO-A[MSLN]_H1.1_L1, MESO-B[MSLN]_H0L0, MESO-C[MSLN]_H1L1, MESO-C[MSLN]_H1.1_L1, MESO-C[MSLN]_H1.2L1, MESO-C[MSLN]_H1.3_L1, MESO-C[MSLN]_H1.4_L1, MESO-C[MSLN]_H1.5_L1, MESO-C[MSLN]_H1.6_L1, MESO-C[MSLN]_H1.7_L1, MESO-C[MSLN]_H1.8_L1, MESO-C[MSLN]_H1.9_L1, MESO-C[MSLN]_H1_L1.1, MESO-C[MSLN]_H1_L1.2, MESO-C[MSLN]_H1_L1.3, MESO-C[MSLN]_H1_L1.4, MESO-C[MSLN]_H1_L1.5, MESO-C[MSLN]_H1_L1.6, MESO-C[MSLN]_H1_L1.7, MESO-C[MSLN]_H1_L1.8, MESO-C[MSLN]_H1_L1.9, MESO-C[MSLN]_H1_L1.10, MESO-C[MSLN]_H1.5_L1.3, MESO-C[MSLN]_H1.6_L1.3, MESO-C[MSLN]_H1.12_L1.9, MESO-C[MSLN]_H1.13_L1.9, MESO-C[MSLN]_H1.3_L1.13, MESO-C[MSLN]_H1.3_L1.14, MESO-C[MSLN]_H1.3_L1.15, MESO-C[MSLN]_H1.3_L1.16, MESO-C[MSLN]_H1.3_L1.17, MESO-C[MSLN]_H1.3_L1.18, MESO-C[MSLN]_H1.3_L1.9, MESO-C[MSLN]_H1.3_L1.5, MESO-C[MSLN]_H1_L1.20, MESO-C[MSLN]_H1.12_L1.20, MESO-C[MSLN]_H1.14_L1.14, MESO-C[MSLN]_H1.15_L1.14, MESO-C[MSLN]_H1.16_L1.14, MESO-C[MSLN]_H1_L1.19, MESO-C[MSLN]_H1_L1.21, MESO-C[MSLN]_H1_L1.22, MESO-C[MSLN]_H1.12_L1.19, MESO-C[MSLN]_H1.12_L1.21, MESO-C[MSLN]_H1.12_L1.22, and MESO-C[MSLN]_H1.12_L1.9 (FIGS. 15-21).

In some embodiments, the 2+1 Fab₂-scFv-Fc format antibody includes skew variants, pI variants, ablation variants, and FcRn variants. Accordingly, some embodiments include 2+1 Fab₂-scFv-Fc formats that comprise: a) a first monomer (the Fab-scFv-Fc side) that comprises the skew variants S364K/E357Q, the ablation variants E233P/L234V/

L235A/G236del/S267K, the FcRn variants M428L/N434S and a variable heavy domain that, with the variable light domain of the common light chain, makes up an Fv that binds to MSLN as outlined herein, and an scFv domain that binds to CD3; b) a second monomer (the Fab-Fc side) that comprises the skew variants L368D/K370S, the pI variants N208D/Q295E/N384D/Q418E/N421D, the ablation variants E233P/L234V/L235A/G236del/S267K, the FcRn variants M428L/N434S and a variable heavy domain that, with variable light domain of the common light chain, makes up an Fv that binds to MSLN as outlined herein; and c) a common light chain comprising a variable light domain and a constant light domain, where numbering is according to EU numbering. In some embodiments, the common light chain and variable heavy domains on each monomer for MSLN binding domains. CD3 binding domain sequences finding particular use in these embodiments include, but are not limited to, H1.30_L1.47, H1.32_L1.47, H1.89_L1.47, H1.90_L1.47, H1.33_L1.47, H1.31_L1.47, L1.47_H1.30, L1.47_H1.30, L1.47_H1.32, L1.47_H1.89, L1.47_H1.90, L1.47_H1.33, and L1.47_H1.31 as well as those depicted in FIGS. 10A-10F. In some embodiments, the MSLN binding domains include the variable heavy and variable light domain of any one of the MSLN binding domains disclosed in FIGS. 15-21. MSLN binding domain sequences that are of particular use in these embodiments include but are not limited to: MESO-A[MSLN]_H1.1_L1, MESO-B[MSLN]_ H0L0, MESO-C[MSLN]_H1L1, MESO-C[MSLN]_ H1.1_L1, MESO-C[MSLN]_H1.2L1, MESO-C[MSLN]_ H1.3_L1, MESO-C[MSLN]_H1.4_L1, MESO-C[MSLN]_ H1.5_L1, MESO-C[MSLN]_H1.6_L1, MESO-C[MSLN]_ H1.7_L1, MESO-C[MSLN]_H1.8_L1, MESO-C[MSLN]_ H1.9_L1, MESO-C[MSLN]_H1_L1.1, MESO-C[MSLN]_ H1_L1.2, MESO-C[MSLN]_H1_L1.3, MESO-C[MSLN]_ H1_L1.4, MESO-C[MSLN]_H1_L1.5, MESO-C[MSLN]_ H1_L1.6, MESO-C[MSLN]_H1_L1.7, MESO-C[MSLN]_ H1_L1.8, MESO-C[MSLN]_H1_L1.9, MESO-C[MSLN]_ H1_L1.10, MESO-C[MSLN]_H1.5_L1.3, MESO-C [MSLN]_H1.6_L1.3, MESO-C[MSLN]_H1.12_L1.9, MESO-C[MSLN]_H1.13_L1.9, MESO-C[MSLN]_ H1.3_L1.13, MESO-C[MSLN]_H1.3_L1.14, MESO-C [MSLN]_H1.3_L1.15, MESO-C[MSLN]_H1.3_L1.16, MESO-C[MSLN]_H1.3_L1.17, MESO-C[MSLN]_ H1.3_L1.18, MESO-C[MSLN]_H1.3_L1.9, MESO-C [MSLN]_H1.3_L1.5, MESO-C[MSLN]_H1_L1.20, MESO-C[MSLN]_H1.12_L1.20, MESO-C[MSLN]_ H1.14_L1.14, MESO-C[MSLN]_H1.15_L1.14, MESO-C [MSLN]_H1.16_L1.14, MESO-C[MSLN]_H1_L1.19, MESO-C[MSLN]_H1_L1.21, MESO-C[MSLN]_ H1_L1.22, MESO-C[MSLN]_H1.12_L1.19, MESO-C [MSLN]_H1.12_L1.21, MESO-C[MSLN]_H1.12_L1.22, and MESO-C[MSLN]_H1.12_L1.9 (FIGS. 15-21).

FIGS. 8A-8C shows some exemplary Fc domain sequences that are useful with the 2+1 Fab₂-scFv-Fc format. The "monomer 1" sequences depicted in FIGS. 8A-8C typically refer to the Fc domain of the "Fab-Fc heavy chain" and the "monomer 2" sequences refer to the Fc domain of the "Fab-scFv-Fc heavy chain." Further, FIG. 9 provides useful CL sequences that can be used with this format.

In some embodiments, the 2+1 Fab₂-scFv-Fc format includes sequences selected from: XENP16249, XENP16250, XENP16253, XENP16827, XENP31693.

In some embodiments, the 2+1 Fab₂-scFv-Fc format comprises sequences selected from: XENP31063, XENP31067, XENP31705, XENP31451, XENP31452, XENP31713, XENP31064, XENP31068, XENP31709, ENP32744, XENP32747, XENP32750, XENP32851, XENP31453, XENP31454, XENP31717, XENP32745, XENP32748, XENP32751, XENP32852, XENP32947, XENP32948, XENP32949, XENP32950, XENP32951, XENP33366, XENP33367, XENP33460, XENP33461, XENP33462, XENP33463, XENP33464, XENP33465, XENP33466, XENP33467, XENP33968, XENP33970, XENP33972, XENP34155, XENP34156, XENP34157, XENP34158, XENP31455, XENP31456, XENP32249, XENP32250, XENP32251, XENP32746, XENP32749, XENP32752, XENP32853, XENP33974, XENP33975, XENP33976, XENP33977, XENP33978, XENP33979, XENP33980, XENP34151, XENP34152, XENP34153, XENP34154, XENP34159, XENP34160, XENP34161, and XENP34162 (FIGS. 28-32).

In some embodiments, the 2+1 Fab₂-scFv-Fc format comprises a variable heavy chain MSLN sequence comprising one or more of the following mutations: S31G, W32Y, M50W, H52N, N53Q, D55G, 194R, T97S, E61Q, E61Y, and/or K100bR.

In some embodiments, the 2+1 Fab₂-scFv-Fc format comprises a variable light chain MSLN sequence comprising one or more of the following mutations: A25S, H27Q, D28S, G30L, S32Y, V33L, T37Q, H55E, T56S, S92Y, Y94T, Y94L, Y94V, Y94I, Y94H, D28S and Y100F.

In some embodiments, the 2+1 Fab₂-scFv-Fc format format includes a MSLN binding domain that includes a MSLN binding domain variable heavy domain selected from any of FIGS. 15-18 and 20-21. In some embodiments, the 2+1 Fab₂-scFv-Fc format includes a MSLN binding domain that includes a MSLN binding domain variable light domain selected from any of FIGS. 15-17 and 19-21. In some embodiments, the 2+1 Fab₂-scFv-Fc format includes a MSLN binding domain that includes a combination of any of the MSLN binding domain variable heavy domains and variable light domains in FIGS. 15-21.

5. Central-Fv

One heterodimeric scaffold that finds particular use in the antibodies described herein is the Central-Fv format. In this embodiment, the format relies on the use of an inserted Fv domain (i.e., the central Fv domain) thus forming an "extra" third antigen binding domain, wherein the Fab portions of the two monomers bind a MSLN and the "extra" central Fv domain binds CD3. The "extra" central Fv domain is inserted between the Fc domain and the CH1-Fv region of the monomers, thus providing a third antigen binding domain (i.e., the "extra" central Fv domain), wherein each monomer contains a component of the "extra" central Fv domain (i.e., one monomer comprises the variable heavy domain and the other a variable light domain of the "extra" central Fv domain).

In this embodiment, one monomer comprises a first heavy chain comprising a first variable heavy domain, a CH1 domain, and Fc domain and an additional variable light domain. The light domain is covalently attached between the C-terminus of the CH1 domain of the heavy constant domain and the N-terminus of the first Fc domain using domain linkers (VH1-CH1-[optional linker]-VL2-hinge-CH2-CH3). The other monomer comprises a first heavy chain comprising a first variable heavy domain, a CH1 domain and Fc domain and an additional variable heavy domain (VH1-CH1-[optional linker]-VH2-hinge-CH2-CH3). The light domain is covalently attached between the C-terminus of the CH1 domain of the heavy constant domain and the N-terminus of the first Fc domain using domain linkers.

This embodiment further utilizes a common light chain comprising a variable light domain and a constant light domain, that associates with the heavy chains to form two identical Fabs that each bind a MSLN. As for many of the embodiments herein, these constructs include skew variants, pI variants, ablation variants, additional Fc variants, etc. as desired and described herein.

The antibodies described herein provide central-Fv formats where the CD3 binding domain sequences are as shown in 10A-10F and the MSLN binding domain sequences are as shown in FIGS. 15-21.

In some embodiments, the MSLN binding domains include the variable heavy and variable light domain of any one of the MSLN binding domains disclosed in FIGS. 15-21.

6. One Armed Central-scFv

One heterodimeric scaffold that finds particular use in the antibodies described herein is the one armed central-scFv format. In this embodiment, one monomer comprises just an Fc domain, while the other monomer includes a Fab domain (a first antigen binding domain), a scFv domain (a second antigen binding domain) and an Fc domain, where the scFv domain is inserted between the Fab domain and the Fc domain. In this format, the Fab portion binds one receptor target and the scFv binds another. In this format, either the Fab portion binds a MSLN and the scFv binds CD3 or vice versa.

In this embodiment, one monomer comprises a first heavy chain comprising a first variable heavy domain, a CH1 domain and Fc domain, with a scFv comprising a scFv variable light domain, an scFv linker and a scFv variable heavy domain. The scFv is covalently attached between the C-terminus of the CH1 domain of the heavy constant domain and the N-terminus of the first Fc domain using domain linkers, in either orientation, VH1-CH1-[optional domain linker]-VH2-scFv linker-VL2-[optional domain linker]-CH2-CH3 or VH1-CH1-[optional domain linker]-VL2-scFv linker-VH2-[optional domain linker]-CH2-CH3. The second monomer comprises an Fc domain (CH2-CH3). This embodiment further utilizes a light chain comprising a variable light domain and a constant light domain that associates with the heavy chain to form a Fab.

As for many of the embodiments herein, these constructs include skew variants, pI variants, ablation variants, additional Fc variants, etc. as desired and described herein.

The antibodies described herein provide central-Fv formats where the CD3 binding domain sequences are as shown in FIG. 10A-10F and the MSLN binding domain sequences are as shown in FIGS. 15-21.

In addition, the Fc domains of the one armed central-scFv format generally include skew variants (e.g. a set of amino acid substitutions as shown in FIGS. 1 and 4, with particularly useful skew variants being selected from the group consisting of S364K/E357Q: L368D/K370S; L368D/K370S: S364K; L368E/K370S: S364K; T411T/E360E/Q362E: D401K; L368D/K370S: S364K/E357L, K370S: S364K/E357Q, T366S/L368A/Y407V: T366W and T366S/L368A/Y407V/Y349C: T366W/S354C), optionally ablation variants (including those shown in FIG. 3), optionally charged scFv linkers (including those shown in FIG. 5) and the heavy chain comprises pI variants (including those shown in FIG. 2).

In some embodiments, the one armed central-scFv format includes skew variants, pI variants, and ablation variants. Accordingly, some embodiments of the one armed central-scFv formats comprise: a) a first monomer that comprises the skew variants S364K/E357Q, the ablation variants E233P/L234V/L235A/G236del/S267K, and a variable heavy domain that, with the variable light domain of the light chain, makes up an Fv that binds to MSLN as outlined herein, and a scFv domain that binds to CD3; b) a second monomer that includes an Fc domain having the skew variants L368D/K370S, the pI variants N208D/Q295E/N384D/Q418E/N421D, the ablation variants E233P/L234V/L235A/G236del/S267K; and c) a light chain comprising a variable light domain and a constant light domain.

In some embodiments, the one armed central-scFv format includes skew variants, pI variants, ablation variants and FcRn variants. Accordingly, some embodiments of the one armed central-scFv formats comprise: a) a first monomer that comprises the skew variants S364K/E357Q, the ablation variants E233P/L234V/L235A/G236del/S267K, the FcRn variants M428L/N434S and a variable heavy domain that, with the variable light domain of the light chain, makes up an Fv that binds to MSLN as outlined herein, and a scFv domain that binds to CD3; b) a second monomer that includes an Fc domain having the skew variants L368D/K370S, the pI variants N208D/Q295E/N384D/Q418E/N421D, the ablation variants E233P/L234V/L235A/G236del/S267K, and the FcRn variants M428L/N434S; and c) a light chain comprising a variable light domain and a constant light domain.

In some embodiments, the MSLN binding domains include the variable heavy and variable light domain of any one of the MSLN binding domains disclosed in FIGS. 15-21.

7. One Armed scFv-mAb

One heterodimeric scaffold that finds particular use in the antibodies described herein is the one armed scFv-mAb format. In this embodiment, one monomer comprises just an Fc domain, while the other monomer uses a scFv domain attached at the N-terminus of the heavy chain, generally through the use of a linker: VH-scFv linker-VL-[optional domain linker]-CH1-hinge-CH2-CH3 or (in the opposite orientation) VL-scFv linker-VH-[optional domain linker]-CH1-hinge-CH2-CH3. In this format, the Fab portions each bind MSLN and the scFv binds CD3. This embodiment further utilizes a light chain comprising a variable light domain and a constant light domain, that associates with the heavy chain to form a Fab. As for many of the embodiments herein, these constructs include skew variants, pI variants, ablation variants, additional Fc variants, etc. as desired and described herein.

The antibodies described herein provide one armed scFv-mAb formats where the CD3 binding domain sequences are as shown in 10A-10F and wherein the MSLN binding domain sequences are as shown in FIGS. 15-21.

In addition, the Fc domains of the one armed scFv-mAb format generally include skew variants (e.g. a set of amino acid substitutions as shown in FIGS. 1 and 4, with particularly useful skew variants being selected from the group consisting of S364K/E357Q: L368D/K370S; L368D/K370S: S364K; L368E/K370S: S364K; T411T/E360E/Q362E: D401K; L368D/K370S: S364K/E357L, K370S: S364K/E357Q, T366S/L368A/Y407V: T366W and T366S/L368A/Y407V/Y349C: T366W/S354C), optionally ablation variants (including those shown in FIG. 3), optionally charged scFv linkers (including those shown in FIG. 5) and the heavy chain comprises pI variants (including those shown in FIG. 2).

In some embodiments, the one armed scFv-mAb format includes skew variants, pI variants, and ablation variants. Accordingly, some embodiments of the one armed scFv-mAb formats comprise: a) a first monomer that comprises the skew variants S364K/E357Q, the ablation variants E233P/L234V/L235A/G236del/S267K, and a variable heavy domain that, with the variable light domain of the light chain, makes up an Fv that binds to MSLN as outlined herein, and a scFv domain that binds to CD3; b) a second monomer that includes an Fc domain having the skew variants L368D/K370S, the pI variants N208D/Q295E/N384D/Q418E/N421D, the ablation variants E233P/L234V/L235A/G236del/S267K; and c) a light chain comprising a variable light domain and a constant light domain.

In some embodiments, the one armed scFv-mAb format includes skew variants, pI variants, ablation variants and FcRn variants. Accordingly, some embodiments one armed scFv-mAb formats comprise: a) a first monomer that comprises the skew variants S364K/E357Q, the ablation variants E233P/L234V/L235A/G236del/S267K, the FcRn variants M428L/N434S and a variable heavy domain that, with the variable light domain of the light chain, makes up an Fv that binds to MSLN as outlined herein, and a scFv domain that binds to CD3; b) a second monomer that includes an Fc domain having the skew variants L368D/K370S, the pI variants N208D/Q295E/N384D/Q418E/N421D, the ablation variants E233P/L234V/L235A/G236del/S267K, and the FcRn variants M428L/N434S; and c) a light chain comprising a variable light domain and a constant light domain.

In some embodiments, the MSLN binding domains include the variable heavy and variable light domain of any one of the MSLN binding domains disclosed in FIGS. 15-21.

8. scFv-mAb

One heterodimeric scaffold that finds particular use in the antibodies described herein is the mAb-scFv format. In this embodiment, the format relies on the use of a N-terminal attachment of a scFv to one of the monomers, thus forming a third antigen binding domain, wherein the Fab portions of the two monomers bind MSLN and the "extra" scFv domain binds CD3.

In this embodiment, the first monomer comprises a first heavy chain (comprising a variable heavy domain and a constant domain), with a N-terminally covalently attached scFv comprising a scFv variable light domain, an scFv linker and a scFv variable heavy domain in either orientation ((VH1-scFv linker-VL1-[optional domain linker]-VH2-CH1-hinge-CH2-CH3) or (with the scFv in the opposite orientation) ((VL1-scFv linker-VH1-[optional domain linker]-VH2-CH1-hinge-CH2-CH3)). This embodiment further utilizes a common light chain comprising a variable light domain and a constant light domain that associates with the heavy chains to form two identical Fabs that bind MSLN. As for many of the embodiments herein, these constructs include skew variants, pI variants, ablation variants, additional Fc variants, etc. as desired and described herein.

The antibodies described herein provide scFv-mAb formats where the CD3 binding domain sequences are as shown in 10A-10F and wherein the MSLN binding domain sequences are as shown in FIGS. 15-21.

In addition, the Fc domains of the scFv-mAb format generally include skew variants (e.g. a set of amino acid substitutions as shown in FIGS. 1 and 4, with particularly useful skew variants being selected from the group consisting of S364K/E357Q: L368D/K370S; L368D/K370S: S364K; L368E/K370S: S364K; T411T/E360E/Q362E: D401K; L368D/K370S: S364K/E357Q, K370S: S364K/E357Q, T366S/L368A/Y407V: T366W and T366S/L368A/Y407V/Y349C: T366W/S354C), optionally ablation variants (including those shown in FIG. 3), optionally charged scFv linkers (including those shown in FIG. 5) and the heavy chain comprises pI variants (including those shown in FIG. 2).

In some embodiments, the scFv-mAb format includes skew variants, pI variants, and ablation variants. Accordingly, some embodiments include scFv-mAb formats that comprise: a) a first monomer that comprises the skew variants S364K/E357Q, the ablation variants E233P/L234V/L235A/G236del/S267K, and a variable heavy domain that, with the variable light domain of the common light chain, makes up an Fv that binds to MSLN as outlined herein, and a scFv domain that binds to CD3; b) a second monomer that comprises the skew variants L368D/K370S, the pI variants N208D/Q295E/N384D/Q418E/N421D, the ablation variants E233P/L234V/L235A/G236del/S267K, and a variable heavy domain that, with the variable light domain of the common light chain, makes up an Fv that binds to MSLN as outlined herein; and c) a common light chain comprising a variable light domain and a constant light domain.

In some embodiments, the scFv-mAb format includes skew variants, pI variants, ablation variants and FcRn variants. Accordingly, some embodiments include scFv-mAb formats that comprise: a) a first monomer that comprises the skew variants S364K/E357Q, the ablation variants E233P/L234V/L235A/G236del/S267K, the FcRn variants M428L/N434S and a variable heavy domain that, with the variable light domain of the common light chain, makes up an Fv that binds to MSLN as outlined herein, and a scFv domain that binds to CD3; b) a second monomer that comprises the skew variants L368D/K370S, the pI variants N208D/Q295E/N384D/Q418E/N421D, the ablation variants E233P/L234V/L235A/G236del/S267K, the FcRn variants M428L/N434S and a variable heavy domain that, with the variable light domain of the common light chain, makes up an Fv that binds to MSLN as outlined herein; and c) a common light chain comprising a variable light domain and a constant light domain.

In some embodiments, the MSLN binding domains include the variable heavy and variable light domain of any one of the MSLN binding domains disclosed in FIGS. 15-21.

9. Dual scFv Formats

The antibodies described herein also provide dual scFv formats as are known in the art. In this embodiment, the MSLN×CD3 heterodimeric bispecific antibody is made up of two scFv-Fc monomers (both in either (VH-scFv linker-VL-[optional domain linker]-CH2-CH3) format or (VL-scFv linker-VH-[optional domain linker]-CH2-CH3) format, or with one monomer in one orientation and the other in the other orientation.

The antibodies described herein provide dual scFv formats where the CD3 binding domain sequences are as shown in FIG. 10A-10F and wherein the MSLN binding domain sequences are as shown in FIGS. 15-21. In some embodiments, the dual scFv format includes skew variants, pI variants, and ablation variants. Accordingly, some embodiments include dual scFv formats that comprise: a) a first monomer that comprises the skew variants S364K/E357Q, the ablation variants E233P/L234V/L235A/G236del/S267K, and a first scFv that binds either CD3 or MSLN; and b) a second monomer that comprises the skew variants L368D/K370S, the pI variants N208D/Q295E/N384D/Q418E/N421D, the ablation variants E233P/L234V/L235A/G236del/S267K, and a second scFv that binds either CD3 or MSLN. In some embodiments, the dual scFv format includes skew variants, pI variants, ablation variants and FcRn variants. In some embodiments, the dual scFv format includes skew variants, pI variants, and ablation variants. Accordingly, some embodiments include dual scFv formats that comprise: a) a first monomer that comprises the skew variants S364K/E357Q, the ablation variants E233P/L234V/L235A/G236del/S267K, the FcRn variants M428L/N434S and a first scFv that binds either CD3 or MSLN; and b) a second monomer that comprises the skew variants L368D/K370S, the pI variants N208D/Q295E/N384D/Q418E/N421D, the ablation variants E233P/L234V/L235A/G236del/S267K, the FcRn variants M428L/N434S and a second scFv that binds either CD3 or MSLN.

In some embodiments, the MSLN binding domains include the variable heavy and variable light domain of any one of the MSLN binding domains disclosed in FIGS. 15-21.

10. Non-Heterodimeric Bispecific Antibodies

As will be appreciated by those in the art, the MSLN and CD3 Fv sequences outlined herein can also be used in both monospecific antibodies (e.g., "traditional monoclonal antibodies") or non-heterodimeric bispecific formats.

CD3 binding domain sequences finding particular use include, but are not limited to H1.30_L1.47, H1.32_L1.47, H1.89_L1.47, H1.90_L1.47, H1.33_L1.47, H1.31_L1.47, L1.47_H1.30, L1.47_H1.30, L1.47_H1.32, L1.47_H1.89, L1.47_H1.90, L1.47_H1.33, and L1.47_H1.31 (FIGS. 10A-10F).

MSLN binding domain sequences that are of particular use include, but are not limited to: MESO-A[MSLN]_ H1.1_L1, MESO-B[MSLN]_H0L0, MESO-C[MSLN]_ H1L1, MESO-C[MSLN]_H1.1_L1, MESO-C[MSLN]_ H1.2L1, MESO-C[MSLN]_H1.3_L1, MESO-C[MSLN]_ H1.4_L1, MESO-C[MSLN]_H1.5_L1, MESO-C[MSLN]_ H1.6_L1, MESO-C[MSLN]_H1.7_L1, MESO-C[MSLN]_ H1.8_L1, MESO-C[MSLN]_H1.9_L1, MESO-C[MSLN]_ H1_L1.1, MESO-C[MSLN]_H1_L1.2, MESO-C[MSLN]_ H1_L1.3, MESO-C[MSLN]_H1_L1.4, MESO-C[MSLN]_ H1_L1.5, MESO-C[MSLN]_H1_L1.6, MESO-C[MSLN]_ H1_L1.7, MESO-C[MSLN]_H1_L1.8, MESO-C[MSLN]_ H1_L1.9, MESO-C[MSLN]_H1_L1.10, MESO-C [MSLN]_ H1.5_L1.3, MESO-C[MSLN]_H1.6_L1.3, MESO-C[MSLN]_H1.12_L1.9, MESO-C[MSLN]_ H1.13_L1.9, MESO-C[MSLN]_H1.3_L1.13, MESO-C [MSLN]_ H1.3_L1.14, MESO-C[MSLN]_H1.3_L1.15, MESO-C[MSLN]_H1.3_L1.16, MESO-C[MSLN]_ H1.3_L1.17, MESO-C[MSLN]_H1.3_L1.18, MESO-C [MSLN]_ H1.3_L1.9, MESO-C[MSLN]_H1.3_L1.5, MESO-C[MSLN]_H1_L1.20, MESO-C[MSLN]_ H1.12_L1.20, MESO-C[MSLN]_H1.14_L1.14, MESO-C [MSLN]_ H1.15_L1.14, MESO-C[MSLN]_H1.16_L1.14, MESO-C[MSLN]_H1_L1.19_, MESO-C[MSLN]_ H1_L1.21, MESO-C[MSLN]_H1_L1.22, MESO-C [MSLN]_ H1.12_L1.19, MESO-C[MSLN]_H1.12_L1.21, MESO-C[MSLN]_H1.12_L1.22, and MESO-C[MSLN]_ H1.12_L1.9 (FIGS. 15-21).

In some embodiments, the MSLN binding domains include the variable heavy and variable light domain of any one of the MSLN binding domains disclosed in FIGS. 15-21.

Suitable non-heterodimeric bispecific formats are known in the art, and include a number of different formats as generally depicted in Spiess et al., Molecular Immunology (67):95-106 (2015) and Kontermann, mAbs 4:2, 182-197 (2012), both of which are expressly incorporated by reference and in particular for the figures, legends and citations to the formats therein.

11. Trident Format

In some embodiments, the bispecific antibodies described herein are in the "Trident" format as generally described in WO2015/184203, hereby expressly incorporated by reference in its entirety and in particular for the Figures, Legends, definitions and sequences of "Heterodimer-Promoting Domains" or "HPDs", including "K-coil" and "E-coil" sequences. Tridents rely on using two different HPDs that associate to form a heterodimeric structure as a component of the structure, see FIG. 1K. In this embodiment, the Trident format include a "traditional" heavy and light chain (e.g., VH1-CH1-hinge-CH2-CH3 and VL1-CL), a third chain comprising a first "diabody-type binding domain" or "DART®", VH2-(linker)-VL3-HPD1 and a fourth chain comprising a second DART®, VH3-(linker)-(linker)-VL2-HPD2. The VH1 and VL1 form a first ABD, the VH2 and VL2 form a second ABD, and the VH3 and VL3 form a third ABD. In some cases, as is shown in FIG. 1K, the second and third ABDs bind the same antigen, in this instance generally MSLN, e.g., bivalently, with the first ABD binding a CD3 monovalently.

In some embodiments, the MSLN binding domains include the variable heavy and variable light domain of any one of the MSLN binding domains disclosed in FIGS. 15-21.

12. Monospecific, Monoclonal Antibodies

As will be appreciated by those in the art, the novel Fv sequences outlined herein can also be used in both monospecific antibodies (e.g., "traditional monoclonal antibodies") or non-heterodimeric bispecific formats. Accordingly, in some embodiments, the antibodies described herein provide monoclonal (monospecific) antibodies comprising the 6 CDRs and/or the vh and vl sequences from the figures, generally with IgG1, IgG2, IgG3 or IgG4 constant regions, with IgG1, IgG2 and IgG4 (including IgG4 constant regions comprising a S228P amino acid substitution) finding particular use in some embodiments. That is, any sequence herein with a "H_L" designation can be linked to the constant region of a human IgG1 antibody.

In some embodiments, the monospecific antibody is a MSLN monospecific antibody. In certain embodiments, the monospecific anti-MSLN antibody includes the 6 CDRs of any of the anti-MSLN antibodies selected from: MESO-A [MSLN]_H1.1_L1, MESO-B[MSLN]_H0L0, MESO-C [MSLN]_H1L1, MESO-C[MSLN]_H1.1_L1, MESO-C [MSLN]_H1.2L1, MESO-C[MSLN]_H1.3_L1, MESO-C [MSLN]_H1.4_L1, MESO-C[MSLN]_H1.5_L1, MESO-C [MSLN]_H1.6_L1, MESO-C[MSLN]_H1.7_L1, MESO-C [MSLN]_H1.8_L1, MESO-C[MSLN]_H1.9_L1, MESO-C [MSLN]_H1_L1.1, MESO-C[MSLN]_H1_L1.2, MESO-C [MSLN]_H1_L1.3, MESO-C[MSLN]_H1_L1.4, MESO-C [MSLN]_H1_L1.5, MESO-C[MSLN]_H1_L1.6, MESO-C [MSLN]_H1_L1.7, MESO-C[MSLN]_H1_L1.8, MESO-C [MSLN]_H1_L1.9, MESO-C[MSLN]_H1_L1.10, MESO-C[MSLN]_H1.5_L1.3, MESO-C[MSLN]_H1.6_L1.3, MESO-C[MSLN]_H1.12_L1.9, MESO-C[MSLN]_ H1.13_L1.9, MESO-C[MSLN]_H1.3_L1.13, MESO-C [MSLN]_H1.3_L1.14, MESO-C[MSLN]_H1.3_L1.15, MESO-C[MSLN]_H1.3_L1.16, MESO-C[MSLN]_ H1.3_L1.17, MESO-C[MSLN]_H1.3_L1.18, MESO-C [MSLN]_H1.3_L1.9, MESO-C[MSLN]_H1.3_L1.5, MESO-C[MSLN]_H1_L1.20, MESO-C[MSLN]_ H1.12_L1.20, MESO-C[MSLN]_H1.14_L1.14, MESO-C [MSLN]_H1.15_L1.14, MESO-C[MSLN]_H1.16_L1.14, MESO-C[MSLN]_H1_L1.19_, MESO-C[MSLN]_ H1_L1.21, MESO-C[MSLN]_H1_L1.22, MESO-C

[MSLN]_H1.12_L1.19, MESO-C[MSLN]_H1.12_L1.21, MESO-C[MSLN]_H1.12_L1.22, and MESO-C[MSLN]_H1.12_L1.9 (FIGS. 15-21).

In some embodiments, the MSLN binding domains include the variable heavy and variable light domain of any one of the MSLN binding domains disclosed in FIGS. 15-21.

G. Antigen Binding Domains

As discussed herein, the subject heterodimeric antibodies include two antigen binding domains (ABDs), each of which bind to MSLN or CD3. As outlined herein, these heterodimeric antibodies can be bispecific and bivalent (each antigen is bound by a single ABD, for example, in the format depicted in FIG. 15A), or bispecific and trivalent (one antigen is bound by a single ABD and the other is bound by two ABDs, for example as depicted in FIG. 15B).

In addition, in general, one of the ABDs comprises a scFv as outlined herein, in an orientation from N- to C-terminus of VH-scFv linker-VL or VL-scFv linker-VH. One or both of the other ABDs, according to the format, generally is a Fab, comprising a VH domain on one protein chain (generally as a component of a heavy chain) and a VL on another protein chain (generally as a component of a light chain).

The disclosure provides a number of ABDs that bind to a number of different checkpoint proteins, as outlined below. As will be appreciated by those in the art, any set of 6 CDRs or VH and VL domains can be in the scFv format or in the Fab format, which is then added to the heavy and light constant domains, where the heavy constant domains comprise variants (including within the CH1 domain as well as the Fc domain). The scFv sequences contained in the sequence listing utilize a particular charged linker, but as outlined herein, uncharged or other charged linkers can be used, including those depicted in FIG. 7.

In addition, as discussed above, the numbering used in the Sequence Listing for the identification of the CDRs is Kabat, however, different numbering can be used, which will change the amino acid sequences of the CDRs as shown in Table 2.

For all of the variable heavy and light domains listed herein, further variants can be made. As outlined herein, in some embodiments the set of 6 CDRs can have from 0, 1, 2, 3, 4 or 5 amino acid modifications (with amino acid substitutions finding particular use), as well as changes in the framework regions of the variable heavy and light domains, as long as the frameworks (excluding the CDRs) retain at least about 80, 85 or 90% identity to a human germline sequence selected from those listed in FIG. 1 of U.S. Pat. No. 7,657,380, which Figure and Legend is incorporated by reference in its entirety herein. Thus, for example, the identical CDRs as described herein can be combined with different framework sequences from human germline sequences, as long as the framework regions retain at least 80, 85 or 90% identity to a human germline sequence selected from those listed in FIG. 1 of U.S. Pat. No. 7,657,380. Alternatively, the CDRs can have amino acid modifications (e.g. from 1, 2, 3, 4 or 5 amino acid modifications in the set of CDRs (that is, the CDRs can be modified as long as the total number of changes in the set of 6 CDRs is less than 6 amino acid modifications, with any combination of CDRs being changed; e.g. there may be one change in VLCDR1, two in VHCDR2, none in VHCDR3, etc.)), as well as having framework region changes, as long as the framework regions retain at least 80, 85 or 90% identity to a human germline sequence selected from those listed in FIG. 1 of U.S. Pat. No. 7,657,380.

1. MSLN Antigen Binding Domains

In some embodiments, one of the ABDs binds MSLN. Suitable sets of 6 CDRs and/or VH and VL domains are depicted in FIGS. 12A-12B, 13, 14, 15, and 16A-16B. In some embodiments, the heterodimeric antibody is a 1+1 Fab-scFv-Fc or 2+1 Fab2-scFv-Fv format antibody (see, e.g., FIGS. 22A and 22B).

In one embodiment, the MSLN antigen binding domain includes the 6 CDRs (i.e., vhCDR1-3 and vlCDR1-3) of a MSLN ABD described herein, including the figures and sequence listing. In exemplary embodiments, the MSLN ABD is one of the following MSLN ABDs: MESO-A [MSLN]_H1.1_L1, MESO-B[MSLN]_H0L0, MESO-C [MSLN]_H1L1, MESO-C[MSLN]_H1.1_L1, MESO-C [MSLN]_H1.2L1, MESO-C[MSLN]_H1.3_L1, MESO-C [MSLN]_H1.4_L1, MESO-C[MSLN]_H1.5_L1, MESO-C [MSLN]_H1.6_L1, MESO-C[MSLN]_H1.7_L1, MESO-C [MSLN]_H1.8_L1, MESO-C[MSLN]_H1.9_L1, MESO-C [MSLN]_H1_L1.1, MESO-C[MSLN]_H1_L1.2, MESO-C [MSLN]_H1_L1.3, MESO-C[MSLN]_H1_L1.4, MESO-C [MSLN]_H1_L1.5, MESO-C[MSLN]_H1_L1.6, MESO-C [MSLN]_H1_L1.7, MESO-C[MSLN]_H1_L1.8, MESO-C [MSLN]_H1_L1.9, MESO-C[MSLN]_H1_L1.10, MESO-C[MSLN]_H1.5_L1.3, MESO-C[MSLN]_H1.6_L1.3, MESO-C[MSLN]_H1.12_L1.9, MESO-C[MSLN]_H1.13_L1.9, MESO-C[MSLN]_H1.3_L1.13, MESO-C[MSLN]_H1.3_L1.14, MESO-C[MSLN]_H1.3_L1.15, MESO-C[MSLN]_H1.3_L1.16, MESO-C[MSLN]_H1.3_L1.17, MESO-C[MSLN]_H1.3_L1.18, MESO-C[MSLN]_H1.3_L1.9, MESO-C[MSLN]_H1.3_L1.5, MESO-C[MSLN]_H1_L1.20, MESO-C[MSLN]_H1.12_L1.20, MESO-C[MSLN]_H1.14_L1.14, MESO-C[MSLN]_H1.15_L1.14, MESO-C[MSLN]_H1.16_L1.14, MESO-C[MSLN]_H1_L1.19_, MESO-C[MSLN]_H1_L1.21, MESO-C[MSLN]_H1_L1.22, MESO-C[MSLN]_H1.12_L1.19, MESO-C[MSLN]_H1.12_L1.21, MESO-C[MSLN]_H1.12_L1.22, and MESO-C[MSLN]_H1.12_L1.9 (FIGS. 15-21). As will be appreciated by those in the art, suitable MSLN binding domains can comprise a set of 6 CDRs as depicted in the Figures, either as they are underlined or, in the case where a different numbering scheme is used as described herein and as shown in Table 2, as the CDRs that are identified using other alignments within the VH and VL sequences of those depicted in FIGS. 15-21. Suitable ABDs can also include the entire VH and VL sequences as depicted in these sequences and Figures, used as scFvs or as Fabs. In many of the embodiments herein that contain an Fv to MSLN, it is the Fab monomer that binds MSLN.

In addition to the parental CDR sets disclosed in the figures and sequence listing that form an ABD to MSLN, the disclosure provides variant CDR sets. In one embodiment, a set of 6 CDRs can have 1, 2, 3, 4 or 5 amino acid changes from the parental CDRs, as long as the MSLN ABD is still able to bind to the target antigen, as measured by at least one of a Biacore™, surface plasmon resonance (SPR) and/or BLI (biolayer interferometry, e.g. Octet® assay) assay, with the latter finding particular use in many embodiments.

In addition to the parental variable heavy and variable light domains disclosed herein that form an ABD to MSLN, the disclosure provides variant VH and VL domains. In one embodiment, the variant VH and VL domains each can have from 1, 2, 3, 4, 5, 6, 7, 8, 9 or 10 amino acid changes from the parental VH and VL domain, as long as the ABD is still able to bind to the target antigen, as measured by at least one of a Biacore™, surface plasmon resonance (SPR) and/or BLI (biolayer interferometry, e.g. Octet® assay) assay, with the latter finding particular use in many embodiments. In another embodiment, the variant VH and VL are at least 90, 95, 97, 98 or 99% identical to the respective parental VH or VL, as long as the ABD is still able to bind to the target antigen, as measured by at least one of a Biacore™, surface plasmon resonance (SPR) and/or BLI (biolayer interferometry, e.g. Octet® assay) assay, with the latter finding particular use in many embodiments.

Some useful embodiments include: XENP16249, XENP16250, XENP16253, XENP16827, XENP31693.

In some embodiments, the present invention comprises sequences selected from: XENP31701, XENP32550, XENP32551, XENP32552, XENP32553, XENP32554, XENP32555, XENP32556, XENP32557, XENP32558, XENP32559, XENP32560, XENP32561, XENP32562, XENP32563, XENP32564, XENP32565, XENP32566, XENP32567, XENP32568, XENP32569, XENP32570, XENP32937, XENP32938, XENP32939, XENP32940, XENP32941, XENP32942, XENP32942, XENP32943, XENP32944, XENP32945, and XENP32946.

In some embodiments, present invention comprises a variable heavy chain MSLN sequence comprising one or more of the following mutations: S31G, W32Y, M50W, H52N, N53Q, D55G, 194R, T97S, E61Q, E61Y, and/or K100bR.

In some embodiments, the present invention comprises a variable light chain MSLN sequence comprising one or more of the following mutations: A25S, H27Q, D28S, G30L, S32Y, V33L, T37Q, H55E, T56S, S92Y, Y94T, Y94L, Y94V, Y94I, Y94H, D28S and Y100F.

In some embodiments, the MSLN binding domain includes a MSLN binding domain variable heavy domain selected from any of FIGS. 15-18 and 20-21. In some embodiments, the MSLN binding domain includes a MSLN binding domain variable light domain selected from any of FIGS. 15-17 and 19-21. In some embodiments, the MSLN binding domain includes a combination of any of the MSLN binding domain variable heavy domains and variable light domains in FIGS. 15-21.

In some embodiments, the MSLN binding domains include the variable heavy and variable light domain of any one of the MSLN binding domains disclosed in FIGS. 15-21.

2, CD3 Antigen Binding Domains

In some embodiments, one of the ABDs binds CD3. Suitable sets of 6 CDRs and/or VH and VL domains, as well as scFv sequences, are depicted in FIGS. 10A-10F and the Sequence Listing. CD3 binding domain sequences that are of particular use include, but are not limited to, anti-CD3 H1.30_L1.47, anti-CD3 H1.32, anti-CD3 L1.47, anti-CD3 H1.89_L1.47, anti-CD3 H1.90_L1.47, anti-CD3 H1.33_L1.47, anti-CD3 H1.31_L1.47, anti-CD3 L1.47_H1.30, anti-CD3 L1.47_H1.30, anti-CD3 L1.47_H1.32, anti-CD3 L1.47_H1.89, anti-CD3 L1.47_H1.90, anti-CD3 L1.47_H1.33, and anti-CD3 L1.47_H1.31 as depicted in FIGS. 10A-10F.

As will be appreciated by those in the art, suitable CD3 binding domains can comprise a set of 6 CDRs as depicted in FIGS. 10A-10F, either as they are underlined or, in the case where a different numbering scheme is used as described herein and as shown in Table 2, as the CDRs that are identified using other alignments within the VH and VL sequences of those depicted in FIGS. 10A-10F. Suitable ABDs can also include the entire VH and VL sequences as depicted in these sequences and Figures, used as scFvs or as Fabs. In many of the embodiments herein that contain an Fv to CD3, it is the scFv monomer that binds CD3.

In addition to the parental CDR sets disclosed in the figures and sequence listing that form an ABD to CD3, the disclosure provides variant CDR sets. In one embodiment, a set of 6 CDRs can have 1, 2, 3, 4 or 5 amino acid changes from the parental CDRs, as long as the CD3 ABD is still able to bind to the target antigen, as measured by at least one of a Biacore™, surface plasmon resonance (SPR) and/or BLI (biolayer interferometry, e.g. Octet® assay) assay, with the latter finding particular use in many embodiments.

In addition to the parental variable heavy and variable light domains disclosed herein that form an ABD to CD3, the disclosure provides variant VH and VL domains. In one embodiment, the variant VH and VL domains each can have from 1, 2, 3, 4, 5, 6, 7, 8, 9 or 10 amino acid changes from the parental VH and VL domain, as long as the ABD is still able to bind to the target antigen, as measured at least one of a Biacore™, surface plasmon resonance (SPR) and/or BLI (biolayer interferometry, e.g. Octet® assay) assay, with the latter finding particular use in many embodiments. In another embodiment, the variant VH and VL are at least 90, 95, 97, 98 or 99% identical to the respective parental VH or VL, as long as the ABD is still able to bind to the target antigen, as measured by at least one of a Biacore™, surface plasmon resonance (SPR) and/or BLI (biolayer interferometry, e.g. Octet® assay) assay, with the latter finding particular use in many embodiments.

H. Useful Embodiments

Useful embodiments include 1+1 Fab-scFv-Fc formats that comprise: a) a first monomer (the "scFv monomer") that comprises a charged scFv linker (with the +H sequence of FIG. 5 being preferred in some embodiments), the skew variants S364K/E357Q, the ablation variants E233P/L234V/L235A/G236del/S267K, and an scFv that binds to CD3 as outlined herein; b) a second monomer (the "Fab monomer") that comprises the skew variants L368D/K370S, the pI variants N208D/Q295E/N384D/Q418E/N421D, the ablation variants E233P/L234V/L235A/G236del/S267K, and a variable heavy domain; and c) a light chain that includes a variable light domain light domain (VL) and a constant light domain (CL), wherein numbering is according to EU numbering. In some embodiments, the variable heavy domain and variable light domain make up a MSLN binding moiety.

Other useful embodiments include 2+1 Fab₂-scFv-Fc formats that comprise: a) a first monomer (the Fab-scFv-Fc side) that comprises the skew variants S364K/E357Q, the ablation variants E233P/L234V/L235A/G236del/S267K, and a variable heavy domain that, with the variable light domain of the common light chain, makes up an Fv that binds to MSLN as outlined herein, and an scFv domain that binds to CD3; b) a second monomer (the Fab-Fc side) that comprises the skew variants L368D/K370S, the pI variants N208D/Q295E/N384D/Q418E/N421D, the ablation variants E233P/L234V/L235A/G236del/S267K, and a variable heavy domain that, with variable light domain of the common light chain, makes up an Fv that binds to MSLN as outlined herein; and c) a common light chain comprising the variable light domain and a constant light domain, where numbering is according to EU numbering. In some embodiments, the common light chain and variable heavy domains on each monomer form MSLN binding domains.

Some useful embodiments include: XENP16248, XENP16833, XENP31697, XENP32550, XENP32551, XENP32552, XENP32553, XENP32554, XENP32555, XENP32556, XENP32557, XENP32558, XENP32559, XENP32560, XENP32561, XENP32562, XENP32563, XENP32564, XENP32565, XENP32566, XENP32567, XENP32568, XENP32569, XENP32570, XENP32937, XENP32938, XENP32939, XENP32940, XENP32941, XENP32942, XENP32943, XENP32944, XENP32945, XENP32946, XENP33888, XENP33889, XENP30764, XENP30765, XENP31701, XENP33969, XENP33971, XENP33973, XENP16251, XENP16834, XENP16252, and XENP16835.

Other useful embodiments include: XENP31063, XENP31067, XENP31705, XENP31451, XENP31452, XENP31713, XENP31064, XENP31068, XENP31709, ENP32744, XENP32747, XENP32750, XENP32851, XENP31453, XENP31454, XENP31717, XENP32745, XENP32748, XENP32751, XENP32852, XENP32947, XENP32948, XENP32949, XENP32950, XENP32951, XENP33366, XENP33367, XENP33460, XENP33461, XENP33462, XENP33463, XENP33464, XENP33465, XENP33466, XENP33467, XENP33968, XENP33970, XENP33972, XENP34155, XENP34156, XENP34157, XENP34158, XENP31455, XENP31456, XENP32249, XENP32250, XENP32251, XENP32746, XENP32749, XENP32752, XENP32853, XENP33974, XENP33975, XENP33976, XENP33977, XENP33978, XENP33979, XENP33980, XENP34151, XENP34152, XENP34153, XENP34154, XENP34159, XENP34160, XENP34161, and XENP34162.

Some useful embodiments include: XENP16249, XENP16250, XENP16253, XENP16827, XENP31693.

In some embodiments, the present invention comprises sequences selected from: XENP31701, XENP32550, XENP32551, XENP32552, XENP32553, XENP32554, XENP32555, XENP32556, XENP32557, XENP32558, XENP32559, XENP32560, XENP32561, XENP32562, XENP32563, XENP32564, XENP32565, XENP32566, XENP32567, XENP32568, XENP32569, XENP32570, XENP32937, XENP32938, XENP32939, XENP32940, XENP32941, XENP32942, XENP32942, XENP32943, XENP32944, XENP32945, and XENP32946.

In some embodiments, present invention comprises a variable heavy chain MSLN sequence comprising one or more of the following mutations: S31G, W32Y, M50W, H52N, N53Q, D55G, 194R, T97S, E61Q, E61Y, and/or K100bR.

In some embodiments, the present invention comprises a variable light chain MSLN sequence comprising one or more of the following mutations: A25S, H27Q, D28S, G30L, S32Y, V33L, T37Q, H55E, T56S, S92Y, Y94T, Y94L, Y94V, Y94I, Y94H, D28S and Y100F.

In some embodiments, the present invention comprises a MSLN binding domain that includes a MSLN binding domain variable heavy domain selected from any of FIGS. 15-18 and 20-21. In some embodiments, the present invention comprises a MSLN binding domain that includes a MSLN binding domain variable light domain selected from any of FIGS. 15-17 and 19-21. In some embodiments, the present invention comprises a MSLN binding domain that includes a combination of any of the MSLN binding domain variable heavy domains and variable light domains in FIGS. 15-21.

In some embodiments, the MSLN binding domains include the variable heavy and variable light domain of any one of the MSLN binding domains disclosed in FIGS. 15-21.

VI. Nucleic Acids of the Invention

The disclosure further provides nucleic acid compositions encoding the anti-MSLN antibodies provided herein, includ-ing, but not limited to, anti-MSLN×anti-CD3 bispecific antibodies and MSLN monospecific antibodies.

As will be appreciated by those in the art, the nucleic acid compositions will depend on the format and scaffold of the heterodimeric protein. Thus, for example, when the format requires three amino acid sequences, such as for the 1+1 Fab-scFv-Fc format (e.g. a first amino acid monomer comprising an Fc domain and a scFv, a second amino acid monomer comprising a heavy chain and a light chain), three nucleic acid sequences can be incorporated into one or more expression vectors for expression. Similarly, some formats (e.g. dual scFv formats such as disclosed in FIG. 1) only two nucleic acids are needed; again, they can be put into one or two expression vectors.

As is known in the art, the nucleic acids encoding the components of the antibodies described herein can be incorporated into expression vectors as is known in the art, and depending on the host cells used to produce the heterodimeric antibodies described herein. Generally the nucleic acids are operably linked to any number of regulatory elements (promoters, origin of replication, selectable markers, ribosomal binding sites, inducers, etc.). The expression vectors can be extra-chromosomal or integrating vectors.

The nucleic acids and/or expression vectors of the antibodies described herein are then transformed into any number of different types of host cells as is well known in the art, including mammalian, bacterial, yeast, insect and/or fungal cells, with mammalian cells (e.g. CHO cells), finding use in many embodiments.

In some embodiments, nucleic acids encoding each monomer and the optional nucleic acid encoding a light chain, as applicable depending on the format, are each contained within a single expression vector, generally under different or the same promoter controls. In embodiments of particular use in the antibodies described herein, each of these two or three nucleic acids are contained on a different expression vector. As shown herein and in 62/025,931, hereby incorporated by reference, different vector ratios can be used to drive heterodimer formation. That is, surprisingly, while the proteins comprise first monomer: second monomer: light chains (in the case of many of the embodiments herein that have three polypeptides comprising the heterodimeric antibody) in a 1:1:2 ratio, these are not the ratios that give the best results.

The heterodimeric antibodies described herein are made by culturing host cells comprising the expression vector(s) as is well known in the art. Once produced, traditional antibody purification steps are done, including an ion exchange chromatography step. As discussed herein, having the pIs of the two monomers differ by at least 0.5 can allow separation by ion exchange chromatography or isoelectric focusing, or other methods sensitive to isoelectric point. That is, the inclusion of pI substitutions that alter the isoelectric point (pI) of each monomer so that such that each monomer has a different pI and the heterodimer also has a distinct pI, thus facilitating isoelectric purification of the "1+1 Fab-scFv-Fc" and "2+1" heterodimers (e.g., anionic exchange columns, cationic exchange columns). These substitutions also aid in the determination and monitoring of any contaminating dual scFv-Fc and mAb homodimers post-purification (e.g., IEF gels, cIEF, and analytical IEX columns).

VII. Biological and Biochemical Functionality of the Heterodimeric Bispecific Antibodies Generally the bispecific MSLN×CD3 antibodies described herein are administered to patients with cancer, and efficacy is assessed, in a number of ways as described herein. Thus, while standard assays of efficacy can be run, such as cancer load, size of tumor, evaluation of presence or extent of metastasis, etc., immuno-oncology treatments can be assessed on the basis of immune status evaluations as well. This can be done in a number of ways, including both in vitro and in vivo assays.

VIII. Treatments

Once made, the compositions of the antibodies described herein find use in a number of applications. MSLN is highly expressed in renal cell carcinoma, accordingly, the heterodimeric compositions of the antibodies described herein find use in the treatment of such MSLN positive cancers.

IX. Antibody Compositions for In Vivo Administration

Formulations of the antibodies used in accordance with the antibodies described herein are prepared for storage by mixing an antibody having the desired degree of purity with optional pharmaceutically acceptable carriers, excipients or stabilizers (Remington's Pharmaceutical Sciences 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™ nonionic surfactant, PLURONICS™ poloxamers or polyethylene glycol (PEG).

X. Administrative Modalities

The antibodies and chemotherapeutic agents described herein are administered to a subject, in accord with known methods, such as intravenous administration as a bolus or by continuous infusion over a period of time.

XI. Treatment Modalities

In the methods described herein, therapy is used to provide a positive therapeutic response with respect to a disease or condition. By "positive therapeutic response" is intended an improvement in the disease or condition, and/or an improvement in the symptoms associated with the disease or condition. For example, a positive therapeutic response would refer to one or more of the following improvements in the disease: (1) a reduction in the number of neoplastic cells; (2) an increase in neoplastic cell death; (3) inhibition of neoplastic cell survival; (5) inhibition (i.e., slowing to some extent, preferably halting) of tumor growth; (6) an increased patient survival rate; and (7) some relief from one or more symptoms associated with the disease or condition.

Positive therapeutic responses in any given disease or condition can be determined by standardized response criteria specific to that disease or condition. Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bone scan imaging, endoscopy, and tumor biopsy sampling including bone marrow aspiration (BMA) and counting of tumor cells in the circulation.

In addition to these positive therapeutic responses, the subject undergoing therapy may experience the beneficial effect of an improvement in the symptoms associated with the disease.

Treatment according to the disclosure includes a "therapeutically effective amount" of the medicaments used. A "therapeutically effective amount" refers to an amount effective, at dosages and for periods of time necessary, to achieve a desired therapeutic result.

A therapeutically effective amount may vary according to factors such as the disease state, age, sex, and weight of the individual, and the ability of the medicaments to elicit a desired response in the individual. A therapeutically effective amount is also one in which any toxic or detrimental effects of the antibody or antibody portion are outweighed by the therapeutically beneficial effects.

A "therapeutically effective amount" for tumor therapy may also be measured by its ability to stabilize the progression of disease. The ability of a compound to inhibit cancer may be evaluated in an animal model system predictive of efficacy in human tumors.

Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

The specification for the dosage unit forms of the disclosure are dictated by and directly dependent on (a) the unique characteristics of the active compound and the particular therapeutic effect to be achieved, and (b) the limitations inherent in the art of compounding such an active compound for the treatment of sensitivity in individuals.

The efficient dosages and the dosage regimens for the bispecific antibodies described herein depend on the disease or condition to be treated and may be determined by the persons skilled in the art.

An exemplary, non-limiting range for a therapeutically effective amount of an bispecific antibody used in the antibodies described herein is about 0.1-100 mg/kg.

All cited references are herein expressly incorporated by reference in their entirety.

Whereas particular embodiments of the disclosure have been described above for purposes of illustration, it will be appreciated by those skilled in the art that numerous variations of the details may be made without departing from the invention as described in the appended claims.

EXAMPLES

Examples are provided below to illustrate the antibodies described herein. These examples are not meant to constrain the antibodies described herein to any particular application or theory of operation. For all constant region positions discussed in the antibodies described herein, numbering is according to the EU index as in Kabat (Kabat et al., 1991, Sequences of Proteins of Immunological Interest, 5th Ed., United States Public Health Service, National Institutes of Health, Bethesda, entirely incorporated by reference). Those skilled in the art of antibodies will appreciate that this convention consists of nonsequential numbering in specific regions of an immunoglobulin sequence, enabling a normalized reference to conserved positions in immunoglobulin families. Accordingly, the positions of any given immunoglobulin as defined by the EU index will not necessarily correspond to its sequential sequence.

General and specific scientific techniques are outlined in US Publications 2015/0307629, 2014/0288275 and WO2014/145806, all of which are expressly incorporated by reference in their entirety and particularly for the techniques outlined therein.

Example 1: Identifying Surrogates for MSLN-Expressing Tumors

To ensure cell line with biologically valid MSLN antigen densities were used to inform the development of the novel anti-MSLNxanti-CD3 bispecific antibodies of the invention, the expression of MSLN on cancer cell lines was correlated to 191 biopsy cores of serous and mucinous ovarian cancer tissues by IHC to identify surrogate cell lines to use in research and development of the novel bispecific antibodies of the invention. Illustrative IHC of biopsy cores are depicted in FIG. 11, and samples were qualitatively scored in-house on a scale of 0-3 with 0 representing little to no MSLN expression and 3 representing high MSLN expression (herein referred to as IHC score; breakdown of score for each core is depicted in FIG. 12). Based on the results, it was determined that the novel bispecific antibodies of the invention should target score 3 and score 2 cell lines as they represent 80% of the patient segment and should not target score 1 cell lines as they resembles normal tissue. Next, endogenous MSLN expression on cancer cell lines were investigated by IHC and flow cytometry, data for which are depicted in FIG. 13. MSLN-transfected A549 cells were found to stain as intensely as ovarian cancer tumors expressing high amounts of MSLN (data not shown). OVCAR-8 cancer cells and ASPC-1 cells represent high and medium MSLN-expressing tumors (score 3 or 2 by IHC). Finally, SKOV3, HT29, MCF7, Huh7, and A549 (parental) cancer cells were found to have MSLN-expression level correlating to non-cancer adjacent tissues and therefore identified as appropriate surrogates of normal tissues.

Example 2: Binding Domains

2A: CD3 Binding Domains

Sequences for CD3 binding domains having different CD3 binding affinities are depicted in FIG. 10.

2B: MSLN Binding Domains

The variable regions of anti-human MSLN binding domains designated MSLN-A, MSLN-B, and MSLN-C are depicted in FIGS. 15-17.

2B (a): Tuning MSLN-C Binding Affinity for MSLN

Variants of MESO-C were engineered by introducing point substitutions into the variable heavy region (VH) and the variable light region (VL) to generate 11 VH variants and 16 VL variants (sequences for which are depicted in FIG. 18 as H1.1-H1.13 and in FIG. 19 as L1.1-L1.18). An additional 4 VL variants were generated by combining useful point substitutions (sequences for which are depicted in FIG. 19 as L1.19-L1.22). WT and variant variable heavy regions were paired with WT and variant variable light regions to generate variant variable regions (Fvs) which were produced in the context of anti-MSLNxanti-CD3 bispecific antibodies. The bispecific antibodies were screened for MSLN binding affinity using Octet®, a BioLayer Interferometry (BLI)-based method. Experimental steps for Octet® generally include the following: Immobilization (capture of ligand to a biosensor); Association (dipping of ligand-coated biosensors into wells containing the analyte); and Dissociation (returning of biosensors to well containing buffer). In an initial screening, anti-human Fc sensors were used to capture the bispecific mAbs and dipped into human MSLN antigen (one concentration to screen large library). The resulting dissociation constant of illustrative variants ($K_D$), association rate (ka), dissociation rate (ka), as well as sensorgram response are depicted in FIG. 20. In further screening of favorite variants identified in the initial screen (and combination variants), bispecific mAbs were dipped into multiple concentrations of human MSLN antigen, data for which are depicted in FIG. 21 (from various screens).

2C: Engineering Anti-MSLNxAnti-CD3 Bispecific Antibodies (bsAbs)

A number of formats for αMSLNxαCD3 bispecific antibodies (bsAbs) were conceived, illustrative formats for which are outlined below and in FIG. 22.

One such format is the 1+1 Fab-scFv-Fc format which comprises a single-chain Fv ("scFv") covalently attached to a first heterodimeric Fc domain, a heavy chain variable region (VH) covalently attached to a complementary second heterodimeric Fc domain, and a light chain (LC) transfected separately so that a Fab domain is formed with the variable heavy domain.

Another format is the 2+1 Fab$_2$-scFv-Fc format which comprises a VH domain covalently attached to a CH1 domain covalently attached to an scFv covalently attached to a first heterodimeric Fc domain (VH-CH1-scFv-Fc), a VH domain covalently attached to a complementary second heterodimeric Fc domain, and a LC transfected separately so that Fab domains are formed with the VH domains.

DNA encoding chains of the αMSLNxαCD3 bsAbs were generated by standard gene synthesis followed by isothermal cloning (Gibson Assembly® molecular cloning method) or subcloning into a pTT5 expression vector containing fusion partners (e.g. domain linkers as depicted in FIG. 6 and/or backbones as depicted in FIGS. 7-9). DNA was transfected into HEK293E cells for expression. Sequences for illustrative αMLSNxαCD3 bsAbs (based on binding domains as described in Example 2B) in the 1+1 Fab-scFv-Fc format and in the 2+1 Fab$_2$-scFv-Fc format are depicted respectively in FIGS. 23-32. A number of formats for αMSLNx αCD3 bispecific antibodies (bsAbs) were conceived, illustrative formats for which are outlined below and in FIG. 19.

One such format is the 1+1 Fab-scFv-Fc format which comprises a single-chain Fv ("scFv") covalently attached to a first heterodimeric Fc domain, a heavy chain variable region (VH) covalently attached to a complementary second heterodimeric Fc domain, and a light chain (LC) transfected separately so that a Fab domain is formed with the variable heavy domain.

Another format is the 2+1 Fab₂-scFv-Fc format which comprises a VH domain covalently attached to a CH1 domain covalently attached to an scFv covalently attached to a first heterodimeric Fc domain (VH-CH1-scFv-Fc), a VH domain covalently attached to a complementary second heterodimeric Fc domain, and a LC transfected separately so that Fab domains are formed with the VH domains.

DNA encoding chains of the αMSLNxαCD3 bsAbs were generated by standard gene synthesis followed by isothermal cloning (Gibson Assembly® molecular cloning method) or subcloning into a pTT5 expression vector containing fusion partners (e.g. domain linkers as depicted in FIG. 6 and/or backbones as depicted in FIGS. 7-9). DNA was transfected into HEK293E cells for expression. Sequences for illustrative αMLSNxαCD3 bsAbs (based on binding domains as described in Example 2B) in the 1+1 Fab-scFv-Fc format and in the 2+1 Fab₂-scFv-Fc format are depicted respectively in FIGS. 20-29.

Example 3: Tuning Anti-MSLNxAnti-CD3 bsAbs to Enhance Selectivity and Therapeutic Index 3A: Higher Valency MSLN Binding Promotes T Cell Activity In initial investigations, the activity of anti-MSLNxanti-CD3 bsAbs in the 1+1 Fab-scFv-Fc format were compared to anti-MSLNxanti-CD3 bsAbs in the 2+1 Fab₂-scFv-Fc format. Test articles were incubated with 10,000 Kuramochi cells and 100,000 human T cells. 5 μL anti-human CD107a-APC were added. Cells were incubated for 24 hours at 37° C., and analyzed by flow cytometry, data for which are presented in FIGS. 33-34. Collectively, the data show that anti-MSLNxanti-CD3 bsAbs in the 2+1 Fab₂-scFv-Fc format promoted activity of CD8⁺ and CD4⁺ T cells (as indicated by degranulation with CD107a, CD25 expression, and CD69 expression) more potently than corresponding 1+1 Fab-scFv-Fc bsAbs.

3B: Tuning MSLN Binding Affinity 3B (a): Reducing MSLN Binding Affinity Promotes Avid Binding in the 2+1 Format Next, the effect of MSLN binding affinity was investigated. 100,000 OVCAR8 (MSLN^high) cells were treated with the indicated concentrations of the indicated test articles. Binding was detected using A647-labelled anti-human Fc mAb, data for which are shown in FIG. 35. The data show that as the MSLN binding affinity is decreased, the 2+1 Fab₂-scFv-Fc format provides more potent binding to OVCAR8 cells than the 1+1 Fab-scFv-Fc format. This indicates that reduction of MSLN binding affinity promotes avid binding by bsAbs in the 2+1 Fab₂-scFv-Fc format to MSLN^high cells, as is readily observable for each of H1_L1.9 (3.9 nM $K_D$), H1.3_L1 (9.2 nM $K_D$), H1. 12_L1.9 (10.2 nM $K_D$), and H1_L1.5 (~12.8 nM $K_D$). Further, XENP32852 and XENP32853 which differ only in CD3 binding affinity have identical binding to OVCAR8 cells confirming that avid binding is due to the MSLN binding domain.

3B (b): Reducing MSLN Binding Affinity Enables Selectivity for Higher Antigen Density Cell Lines Having determined that reducing MSLN binding affinity promoted avid binding in the 2+1 Fab₂-scFv-Fc format to MSLN^high cells, the next step was to determine whether this subsequently conveys selective activity on higher density cell lines.

Accordingly in a first experiment, the 2+1 Fab₂-scFv-Fc bsAbs investigated in Example 3B (a) were further probed in an RTCC assay. Cancer cells with varying MSLN densities (A549, HT29, MCF7, OVCAR8, and SKOV3) were transduced to constitutively express luciferase. Luciferase released from dead cancer cells rapidly degrades in assay media, so live target cells can be quantified based on luminescence readout. The luciferase-transduced cancer cells were incubated with T cells (effector: target ratio 10:1) for 24 hours. Test articles were added to the cells and incubated for 48 additional hours. Following incubation, Bio-Glo™ Luciferase reagent (PROMEGA™ Corporation, Madison, WI.) was added and plates were read with the Envision® Reader plate reader on luminescence setting. % RTCC was calculated by 1-(Raw Value/PBS AVG))*100. Data depicting dose-dependent induction of RTCC by the test articles on the various cells lines are depicted in FIG. 36. The data show that at high MSLN binding affinity, the 2+1 bsAbs induced potent RTCC on MSLN^high OVCAR8 cell lines as well as MSLN^low SKOV3 and HT29 cell lines. However, as MSLN binding affinity is reduced, the RTCC potency of the 2+1 bsAbs on the MSLN^low cell lines is reduced. However, there is room for further improvement in selectivity for MSLN^med/high cells.

Accordingly in another set of experiments, 2+1 Fab₂-scFv-Fc anti-MSLNxanti-CD3 bsAbs having further reduced MSLN affinity were explored. In one set of experiments, RTCC was assessed as described above using luciferase-transduced cancer cells. In a second experiment, RTCC was assessed using xCELLigence® Real Time Cell Analysis instrument (ACEA Biosciences™, San Diego, CA). Data from each experiment are depicted in FIGS. 37-38. The data show that XENP33366 having 90.4 nM MSLN binding affinity enabled improved selectivity for MSLN^high OVCAR8, as indicated by reduced potency in killing of SKOV3 cells and more potent killing of OVCAR8. XENP33367 having 246 nM MSLN binding affinity demonstrated little to no RTCC activity on MSLN^low cells, but was also less potent on OVCAR8 than XENP33366. Notably, the data also show that even with the drastic reduction in MSLN binding affinity to enhance selectivity, RTCC activity on ASPC-1, a cancer cell line with ~36K surface MSLN expression and a lower cancer IHC score (Score 2), was not compromised.

In yet another set of experiments, T cells were treated with a dose titration of the above test articles and various cancer cell lines (effector: target ratio 10:1) for 24 hours and assessed for proliferation, degranulation, and activation (as indicated by percentage CD3⁺ T cells respectively staining for Ki67, CD107a, and CD25), data for which are depicted in FIGS. 39-41. Notably, each of the three bispecific antibodies enabled proliferation in the presence of Score 3 and Score 2 cell lines, but not in the presence of Score 1 cell lines. Consistent with the RTCC data above, reduction in MSLN binding affinity reduced T cell degranulation and activation in the presence of Score 1 cell lines. Importantly even at drastically reduced MSLN binding affinity (i.e. for XENP33367), T cell proliferation, degranulation, and activation were not compromised for Score 3 and Score 2 cancer cell lines.

3C: Tuning CD3 Binding Affinity

Another approach explored for optimizing the anti-MSLN×anti-CD3 bispecific antibodies was tuning CD3 binding affinity. Accordingly, anti-MSLN×anti-CD3 bs Abs in the 2+1 Fab$_2$-scFv-Fc format having either CD3 High-Int #1 or CD3 High-Int #2 binding domains were investigated in an RTCC assay. RTCC was assessed as described above using luciferase-transduced cancer cells, data for which are depicted in FIG. 42. Collectively, the data show that reducing the CD3 binding affinity may also convey selective targeting to high expressing cell lines (even with higher affinity MSLN binding).

While exemplary embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCE LISTING

```
Sequence total quantity: 618
SEQ ID NO: 1              moltype = AA  length = 20
FEATURE                   Location/Qualifiers
REGION                    1..20
                          note = Description of Artificial Sequence: Synthetic peptide
source                    1..20
                          mol_type = protein
                          organism = synthetic construct
SEQUENCE: 1
GKPGSGKPGS GKPGSGKPGS                                              20

SEQ ID NO: 2              moltype = AA  length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 2
GGGGS                                                              5

SEQ ID NO: 3              moltype = AA  length = 5
FEATURE                   Location/Qualifiers
REGION                    1..5
                          note = Description of Artificial Sequence: Synthetic peptide
REGION                    1..5
                          note = See specification as filed for detailed description
                           of substitutions and preferred embodiments
source                    1..5
                          mol_type = protein
                          organism = synthetic construct
SEQUENCE: 3
GSGGS                                                              5

SEQ ID NO: 4              moltype = AA  length = 4
FEATURE                   Location/Qualifiers
REGION                    1..4
                          note = Description of Artificial Sequence: Synthetic peptide
REGION                    1..4
                          note = See specification as filed for detailed description
                           of substitutions and preferred embodiments
source                    1..4
                          mol_type = protein
                          organism = synthetic construct
SEQUENCE: 4
GGGS                                                              4

SEQ ID NO: 5              moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 5
GGGGSGGGGS GGGGS                                                   15

SEQ ID NO: 6              moltype = AA  length = 18
FEATURE                   Location/Qualifiers
REGION                    1..18
                          note = Description of Artificial Sequence: Synthetic peptide
source                    1..18
```

```
                          mol_type = protein
                          organism = synthetic construct
SEQUENCE: 6
GSTSGSGKPG SGEGSTKG                                              18

SEQ ID NO: 7             moltype = AA   length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 7
IRPRAIGGSK PRVA                                                  14

SEQ ID NO: 8             moltype = AA   length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 8
GKGGSGKGGS GKGGS                                                 15

SEQ ID NO: 9             moltype = AA   length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 9
GGKGSGGKGS GGKGS                                                 15

SEQ ID NO: 10            moltype = AA   length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 10
GGGKSGGGKS GGGKS                                                 15

SEQ ID NO: 11            moltype = AA   length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 11
GKGKSGKGKS GKGKS                                                 15

SEQ ID NO: 12            moltype = AA   length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 12
GGGKSGGKGS GKGGS                                                 15

SEQ ID NO: 13            moltype = AA   length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 13
GKPGSGKPGS GKPGS                                                 15

SEQ ID NO: 14            moltype = AA   length = 20
FEATURE                  Location/Qualifiers
REGION                   1..20
                         note = Description of Artificial Sequence: Synthetic peptide
```

-continued

```
source                    1..20
                          mol_type = protein
                          organism = synthetic construct
SEQUENCE: 14
GKGKSGKGKS GKGKSGKGKS                                              20

SEQ ID NO: 15             moltype = AA  length = 20
FEATURE                   Location/Qualifiers
REGION                    1..20
                          note = Description of Artificial Sequence: Synthetic peptide
source                    1..20
                          mol_type = protein
                          organism = synthetic construct
SEQUENCE: 15
GGGGSGGGGS GGGGSGGGGS                                              20

SEQ ID NO: 16             moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 16
STAGDTHLGG EDFD                                                    14

SEQ ID NO: 17             moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 17
GEGGSGEGGS GEGGS                                                   15

SEQ ID NO: 18             moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 18
GGEGSGGEGS GGEGS                                                   15

SEQ ID NO: 19             moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 19
GGGESGGGES GGGES                                                   15

SEQ ID NO: 20             moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 20
GEGESGEGES GEGES                                                   15

SEQ ID NO: 21             moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 21
GGGESGGEGS GEGGS                                                   15

SEQ ID NO: 22             moltype = AA  length = 20
FEATURE                   Location/Qualifiers
REGION                    1..20
```

-continued

```
                            note = Description of Artificial Sequence: Synthetic peptide
source                      1..20
                            mol_type = protein
                            organism = synthetic construct
SEQUENCE: 22
GEGESGEGES GEGESGEGES                                                      20

SEQ ID NO: 23               moltype = AA  length = 19
FEATURE                     Location/Qualifiers
REGION                      1..19
                            note = Description of Artificial Sequence: Synthetic peptide
source                      1..19
                            mol_type = protein
                            organism = synthetic construct
SEQUENCE: 23
PRGASKSGSA SQTGSAPGS                                                       19

SEQ ID NO: 24               moltype = AA  length = 19
FEATURE                     Location/Qualifiers
REGION                      1..19
                            note = Description of Artificial Sequence: Synthetic peptide
source                      1..19
                            mol_type = protein
                            organism = synthetic construct
SEQUENCE: 24
GTAAAGAGAA GGAAAGAAG                                                       19

SEQ ID NO: 25               moltype = AA  length = 19
FEATURE                     Location/Qualifiers
REGION                      1..19
                            note = Description of Artificial Sequence: Synthetic peptide
source                      1..19
                            mol_type = protein
                            organism = synthetic construct
SEQUENCE: 25
GTSGSSGSGS GGSGSGGGG                                                       19

SEQ ID NO: 26               moltype = AA  length = 10
FEATURE                     Location/Qualifiers
REGION                      1..10
                            note = Description of Artificial Sequence: Synthetic peptide
source                      1..10
                            mol_type = protein
                            organism = synthetic construct
SEQUENCE: 26
GGGGSGGGGS                                                                 10

SEQ ID NO: 27               moltype = AA  length = 25
FEATURE                     Location/Qualifiers
REGION                      1..25
                            note = Description of Artificial Sequence: Synthetic peptide
source                      1..25
                            mol_type = protein
                            organism = synthetic construct
SEQUENCE: 27
GGGGSGGGGS GGGGSGGGGS GGGGS                                                25

SEQ ID NO: 28               moltype = AA  length = 30
FEATURE                     Location/Qualifiers
REGION                      1..30
                            note = Description of Artificial Sequence: Synthetic
                             polypeptide
source                      1..30
                            mol_type = protein
                            organism = synthetic construct
SEQUENCE: 28
GGGGSGGGGS GGGGSGGGGS GGGGSGGGGS                                           30

SEQ ID NO: 29               moltype = AA  length = 35
FEATURE                     Location/Qualifiers
REGION                      1..35
                            note = Description of Artificial Sequence: Synthetic
                             polypeptide
source                      1..35
                            mol_type = protein
                            organism = synthetic construct
SEQUENCE: 29
GGGGSGGGGS GGGGSGGGGS GGGGSGGGGS GGGGS                                     35
```

-continued

```
SEQ ID NO: 30            moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 30
GGGGA                                                              5

SEQ ID NO: 31            moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 31
GGGGAGGGGA                                                         10

SEQ ID NO: 32            moltype = AA  length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 32
GGGGAGGGGA GGGGA                                                   15

SEQ ID NO: 33            moltype = AA  length = 20
FEATURE                  Location/Qualifiers
REGION                   1..20
                         note = Description of Artificial Sequence: Synthetic peptide
source                   1..20
                         mol_type = protein
                         organism = synthetic construct
SEQUENCE: 33
GGGGAGGGGA GGGGAGGGGA                                              20

SEQ ID NO: 34            moltype = AA  length = 25
FEATURE                  Location/Qualifiers
REGION                   1..25
                         note = Description of Artificial Sequence: Synthetic peptide
source                   1..25
                         mol_type = protein
                         organism = synthetic construct
SEQUENCE: 34
GGGGAGGGGA GGGGAGGGGA GGGGA                                        25

SEQ ID NO: 35            moltype = AA  length = 30
FEATURE                  Location/Qualifiers
REGION                   1..30
                         note = Description of Artificial Sequence: Synthetic
                          polypeptide
source                   1..30
                         mol_type = protein
                         organism = synthetic construct
SEQUENCE: 35
GGGGAGGGGA GGGGAGGGGA GGGGAGGGGA                                   30

SEQ ID NO: 36            moltype = AA  length = 35
FEATURE                  Location/Qualifiers
REGION                   1..35
                         note = Description of Artificial Sequence: Synthetic
                          polypeptide
source                   1..35
                         mol_type = protein
                         organism = synthetic construct
SEQUENCE: 36
GGGGAGGGGA GGGGAGGGGA GGGGAGGGGA GGGGA                             35

SEQ ID NO: 37            moltype = AA  length = 30
FEATURE                  Location/Qualifiers
REGION                   1..30
                         note = Description of Artificial Sequence: Synthetic
                          polypeptide
source                   1..30
                         mol_type = protein
```

```
                          organism = synthetic construct
SEQUENCE: 37
DPALVHQRPA PPGGGGSGGG GSGGGGSGGG                                     30

SEQ ID NO: 38            moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 38
GKPGS                                                               5

SEQ ID NO: 39            moltype = AA  length = 25
FEATURE                  Location/Qualifiers
REGION                   1..25
                         note = Description of Artificial Sequence: Synthetic peptide
source                   1..25
                         mol_type = protein
                         organism = synthetic construct
SEQUENCE: 39
GKPGSGKPGS GKPGSGKPGS GKPGS                                         25

SEQ ID NO: 40            moltype = AA  length = 30
FEATURE                  Location/Qualifiers
REGION                   1..30
                         note = Description of Artificial Sequence: Synthetic
                          polypeptide
source                   1..30
                         mol_type = protein
                         organism = synthetic construct
SEQUENCE: 40
GKPGSGKPGS GKPGSGKPGS GKPGSGKPGS                                    30

SEQ ID NO: 41            moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 41
GGGES                                                               5

SEQ ID NO: 42            moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 42
KTHTCPPCP                                                           9

SEQ ID NO: 43            moltype = AA  length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 43
EPKSSDKTHT CPPCP                                                    15

SEQ ID NO: 44            moltype = AA  length = 19
FEATURE                  Location/Qualifiers
REGION                   1..19
                         note = Description of Artificial Sequence: Synthetic peptide
source                   1..19
                         mol_type = protein
                         organism = synthetic construct
SEQUENCE: 44
GGGGSGGGGS KTHTCPPCP                                                19

SEQ ID NO: 45            moltype = AA  length = 19
FEATURE                  Location/Qualifiers
REGION                   1..19
                         note = Description of Artificial Sequence: Synthetic peptide
```

```
source                    1..19
                          mol_type = protein
                          organism = synthetic construct
SEQUENCE: 45
GKPGSGKPGS KTHTCPPCP                                                    19

SEQ ID NO: 46             moltype = AA  length = 14
FEATURE                   Location/Qualifiers
REGION                    1..14
                          note = Description of Artificial Sequence: Synthetic peptide
source                    1..14
                          mol_type = protein
                          organism = synthetic construct
SEQUENCE: 46
GKPGSKTHTC PPCP                                                         14

SEQ ID NO: 47             moltype = AA  length = 329
FEATURE                   Location/Qualifiers
REGION                    1..329
                          note = Description of Artificial Sequence: Synthetic
                           polypeptide
REGION                    1..329
                          note = 1 + 1 Fab-scFv-Fc Backbone 1 Fab-Fc Side
source                    1..329
                          mol_type = protein
                          organism = synthetic construct
SEQUENCE: 47
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS DTKVDKKVEP KSCDKTHTCP PCPAPPVAGP  120
SVFLFPPKPK DTLMISRTPE VTCVVVDVKH EDPEVKFNWY VDGVEVHNAK TKPREEEYNS  180
TYRVVSVLTV LHQDWLNGKE YKCKVSNKAL PAPIEKTISK AKGQPREPQV YTLPPSREEM  240
TKNQVSLTCD VSGFYPSDIA VEWESDGQPE NNYKTTPPVL DSDGSFFLYS KLTVDKSRWE  300
QGDVFSCSVM HEALHNHYTQ KSLSLSPGK                                     329

SEQ ID NO: 48             moltype = AA  length = 231
FEATURE                   Location/Qualifiers
REGION                    1..231
                          note = Description of Artificial Sequence: Synthetic
                           polypeptide
REGION                    1..231
                          note = 1 + 1 Fab-scFv-Fc Backbone 1 scFv-Fc Side
source                    1..231
                          mol_type = protein
                          organism = synthetic construct
SEQUENCE: 48
EPKSSDKTHT CPPCPAPPVA GPSVFLFPPK PKDTLMISRT PEVTCVVVDV KHEDPEVKFN  60
WYVDGVEVHN AKTKPREEQY NSTYRVVSVL TVLHQDWLNG KEYKCKVSNK ALPAPIEKTI  120
SKAKGQPREP QVYTLPPSRE QMTKNQVKLT CLVKGFYPSD IAVEWESNGQ PENNYKTTPP  180
VLDSDGSFFL YSKLTVDKSR WQQGNVFSCS VMHEALHNHY TQKSLSLSPG K            231

SEQ ID NO: 49             moltype = AA  length = 329
FEATURE                   Location/Qualifiers
REGION                    1..329
                          note = Description of Artificial Sequence: Synthetic
                           polypeptide
REGION                    1..329
                          note = 1 + 1 Fab-scFv-Fc Backbone 2 Fab-Fc Side
source                    1..329
                          mol_type = protein
                          organism = synthetic construct
SEQUENCE: 49
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS DTKVDKKVEP KSCDKTHTCP PCPAPPVAGP  120
SVFLFPPKPK DTLMISRTPE VTCVVVDVKH EDPEVKFNWY VDGVEVHNAK TKPREEEYNS  180
TYRVVSVLTV LHQDWLNGKE YKCKVSNKAL PAPIEKTISK AKGQPREPQV YTLPPSREEM  240
TKNQVSLTCD VSGFYPSDIA VEWESDGQPE NNYKTTPPVL DSDGSFFLYS KLTVDKSRWE  300
QGDVFSCSVM HEALHNHYTQ KSLSLSPGK                                     329

SEQ ID NO: 50             moltype = AA  length = 231
FEATURE                   Location/Qualifiers
REGION                    1..231
                          note = Description of Artificial Sequence: Synthetic
                           polypeptide
REGION                    1..231
                          note = 1 + 1 Fab-scFv-Fc Backbone 2 scFv-Fc Side
source                    1..231
                          mol_type = protein
                          organism = synthetic construct
SEQUENCE: 50
```

-continued

```
EPKSSDKTHT CPPCPAPPVA GPSVFLFPPK PKDTLMISRT PEVTCVVVDV KHEDPEVKFN    60
WYVDGVEVHN AKTKPREEQY NSTYRVVSVL TVLHQDWLNG KEYKCKVSNK ALPAPIEKTI   120
SKAKGQPREP QVYTLPPSRE EMTKNQVKLT CLVKGFYPSD IAVEWESNGQ PENNYKTTPP   180
VLDSDGSFFL YSKLTVDKSR WQQGNVFSCS VMHEALHNHY TQKSLSLSPG K            231

SEQ ID NO: 51            moltype = AA  length = 329
FEATURE                  Location/Qualifiers
REGION                   1..329
                         note = Description of Artificial Sequence: Synthetic
                          polypeptide
REGION                   1..329
                         note = 1 + 1 Fab-scFv-Fc Backbone 3 Fab-Fc Side
source                   1..329
                         mol_type = protein
                         organism = synthetic construct
SEQUENCE: 51
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS DTKVDKKVEP KSCDKTHTCP PCPAPPVAGP   120
SVFLFPPKPK DTLMISRTPE VTCVVVDVKH EDPEVKFNWY VDGVEVHNAK TKPREEEYNS   180
TYRVVSVLTV LHQDWLNGKE YKCKVSNKAL PAPIEKTISK AKGQPREPQV YTLPPSREEM   240
TKNQVSLTCE VSGFYPSDIA VEWESDGQPE NNYKTTPPVL DSDGSFFLYS KLTVDKSRWE   300
QGDVFSCSVM HEALHNHYTQ KSLSLSPGK                                     329

SEQ ID NO: 52            moltype = AA  length = 231
FEATURE                  Location/Qualifiers
REGION                   1..231
                         note = Description of Artificial Sequence: Synthetic
                          polypeptide
REGION                   1..231
                         note = 1 + 1 Fab-scFv-Fc Backbone 3 scFv-Fc Side
source                   1..231
                         mol_type = protein
                         organism = synthetic construct
SEQUENCE: 52
EPKSSDKTHT CPPCPAPPVA GPSVFLFPPK PKDTLMISRT PEVTCVVVDV KHEDPEVKFN    60
WYVDGVEVHN AKTKPREEQY NSTYRVVSVL TVLHQDWLNG KEYKCKVSNK ALPAPIEKTI   120
SKAKGQPREP QVYTLPPSRE EMTKNQVKLT CLVKGFYPSD IAVEWESNGQ PENNYKTTPP   180
VLDSDGSFFL YSKLTVDKSR WQQGNVFSCS VMHEALHNHY TQKSLSLSPG K            231

SEQ ID NO: 53            moltype = AA  length = 329
FEATURE                  Location/Qualifiers
REGION                   1..329
                         note = Description of Artificial Sequence: Synthetic
                          polypeptide
REGION                   1..329
                         note = 1 + 1 Fab-scFv-Fc Backbone 4 Fab-Fc Side
source                   1..329
                         mol_type = protein
                         organism = synthetic construct
SEQUENCE: 53
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS DTKVDKKVEP KSCDKTHTCP PCPAPPVAGP   120
SVFLFPPKPK DTLMISRTPE VTCVVVDVKH EDPEVKFNWY VDGVEVHNAK TKPREEEYNS   180
TYRVVSVLTV LHQDWLNGKE YKCKVSNKAL PAPIEKTISK AKGQPREPQV YTLPPSREEM   240
TENEVSLTCL VKGFYPSDIA VEWESDGQPE NNYKTTPPVL DSDGSFFLYS KLEVDKSRWE   300
QGDVFSCSVM HEALHNHYTQ KSLSLSPGK                                     329

SEQ ID NO: 54            moltype = AA  length = 231
FEATURE                  Location/Qualifiers
REGION                   1..231
                         note = Description of Artificial Sequence: Synthetic
                          polypeptide
REGION                   1..231
                         note = 1 + 1 Fab-scFv-Fc Backbone 4 scFv-Fc Side
source                   1..231
                         mol_type = protein
                         organism = synthetic construct
SEQUENCE: 54
EPKSSDKTHT CPPCPAPPVA GPSVFLFPPK PKDTLMISRT PEVTCVVVDV KHEDPEVKFN    60
WYVDGVEVHN AKTKPREEQY NSTYRVVSVL TVLHQDWLNG KEYKCKVSNK ALPAPIEKTI   120
SKAKGQPREP QVYTLPPSRE EMTKNQVSLT CLVKGFYPSD IAVEWESNGQ PENNYKTTPP   180
VLDSKGSFFL YSKLTVDKSR WQQGNVFSCS VMHEALHNHY TQKSLSLSPG K            231

SEQ ID NO: 55            moltype = AA  length = 329
FEATURE                  Location/Qualifiers
REGION                   1..329
                         note = Description of Artificial Sequence: Synthetic
                          polypeptide
REGION                   1..329
```

```
                          note = 1 + 1 Fab-scFv-Fc Backbone 5 Fab-Fc Side
source                    1..329
                          mol_type = protein
                          organism = synthetic construct
SEQUENCE: 55
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS DTKVDKKVEP KSCDKTHTCP PCPAPPVAGP  120
SVFLFPPKPK DTLMISRTPE VTCVVVDVKH EDPEVKFNWY VDGVEVHNAK TKPREEEYNS  180
TYRVVSVLTV LHQDWLNGKE YKCKVSNKAL PAPIEKTISK AKGQPREPQV YTLPPSRDEL  240
TKNQVSLTCD VSGFYPSDIA VEWESDGQPE NNYKTTPPVL DSDGSFFLYS KLTVDKSRWE  300
QGDVFSCSVM HEALHNHYTQ KSLSLSPGK                                    329

SEQ ID NO: 56           moltype = AA  length = 231
FEATURE                 Location/Qualifiers
REGION                  1..231
                        note = Description of Artificial Sequence: Synthetic
                         polypeptide
REGION                  1..231
                        note = 1 + 1 Fab-scFv-Fc Backbone 5 scFv-Fc Side
source                  1..231
                        mol_type = protein
                        organism = synthetic construct
SEQUENCE: 56
EPKSSDKTHT CPPCPAPPVA GPSVFLFPPK PKDTLMISRT PEVTCVVVDV KHEDPEVKFN  60
WYVDGVEVHN AKTKPREEQY NSTYRVVSVL TVLHQDWLNG KEYKCKVSNK ALPAPIEKTI  120
SKAKGQPREP QVYTLPPSRD QLTKNQVKLT CLVKGFYPSD IAVEWESNGQ PENNYKTTPP  180
VLDSDGSFFL YSKLTVDKSR WQQGNVFSCS VMHEALHNHY TQKSLSLSPG K           231

SEQ ID NO: 57           moltype = AA  length = 329
FEATURE                 Location/Qualifiers
REGION                  1..329
                        note = Description of Artificial Sequence: Synthetic
                         polypeptide
REGION                  1..329
                        note = 1 + 1 Fab-scFv-Fc Backbone 6 Fab-Fc Side
source                  1..329
                        mol_type = protein
                        organism = synthetic construct
SEQUENCE: 57
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS DTKVDKKVEP KSCDKTHTCP PCPAPPVAGP  120
SVFLFPPKPK DTLMISRTPE VTCVVVDVKH EDPEVKFNWY VDGVEVHNAK TKPREEEYAS  180
TYRVVSVLTV LHQDWLNGKE YKCKVSNKAL PAPIEKTISK AKGQPREPQV YTLPPSREEM  240
TKNQVSLTCD VSGFYPSDIA VEWESDGQPE NNYKTTPPVL DSDGSFFLYS KLTVDKSRWE  300
QGDVFSCSVM HEALHNHYTQ KSLSLSPGK                                    329

SEQ ID NO: 58           moltype = AA  length = 231
FEATURE                 Location/Qualifiers
REGION                  1..231
                        note = Description of Artificial Sequence: Synthetic
                         polypeptide
REGION                  1..231
                        note = 1 + 1 Fab-scFv-Fc Backbone 6 scFv-Fc Side
source                  1..231
                        mol_type = protein
                        organism = synthetic construct
SEQUENCE: 58
EPKSSDKTHT CPPCPAPPVA GPSVFLFPPK PKDTLMISRT PEVTCVVVDV KHEDPEVKFN  60
WYVDGVEVHN AKTKPREEQY ASTYRVVSVL TVLHQDWLNG KEYKCKVSNK ALPAPIEKTI  120
SKAKGQPREP QVYTLPPSRE QMTKNQVKLT CLVKGFYPSD IAVEWESNGQ PENNYKTTPP  180
VLDSDGSFFL YSKLTVDKSR WQQGNVFSCS VMHEALHNHY TQKSLSLSPG K           231

SEQ ID NO: 59           moltype = AA  length = 329
FEATURE                 Location/Qualifiers
REGION                  1..329
                        note = Description of Artificial Sequence: Synthetic
                         polypeptide
REGION                  1..329
                        note = 1 + 1 Fab-scFv-Fc Backbone 7 Fab-Fc Side
source                  1..329
                        mol_type = protein
                        organism = synthetic construct
SEQUENCE: 59
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS DTKVDKKVEP KSCDKTHTCP PCPAPPVAGP  120
SVFLFPPKPK DTLMISRTPE VTCVVVDVKH EDPEVKFNWY VDGVEVHNAK TKPREEEYSS  180
TYRVVSVLTV LHQDWLNGKE YKCKVSNKAL PAPIEKTISK AKGQPREPQV YTLPPSREEM  240
TKNQVSLTCD VSGFYPSDIA VEWESDGQPE NNYKTTPPVL DSDGSFFLYS KLTVDKSRWE  300
QGDVFSCSVM HEALHNHYTQ KSLSLSPGK                                    329
```

```
SEQ ID NO: 60          moltype = AA  length = 231
FEATURE                Location/Qualifiers
REGION                 1..231
                       note = Description of Artificial Sequence: Synthetic
                        polypeptide
REGION                 1..231
                       note = 1 + 1 Fab-scFv-Fc Backbone 7 scFv-Fc Side
source                 1..231
                       mol_type = protein
                       organism = synthetic construct
SEQUENCE: 60
EPKSSDKTHT CPPCPAPPVA GPSVFLFPPK PKDTLMISRT PEVTCVVVDV KHEDPEVKFN  60
WYVDGVEVHN AKTKPREEQY SSTYRVVSVL TVLHQDWLNG KEYKCKVSNK ALPAPIEKTI  120
SKAKGQPREP QVYTLPPSRE QMTKNQVKLT CLVKGFYPSD IAVEWESNGQ PENNYKTTPP  180
VLDSDGSFFL YSKLTVDKSR WQQGNVFSCS VMHEALHNHY TQKSLSLSPG K           231

SEQ ID NO: 61          moltype = AA  length = 327
FEATURE                Location/Qualifiers
REGION                 1..327
                       note = Description of Artificial Sequence: Synthetic
                        polypeptide
REGION                 1..327
                       note = 1 + 1 Fab-scFv-Fc Backbone 8 Fab-Fc Side
source                 1..327
                       mol_type = protein
                       organism = synthetic construct
SEQUENCE: 61
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS DTKVDKRVES KYGPPCPPCP APEFLGGPSV  120
FLFPPKPKDT LMISRTPEVT CVVVDVSQED PEVQFNWYVD GVEVHNAKTK PREEEFNSTY  180
RVVSVLTVLH QDWLNGKEYK CKVSNKGLPS SIEKTISKAK GQPREPQVYT LPPSQEEMTK  240
NQVSLTCDVS GFYPSDIAVE WESDGQPENN YKTTPPVLDS DGSFFLYSRL TVDKSRWEEG  300
DVFSCSVMHE ALHNHYTQKS LSLSLGK                                     327

SEQ ID NO: 62          moltype = AA  length = 229
FEATURE                Location/Qualifiers
REGION                 1..229
                       note = Description of Artificial Sequence: Synthetic
                        polypeptide
REGION                 1..229
                       note = 1 + 1 Fab-scFv-Fc Backbone 8 scFv-Fc Side
source                 1..229
                       mol_type = protein
                       organism = synthetic construct
SEQUENCE: 62
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEQM TKNQVKLTCL VKGFYPSDIA VEWESNGQPE NNYKTTPPVL  180
DSDGSFFLYS RLTVDKSRWQ EGNVFSCSVM HEALHNHYTQ KSLSLSLGK             229

SEQ ID NO: 63          moltype = AA  length = 326
FEATURE                Location/Qualifiers
REGION                 1..326
                       note = Description of Artificial Sequence: Synthetic
                        polypeptide
REGION                 1..326
                       note = 1 + 1 Fab-scFv-Fc Backbone 9 Fab-Fc Side
source                 1..326
                       mol_type = protein
                       organism = synthetic construct
SEQUENCE: 63
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS DTKVDKTVER KCCVECPPCP APPVAGPSVF  120
LFPPKPKDTL MISRTPEVTC VVVDVSHEDP EVQFNWYVDG VEVHNAKTKP REEEFNSTFR  180
VVSVLTVVHQ DWLNGKEYKC KVSNKGLPAP IEKTISKTKG QPREPQVYTL PPSREEMTKN  240
QVSLTCDVSG FYPSDIAVEW ESDGQPENNY KTTPPMLDSD GSFFLYSKLT VDKSRWEQGD  300
VFSCSVMHEA LHNHYTQKSL SLSPGK                                      326

SEQ ID NO: 64          moltype = AA  length = 228
FEATURE                Location/Qualifiers
REGION                 1..228
                       note = Description of Artificial Sequence: Synthetic
                        polypeptide
REGION                 1..228
                       note = 1 + 1 Fab-scFv-Fc Backbone 9 scFv-Fc Side
source                 1..228
                       mol_type = protein
                       organism = synthetic construct
```

```
SEQUENCE: 64
ERKCCVECPP CPAPPVAGPS VFLFPPKPKD TLMISRTPEV TCVVVDVSHE DPEVQFNWYV   60
DGVEVHNAKT KPREEQFNST FRVVSVLTVV HQDWLNGKEY KCKVSNKGLP APIEKTISKT  120
KGQPREPQVY TLPPSREQMT KNQVKLTCLV KGFYPSDIAV EWESNGQPEN NYKTTPPMLD  180
SDGSFFLYSK LTVDKSRWQQ GNVFSCSVMH EALHNHYTQK SLSLSPGK              228

SEQ ID NO: 65          moltype = AA   length = 326
FEATURE                Location/Qualifiers
REGION                 1..326
                       note = Description of Artificial Sequence: Synthetic
                        polypeptide
REGION                 1..326
                       note = 1 + 1 Fab-scFv-Fc Backbone 10 Fab-Fc Side
source                 1..326
                       mol_type = protein
                       organism = synthetic construct
SEQUENCE: 65
ASTKGPSVFP LAPCSRSTSE STAALGCLVK DYFPEPVTVS WNSGALTSGV HTFPAVLQSS   60
GLYSLSSVVT VPSSNFGTQT YTCNVDHKPS DTKVDKTVER KCCVECPPCP APPVAGPSVF  120
LFPPKPKDTL MISRTPEVTC VVVDVKHEDP EVQFNWYVDG VEVHNAKTKP REEEFNSTFR  180
VVSVLTVVHQ DWLNGKEYKC KVSNKGLPAP IEKTISKTKG QPREPQVYTL PPSREEMTKN  240
QVSLTCDVSG FYPSDIAVEW ESDGQPENNY KTTPPMLDSD GSFFLYSKLT VDKSRWEQGD  300
VFSCSVMHEA LHNHYTQKSL SLSPGK                                       326

SEQ ID NO: 66          moltype = AA   length = 228
FEATURE                Location/Qualifiers
REGION                 1..228
                       note = Description of Artificial Sequence: Synthetic
                        polypeptide
REGION                 1..228
                       note = 1 + 1 Fab-scFv-Fc Backbone 10 scFv-Fc Side
source                 1..228
                       mol_type = protein
                       organism = synthetic construct
SEQUENCE: 66
ERKCCVECPP CPAPPVAGPS VFLFPPKPKD TLMISRTPEV TCVVVDVKHE DPEVQFNWYV   60
DGVEVHNAKT KPREEQFNST FRVVSVLTVV HQDWLNGKEY KCKVSNKGLP APIEKTISKT  120
KGQPREPQVY TLPPSREQMT KNQVKLTCLV KGFYPSDIAV EWESNGQPEN NYKTTPPMLD  180
SDGSFFLYSK LTVDKSRWQQ GNVFSCSVMH EALHNHYTQK SLSLSPGK              228

SEQ ID NO: 67          moltype = AA   length = 329
FEATURE                Location/Qualifiers
REGION                 1..329
                       note = Description of Artificial Sequence: Synthetic
                        polypeptide
REGION                 1..329
                       note = 1 + 1 Fab-scFv-Fc Backbone 11 Fab-Fc Side
source                 1..329
                       mol_type = protein
                       organism = synthetic construct
SEQUENCE: 67
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS DTKVDKKVEP KSCDKTHTCP PCPAPPVAGP  120
SVFLFPPKPK DTLMISRTPE VTCVVVDVKH EDPEVKFNWY VDGVEVHNAK TKPREEEYNS  180
TYRVVSVLTV LHQDWLNGKE YKCKVSNKAL PAPIEKTISK AKGQPREPQV YTLPPSREEM  240
TKNQVSLTCD VSGFYPSDIA VEWESDGQPE NNYKTTPPVL DSDGSFFLYS KLTVDKSRWE  300
QGDVFSCSVL HEALHSHYTQ KSLSLSPGK                                    329

SEQ ID NO: 68          moltype = AA   length = 231
FEATURE                Location/Qualifiers
REGION                 1..231
                       note = Description of Artificial Sequence: Synthetic
                        polypeptide
REGION                 1..231
                       note = 1 + 1 Fab-scFv-Fc Backbone 11 scFv-Fc Side
source                 1..231
                       mol_type = protein
                       organism = synthetic construct
SEQUENCE: 68
EPKSSDKTHT CPPCPAPPVA GPSVFLFPPK PKDTLMISRT PEVTCVVVDV KHEDPEVKFN   60
WYVDGVEVHN AKTKPREEQY NSTYRVVSVL TVLHQDWLNG KEYKCKVSNK ALPAPIEKTI  120
SKAKGQPREP QVYTLPPSRE QMTKNQVKLT CLVKGFYPSD IAVEWESNGQ PENNYKTTPP  180
VLDSDGSFFL YSKLTVDKSR WQQGNVFSCS VLHEALHSHY TQKSLSLSPG K          231

SEQ ID NO: 69          moltype = AA   length = 329
FEATURE                Location/Qualifiers
REGION                 1..329
                       note = Description of Artificial Sequence: Synthetic
                        polypeptide
```

```
REGION                    1..329
                          note = 1 + 1 Fab-scFv-Fc Backbone 12 Fab-Fc Side
source                    1..329
                          mol_type = protein
                          organism = synthetic construct
SEQUENCE: 69
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPPVAGP  120
SVFLFPPKPK DTLMISRTPE VTCVVVDVKH EDPEVKFNWY VDGVEVHNAK TKPREEQYNS  180
TYRVVSVLTV LHQDWLNGKE YKCKVSNKAL PAPIEKTISK AKGQPREPQV YTLPPSREEM  240
TKNQVSLTCD VAGFYPSDIA VEWESNGQPE NNYKTTPPVL DSDGSFFLYS KLTVDKSRWQ  300
QGNVFSCSVM HEALHNHYTQ KSLSLSPGK                                    329

SEQ ID NO: 70             moltype = AA  length = 231
FEATURE                   Location/Qualifiers
REGION                    1..231
                          note = Description of Artificial Sequence: Synthetic
                           polypeptide
REGION                    1..231
                          note = 1 + 1 Fab-scFv-Fc Backbone 12 scFv-Fc Side
source                    1..231
                          mol_type = protein
                          organism = synthetic construct
SEQUENCE: 70
ERKSSDKTHT CPPRPAPPVA GPSVFLFPPK PKDTLMISRT PEVTCVVVDV KHEDPEVKFK  60
WYVDGVEVHN AKTKPREEQY NSTYRVVSVL TVLHQDWLNG KEYKCKVSNK ALPAPIEKTI  120
SKAKGQPREP QVYTLPPSRE QMTKNQVKLT CLVKGFYPSD IAVEWESNGQ PENNYKTTPP  180
VLDSDGSFFL YSKLTVDKSR WQQGNVFSCS VMHEALHNHY TQKSLSLSPG K           231

SEQ ID NO: 71             moltype = AA  length = 329
FEATURE                   Location/Qualifiers
REGION                    1..329
                          note = Description of Artificial Sequence: Synthetic
                           polypeptide
REGION                    1..329
                          note = 2 + 1 Fab2-scFv-Fc Backbone 1 Fab-Fc Side
source                    1..329
                          mol_type = protein
                          organism = synthetic construct
SEQUENCE: 71
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS DTKVDKKVEP KSCDKTHTCP PCPAPPVAGP  120
SVFLFPPKPK DTLMISRTPE VTCVVVDVKH EDPEVKFNWY VDGVEVHNAK TKPREEEYNS  180
TYRVVSVLTV LHQDWLNGKE YKCKVSNKAL PAPIEKTISK AKGQPREPQV YTLPPSREEM  240
TKNQVSLTCD VSGFYPSDIA VEWESDGQPE NNYKTTPPVL DSDGSFFLYS KLTVDKSRWE  300
QGDVFSCSVM HEALHNHYTQ KSLSLSPGK                                    329

SEQ ID NO: 72             moltype = AA  length = 216
FEATURE                   Location/Qualifiers
REGION                    1..216
                          note = Description of Artificial Sequence: Synthetic
                           polypeptide
REGION                    1..216
                          note = 2 + 1 Fab2-scFv-Fc Backbone 1 Fab-scFv-Fc Side
source                    1..216
                          mol_type = protein
                          organism = synthetic construct
SEQUENCE: 72
APPVAGPSVF LFPPKPKDTL MISRTPEVTC VVVDVKHEDP EVKFNWYVDG VEVHNAKTKP  60
REEQYNSTYR VVSVLTVLHQ DWLNGKEYKC KVSNKALPAP IEKTISKAKG QPREPQVYTL  120
PPSREQMTKN QVKLTCLVKG FYPSDIAVEW ESNGQPENNY KTTPPVLDSD GSFFLYSKLT  180
VDKSRWQQGN VFSCSVMHEA LHNHYTQKSL SLSPGK                            216

SEQ ID NO: 73             moltype = AA  length = 329
FEATURE                   Location/Qualifiers
REGION                    1..329
                          note = Description of Artificial Sequence: Synthetic
                           polypeptide
REGION                    1..329
                          note = 2 + 1 Fab2-scFv-Fc Backbone 2 Fab-Fc Side
source                    1..329
                          mol_type = protein
                          organism = synthetic construct
SEQUENCE: 73
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS DTKVDKKVEP KSCDKTHTCP PCPAPPVAGP  120
SVFLFPPKPK DTLMISRTPE VTCVVVDVKH EDPEVKFNWY VDGVEVHNAK TKPREEEYNS  180
TYRVVSVLTV LHQDWLNGKE YKCKVSNKAL PAPIEKTISK AKGQPREPQV YTLPPSREEM  240
TKNQVSLTCD VSGFYPSDIA VEWESDGQPE NNYKTTPPVL DSDGSFFLYS KLTVDKSRWE  300
```

```
QGDVFSCSVM HEALHNHYTQ KSLSLSPGK                                          329

SEQ ID NO: 74           moltype = AA   length = 216
FEATURE                 Location/Qualifiers
REGION                  1..216
                        note = Description of Artificial Sequence: Synthetic
                         polypeptide
REGION                  1..216
                        note = 2 + 1 Fab2-scFv-Fc Backbone 2 Fab-scFv-Fc Side
source                  1..216
                        mol_type = protein
                        organism = synthetic construct
SEQUENCE: 74
APPVAGPSVF LFPPKPKDTL MISRTPEVTC VVVDVKHEDP EVKFNWYVDG VEVHNAKTKP     60
REEQYNSTYR VVSVLTVLHQ DWLNGKEYKC KVSNKALPAP IEKTISKAKG QPREPQVYTL     120
PPSREEMTKN QVKLTCLVKG FYPSDIAVEW ESNGQPENNY KTTPPVLDSD GSFFLYSKLT     180
VDKSRWQQGN VFSCSVMHEA LHNHYTQKSL SLSPGK                               216

SEQ ID NO: 75           moltype = AA   length = 329
FEATURE                 Location/Qualifiers
REGION                  1..329
                        note = Description of Artificial Sequence: Synthetic
                         polypeptide
REGION                  1..329
                        note = 2 + 1 Fab2-scFv-Fc Backbone 3 Fab-Fc Side
source                  1..329
                        mol_type = protein
                        organism = synthetic construct
SEQUENCE: 75
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS DTKVDKKVEP KSCDKTHTCP PCPAPPVAGP     120
SVFLFPPKPK DTLMISRTPE VTCVVVDVKH EDPEVKFNWY VDGVEVHNAK TKPREEEYNS     180
TYRVVSVLTV LHQDWLNGKE YKCKVSNKAL PAPIEKTISK AKGQPREPQV YTLPPSREEM     240
TKNQVSLTCE VSGFYPSDIA VEWESDGQPE NNYKTTPPVL DSDGSFFLYS KLTVDKSRWE     300
QGDVFSCSVM HEALHNHYTQ KSLSLSPGK                                       329

SEQ ID NO: 76           moltype = AA   length = 216
FEATURE                 Location/Qualifiers
REGION                  1..216
                        note = Description of Artificial Sequence: Synthetic
                         polypeptide
REGION                  1..216
                        note = 2 + 1 Fab2-scFv-Fc Backbone 3 Fab-scFv-Fc Side
source                  1..216
                        mol_type = protein
                        organism = synthetic construct
SEQUENCE: 76
APPVAGPSVF LFPPKPKDTL MISRTPEVTC VVVDVKHEDP EVKFNWYVDG VEVHNAKTKP     60
REEQYNSTYR VVSVLTVLHQ DWLNGKEYKC KVSNKALPAP IEKTISKAKG QPREPQVYTL     120
PPSREEMTKN QVKLTCLVKG FYPSDIAVEW ESNGQPENNY KTTPPVLDSD GSFFLYSKLT     180
VDKSRWQQGN VFSCSVMHEA LHNHYTQKSL SLSPGK                               216

SEQ ID NO: 77           moltype = AA   length = 329
FEATURE                 Location/Qualifiers
REGION                  1..329
                        note = Description of Artificial Sequence: Synthetic
                         polypeptide
REGION                  1..329
                        note = 2 + 1 Fab2-scFv-Fc Backbone 4 Fab-Fc Side
source                  1..329
                        mol_type = protein
                        organism = synthetic construct
SEQUENCE: 77
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS DTKVDKKVEP KSCDKTHTCP PCPAPPVAGP     120
SVFLFPPKPK DTLMISRTPE VTCVVVDVKH EDPEVKFNWY VDGVEVHNAK TKPREEEYNS     180
TYRVVSVLTV LHQDWLNGKE YKCKVSNKAL PAPIEKTISK AKGQPREPQV YTLPPSREEM     240
TENEVSLTCL VKGFYPSDIA VEWESDGQPE NNYKTTPPVL DSDGSFFLYS KLEVDKSRWE     300
QGDVFSCSVM HEALHNHYTQ KSLSLSPGK                                       329

SEQ ID NO: 78           moltype = AA   length = 216
FEATURE                 Location/Qualifiers
REGION                  1..216
                        note = Description of Artificial Sequence: Synthetic
                         polypeptide
REGION                  1..216
                        note = 2 + 1 Fab2-scFv-Fc Backbone 4 Fab-scFv-Fc Side
source                  1..216
                        mol_type = protein
```

```
                          organism = synthetic construct
SEQUENCE: 78
APPVAGPSVF LFPPKPKDTL MISRTPEVTC VVVDVKHEDP EVKFNWYVDG VEVHNAKTKP  60
REEQYNSTYR VVSVLTVLHQ DWLNGKEYKC KVSNKALPAP IEKTISKAKG QPREPQVYTL  120
PPSREEMTKN QVSLTCLVKG FYPSDIAVEW ESNGQPENNY KTTPPVLDSK GSFFLYSKLT  180
VDKSRWQQGN VFSCSVMHEA LHNHYTQKSL SLSPGK                            216

SEQ ID NO: 79           moltype = AA  length = 329
FEATURE                 Location/Qualifiers
REGION                  1..329
                        note = Description of Artificial Sequence: Synthetic
                         polypeptide
REGION                  1..329
                        note = 2 + 1 Fab2-scFv-Fc Backbone 5 Fab-Fc Side
source                  1..329
                        mol_type = protein
                        organism = synthetic construct
SEQUENCE: 79
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS DTKVDKKVEP KSCDKTHTCP PCPAPPVAGP  120
SVFLFPPKPK DTLMISRTPE VTCVVVDVKH EDPEVKFNWY VDGVEVHNAK TKPREEEYNS  180
TYRVVSVLTV LHQDWLNGKE YKCKVSNKAL PAPIEKTISK AKGQPREPQV YTLPPSRDEL  240
TKNQVSLTCD VSGFYPSDIA VEWESDGQPE NNYKTTPPVL DSDGSFFLYS KLTVDKSRWE  300
QGDVFSCSVM HEALHNHYTQ KSLSLSPGK                                    329

SEQ ID NO: 80           moltype = AA  length = 216
FEATURE                 Location/Qualifiers
REGION                  1..216
                        note = Description of Artificial Sequence: Synthetic
                         polypeptide
REGION                  1..216
                        note = 2 + 1 Fab2-scFv-Fc Backbone 5 Fab-scFv-Fc Side
source                  1..216
                        mol_type = protein
                        organism = synthetic construct
SEQUENCE: 80
APPVAGPSVF LFPPKPKDTL MISRTPEVTC VVVDVKHEDP EVKFNWYVDG VEVHNAKTKP  60
REEQYNSTYR VVSVLTVLHQ DWLNGKEYKC KVSNKALPAP IEKTISKAKG QPREPQVYTL  120
PPSRDQLTKN QVKLTCLVKG FYPSDIAVEW ESNGQPENNY KTTPPVLDSD GSFFLYSKLT  180
VDKSRWQQGN VFSCSVMHEA LHNHYTQKSL SLSPGK                            216

SEQ ID NO: 81           moltype = AA  length = 329
FEATURE                 Location/Qualifiers
REGION                  1..329
                        note = Description of Artificial Sequence: Synthetic
                         polypeptide
REGION                  1..329
                        note = 2 + 1 Fab2-scFv-Fc Backbone 6 Fab-Fc Side
source                  1..329
                        mol_type = protein
                        organism = synthetic construct
SEQUENCE: 81
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS DTKVDKKVEP KSCDKTHTCP PCPAPPVAGP  120
SVFLFPPKPK DTLMISRTPE VTCVVVDVKH EDPEVKFNWY VDGVEVHNAK TKPREEEYAS  180
TYRVVSVLTV LHQDWLNGKE YKCKVSNKAL PAPIEKTISK AKGQPREPQV YTLPPSREEM  240
TKNQVSLTCD VSGFYPSDIA VEWESDGQPE NNYKTTPPVL DSDGSFFLYS KLTVDKSRWE  300
QGDVFSCSVM HEALHNHYTQ KSLSLSPGK                                    329

SEQ ID NO: 82           moltype = AA  length = 216
FEATURE                 Location/Qualifiers
REGION                  1..216
                        note = Description of Artificial Sequence: Synthetic
                         polypeptide
REGION                  1..216
                        note = 2 + 1 Fab2-scFv-Fc Backbone 6 Fab-scFv-Fc Side
source                  1..216
                        mol_type = protein
                        organism = synthetic construct
SEQUENCE: 82
APPVAGPSVF LFPPKPKDTL MISRTPEVTC VVVDVKHEDP EVKFNWYVDG VEVHNAKTKP  60
REEQYASTYR VVSVLTVLHQ DWLNGKEYKC KVSNKALPAP IEKTISKAKG QPREPQVYTL  120
PPSREQMTKN QVKLTCLVKG FYPSDIAVEW ESNGQPENNY KTTPPVLDSD GSFFLYSKLT  180
VDKSRWQQGN VFSCSVMHEA LHNHYTQKSL SLSPGK                            216

SEQ ID NO: 83           moltype = AA  length = 329
FEATURE                 Location/Qualifiers
REGION                  1..329
                        note = Description of Artificial Sequence: Synthetic
```

```
                              polypeptide
REGION                        1..329
                              note = 2 + 1 Fab2-scFv-Fc Backbone 7 Fab-Fc Side
source                        1..329
                              mol_type = protein
                              organism = synthetic construct
SEQUENCE: 83
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS DTKVDKKVEP KSCDKTHTCP PCPAPPVAGP  120
SVFLFPPKPK DTLMISRTPE VTCVVVDVKH EDPEVKFNWY VDGVEVHNAK TKPREEEYSS  180
TYRVVSVLTV LHQDWLNGKE YKCKVSNKAL PAPIEKTISK AKGQPREPQV YTLPPSREEM  240
TKNQVSLTCD VSGFYPSDIA VEWESDGQPE NNYKTTPPVL DSDGSFFLYS KLTVDKSRWE  300
QGDVFSCSVM HEALHNHYTQ KSLSLSPGK                                    329

SEQ ID NO: 84             moltype = AA  length = 216
FEATURE                   Location/Qualifiers
REGION                    1..216
                          note = Description of Artificial Sequence: Synthetic
                           polypeptide
REGION                    1..216
                          note = 2 + 1 Fab2-scFv-Fc Backbone 7 Fab-scFv-Fc Side
source                    1..216
                          mol_type = protein
                          organism = synthetic construct
SEQUENCE: 84
APPVAGPSVF LFPPKPKDTL MISRTPEVTC VVVDVKHEDP EVKFNWYVDG VEVHNAKTKP  60
REEQYSSTYR VVSVLTVLHQ DWLNGKEYKC KVSNKALPAP IEKTISKAKG QPREPQVYTL  120
PPSREQMTKN QVKLTCLVKG FYPSDIAVEW ESNGQPENNY KTTPPVLDSD GSFFLYSKLT  180
VDKSRWQQGN VFSCSVMHEA LHNHYTQKSL SLSPGK                            216

SEQ ID NO: 85             moltype = AA  length = 329
FEATURE                   Location/Qualifiers
REGION                    1..329
                          note = Description of Artificial Sequence: Synthetic
                           polypeptide
REGION                    1..329
                          note = 2 + 1 Fab2-scFv-Fc Backbone 8 Fab-Fc Side
source                    1..329
                          mol_type = protein
                          organism = synthetic construct
SEQUENCE: 85
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS DTKVDKKVEP KSCDKTHTCP PCPAPPVAGP  120
SVFLFPPKPK DTLMISRTPE VTCVVVDVKH EDPEVKFNWY VDGVEVHNAK TKPREEEYNS  180
TYRVVSVLTV LHQDWLNGKE YKCKVSNKAL PAPIEKTISK AKGQPREPQV YTLPPSREEM  240
TKNQVSLTCD VSGFYPSDIA VEWESDGQPE NNYKTTPPVL DSDGSFFLYS KLTVDKSRWE  300
QGDVFSCSVL HEALHSHYTQ KSLSLSPGK                                    329

SEQ ID NO: 86             moltype = AA  length = 216
FEATURE                   Location/Qualifiers
REGION                    1..216
                          note = Description of Artificial Sequence: Synthetic
                           polypeptide
REGION                    1..216
                          note = 2 + 1 Fab2-scFv-Fc Backbone 8 Fab-scFv-Fc Side
source                    1..216
                          mol_type = protein
                          organism = synthetic construct
SEQUENCE: 86
APPVAGPSVF LFPPKPKDTL MISRTPEVTC VVVDVKHEDP EVKFNWYVDG VEVHNAKTKP  60
REEQYNSTYR VVSVLTVLHQ DWLNGKEYKC KVSNKALPAP IEKTISKAKG QPREPQVYTL  120
PPSREQMTKN QVKLTCLVKG FYPSDIAVEW ESNGQPENNY KTTPPVLDSD GSFFLYSKLT  180
VDKSRWQQGN VFSCSVLHEA LHSHYTQKSL SLSPGK                            216

SEQ ID NO: 87             moltype = AA  length = 329
FEATURE                   Location/Qualifiers
REGION                    1..329
                          note = Description of Artificial Sequence: Synthetic
                           polypeptide
REGION                    1..329
                          note = 2 + 1 Fab2-scFv-Fc Backbone 9 Fab-Fc Side
source                    1..329
                          mol_type = protein
                          organism = synthetic construct
SEQUENCE: 87
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPPVAGP  120
SVFLFPPKPK DTLMISRTPE VTCVVVDVKH EDPEVKFNWY VDGVEVHNAK TKPREEQYNS  180
TYRVVSVLTV LHQDWLNGKE YKCKVSNKAL PAPIEKTISK AKGQPREPQV YTLPPSREEM  240
```

```
TKNQVSLTCD VAGFYPSDIA VEWESNGQPE NNYKTTPPVL DSDGSFFLYS KLTVDKSRWQ    300
QGNVFSCSVM HEALHNHYTQ KSLSLSPGK                                       329

SEQ ID NO: 88            moltype = AA   length = 216
FEATURE                  Location/Qualifiers
REGION                   1..216
                         note = Description of Artificial Sequence: Synthetic
                          polypeptide
REGION                   1..216
                         note = 2 + 1 Fab2-scFv-Fc Backbone 9 Fab-scFv-Fc Side
source                   1..216
                         mol_type = protein
                         organism = synthetic construct
SEQUENCE: 88
APPVAGPSVF LFPPKPKDTL MISRTPEVTC VVVDVKHEDP EVKFKWYVDG VEVHNAKTKP    60
REEQYNSTYR VVSVLTVLHQ DWLNGKEYKC KVSNKALPAP IEKTISKAKG QPREPQVYTL    120
PPSREQMTKN QVKLTCLVKG FYPSDIAVEW ESNGQPENNY KTTPPVLDSD GSFFLYSKLT    180
VDKSRWQQGN VFSCSVMHEA LHNHYTQKSL SLSPGK                              216

SEQ ID NO: 89            moltype = AA   length = 107
FEATURE                  Location/Qualifiers
REGION                   1..107
                         note = Description of Artificial Sequence: Synthetic
                          polypeptide
REGION                   1..107
                         note = Constant Light Domain - Kappa
source                   1..107
                         mol_type = protein
                         organism = synthetic construct
SEQUENCE: 89
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                  107

SEQ ID NO: 90            moltype = AA   length = 106
FEATURE                  Location/Qualifiers
REGION                   1..106
                         note = Description of Artificial Sequence: Synthetic
                          polypeptide
REGION                   1..106
                         note = Constant Light Domain - Lambda
source                   1..106
                         mol_type = protein
                         organism = synthetic construct
SEQUENCE: 90
GQPKAAPSVT LFPPSSEELQ ANKATLVCLI SDFYPGAVTV AWKADSSPVK AGVETTTPSK    60
QSNNKYAASS YLSLTPEQWK SHRSYSCQVT HEGSTVEKTV APTECS                   106

SEQ ID NO: 91            moltype = AA   length = 254
FEATURE                  Location/Qualifiers
REGION                   1..254
                         note = Description of Artificial Sequence: Synthetic
                          polypeptide
REGION                   1..254
                         note = CD3 High - [anti-CD3]_H1.30_L1.47_scFv scFv
source                   1..254
                         mol_type = protein
                         organism = synthetic construct
SEQUENCE: 91
EVQLVESGGG LVQPGGSLRL SCAASGFTFS TYAMNWVRQA PGKGLEWVGR IRSKYNNYAT    60
YYADSVKGRF TISRDDSKNT LYLQMNSLRA EDTAVYYCVR HGNFGDSYVS WFAYWGQGTL    120
VTVSSGKPGS GKPGSGKPGS GKPGSQAVVT QEPSLTVSPG GTVTLTCGSS TGAVTSNYA     180
NWVQQKPGKS PRGLIGGTNK RAPGVPARFS GSLLGGKAAL TISGAQPEDE ADYYCALWYS    240
NHWVFGGGTK LTVL                                                      254

SEQ ID NO: 92            moltype = AA   length = 125
FEATURE                  Location/Qualifiers
REGION                   1..125
                         note = Description of Artificial Sequence: Synthetic
                          polypeptide
REGION                   1..125
                         note = CD3 High - [anti-CD3]_H1.30_L1.47_scFv Variable
                          Heavy (vh) Domain
source                   1..125
                         mol_type = protein
                         organism = synthetic construct
SEQUENCE: 92
EVQLVESGGG LVQPGGSLRL SCAASGFTFS TYAMNWVRQA PGKGLEWVGR IRSKYNNYAT    60
YYADSVKGRF TISRDDSKNT LYLQMNSLRA EDTAVYYCVR HGNFGDSYVS WFAYWGQGTL    120
VTVSS                                                                125
```

```
SEQ ID NO: 93          moltype = AA   length = 5
FEATURE                Location/Qualifiers
REGION                 1..5
                       note = Description of Artificial Sequence: Synthetic peptide
REGION                 1..5
                       note = CD3 High - [anti-CD3]_H1.30_L1.47_scFv vhCDR1
source                 1..5
                       mol_type = protein
                       organism = synthetic construct
SEQUENCE: 93
TYAMN                                                                    5

SEQ ID NO: 94          moltype = AA   length = 19
FEATURE                Location/Qualifiers
REGION                 1..19
                       note = Description of Artificial Sequence: Synthetic peptide
REGION                 1..19
                       note = CD3 High - [anti-CD3]_H1.30_L1.47_scFv vhCDR2
source                 1..19
                       mol_type = protein
                       organism = synthetic construct
SEQUENCE: 94
RIRSKYNNYA TYYADSVKG                                                     19

SEQ ID NO: 95          moltype = AA   length = 14
FEATURE                Location/Qualifiers
REGION                 1..14
                       note = Description of Artificial Sequence: Synthetic peptide
REGION                 1..14
                       note = CD3 High - [anti-CD3]_H1.30_L1.47_scFv vhCDR3
source                 1..14
                       mol_type = protein
                       organism = synthetic construct
SEQUENCE: 95
HGNFGDSYVS WFAY                                                          14

SEQ ID NO: 96          moltype = AA   length = 109
FEATURE                Location/Qualifiers
REGION                 1..109
                       note = Description of Artificial Sequence: Synthetic
                        polypeptide
REGION                 1..109
                       note = CD3 High - [anti-CD3]_H1.30_L1.47_scFv Variable
                        Light (vl) Domain
source                 1..109
                       mol_type = protein
                       organism = synthetic construct
SEQUENCE: 96
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVL           109

SEQ ID NO: 97          moltype = AA   length = 14
FEATURE                Location/Qualifiers
REGION                 1..14
                       note = Description of Artificial Sequence: Synthetic peptide
REGION                 1..14
                       note = CD3 High - [anti-CD3]_H1.30_L1.47_scFv vlCDR1
source                 1..14
                       mol_type = protein
                       organism = synthetic construct
SEQUENCE: 97
GSSTGAVTTS NYAN                                                          14

SEQ ID NO: 98          moltype = AA   length = 7
FEATURE                Location/Qualifiers
REGION                 1..7
                       note = Description of Artificial Sequence: Synthetic peptide
REGION                 1..7
                       note = CD3 High - [anti-CD3]_H1.30_L1.47_scFv vlCDR2
source                 1..7
                       mol_type = protein
                       organism = synthetic construct
SEQUENCE: 98
GTNKRAP                                                                  7

SEQ ID NO: 99          moltype = AA   length = 9
FEATURE                Location/Qualifiers
REGION                 1..9
```

```
                            note = Description of Artificial Sequence: Synthetic peptide
REGION                      1..9
                            note = CD3 High - [anti-CD3]_H1.30_L1.47_scFv vlCDR3
source                      1..9
                            mol_type = protein
                            organism = synthetic construct
SEQUENCE: 99
ALWYSNHWV                                                                        9

SEQ ID NO: 100              moltype = AA  length = 20
FEATURE                     Location/Qualifiers
REGION                      1..20
                            note = Description of Artificial Sequence: Synthetic peptide
REGION                      1..20
                            note = CD3 High - [anti-CD3]_H1.30_L1.47_scFv Linker
source                      1..20
                            mol_type = protein
                            organism = synthetic construct
SEQUENCE: 100
GKPGSGKPGS GKPGSGKPGS                                                            20

SEQ ID NO: 101              moltype = AA  length = 254
FEATURE                     Location/Qualifiers
REGION                      1..254
                            note = Description of Artificial Sequence: Synthetic
                             polypeptide
REGION                      1..254
                            note = CD3 High-Int #1 - [anti-CD3]_H1.32_L1.47_scFv scFv
source                      1..254
                            mol_type = protein
                            organism = synthetic construct
SEQUENCE: 101
EVQLVESGGG LVQPGGSLRL SCAASGFTFS TYAMNWVRQA PGKGLEWVGR IRSKANNYAT   60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVL                                                    254

SEQ ID NO: 102              moltype = AA  length = 125
FEATURE                     Location/Qualifiers
REGION                      1..125
                            note = Description of Artificial Sequence: Synthetic
                             polypeptide
REGION                      1..125
                            note = CD3 High-Int #1 - [anti-CD3]_H1.32_L1.47_scFv
                             Variable Heav y (vh) Domain
source                      1..125
                            mol_type = protein
                            organism = synthetic construct
SEQUENCE: 102
EVQLVESGGG LVQPGGSLRL SCAASGFTFS TYAMNWVRQA PGKGLEWVGR IRSKANNYAT   60
YYADSVKGRF TISRDDSKNT LYLQMNSLRA EDTAVYYCVR HGNFGDSYVS WFAYWGQGTL  120
VTVSS                                                              125

SEQ ID NO: 103              moltype = AA  length = 5
FEATURE                     Location/Qualifiers
REGION                      1..5
                            note = Description of Artificial Sequence: Synthetic peptide
REGION                      1..5
                            note = CD3 High-Int #1 - [anti-CD3]_H1.32_L1.47_scFv vhCDR1
source                      1..5
                            mol_type = protein
                            organism = synthetic construct
SEQUENCE: 103
TYAMN                                                                            5

SEQ ID NO: 104              moltype = AA  length = 19
FEATURE                     Location/Qualifiers
REGION                      1..19
                            note = Description of Artificial Sequence: Synthetic peptide
REGION                      1..19
                            note = CD3 High-Int #1 - [anti-CD3]_H1.32_L1.47_scFv vhCDR2
source                      1..19
                            mol_type = protein
                            organism = synthetic construct
SEQUENCE: 104
RIRSKANNYA TYYADSVKG                                                            19

SEQ ID NO: 105              moltype = AA  length = 14
```

| FEATURE | Location/Qualifiers |
|---|---|
| REGION | 1..14 |
| | note = Description of Artificial Sequence: Synthetic peptide |
| REGION | 1..14 |
| | note = CD3 High-Int #1 - [anti-CD3]_H1.32_L1.47_scFv vhCDR3 |
| source | 1..14 |
| | mol_type = protein |
| | organism = synthetic construct |

SEQUENCE: 105
HGNFGDSYVS WFAY                                                          14

SEQ ID NO: 106      moltype = AA  length = 109
FEATURE             Location/Qualifiers
REGION              1..109
                    note = Description of Artificial Sequence: Synthetic
                    polypeptide
REGION              1..109
                    note = CD3 High-Int #1 - [anti-CD3]_H1.32_L1.47_scFv
                    Variable Ligh t (vl) Domain
source              1..109
                    mol_type = protein
                    organism = synthetic construct
SEQUENCE: 106
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVL           109

SEQ ID NO: 107      moltype = AA  length = 14
FEATURE             Location/Qualifiers
REGION              1..14
                    note = Description of Artificial Sequence: Synthetic peptide
REGION              1..14
                    note = CD3 High-Int #1 - [anti-CD3]_H1.32_L1.47_scFv vlCDR1
source              1..14
                    mol_type = protein
                    organism = synthetic construct
SEQUENCE: 107
GSSTGAVTTS NYAN                                                          14

SEQ ID NO: 108      moltype = AA  length = 7
FEATURE             Location/Qualifiers
REGION              1..7
                    note = Description of Artificial Sequence: Synthetic peptide
REGION              1..7
                    note = CD3 High-Int #1 - [anti-CD3]_H1.32_L1.47_scFv vlCDR2
source              1..7
                    mol_type = protein
                    organism = synthetic construct
SEQUENCE: 108
GTNKRAP                                                                  7

SEQ ID NO: 109      moltype = AA  length = 9
FEATURE             Location/Qualifiers
REGION              1..9
                    note = Description of Artificial Sequence: Synthetic peptide
REGION              1..9
                    note = CD3 High-Int #1 - [anti-CD3]_H1.32_L1.47_scFv vlCDR3
source              1..9
                    mol_type = protein
                    organism = synthetic construct
SEQUENCE: 109
ALWYSNHWV                                                                9

SEQ ID NO: 110      moltype = AA  length = 20
FEATURE             Location/Qualifiers
REGION              1..20
                    note = Description of Artificial Sequence: Synthetic peptide
REGION              1..20
                    note = CD3 High-Int #1 - [anti-CD3]_H1.32_L1.47_scFv Linker
source              1..20
                    mol_type = protein
                    organism = synthetic construct
SEQUENCE: 110
GKPGSGKPGS GKPGSGKPGS                                                    20

SEQ ID NO: 111      moltype = AA  length = 254
FEATURE             Location/Qualifiers
REGION              1..254
                    note = Description of Artificial Sequence: Synthetic
                    polypeptide -continued

```
REGION                     1..254
                           note = CD3 High-Int #2 - [anti-CD3]_H1.89_L1.47_scFv scFv
source                     1..254
                           mol_type = protein
                           organism = synthetic construct
SEQUENCE: 111
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDEYVS WFAYWGQGTL   120
VTVSSGKPGS GKPGSGKPGS GKPGSQAVVT QEPSLTVSPG GTVTLTCGSS TGAVTTSNYA   180
NWVQQKPGKS PRGLIGGTNK RAPGVPARFS GSLLGGKAAL TISGAQPEDE ADYYCALWYS   240
NHWVFGGGTK LTVL                                                     254

SEQ ID NO: 112             moltype = AA  length = 125
FEATURE                    Location/Qualifiers
REGION                     1..125
                           note = Description of Artificial Sequence: Synthetic
                            polypeptide
REGION                     1..125
                           note = CD3 High-Int #2 - [anti-CD3]_H1.89_L1.47_scFv
                            Variable Heav y (vh) Domain
source                     1..125
                           mol_type = protein
                           organism = synthetic construct
SEQUENCE: 112
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDEYVS WFAYWGQGTL   120
VTVSS                                                               125

SEQ ID NO: 113             moltype = AA  length = 5
FEATURE                    Location/Qualifiers
REGION                     1..5
                           note = Description of Artificial Sequence: Synthetic peptide
REGION                     1..5
                           note = CD3 High-Int #2 - [anti-CD3]_H1.89_L1.47_scFv vhCDR1
source                     1..5
                           mol_type = protein
                           organism = synthetic construct
SEQUENCE: 113
TYAMN                                                                 5

SEQ ID NO: 114             moltype = AA  length = 19
FEATURE                    Location/Qualifiers
REGION                     1..19
                           note = Description of Artificial Sequence: Synthetic peptide
REGION                     1..19
                           note = CD3 High-Int #2 - [anti-CD3]_H1.89_L1.47_scFv vhCDR2
source                     1..19
                           mol_type = protein
                           organism = synthetic construct
SEQUENCE: 114
RIRSKYNNYA TYYADSVKG                                                 19

SEQ ID NO: 115             moltype = AA  length = 14
FEATURE                    Location/Qualifiers
REGION                     1..14
                           note = Description of Artificial Sequence: Synthetic peptide
REGION                     1..14
                           note = CD3 High-Int #2 - [anti-CD3]_H1.89_L1.47_scFv vhCDR3
source                     1..14
                           mol_type = protein
                           organism = synthetic construct
SEQUENCE: 115
HGNFGDEYVS WFAY                                                      14

SEQ ID NO: 116             moltype = AA  length = 109
FEATURE                    Location/Qualifiers
REGION                     1..109
                           note = Description of Artificial Sequence: Synthetic
                            polypeptide
REGION                     1..109
                           note = CD3 High-Int #2 - [anti-CD3]_H1.89_L1.47_scFv
                            Variable Ligh t (vl) Domain
source                     1..109
                           mol_type = protein
                           organism = synthetic construct
SEQUENCE: 116
QAVVTQEPSL TVSPGGTVTL TCGSSTGAVT TSNYANWVQQ KPGKSPRGLI GGTNKRAPGV   60
PARFSGSLLG GKAALTISGA QPEDEADYYC ALWYSNHWVF GGGTKLTVL              109
```

```
SEQ ID NO: 117            moltype = AA   length = 14
FEATURE                   Location/Qualifiers
REGION                    1..14
                          note = Description of Artificial Sequence: Synthetic peptide
REGION                    1..14
                          note = CD3 High-Int #2 - [anti-CD3]_H1.89_L1.47_scFv vlCDR1
source                    1..14
                          mol_type = protein
                          organism = synthetic construct
SEQUENCE: 117
GSSTGAVTTS NYAN                                                              14

SEQ ID NO: 118            moltype = AA   length = 7
FEATURE                   Location/Qualifiers
REGION                    1..7
                          note = Description of Artificial Sequence: Synthetic peptide
REGION                    1..7
                          note = CD3 High-Int #2 - [anti-CD3]_H1.89_L1.47_scFv vlCDR2
source                    1..7
                          mol_type = protein
                          organism = synthetic construct
SEQUENCE: 118
GTNKRAP                                                                       7

SEQ ID NO: 119            moltype = AA   length = 9
FEATURE                   Location/Qualifiers
REGION                    1..9
                          note = Description of Artificial Sequence: Synthetic peptide
REGION                    1..9
                          note = CD3 High-Int #2 - [anti-CD3]_H1.89_L1.47_scFv vlCDR3
source                    1..9
                          mol_type = protein
                          organism = synthetic construct
SEQUENCE: 119
ALWYSNHWV                                                                     9

SEQ ID NO: 120            moltype = AA   length = 20
FEATURE                   Location/Qualifiers
REGION                    1..20
                          note = Description of Artificial Sequence: Synthetic peptide
REGION                    1..20
                          note = CD3 High-Int #2 - [anti-CD3]_H1.89_L1.47_scFv Linker
source                    1..20
                          mol_type = protein
                          organism = synthetic construct
SEQUENCE: 120
GKPGSGKPGS GKPGSGKPGS                                                        20

SEQ ID NO: 121            moltype = AA   length = 254
FEATURE                   Location/Qualifiers
REGION                    1..254
                          note = Description of Artificial Sequence: Synthetic
                          polypeptide
REGION                    1..254
                          note = CD3 High-Int - [anti-CD3]_H1.90_L1.47_scFv scFv
source                    1..254
                          mol_type = protein
                          organism = synthetic construct
SEQUENCE: 121
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDPYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVL                                                    254

SEQ ID NO: 122            moltype = AA   length = 125
FEATURE                   Location/Qualifiers
REGION                    1..125
                          note = Description of Artificial Sequence: Synthetic
                          polypeptide
REGION                    1..125
                          note = CD3 High-Int - [anti-CD3]_H1.90_L1.47_scFv Variable
                          Heavy ( vh) Domain
source                    1..125
                          mol_type = protein
                          organism = synthetic construct
SEQUENCE: 122
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDPYVS WFAYWGQGTL  120
```

```
VTVSS                                                                    125

SEQ ID NO: 123          moltype = AA   length = 5
FEATURE                 Location/Qualifiers
REGION                  1..5
                        note = Description of Artificial Sequence: Synthetic peptide
REGION                  1..5
                        note = CD3 High-Int - [anti-CD3]_H1.90_L1.47_scFv vhCDR1
source                  1..5
                        mol_type = protein
                        organism = synthetic construct
SEQUENCE: 123
TYAMN                                                                    5

SEQ ID NO: 124          moltype = AA   length = 19
FEATURE                 Location/Qualifiers
REGION                  1..19
                        note = Description of Artificial Sequence: Synthetic peptide
REGION                  1..19
                        note = CD3 High-Int - [anti-CD3]_H1.90_L1.47_scFv vhCDR2
source                  1..19
                        mol_type = protein
                        organism = synthetic construct
SEQUENCE: 124
RIRSKYNNYA TYYADSVKG                                                     19

SEQ ID NO: 125          moltype = AA   length = 14
FEATURE                 Location/Qualifiers
REGION                  1..14
                        note = Description of Artificial Sequence: Synthetic peptide
REGION                  1..14
                        note = CD3 High-Int - [anti-CD3]_H1.90_L1.47_scFv vhCDR3
source                  1..14
                        mol_type = protein
                        organism = synthetic construct
SEQUENCE: 125
HGNFGDPYVS WFAY                                                          14

SEQ ID NO: 126          moltype = AA   length = 109
FEATURE                 Location/Qualifiers
REGION                  1..109
                        note = Description of Artificial Sequence: Synthetic
                         polypeptide
REGION                  1..109
                        note = CD3 High-Int - [anti-CD3]_H1.90_L1.47_scFv Variable
                         Light ( vl) Domain
source                  1..109
                        mol_type = protein
                        organism = synthetic construct
SEQUENCE: 126
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVL          109

SEQ ID NO: 127          moltype = AA   length = 14
FEATURE                 Location/Qualifiers
REGION                  1..14
                        note = Description of Artificial Sequence: Synthetic peptide
REGION                  1..14
                        note = CD3 High-Int - [anti-CD3]_H1.90_L1.47_scFv vlCDR1
source                  1..14
                        mol_type = protein
                        organism = synthetic construct
SEQUENCE: 127
GSSTGAVTTS NYAN                                                          14

SEQ ID NO: 128          moltype = AA   length = 7
FEATURE                 Location/Qualifiers
REGION                  1..7
                        note = Description of Artificial Sequence: Synthetic peptide
REGION                  1..7
                        note = CD3 High-Int - [anti-CD3]_H1.90_L1.47_scFv vlCDR2
source                  1..7
                        mol_type = protein
                        organism = synthetic construct
SEQUENCE: 128
GTNKRAP                                                                  7

SEQ ID NO: 129          moltype = AA   length = 9
FEATURE                 Location/Qualifiers
```

```
REGION              1..9
                    note = Description of Artificial Sequence: Synthetic peptide
REGION              1..9
                    note = CD3 High-Int - [anti-CD3]_H1.90_L1.47_scFv vlCDR3
source              1..9
                    mol_type = protein
                    organism = synthetic construct
SEQUENCE: 129
ALWYSNHWV                                                                    9

SEQ ID NO: 130      moltype = AA  length = 20
FEATURE             Location/Qualifiers
REGION              1..20
                    note = Description of Artificial Sequence: Synthetic peptide
REGION              1..20
                    note = CD3 High-Int - [anti-CD3]_H1.90_L1.47_scFv Linker
source              1..20
                    mol_type = protein
                    organism = synthetic construct
SEQUENCE: 130
GKPGSGKPGS GKPGSGKPGS                                                       20

SEQ ID NO: 131      moltype = AA  length = 254
FEATURE             Location/Qualifiers
REGION              1..254
                    note = Description of Artificial Sequence: Synthetic
                     polypeptide
REGION              1..254
                    note = Anti-CD3-Intermediate - [anti-CD3]_H1.33_L1.47_scFv
                     scFv
source              1..254
                    mol_type = protein
                    organism = synthetic construct
SEQUENCE: 131
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS WFDYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVL                                                    254

SEQ ID NO: 132      moltype = AA  length = 125
FEATURE             Location/Qualifiers
REGION              1..125
                    note = Description of Artificial Sequence: Synthetic
                     polypeptide
REGION              1..125
                    note = Anti-CD3-Intermediate - [anti-CD3]_H1.33_L1.47_scFv
                     Variabl e Heavy (vh) Domain
source              1..125
                    mol_type = protein
                    organism = synthetic construct
SEQUENCE: 132
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS WFDYWGQGTL  120
VTVSS                                                              125

SEQ ID NO: 133      moltype = AA  length = 5
FEATURE             Location/Qualifiers
REGION              1..5
                    note = Description of Artificial Sequence: Synthetic peptide
REGION              1..5
                    note = Anti-CD3-Intermediate - [anti-CD3]_H1.33_L1.47_scFv
                     vhCDR1
source              1..5
                    mol_type = protein
                    organism = synthetic construct
SEQUENCE: 133
TYAMN                                                                        5

SEQ ID NO: 134      moltype = AA  length = 19
FEATURE             Location/Qualifiers
REGION              1..19
                    note = Description of Artificial Sequence: Synthetic peptide
REGION              1..19
                    note = Anti-CD3-Intermediate - [anti-CD3]_H1.33_L1.47_scFv
                     vhCDR2
source              1..19
                    mol_type = protein
                    organism = synthetic construct
```

-continued

```
SEQUENCE: 134
RIRSKYNNYA TYYADSVKG                                                        19

SEQ ID NO: 135          moltype = AA  length = 14
FEATURE                 Location/Qualifiers
REGION                  1..14
                        note = Description of Artificial Sequence: Synthetic peptide
REGION                  1..14
                        note = Anti-CD3-Intermediate - [anti-CD3]_H1.33_L1.47_scFv
                          vhCDR3
source                  1..14
                        mol_type = protein
                        organism = synthetic construct
SEQUENCE: 135
HGNFGDSYVS WFDY                                                             14

SEQ ID NO: 136          moltype = AA  length = 109
FEATURE                 Location/Qualifiers
REGION                  1..109
                        note = Description of Artificial Sequence: Synthetic
                          polypeptide
REGION                  1..109
                        note = Anti-CD3-Intermediate - [anti-CD3]_H1.33_L1.47_scFv
                          Variabl e Light (vl) Domain
source                  1..109
                        mol_type = protein
                        organism = synthetic construct
SEQUENCE: 136
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVL              109

SEQ ID NO: 137          moltype = AA  length = 14
FEATURE                 Location/Qualifiers
REGION                  1..14
                        note = Description of Artificial Sequence: Synthetic peptide
REGION                  1..14
                        note = Anti-CD3-Intermediate - [anti-CD3]_H1.33_L1.47_scFv
                          vlCDR1
source                  1..14
                        mol_type = protein
                        organism = synthetic construct
SEQUENCE: 137
GSSTGAVTTS NYAN                                                             14

SEQ ID NO: 138          moltype = AA  length = 7
FEATURE                 Location/Qualifiers
REGION                  1..7
                        note = Description of Artificial Sequence: Synthetic peptide
REGION                  1..7
                        note = Anti-CD3-Intermediate - [anti-CD3]_H1.33_L1.47_scFv
                          vlCDR2
source                  1..7
                        mol_type = protein
                        organism = synthetic construct
SEQUENCE: 138
GTNKRAP                                                                     7

SEQ ID NO: 139          moltype = AA  length = 9
FEATURE                 Location/Qualifiers
REGION                  1..9
                        note = Description of Artificial Sequence: Synthetic peptide
REGION                  1..9
                        note = Anti-CD3-Intermediate - [anti-CD3]_H1.33_L1.47_scFv
                          vlCDR3
source                  1..9
                        mol_type = protein
                        organism = synthetic construct
SEQUENCE: 139
ALWYSNHWV                                                                   9

SEQ ID NO: 140          moltype = AA  length = 20
FEATURE                 Location/Qualifiers
REGION                  1..20
                        note = Description of Artificial Sequence: Synthetic peptide
REGION                  1..20
                        note = Anti-CD3-Intermediate - [anti-CD3]_H1.33_L1.47_scFv
                          Linker
source                  1..20
                        mol_type = protein
```

```
                          organism = synthetic construct
SEQUENCE: 140
GKPGSGKPGS GKPGSGKPGS                                                    20

SEQ ID NO: 141           moltype = AA   length = 254
FEATURE                  Location/Qualifiers
REGION                   1..254
                         note = Description of Artificial Sequence: Synthetic
                          polypeptide
REGION                   1..254
                         note = CD3 High-Int - [anti-CD3]_H1.31_L1.47_scFv scFv
source                   1..254
                         mol_type = protein
                         organism = synthetic construct
SEQUENCE: 141
EVQLVESGGG LVQPGGSLRL SCAASGFTFS TYAMSWVRQA PGKGLEWVGR IRSKYNNYAT  60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVL                                                    254

SEQ ID NO: 142           moltype = AA   length = 125
FEATURE                  Location/Qualifiers
REGION                   1..125
                         note = Description of Artificial Sequence: Synthetic
                          polypeptide
REGION                   1..125
                         note = CD3 High-Int - [anti-CD3]_H1.31_L1.47_scFv Variable
                          Heavy ( vh) Domain
source                   1..125
                         mol_type = protein
                         organism = synthetic construct
SEQUENCE: 142
EVQLVESGGG LVQPGGSLRL SCAASGFTFS TYAMSWVRQA PGKGLEWVGR IRSKYNNYAT  60
YYADSVKGRF TISRDDSKNT LYLQMNSLRA EDTAVYYCVR HGNFGDSYVS WFAYWGQGTL  120
VTVSS                                                              125

SEQ ID NO: 143           moltype = AA   length = 5
FEATURE                  Location/Qualifiers
REGION                   1..5
                         note = Description of Artificial Sequence: Synthetic peptide
REGION                   1..5
                         note = CD3 High-Int - [anti-CD3]_H1.31_L1.47_scFv vhCDR1
source                   1..5
                         mol_type = protein
                         organism = synthetic construct
SEQUENCE: 143
TYAMS                                                              5

SEQ ID NO: 144           moltype = AA   length = 19
FEATURE                  Location/Qualifiers
REGION                   1..19
                         note = Description of Artificial Sequence: Synthetic peptide
REGION                   1..19
                         note = CD3 High-Int - [anti-CD3]_H1.31_L1.47_scFv vhCDR2
source                   1..19
                         mol_type = protein
                         organism = synthetic construct
SEQUENCE: 144
RIRSKYNNYA TYYADSVKG                                               19

SEQ ID NO: 145           moltype = AA   length = 14
FEATURE                  Location/Qualifiers
REGION                   1..14
                         note = Description of Artificial Sequence: Synthetic peptide
REGION                   1..14
                         note = CD3 High-Int - [anti-CD3]_H1.31_L1.47_scFv vhCDR3
source                   1..14
                         mol_type = protein
                         organism = synthetic construct
SEQUENCE: 145
HGNFGDSYVS WFAY                                                    14

SEQ ID NO: 146           moltype = AA   length = 109
FEATURE                  Location/Qualifiers
REGION                   1..109
                         note = Description of Artificial Sequence: Synthetic
                          polypeptide
REGION                   1..109
```

-continued

```
                        note = CD3 High-Int - [anti-CD3]_H1.31_L1.47_scFv Variable
                         Light ( vl) Domain
source                  1..109
                        mol_type = protein
                        organism = synthetic construct
SEQUENCE: 146
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVL                109

SEQ ID NO: 147          moltype = AA  length = 14
FEATURE                 Location/Qualifiers
REGION                  1..14
                        note = Description of Artificial Sequence: Synthetic peptide
REGION                  1..14
                        note = CD3 High-Int - [anti-CD3]_H1.31_L1.47_scFv vlCDR1
source                  1..14
                        mol_type = protein
                        organism = synthetic construct
SEQUENCE: 147
GSSTGAVTTS NYAN                                                     14

SEQ ID NO: 148          moltype = AA  length = 7
FEATURE                 Location/Qualifiers
REGION                  1..7
                        note = Description of Artificial Sequence: Synthetic peptide
REGION                  1..7
                        note = CD3 High-Int - [anti-CD3]_H1.31_L1.47_scFv vlCDR2
source                  1..7
                        mol_type = protein
                        organism = synthetic construct
SEQUENCE: 148
GTNKRAP                                                             7

SEQ ID NO: 149          moltype = AA  length = 9
FEATURE                 Location/Qualifiers
REGION                  1..9
                        note = Description of Artificial Sequence: Synthetic peptide
REGION                  1..9
                        note = CD3 High-Int - [anti-CD3]_H1.31_L1.47_scFv vlCDR3
source                  1..9
                        mol_type = protein
                        organism = synthetic construct
SEQUENCE: 149
ALWYSNHWV                                                           9

SEQ ID NO: 150          moltype = AA  length = 20
FEATURE                 Location/Qualifiers
REGION                  1..20
                        note = Description of Artificial Sequence: Synthetic peptide
REGION                  1..20
                        note = CD3 High-Int - [anti-CD3]_H1.31_L1.47_scFv Linker
source                  1..20
                        mol_type = protein
                        organism = synthetic construct
SEQUENCE: 150
GKPGSGKPGS GKPGSGKPGS                                               20

SEQ ID NO: 151          moltype = AA  length = 254
FEATURE                 Location/Qualifiers
REGION                  1..254
                        note = Description of Artificial Sequence: Synthetic
                         polypeptide
REGION                  1..254
                        note = CD3 High[VL-VH] - [anti-CD3]_L1.47_ H1.30_scFv scFv
source                  1..254
                        mol_type = protein
                        organism = synthetic construct
SEQUENCE: 151
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVLG KPGSGKPGSG  120
KPGSGKPGSE VQLVESGGGL VQPGGSLRLS CAASGFTFST YAMNWVRQAP GKGLEWVGRI  180
RSKYNNYATY YADSVKGRFT ISRDDSKNTL YLQMNSLRAE DTAVYYCVRH GNFGDSYVSW  240
FAYWGQGTLV TVSS                                                     254

SEQ ID NO: 152          moltype = AA  length = 109
FEATURE                 Location/Qualifiers
REGION                  1..109
                        note = Description of Artificial Sequence: Synthetic
                         polypeptide
```

-continued

```
REGION                    1..109
                          note = CD3 High[VL-VH] - [anti-CD3]_L1.47_ H1.30_scFv
                          Variable Lig ht (vl) Domain
source                    1..109
                          mol_type = protein
                          organism = synthetic construct
SEQUENCE: 152
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVL              109

SEQ ID NO: 153            moltype = AA  length = 14
FEATURE                   Location/Qualifiers
REGION                    1..14
                          note = Description of Artificial Sequence: Synthetic peptide
REGION                    1..14
                          note = CD3 High[VL-VH] - [anti-CD3]_L1.47_ H1.30_scFv vlCDR1
source                    1..14
                          mol_type = protein
                          organism = synthetic construct
SEQUENCE: 153
GSSTGAVTTS NYAN                                                    14

SEQ ID NO: 154            moltype = AA  length = 7
FEATURE                   Location/Qualifiers
REGION                    1..7
                          note = Description of Artificial Sequence: Synthetic peptide
REGION                    1..7
                          note = CD3 High[VL-VH] - [anti-CD3]_L1.47_ H1.30_scFv vlCDR2
source                    1..7
                          mol_type = protein
                          organism = synthetic construct
SEQUENCE: 154
GTNKRAP                                                            7

SEQ ID NO: 155            moltype = AA  length = 9
FEATURE                   Location/Qualifiers
REGION                    1..9
                          note = Description of Artificial Sequence: Synthetic peptide
REGION                    1..9
                          note = CD3 High[VL-VH] - [anti-CD3]_L1.47_ H1.30_scFv vlCDR3
source                    1..9
                          mol_type = protein
                          organism = synthetic construct
SEQUENCE: 155
ALWYSNHWV                                                          9

SEQ ID NO: 156            moltype = AA  length = 125
FEATURE                   Location/Qualifiers
REGION                    1..125
                          note = Description of Artificial Sequence: Synthetic
                          polypeptide
REGION                    1..125
                          note = CD3 High[VL-VH] - [anti-CD3]_L1.47_ H1.30_scFv
                          Variable Hea vy (vh) Domain
source                    1..125
                          mol_type = protein
                          organism = synthetic construct
SEQUENCE: 156
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS WFAYWGQGTL  120
VTVSS                                                              125

SEQ ID NO: 157            moltype = AA  length = 5
FEATURE                   Location/Qualifiers
REGION                    1..5
                          note = Description of Artificial Sequence: Synthetic peptide
REGION                    1..5
                          note = CD3 High[VL-VH] - [anti-CD3]_L1.47_ H1.30_scFv vhCDR1
source                    1..5
                          mol_type = protein
                          organism = synthetic construct
SEQUENCE: 157
TYAMN                                                              5

SEQ ID NO: 158            moltype = AA  length = 19
FEATURE                   Location/Qualifiers
REGION                    1..19
                          note = Description of Artificial Sequence: Synthetic peptide
REGION                    1..19
```

```
                            note = CD3 High[VL-VH] - [anti-CD3]_L1.47_ H1.30_scFv vhCDR2
source                      1..19
                            mol_type = protein
                            organism = synthetic construct
SEQUENCE: 158
RIRSKYNNYA TYYADSVKG                                                    19

SEQ ID NO: 159              moltype = AA  length = 14
FEATURE                     Location/Qualifiers
REGION                      1..14
                            note = Description of Artificial Sequence: Synthetic peptide
REGION                      1..14
                            note = CD3 High[VL-VH] - [anti-CD3]_L1.47_ H1.30_scFv vhCDR3
source                      1..14
                            mol_type = protein
                            organism = synthetic construct
SEQUENCE: 159
HGNFGDSYVS WFAY                                                         14

SEQ ID NO: 160              moltype = AA  length = 20
FEATURE                     Location/Qualifiers
REGION                      1..20
                            note = Description of Artificial Sequence: Synthetic peptide
REGION                      1..20
                            note = CD3 High[VL-VH] - [anti-CD3]_L1.47_ H1.30_scFv Linker
source                      1..20
                            mol_type = protein
                            organism = synthetic construct
SEQUENCE: 160
GKPGSGKPGS GKPGSGKPGS                                                   20

SEQ ID NO: 161              moltype = AA  length = 254
FEATURE                     Location/Qualifiers
REGION                      1..254
                            note = Description of Artificial Sequence: Synthetic
                             polypeptide
REGION                      1..254
                            note = CD3 High-Int #1[VL-VH] - [anti-CD3]_L1.47_
                             H1.32_scFv scFv
source                      1..254
                            mol_type = protein
                            organism = synthetic construct
SEQUENCE: 161
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVLG KPGSGKPGSG  120
KPGSGKPGSE VQLVESGGGL VQPGGSLRLS CAASGFTFST YAMNWVRQAP GKGLEWVGRI  180
RSKANNYATY YADSVKGRFT ISRDDSKNTL YLQMNSLRAE DTAVYYCVRH GNFGDSYVSW  240
FAYWGQGTLV TVSS                                                    254

SEQ ID NO: 162              moltype = AA  length = 109
FEATURE                     Location/Qualifiers
REGION                      1..109
                            note = Description of Artificial Sequence: Synthetic
                             polypeptide
REGION                      1..109
                            note = CD3 High-Int #1[VL-VH] - [anti-CD3]_L1.47_
                             H1.32_scFv Varia ble Light (vl) Domain
source                      1..109
                            mol_type = protein
                            organism = synthetic construct
SEQUENCE: 162
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVL              109

SEQ ID NO: 163              moltype = AA  length = 14
FEATURE                     Location/Qualifiers
REGION                      1..14
                            note = Description of Artificial Sequence: Synthetic peptide
REGION                      1..14
                            note = CD3 High-Int #1[VL-VH] - [anti-CD3]_L1.47_
                             H1.32_scFv vlCDR 1
source                      1..14
                            mol_type = protein
                            organism = synthetic construct
SEQUENCE: 163
GSSTGAVTTS NYAN                                                         14

SEQ ID NO: 164              moltype = AA  length = 7
FEATURE                     Location/Qualifiers
```

-continued

```
REGION                    1..7
                          note = Description of Artificial Sequence: Synthetic peptide
REGION                    1..7
                          note = CD3 High-Int #1[VL-VH] - [anti-CD3]_L1.47_
                          H1.32_scFv vlCDR 2
source                    1..7
                          mol_type = protein
                          organism = synthetic construct
SEQUENCE: 164
GTNKRAP                                                                     7

SEQ ID NO: 165            moltype = AA  length = 9
FEATURE                   Location/Qualifiers
REGION                    1..9
                          note = Description of Artificial Sequence: Synthetic peptide
REGION                    1..9
                          note = CD3 High-Int #1[VL-VH] - [anti-CD3]_L1.47_
                          H1.32_scFv vlCDR 3
source                    1..9
                          mol_type = protein
                          organism = synthetic construct
SEQUENCE: 165
ALWYSNHWV                                                                   9

SEQ ID NO: 166            moltype = AA  length = 125
FEATURE                   Location/Qualifiers
REGION                    1..125
                          note = Description of Artificial Sequence: Synthetic
                          polypeptide
REGION                    1..125
                          note = CD3 High-Int #1[VL-VH] - [anti-CD3]_L1.47_
                          H1.32_scFv Varia ble Heavy (vh) Domain
source                    1..125
                          mol_type = protein
                          organism = synthetic construct
SEQUENCE: 166
EVQLVESGGG LVQPGGSLRL SCAASGFTFS TYAMNWVRQA PGKGLEWVGR IRSKANNYAT   60
YYADSVKGRF TISRDDSKNT LYLQMNSLRA EDTAVYYCVR HGNFGDSYVS WFAYWGQGTL  120
VTVSS                                                                     125

SEQ ID NO: 167            moltype = AA  length = 5
FEATURE                   Location/Qualifiers
REGION                    1..5
                          note = Description of Artificial Sequence: Synthetic peptide
REGION                    1..5
                          note = CD3 High-Int #1[VL-VH] - [anti-CD3]_L1.47_
                          H1.32_scFv vhCDR 1
source                    1..5
                          mol_type = protein
                          organism = synthetic construct
SEQUENCE: 167
TYAMN                                                                       5

SEQ ID NO: 168            moltype = AA  length = 19
FEATURE                   Location/Qualifiers
REGION                    1..19
                          note = Description of Artificial Sequence: Synthetic peptide
REGION                    1..19
                          note = CD3 High-Int #1[VL-VH] - [anti-CD3]_L1.47_
                          H1.32_scFv vhCDR 2
source                    1..19
                          mol_type = protein
                          organism = synthetic construct
SEQUENCE: 168
RIRSKANNYA TYYADSVKG                                                       19

SEQ ID NO: 169            moltype = AA  length = 14
FEATURE                   Location/Qualifiers
REGION                    1..14
                          note = Description of Artificial Sequence: Synthetic peptide
REGION                    1..14
                          note = CD3 High-Int #1[VL-VH] - [anti-CD3]_L1.47_
                          H1.32_scFv vhCDR 3
source                    1..14
                          mol_type = protein
                          organism = synthetic construct
SEQUENCE: 169
HGNFGDSYVS WFAY                                                            14
```

```
SEQ ID NO: 170          moltype = AA   length = 20
FEATURE                 Location/Qualifiers
REGION                  1..20
                        note = Description of Artificial Sequence: Synthetic peptide
REGION                  1..20
                        note = CD3 High-Int #1[VL-VH] - [anti-CD3]_L1.47_
                        H1.32_scFv Linke r
source                  1..20
                        mol_type = protein
                        organism = synthetic construct
SEQUENCE: 170
GKPGSGKPGS GKPGSGKPGS                                                     20

SEQ ID NO: 171          moltype = AA   length = 254
FEATURE                 Location/Qualifiers
REGION                  1..254
                        note = Description of Artificial Sequence: Synthetic
                        polypeptide
REGION                  1..254
                        note = CD3 High-Int #2[VL-VH] - [anti-CD3]_L1.47_
                        H1.89_scFv scFv
source                  1..254
                        mol_type = protein
                        organism = synthetic construct
SEQUENCE: 171
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVLG KPGSGKPGSG  120
KPGSGKPGSE VQLVESGGGL VQPGGSLRLS CAASGFTFST YAMNWVRQAP GKGLEWVGRI  180
RSKYNNYATY YADSVKGRFT ISRDDSKNTL YLQMNSLRAE DTAVYYCVRH GNFGDEYVSW  240
FAYWGQGTLV TVSS                                                    254

SEQ ID NO: 172          moltype = AA   length = 109
FEATURE                 Location/Qualifiers
REGION                  1..109
                        note = Description of Artificial Sequence: Synthetic
                        polypeptide
REGION                  1..109
                        note = CD3 High-Int #2[VL-VH] - [anti-CD3]_L1.47_
                        H1.89_scFv Varia ble Light (vl) Domain
source                  1..109
                        mol_type = protein
                        organism = synthetic construct
SEQUENCE: 172
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVL              109

SEQ ID NO: 173          moltype = AA   length = 14
FEATURE                 Location/Qualifiers
REGION                  1..14
                        note = Description of Artificial Sequence: Synthetic peptide
REGION                  1..14
                        note = CD3 High-Int #2[VL-VH] - [anti-CD3]_L1.47_
                        H1.89_scFv vlCDR 1
source                  1..14
                        mol_type = protein
                        organism = synthetic construct
SEQUENCE: 173
GSSTGAVTTS NYAN                                                    14

SEQ ID NO: 174          moltype = AA   length = 7
FEATURE                 Location/Qualifiers
REGION                  1..7
                        note = Description of Artificial Sequence: Synthetic peptide
REGION                  1..7
                        note = CD3 High-Int #2[VL-VH] - [anti-CD3]_L1.47_
                        H1.89_scFv vlCDR 2
source                  1..7
                        mol_type = protein
                        organism = synthetic construct
SEQUENCE: 174
GTNKRAP                                                            7

SEQ ID NO: 175          moltype = AA   length = 9
FEATURE                 Location/Qualifiers
REGION                  1..9
                        note = Description of Artificial Sequence: Synthetic peptide
REGION                  1..9
                        note = CD3 High-Int #2[VL-VH] - [anti-CD3]_L1.47_
                        H1.89_scFv vlCDR 3
```

-continued

```
source                    1..9
                          mol_type = protein
                          organism = synthetic construct
SEQUENCE: 175
ALWYSNHWV                                                          9

SEQ ID NO: 176            moltype = AA   length = 125
FEATURE                   Location/Qualifiers
REGION                    1..125
                          note = Description of Artificial Sequence: Synthetic
                          polypeptide
REGION                    1..125
                          note = CD3 High-Int #2[VL-VH] - [anti-CD3]_L1.47_
                          H1.89_scFv Varia ble Heavy (vh) Domain
source                    1..125
                          mol_type = protein
                          organism = synthetic construct
SEQUENCE: 176
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDEYVS WFAYWGQGTL   120
VTVSS                                                              125

SEQ ID NO: 177            moltype = AA   length = 5
FEATURE                   Location/Qualifiers
REGION                    1..5
                          note = Description of Artificial Sequence: Synthetic peptide
REGION                    1..5
                          note = CD3 High-Int #2[VL-VH] - [anti-CD3]_L1.47_
                          H1.89_scFv vhCDR 1
source                    1..5
                          mol_type = protein
                          organism = synthetic construct
SEQUENCE: 177
TYAMN                                                              5

SEQ ID NO: 178            moltype = AA   length = 19
FEATURE                   Location/Qualifiers
REGION                    1..19
                          note = Description of Artificial Sequence: Synthetic peptide
REGION                    1..19
                          note = CD3 High-Int #2[VL-VH] - [anti-CD3]_L1.47_
                          H1.89_scFv vhCDR 2
source                    1..19
                          mol_type = protein
                          organism = synthetic construct
SEQUENCE: 178
RIRSKYNNYA TYYADSVKG                                               19

SEQ ID NO: 179            moltype = AA   length = 14
FEATURE                   Location/Qualifiers
REGION                    1..14
                          note = Description of Artificial Sequence: Synthetic peptide
REGION                    1..14
                          note = CD3 High-Int #2[VL-VH] - [anti-CD3]_L1.47_
                          H1.89_scFv vhCDR 3
source                    1..14
                          mol_type = protein
                          organism = synthetic construct
SEQUENCE: 179
HGNFGDEYVS WFAY                                                    14

SEQ ID NO: 180            moltype = AA   length = 20
FEATURE                   Location/Qualifiers
REGION                    1..20
                          note = Description of Artificial Sequence: Synthetic peptide
REGION                    1..20
                          note = CD3 High-Int #2[VL-VH] - [anti-CD3]_L1.47_
                          H1.89_scFv Linke r
source                    1..20
                          mol_type = protein
                          organism = synthetic construct
SEQUENCE: 180
GKPGSGKPGS GKPGSGKPGS                                              20

SEQ ID NO: 181            moltype = AA   length = 254
FEATURE                   Location/Qualifiers
REGION                    1..254
                          note = Description of Artificial Sequence: Synthetic
                          polypeptide
```

-continued

```
REGION                     1..254
                           note = CD3 High-Int[VL-VH] - [anti-CD3]_L1.47_ H1.90_scFv
                             scFv
source                     1..254
                           mol_type = protein
                           organism = synthetic construct
SEQUENCE: 181
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVLG KPGSGKPGSG  120
KPGSGKPGSE VQLVESGGGL VQPGGSLRLS CAASGFTFST YAMNWVRQAP GKGLEWVGRI  180
RSKYNNYATY YADSVKGRFT ISRDDSKNTL YLQMNSLRAE DTAVYYCVRH GNFGDPYVSW  240
FAYWGQGTLV TVSS                                                    254

SEQ ID NO: 182            moltype = AA  length = 109
FEATURE                   Location/Qualifiers
REGION                    1..109
                          note = Description of Artificial Sequence: Synthetic
                            polypeptide
REGION                    1..109
                          note = CD3 High-Int[VL-VH] - [anti-CD3]_L1.47_ H1.90_scFv
                            Variable Light (vl) Domain
source                    1..109
                          mol_type = protein
                          organism = synthetic construct
SEQUENCE: 182
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVL              109

SEQ ID NO: 183            moltype = AA  length = 14
FEATURE                   Location/Qualifiers
REGION                    1..14
                          note = Description of Artificial Sequence: Synthetic peptide
REGION                    1..14
                          note = CD3 High-Int[VL-VH] - [anti-CD3]_L1.47_ H1.90_scFv
                            vlCDR1
source                    1..14
                          mol_type = protein
                          organism = synthetic construct
SEQUENCE: 183
GSSTGAVTTS NYAN                                                    14

SEQ ID NO: 184            moltype = AA  length = 7
FEATURE                   Location/Qualifiers
REGION                    1..7
                          note = Description of Artificial Sequence: Synthetic peptide
REGION                    1..7
                          note = CD3 High-Int[VL-VH] - [anti-CD3]_L1.47_ H1.90_scFv
                            vlCDR2
source                    1..7
                          mol_type = protein
                          organism = synthetic construct
SEQUENCE: 184
GTNKRAP                                                            7

SEQ ID NO: 185            moltype = AA  length = 9
FEATURE                   Location/Qualifiers
REGION                    1..9
                          note = Description of Artificial Sequence: Synthetic peptide
REGION                    1..9
                          note = CD3 High-Int[VL-VH] - [anti-CD3]_L1.47_ H1.90_scFv
                            vlCDR3
source                    1..9
                          mol_type = protein
                          organism = synthetic construct
SEQUENCE: 185
ALWYSNHWV                                                          9

SEQ ID NO: 186            moltype = AA  length = 125
FEATURE                   Location/Qualifiers
REGION                    1..125
                          note = Description of Artificial Sequence: Synthetic
                            polypeptide
REGION                    1..125
                          note = CD3 High-Int[VL-VH] - [anti-CD3]_L1.47_ H1.90_scFv
                            Variable Heavy (vh) Domain
source                    1..125
                          mol_type = protein
                          organism = synthetic construct
SEQUENCE: 186
```

-continued

```
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDPYVS WFAYWGQGTL  120
VTVSS                                                              125

SEQ ID NO: 187          moltype = AA  length = 5
FEATURE                 Location/Qualifiers
REGION                  1..5
                        note = Description of Artificial Sequence: Synthetic peptide
REGION                  1..5
                        note = CD3 High-Int[VL-VH] - [anti-CD3]_L1.47_ H1.90_ scFv
                         vhCDR1
source                  1..5
                        mol_type = protein
                        organism = synthetic construct
SEQUENCE: 187
TYAMN                                                               5

SEQ ID NO: 188          moltype = AA  length = 19
FEATURE                 Location/Qualifiers
REGION                  1..19
                        note = Description of Artificial Sequence: Synthetic peptide
REGION                  1..19
                        note = CD3 High-Int[VL-VH] - [anti-CD3]_L1.47_ H1.90_ scFv
                         vhCDR2
source                  1..19
                        mol_type = protein
                        organism = synthetic construct
SEQUENCE: 188
RIRSKYNNYA TYYADSVKG                                                19

SEQ ID NO: 189          moltype = AA  length = 14
FEATURE                 Location/Qualifiers
REGION                  1..14
                        note = Description of Artificial Sequence: Synthetic peptide
REGION                  1..14
                        note = CD3 High-Int[VL-VH] - [anti-CD3]_L1.47_ H1.90_ scFv
                         vhCDR3
source                  1..14
                        mol_type = protein
                        organism = synthetic construct
SEQUENCE: 189
HGNFGDPYVS WFAY                                                     14

SEQ ID NO: 190          moltype = AA  length = 20
FEATURE                 Location/Qualifiers
REGION                  1..20
                        note = Description of Artificial Sequence: Synthetic peptide
REGION                  1..20
                        note = CD3 High-Int[VL-VH] - [anti-CD3]_L1.47_ H1.90_ scFv
                         Linker
source                  1..20
                        mol_type = protein
                        organism = synthetic construct
SEQUENCE: 190
GKPGSGKPGS GKPGSGKPGS                                               20

SEQ ID NO: 191          moltype = AA  length = 254
FEATURE                 Location/Qualifiers
REGION                  1..254
                        note = Description of Artificial Sequence: Synthetic
                         polypeptide
REGION                  1..254
                        note = Anti-CD3-Intermediate[VL-VH] - [anti-CD3]_L1.47_
                         H1.33_scFv scFv
source                  1..254
                        mol_type = protein
                        organism = synthetic construct
SEQUENCE: 191
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVLG KPGSGKPGSG  120
KPGSGKPGSE VQLVESGGGL VQPGGSLRLS CAASGFTFST YAMNWVRQAP GKGLEWVGRI  180
RSKYNNYATY YADSVKGRFT ISRDDSKNTL YLQMNSLRAE DTAVYYCVRH GNFGDSYVSW  240
FDYWGQGTLV TVSS                                                    254

SEQ ID NO: 192          moltype = AA  length = 109
FEATURE                 Location/Qualifiers
REGION                  1..109
                        note = Description of Artificial Sequence: Synthetic
                         polypeptide
```

```
REGION                    1..109
                          note = Anti-CD3-Intermediate[VL-VH] - [anti-CD3]_L1.47_
                          H1.33_scFv Variable Light (vl) Domain
source                    1..109
                          mol_type = protein
                          organism = synthetic construct
SEQUENCE: 192
QAVVTQEPSL TVSPGGTVTL TCGSSTGAVT TSNYANWVQQ KPGKSPRGLI GGTNKRAPGV   60
PARFSGSLLG GKAALTISGA QPEDEADYYC ALWYSNHWVF GGGTKLTVL              109

SEQ ID NO: 193            moltype = AA  length = 14
FEATURE                   Location/Qualifiers
REGION                    1..14
                          note = Description of Artificial Sequence: Synthetic peptide
REGION                    1..14
                          note = Anti-CD3-Intermediate[VL-VH] - [anti-CD3]_L1.47_
                          H1.33_scFv vlCDR1
source                    1..14
                          mol_type = protein
                          organism = synthetic construct
SEQUENCE: 193
GSSTGAVTTS NYAN                                                    14

SEQ ID NO: 194            moltype = AA  length = 7
FEATURE                   Location/Qualifiers
REGION                    1..7
                          note = Description of Artificial Sequence: Synthetic peptide
REGION                    1..7
                          note = Anti-CD3-Intermediate[VL-VH] - [anti-CD3]_L1.47_
                          H1.33_scFv vlCDR2
source                    1..7
                          mol_type = protein
                          organism = synthetic construct
SEQUENCE: 194
GTNKRAP                                                            7

SEQ ID NO: 195            moltype = AA  length = 9
FEATURE                   Location/Qualifiers
REGION                    1..9
                          note = Description of Artificial Sequence: Synthetic peptide
REGION                    1..9
                          note = Anti-CD3-Intermediate[VL-VH] - [anti-CD3]_L1.47_
                          H1.33_scFv vlCDR3
source                    1..9
                          mol_type = protein
                          organism = synthetic construct
SEQUENCE: 195
ALWYSNHWV                                                          9

SEQ ID NO: 196            moltype = AA  length = 125
FEATURE                   Location/Qualifiers
REGION                    1..125
                          note = Description of Artificial Sequence: Synthetic
                          polypeptide
REGION                    1..125
                          note = Anti-CD3-Intermediate[VL-VH] - [anti-CD3]_L1.47_
                          H1.33_scFv Variable Heavy (vh) Domain
source                    1..125
                          mol_type = protein
                          organism = synthetic construct
SEQUENCE: 196
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFDYWGQGTL  120
VTVSS                                                             125

SEQ ID NO: 197            moltype = AA  length = 5
FEATURE                   Location/Qualifiers
REGION                    1..5
                          note = Description of Artificial Sequence: Synthetic peptide
REGION                    1..5
                          note = Anti-CD3-Intermediate[VL-VH] - [anti-CD3]_L1.47_
                          H1.33_scFv vhCDR1
source                    1..5
                          mol_type = protein
                          organism = synthetic construct
SEQUENCE: 197
TYAMN                                                             5

SEQ ID NO: 198            moltype = AA  length = 19
```

-continued

```
FEATURE               Location/Qualifiers
REGION                1..19
                      note = Description of Artificial Sequence: Synthetic peptide
REGION                1..19
                      note = Anti-CD3-Intermediate[VL-VH] - [anti-CD3]_L1.47_
                      H1.33_scFv vhCDR2
source                1..19
                      mol_type = protein
                      organism = synthetic construct
SEQUENCE: 198
RIRSKYNNYA TYYADSVKG                                                    19

SEQ ID NO: 199        moltype = AA  length = 14
FEATURE               Location/Qualifiers
REGION                1..14
                      note = Description of Artificial Sequence: Synthetic peptide
REGION                1..14
                      note = Anti-CD3-Intermediate[VL-VH] - [anti-CD3]_L1.47_
                      H1.33_scFv vhCDR3
source                1..14
                      mol_type = protein
                      organism = synthetic construct
SEQUENCE: 199
HGNFGDSYVS WFDY                                                         14

SEQ ID NO: 200        moltype = AA  length = 20
FEATURE               Location/Qualifiers
REGION                1..20
                      note = Description of Artificial Sequence: Synthetic peptide
REGION                1..20
                      note = Anti-CD3-Intermediate[VL-VH] - [anti-CD3]_L1.47_
                      H1.33_scFv Linker
source                1..20
                      mol_type = protein
                      organism = synthetic construct
SEQUENCE: 200
GKPGSGKPGS GKPGSGKPGS                                                   20

SEQ ID NO: 201        moltype = AA  length = 254
FEATURE               Location/Qualifiers
REGION                1..254
                      note = Description of Artificial Sequence: Synthetic
                      polypeptide
REGION                1..254
                      note = CD3 High-Int[VL-VH] - [anti-CD3]_L1.47_ H1.31_scFv
                      scFv
source                1..254
                      mol_type = protein
                      organism = synthetic construct
SEQUENCE: 201
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVLG KPGSGKPGSG  120
KPGSGKPGSE VQLVESGGGL VQPGGSLRLS CAASGFTFST YAMSWVRQAP GKGLEWVGRI  180
RSKYNNYATY YADSVKGRFT ISRDDSKNTL YLQMNSLRAE DTAVYYCVRH GNFGDSYVSW  240
FAYWGQGTLV TVSS                                                    254

SEQ ID NO: 202        moltype = AA  length = 109
FEATURE               Location/Qualifiers
REGION                1..109
                      note = Description of Artificial Sequence: Synthetic
                      polypeptide
REGION                1..109
                      note = CD3 High-Int[VL-VH] - [anti-CD3]_L1.47_ H1.31_scFv
                      Variable Light (vl) Domain
source                1..109
                      mol_type = protein
                      organism = synthetic construct
SEQUENCE: 202
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVL              109

SEQ ID NO: 203        moltype = AA  length = 14
FEATURE               Location/Qualifiers
REGION                1..14
                      note = Description of Artificial Sequence: Synthetic peptide
REGION                1..14
                      note = CD3 High-Int[VL-VH] - [anti-CD3]_L1.47_ H1.31_scFv
                      vlCDR1
source                1..14
```

```
                        mol_type = protein
                        organism = synthetic construct
SEQUENCE: 203
GSSTGAVTTS NYAN                                              14

SEQ ID NO: 204          moltype = AA  length = 7
FEATURE                 Location/Qualifiers
REGION                  1..7
                        note = Description of Artificial Sequence: Synthetic peptide
REGION                  1..7
                        note = CD3 High-Int[VL-VH] - [anti-CD3]_L1.47_ H1.31_scFv
                         vlCDR2
source                  1..7
                        mol_type = protein
                        organism = synthetic construct
SEQUENCE: 204
GTNKRAP                                                       7

SEQ ID NO: 205          moltype = AA  length = 9
FEATURE                 Location/Qualifiers
REGION                  1..9
                        note = Description of Artificial Sequence: Synthetic peptide
REGION                  1..9
                        note = CD3 High-Int[VL-VH] - [anti-CD3]_L1.47_ H1.31_scFv
                         vlCDR3
source                  1..9
                        mol_type = protein
                        organism = synthetic construct
SEQUENCE: 205
ALWYSNHWV                                                     9

SEQ ID NO: 206          moltype = AA  length = 125
FEATURE                 Location/Qualifiers
REGION                  1..125
                        note = Description of Artificial Sequence: Synthetic
                         polypeptide
REGION                  1..125
                        note = CD3 High-Int[VL-VH] - [anti-CD3]_L1.47_ H1.31_scFv
                         Variable Heavy (vh) Domain
source                  1..125
                        mol_type = protein
                        organism = synthetic construct
SEQUENCE: 206
EVQLVESGGG LVQPGGSLRL SCAASGFTFS TYAMSWVRQA PGKGLEWVGR IRSKYNNYAT  60
YYADSVKGRF TISRDDSKNT LYLQMNSLRA EDTAVYYCVR HGNFGDSYVS WFAYWGQGTL 120
VTVSS                                                       125

SEQ ID NO: 207          moltype = AA  length = 5
FEATURE                 Location/Qualifiers
REGION                  1..5
                        note = Description of Artificial Sequence: Synthetic peptide
REGION                  1..5
                        note = CD3 High-Int[VL-VH] - [anti-CD3]_L1.47_ H1.31_scFv
                         vhCDR1
source                  1..5
                        mol_type = protein
                        organism = synthetic construct
SEQUENCE: 207
TYAMS                                                         5

SEQ ID NO: 208          moltype = AA  length = 19
FEATURE                 Location/Qualifiers
REGION                  1..19
                        note = Description of Artificial Sequence: Synthetic peptide
REGION                  1..19
                        note = CD3 High-Int[VL-VH] - [anti-CD3]_L1.47_ H1.31_scFv
                         vhCDR2
source                  1..19
                        mol_type = protein
                        organism = synthetic construct
SEQUENCE: 208
RIRSKYNNYA TYYADSVKG                                          19

SEQ ID NO: 209          moltype = AA  length = 14
FEATURE                 Location/Qualifiers
REGION                  1..14
                        note = Description of Artificial Sequence: Synthetic peptide
REGION                  1..14
                        note = CD3 High-Int[VL-VH] - [anti-CD3]_L1.47_ H1.31_scFv
```

-continued

```
                        vhCDR3
source                  1..14
                        mol_type = protein
                        organism = synthetic construct
SEQUENCE: 209
HGNFGDSYVS WFAY                                                    14

SEQ ID NO: 210          moltype = AA  length = 20
FEATURE                 Location/Qualifiers
REGION                  1..20
                        note = Description of Artificial Sequence: Synthetic peptide
REGION                  1..20
                        note = CD3 High-Int[VL-VH] - [anti-CD3]_L1.47_ H1.31_scFv
                         Linker
source                  1..20
                        mol_type = protein
                        organism = synthetic construct
SEQUENCE: 210
GKPGSGKPGS GKPGSGKPGS                                              20

SEQ ID NO: 211          moltype = AA  length = 875
FEATURE                 Location/Qualifiers
REGION                  1..875
                        note = sp4638
source                  1..875
                        mol_type = protein
                        organism = Homo sapiens
SEQUENCE: 211
MESTLTLATE QPVKKNTLKK YKIACIVLLA LLVIMSLGLG LGLGLRKLEK QGSCRKKCFD  60
ASFRGLENCR CDVACKDRGD CCWDFEDTCV ESTRIWMCNK FRCGETRLEA SLCSCSDDCL  120
QRKDCCADYK SVCQGETSWL EENCDTAQQS QCPEGFDLPP VILFSMDGFR AEYLYTWDTL  180
MPNINKLKTC GIHSKYMRAM YPTKTFPNHY TIVTGLYPES HGIIDNNMYD VNLNKNFSLS  240
SKEQNNPAWW HGQPMWLTAM YQGLKAATYF WPGSEVAING SFPSIYMPYN GSVPFEERIS  300
TLLKWLDLPK AERPRFYTMY FEEPDSSGHA GGPVSARVIK ALQVVDHAFG MLMEGLKQRN  360
LHNCVNIILL ADHGMDQTYC NKMEYMTDYF PRINFFYMYE GPAPRIRAHN IPHDFFSFNS  420
EEIVRNLSCR KPDQHFKPYL TPDLPKRLHY AKNVRIDKVH LFVDQQWLAV RSKSNTNCGG  480
GNHGYNNEFR SMEAIFLAHG PSFKEKTEVE PFENIEVYNL MCDLLRIQPA PNNGTHGSLN  540
HLLKVPFYEP SHAEEVSKFS VCGFANPLPT ESLDCFCPHL QNSTQLEQVN QMLNLTQEEI  600
TATVKVNLPF GRPRVLQKNV DHCLLYHREY VSGFGKAMRM PMWSSYTVPQ LGDTSPLPPT  660
VPDCLRADVR VPPSESQKCS FYLADKNITH GFLYPPASNR TSDSQYDALI TSNLVPMYEE  720
FRKMWDYFHS VLLIKHATER NGVNVVSGPI FDYNYDGHFD APDEITKHLA NTDVPIPTHY  780
FVVLTSCKNK SHTPENCPGW LDVLPFIIPH RPTNVESCPE GKPEALWVEE RFTAHIARVR  840
DVELLTGLDF YQDKVQPVSE ILQLKTYLPT FETTI                             875

SEQ ID NO: 212          moltype = AA  length = 845
FEATURE                 Location/Qualifiers
REGION                  1..845
                        note = sp4638[31]-875
source                  1..845
                        mol_type = protein
                        organism = Homo sapiens
SEQUENCE: 212
LLVIMSLGLG LGLGLRKLEK QGSCRKKCFD ASFRGLENCR CDVACKDRGD CCWDFEDTCV  60
ESTRIWMCNK FRCGETRLEA SLCSCSDDCL QRKDCCADYK SVCQGETSWL EENCDTAQQS  120
QCPEGFDLPP VILFSMDGFR AEYLYTWDTL MPNINKLKTC GIHSKYMRAM YPTKTFPNHY  180
TIVTGLYPES HGIIDNNMYD VNLNKNFSLS SKEQNNPAWW HGQPMWLTAM YQGLKAATYF  240
WPGSEVAING SFPSIYMPYN GSVPFEERIS TLLKWLDLPK AERPRFYTMY FEEPDSSGHA  300
GGPVSARVIK ALQVVDHAFG MLMEGLKQRN LHNCVNIILL ADHGMDQTYC NKMEYMTDYF  360
PRINFFYMYE GPAPRIRAHN IPHDFFSFNS EEIVRNLSCR KPDQHFKPYL TPDLPKRLHY  420
AKNVRIDKVH LFVDQQWLAV RSKSNTNCGG GNHGYNNEFR SMEAIFLAHG PSFKEKTEVE  480
PFENIEVYNL MCDLLRIQPA PNNGTHGSLN HLLKVPFYEP SHAEEVSKFS VCGFANPLPT  540
ESLDCFCPHL QNSTQLEQVN QMLNLTQEEI TATVKVNLPF GRPRVLQKNV DHCLLYHREY  600
VSGFGKAMRM PMWSSYTVPQ LGDTSPLPPT VPDCLRADVR VPPSESQKCS FYLADKNITH  660
GFLYPPASNR TSDSQYDALI TSNLVPMYEE FRKMWDYFHS VLLIKHATER NGVNVVSGPI  720
FDYNYDGHFD APDEITKHLA NTDVPIPTHY FVVLTSCKNK SHTPENCPGW LDVLPFIIPH  780
RPTNVESCPE GKPEALWVEE RFTAHIARVR DVELLTGLDF YQDKVQPVSE ILQLKTYLPT  840
FETTI                                                             845

SEQ ID NO: 213          moltype = AA  length = 874
FEATURE                 Location/Qualifiers
REGION                  1..874
                        note = spDYE8
source                  1..874
                        mol_type = protein
                        organism = Mus musculus
SEQUENCE: 213
MDSRLALATE EPIKKDSLKK YKILCVVLLA LLVIVSLGLG LGLGLRKPEE QGSCRKKCFD  60
SSHRGLEGCR CDSGCTGRGD CCWDFEDTCV KSTQIWTCNL FRCGENRLET ALCSCADDCL  120
QRKDCCADYK TVCQGESPWV TEACASSQEP QCPPGFDLPP VILFSMDGFR AEYLQTWSTL  180
```

```
LPNINKLKTC GIHSKYMRAM YPTKTFPNHY TIVTGLYPES HGIIDNNMYD VHLNKNFSLS  240
SVEKSNPAWW SGQPIWLTAM YQGLKAACYY WPGSDVAVNG SFPTIYRNYS NSVPYERRIT  300
TLLQWLDLPK ADRPSFYTIY VEEPDSAGHS SGPVSAGVIK ALQSVDNAFG MLMEGLKQRN  360
LHNCVNIIVL ADHGMDQTSC DRVEYMTDYF PKINFYMYQG PAPRIRTRNI PQDFFTFNSE  420
EIVRNLSCRK PDQHFKPYLT PDLPKRLHYA KNVRIDKAHL MVDRQWLAFR SKGSSNCGGG  480
THGYNNEFKS MEAIFLAHGP SFIEKTVIEP FENIEVYNLL CDLLHIEPAP NNGTHGSLNH  540
LLKTPFYKPS HAGELSTPAD CGFTTPLPTD PLDCSCPALQ NTPGLEEQAN QRLNLSEGEV  600
AATVKANLPF GRPRVMQKNG DHCLLYHRDY ISGYGKAMKM PMWSSYTVLK PGDTSSLPPT  660
VPDCLRADVR VAPSESQKCS FYLADKNITH GFLYPAIKGT NESRYDALIT SNLVPMYKEF  720
KKMWDYFHEV LLIKYAIERN GLNVVSGPIF DYNYDGHFDA PDEITQYVAG TDVPIPTHYF  780
VVLTSCKDQT HTPDSCPGWL DVLPFIVPHR PTNIESCSEN KTEDLWVEER FQAHAARVRD  840
VELLTGLDFY QEKAQPVSQI LQLKTYLPTF ETII                              874

SEQ ID NO: 214            moltype = AA  length = 844
FEATURE                   Location/Qualifiers
REGION                    1..844
                          note = spDYE8[31]-874
source                    1..844
                          mol_type = protein
                          organism = Mus musculus
SEQUENCE: 214
LLVIVSLGLG LGLGLRKPEE QGSCRKKCFD SSHRGLEGCR CDSGCTGRGD CCWDFEDTCV  60
KSTQIWTCNL FRCGENRLET ALCSCADDCL QRKDCCADYK TVCQGESPWV TEACASSQEP  120
QCPPGFDLPP VILFSMDGFR AEYLQTWSTL LPNINKLKTC GIHSKYMRAM YPTKTFPNHY  180
TIVTGLYPES HGIIDNNMYD VHLNKNFSLS SVEKSNPAWW SGQPIWLTAM YQGLKAACYY  240
WPGSDVAVNG SFPTIYRNYS NSVPYERRIT TLLQWLDLPK ADRPSFYTIY VEEPDSAGHS  300
SGPVSAGVIK ALQSVDNAFG MLMEGLKQRN LHNCVNIIVL ADHGMDQTSC DRVEYMTDYF  360
PKINFYMYQG PAPRIRTRNI PQDFFTFNSE EIVRNLSCRK PDQHFKPYLT PDLPKRLHYA  420
KNVRIDKAHL MVDRQWLAFR SKGSSNCGGG THGYNNEFKS MEAIFLAHGP SFIEKTVIEP  480
FENIEVYNLL CDLLHIEPAP NNGTHGSLNH LLKTPFYKPS HAGELSTPAD CGFTTPLPTD  540
PLDCSCPALQ NTPGLEEQAN QRLNLSEGEV AATVKANLPF GRPRVMQKNG DHCLLYHRDY  600
ISGYGKAMKM PMWSSYTVLK PGDTSSLPPT VPDCLRADVR VAPSESQKCS FYLADKNITH  660
GFLYPAIKGT NESRYDALIT SNLVPMYKEF KKMWDYFHEV LLIKYAIERN GLNVVSGPIF  720
DYNYDGHFDA PDEITQYVAG TDVPIPTHYF VVLTSCKDQT HTPDSCPGWL DVLPFIVPHR  780
PTNIESCSEN KTEDLWVEER FQAHAARVRD VELLTGLDFY QEKAQPVSQI LQLKTYLPTF  840
ETII                                                              844

SEQ ID NO: 215            moltype = AA  length = 874
FEATURE                   Location/Qualifiers
REGION                    1..874
                          note = tr^A2K5TKP4
source                    1..874
                          mol_type = protein
                          organism = Macaca fascicularis
SEQUENCE: 215
MESMLTLATE QPVKKNTLKK YKIACIVLLA LLVIMSLGLG LGLGLRKLEK QGSCRKKCFD  60
ASFRGLENCR CDVACEDRGD CCWDFEDTCV ESTRIWTCNK FRCGETRLEA SLCSCSDDCL  120
QRKDCCADYK SVCQGETSWL EENCDTAQQS QCPEGFDLPP VILFSMDGFR AEYLYTWDTL  180
MPNINKLKTC GIHSKYMRAM YPTKTFPNHY TIVTGLYPES HGIIDNNMYD VNLNKNFSLS  240
SEEQNNPAWW HGQPMWLTAM YQGLKAATYF WPGSEVAING SFPSIYMPYN RSVPYEERIS  300
TLLKWLDLPK AERPSFYTMY FEEPDSSGHA GGPVSARVIK ALQVVDHAFG MLMEGLKQRN  360
LHNCVNIILL ADHGMDQTYC NKMEYMTDYF PRINFYMYEG PAPRIRALNV PHDFFSCKYE  420
DTYMKKRCRK PDQHFKPYLT PDLPKRLHYA KNVRIDKVHL FVDRQWLAVG SKSNTNCGGG  480
NHGYNNEFRS MEAIFLAHGP SFKEKTEVEP FENIEVYNLM CDLLRIQPAP NNGTRGSLNH  540
LLKVPFYEPS HAEEVSKFSV CGFANPLPTN NLSCLCPHLQ NSIQLEQVNQ MLNLTQEEIT  600
ATVKVNLPFG RPRVLQKNVD NCLLYHREYV SGFGKAMRMP MWSSYTVPQL GDTSPLPPTV  660
PDCLRADVRV PPSESQKCSF YLADENITHG FLYPPAINRT SDSQYDALIM SNLVPMYEEF  720
RKMWDYFHSV LLIKHATERN GVNVVSGPIF DYNYDGHFDA PEEITKHIAN TDIPIPTHYF  780
VVLTSCKNKS HTPENCPGWL DVLPFIIPHR PTNVESCPEG KPEALWVEER FTAHIARVRD  840
VELLTGLDFY QDKAQPVSEI LQLKTYLPTF ETTI                              874

SEQ ID NO: 216            moltype = AA  length = 844
FEATURE                   Location/Qualifiers
REGION                    1..844
                          note = tr^A2K5TKP4[31]-874
source                    1..844
                          mol_type = protein
                          organism = Macaca fascicularis
SEQUENCE: 216
LLVIMSLGLG LGLGLRKLEK QGSCRKKCFD ASFRGLENCR CDVACEDRGD CCWDFEDTCV  60
ESTRIWTCNK FRCGETRLEA SLCSCSDDCL QRKDCCADYK SVCQGETSWL EENCDTAQQS  120
QCPEGFDLPP VILFSMDGFR AEYLYTWDTL MPNINKLKTC GIHSKYMRAM YPTKTFPNHY  180
TIVTGLYPES HGIIDNNMYD VNLNKNFSLS SEEQNNPAWW HGQPMWLTAM YQGLKAATYF  240
WPGSEVAING SFPSIYMPYN RSVPYEERIS TLLKWLDLPK AERPSFYTMY FEEPDSSGHA  300
GGPVSARVIK ALQVVDHAFG MLMEGLKQRN LHNCVNIILL ADHGMDQTYC NKMEYMTDYF  360
PRINFYMYEG PAPRIRALNV PHDFFSCKYE DTYMKKRCRK PDQHFKPYLT PDLPKRLHYA  420
KNVRIDKVHL FVDRQWLAVG SKSNTNCGGG NHGYNNEFRS MEAIFLAHGP SFKEKTEVEP  480
FENIEVYNLM CDLLRIQPAP NNGTRGSLNH LLKVPFYEPS HAEEVSKFSV CGFANPLPTN  540
NLSCLCPHLQ NSIQLEQVNQ MLNLTQEEIT ATVKVNLPFG RPRVLQKNVD NCLLYHREYV  600
```

```
SGFGKAMRMP MWSSYTVPQL GDTSPLPPTV PDCLRADVRV PPSESQKCSF YLADENITHG   660
FLYPPAINRT SDSQYDALIM SNLVPMYEEF RKMWDYFHSV LLIKHATERN GVNVVSGPIF   720
DYNYDGHFDA PEEITKHIAN TDIPIPTHYF VVLTSCKNKS HTPENCPGWL DVLPFIIPHR   780
PTNVESCPEG KPEALWVEER FTAHIARVRD VELLTGLDFY QDKAQPVSEI LQLKTYLPTF   840
ETTI                                                                844

SEQ ID NO: 217              moltype = AA   length = 124
FEATURE                     Location/Qualifiers
REGION                      1..124
                            note = Description of Artificial Sequence: Synthetic
                             polypeptide
REGION                      1..124
                            note = MESO-A[MSLN]_H1.1_L1 Variable heavy (vh) domain
source                      1..124
                            mol_type = protein
                            organism = synthetic construct
SEQUENCE: 217
EVQLVESGGG LVQPGGSLKL SCAASGFDFS RYWMSWVRQA PGKGLEWVSE INPDSSTIVY   60
TPSVKGRFTI SRDNAKNSLY LQMNSLRAED TAVYYCARRG SHYYGYRTGY FDVWGAGTTV   120
TVSS                                                                124

SEQ ID NO: 218              moltype = AA   length = 5
FEATURE                     Location/Qualifiers
REGION                      1..5
                            note = Description of Artificial Sequence: Synthetic peptide
REGION                      1..5
                            note = MESO-A[MSLN]_H1.1_L1 vhCDR1
source                      1..5
                            mol_type = protein
                            organism = synthetic construct
SEQUENCE: 218
RYWMS                                                               5

SEQ ID NO: 219              moltype = AA   length = 17
FEATURE                     Location/Qualifiers
REGION                      1..17
                            note = Description of Artificial Sequence: Synthetic peptide
REGION                      1..17
                            note = MESO-A[MSLN]_H1.1_L1 vhCDR2
source                      1..17
                            mol_type = protein
                            organism = synthetic construct
SEQUENCE: 219
EINPDSSTIV YTPSVKG                                                  17

SEQ ID NO: 220              moltype = AA   length = 15
FEATURE                     Location/Qualifiers
REGION                      1..15
                            note = Description of Artificial Sequence: Synthetic peptide
REGION                      1..15
                            note = MESO-A[MSLN]_H1.1_L1 vhCDR3
source                      1..15
                            mol_type = protein
                            organism = synthetic construct
SEQUENCE: 220
RGSHYYGYRT GYFDV                                                    15

SEQ ID NO: 221              moltype = AA   length = 106
FEATURE                     Location/Qualifiers
REGION                      1..106
                            note = Description of Artificial Sequence: Synthetic
                             polypeptide
REGION                      1..106
                            note = MESO-A[MSLN]_H1.1_L1 Variable light (vl) domain
source                      1..106
                            mol_type = protein
                            organism = synthetic construct
SEQUENCE: 221
DVVLTQSPAT LSLSPGERAT LSCRASSSVS YMYWHQQKPD QSPKLLIYDT SNLASGVPVR   60
FSGSGSGTDY TLTISSLEPE DFAVYYCQQW SSYPPTFGGG TKLEIK                  106

SEQ ID NO: 222              moltype = AA   length = 10
FEATURE                     Location/Qualifiers
REGION                      1..10
                            note = Description of Artificial Sequence: Synthetic peptide
REGION                      1..10
                            note = MESO-A[MSLN]_H1.1_L1 vlCDR1
source                      1..10
                            mol_type = protein
```

```
                       organism = synthetic construct
SEQUENCE: 222
RASSSVSYMY                                                        10

SEQ ID NO: 223         moltype = AA  length = 7
FEATURE                Location/Qualifiers
REGION                 1..7
                       note = Description of Artificial Sequence: Synthetic peptide
REGION                 1..7
                       note = MESO-A[MSLN]_H1.1_L1 vlCDR2
source                 1..7
                       mol_type = protein
                       organism = synthetic construct
SEQUENCE: 223
DTSNLAS                                                           7

SEQ ID NO: 224         moltype = AA  length = 9
FEATURE                Location/Qualifiers
REGION                 1..9
                       note = Description of Artificial Sequence: Synthetic peptide
REGION                 1..9
                       note = MESO-A[MSLN]_H1.1_L1 vlCDR3
source                 1..9
                       mol_type = protein
                       organism = synthetic construct
SEQUENCE: 224
QQWSSYPPT                                                         9

SEQ ID NO: 225         moltype = AA  length = 454
FEATURE                Location/Qualifiers
REGION                 1..454
                       note = Description of Artificial Sequence: Synthetic
                        polypeptide
REGION                 1..454
                       note = XENP16249 Chain 1 - MESO-A[MSLN]_H1.1_IgG1 Heavy
                        Chain
source                 1..454
                       mol_type = protein
                       organism = synthetic construct
SEQUENCE: 225
EVQLVESGGG LVQPGGSLKL SCAASGFDFS RYWMSWVRQA PGKGLEWVSE INPDSSTIVY  60
TPSVKGRFTI SRDNAKNSLY LQMNSLRAED TAVYYCARRG SHYYGYRTGY FDVWGAGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SREEMTKNQV SLTCLVKGFY PSDIAVEWES NGQPENNYKT TPPVLDSDGS FFLYSKLTVD  420
KSRWQQGNVF SCSVMHEALH NHYTQKSLSL SPGK                             454

SEQ ID NO: 226         moltype = AA  length = 213
FEATURE                Location/Qualifiers
REGION                 1..213
                       note = Description of Artificial Sequence: Synthetic
                        polypeptide
REGION                 1..213
                       note = XENP16249 Chain 2 - MESO-A[MSLN]_L1 Light Chain
source                 1..213
                       mol_type = protein
                       organism = synthetic construct
SEQUENCE: 226
DVVLTQSPAT LSLSPGERAT LSCRASSSVS YMYWHQQKPD QSPKLLIYDT SNLASGVPVR  60
FSGSGSGTDY TLTISSLEPE DFAVYYCQQW SSYPPTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 227         moltype = AA  length = 453
FEATURE                Location/Qualifiers
REGION                 1..453
                       note = Description of Artificial Sequence: Synthetic
                        polypeptide
REGION                 1..453
                       note = XENP16250 Chain 1 -
                        MESO-A[MSLN]_H1.1_IgG1_PVA_/S267K Heav y Chain
source                 1..453
                       mol_type = protein
                       organism = synthetic construct
SEQUENCE: 227
EVQLVESGGG LVQPGGSLKL SCAASGFDFS RYWMSWVRQA PGKGLEWVSE INPDSSTIVY  60
TPSVKGRFTI SRDNAKNSLY LQMNSLRAED TAVYYCARRG SHYYGYRTGY FDVWGAGTTV  120
```

```
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPP  240
VAGPSVFLFP PKPKDTLMIS RTPEVTCVVV DVKHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                                453

SEQ ID NO: 228              moltype = AA  length = 213
FEATURE                    Location/Qualifiers
REGION                     1..213
                           note = Description of Artificial Sequence: Synthetic
                            polypeptide
REGION                     1..213
                           note = XENP16250 Chain 2 - MESO-A[MSLN]_L1 Light Chain
source                     1..213
                           mol_type = protein
                           organism = synthetic construct
SEQUENCE: 228
DVVLTQSPAT LSLSPGERAT LSCRASSSVS YMYWHQQKPD QSPKLLIYDT SNLASGVPVR  60
FSGSGSGTDY TLTISSLEPE DFAVYYCQQW SSYPPTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                                213

SEQ ID NO: 229              moltype = AA  length = 453
FEATURE                    Location/Qualifiers
REGION                     1..453
                           note = Description of Artificial Sequence: Synthetic
                            polypeptide
REGION                     1..453
                           note = XENP16253 Chain 1 -
                            MESO-A[MSLN]_H1.1_IgG1_pI(-)_Isosteric_
                            A_/PVA_/S267K/L368D/K370S Heavy Chain
source                     1..453
                           mol_type = protein
                           organism = synthetic construct
SEQUENCE: 229
EVQLVESGGG LVQPGGSLKL SCAASGFDFS RYWMSWVRQA PGKGLEWVSE INPDSSTIVY  60
TPSVKGRFTI SRDNAKNSLY LQMNSLRAED TAVYYCARRG SHYYGYRTGY FDVWGAGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSDTKVDK KVEPKSCDKT HTCPPCPAPP  240
VAGPSVFLFP PKPKDTLMIS RTPEVTCVVV DVKHEDPEVK FNWYVDGVEV HNAKTKPREE  300
EYNSTYRVVS VLTVLHQDWL NGKEYKCKVS NKALPAPIEK TISKAKGQPR EPQVYTLPPS  360
REEMTKNQVS LTCDVSGFYP SDIAVEWESD GQPENNYKTT PPVLDSDGSF FLYSKLTVDK  420
SRWEQGDVFS CSVMHEALHN HYTQKSLSLS PGK                                453

SEQ ID NO: 230              moltype = AA  length = 213
FEATURE                    Location/Qualifiers
REGION                     1..213
                           note = Description of Artificial Sequence: Synthetic
                            polypeptide
REGION                     1..213
                           note = XENP16253 Chain 2 - MESO-A[MSLN]_L1 Light Chain
source                     1..213
                           mol_type = protein
                           organism = synthetic construct
SEQUENCE: 230
DVVLTQSPAT LSLSPGERAT LSCRASSSVS YMYWHQQKPD QSPKLLIYDT SNLASGVPVR  60
FSGSGSGTDY TLTISSLEPE DFAVYYCQQW SSYPPTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                                213

SEQ ID NO: 231              moltype = AA  length = 123
FEATURE                    Location/Qualifiers
REGION                     1..123
                           note = Description of Artificial Sequence: Synthetic
                            polypeptide
REGION                     1..123
                           note = MESO-B[MSLN]_H0L0 Variable heavy (vh) domain
source                     1..123
                           mol_type = protein
                           organism = synthetic construct
SEQUENCE: 231
QVQLQQSGPG LVTPSQTLSL TCAISGDSVS SNSATWNWIR QSPSRGLEWL GRTYYRSKWY  60
NDYAVSVKSR MSINPDTSKN QFSLQLNSVT PEDTAVYYCA RGMMTYYYGM DVWGQGTTVT  120
VSS                                                                123

SEQ ID NO: 232              moltype = AA  length = 7
FEATURE                    Location/Qualifiers
REGION                     1..7
```

```
                          note = Description of Artificial Sequence: Synthetic peptide
REGION                    1..7
                          note = MESO-B[MSLN]_H0L0 vhCDR1
source                    1..7
                          mol_type = protein
                          organism = synthetic construct
SEQUENCE: 232
SNSATWN                                                                        7

SEQ ID NO: 233            moltype = AA  length = 18
FEATURE                   Location/Qualifiers
REGION                    1..18
                          note = Description of Artificial Sequence: Synthetic peptide
REGION                    1..18
                          note = MESO-B[MSLN]_H0L0 vhCDR2
source                    1..18
                          mol_type = protein
                          organism = synthetic construct
SEQUENCE: 233
RTYYRSKWYN DYAVSVKS                                                            18

SEQ ID NO: 234            moltype = AA  length = 11
FEATURE                   Location/Qualifiers
REGION                    1..11
                          note = Description of Artificial Sequence: Synthetic peptide
REGION                    1..11
                          note = MESO-B[MSLN]_H0L0 vhCDR3
source                    1..11
                          mol_type = protein
                          organism = synthetic construct
SEQUENCE: 234
GMMTYYYGMD V                                                                   11

SEQ ID NO: 235            moltype = AA  length = 115
FEATURE                   Location/Qualifiers
REGION                    1..115
                          note = Description of Artificial Sequence: Synthetic
                           polypeptide
REGION                    1..115
                          note = MESO-B[MSLN]_H0L0 Variable light (vl) domain
source                    1..115
                          mol_type = protein
                          organism = synthetic construct
SEQUENCE: 235
QPVLTQSSSL SASPGASASL TCTLRSGINV GPYRIYWYQQ KPGSPPQYLL NYKSDSDKQQ  60
GSGVPSRFSG SKDASANAGV LLISGLRSED EADYYCMIWH SSAAVFGGGT QLTVL         115

SEQ ID NO: 236            moltype = AA  length = 14
FEATURE                   Location/Qualifiers
REGION                    1..14
                          note = Description of Artificial Sequence: Synthetic peptide
REGION                    1..14
                          note = MESO-B[MSLN]_H0L0 vlCDR1
source                    1..14
                          mol_type = protein
                          organism = synthetic construct
SEQUENCE: 236
TLRSGINVGP YRIY                                                                14

SEQ ID NO: 237            moltype = AA  length = 7
FEATURE                   Location/Qualifiers
REGION                    1..7
                          note = Description of Artificial Sequence: Synthetic peptide
REGION                    1..7
                          note = MESO-B[MSLN]_H0L0 vlCDR2
source                    1..7
                          mol_type = protein
                          organism = synthetic construct
SEQUENCE: 237
SDKQQGS                                                                        7

SEQ ID NO: 238            moltype = AA  length = 9
FEATURE                   Location/Qualifiers
REGION                    1..9
                          note = Description of Artificial Sequence: Synthetic peptide
REGION                    1..9
                          note = MESO-B[MSLN]_H0L0 vlCDR3
source                    1..9
                          mol_type = protein
```

```
                        organism = synthetic construct
SEQUENCE: 238
MIWHSSAAV                                                        9

SEQ ID NO: 239          moltype = AA  length = 453
FEATURE                 Location/Qualifiers
REGION                  1..453
                        note = Description of Artificial Sequence: Synthetic
                         polypeptide
REGION                  1..453
                        note = XENP16827 Chain 1 - MESO-B[MSLN]_H0_IgG1 Heavy Chain
source                  1..453
                        mol_type = protein
                        organism = synthetic construct
SEQUENCE: 239
QVQLQQSGPG LVTPSQTLSL TCAISGDSVS SNSATWNWIR QSPSRGLEWL GRTYYRSKWY  60
NDYAVSVKSR MSINPDTSKN QFSLQLNSVT PEDTAVYYCA RGMMTYYYGM DVWGQGTTVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                              453

SEQ ID NO: 240          moltype = AA  length = 221
FEATURE                 Location/Qualifiers
REGION                  1..221
                        note = Description of Artificial Sequence: Synthetic
                         polypeptide
REGION                  1..221
                        note = XENP16827 Chain 2 - MESO-B[MSLN]_L0 Light Chain
source                  1..221
                        mol_type = protein
                        organism = synthetic construct
SEQUENCE: 240
QPVLTQSSSL SASPGASASL TCTLRSGINV GPYRIYWYQQ KPGSPPQYLL NYKSDSDKQQ  60
GSGVPSRFSG SKDASANAGV LLISGLRSED EADYYCMIWH SSAAVFGGGT QLTVLGQPKA  120
APSVTLFPPS SEELQANKAT LVCLISDFYP GAVTVAWKAD SSPVKAGVET TTPSKQSNNK  180
YAASSYLSLT PEQWKSHRSY SCQVTHEGST VEKTVAPTEC S                     221

SEQ ID NO: 241          moltype = AA  length = 120
FEATURE                 Location/Qualifiers
REGION                  1..120
                        note = Description of Artificial Sequence: Synthetic
                         polypeptide
REGION                  1..120
                        note = MESO-C[MSLN]_H1L1 Variable heavy (vh) domain
source                  1..120
                        mol_type = protein
                        organism = synthetic construct
SEQUENCE: 241
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120

SEQ ID NO: 242          moltype = AA  length = 5
FEATURE                 Location/Qualifiers
REGION                  1..5
                        note = Description of Artificial Sequence: Synthetic peptide
REGION                  1..5
                        note = MESO-C[MSLN]_H1L1 vhCDR1
source                  1..5
                        mol_type = protein
                        organism = synthetic construct
SEQUENCE: 242
SYWMH                                                             5

SEQ ID NO: 243          moltype = AA  length = 17
FEATURE                 Location/Qualifiers
REGION                  1..17
                        note = Description of Artificial Sequence: Synthetic peptide
REGION                  1..17
                        note = MESO-C[MSLN]_H1L1 vhCDR2
source                  1..17
                        mol_type = protein
                        organism = synthetic construct
SEQUENCE: 243
MIHPNSDNTI YYEKFQG                                                17

SEQ ID NO: 244          moltype = AA  length = 11
```

```
FEATURE              Location/Qualifiers
REGION               1..11
                     note = Description of Artificial Sequence: Synthetic peptide
REGION               1..11
                     note = MESO-C[MSLN]_H1L1 vhCDR3
source               1..11
                     mol_type = protein
                     organism = synthetic construct
SEQUENCE: 244
IITPVVPKFD Y                                                           11

SEQ ID NO: 245       moltype = AA  length = 107
FEATURE              Location/Qualifiers
REGION               1..107
                     note = Description of Artificial Sequence: Synthetic
                      polypeptide
REGION               1..107
                     note = MESO-C[MSLN]_H1L1 Variable light (vl) domain
source               1..107
                     mol_type = protein
                     organism = synthetic construct
SEQUENCE: 245
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSYPLTFGA GTKLEIK                107

SEQ ID NO: 246       moltype = AA  length = 11
FEATURE              Location/Qualifiers
REGION               1..11
                     note = Description of Artificial Sequence: Synthetic peptide
REGION               1..11
                     note = MESO-C[MSLN]_H1L1 vlCDR1
source               1..11
                     mol_type = protein
                     organism = synthetic construct
SEQUENCE: 246
KASHDVGTSV A                                                          11

SEQ ID NO: 247       moltype = AA  length = 7
FEATURE              Location/Qualifiers
REGION               1..7
                     note = Description of Artificial Sequence: Synthetic peptide
REGION               1..7
                     note = MESO-C[MSLN]_H1L1 vlCDR2
source               1..7
                     mol_type = protein
                     organism = synthetic construct
SEQUENCE: 247
WASTRHT                                                                7

SEQ ID NO: 248       moltype = AA  length = 9
FEATURE              Location/Qualifiers
REGION               1..9
                     note = Description of Artificial Sequence: Synthetic peptide
REGION               1..9
                     note = MESO-C[MSLN]_H1L1 vlCDR3
source               1..9
                     mol_type = protein
                     organism = synthetic construct
SEQUENCE: 248
QQYSSYPLT                                                              9

SEQ ID NO: 249       moltype = AA  length = 449
FEATURE              Location/Qualifiers
REGION               1..449
                     note = Description of Artificial Sequence: Synthetic
                      polypeptide
REGION               1..449
                     note = XENP31693 Chain 1 - MESO-C[MSLN]_H1_IgG1_PVA_/S267K
                      Heavy C hain
source               1..449
                     mol_type = protein
                     organism = synthetic construct
SEQUENCE: 249
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPPVAGP  240
SVFLFPPKPK DTLMISRTPE VTCVVVDVKH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
```

-continued

```
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                     449

SEQ ID NO: 250          moltype = AA  length = 214
FEATURE                 Location/Qualifiers
REGION                  1..214
                        note = Description of Artificial Sequence: Synthetic
                         polypeptide
REGION                  1..214
                        note = XENP31693 Chain 2 - MESO-C[MSLN]_L1 Light Chain
source                  1..214
                        mol_type = protein
                        organism = synthetic construct
SEQUENCE: 250
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 251          moltype = AA  length = 120
FEATURE                 Location/Qualifiers
REGION                  1..120
                        note = Description of Artificial Sequence: Synthetic
                         polypeptide
REGION                  1..120
                        note = MESO-C[MSLN]_H1.1 Variable Heavy
source                  1..120
                        mol_type = protein
                        organism = synthetic construct
SEQUENCE: 251
QVQLVQSGAE VKKPGASVKV SCKASGYTFT GYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120

SEQ ID NO: 252          moltype = AA  length = 120
FEATURE                 Location/Qualifiers
REGION                  1..120
                        note = Description of Artificial Sequence: Synthetic
                         polypeptide
REGION                  1..120
                        note = MESO-C[MSLN]_H1.2 Variable Heavy
source                  1..120
                        mol_type = protein
                        organism = synthetic construct
SEQUENCE: 252
QVQLVQSGAE VKKPGASVKV SCKASGYTFT SYYMHWVRQA PGQGLEWMGM IHPNSDNTIY  60
YEKFQGRVTM TVDKSISTAY MELSRLRSDD TAVYYCAIII TPVVPKFDYW GQGTLVTVSS  120

SEQ ID NO: 253          moltype = AA  length = 120
FEATURE                 Location/Qualifiers
REGION                  1..120
                        note = Description of Artificial Sequence: Synthetic
                         polypeptide
REGION                  1..120
                        note = MESO-C[MSLN]_H1.3 Variable Heavy
source                  1..120
                        mol_type = protein
                        organism = synthetic construct
SEQUENCE: 253
QVQLVQSGAE VKKPGASVKV SCKASGYTFT SYWMHWVRQA PGQGLEWMGW IHPNSDNTIY  60
YEKFQGRVTM TVDKSISTAY MELSRLRSDD TAVYYCAIII TPVVPKFDYW GQGTLVTVSS  120

SEQ ID NO: 254          moltype = AA  length = 120
FEATURE                 Location/Qualifiers
REGION                  1..120
                        note = Description of Artificial Sequence: Synthetic
                         polypeptide
REGION                  1..120
                        note = MESO-C[MSLN]_H1.4 Variable Heavy
source                  1..120
                        mol_type = protein
                        organism = synthetic construct
SEQUENCE: 254
QVQLVQSGAE VKKPGASVKV SCKASGYTFT SYWMHWVRQA PGQGLEWMGM INPNSDNTIY  60
YEKFQGRVTM TVDKSISTAY MELSRLRSDD TAVYYCAIII TPVVPKFDYW GQGTLVTVSS  120

SEQ ID NO: 255          moltype = AA  length = 120
FEATURE                 Location/Qualifiers
REGION                  1..120
                        note = Description of Artificial Sequence: Synthetic
```

-continued

```
                        polypeptide
REGION                  1..120
                        note = MESO-C[MSLN]_H1.5 Variable Heavy
source                  1..120
                        mol_type = protein
                        organism = synthetic construct
SEQUENCE: 255
QVQLVQSGAE VKKPGASVKV SCKASGYTFT SYWMHWVRQA PGQGLEWMGM IHPQSDNTIY  60
YEKFQGRVTM TVDKSISTAY MELSRLRSDD TAVYYCAIII TPVVPKFDYW GQGTLVTVSS  120

SEQ ID NO: 256          moltype = AA  length = 120
FEATURE                 Location/Qualifiers
REGION                  1..120
                        note = Description of Artificial Sequence: Synthetic
                         polypeptide
REGION                  1..120
                        note = MESO-C[MSLN]_H1.6 Variable Heavy
source                  1..120
                        mol_type = protein
                        organism = synthetic construct
SEQUENCE: 256
QVQLVQSGAE VKKPGASVKV SCKASGYTFT SYWMHWVRQA PGQGLEWMGM IHPNSGNTIY  60
YEKFQGRVTM TVDKSISTAY MELSRLRSDD TAVYYCAIII TPVVPKFDYW GQGTLVTVSS  120

SEQ ID NO: 257          moltype = AA  length = 120
FEATURE                 Location/Qualifiers
REGION                  1..120
                        note = Description of Artificial Sequence: Synthetic
                         polypeptide
REGION                  1..120
                        note = MESO-C[MSLN]_H1.7 Variable Heavy
source                  1..120
                        mol_type = protein
                        organism = synthetic construct
SEQUENCE: 257
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCARII TPVVPKFDYW GQGTLVTVSS  120

SEQ ID NO: 258          moltype = AA  length = 120
FEATURE                 Location/Qualifiers
REGION                  1..120
                        note = Description of Artificial Sequence: Synthetic
                         polypeptide
REGION                  1..120
                        note = MESO-C[MSLN]_H1.8 Variable Heavy
source                  1..120
                        mol_type = protein
                        organism = synthetic construct
SEQUENCE: 258
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII SPVVPKFDYW GQGTLVTVSS  120

SEQ ID NO: 259          moltype = AA  length = 120
FEATURE                 Location/Qualifiers
REGION                  1..120
                        note = Description of Artificial Sequence: Synthetic
                         polypeptide
REGION                  1..120
                        note = MESO-C[MSLN]_H1.9 Variable Heavy
source                  1..120
                        mol_type = protein
                        organism = synthetic construct
SEQUENCE: 259
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPRFDYW GQGTLVTVSS  120

SEQ ID NO: 260          moltype = AA  length = 120
FEATURE                 Location/Qualifiers
REGION                  1..120
                        note = Description of Artificial Sequence: Synthetic
                         polypeptide
REGION                  1..120
                        note = MESO-C[MSLN]_H1.12 Variable Heavy
source                  1..120
                        mol_type = protein
                        organism = synthetic construct
SEQUENCE: 260
QVQLVQSGAE VKKPGASVKV SCKASGYTFT SYWMHWVRQA PGQGLEWMGM IHPNSDNTIY  60
YQKFQGRVTM TVDKSISTAY MELSRLRSDD TAVYYCAIII TPVVPKFDYW GQGTLVTVSS  120
```

-continued

```
SEQ ID NO: 261            moltype = AA  length = 120
FEATURE                   Location/Qualifiers
REGION                    1..120
                          note = Description of Artificial Sequence: Synthetic
                           polypeptide
REGION                    1..120
                          note = MESO-C[MSLN]_H1.13 Variable Heavy
source                    1..120
                          mol_type = protein
                          organism = synthetic construct
SEQUENCE: 261
QVQLVQSGAE VKKPGASVKV SCKASGYTFT SYWMHWVRQA PGQGLEWMGM IHPNSDNTIY   60
YYKFQGRVTM TVDKSISTAY MELSRLRSDD TAVYYCAIII TPVVPKFDYW GQGTLVTVSS  120

SEQ ID NO: 262            moltype = AA  length = 107
FEATURE                   Location/Qualifiers
REGION                    1..107
                          note = Description of Artificial Sequence: Synthetic
                           polypeptide
REGION                    1..107
                          note = MESO-C[MSLN]_L1.1 Variable Light
source                    1..107
                          mol_type = protein
                          organism = synthetic construct
SEQUENCE: 262
DIVMTQSPDS LAVSLGERAT INCKSSHDVG TSVAWYQQKP GQSPKLLIYW ASTRHTGVPD   60
RFTGSGSGTD FTLTISSLQA EDVAVYFCQQ YSSYPLTFGA GTKLEIK              107

SEQ ID NO: 263            moltype = AA  length = 107
FEATURE                   Location/Qualifiers
REGION                    1..107
                          note = Description of Artificial Sequence: Synthetic
                           polypeptide
REGION                    1..107
                          note = MESO-C[MSLN]_L1.2 Variable Light
source                    1..107
                          mol_type = protein
                          organism = synthetic construct
SEQUENCE: 263
DIVMTQSPDS LAVSLGERAT INCKASQDVG TSVAWYQQKP GQSPKLLIYW ASTRHTGVPD   60
RFTGSGSGTD FTLTISSLQA EDVAVYFCQQ YSSYPLTFGA GTKLEIK              107

SEQ ID NO: 264            moltype = AA  length = 107
FEATURE                   Location/Qualifiers
REGION                    1..107
                          note = Description of Artificial Sequence: Synthetic
                           polypeptide
REGION                    1..107
                          note = MESO-C[MSLN]_L1.3 Variable Light
source                    1..107
                          mol_type = protein
                          organism = synthetic construct
SEQUENCE: 264
DIVMTQSPDS LAVSLGERAT INCKASHSVG TSVAWYQQKP GQSPKLLIYW ASTRHTGVPD   60
RFTGSGSGTD FTLTISSLQA EDVAVYFCQQ YSSYPLTFGA GTKLEIK              107

SEQ ID NO: 265            moltype = AA  length = 107
FEATURE                   Location/Qualifiers
REGION                    1..107
                          note = Description of Artificial Sequence: Synthetic
                           polypeptide
REGION                    1..107
                          note = MESO-C[MSLN]_L1.4 Variable Light
source                    1..107
                          mol_type = protein
                          organism = synthetic construct
SEQUENCE: 265
DIVMTQSPDS LAVSLGERAT INCKASHDVL TSVAWYQQKP GQSPKLLIYW ASTRHTGVPD   60
RFTGSGSGTD FTLTISSLQA EDVAVYFCQQ YSSYPLTFGA GTKLEIK              107

SEQ ID NO: 266            moltype = AA  length = 107
FEATURE                   Location/Qualifiers
REGION                    1..107
                          note = Description of Artificial Sequence: Synthetic
                           polypeptide
REGION                    1..107
                          note = MESO-C[MSLN]_L1.5 Variable Light
source                    1..107
```

```
                             mol_type = protein
                             organism = synthetic construct
SEQUENCE: 266
DIVMTQSPDS LAVSLGERAT INCKASHDVG TYVAWYQQKP GQSPKLLIYW ASTRHTGVPD    60
RFTGSGSGTD FTLTISSLQA EDVAVYFCQQ YSSYPLTFGA GTKLEIK                  107

SEQ ID NO: 267           moltype = AA  length = 107
FEATURE                  Location/Qualifiers
REGION                   1..107
                         note = Description of Artificial Sequence: Synthetic
                          polypeptide
REGION                   1..107
                         note = MESO-C[MSLN]_L1.6 Variable Light
source                   1..107
                         mol_type = protein
                         organism = synthetic construct
SEQUENCE: 267
DIVMTQSPDS LAVSLGERAT INCKASHDVG TSLAWYQQKP GQSPKLLIYW ASTRHTGVPD    60
RFTGSGSGTD FTLTISSLQA EDVAVYFCQQ YSSYPLTFGA GTKLEIK                  107

SEQ ID NO: 268           moltype = AA  length = 107
FEATURE                  Location/Qualifiers
REGION                   1..107
                         note = Description of Artificial Sequence: Synthetic
                          polypeptide
REGION                   1..107
                         note = MESO-C[MSLN]_L1.7 Variable Light
source                   1..107
                         mol_type = protein
                         organism = synthetic construct
SEQUENCE: 268
DIVMTQSPDS LAVSLGERAT INCKASHDVG TSVAWYQQKP GQSPKLLIYW ASTRETGVPD    60
RFTGSGSGTD FTLTISSLQA EDVAVYFCQQ YSSYPLTFGA GTKLEIK                  107

SEQ ID NO: 269           moltype = AA  length = 107
FEATURE                  Location/Qualifiers
REGION                   1..107
                         note = Description of Artificial Sequence: Synthetic
                          polypeptide
REGION                   1..107
                         note = MESO-C[MSLN]_L1.8 Variable Light
source                   1..107
                         mol_type = protein
                         organism = synthetic construct
SEQUENCE: 269
DIVMTQSPDS LAVSLGERAT INCKASHDVG TSVAWYQQKP GQSPKLLIYW ASTRHSGVPD    60
RFTGSGSGTD FTLTISSLQA EDVAVYFCQQ YSSYPLTFGA GTKLEIK                  107

SEQ ID NO: 270           moltype = AA  length = 107
FEATURE                  Location/Qualifiers
REGION                   1..107
                         note = Description of Artificial Sequence: Synthetic
                          polypeptide
REGION                   1..107
                         note = MESO-C[MSLN]_L1.9 Variable Light
source                   1..107
                         mol_type = protein
                         organism = synthetic construct
SEQUENCE: 270
DIVMTQSPDS LAVSLGERAT INCKASHDVG TSVAWYQQKP GQSPKLLIYW ASTRHTGVPD    60
RFTGSGSGTD FTLTISSLQA EDVAVYFCQQ YYSYPLTFGA GTKLEIK                  107

SEQ ID NO: 271           moltype = AA  length = 107
FEATURE                  Location/Qualifiers
REGION                   1..107
                         note = Description of Artificial Sequence: Synthetic
                          polypeptide
REGION                   1..107
                         note = MESO-C[MSLN]_L1.10 Variable Light
source                   1..107
                         mol_type = protein
                         organism = synthetic construct
SEQUENCE: 271
DIVMTQSPDS LAVSLGERAT INCKASHDVG TSVAWYQQKP GQSPKLLIYW ASTRHTGVPD    60
RFTGSGSGTD FTLTISSLQA EDVAVYFCQQ YSSTPLTFGA GTKLEIK                  107

SEQ ID NO: 272           moltype = AA  length = 107
FEATURE                  Location/Qualifiers
REGION                   1..107
```

-continued

```
                        note = Description of Artificial Sequence: Synthetic
                         polypeptide
REGION                  1..107
                        note = MESO-C[MSLN]_L1.13 Variable Light
source                  1..107
                        mol_type = protein
                        organism = synthetic construct
SEQUENCE: 272
DIVMTQSPDS LAVSLGERAT INCKASHDVG QSVAWYQQKP GQSPKLLIYW ASTRHTGVPD  60
RFTGSGSGTD FTLTISSLQA EDVAVYFCQQ YSSYPLTFGA GTKLEIK                107

SEQ ID NO: 273          moltype = AA  length = 107
FEATURE                 Location/Qualifiers
REGION                  1..107
                        note = Description of Artificial Sequence: Synthetic
                         polypeptide
REGION                  1..107
                        note = MESO-C[MSLN]_L1.14 Variable Light
source                  1..107
                        mol_type = protein
                        organism = synthetic construct
SEQUENCE: 273
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSFPLTFGA GTKLEIK                107

SEQ ID NO: 274          moltype = AA  length = 107
FEATURE                 Location/Qualifiers
REGION                  1..107
                        note = Description of Artificial Sequence: Synthetic
                         polypeptide
REGION                  1..107
                        note = MESO-C[MSLN]_L1.15 Variable Light
source                  1..107
                        mol_type = protein
                        organism = synthetic construct
SEQUENCE: 274
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSLPLTFGA GTKLEIK                107

SEQ ID NO: 275          moltype = AA  length = 107
FEATURE                 Location/Qualifiers
REGION                  1..107
                        note = Description of Artificial Sequence: Synthetic
                         polypeptide
REGION                  1..107
                        note = MESO-C[MSLN]_L1.16 Variable Light
source                  1..107
                        mol_type = protein
                        organism = synthetic construct
SEQUENCE: 275
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSVPLTFGA GTKLEIK                107

SEQ ID NO: 276          moltype = AA  length = 107
FEATURE                 Location/Qualifiers
REGION                  1..107
                        note = Description of Artificial Sequence: Synthetic
                         polypeptide
REGION                  1..107
                        note = MESO-C[MSLN]_L1.17 Variable Light
source                  1..107
                        mol_type = protein
                        organism = synthetic construct
SEQUENCE: 276
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSIPLTFGA GTKLEIK                107

SEQ ID NO: 277          moltype = AA  length = 107
FEATURE                 Location/Qualifiers
REGION                  1..107
                        note = Description of Artificial Sequence: Synthetic
                         polypeptide
REGION                  1..107
                        note = MESO-C[MSLN]_L1.18 Variable Light
source                  1..107
                        mol_type = protein
                        organism = synthetic construct
SEQUENCE: 277
DIVMTQSPDS LAVSLGERAT INCKASHDVG TSVAWYQQKP GQSPKLLIYW ASTRHTGVPD  60
```

```
RFTGSGSGTD FTLTISSLQA EDVAVYFCQQ YSSHPLTFGA GTKLEIK                              107

SEQ ID NO: 278          moltype = AA   length = 107
FEATURE                 Location/Qualifiers
REGION                  1..107
                        note = Description of Artificial Sequence: Synthetic
                         polypeptide
REGION                  1..107
                        note = MESO-C[MSLN]_L1.19 Variable Light
source                  1..107
                        mol_type = protein
                        organism = synthetic construct
SEQUENCE: 278
DIVMTQSPDS LAVSLGERAT INCKASHDVG TYVAWYQQKP GQSPKLLIYW ASTRHTGVPD  60
RFTGSGSGTD FTLTISSLQA EDVAVYFCQQ YYSYPLTFGA GTKLEIK                              107

SEQ ID NO: 279          moltype = AA   length = 107
FEATURE                 Location/Qualifiers
REGION                  1..107
                        note = Description of Artificial Sequence: Synthetic
                         polypeptide
REGION                  1..107
                        note = MESO-C[MSLN]_L1.20 Variable Light
source                  1..107
                        mol_type = protein
                        organism = synthetic construct
SEQUENCE: 279
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YYSFPLTFGA GTKLEIK                              107

SEQ ID NO: 280          moltype = AA   length = 107
FEATURE                 Location/Qualifiers
REGION                  1..107
                        note = Description of Artificial Sequence: Synthetic
                         polypeptide
REGION                  1..107
                        note = MESO-C[MSLN]_L1.21 Variable Light
source                  1..107
                        mol_type = protein
                        organism = synthetic construct
SEQUENCE: 280
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YYSVPLTFGA GTKLEIK                              107

SEQ ID NO: 281          moltype = AA   length = 107
FEATURE                 Location/Qualifiers
REGION                  1..107
                        note = Description of Artificial Sequence: Synthetic
                         polypeptide
REGION                  1..107
                        note = MESO-C[MSLN]_L1.22 Variable Light
source                  1..107
                        mol_type = protein
                        organism = synthetic construct
SEQUENCE: 281
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YYSIPLTFGA GTKLEIK                              107

SEQ ID NO: 282          moltype = AA   length = 453
FEATURE                 Location/Qualifiers
REGION                  1..453
                        note = Description of Artificial Sequence: Synthetic
                         polypeptide
REGION                  1..453
                        note = XENP16248 Chain 1 -
                         MESO-A[MSLN]_H1.1_IgG1_pI(-)_Isosteric_
                         A_/PVA_/S267K/L368D/K370S
source                  1..453
                        mol_type = protein
                        organism = synthetic construct
SEQUENCE: 282
EVQLVESGGG LVQPGGSLKL SCAASGFDFS RYWMSWVRQA PGKGLEWVSE INPDSSTIVY  60
TPSVKGRFTI SRDNAKNSLY LQMNSLRAED TAVYYCARRG SHYYGYRTGY FDVWGAGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSDTKVDK KVEPKSCDKT HTCPPCPAPP  240
VAGPSVFLFP PKPKDTLMIS RTPEVTCVVV DVKHEDPEVK FNWYVDGVEV HNAKTKPREE  300
EYNSTYRVVS VLTVLHQDWL NGKEYKCKVS NKALPAPIEK TISKAKGQPR EPQVYTLPPS  360
REEMTKNQVS LTCDVSGFYP SDIAVEWESD GQPENNYKTT PPVLDSDGSF FLYSKLTVDK  420
SRWEQGDVFS CSVMHEALHN HYTQKSLSLS PGK                                             453
```

-continued

```
SEQ ID NO: 283            moltype = AA  length = 485
FEATURE                   Location/Qualifiers
REGION                    1..485
                          note = Description of Artificial Sequence: Synthetic
                          polypeptide
REGION                    1..485
                          note = XENP16248 Chain 2 -
                          [CD3]_H1.30_L1.47_scFv(GKPGS)4_Fc(216)_
                          IgG1_C220S/PVA_/S267K/S364K/E357Q
source                    1..485
                          mol_type = protein
                          organism = synthetic construct
SEQUENCE: 283
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 284            moltype = AA  length = 213
FEATURE                   Location/Qualifiers
REGION                    1..213
                          note = Description of Artificial Sequence: Synthetic
                          polypeptide
REGION                    1..213
                          note = XENP16248 Chain 3 - MESO-A[MSLN]_L1 Light Chain
source                    1..213
                          mol_type = protein
                          organism = synthetic construct
SEQUENCE: 284
DVVLTQSPAT LSLSPGERAT LSCRASSSVS YMYWHQQKPD QSPKLLIYDT SNLASGVPVR   60
FSGSGSGTDY TLTISSLEPE DFAVYYCQQW SSYPPTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 285            moltype = AA  length = 452
FEATURE                   Location/Qualifiers
REGION                    1..452
                          note = Description of Artificial Sequence: Synthetic
                          polypeptide
REGION                    1..452
                          note = XENP16833 Chain 1 -
                          MESO-B[MSLN]_H0L0_Fab_IgG1_pI(-)_Isoste
                          ric_A_/PVA_/S267K/L368D/K370S
source                    1..452
                          mol_type = protein
                          organism = synthetic construct
SEQUENCE: 285
QVQLQQSGPG LVTPSQTLSL TCAISGDSVS SNSATWNWIR QSPSRGLEWL GRTYYRSKWY   60
NDYAVSVKSR MSINPDTSKN QFSLQLNSVT PEDTAVYYCA RGMMTYYYGM DVWGQGTTVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSDTKVDKK VEPKSCDKTH TCPPCPAPPV  240
AGPSVFLFPP KPKDTLMISR TPEVTCVVVD VKHEDPEVKF NWYVDGVEVH NAKTKPREEE  300
YNSTYRVVSV LTVLHQDWLN GKEYKCKVSN KALPAPIEKT ISKAKGQPRE PQVYTLPPSR  360
EEMTKNQVSL TCDVSGFYPS DIAVEWESDG QPENNYKTTP PVLDSDGSFF LYSKLTVDKS  420
RWEQGDVFSC SVMHEALHNH YTQKSLSLSP GK                                452

SEQ ID NO: 286            moltype = AA  length = 485
FEATURE                   Location/Qualifiers
REGION                    1..485
                          note = Description of Artificial Sequence: Synthetic
                          polypeptide
REGION                    1..485
                          note = XENP16833 Chain 2 -
                          [CD3]_H1.30_L1.47_scFv(GKPGS)4_Fc(216)_
                          IgG1_C220S/PVA_/S267K/S364K/E357Q
source                    1..485
                          mol_type = protein
                          organism = synthetic construct
SEQUENCE: 286
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
```

```
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 287            moltype = AA  length = 221
FEATURE                   Location/Qualifiers
REGION                    1..221
                          note = Description of Artificial Sequence: Synthetic
                           polypeptide
REGION                    1..221
                          note = XENP16833 Chain 3 - MESO-B[MSLN]_L0 Light Chain
source                    1..221
                          mol_type = protein
                          organism = synthetic construct
SEQUENCE: 287
QPVLTQSSSL SASPGASASL TCTLRSGINV GPYRIYWYQQ KPGSPPQYLL NYKSDSDKQQ  60
GSGVPSRFSG SKDASANAGV LLISGLRSED EADYYCMIWH SSAAVFGGGT QLTVLGQPKA  120
APSVTLFPPS SEELQANKAT LVCLISDFYP GAVTVAWKAD SSPVKAGVET TTPSKQSNNK  180
YAASSYLSLT PEQWKSHRSY SCQVTHEGST VEKTVAPTEC S                     221

SEQ ID NO: 288            moltype = AA  length = 449
FEATURE                   Location/Qualifiers
REGION                    1..449
                          note = Description of Artificial Sequence: Synthetic
                           polypeptide
REGION                    1..449
                          note = XENP31697 Chain 1 -
                           MESO-C[MSLN]_H1_IgG1_pI(-)_Isosteric_A_
                           /PVA_/S267K/L368D/K370S
source                    1..449
                          mol_type = protein
                          organism = synthetic construct
SEQUENCE: 288
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPPKP KDTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 289            moltype = AA  length = 485
FEATURE                   Location/Qualifiers
REGION                    1..485
                          note = Description of Artificial Sequence: Synthetic
                           polypeptide
REGION                    1..485
                          note = XENP31697 Chain 2 -
                           [CD3]_H1.30_L1.47_scFv(GKPGS)4_Fc(216)_
                           IgG1_C220S/PVA_/S267K/S364K/E357Q
source                    1..485
                          mol_type = protein
                          organism = synthetic construct
SEQUENCE: 289
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 290            moltype = AA  length = 214
FEATURE                   Location/Qualifiers
REGION                    1..214
                          note = Description of Artificial Sequence: Synthetic
                           polypeptide
REGION                    1..214
                          note = XENP31697 Chain 3 - MESO-C[MSLN]_L1 Light Chain
source                    1..214
                          mol_type = protein
                          organism = synthetic construct
SEQUENCE: 290
DIVMTQSPDS LAVSLGERAT INCKASHDVG TSVAWYQQKP GQSPKLLIYW ASTRHTGVPD  60
```

```
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 291              moltype = AA  length = 449
FEATURE                     Location/Qualifiers
REGION                      1..449
                            note = Description of Artificial Sequence: Synthetic
                             polypeptide
REGION                      1..449
                            note = XENP32550 Chain 1 -
                             MESO-C[MSLN]_H1.1_IgG1_pI(-)_Isosteric_
                             A_/PVA_/S267K/L368D/K370S
source                      1..449
                            mol_type = protein
                            organism = synthetic construct
SEQUENCE: 291
QVQLVQSGAE VKKPGASVKV SCKASGYTFT GYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 292              moltype = AA  length = 485
FEATURE                     Location/Qualifiers
REGION                      1..485
                            note = Description of Artificial Sequence: Synthetic
                             polypeptide
REGION                      1..485
                            note = XENP32550 Chain 2 -
                             MESO-C[MSLN]_H1.1_[CD3]_H1.30_L1.47_scF
                             v(GKPGS)4_Fc(216)_IgG1_C220S/PVA_/S267K/S364K/E357Q
source                      1..485
                            mol_type = protein
                            organism = synthetic construct
SEQUENCE: 292
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 293              moltype = AA  length = 214
FEATURE                     Location/Qualifiers
REGION                      1..214
                            note = Description of Artificial Sequence: Synthetic
                             polypeptide
REGION                      1..214
                            note = XENP32550 Chain 3 - MESO-C[MSLN]_L1 Light Chain
source                      1..214
                            mol_type = protein
                            organism = synthetic construct
SEQUENCE: 293
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 294              moltype = AA  length = 449
FEATURE                     Location/Qualifiers
REGION                      1..449
                            note = Description of Artificial Sequence: Synthetic
                             polypeptide
REGION                      1..449
                            note = XENP32551 Chain 1 -
                             MESO-C[MSLN]_H1.2_IgG1_pI(-)_Isosteric_
                             A_/PVA_/S267K/L368D/K370S
source                      1..449
                            mol_type = protein
                            organism = synthetic construct
SEQUENCE: 294
QVQLVQSGAE VKKPGASVKV SCKASGYTFT SYYMHWVRQA PGQGLEWMGM IHPNSDNTIY  60
```

```
YEKFQGRVTM TVDKSISTAY MELSRLRSDD TAVYYCAIII TPVVPKFDYW GQGTLVTVSS      120
ASTKGPSVFP LAPSSKSTSG GTAALGCLVK DYFPEPVTVS WNSGALTSGV HTFPAVLQSS      180
GLYSLSSVVT VPSSSLGTQT YICNVNHKPS DTKVDKKVEP KSCDKTHTCP PCPAPPVAGP      240
SVFLFPPKPK DTLMISRTPE VTCVVVDVKH EDPEVKFNWY VDGVEVHNAK TKPREEEYNS      300
TYRVVSVLTV LHQDWLNGKE YKCKVSNKAL PAPIEKTISK AKGQPREPQV YTLPPSREEM      360
TKNQVSLTCD VSGFYPSDIA VEWESDGQPE NNYKTTPPVL DSDGSFFLYS KLTVDKSRWE      420
QGDVFSCSVM HEALHNHYTQ KSLSLSPGK                                        449

SEQ ID NO: 295            moltype = AA  length = 485
FEATURE                   Location/Qualifiers
REGION                    1..485
                          note = Description of Artificial Sequence: Synthetic
                          polypeptide
REGION                    1..485
                          note = XENP32551 Chain 2 -
                          MESO-C[MSLN]_H1.2_[CD3]_H1.30_L1.47_scF
                          v(GKPGS)4_Fc(216)_IgG1_C220S/PVA_/S267K/S364K/E357Q
source                    1..485
                          mol_type = protein
                          organism = synthetic construct
SEQUENCE: 295
EVQLVESGGG LVQPGGSLRL SCAASGFTFS TYAMNWVRQA PGKGLEWVGR IRSKYNNYAT       60
YYADSVKGRF TISRDDSKNT LYLQMNSLRA EDTAVYYCVR HGNFGDSYVS WFAYWGQGTL      120
VTVSSGKPGS GKPGSGKPGS GKPGSQAVVT QEPSLTVSPG GTVTLTCGSS TGAVTTSNYA      180
NWVQQKPGKS PRGLIGGTNK RAPGVPARFS GSLLGGKAAL TISGAQPEDE ADYYCALWYS      240
NHWVFGGGTK LTVLEPKSSD KTHTCPPCPA PPVAGPSVFL FPPKPKDTLM ISRTPEVTCV      300
VVDVKHEDPE VKFNWYVDGV EVHNAKTKPR EEQYNSTYRV VSVLTVLHQD WLNGKEYKCK      360
VSNKALPAPI EKTISKAKGQ PREPQVYTLP PSREQMTKNQ VKLTCLVKGF YPSDIAVEWE      420
SNGQPENNYK TTPPVLDSDG SFFLYSKLTV DKSRWQQGNV FSCSVMHEAL HNHYTQKSLS      480
LSPGK                                                                  485

SEQ ID NO: 296            moltype = AA  length = 214
FEATURE                   Location/Qualifiers
REGION                    1..214
                          note = Description of Artificial Sequence: Synthetic
                          polypeptide
REGION                    1..214
                          note = XENP32551 Chain 3 - MESO-C[MSLN]_L1 Light Chain
source                    1..214
                          mol_type = protein
                          organism = synthetic construct
SEQUENCE: 296
DIVMTQSPDS LAVSLGERAT INCKASHDVG TSVAWYQQKP GQSPKLLIYW ASTRHTGVPD       60
RFTGSGSGTD FTLTISSLQA EDVAVYFCQQ YSSYPLTFGA GTKLEIKRTV AAPSVFIFPP      120
SDEQLKSGTA SVVCLLNNFY PREAKVQWKV DNALQSGNSQ ESVTEQDSKD STYSLSSTLT      180
LSKADYEKHK VYACEVTHQG LSSPVTKSFN RGEC                                  214

SEQ ID NO: 297            moltype = AA  length = 449
FEATURE                   Location/Qualifiers
REGION                    1..449
                          note = Description of Artificial Sequence: Synthetic
                          polypeptide
REGION                    1..449
                          note = XENP32552 Chain 1 -
                          MESO-C[MSLN]_H1.3_IgG1_pI(-)_Isosteric_
                          A_/PVA_/S267K/L368D/K370S
source                    1..449
                          mol_type = protein
                          organism = synthetic construct
SEQUENCE: 297
QVQLVQSGAE VKKPGASVKV SCKASGYTFT SYWMHWVRQA PGQGLEWMGW IHPNSDNTIY       60
YEKFQGRVTM TVDKSISTAY MELSRLRSDD TAVYYCAIII TPVVPKFDYW GQGTLVTVSS      120
ASTKGPSVFP LAPSSKSTSG GTAALGCLVK DYFPEPVTVS WNSGALTSGV HTFPAVLQSS      180
GLYSLSSVVT VPSSSLGTQT YICNVNHKPS DTKVDKKVEP KSCDKTHTCP PCPAPPVAGP      240
SVFLFPPKPK DTLMISRTPE VTCVVVDVKH EDPEVKFNWY VDGVEVHNAK TKPREEEYNS      300
TYRVVSVLTV LHQDWLNGKE YKCKVSNKAL PAPIEKTISK AKGQPREPQV YTLPPSREEM      360
TKNQVSLTCD VSGFYPSDIA VEWESDGQPE NNYKTTPPVL DSDGSFFLYS KLTVDKSRWE      420
QGDVFSCSVM HEALHNHYTQ KSLSLSPGK                                        449

SEQ ID NO: 298            moltype = AA  length = 485
FEATURE                   Location/Qualifiers
REGION                    1..485
                          note = Description of Artificial Sequence: Synthetic
                          polypeptide
REGION                    1..485
                          note = XENP32552 Chain 2 -
                          MESO-C[MSLN]_H1.3_[CD3]_H1.30_L1.47_scF
                          v(GKPGS)4_Fc(216)_IgG1_C220S/PVA_/S267K/S364K/E357Q
source                    1..485
```

-continued

```
                          mol_type = protein
                          organism = synthetic construct
SEQUENCE: 298
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 299          moltype = AA  length = 214
FEATURE                 Location/Qualifiers
REGION                  1..214
                        note = Description of Artificial Sequence: Synthetic
                        polypeptide
REGION                  1..214
                        note = XENP32552 Chain 3 - MESO-C[MSLN]_L1 Light Chain
source                  1..214
                        mol_type = protein
                        organism = synthetic construct
SEQUENCE: 299
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 300          moltype = AA  length = 449
FEATURE                 Location/Qualifiers
REGION                  1..449
                        note = Description of Artificial Sequence: Synthetic
                        polypeptide
REGION                  1..449
                        note = XENP32553 Chain 1 -
                        MESO-C[MSLN]_H1.4_IgG1_pI(-)_Isosteric_
                        A_/PVA_/S267K/L368D/K370S
source                  1..449
                        mol_type = protein
                        organism = synthetic construct
SEQUENCE: 300
QVQLVQSGAE VKKPGASVKV SCKASGYTFT SYWMHWVRQA PGQGLEWMGM INPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                   449

SEQ ID NO: 301          moltype = AA  length = 485
FEATURE                 Location/Qualifiers
REGION                  1..485
                        note = Description of Artificial Sequence: Synthetic
                        polypeptide
REGION                  1..485
                        note = XENP32553 Chain 2 -
                        MESO-C[MSLN]_H1.4_[CD3]_H1.30_L1.47_scF
                        v(GKPGS)4_Fc(216)_IgG1_C220S/PVA_/S267K/S364K/E357Q
source                  1..485
                        mol_type = protein
                        organism = synthetic construct
SEQUENCE: 301
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 302          moltype = AA  length = 214
FEATURE                 Location/Qualifiers
REGION                  1..214
                        note = Description of Artificial Sequence: Synthetic
                        polypeptide
```

```
REGION                    1..214
                          note = XENP32553 Chain 3 - MESO-C[MSLN]_L1 Light Chain
source                    1..214
                          mol_type = protein
                          organism = synthetic construct
SEQUENCE: 302
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 303            moltype = AA  length = 449
FEATURE                   Location/Qualifiers
REGION                    1..449
                          note = Description of Artificial Sequence: Synthetic
                           polypeptide
REGION                    1..449
                          note = XENP32554 Chain 1 -
                           MESO-C[MSLN]_H1.5_IgG1_pI(-)_Isosteric_
                           A_/PVA_/S267K/L368D/K370S
source                    1..449
                          mol_type = protein
                          organism = synthetic construct
SEQUENCE: 303
QVQLVQSGAE VKKPGASVKV SCKASGYTFT SYWMHWVRQA PGQGLEWMGM IHPQSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 304            moltype = AA  length = 485
FEATURE                   Location/Qualifiers
REGION                    1..485
                          note = Description of Artificial Sequence: Synthetic
                           polypeptide
REGION                    1..485
                          note = XENP32554 Chain 2 -
                           MESO-C[MSLN]_H1.5_[CD3]_H1.30_L1.47_scF
                           v(GKPGS)4_Fc(216)_IgG1_C220S/PVA_/S267K/S364K/E357Q
source                    1..485
                          mol_type = protein
                          organism = synthetic construct
SEQUENCE: 304
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 305            moltype = AA  length = 214
FEATURE                   Location/Qualifiers
REGION                    1..214
                          note = Description of Artificial Sequence: Synthetic
                           polypeptide
REGION                    1..214
                          note = XENP32554 Chain 3 - MESO-C[MSLN]_L1 Light Chain
source                    1..214
                          mol_type = protein
                          organism = synthetic construct
SEQUENCE: 305
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 306            moltype = AA  length = 449
FEATURE                   Location/Qualifiers
REGION                    1..449
                          note = Description of Artificial Sequence: Synthetic
                           polypeptide
REGION                    1..449
                          note = XENP32555 Chain 1 -
```

-continued

```
                        MESO-C[MSLN]_H1.6_IgG1_pI(-)_Isosteric_
                        A_/PVA_/S267K/L368D/K370S
source                  1..449
                        mol_type = protein
                        organism = synthetic construct
SEQUENCE: 306
QVQLVQSGAE VKKPGASVKV SCKASGYTFT SYWMHWVRQA PGQGLEWMGM IHPNSGNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 307         moltype = AA  length = 485
FEATURE                Location/Qualifiers
REGION                 1..485
                       note = Description of Artificial Sequence: Synthetic
                        polypeptide
REGION                 1..485
                       note = XENP32555 Chain 2 -
                        MESO-C[MSLN]_H1.6_[CD3]_H1.30_L1.47_scF
                        v(GKPGS)4_Fc(216)_IgG1_C220S/PVA_/S267K/S364K/E357Q
source                 1..485
                       mol_type = protein
                       organism = synthetic construct
SEQUENCE: 307
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                              485

SEQ ID NO: 308         moltype = AA  length = 214
FEATURE                Location/Qualifiers
REGION                 1..214
                       note = Description of Artificial Sequence: Synthetic
                        polypeptide
REGION                 1..214
                       note = XENP32555 Chain 3 - MESO-C[MSLN]_L1 Light Chain
source                 1..214
                       mol_type = protein
                       organism = synthetic construct
SEQUENCE: 308
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 309         moltype = AA  length = 449
FEATURE                Location/Qualifiers
REGION                 1..449
                       note = Description of Artificial Sequence: Synthetic
                        polypeptide
REGION                 1..449
                       note = XENP32556 Chain 1 -
                        MESO-C[MSLN]_H1.7_IgG1_pI(-)_Isosteric_
                        A_/PVA_/S267K/L368D/K370S
source                 1..449
                       mol_type = protein
                       organism = synthetic construct
SEQUENCE: 309
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCARII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 310         moltype = AA  length = 485
FEATURE                Location/Qualifiers
REGION                 1..485
```

```
                              note = Description of Artificial Sequence: Synthetic
                               polypeptide
REGION                        1..485
                              note = XENP32556 Chain 2 -
                               MESO-C[MSLN]_H1.7_[CD3]_H1.30_L1.47_scF
                               v(GKPGS)4_Fc(216)_IgG1_C220S/PVA_/S267K/S364K/E357Q
source                        1..485
                              mol_type = protein
                              organism = synthetic construct
SEQUENCE: 310
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                              485

SEQ ID NO: 311                moltype = AA  length = 214
FEATURE                       Location/Qualifiers
REGION                        1..214
                              note = Description of Artificial Sequence: Synthetic
                               polypeptide
REGION                        1..214
                              note = XENP32556 Chain 3 - MESO-C[MSLN]_L1 Light Chain
source                        1..214
                              mol_type = protein
                              organism = synthetic construct
SEQUENCE: 311
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 312                moltype = AA  length = 449
FEATURE                       Location/Qualifiers
REGION                        1..449
                              note = Description of Artificial Sequence: Synthetic
                               polypeptide
REGION                        1..449
                              note = XENP32557 Chain 1 -
                               MESO-C[MSLN]_H1.8_IgG1_pI(-)_Isosteric_
                               A_/PVA_/S267K/L368D/K370S
source                        1..449
                              mol_type = protein
                              organism = synthetic construct
SEQUENCE: 312
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII SPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 313                moltype = AA  length = 485
FEATURE                       Location/Qualifiers
REGION                        1..485
                              note = Description of Artificial Sequence: Synthetic
                               polypeptide
REGION                        1..485
                              note = XENP32557 Chain 2 -
                               MESO-C[MSLN]_H1.8_[CD3]_H1.30_L1.47_scF
                               v(GKPGS)4_Fc(216)_IgG1_C220S/PVA_/S267K/S364K/E357Q
source                        1..485
                              mol_type = protein
                              organism = synthetic construct
SEQUENCE: 313
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
```

-continued

```
LSPGK                                                                485

SEQ ID NO: 314          moltype = AA   length = 214
FEATURE                 Location/Qualifiers
REGION                  1..214
                        note = Description of Artificial Sequence: Synthetic
                         polypeptide
REGION                  1..214
                        note = XENP32557 Chain 3 - MESO-C[MSLN]_L1 Light Chain
source                  1..214
                        mol_type = protein
                        organism = synthetic construct
SEQUENCE: 314
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 315          moltype = AA   length = 449
FEATURE                 Location/Qualifiers
REGION                  1..449
                        note = Description of Artificial Sequence: Synthetic
                         polypeptide
REGION                  1..449
                        note = XENP32558 Chain 1 -
                         MESO-C[MSLN]_H1.9_IgG1_pI(-)_Isosteric_
                         A_/PVA_/S267K/L368D/K370S
source                  1..449
                        mol_type = protein
                        organism = synthetic construct
SEQUENCE: 315
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPRFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 316          moltype = AA   length = 485
FEATURE                 Location/Qualifiers
REGION                  1..485
                        note = Description of Artificial Sequence: Synthetic
                         polypeptide
REGION                  1..485
                        note = XENP32558 Chain 2 -
                         MESO-C[MSLN]_H1.9_[CD3]_H1.30_L1.47_scF
                         v(GKPGS)4_Fc(216)_IgG1_C220S/PVA_/S267K/S364K/E357Q
source                  1..485
                        mol_type = protein
                        organism = synthetic construct
SEQUENCE: 316
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 317          moltype = AA   length = 214
FEATURE                 Location/Qualifiers
REGION                  1..214
                        note = Description of Artificial Sequence: Synthetic
                         polypeptide
REGION                  1..214
                        note = XENP32558 Chain 3 - MESO-C[MSLN]_L1 Light Chain
source                  1..214
                        mol_type = protein
                        organism = synthetic construct
SEQUENCE: 317
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

-continued

```
SEQ ID NO: 318          moltype = AA  length = 449
FEATURE                 Location/Qualifiers
REGION                  1..449
                        note = Description of Artificial Sequence: Synthetic
                        polypeptide
REGION                  1..449
                        note = XENP32559 Chain 1 -
                        MESO-C[MSLN]_H1_IgG1_pI(-)_Isosteric_A_
                        /PVA_/S267K/L368D/K370S
source                  1..449
                        mol_type = protein
                        organism = synthetic construct
SEQUENCE: 318
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 319          moltype = AA  length = 485
FEATURE                 Location/Qualifiers
REGION                  1..485
                        note = Description of Artificial Sequence: Synthetic
                        polypeptide
REGION                  1..485
                        note = XENP32559 Chain 2 -
                        MESO-C[MSLN]_H1_[CD3]_H1.30_L1.47_scFv(
                        GKPGS)4_Fc(216)_IgG1_C220S/PVA_/S267K/S364K/E357Q
source                  1..485
                        mol_type = protein
                        organism = synthetic construct
SEQUENCE: 319
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                              485

SEQ ID NO: 320          moltype = AA  length = 214
FEATURE                 Location/Qualifiers
REGION                  1..214
                        note = Description of Artificial Sequence: Synthetic
                        polypeptide
REGION                  1..214
                        note = XENP32559 Chain 3 - MESO-C[MSLN]_L1.1 Light Chain
source                  1..214
                        mol_type = protein
                        organism = synthetic construct
SEQUENCE: 320
DIVMTQSPDS LAVSLGERAT INCKSSHDVG TSVAWYQQKP GQSPKLLIYW ASTRHTGVPD   60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 321          moltype = AA  length = 449
FEATURE                 Location/Qualifiers
REGION                  1..449
                        note = Description of Artificial Sequence: Synthetic
                        polypeptide
REGION                  1..449
                        note = XENP32560 Chain 1 -
                        MESO-C[MSLN]_H1_IgG1_pI(-)_Isosteric_A_
                        /PVA_/S267K/L368D/K370S
source                  1..449
                        mol_type = protein
                        organism = synthetic construct
SEQUENCE: 321
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
```

```
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 322            moltype = AA  length = 485
FEATURE                   Location/Qualifiers
REGION                    1..485
                          note = Description of Artificial Sequence: Synthetic
                          polypeptide
REGION                    1..485
                          note = XENP32560 Chain 2 -
                          MESO-C[MSLN]_H1_[CD3]_H1.30_L1.47_scFv(
                          GKPGS)4_Fc(216)_IgG1_C220S/PVA_/S267K/S364K/E357Q
source                    1..485
                          mol_type = protein
                          organism = synthetic construct
SEQUENCE: 322
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 323            moltype = AA  length = 214
FEATURE                   Location/Qualifiers
REGION                    1..214
                          note = Description of Artificial Sequence: Synthetic
                          polypeptide
REGION                    1..214
                          note = XENP32560 Chain 3 - MESO-C[MSLN]_L1.2 Light Chain
source                    1..214
                          mol_type = protein
                          organism = synthetic construct
SEQUENCE: 323
DIVMTQSPDS LAVSLGERAT INCKASQDVG TSVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 324            moltype = AA  length = 449
FEATURE                   Location/Qualifiers
REGION                    1..449
                          note = Description of Artificial Sequence: Synthetic
                          polypeptide
REGION                    1..449
                          note = XENP32561 Chain 1 -
                          MESO-C[MSLN]_H1_IgG1_pI(-)_Isosteric_A_
                          /PVA_/S267K/L368D/K370S
source                    1..449
                          mol_type = protein
                          organism = synthetic construct
SEQUENCE: 324
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVPKFDYW GQGTLVTVSS   120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 325            moltype = AA  length = 485
FEATURE                   Location/Qualifiers
REGION                    1..485
                          note = Description of Artificial Sequence: Synthetic
                          polypeptide
REGION                    1..485
                          note = XENP32561 Chain 2 -
                          MESO-C[MSLN]_H1_[CD3]_H1.30_L1.47_scFv(
                          GKPGS)4_Fc(216)_IgG1_C220S/PVA_/S267K/S364K/E357Q
source                    1..485
                          mol_type = protein
                          organism = synthetic construct
SEQUENCE: 325
EVQLVESGGG LVQPGGSLRL SCAASGFTFS TYAMNWVRQA PGKGLEWVGR IRSKYNNYAT  60
```

```
YYADSVKGRF TISRDDSKNT LYLQMNSLRA EDTAVYYCVR HGNFGDSYVS WFAYWGQGTL   120
VTVSSGKPGS GKPGSGKPGS GKPGSQAVVT QEPSLTVSPG GTVTLTCGSS TGAVTTSNYA   180
NWVQQKPGKS PRGLIGGTNK RAPGVPARFS GSLLGGKAAL TISGAQPEDE ADYYCALWYS   240
NHWVFGGGTK LTVLEPKSSD KTHTCPPCPA PPVAGPSVFL FPPKPKDTLM ISRTPEVTCV   300
VVDVKHEDPE VKFNWYVDGV EVHNAKTKPR EEQYNSTYRV VSVLTVLHQD WLNGKEYKCK   360
VSNKALPAPI EKTISKAKGQ PREPQVYTLP PSREQMTKNQ VKLTCLVKGF YPSDIAVEWE   420
SNGQPENNYK TTPPVLDSDG SFFLYSKLTV DKSRWQQGNV FSCSVMHEAL HNHYTQKSLS   480
LSPGK                                                                485
```

```
SEQ ID NO: 326            moltype = AA  length = 214
FEATURE                   Location/Qualifiers
REGION                    1..214
                          note = Description of Artificial Sequence: Synthetic
                           polypeptide
REGION                    1..214
                          note = XENP32561 Chain 3 - MESO-C[MSLN]_L1.3 Light Chain
source                    1..214
                          mol_type = protein
                          organism = synthetic construct
SEQUENCE: 326
DIVMTQSPDS LAVSLGERAT INCKASHSVG TSVAWYQQKP GQSPKLLIYW ASTRHTGVPD   60
RFTGSGSGTD FTLTISSLQA EDVAVYFCQQ YSSYPLTFGA GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                                214
```

```
SEQ ID NO: 327            moltype = AA  length = 449
FEATURE                   Location/Qualifiers
REGION                    1..449
                          note = Description of Artificial Sequence: Synthetic
                           polypeptide
REGION                    1..449
                          note = XENP32562 Chain 1 -
                           MESO-C[MSLN]_H1_IgG1_pI(-)_Isosteric_A_
                           /PVA_/S267K/L368D/K370S
source                    1..449
                          mol_type = protein
                          organism = synthetic construct
SEQUENCE: 327
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                      449
```

```
SEQ ID NO: 328            moltype = AA  length = 485
FEATURE                   Location/Qualifiers
REGION                    1..485
                          note = Description of Artificial Sequence: Synthetic
                           polypeptide
REGION                    1..485
                          note = XENP32562 Chain 2 -
                           MESO-C[MSLN]_H1_[CD3]_H1.30_L1.47_scFv(
                           GKPGS)4_Fc(216)_IgG1_C220S/PVA_/S267K/S364K/E357Q
source                    1..485
                          mol_type = protein
                          organism = synthetic construct
SEQUENCE: 328
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFAYWGQGTL   120
VTVSSGKPGS GKPGSGKPGS GKPGSQAVVT QEPSLTVSPG GTVTLTCGSS TGAVTTSNYA   180
NWVQQKPGKS PRGLIGGTNK RAPGVPARFS GSLLGGKAAL TISGAQPEDE ADYYCALWYS   240
NHWVFGGGTK LTVLEPKSSD KTHTCPPCPA PPVAGPSVFL FPPKPKDTLM ISRTPEVTCV   300
VVDVKHEDPE VKFNWYVDGV EVHNAKTKPR EEQYNSTYRV VSVLTVLHQD WLNGKEYKCK   360
VSNKALPAPI EKTISKAKGQ PREPQVYTLP PSREQMTKNQ VKLTCLVKGF YPSDIAVEWE   420
SNGQPENNYK TTPPVLDSDG SFFLYSKLTV DKSRWQQGNV FSCSVMHEAL HNHYTQKSLS   480
LSPGK                                                                485
```

```
SEQ ID NO: 329            moltype = AA  length = 214
FEATURE                   Location/Qualifiers
REGION                    1..214
                          note = Description of Artificial Sequence: Synthetic
                           polypeptide
REGION                    1..214
                          note = XENP32562 Chain 3 - MESO-C[MSLN]_L1.4 Light Chain
source                    1..214
                          mol_type = protein
```

```
                        organism = synthetic construct
SEQUENCE: 329
DIVMTQSPDS LAVSLGERAT INCKASHDVL TSVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 330          moltype = AA  length = 449
FEATURE                 Location/Qualifiers
REGION                  1..449
                        note = Description of Artificial Sequence: Synthetic
                         polypeptide
REGION                  1..449
                        note = XENP32563 Chain 1 -
                         MESO-C[MSLN]_H1_IgG1_pI(-)_Isosteric_A_
                         /PVA_/S267K/L368D/K370S
source                  1..449
                        mol_type = protein
                        organism = synthetic construct
SEQUENCE: 330
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 331          moltype = AA  length = 485
FEATURE                 Location/Qualifiers
REGION                  1..485
                        note = Description of Artificial Sequence: Synthetic
                         polypeptide
REGION                  1..485
                        note = XENP32563 Chain 2 -
                         MESO-C[MSLN]_H1_[CD3]_H1.30_L1.47_scFv(
                         GKPGS)4_Fc(216)_IgG1_C220S/PVA_/S267K/S364K/E357Q
source                  1..485
                        mol_type = protein
                        organism = synthetic construct
SEQUENCE: 331
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 332          moltype = AA  length = 214
FEATURE                 Location/Qualifiers
REGION                  1..214
                        note = Description of Artificial Sequence: Synthetic
                         polypeptide
REGION                  1..214
                        note = XENP32563 Chain 3 - MESO-C[MSLN]_L1.5 Light Chain
source                  1..214
                        mol_type = protein
                        organism = synthetic construct
SEQUENCE: 332
DIVMTQSPDS LAVSLGERAT INCKASHDVG TYVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 333          moltype = AA  length = 449
FEATURE                 Location/Qualifiers
REGION                  1..449
                        note = Description of Artificial Sequence: Synthetic
                         polypeptide
REGION                  1..449
                        note = XENP32564 Chain 1 -
                         MESO-C[MSLN]_H1_IgG1_pI(-)_Isosteric_A_
                         /PVA_/S267K/L368D/K370S
source                  1..449
                        mol_type = protein
```

```
                        organism = synthetic construct
SEQUENCE: 333
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 334          moltype = AA  length = 485
FEATURE                 Location/Qualifiers
REGION                  1..485
                        note = Description of Artificial Sequence: Synthetic
                         polypeptide
REGION                  1..485
                        note = XENP32564 Chain 2 -
                         MESO-C[MSLN]_H1_[CD3]_H1.30_L1.47_scFv(
                         GKPGS)4_Fc(216)_IgG1_C220S/PVA_/S267K/S364K/E357Q
source                  1..485
                        mol_type = protein
                        organism = synthetic construct
SEQUENCE: 334
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYFCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 335          moltype = AA  length = 214
FEATURE                 Location/Qualifiers
REGION                  1..214
                        note = Description of Artificial Sequence: Synthetic
                         polypeptide
REGION                  1..214
                        note = XENP32564 Chain 3 - MESO-C[MSLN]_L1.6 Light Chain
source                  1..214
                        mol_type = protein
                        organism = synthetic construct
SEQUENCE: 335
DIVMTQSPDS LAVSLGERAT INCKASHDVG TSLAWYQQKP GQSPKLLIYW ASTRHTGVPD   60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 336          moltype = AA  length = 449
FEATURE                 Location/Qualifiers
REGION                  1..449
                        note = Description of Artificial Sequence: Synthetic
                         polypeptide
REGION                  1..449
                        note = XENP32565 Chain 1 -
                         MESO-C[MSLN]_H1_IgG1_pI(-)_Isosteric_A_
                         /PVA_/S267K/L368D/K370S
source                  1..449
                        mol_type = protein
                        organism = synthetic construct
SEQUENCE: 336
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 337          moltype = AA  length = 485
FEATURE                 Location/Qualifiers
REGION                  1..485
                        note = Description of Artificial Sequence: Synthetic
                         polypeptide
REGION                  1..485
                        note = XENP32565 Chain 2 -
```

```
                             MESO-C[MSLN]_H1_[CD3]_H1.30_L1.47_scFv(
                             GKPGS)4_Fc(216)_IgG1_C220S/PVA_/S267K/S364K/E357Q
source                       1..485
                             mol_type = protein
                             organism = synthetic construct
SEQUENCE: 337
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 338              moltype = AA  length = 214
FEATURE                     Location/Qualifiers
REGION                      1..214
                            note = Description of Artificial Sequence: Synthetic
                            polypeptide
REGION                      1..214
                            note = XENP32565 Chain 3 - MESO-C[MSLN]_L1.7 Light Chain
source                      1..214
                            mol_type = protein
                            organism = synthetic construct
SEQUENCE: 338
DIVMTQSPDS LAVSLGERAT INCKASHDVG TSVAWYQQKP GQSPKLLIYW ASTRETGVPD   60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 339              moltype = AA  length = 449
FEATURE                     Location/Qualifiers
REGION                      1..449
                            note = Description of Artificial Sequence: Synthetic
                            polypeptide
REGION                      1..449
                            note = XENP32566 Chain 1 -
                            MESO-C[MSLN]_H1_IgG1_pI(-)_Isosteric_A_
                            /PVA_/S267K/L368D/K370S
source                      1..449
                            mol_type = protein
                            organism = synthetic construct
SEQUENCE: 339
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 340              moltype = AA  length = 485
FEATURE                     Location/Qualifiers
REGION                      1..485
                            note = Description of Artificial Sequence: Synthetic
                            polypeptide
REGION                      1..485
                            note = XENP32566 Chain 2 -
                            MESO-C[MSLN]_H1_[CD3]_H1.30_L1.47_scFv(
                            GKPGS)4_Fc(216)_IgG1_C220S/PVA_/S267K/S364K/E357Q
source                      1..485
                            mol_type = protein
                            organism = synthetic construct
SEQUENCE: 340
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 341              moltype = AA  length = 214
FEATURE                     Location/Qualifiers
```

-continued

```
REGION                    1..214
                          note = Description of Artificial Sequence: Synthetic
                           polypeptide
REGION                    1..214
                          note = XENP32566 Chain 3 - MESO-C[MSLN]_L1.8 Light Chain
source                    1..214
                          mol_type = protein
                          organism = synthetic construct
SEQUENCE: 341
DIVMTQSPDS LAVSLGERAT INCKASHDVG TSVAWYQQKP GQSPKLLIYW ASTRHSGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 342            moltype = AA   length = 449
FEATURE                   Location/Qualifiers
REGION                    1..449
                          note = Description of Artificial Sequence: Synthetic
                           polypeptide
REGION                    1..449
                          note = XENP32567 Chain 1 -
                          MESO-C[MSLN]_H1_IgG1_pI(-)_Isosteric_A_
                          /PVA_/S267K/L368D/K370S
source                    1..449
                          mol_type = protein
                          organism = synthetic construct
SEQUENCE: 342
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 343            moltype = AA   length = 485
FEATURE                   Location/Qualifiers
REGION                    1..485
                          note = Description of Artificial Sequence: Synthetic
                           polypeptide
REGION                    1..485
                          note = XENP32567 Chain 2 -
                          MESO-C[MSLN]_H1_[CD3]_H1.30_L1.47_scFv(
                          GKPGS)4_Fc(216)_IgG1_C220S/PVA_/S267K/S364K/E357Q
source                    1..485
                          mol_type = protein
                          organism = synthetic construct
SEQUENCE: 343
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 344            moltype = AA   length = 214
FEATURE                   Location/Qualifiers
REGION                    1..214
                          note = Description of Artificial Sequence: Synthetic
                           polypeptide
REGION                    1..214
                          note = XENP32567 Chain 3 - MESO-C[MSLN]_L1.9 Light Chain
source                    1..214
                          mol_type = protein
                          organism = synthetic construct
SEQUENCE: 344
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YYSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 345            moltype = AA   length = 449
FEATURE                   Location/Qualifiers
REGION                    1..449
                          note = Description of Artificial Sequence: Synthetic
```

-continued

```
                              polypeptide
REGION                        1..449
                              note = XENP32568 Chain 1 -
                               MESO-C[MSLN]_H1_IgG1_pI(-)_Isosteric_A_
                               /PVA_/S267K/L368D/K370S
source                        1..449
                              mol_type = protein
                              organism = synthetic construct
SEQUENCE: 345
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                     449

SEQ ID NO: 346                moltype = AA  length = 485
FEATURE                       Location/Qualifiers
REGION                        1..485
                              note = Description of Artificial Sequence: Synthetic
                               polypeptide
REGION                        1..485
                              note = XENP32568 Chain 2 -
                               MESO-C[MSLN]_H1_[CD3]_H1.30_L1.47_scFv(
                               GKPGS)4_Fc(216)_IgG1_C220S/PVA_/S267K/S364K/E357Q
source                        1..485
                              mol_type = protein
                              organism = synthetic construct
SEQUENCE: 346
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                              485

SEQ ID NO: 347                moltype = AA  length = 214
FEATURE                       Location/Qualifiers
REGION                        1..214
                              note = Description of Artificial Sequence: Synthetic
                               polypeptide
REGION                        1..214
                              note = XENP32568 Chain 3 - MESO-C[MSLN]_L1.10 Light Chain
source                        1..214
                              mol_type = protein
                              organism = synthetic construct
SEQUENCE: 347
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSTPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 348                moltype = AA  length = 449
FEATURE                       Location/Qualifiers
REGION                        1..449
                              note = Description of Artificial Sequence: Synthetic
                               polypeptide
REGION                        1..449
                              note = XENP32569 Chain 1 -
                               MESO-C[MSLN]_H1.5_IgG1_pI(-)_Isosteric_
                               A_/PVA_/S267K/L368D/K370S
source                        1..449
                              mol_type = protein
                              organism = synthetic construct
SEQUENCE: 348
QVQLVQSGAE VKKPGASVKV SCKASGYTFT SYWMHWVRQA PGQGLEWMGM IHPQSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                     449
```

-continued

```
SEQ ID NO: 349          moltype = AA  length = 485
FEATURE                 Location/Qualifiers
REGION                  1..485
                        note = Description of Artificial Sequence: Synthetic
                        polypeptide
REGION                  1..485
                        note = XENP32569 Chain 2 -
                        MESO-C[MSLN]_H1.5_[CD3]_H1.30_L1.47_scF
                        v(GKPGS)4_Fc(216)_IgG1_C220S/PVA_/S267K/S364K/E357Q
source                  1..485
                        mol_type = protein
                        organism = synthetic construct
SEQUENCE: 349
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                            485

SEQ ID NO: 350          moltype = AA  length = 214
FEATURE                 Location/Qualifiers
REGION                  1..214
                        note = Description of Artificial Sequence: Synthetic
                        polypeptide
REGION                  1..214
                        note = XENP32569 Chain 3 - MESO-C[MSLN]_L1.3 Light Chain
source                  1..214
                        mol_type = protein
                        organism = synthetic construct
SEQUENCE: 350
DIVMTQSPDS LAVSLGERAT INCKASHSVG TSVAWYQQKP GQSPKLLIYW ASTRHTGVPD   60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 351          moltype = AA  length = 449
FEATURE                 Location/Qualifiers
REGION                  1..449
                        note = Description of Artificial Sequence: Synthetic
                        polypeptide
REGION                  1..449
                        note = XENP32570 Chain 1 -
                        MESO-C[MSLN]_H1.6_IgG1_pI(-)_Isosteric_
                        A_/PVA_/S267K/L368D/K370S
source                  1..449
                        mol_type = protein
                        organism = synthetic construct
SEQUENCE: 351
QVQLVQSGAE VKKPGASVKV SCKASGYTFT SYWMHWVRQA PGQGLEWMGM IHPNSGNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                   449

SEQ ID NO: 352          moltype = AA  length = 485
FEATURE                 Location/Qualifiers
REGION                  1..485
                        note = Description of Artificial Sequence: Synthetic
                        polypeptide
REGION                  1..485
                        note = XENP32570 Chain 2 -
                        MESO-C[MSLN]_H1.6_[CD3]_H1.30_L1.47_scF
                        v(GKPGS)4_Fc(216)_IgG1_C220S/PVA_/S267K/S364K/E357Q
source                  1..485
                        mol_type = protein
                        organism = synthetic construct
SEQUENCE: 352
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
```

-continued

```
VVDVKHEDPE VKFNWYVDGV EVHNAKTKPR EEQYNSTYRV VSVLTVLHQD WLNGKEYKCK   360
VSNKALPAPI EKTISKAKGQ PREPQVYTLP PSREQMTKNQ VKLTCLVKGF YPSDIAVEWE   420
SNGQPENNYK TTPPVLDSDG SFFLYSKLTV DKSRWQQGNV FSCSVMHEAL HNHYTQKSLS   480
LSPGK                                                              485

SEQ ID NO: 353          moltype = AA  length = 214
FEATURE                 Location/Qualifiers
REGION                  1..214
                        note = Description of Artificial Sequence: Synthetic
                         polypeptide
REGION                  1..214
                        note = XENP32570 Chain 3 - MESO-C[MSLN]_L1.3 Light Chain
source                  1..214
                        mol_type = protein
                        organism = synthetic construct
SEQUENCE: 353
DIVMTQSPDS LAVSLGERAT INCKASHSVG TSVAWYQQKP GQSPKLLIYW ASTRHTGVPD   60
RFTGSGSGTD FTLTISSLQA EDVAVYFCQQ YSSYPLTFGA GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 354          moltype = AA  length = 449
FEATURE                 Location/Qualifiers
REGION                  1..449
                        note = Description of Artificial Sequence: Synthetic
                         polypeptide
REGION                  1..449
                        note = XENP32937 Chain 1 -
                         MESO-C[MSLN]_H1.12_IgG1_pI(-)_Isosteric
                         _A_/PVA_/S267K/L368D/K370S
source                  1..449
                        mol_type = protein
                        organism = synthetic construct
SEQUENCE: 354
QVQLVQSGAE VKKPGASVKV SCKASGYTFT SYWMHWVRQA PGQGLEWMGM IHPNSDNTIY   60
YQKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                    449

SEQ ID NO: 355          moltype = AA  length = 485
FEATURE                 Location/Qualifiers
REGION                  1..485
                        note = Description of Artificial Sequence: Synthetic
                         polypeptide
REGION                  1..485
                        note = XENP32937 Chain 2 -
                         MESO-C[MSLN]_H1.12_[CD3]_H1.30_L1.47_sc
                         Fv(GKPGS)4-IgG1_pI(-)_Isosteric_A_/PVA_/S267K/L368D/K370S-F
                         c(216)_IgG1_C220S/PVA_/S267K/S364K/E357Q
source                  1..485
                        mol_type = protein
                        organism = synthetic construct
SEQUENCE: 355
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFAYWGQGTL   120
VTVSSGKPGS GKPGSGKPGS GKPGSQAVVT QEPSLTVSPG GTVTLTCGSS TGAVTTSNYA   180
NWVQQKPGKS PRGLIGGTNK RAPGVPARFS GSLLGGKAAL TISGAQPEDE ADYYCALWYS   240
NHWVFGGGTK LTVLEPKSSD KTHTCPPCPA PPVAGPSVFL FPPKPKDTLM ISRTPEVTCV   300
VVDVKHEDPE VKFNWYVDGV EVHNAKTKPR EEQYNSTYRV VSVLTVLHQD WLNGKEYKCK   360
VSNKALPAPI EKTISKAKGQ PREPQVYTLP PSREQMTKNQ VKLTCLVKGF YPSDIAVEWE   420
SNGQPENNYK TTPPVLDSDG SFFLYSKLTV DKSRWQQGNV FSCSVMHEAL HNHYTQKSLS   480
LSPGK                                                              485

SEQ ID NO: 356          moltype = AA  length = 214
FEATURE                 Location/Qualifiers
REGION                  1..214
                        note = Description of Artificial Sequence: Synthetic
                         polypeptide
REGION                  1..214
                        note = XENP32937 Chain 3 - MESO-C[MSLN]_L1.9 Light Chain
source                  1..214
                        mol_type = protein
                        organism = synthetic construct
SEQUENCE: 356
DIVMTQSPDS LAVSLGERAT INCKASHDVG TSVAWYQQKP GQSPKLLIYW ASTRHTGVPD   60
```

```
RFTGSGSGTD FTLTISSLQA EDVAVYFCQQ YYSYPLTFGA GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 357          moltype = AA  length = 449
FEATURE                 Location/Qualifiers
REGION                  1..449
                        note = Description of Artificial Sequence: Synthetic
                         polypeptide
REGION                  1..449
                        note = XENP32938 Chain 1 -
                         MESO-C[MSLN]_H1.13_IgG1_pI(-)_Isosteric
                         _A_/PVA_/S267K/L368D/K370S
source                  1..449
                        mol_type = protein
                        organism = synthetic construct
SEQUENCE: 357
QVQLVQSGAE VKKPGASVKV SCKASGYTFT SYWMHWVRQA PGQGLEWMGM IHPNSDNTIY    60
YYKFQGRVTM TVDKSISTAY MELSRLRSDD TAVYYCAIII TPVVPKFDYW GQGTLVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS DTKVDKKVEP KSCDKTHTCP PCPAPPVAGP    240
SVFLFPPKPK DTLMISRTPE VTCVVVDVKH EDPEVKFNWY VDGVEVHNAK TKPREEEYNS    300
TYRVVSVLTV LHQDWLNGKE YKCKVSNKAL PAPIEKTISK AKGQPREPQV YTLPPSREEM    360
TKNQVSLTCD VSGFYPSDIA VEWESDGQPE NNYKTTPPVL DSDGSFFLYS KLTVDKSRWE    420
QGDVFSCSVM HEALHNHYTQ KSLSLSPGK                                     449

SEQ ID NO: 358          moltype = AA  length = 485
FEATURE                 Location/Qualifiers
REGION                  1..485
                        note = Description of Artificial Sequence: Synthetic
                         polypeptide
REGION                  1..485
                        note = XENP32938 Chain 2 -
                         MESO-C[MSLN]_H1.13_[CD3]_H1.30_L1.47_sc
                         Fv(GKPGS)4-IgG1_pI(-)_Isosteric_A_/PVA_/S267K/L368D/K370S-F
                         c(216)_IgG1_C220S/PVA_/S267K/S364K/E357Q
source                  1..485
                        mol_type = protein
                        organism = synthetic construct
SEQUENCE: 358
EVQLVESGGG LVQPGGSLRL SCAASGFTFS TYAMNWVRQA PGKGLEWVGR IRSKYNNYAT    60
YYADSVKGRF TISRDDSKNT LYLQMNSLRA EDTAVYYCVR HGNFGDSYVS WFAYWGQGTL    120
VTVSSGKPGS GKPGSGKPGS GKPGSQAVVT QEPSLTVSPG GTVTLTCGSS TGAVTTSNYA    180
NWVQQKPGKS PRGLIGGTNK RAPGVPARFS GSLLGGKAAL TISGAQPEDE ADYYCALWYS    240
NHWVFGGGTK LTVLEPKSSD KTHTCPPCPA PPVAGPSVFL FPPKPKDTLM ISRTPEVTCV    300
VVDVKHEDPE VKFNWYVDGV EVHNAKTKPR EEQYNSTYRV VSVLTVLHQD WLNGKEYKCK    360
VSNKALPAPI EKTISKAKGQ PREPQVYTLP PSREQMTKNQ VKLTCLVKGF YPSDIAVEWE    420
SNGQPENNYK TTPPVLDSDG SFFLYSKLTV DKSRWQQGNV FSCSVMHEAL HNHYTQKSLS    480
LSPGK                                                               485

SEQ ID NO: 359          moltype = AA  length = 214
FEATURE                 Location/Qualifiers
REGION                  1..214
                        note = Description of Artificial Sequence: Synthetic
                         polypeptide
REGION                  1..214
                        note = XENP32938 Chain 3 - MESO-C[MSLN]_L1.9 Light Chain
source                  1..214
                        mol_type = protein
                        organism = synthetic construct
SEQUENCE: 359
DIVMTQSPDS LAVSLGERAT INCKASHDVG TSVAWYQQKP GQSPKLLIYW ASTRHTGVPD    60
RFTGSGSGTD FTLTISSLQA EDVAVYFCQQ YYSYPLTFGA GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 360          moltype = AA  length = 449
FEATURE                 Location/Qualifiers
REGION                  1..449
                        note = Description of Artificial Sequence: Synthetic
                         polypeptide
REGION                  1..449
                        note = XENP32939 Chain 1 -
                         MESO-C[MSLN]_H1.3_IgG1_pI(-)_Isosteric_
                         A_/PVA_/S267K/L368D/K370S
source                  1..449
                        mol_type = protein
                        organism = synthetic construct
SEQUENCE: 360
```

```
QVQLVQSGAE VKKPGASVKV SCKASGYTFT SYWMHWVRQA PGQGLEWMGW IHPNSDNTIY    60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                     449
```

SEQ ID NO: 361             moltype = AA   length = 485
FEATURE                    Location/Qualifiers
REGION                     1..485
                            note = Description of Artificial Sequence: Synthetic
                            polypeptide
REGION                     1..485
                            note = XENP32939 Chain 2 -
                            MESO-C[MSLN]_H1.3_[CD3]_H1.30_L1.47_scF
                            v(GKPGS)4-IgG1_pI(-)_Isosteric_A_/PVA_/S267K/L368D/K370S-Fc
                            (216)_IgG1_C220S/PVA_/S267K/S364K/E357Q
source                     1..485
                            mol_type = protein
                            organism = synthetic construct
SEQUENCE: 361

```
EVQLVESGGG LVQPGGSLRL SCAASGFTFS TYAMNWVRQA PGKGLEWVGR IRSKYNNYAT    60
YYADSVKGRF TISRDDSKNT LYLQMNSLRA EDTAVYYCVR HGNFGDSYVS WFAYWGQGTL   120
VTVSSGKPGS GKPGSGKPGS GKPGSQAVVT QEPSLTVSPG GTVTLTCGSS TGAVTTSNYA   180
NWVQQKPGKS PRGLIGGTNK RAPGVPARFS GSLLGGKAAL TISGAQPEDE ADYYCALWYS   240
NHWVFGGGTK LTVLEPKSSD KTHTCPPCPA PPVAGPSVFL FPPKPKDTLM ISRTPEVTCV   300
VVDVKHEDPE VKFNWYVDGV EVHNAKTKPR EEQYNSTYRV VSVLTVLHQD WLNGKEYKCK   360
VSNKALPAPI EKTISKAKGQ PREPQVYTLP PSREQMTKNQ VKLTCLVKGF YPSDIAVEWE   420
SNGQPENNYK TTPPVLDSDG SFFLYSKLTV DKSRWQQGNV FSCSVMHEAL HNHYTQKSLS   480
LSPGK                                                              485
```

SEQ ID NO: 362             moltype = AA   length = 214
FEATURE                    Location/Qualifiers
REGION                     1..214
                            note = Description of Artificial Sequence: Synthetic
                            polypeptide
REGION                     1..214
                            note = XENP32939 Chain 3 - MESO-C[MSLN]_L1.13 Light Chain
source                     1..214
                            mol_type = protein
                            organism = synthetic construct
SEQUENCE: 362

```
DIVMTQSPDS LAVSLGERAT INCKASHDVG QSVAWYQQKP GQSPKLLIYW ASTRHTGVPD    60
RFTGSGSGTD FTLTISSLQA EDVAVYFCQQ YSSYPLTFGA GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214
```

SEQ ID NO: 363             moltype = AA   length = 449
FEATURE                    Location/Qualifiers
REGION                     1..449
                            note = Description of Artificial Sequence: Synthetic
                            polypeptide
REGION                     1..449
                            note = XENP32940 Chain 1 -
                            MESO-C[MSLN]_H1.3_IgG1_pI(-)_Isosteric_
                            A_/PVA_/S267K/L368D/K370S
source                     1..449
                            mol_type = protein
                            organism = synthetic construct
SEQUENCE: 363

```
QVQLVQSGAE VKKPGASVKV SCKASGYTFT SYWMHWVRQA PGQGLEWMGW IHPNSDNTIY    60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                     449
```

SEQ ID NO: 364             moltype = AA   length = 485
FEATURE                    Location/Qualifiers
REGION                     1..485
                            note = Description of Artificial Sequence: Synthetic
                            polypeptide
REGION                     1..485
                            note = XENP32940 Chain 2 -
                            MESO-C[MSLN]_H1.3_[CD3]_H1.30_L1.47_scF -continued

```
                              v(GKPGS)4-IgG1_pI(-)_Isosteric_A_/PVA_/S267K/L368D/K370S-Fc
                              (216)_IgG1_C220S/PVA_/S267K/S364K/E357Q
source                        1..485
                              mol_type = protein
                              organism = synthetic construct
SEQUENCE: 364
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFAYWGQGTL   120
VTVSSGKPGS GKPGSGKPGS GKPGSQAVVT QEPSLTVSPG GTVTLTCGSS TGAVTTSNYA   180
NWVQQKPGKS PRGLIGGTNK RAPGVPARFS GSLLGGKAAL TISGAQPEDE ADYYCALWYS   240
NHWVFGGGTK LTVLEPKSSD KTHTCPPCPA PPVAGPSVFL FPPKPKDTLM ISRTPEVTCV   300
VVDVKHEDPE VKFNWYVDGV EVHNAKTKPR EEQYNSTYRV VSVLTVLHQD WLNGKEYKCK   360
VSNKALPAPI EKTISKAKGQ PREPQVYTLP PSREQMTKNQ VKLTCLVKGF YPSDIAVEWE   420
SNGQPENNYK TTPPVLDSDG SFFLYSKLTV DKSRWQQGNV FSCSVMHEAL HNHYTQKSLS   480
LSPGK                                                              485

SEQ ID NO: 365           moltype = AA  length = 214
FEATURE                  Location/Qualifiers
REGION                   1..214
                         note = Description of Artificial Sequence: Synthetic
                         polypeptide
REGION                   1..214
                         note = XENP32940 Chain 3 - MESO-C[MSLN]_L1.14 Light Chain
source                   1..214
                         mol_type = protein
                         organism = synthetic construct
SEQUENCE: 365
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YSSFPLTFGA GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 366           moltype = AA  length = 449
FEATURE                  Location/Qualifiers
REGION                   1..449
                         note = Description of Artificial Sequence: Synthetic
                         polypeptide
REGION                   1..449
                         note = XENP32941 Chain 1 -
                         MESO-C[MSLN]_H1.3_IgG1_pI(-)_Isosteric_
                         A_/PVA_/S267K/L368D/K370S
source                   1..449
                         mol_type = protein
                         organism = synthetic construct
SEQUENCE: 366
QVQLVQSGAE VKKPGASVKV SCKASGYTFT SYWMHWVRQA PGQGLEWMGW IHPNSDNTIY   60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                    449

SEQ ID NO: 367           moltype = AA  length = 485
FEATURE                  Location/Qualifiers
REGION                   1..485
                         note = Description of Artificial Sequence: Synthetic
                         polypeptide
REGION                   1..485
                         note = XENP32941 Chain 2 -
                         MESO-C[MSLN]_H1.3_[CD3]_H1.30_L1.47_scF
                         v(GKPGS)4-IgG1_pI(-)_Isosteric_A_/PVA_/S267K/L368D/K370S-Fc
                         (216)_IgG1_C220S/PVA_/S267K/S364K/E357Q
source                   1..485
                         mol_type = protein
                         organism = synthetic construct
SEQUENCE: 367
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFAYWGQGTL   120
VTVSSGKPGS GKPGSGKPGS GKPGSQAVVT QEPSLTVSPG GTVTLTCGSS TGAVTTSNYA   180
NWVQQKPGKS PRGLIGGTNK RAPGVPARFS GSLLGGKAAL TISGAQPEDE ADYYCALWYS   240
NHWVFGGGTK LTVLEPKSSD KTHTCPPCPA PPVAGPSVFL FPPKPKDTLM ISRTPEVTCV   300
VVDVKHEDPE VKFNWYVDGV EVHNAKTKPR EEQYNSTYRV VSVLTVLHQD WLNGKEYKCK   360
VSNKALPAPI EKTISKAKGQ PREPQVYTLP PSREQMTKNQ VKLTCLVKGF YPSDIAVEWE   420
SNGQPENNYK TTPPVLDSDG SFFLYSKLTV DKSRWQQGNV FSCSVMHEAL HNHYTQKSLS   480
LSPGK                                                              485

SEQ ID NO: 368           moltype = AA  length = 214
```

-continued

```
FEATURE           Location/Qualifiers
REGION            1..214
                  note = Description of Artificial Sequence: Synthetic
                   polypeptide
REGION            1..214
                  note = XENP32941 Chain 3 - MESO-C[MSLN]_L1.15 Light Chain
source            1..214
                  mol_type = protein
                  organism = synthetic construct
SEQUENCE: 368
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSLPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 369        moltype = AA  length = 449
FEATURE           Location/Qualifiers
REGION            1..449
                  note = Description of Artificial Sequence: Synthetic
                   polypeptide
REGION            1..449
                  note = XENP32942 Chain 1 -
                   MESO-C[MSLN]_H1.3_IgG1_pI(-)_Isosteric_
                   A_/PVA_/S267K/L368D/K370S
source            1..449
                  mol_type = protein
                  organism = synthetic construct
SEQUENCE: 369
QVQLVQSGAE VKKPGASVKV SCKASGYTFT SYWMHWVRQA PGQGLEWMGW IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 370        moltype = AA  length = 485
FEATURE           Location/Qualifiers
REGION            1..485
                  note = Description of Artificial Sequence: Synthetic
                   polypeptide
REGION            1..485
                  note = XENP32942 Chain 2 -
                   MESO-C[MSLN]_H1.3_[CD3]_H1.30_L1.47_scF
                   v(GKPGS)4_Fc(216)_IgG1_C220S/PVA_/S267K/S364K/E357Q
source            1..485
                  mol_type = protein
                  organism = synthetic construct
SEQUENCE: 370
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 371        moltype = AA  length = 214
FEATURE           Location/Qualifiers
REGION            1..214
                  note = Description of Artificial Sequence: Synthetic
                   polypeptide
REGION            1..214
                  note = XENP32942 Chain 3 - MESO-C[MSLN]_L1.16 Light Chain
source            1..214
                  mol_type = protein
                  organism = synthetic construct
SEQUENCE: 371
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSVPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 372        moltype = AA  length = 449
FEATURE           Location/Qualifiers
REGION            1..449
```

-continued

```
                            note = Description of Artificial Sequence: Synthetic
                             polypeptide
REGION                      1..449
                            note = XENP32943 Chain 1 -
                             MESO-C[MSLN]_H1.3_IgG1_pI(-)_Isosteric_
                             A_/PVA_/S267K/L368D/K370S
source                      1..449
                            mol_type = protein
                            organism = synthetic construct
SEQUENCE: 372
QVQLVQSGAE VKKPGASVKV SCKASGYTFT SYWMHWVRQA PGQGLEWMGW IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 373              moltype = AA  length = 485
FEATURE                     Location/Qualifiers
REGION                      1..485
                            note = Description of Artificial Sequence: Synthetic
                             polypeptide
REGION                      1..485
                            note = XENP32943 Chain 2 -
                             MESO-C[MSLN]_H1.3_[CD3]_H1.30_L1.47_scF
                             v(GKPGS)4-IgG1_pI(-)_Isosteric_A_/PVA_/S267K/L368D/K370S-Fc
                             (216)_IgG1_C220S/PVA_/S267K/S364K/E357Q
source                      1..485
                            mol_type = protein
                            organism = synthetic construct
SEQUENCE: 373
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 374              moltype = AA  length = 214
FEATURE                     Location/Qualifiers
REGION                      1..214
                            note = Description of Artificial Sequence: Synthetic
                             polypeptide
REGION                      1..214
                            note = XENP32943 Chain 3 - MESO-C[MSLN]_L1.17 Light Chain
source                      1..214
                            mol_type = protein
                            organism = synthetic construct
SEQUENCE: 374
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSIPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 375              moltype = AA  length = 449
FEATURE                     Location/Qualifiers
REGION                      1..449
                            note = Description of Artificial Sequence: Synthetic
                             polypeptide
REGION                      1..449
                            note = XENP32944 Chain 1 -
                             MESO-C[MSLN]_H1.3_IgG1_pI(-)_Isosteric_
                             A_/PVA_/S267K/L368D/K370S
source                      1..449
                            mol_type = protein
                            organism = synthetic construct
SEQUENCE: 375
QVQLVQSGAE VKKPGASVKV SCKASGYTFT SYWMHWVRQA PGQGLEWMGW IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
```

```
QGDVFSCSVM HEALHNHYTQ KSLSLSPGK                                        449

SEQ ID NO: 376          moltype = AA  length = 485
FEATURE                 Location/Qualifiers
REGION                  1..485
                        note = Description of Artificial Sequence: Synthetic
                         polypeptide
REGION                  1..485
                        note = XENP32944 Chain 2 -
                         MESO-C[MSLN]_H1.3_[CD3]_H1.30_L1.47_scF
                         v(GKPGS)4-IgG1_pI(-)_Isosteric_A_/PVA_/S267K/L368D/K370S-Fc
                         (216)_IgG1_C220S/PVA_/S267K/S364K/E357Q
source                  1..485
                        mol_type = protein
                        organism = synthetic construct
SEQUENCE: 376
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                               485

SEQ ID NO: 377          moltype = AA  length = 214
FEATURE                 Location/Qualifiers
REGION                  1..214
                        note = Description of Artificial Sequence: Synthetic
                         polypeptide
REGION                  1..214
                        note = XENP32944 Chain 3 - MESO-C[MSLN]_L1.18 Light Chain
source                  1..214
                        mol_type = protein
                        organism = synthetic construct
SEQUENCE: 377
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSHPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 378          moltype = AA  length = 449
FEATURE                 Location/Qualifiers
REGION                  1..449
                        note = Description of Artificial Sequence: Synthetic
                         polypeptide
REGION                  1..449
                        note = XENP32945 Chain 1 -
                         MESO-C[MSLN]_H1.3_IgG1_pI(-)_Isosteric_
                         A_/PVA_/S267K/L368D/K370S
source                  1..449
                        mol_type = protein
                        organism = synthetic construct
SEQUENCE: 378
QVQLVQSGAE VKKPGASVKV SCKASGYTFT SYWMHWVRQA PGQGLEWMGW IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                     449

SEQ ID NO: 379          moltype = AA  length = 485
FEATURE                 Location/Qualifiers
REGION                  1..485
                        note = Description of Artificial Sequence: Synthetic
                         polypeptide
REGION                  1..485
                        note = XENP32945 Chain 2 -
                         MESO-C[MSLN]_H1.3_[CD3]_H1.30_L1.47_scF
                         v(GKPGS)4-IgG1_pI(-)_Isosteric_A_/PVA_/S267K/L368D/K370S-Fc
                         (216)_IgG1_C220S/PVA_/S267K/S364K/E357Q
source                  1..485
                        mol_type = protein
                        organism = synthetic construct
SEQUENCE: 379
EVQLVESGGG LVQPGGSLRL SCAASGFTFS TYAMNWVRQA PGKGLEWVGR IRSKYNNYAT  60
```

```
YYADSVKGRF TISRDDSKNT LYLQMNSLRA EDTAVYYCVR HGNFGDSYVS WFAYWGQGTL   120
VTVSSGKPGS GKPGSGKPGS GKPGSQAVVT QEPSLTVSPG GTVTLTCGSS TGAVTTSNYA   180
NWVQQKPGKS PRGLIGGTNK RAPGVPARFS GSLLGGKAAL TISGAQPEDE ADYYCALWYS   240
NHWVFGGGTK LTVLEPKSSD KTHTCPPCPA PPVAGPSVFL FPPKPKDTLM ISRTPEVTCV   300
VVDVKHEDPE VKFNWYVDGV EVHNAKTKPR EEQYNSTYRV VSVLTVLHQD WLNGKEYKCK   360
VSNKALPAPI EKTISKAKGQ PREPQVYTLP PSREQMTKNQ VKLTCLVKGF YPSDIAVEWE   420
SNGQPENNYK TTPPVLDSDG SFFLYSKLTV DKSRWQQGNV FSCSVMHEAL HNHYTQKSLS   480
LSPGK                                                              485
```

```
SEQ ID NO: 380              moltype = AA  length = 214
FEATURE                     Location/Qualifiers
REGION                      1..214
                            note = Description of Artificial Sequence: Synthetic
                             polypeptide
REGION                      1..214
                            note = XENP32945 Chain 3 - MESO-C[MSLN]_L1.9 Light Chain
source                      1..214
                            mol_type = protein
                            organism = synthetic construct
SEQUENCE: 380
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YYSYPLTFGG GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214
```

```
SEQ ID NO: 381              moltype = AA  length = 449
FEATURE                     Location/Qualifiers
REGION                      1..449
                            note = Description of Artificial Sequence: Synthetic
                             polypeptide
REGION                      1..449
                            note = XENP32946 Chain 1 -
                             MESO-C[MSLN]_H1.3_IgG1_pI(-)_Isosteric_
                             A_/PVA_/S267K/L368D/K370S
source                      1..449
                            mol_type = protein
                            organism = synthetic construct
SEQUENCE: 381
QVQLVQSGAE VKKPGASVKV SCKASGYTFT SYWMHWVRQA PGQGLEWMGW IHPNSDNTIY   60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                    449
```

```
SEQ ID NO: 382              moltype = AA  length = 485
FEATURE                     Location/Qualifiers
REGION                      1..485
                            note = Description of Artificial Sequence: Synthetic
                             polypeptide
REGION                      1..485
                            note = XENP32946 Chain 2 -
                             MESO-C[MSLN]_H1.3_[CD3]_H1.30_L1.47_scF
                             v(GKPGS)4-IgG1_pI(-)_Isosteric_A_/PVA_/S267K/L368D/K370S-Fc
                             (216)_IgG1_C220S/PVA_/S267K/S364K/E357Q
source                      1..485
                            mol_type = protein
                            organism = synthetic construct
SEQUENCE: 382
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFAYWGQGTL   120
VTVSSGKPGS GKPGSGKPGS GKPGSQAVVT QEPSLTVSPG GTVTLTCGSS TGAVTTSNYA   180
NWVQQKPGKS PRGLIGGTNK RAPGVPARFS GSLLGGKAAL TISGAQPEDE ADYYCALWYS   240
NHWVFGGGTK LTVLEPKSSD KTHTCPPCPA PPVAGPSVFL FPPKPKDTLM ISRTPEVTCV   300
VVDVKHEDPE VKFNWYVDGV EVHNAKTKPR EEQYNSTYRV VSVLTVLHQD WLNGKEYKCK   360
VSNKALPAPI EKTISKAKGQ PREPQVYTLP PSREQMTKNQ VKLTCLVKGF YPSDIAVEWE   420
SNGQPENNYK TTPPVLDSDG SFFLYSKLTV DKSRWQQGNV FSCSVMHEAL HNHYTQKSLS   480
LSPGK                                                              485
```

```
SEQ ID NO: 383              moltype = AA  length = 214
FEATURE                     Location/Qualifiers
REGION                      1..214
                            note = Description of Artificial Sequence: Synthetic
                             polypeptide
REGION                      1..214
                            note = XENP32946 Chain 3 - MESO-C[MSLN]_L1.5 Light Chain
source                      1..214
```

```
                              mol_type = protein
                              organism = synthetic construct
SEQUENCE: 383
DIVMTQSPDS LAVSLGERAT INCKASHDVG TYVAWYQQKP GQSPKLLIYW ASTRHTGVPD    60
RFTGSGSGTD FTLTISSLQA EDVAVYFCQQ YSSYPLTFGA GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 384              moltype = AA  length = 485
FEATURE                     Location/Qualifiers
REGION                      1..485
                            note = Description of Artificial Sequence: Synthetic
                             polypeptide
REGION                      1..485
                            note = XENP33888 Chain 1 -
                             MESO-C[MSLN]_H1_IgG1_pI(-)_Isosteric_A_
                             /PVA_/S267K/L368D/K370S
source                      1..485
                            mol_type = protein
                            organism = synthetic construct
SEQUENCE: 384
EVQLVESGGG LVQPGGSLRL SCAASGFTFS TYAMNWVRQA PGKGLEWVGR IRSKYNNYAT    60
YYADSVKGRF TISRDDSKNT LYLQMNSLRA EDTAVYYCVR HGNFGDSYVS WFAYWGQGTL   120
VTVSSGKPGS GKPGSGKPGS GKPGSQAVVT QEPSLTVSPG GTVTLTCGSS TGAVTTSNYA   180
NWVQQKPGKS PRGLIGGTNK RAPGVPARFS GSLLGGKAAL TISGAQPEDE ADYYCALWYS   240
NHWVFGGGTK LTVLEPKSSD KTHTCPPCPA PPVAGPSVFL FPPKPKDTLM ISRTPEVTCV   300
VVDVKHEDPE VKFNWYVDGV EVHNAKTKPR EEQYNSTYRV VSVLTVLHQD WLNGKEYKCK   360
VSNKALPAPI EKTISKAKGQ PREPQVYTLP PSREQMTKNQ VKLTCLVKGF YPSDIAVEWE   420
SNGQPENNYK TTPPVLDSDG SFFLYSKLTV DKSRWQQGNV FSCSVMHEAL HNHYTQKSLS   480
LSPGK                                                              485

SEQ ID NO: 385              moltype = AA  length = 449
FEATURE                     Location/Qualifiers
REGION                      1..449
                            note = Description of Artificial Sequence: Synthetic
                             polypeptide
REGION                      1..449
                            note = XENP33888 Chain 2 -
                             [CD3]_H1.30_L1.47_scFv(GKPGS)4_Fc(216)_
                             IgG1_C220S/PVA_/S267K/S364K/E357Q
source                      1..449
                            mol_type = protein
                            organism = synthetic construct
SEQUENCE: 385
QVQLVQSGAE VKKPGASVKV SCKASGYTFT SYWMHWVRQA PGQGLEWMGM IHPNSDNTIY    60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                    449

SEQ ID NO: 386              moltype = AA  length = 214
FEATURE                     Location/Qualifiers
REGION                      1..214
                            note = Description of Artificial Sequence: Synthetic
                             polypeptide
REGION                      1..214
                            note = XENP33888 Chain 3 - MESO-C[MSLN]_L1.20 Light Chain
source                      1..214
                            mol_type = protein
                            organism = synthetic construct
SEQUENCE: 386
DIVMTQSPDS LAVSLGERAT INCKASHDVG TSVAWYQQKP GQSPKLLIYW ASTRHTGVPD    60
RFTGSGSGTD FTLTISSLQA EDVAVYFCQQ YSFPLTFGA GTKLEIKRTV AAPSVFIFPP    120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 387              moltype = AA  length = 485
FEATURE                     Location/Qualifiers
REGION                      1..485
                            note = Description of Artificial Sequence: Synthetic
                             polypeptide
REGION                      1..485
                            note = XENP33889 Chain 1 -
                             MESO-C[MSLN]_H1.12_IgG1_pI(-)_Isosteric
                             _A_/PVA_/S267K/L368D/K370S
source                      1..485
```

```
                     mol_type = protein
                     organism = synthetic construct
SEQUENCE: 387
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 388          moltype = AA  length = 449
FEATURE                 Location/Qualifiers
REGION                  1..449
                        note = Description of Artificial Sequence: Synthetic
                        polypeptide
REGION                  1..449
                        note = XENP33889 Chain 2 -
                        [CD3]_H1.30_L1.47_scFv(GKPGS)4_Fc(216)_
                        IgG1_C220S/PVA_/S267K/S364K/E357Q
source                  1..449
                        mol_type = protein
                        organism = synthetic construct
SEQUENCE: 388
QVQLVQSGAE VKKPGASVKV SCKASGYTFT SYWMHWVRQA PGQGLEWMGM IHPNSDNTIY   60
YQKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 389          moltype = AA  length = 214
FEATURE                 Location/Qualifiers
REGION                  1..214
                        note = Description of Artificial Sequence: Synthetic
                        polypeptide
REGION                  1..214
                        note = XENP33889 Chain 3 - MESO-C[MSLN]_L1.20 Light Chain
source                  1..214
                        mol_type = protein
                        organism = synthetic construct
SEQUENCE: 389
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YYSFPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 390          moltype = AA  length = 453
FEATURE                 Location/Qualifiers
REGION                  1..453
                        note = Description of Artificial Sequence: Synthetic
                        polypeptide
REGION                  1..453
                        note = XENP30764 Chain 1 -
                        MESO-A[MSLN]_H1.1_L1_Fab_IgG1_pI(-)_Iso
                        steric_A_/PVA_/S267K/L368D/K370S
source                  1..453
                        mol_type = protein
                        organism = synthetic construct
SEQUENCE: 390
EVQLVESGGG LVQPGGSLKL SCAASGFDFS RYWMSWVRQA PGKGLEWVSE INPDSSTIVY   60
TPSVKGRFTI SRDNAKNSLY LQMNSLRAED TAVYYCARRG SHYYGYRTGY FDVWGAGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSDTKVDK KVEPKSCDKT HTCPPCPAPP  240
VAGPSVFLFP PKPKDTLMIS RTPEVTCVVV DVKHEDPEVK FNWYVDGVEV HNAKTKPREE  300
EYNSTYRVVS VLTVLHQDWL NGKEYKCKVS NKALPAPIEK TISKAKGQPR EPQVYTLPPS  360
REEMTKNQVS LTCDVSGFYP SDIAVEWESD GQPENNYKTT PPVLDSDGSF FLYSKLTVDK  420
SRWEQGDVFS CSVMHEALHN HYTQKSLSLS PGK                              453

SEQ ID NO: 391          moltype = AA  length = 485
FEATURE                 Location/Qualifiers
REGION                  1..485
                        note = Description of Artificial Sequence: Synthetic
                        polypeptide
REGION                  1..485
```

```
                              note = XENP30764 Chain 2 -
                              [CD3]_H1.32_L1.47_scFv(GKPGS)4_Fc(216)_
                              IgG1_C220S/PVA_/S267K/S364K/E357Q
source                        1..485
                              mol_type = protein
                              organism = synthetic construct
SEQUENCE: 391
EVQLVESGGG LVQPGGSLRL SCAASGFTFS TYAMNWVRQA PGKGLEWVGR IRSKANNYAT   60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                              485

SEQ ID NO: 392            moltype = AA  length = 213
FEATURE                   Location/Qualifiers
REGION                    1..213
                          note = Description of Artificial Sequence: Synthetic
                          polypeptide
REGION                    1..213
                          note = XENP30764 Chain 3 - MESO-A[MSLN]_L1 Light Chain
source                    1..213
                          mol_type = protein
                          organism = synthetic construct
SEQUENCE: 392
DVVLTQSPAT LSLSPGERAT LSCRASSSVS YMYWHQQKPD QSPKLLIYDT SNLASGVPVR   60
FSGSGSGTDY TLTISSLEPE DFAVYYCQQW SSYPPTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                                213

SEQ ID NO: 393            moltype = AA  length = 452
FEATURE                   Location/Qualifiers
REGION                    1..452
                          note = Description of Artificial Sequence: Synthetic
                          polypeptide
REGION                    1..452
                          note = XENP30765 Chain 1 -
                          MESO-B[MSLN]_H0L0_Fab_IgG1_pI(-)_Isoste
                          ric_A_/PVA_/S267K/L368D/K370S
source                    1..452
                          mol_type = protein
                          organism = synthetic construct
SEQUENCE: 393
QVQLQQSGPG LVTPSQTLSL TCAISGDSVS SNSATWNWIR QSPSRGLEWL GRTYYRSKWY   60
NDYAVSVKSR MSINPDTSKN QFSLQLNSVT PEDTAVYYCA RGMMTYYYGM DVWGQGTTVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSDTKVDKK VEPKSCDKTH TCPPCPAPPV  240
AGPSVFLFPP KPKDTLMISR TPEVTCVVVD VKHEDPEVKF NWYVDGVEVH NAKTKPREEE  300
YNSTYRVVSV LTVLHQDWLN GKEYKCKVSN KALPAPIEKT ISKAKGQPRE PQVYTLPPSR  360
EEMTKNQVSL TCDVSGFYPS DIAVEWESDG QPENNYKTTP PVLDSDGSFF LYSKLTVDKS  420
RWEQGDVFSC SVMHEALHNH YTQKSLSLSP GK                                452

SEQ ID NO: 394            moltype = AA  length = 485
FEATURE                   Location/Qualifiers
REGION                    1..485
                          note = Description of Artificial Sequence: Synthetic
                          polypeptide
REGION                    1..485
                          note = XENP30765 Chain 2 -
                          [CD3]_H1.32_L1.47_scFv(GKPGS)4_Fc(216)_
                          IgG1_C220S/PVA_/S267K/S364K/E357Q
source                    1..485
                          mol_type = protein
                          organism = synthetic construct
SEQUENCE: 394
EVQLVESGGG LVQPGGSLRL SCAASGFTFS TYAMNWVRQA PGKGLEWVGR IRSKANNYAT   60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                              485

SEQ ID NO: 395            moltype = AA  length = 221
```

```
FEATURE                 Location/Qualifiers
REGION                  1..221
                        note = Description of Artificial Sequence: Synthetic
                         polypeptide
REGION                  1..221
                        note = XENP30765 Chain 3 - MESO-B[MSLN]_L0 Light Chain
source                  1..221
                        mol_type = protein
                        organism = synthetic construct
SEQUENCE: 395
QPVLTQSSSL SASPGASASL TCTLRSGINV GPYRIYWYQQ KPGSPPQYLL NYKSDSDKQQ  60
GSGVPSRFSG SKDASANAGV LLISGLRSED EADYYCMIWH SSAAVFGGGT QLTVLGQPKA  120
APSVTLFPPS SEELQANKAT LVCLISDFYP GAVTVAWKAD SSPVKAGVET TTPSKQSNNK  180
YAASSYLSLT PEQWKSHRSY SCQVTHEGST VEKTVAPTEC S                     221

SEQ ID NO: 396          moltype = AA  length = 449
FEATURE                 Location/Qualifiers
REGION                  1..449
                        note = Description of Artificial Sequence: Synthetic
                         polypeptide
REGION                  1..449
                        note = XENP31701 Chain 1 -
                         MESO-C[MSLN]_H1_IgG1_pI(-)_Isosteric_A_
                         /PVA_/S267K/L368D/K370S
source                  1..449
                        mol_type = protein
                        organism = synthetic construct
SEQUENCE: 396
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 397          moltype = AA  length = 485
FEATURE                 Location/Qualifiers
REGION                  1..485
                        note = Description of Artificial Sequence: Synthetic
                         polypeptide
REGION                  1..485
                        note = XENP31701 Chain 2 -
                         [CD3]_H1.32_L1.47_scFv(GKPGS)4_Fc(216)_
                         IgG1_C220S/PVA_/S267K/S364K/E357Q
source                  1..485
                        mol_type = protein
                        organism = synthetic construct
SEQUENCE: 397
EVQLVESGGG LVQPGGSLRL SCAASGFTFS TYAMNWVRQA PGKGLEWVGR IRSKANNYAT  60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 398          moltype = AA  length = 214
FEATURE                 Location/Qualifiers
REGION                  1..214
                        note = Description of Artificial Sequence: Synthetic
                         polypeptide
REGION                  1..214
                        note = XENP31701 Chain 3 - MESO-C[MSLN]_L1 Light Chain
source                  1..214
                        mol_type = protein
                        organism = synthetic construct
SEQUENCE: 398
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 399          moltype = AA  length = 449
FEATURE                 Location/Qualifiers
REGION                  1..449
```

-continued

```
                        note = Description of Artificial Sequence: Synthetic
                         polypeptide
REGION                  1..449
                        note = XENP33969 Chain 1 -
                         MESO-C[MSLN]_H1.14_IgG1_pI(-)_Isosteric
                         _A_PVA_/S267K/L368D/K370S
source                  1..449
                        mol_type = protein
                        organism = synthetic construct
SEQUENCE: 399
QVQLVQSGAE VKKPGASVKV SCKASGYTFT SYWMHWVRQA PGQGLEWMGW IHPQSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 400            moltype = AA   length = 485
FEATURE                   Location/Qualifiers
REGION                    1..485
                          note = Description of Artificial Sequence: Synthetic
                           polypeptide
REGION                    1..485
                          note = XENP33969 Chain 2 -
                           [CD3]_L1.47_H1.32_scFv(GKPGS)4_Fc(216)_
                           IgG1_C220S/PVA_/S267K/S364K/E357Q
source                    1..485
                          mol_type = protein
                          organism = synthetic construct
SEQUENCE: 400
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVLG KPGSGKPGSG  120
KPGSGKPGSE VQLVESGGGL VQPGGSLRLS CAASGFTFST YAMNWVRQAP GKGLEWVGRI  180
RSKANNYATY YADSVKGRFT ISRDDSKNTL YLQMNSLRAE DTAVYYCVRH GNFGDSYVSW  240
FAYWGQGTLV TVSSEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 401            moltype = AA   length = 214
FEATURE                   Location/Qualifiers
REGION                    1..214
                          note = Description of Artificial Sequence: Synthetic
                           polypeptide
REGION                    1..214
                          note = XENP33969 Chain 3 - MESO-C[MSLN]_L1.14 Light Chain
source                    1..214
                          mol_type = protein
                          organism = synthetic construct
SEQUENCE: 401
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSFPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 402            moltype = AA   length = 449
FEATURE                   Location/Qualifiers
REGION                    1..449
                          note = Description of Artificial Sequence: Synthetic
                           polypeptide
REGION                    1..449
                          note = XENP33971 Chain 1 -
                           MESO-C[MSLN]_H1.15_IgG1_pI(-)_Isosteric
                           _A_PVA_/S267K/L368D/K370S
source                    1..449
                          mol_type = protein
                          organism = synthetic construct
SEQUENCE: 402
QVQLVQSGAE VKKPGASVKV SCKASGYTFT SYWMHWVRQA PGQGLEWMGW IHPNSDNTIY  60
YEKFQGRVTM TVDKSISTAY MELSRLRSDD TAVYYCARII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449
```

-continued

```
SEQ ID NO: 403             moltype = AA  length = 485
FEATURE                    Location/Qualifiers
REGION                     1..485
                           note = Description of Artificial Sequence: Synthetic
                            polypeptide
REGION                     1..485
                           note = XENP33971 Chain 2 -
                            [CD3]_L1.47_H1.32_scFv(GKPGS)4_Fc(216)_
                            IgG1_C220S/PVA_/S267K/S364K/E357Q
source                     1..485
                           mol_type = protein
                           organism = synthetic construct
SEQUENCE: 403
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVLG KPGSGKPGSG  120
KPGSGKPGSE VQLVESGGGL VQPGGSLRLS CAASGFTFST YAMNWVRQAP GKGLEWVGRI  180
RSKANNYATY YADSVKGRFT ISRDDSKNTL YLQMNSLRAE DTAVYYCVRH GNFGDSYVSW  240
FAYWGQGTLV TVSSEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 404             moltype = AA  length = 214
FEATURE                    Location/Qualifiers
REGION                     1..214
                           note = Description of Artificial Sequence: Synthetic
                            polypeptide
REGION                     1..214
                           note = XENP33971 Chain 3 - MESO-C[MSLN]_L1.14 Light Chain
source                     1..214
                           mol_type = protein
                           organism = synthetic construct
SEQUENCE: 404
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSFPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 405             moltype = AA  length = 449
FEATURE                    Location/Qualifiers
REGION                     1..449
                           note = Description of Artificial Sequence: Synthetic
                            polypeptide
REGION                     1..449
                           note = XENP33973 Chain 1 -
                            MESO-C[MSLN]_H1.16_IgG1_pI(-)_Isosteric
                            _A_PVA_/S267K/L368D/K370S
source                     1..449
                           mol_type = protein
                           organism = synthetic construct
SEQUENCE: 405
QVQLVQSGAE VKKPGASVKV SCKASGYTFT SYWMHWVRQA PGQGLEWMGW IHPQSDNTIY  60
YEKFQGRVTM TVDKSISTAY MELSRLRSDD TAVYYCARII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                   449

SEQ ID NO: 406             moltype = AA  length = 485
FEATURE                    Location/Qualifiers
REGION                     1..485
                           note = Description of Artificial Sequence: Synthetic
                            polypeptide
REGION                     1..485
                           note = XENP33973 Chain 2 -
                            [CD3]_L1.47_H1.32_scFv(GKPGS)4_Fc(216)_
                            IgG1_C220S/PVA_/S267K/S364K/E357Q
source                     1..485
                           mol_type = protein
                           organism = synthetic construct
SEQUENCE: 406
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVLG KPGSGKPGSG  120
KPGSGKPGSE VQLVESGGGL VQPGGSLRLS CAASGFTFST YAMNWVRQAP GKGLEWVGRI  180
RSKANNYATY YADSVKGRFT ISRDDSKNTL YLQMNSLRAE DTAVYYCVRH GNFGDSYVSW  240
```

-continued

```
FAYWGQGTLV TVSSEPKSSD KTHTCPPCPA PPVAGPSVFL FPPKPKDTLM ISRTPEVTCV   300
VVDVKHEDPE VKFNWYVDGV EVHNAKTKPR EEQYNSTYRV VSVLTVLHQD WLNGKEYKCK   360
VSNKALPAPI EKTISKAKGQ PREPQVYTLP PSREQMTKNQ VKLTCLVKGF YPSDIAVEWE   420
SNGQPENNYK TTPPVLDSDG SFFLYSKLTV DKSRWQQGNV FSCSVMHEAL HNHYTQKSLS   480
LSPGK                                                              485

SEQ ID NO: 407           moltype = AA  length = 214
FEATURE                  Location/Qualifiers
REGION                   1..214
                         note = Description of Artificial Sequence: Synthetic
                          polypeptide
REGION                   1..214
                         note = XENP33973 Chain 3 - MESO-C[MSLN]_L1.14 Light Chain
source                   1..214
                         mol_type = protein
                         organism = synthetic construct
SEQUENCE: 407
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YSSFPLTFGA GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 408           moltype = AA  length = 453
FEATURE                  Location/Qualifiers
REGION                   1..453
                         note = Description of Artificial Sequence: Synthetic
                          polypeptide
REGION                   1..453
                         note = XENP16251 Chain 1 -
                          MESO-A[MSLN]_H1.1_L1_Fab_IgG1_pI(-)_Iso
                          steric_A_/PVA_/S267K/L368D/K370S
source                   1..453
                         mol_type = protein
                         organism = synthetic construct
SEQUENCE: 408
EVQLVESGGG LVQPGGSLKL SCAASGFDFS RYWMSWVRQA PGKGLEWVSE INPDSSTIVY   60
TPSVKGRFTI SRDNAKNSLY LQMNSLRAED TAVYYCARRG SHYYGYRTGY FDVWGAGTTV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSDTKVDK KVEPKSCDKT HTCPPCPAPP   240
VAGPSVFLFP PKPKDTLMIS RTPEVTCVVV DVKHEDPEVK FNWYVDGVEV HNAKTKPREE   300
EYNSTYRVVS VLTVLHQDWL NGKEYKCKVS NKALPAPIEK TISKAKGQPR EPQVYTLPPS   360
REEMTKNQVS LTCDVSGFYP SDIAVEWESD GQPENNYKTT PPVLDSDGSF FLYSKLTVDK   420
SRWEQGDVFS CSVMHEALHN HYTQKSLSLS PGK                              453

SEQ ID NO: 409           moltype = AA  length = 485
FEATURE                  Location/Qualifiers
REGION                   1..485
                         note = Description of Artificial Sequence: Synthetic
                          polypeptide
REGION                   1..485
                         note = XENP16251 Chain 2 -
                          [CD3]_H1.33_L1.47_scFv(GKPGS)4_Fc(216)_
                          IgG1_C220S/PVA_/S267K/S364K/E357Q
source                   1..485
                         mol_type = protein
                         organism = synthetic construct
SEQUENCE: 409
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFDYWGQGTL   120
VTVSSGKPGS GKPGSGKPGS GKPGSQAVVT QEPSLTVSPG GTVTLTCGSS TGAVTTSNYA   180
NWVQQKPGKS PRGLIGGTNK RAPGVPARFS GSLLGGKAAL TISGAQPEDE ADYYCALWYS   240
NHWVFGGGTK LTVLEPKSSD KTHTCPPCPA PPVAGPSVFL FPPKPKDTLM ISRTPEVTCV   300
VVDVKHEDPE VKFNWYVDGV EVHNAKTKPR EEQYNSTYRV VSVLTVLHQD WLNGKEYKCK   360
VSNKALPAPI EKTISKAKGQ PREPQVYTLP PSREQMTKNQ VKLTCLVKGF YPSDIAVEWE   420
SNGQPENNYK TTPPVLDSDG SFFLYSKLTV DKSRWQQGNV FSCSVMHEAL HNHYTQKSLS   480
LSPGK                                                              485

SEQ ID NO: 410           moltype = AA  length = 213
FEATURE                  Location/Qualifiers
REGION                   1..213
                         note = Description of Artificial Sequence: Synthetic
                          polypeptide
REGION                   1..213
                         note = XENP16251 Chain 3 - MESO-A[MSLN]_L1 Light Chain
source                   1..213
                         mol_type = protein
                         organism = synthetic construct
SEQUENCE: 410
DVVLTQSPAT LSLSPGERAT LSCRASSSVS YMYWHQQKPD QSPKLLIYDT SNLASGVPVR   60
```

-continued

```
FSGSGSGTDY TLTISSLEPE DFAVYYCQQW SSYPPTFGGG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 411          moltype = AA   length = 452
FEATURE                 Location/Qualifiers
REGION                  1..452
                        note = Description of Artificial Sequence: Synthetic
                        polypeptide
REGION                  1..452
                        note = XENP16834 Chain 1 -
                        MESO-B[MSLN]_H0L0_Fab_IgG1_pI(-)_Isoste
                        ric_A_/PVA_/S267K/L368D/K370S
source                  1..452
                        mol_type = protein
                        organism = synthetic construct
SEQUENCE: 411
QVQLQQSGPG LVTPSQTLSL TCAISGDSVS SNSATWNWIR QSPSRGLEWL GRTYYRSKWY   60
NDYAVSVKSR MSINPDTSKN QFSLQLNSVT PEDTAVYYCA RGMMTYYYGM DVWGQGTTVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSDTKVDKK VEPKSCDKTH TCPPCPAPPV   240
AGPSVFLFPP KPKDTLMISR TPEVTCVVVD VKHEDPEVKF NWYVDGVEVH NAKTKPREEE   300
YNSTYRVVSV LTVLHQDWLN GKEYKCKVSN KALPAPIEKT ISKAKGQPRE PQVYTLPPSR   360
EEMTKNQVSL TCDVSGFYPS DIAVEWESDG QPENNYKTTP PVLDSDGSFF LYSKLTVDKS   420
RWEQGDVFSC SVMHEALHNH YTQKSLSLSP GK                                452

SEQ ID NO: 412          moltype = AA   length = 485
FEATURE                 Location/Qualifiers
REGION                  1..485
                        note = Description of Artificial Sequence: Synthetic
                        polypeptide
REGION                  1..485
                        note = XENP16834 Chain 2 -
                        [CD3]_H1.33_L1.47_scFv(GKPGS)4_Fc(216)_
                        IgG1_C220S/PVA_/S267K/S364K/E357Q
source                  1..485
                        mol_type = protein
                        organism = synthetic construct
SEQUENCE: 412
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFDYWGQGTL   120
VTVSSGKPGS GKPGSGKPGS GKPGSQAVVT QEPSLTVSPG GTVTLTCGSS TGAVTTSNYA   180
NWVQQKPGQS PRGLIGGTNK RAPGVPARFS GSLLGGKAAL TISGAQPEDE ADYYCALWYS   240
NHWVFGGGTK LTVLPKSSD KTHTCPPCPA PPVAGPSVFL FPPKPKDTLM ISRTPEVTCV   300
VVDVKHEDPE VKFNWYVDGV EVHNAKTKPR EEQYNSTYRV VSVLTVLHQD WLNGKEYKCK   360
VSNKALPAPI EKTISKAKGQ PREPQVYTLP PSREQMTKNQ VKLTCLVKGF YPSDIAVEWE   420
SNGQPENNYK TTPPVLDSDG SFFLYSKLTV DKSRWQQGNV FSCSVMHEAL HNHYTQKSLS   480
LSPGK                                                              485

SEQ ID NO: 413          moltype = AA   length = 221
FEATURE                 Location/Qualifiers
REGION                  1..221
                        note = Description of Artificial Sequence: Synthetic
                        polypeptide
REGION                  1..221
                        note = XENP16834 Chain 3 - MESO-B[MSLN]_L0 Light Chain
source                  1..221
                        mol_type = protein
                        organism = synthetic construct
SEQUENCE: 413
QPVLTQSSSL SASPGASASL TCTLRSGINV GPYRIYWYQQ KPGSPPQYLL NYKSDSDKQQ   60
GSGVPSRFSG SKDASANAGV LLISGLRSED EADYYCMIWH SSAAVFGGGT QLTVLGQPKA   120
APSVTLFPPS SEELQANKAT LVCLISDFYP GAVTVAWKAD SSPVKAGVET TTPSKQSNNK   180
YAASSYLSLT PEQWKSHRSY SCQVTHEGST VEKTVAPTEC S                       221

SEQ ID NO: 414          moltype = AA   length = 453
FEATURE                 Location/Qualifiers
REGION                  1..453
                        note = Description of Artificial Sequence: Synthetic
                        polypeptide
REGION                  1..453
                        note = XENP16252 Chain 1 -
                        MESO-A[MSLN]_H1.1_L1_Fab_IgG1_pI(-)_Iso
                        steric_A_/PVA_/S267K/L368D/K370S
source                  1..453
                        mol_type = protein
                        organism = synthetic construct
SEQUENCE: 414
EVQLVESGGG LVQPGGSLKL SCAASGFDFS RYWMSWVRQA PGKGLEWVSE INPDSSTIVY   60
```

```
TPSVKGRFTI SRDNAKNSLY LQMNSLRAED TAVYYCARRG SHYYGYRTGY FDVWGAGTTV    120
TVSSASTKGP SVFPLAPSSK STSGGTAALG CLVKDYFPEP VTVSWNSGAL TSGVHTFPAV    180
LQSSGLYSLS SVVTVPSSSL GTQTYICNVN HKPSDTKVDK KVEPKSCDKT HTCPPCPAPP    240
VAGPSVFLFP PKPKDTLMIS RTPEVTCVVV DVKHEDPEVK FNWYVDGVEV HNAKTKPREE    300
EYNSTYRVVS VLTVLHQDWL NGKEYKCKVS NKALPAPIEK TISKAKGQPR EPQVYTLPPS    360
REEMTKNQVS LTCDVSGFYP SDIAVEWESD GQPENNYKTT PPVLDSDGSF FLYSKLTVDK    420
SRWEQGDVFS CSVMHEALHN HYTQKSLSLS PGK                                 453

SEQ ID NO: 415              moltype = AA  length = 485
FEATURE                     Location/Qualifiers
REGION                      1..485
                            note = Description of Artificial Sequence: Synthetic
                             polypeptide
REGION                      1..485
                            note = XENP16252 Chain 2 -
                             [CD3]_H1.31_L1.47_scFv(GKPGS)4_Fc(216)_
                             IgG1_C220S/PVA_/S267K/S364K/E357Q
source                      1..485
                            mol_type = protein
                            organism = synthetic construct
SEQUENCE: 415
EVQLVESGGG LVQPGGSLRL SCAASGFTFS TYAMSWVRQA PGKGLEWVGR IRSKYNNYAT     60
YYADSVKGRF TISRDDSKNT LYLQMNSLRA EDTAVYYCVR HGNFGDSYVS WFAYWGQGTL    120
VTVSSGKPGS GKPGSGKPGS GKPGSQAVVT QEPSLTVSPG GTVTLTCGSS TGAVTTSNYA    180
NWVQQKPGKS PRGLIGGTNK RAPGVPARFS GSLLGGKAAL TISGAQPEDE ADYYCALWYS    240
NHWVFGGGTK LTVLEPKSSD KTHTCPPCPA PPVAGPSVFL FPPKPKDTLM ISRTPEVTCV    300
VVDVKHEDPE VKFNWYVDGV EVHNAKTKPR EEQYNSTYRV VSVLTVLHQD WLNGKEYKCK    360
VSNKALPAPI EKTISKAKGQ PREPQVYTLP PSREQMTKNQ VKLTCLVKGF YPSDIAVEWE    420
SNGQPENNYK TTPPVLDSDG SFFLYSKLTV DKSRWQQGNV FSCSVMHEAL HNHYTQKSLS    480
LSPGK                                                                485

SEQ ID NO: 416              moltype = AA  length = 213
FEATURE                     Location/Qualifiers
REGION                      1..213
                            note = Description of Artificial Sequence: Synthetic
                             polypeptide
REGION                      1..213
                            note = XENP16252 Chain 3 - MESO-A[MSLN]_L1 Light Chain
source                      1..213
                            mol_type = protein
                            organism = synthetic construct
SEQUENCE: 416
DVVLTQSPAT LSLSPGERAT LSCRASSSVS YMYWHQQKPD QSPKLLIYDT SNLASGVPVR     60
FSGSGSGTDY TLTISSLEPE DFAVYYCQQW SSYPPTFGGG TKLEIKRTVA APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GEC                                 213

SEQ ID NO: 417              moltype = AA  length = 452
FEATURE                     Location/Qualifiers
REGION                      1..452
                            note = Description of Artificial Sequence: Synthetic
                             polypeptide
REGION                      1..452
                            note = XENP16835 Chain 1 -
                             MESO-B[MSLN]_H0L0_Fab_IgG1_pI(-)_Isoste
                             ric_A_/PVA_/S267K/L368D/K370S
source                      1..452
                            mol_type = protein
                            organism = synthetic construct
SEQUENCE: 417
QVQLQQSGPG LVTPSQTLSL TCAISGDSVS SNSATWNWIR QSPSRGLEWL GRTYYRSKWY     60
NDYAVSVKSR MSINPDTSKN QFSLQLNSVT PEDTAVYYCA RGMMTYYYGM DVWGQGTTVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSDTKVDKK VEPKSCDKTH TCPPCPAPPV    240
AGPSVFLFPP KPKDTLMISR TPEVTCVVVD VKHEDPEVKF NWYVDGVEVH NAKTKPREEE    300
YNSTYRVVSV LTVLHQDWLN GKEYKCKVSN KALPAPIEKT ISKAKGQPRE PQVYTLPPSR    360
EEMTKNQVSL TCDVSGFYPS DIAVEWESDG QPENNYKTTP PVLDSDGSFF LYSKLTVDKS    420
RWEQGDVFSC SVMHEALHNH YTQKSLSLSP GK                                  452

SEQ ID NO: 418              moltype = AA  length = 485
FEATURE                     Location/Qualifiers
REGION                      1..485
                            note = Description of Artificial Sequence: Synthetic
                             polypeptide
REGION                      1..485
                            note = XENP16835 Chain 2 -
                             [CD3]_H1.31_L1.47_scFv(GKPGS)4_Fc(216)_
                             IgG1_C220S/PVA_/S267K/S364K/E357Q
source                      1..485
```

```
                              mol_type = protein
                              organism = synthetic construct
SEQUENCE: 418
EVQLVESGGG LVQPGGSLRL SCAASGFTFS TYAMSWVRQA PGKGLEWVGR IRSKYNNYAT   60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PPVAGPSVFL FPPKPKDTLM ISRTPEVTCV  300
VVDVKHEDPE VKFNWYVDGV EVHNAKTKPR EEQYNSTYRV VSVLTVLHQD WLNGKEYKCK  360
VSNKALPAPI EKTISKAKGQ PREPQVYTLP PSREQMTKNQ VKLTCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 419           moltype = AA  length = 221
FEATURE                  Location/Qualifiers
REGION                   1..221
                         note = Description of Artificial Sequence: Synthetic
                          polypeptide
REGION                   1..221
                         note = XENP16835 Chain 3 - MESO-B[MSLN]_L0 Light Chain
source                   1..221
                         mol_type = protein
                         organism = synthetic construct
SEQUENCE: 419
QPVLTQSSSL SASPGASASL TCTLRSGINV GPYRIYWYQQ KPGSPPQYLL NYKSDSDKQQ   60
GSGVPSRFSG SKDASANAGV LLISGLRSED EADYYCMIWH SSAAVFGGGT QLTVLGQPKA  120
APSVTLFPPS SEELQANKAT LVCLISDFYP GAVTVAWKAD SSPVKAGVET TTPSKQSNNK  180
YAASSYLSLT PEQWKSHRSY SCQVTHEGST VEKTVAPTEC S                     221

SEQ ID NO: 420           moltype = AA  length = 453
FEATURE                  Location/Qualifiers
REGION                   1..453
                         note = Description of Artificial Sequence: Synthetic
                          polypeptide
REGION                   1..453
                         note = XENP31063 Chain 1 -
                          MESO-A[MSLN]_H1.1_IgG1_pI(-)_Isosteric_
                          A_/PVA_/S267K/L368D/K370S
source                   1..453
                         mol_type = protein
                         organism = synthetic construct
SEQUENCE: 420
EVQLVESGGG LVQPGGSLKL SCAASGFDFS RYWMSWVRQA PGKGLEWVSE INPDSSTIVY   60
TPSVKGRFTI SRDNAKNSLY LQMNSLRAED TAVYYCARRG SHYYGYRTGY FDVWGAGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSDTKVDK KVEPKSCDKT HTCPPCPAPP  240
VAGPSVFLFP PKPKDTLMIS RTPEVTCVVV DVKHEDPEVK FNWYVDGVEV HNAKTKPREE  300
EYNSTYRVVS VLTVLHQDWL NGKEYKCKVS NKALPAPIEK TISKAKGQPR EPQVYTLPPS  360
REEMTKNQVS LTCDVSGFYP SDIAVEWESD GQPENNYKTT PPVLDSDGSF FLYSKLTVDK  420
SRWEQGDVFS CSVMHEALHN HYTQKSLSLS PGK                             453

SEQ ID NO: 421           moltype = AA  length = 726
FEATURE                  Location/Qualifiers
REGION                   1..726
                         note = Description of Artificial Sequence: Synthetic
                          polypeptide
REGION                   1..726
                         note = XENP31063 Chain 2 -
                          MESO-A[MSLN]_H1.1_[CD3]_H1.30_L1.47_scF
                          v(GKPGS)4_Fc(216)_IgG1_C220S/PVA_/S267K/S364K/E357Q
source                   1..726
                         mol_type = protein
                         organism = synthetic construct
SEQUENCE: 421
EVQLVESGGG LVQPGGSLKL SCAASGFDFS RYWMSWVRQA PGKGLEWVSE INPDSSTIVY   60
TPSVKGRFTI SRDNAKNSLY LQMNSLRAED TAVYYCARRG SHYYGYRTGY FDVWGAGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCGGG GSGGGGSEVQ  240
LVESGGGLVQ PGGSLRLSCA ASGFTFSTYA MNWVRQAPGK GLEWVGRIRS KYNNYATYYA  300
DSVKGRFTIS RDDSKNTLYL QMNSLRAEDT AVYYCVRHGN FGDSYVSWFA YWGQGTLVTV  360
SSGKPGSGKP GSGKPGSGKP GSQAVVTQEP SLTVSPGGTV TLTCGSSTGA VTTSNYANWV  420
QQKPGKSPRG LIGGTNKRAP GVPARFSGSL LGGKAALTIS GAQPEDEADY YCALWYSNHW  480
VFGGGTKLTV LGGGGSGGGG SKTHTCPPCP APPVAGPSVF LFPPKPKDTL MISRTPEVTC  540
VVVDVKHEDP EVKFNWYVDG VEVHNAKTKP REEQYNSTYR VVSVLTVLHQ DWLNGKEYKC  600
KVSNKALPAP IEKTISKAKG QPREPQVYTL PPSREQMTKN QVKLTCLVKG FYPSDIAVEW  660
ESNGQPENNY KTTPPVLDSD GSFFLYSKLT VDKSRWQQGN VFSCSVMHEA LHNHYTQKSL  720
SLSPGK                                                          726

SEQ ID NO: 422           moltype = AA  length = 213
```

-continued

```
FEATURE            Location/Qualifiers
REGION             1..213
                   note = Description of Artificial Sequence: Synthetic
                    polypeptide
REGION             1..213
                   note = XENP31063 Chain 3 - MESO-A[MSLN]_L1 Light Chain
source             1..213
                   mol_type = protein
                   organism = synthetic construct
SEQUENCE: 422
DVVLTQSPAT LSLSPGERAT LSCRASSSVS YMYWHQQKPD QSPKLLIYDT SNLASGVPVR    60
FSGSGSGTDY TLTISSLEPE DFAVYYCQQW SSYPPTFGGG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 423     moltype = AA   length = 452
FEATURE            Location/Qualifiers
REGION             1..452
                   note = Description of Artificial Sequence: Synthetic
                    polypeptide
REGION             1..452
                   note = XENP31067 Chain 1 -
                    MESO-B[MSLN]_H0_IgG1_pI(-)_Isosteric_A_
                    /PVA_/S267K/L368D/K370S
source             1..452
                   mol_type = protein
                   organism = synthetic construct
SEQUENCE: 423
QVQLQQSGPG LVTPSQTLSL TCAISGDSVS SNSATWNWIR QSPSRGLEWL GRTYYRSKWY    60
NDYAVSVKSR MSINPDTSKN QFSLQLNSVT PEDTAVYYCA RGMMTYYYGM DVWGQGTTVT   120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSDTKVDKK VEPKSCDKTH TCPPCPAPPV   240
AGPSVFLFPP KPKDTLMISR TPEVTCVVVD VKHEDPEVKF NWYVDGVEVH NAKTKPREEE   300
YNSTYRVVSV LTVLHQDWLN GKEYKCKVSN KALPAPIEKT ISKAKGQPRE PQVYTLPPSR   360
EEMTKNQVSL TCDVSGFYPS DIAVEWESDG QPENNYKTTP PVLDSDGSFF LYSKLTVDKS   420
RWEQGDVFSC SVMHEALHNH YTQKSLSLSP GK                                 452

SEQ ID NO: 424     moltype = AA   length = 725
FEATURE            Location/Qualifiers
REGION             1..725
                   note = Description of Artificial Sequence: Synthetic
                    polypeptide
REGION             1..725
                   note = XENP31067 Chain 2 -
                    MESO-B[MSLN]_H0_[CD3]_H1.30_L1.47_scFv(
                    GKPGS)4_Fc(216)_IgG1_C220S/PVA_/S267K/S364K/E357Q
source             1..725
                   mol_type = protein
                   organism = synthetic construct
SEQUENCE: 424
QVQLQQSGPG LVTPSQTLSL TCAISGDSVS SNSATWNWIR QSPSRGLEWL GRTYYRSKWY    60
NDYAVSVKSR MSINPDTSKN QFSLQLNSVT PEDTAVYYCA RGMMTYYYGM DVWGQGTTVT   120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCGGGG SGGGGSEVQL   240
VESGGGLVQP GGSLRLSCAA SGFTFSTYAM NWVRQAPGKG LEWVGRIRSK YNNYATYYAD   300
SVKGRFTISR DDSKNTLYLQ MNSLRAEDTA VYYCVRHGNF GDSYVSWFAY WGQGTLVTVS   360
SGKPGSGKPG SGKPGSGKPG SQAVVTQEPS LTVSPGGTVT LTCGSSTGAV TTSNYANWVQ   420
QKPGKSPRGL IGGTNKRAPG VPARFSGSLL GGKAALTISG AQPEDEADYY CALWYSNHWV   480
FGGGTKLTVL GGGSGGGGS KTHTCPPCPA PPVAGPSVFL FPPKPKDTLM ISRTPEVTCV   540
VVDVKHEDPE VKFNWYVDGV EVHNAKTKPR EEQYNSTYRV VSVLTVLHQD WLNGKEYKCK   600
VSNKALPAPI EKTISKAKGQ PREPQVYTLP PSREQMTKNQ VKLTCLVKGF YPSDIAVEWE   660
SNGQPENNYK TTPPVLDSDG SFFLYSKLTV DKSRWQQGNV FSCSVMHEAL HNHYTQKSLS   720
LSPGK                                                              725

SEQ ID NO: 425     moltype = AA   length = 221
FEATURE            Location/Qualifiers
REGION             1..221
                   note = Description of Artificial Sequence: Synthetic
                    polypeptide
REGION             1..221
                   note = XENP31067 Chain 3 - MESO-B[MSLN]_L0 Light Chain
source             1..221
                   mol_type = protein
                   organism = synthetic construct
SEQUENCE: 425
QPVLTQSSSL SASPGASASL TCTLRSGINV GPYRIYWYQQ KPGSPPQYLL NYKSDSDKQQ    60
GSGVPSRFSG SKDASANAGV LLISGLRSED EADYYCMIWH SSAAVFGGGT QLTVLGQPKA   120
APSVTLFPPS SEELQANKAT LVCLISDFYP GAVTVAWKAD SSPVKAGVET TTPSKQSNNK   180
YAASSYLSLT PEQWKSHRSY SCQVTHEGST VEKTVAPTEC S                       221
```

```
SEQ ID NO: 426          moltype = AA   length = 449
FEATURE                 Location/Qualifiers
REGION                  1..449
                        note = Description of Artificial Sequence: Synthetic
                        polypeptide
REGION                  1..449
                        note = XENP31705 Chain 1 -
                        MESO-C[MSLN]_H1_IgG1_pI(-)_Isosteric_A_
                        /PVA_/S267K/L368D/K370S
source                  1..449
                        mol_type = protein
                        organism = synthetic construct
SEQUENCE: 426
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                     449

SEQ ID NO: 427          moltype = AA   length = 722
FEATURE                 Location/Qualifiers
REGION                  1..722
                        note = Description of Artificial Sequence: Synthetic
                        polypeptide
REGION                  1..722
                        note = XENP31705 Chain 2 -
                        MESO-C[MSLN]_H1_[CD3]_H1.30_L1.47_scFv(
                        GKPGS)4_Fc(216)_IgG1_C220S/PVA_/S267K/S364K/E357Q
source                  1..722
                        mol_type = protein
                        organism = synthetic construct
SEQUENCE: 427
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSEVQLVES  240
GGGLVQPGGS LRLSCAASGF TFSTYAMNWV RQAPGKGLEW VGRIRSKYNN YATYYADSVK  300
GRFTISRDDS KNTLYLQMNS LRAEDTAVYY CVRHGNFGDS YVSWFAYWGQ GTLVTVSSGK  360
PGSGKPGSGK PGSGKPGSQA VVTQEPSLTV SPGGTVTLTC GSSTGAVTTS NYANWVQQKP  420
GKSPRGLIGG TNKRAPGVPA RFSGSLLGGK AALTISGAQP EDEADYYCAL WYSNHWVFGG  480
GTKLTVLGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                                 722

SEQ ID NO: 428          moltype = AA   length = 214
FEATURE                 Location/Qualifiers
REGION                  1..214
                        note = Description of Artificial Sequence: Synthetic
                        polypeptide
REGION                  1..214
                        note = XENP31705 Chain 3 - MESO-C[MSLN]_L1 Light Chain
source                  1..214
                        mol_type = protein
                        organism = synthetic construct
SEQUENCE: 428
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 429          moltype = AA   length = 453
FEATURE                 Location/Qualifiers
REGION                  1..453
                        note = Description of Artificial Sequence: Synthetic
                        polypeptide
REGION                  1..453
                        note = XENP31451 Chain 1 -
                        MESO-A[MSLN]_H1.1_IgG1_pI(-)_Isosteric_
                        A_/PVA_/S267K/L368D/K370S
source                  1..453
                        mol_type = protein
                        organism = synthetic construct
SEQUENCE: 429
```

```
EVQLVESGGG LVQPGGSLKL SCAASGFDFS RYWMSWVRQA PGKGLEWVSE INPDSSTIVY   60
TPSVKGRFTI SRDNAKNSLY LQMNSLRAED TAVYYCARRG SHYYGYRTGY FDVWGAGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSDTKVDK KVEPKSCDKT HTCPPCPAPP  240
VAGPSVFLFP PKPKDTLMIS RTPEVTCVVV DVKHEDPEVK FNWYVDGVEV HNAKTKPREE  300
EYNSTYRVVS VLTVLHQDWL NGKEYKCKVS NKALPAPIEK TISKAKGQPR EPQVYTLPPS  360
REEMTKNQVS LTCDVSGFYP SDIAVEWESD GQPENNYKTT PPVLDSDGSF FLYSKLTVDK  420
SRWEQGDVFS CSVMHEALHN HYTQKSLSLS PGK                               453
```

```
SEQ ID NO: 430              moltype = AA   length = 726
FEATURE                     Location/Qualifiers
REGION                      1..726
                            note = Description of Artificial Sequence: Synthetic
                             polypeptide
REGION                      1..726
                            note = XENP31451 Chain 2 -
                             MESO-A[MSLN]_H1.1_(G4S)2_[CD3]_L1.47_H1
                             .30_scFv(GKPGS)4_Fc(216)_IgG1_C220S/PVA_/S267K/S364K/E357Q
source                      1..726
                            mol_type = protein
                            organism = synthetic construct
SEQUENCE: 430
EVQLVESGGG LVQPGGSLKL SCAASGFDFS RYWMSWVRQA PGKGLEWVSE INPDSSTIVY   60
TPSVKGRFTI SRDNAKNSLY LQMNSLRAED TAVYYCARRG SHYYGYRTGY FDVWGAGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCGGG GSGGGGSQAV  240
VTQEPSLTVS PGGTVTLTCG SSTGAVTTSN YANWVQQKPG KSPRGLIGGT NKRAPGVPAR  300
FSGSLLGGKA ALTISGAQPE DEADYYCALW YSNHWVFGGG TKLTVLGKPG SGKPGSGKPG  360
SGKPGSEVQL VESGGGLVQP GGSLRLSCAA SGFTFSTYAM NWVRQAPGKG LEWVGRIRSK  420
YNNYATYYAD SVKGRFTISR DDSKNTLYLQ MNSLRAEDTA VYYCVRHGNF GDSYVSWFAY  480
WGQGTLVTVS SGGGGSGGGG SKTHTCPPCP APPVAGPSVF LFPPKPKDTL MISRTPEVTC  540
VVVDVKHEDP EVKFNWYVDG VEVHNAKTKP REEQYNSTYR VVSVLTVLHQ DWLNGKEYKC  600
KVSNKALPAP IEKTISKAKG QPREPQVYTL PPSREQMTKN QVKLTCLVKG FYPSDIAVEW  660
ESNGQPENNY KTTPPVLDSD GSFFLYSKLT VDKSRWQQGN VFSCSVMHEA LHNHYTQKSL  720
SLSPGK                                                             726
```

```
SEQ ID NO: 431              moltype = AA   length = 213
FEATURE                     Location/Qualifiers
REGION                      1..213
                            note = Description of Artificial Sequence: Synthetic
                             polypeptide
REGION                      1..213
                            note = XENP31451 Chain 3 - MESO-A[MSLN]_L1 Light Chain
source                      1..213
                            mol_type = protein
                            organism = synthetic construct
SEQUENCE: 431
DVVLTQSPAT LSLSPGERAT LSCRASSSVS YMYWHQQKPD QSPKLLIYDT SNLASGVPVR   60
FSGSGSGTDY TLTISSLEPE DFAVYYCQQW SSYPPTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213
```

```
SEQ ID NO: 432              moltype = AA   length = 452
FEATURE                     Location/Qualifiers
REGION                      1..452
                            note = Description of Artificial Sequence: Synthetic
                             polypeptide
REGION                      1..452
                            note = XENP31452 Chain 1 -
                             MESO-B[MSLN]_H0_IgG1_pI(-)_Isosteric_A_
                             /PVA_/S267K/L368D/K370S
source                      1..452
                            mol_type = protein
                            organism = synthetic construct
SEQUENCE: 432
QVQLQQSGPG LVTPSQTLSL TCAISGDSVS SNSATWNWIR QSPSRGLEWL GRTYYRSKWY   60
NDYAVSVKSR MSINPDTSKN QFSLQLNSVT PEDTAVYYCA RGMMTYYYGM DVWGQGTTVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSDTKVDKK VEPKSCDKTH TCPPCPAPPV  240
AGPSVFLFPP KPKDTLMISR TPEVTCVVVD VKHEDPEVKF NWYVDGVEVH NAKTKPREEE  300
YNSTYRVVSV LTVLHQDWLN GKEYKCKVSN KALPAPIEKT ISKAKGQPRE PQVYTLPPSR  360
EEMTKNQVSL TCDVSGFYPS DIAVEWESDG QPENNYKTTP PVLDSDGSFF LYSKLTVDKS  420
RWEQGDVFSC SVMHEALHNH YTQKSLSLSP GK                                452
```

```
SEQ ID NO: 433              moltype = AA   length = 725
FEATURE                     Location/Qualifiers
REGION                      1..725
                            note = Description of Artificial Sequence: Synthetic
                             polypeptide
```

-continued

```
REGION                    1..725
                          note = XENP31452 Chain 2 -
                           MESO-B[MSLN]_H0_(G4S)2_[CD3]_L1.47_H1.3
                           0_scFv(GKPGS)4_Fc(216)_IgG1_C220S/PVA_/S267K/S364K/E357Q
source                    1..725
                          mol_type = protein
                          organism = synthetic construct
SEQUENCE: 433
QVQLQQSGPG LVTPSQTLSL TCAISGDSVS SNSATWNWIR QSPSRGLEWL GRTYYRSKWY   60
NDYAVSVKSR MSINPDTSKN QFSLQLNSVT PEDTAVYYCA RGMMTYYYGM DVWGQGTTVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCGGGG SGGGGSQAVV  240
TQEPSLTVSP GGTVTLTCGS STGAVTTSNY ANWVQQKPGK SPRGLIGGTN KRAPGVPARF  300
SGSLLGGKAA LTISGAQPED EADYYCALWY SNHWVFGGGT KLTVLGKPGS GKPGSGKPGS  360
GKPGSEVQLV ESGGGLVQPG GSLRLSCAAS GFTFSTYAMN WVRQAPGKGL EWVGRIRSKY  420
NNYATYYADS VKGRFTISRD DSKNTLYLQM NSLRAEDTAV YYCVRHGNFG DSYVSWFAYW  480
GQGTLVTVSS GGGGSGGGGS KTHTCPPCPA PPVAGPSVFL FPPKPKDTLM ISRTPEVTCV  540
VVDVKHEDPE VKFNWYVDGV EVHNAKTKPR EEQYNSTYRV VSVLTVLHQD WLNGKEYKCK  600
VSNKALPAPI EKTISKAKGQ PREPQVYTLP PSREQMTKNQ VKLTCLVKGF YPSDIAVEWE  660
SNGQPENNYK TTPPVLDSDG SFFLYSKLTV DKSRWQQGNV FSCSVMHEAL HNHYTQKSLS  720
LSPGK                                                             725

SEQ ID NO: 434            moltype = AA  length = 221
FEATURE                   Location/Qualifiers
REGION                    1..221
                          note = Description of Artificial Sequence: Synthetic
                           polypeptide
REGION                    1..221
                          note = XENP31452 Chain 3 - MESO-B[MSLN]_L0 Light Chain
source                    1..221
                          mol_type = protein
                          organism = synthetic construct
SEQUENCE: 434
QPVLTQSSSL SASPGASASL TCTLRSGINV GPYRIYWYQQ KPGSPPQYLL NYKSDSDKQQ   60
GSGVPSRFSG SKDASANAGV LLISGLRSED EADYYCMIWH SSAAVFGGGT QLTVLGQPKA  120
APSVTLFPPS SEELQANKAT LVCLISDFYP GAVTVAWKAD SSPVKAGVET TTPSKQSNNK  180
YAASSYLSLT PEQWKSHRSY SCQVTHEGST VEKTVAPTEC S                     221

SEQ ID NO: 435            moltype = AA  length = 449
FEATURE                   Location/Qualifiers
REGION                    1..449
                          note = Description of Artificial Sequence: Synthetic
                           polypeptide
REGION                    1..449
                          note = XENP31713 Chain 1 -
                           MESO-C[MSLN]_H1_IgG1_pI(-)_Isosteric_A_
                           /PVA_/S267K/L368D/K370S
source                    1..449
                          mol_type = protein
                          organism = synthetic construct
SEQUENCE: 435
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                   449

SEQ ID NO: 436            moltype = AA  length = 722
FEATURE                   Location/Qualifiers
REGION                    1..722
                          note = Description of Artificial Sequence: Synthetic
                           polypeptide
REGION                    1..722
                          note = XENP31713 Chain 2 -
                           MESO-C[MSLN]_H1_[CD3]_L1.47_H1.30_scFv(
                           GKPGS)4_Fc(216)_IgG1_C220S/PVA_/S267K/S364K/E357Q
source                    1..722
                          mol_type = protein
                          organism = synthetic construct
SEQUENCE: 436
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
```

```
GSEVQLVESG GGLVQPGGSL RLSCAASGFT FSTYAMNWVR QAPGKGLEWV GRIRSKYNNY   420
ATYYADSVKG RFTISRDDSK NTLYLQMNSL RAEDTAVYYC VRHGNFGDSY VSWFAYWGQG   480
TLVTVSSGGG GSGGGGSKTH TCPPCPAPPV AGPSVFLFPP KPKDTLMISR TPEVTCVVVD   540
VKHEDPEVKF NWYVDGVEVH NAKTKPREEQ YNSTYRVVSV LTVLHQDWLN GKEYKCKVSN   600
KALPAPIEKT ISKAKGQPRE PQVYTLPPSR EQMTKNQVKL TCLVKGFYPS DIAVEWESNG   660
QPENNYKTTP PVLDSDGSFF LYSKLTVDKS RWQQGNVFSC SVMHEALHNH YTQKSLSLSP   720
GK                                                                 722

SEQ ID NO: 437          moltype = AA  length = 214
FEATURE                 Location/Qualifiers
REGION                  1..214
                        note = Description of Artificial Sequence: Synthetic
                         polypeptide
REGION                  1..214
                        note = XENP31713 Chain 3 - MESO-C[MSLN]_L1 Light Chain
source                  1..214
                        mol_type = protein
                        organism = synthetic construct
SEQUENCE: 437
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YSSYPLTFGA GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 438          moltype = AA  length = 453
FEATURE                 Location/Qualifiers
REGION                  1..453
                        note = Description of Artificial Sequence: Synthetic
                         polypeptide
REGION                  1..453
                        note = XENP31064 Chain 1 -
                         MESO-A[MSLN]_H1.1_IgG1_pI(-)_Isosteric_
                         A_/PVA_/S267K/L368D/K370S
source                  1..453
                        mol_type = protein
                        organism = synthetic construct
SEQUENCE: 438
EVQLVESGGG LVQPGGSLKL SCAASGFDFS RYWMSWVRQA PGKGLEWVSE INPDSSTIVY   60
TPSVKGRFTI SRDNAKNSLY LQMNSLRAED TAVYYCARRG SHYYGYRTGY FDVWGAGTTV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSDTKVDK KVEPKSCDKT HTCPPCPAPP   240
VAGPSVFLFP PKPKDTLMIS RTPEVTCVVV DVKHEDPEVK FNWYVDGVEV HNAKTKPREE   300
EYNSTYRVVS VLTVLHQDWL NGKEYKCKVS NKALPAPIEK TISKAKGQPR EPQVYTLPPS   360
REEMTKNQVS LTCDVSGFYP SDIAVEWESD GQPENNYKTT PPVLDSDGSF FLYSKLTVDK   420
SRWEQGDVFS CSVMHEALHN HYTQKSLSLS PGK                              453

SEQ ID NO: 439          moltype = AA  length = 726
FEATURE                 Location/Qualifiers
REGION                  1..726
                        note = Description of Artificial Sequence: Synthetic
                         polypeptide
REGION                  1..726
                        note = XENP31064 Chain 2 -
                         MESO-A[MSLN]_H1.1_[CD3]_H1.32_L1.47_scF
                         v(GKPGS)4_Fc(216)_IgG1_C220S/PVA_/S267K/S364K/E357Q
source                  1..726
                        mol_type = protein
                        organism = synthetic construct
SEQUENCE: 439
EVQLVESGGG LVQPGGSLKL SCAASGFDFS RYWMSWVRQA PGKGLEWVSE INPDSSTIVY   60
TPSVKGRFTI SRDNAKNSLY LQMNSLRAED TAVYYCARRG SHYYGYRTGY FDVWGAGTTV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK KVEPKSCGGG GSGGGGSEVQ   240
LVESGGGLVQ PGGSLRLSCA ASGFTFSTYA MNWVRQAPGK GLEWVGRIRS KANNYATYYA   300
DSVKGRFTIS RDDSKNTLYL QMNSLRAEDT AVYYCVRHGN FGDSYVSWFA YWGQGTLVTV   360
SSGKPGSGKP GSGKPGSGKP GSQAVVTQEP SLTVSPGGTV TLTCGSSTGA VTTSNYANWV   420
QQKPGKSPRG LIGGTNKRAP GVPARFSGSL LGGKAALTIS GAQPEDEADY YCALWYSNHW   480
VFGGGTKLTV LGGGGSGGGG SKTHTCPPCP APPVAGPSVF LFPPKPKDTL MISRTPEVTC   540
VVVDVKHEDP EVKFNWYVDG VEVHNAKTKP REEQYNSTYR VVSVLTVLHQ DWLNGKEYKC   600
KVSNKALPAP IEKTISKAKG QPREPQVYTL PPSREQMTKN QVKLTCLVKG FYPSDIAVEW   660
ESNGQPENNY KTTPPVLDSD GSFFLYSKLT VDKSRWQQGN VFSCSVMHEA LHNHYTQKSL   720
SLSPGK                                                             726

SEQ ID NO: 440          moltype = AA  length = 213
FEATURE                 Location/Qualifiers
REGION                  1..213
                        note = Description of Artificial Sequence: Synthetic
                         polypeptide
REGION                  1..213
```

```
                              note = XENP31064 Chain 3 - MESO-A[MSLN]_L1 Light Chain
source                        1..213
                              mol_type = protein
                              organism = synthetic construct
SEQUENCE: 440
DVVLTQSPAT LSLSPGERAT LSCRASSSVS YMYWHQQKPD QSPKLLIYDT SNLASGVPVR   60
FSGSGSGTDY TLTISSLEPE DFAVYYCQQW SSYPPTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 441                moltype = AA  length = 452
FEATURE                       Location/Qualifiers
REGION                        1..452
                              note = Description of Artificial Sequence: Synthetic
                               polypeptide
REGION                        1..452
                              note = XENP31068 Chain 1 -
                               MESO-B[MSLN]_H0_IgG1_pI(-)_Isosteric_A_
                               /PVA_/S267K/L368D/K370S
source                        1..452
                              mol_type = protein
                              organism = synthetic construct
SEQUENCE: 441
QVQLQQSGPG LVTPSQTLSL TCAISGDSVS SNSATWNWIR QSPSRGLEWL GRTYYRSKWY   60
NDYAVSVKSR MSINPDTSKN QFSLQLNSVT PEDTAVYYCA RGMMTYYYGM DVWGQGTTVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSDTKVDKK VEPKSCDKTH TCPPCPAPPV  240
AGPSVFLFPP KPKDTLMISR TPEVTCVVVD VKHEDPEVKF NWYVDGVEVH NAKTKPREEE  300
YNSTYRVVSV LTVLHQDWLN GKEYKCKVSN KALPAPIEKT ISKAKGQPRE PQVYTLPPSR  360
EEMTKNQVSL TCDVSGFYPS DIAVEWESDG QPENNYKTTP PVLDSDGSFF LYSKLTVDKS  420
RWEQGDVFSC SVMHEALHNH YTQKSLSLSP GK                                452

SEQ ID NO: 442                moltype = AA  length = 725
FEATURE                       Location/Qualifiers
REGION                        1..725
                              note = Description of Artificial Sequence: Synthetic
                               polypeptide
REGION                        1..725
                              note = XENP31068 Chain 2 -
                               MESO-B[MSLN]_H0_[CD3]_H1.32_L1.47_scFv(
                               GKPGS)4_Fc(216)_IgG1_C220S/PVA_/S267K/S364K/E357Q
source                        1..725
                              mol_type = protein
                              organism = synthetic construct
SEQUENCE: 442
QVQLQQSGPG LVTPSQTLSL TCAISGDSVS SNSATWNWIR QSPSRGLEWL GRTYYRSKWY   60
NDYAVSVKSR MSINPDTSKN QFSLQLNSVT PEDTAVYYCA RGMMTYYYGM DVWGQGTTVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCGGGG SGGGGSEVQL  240
VESGGGLVQP GGSLRLSCAA SGFTFSTYAM NWVRQAPGKG LEWVGRIRSK ANNYATYYAD  300
SVKGRFTISR DDSKNTLYLQ MNSLRAEDTA VYYCVRHGNF GDSYVSWFAY WGQGTLVTVS  360
SGKPGSGKPG SGKPGSGKPG SQAVVTQEPS LTVSPGGTVT LTCGSSTGAV TTSNYANWVQ  420
QKPGKSPRGL IGGTNKRAPG VPARFSGSLL GGKAALTISG AQPEDEADYY CALWYSNHWV  480
FGGGTKLTVL GGGGSGGGGS KTHTCPPCPA PPVAGPSVFL FPPKPKDTLM ISRTPEVTCV  540
VVDVKHEDPE VKFNWYVDGV EVHNAKTKPR EEQYNSTYRV VSVLTVLHQD WLNGKEYKCK  600
VSNKALPAPI EKTISKAKGQ PREPQVYTLP PSREQMTKNQ VKLTCLVKGF YPSDIAVEWE  660
SNGQPENNYK TTPPVLDSDG SFFLYSKLTV DKSRWQQGNV FSCSVMHEAL HNHYTQKSLS  720
LSPGK                                                             725

SEQ ID NO: 443                moltype = AA  length = 221
FEATURE                       Location/Qualifiers
REGION                        1..221
                              note = Description of Artificial Sequence: Synthetic
                               polypeptide
REGION                        1..221
                              note = XENP31068 Chain 3 - MESO-B[MSLN]_L0 Light Chain
source                        1..221
                              mol_type = protein
                              organism = synthetic construct
SEQUENCE: 443
QPVLTQSSSL SASPGASASL TCTLRSGINV GPYRIYWYQQ KPGSPPQYLL NYKSDSDKQQ   60
GSGVPSRFSG SKDASANAGV LLISGLRSED EADYYCMIWH SSAAVFGGGT QLTVLGQPKA  120
APSVTLFPPS SEELQANKAT LVCLISDFYP GAVTVAWKAD SSPVKAGVET TTPSKQSNNK  180
YAASSYLSLT PEQWKSHRSY SCQVTHEGST VEKTVAPTEC S                     221

SEQ ID NO: 444                moltype = AA  length = 449
FEATURE                       Location/Qualifiers
REGION                        1..449
                              note = Description of Artificial Sequence: Synthetic
```

```
                          polypeptide
REGION                    1..449
                          note = XENP31709 Chain 1 -
                           MESO-C[MSLN]_H1_IgG1_pI(-)_Isosteric_A_
                           /PVA_/S267K/L368D/K370S
source                    1..449
                          mol_type = protein
                          organism = synthetic construct
SEQUENCE: 444
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 445           moltype = AA  length = 722
FEATURE                  Location/Qualifiers
REGION                   1..722
                         note = Description of Artificial Sequence: Synthetic
                          polypeptide
REGION                   1..722
                         note = XENP31709 Chain 2 -
                          MESO-C[MSLN]_H1_[CD3]_H1.32_L1.47_scFv(
                          GKPGS)4_Fc(216)_IgG1_C220S/PVA_/S267K/S364K/E357Q
source                   1..722
                         mol_type = protein
                         organism = synthetic construct
SEQUENCE: 445
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSEVQLVES  240
GGGLVQPGGS LRLSCAASGF TFSTYAMNWV RQAPGKGLEW VGRIRSKANN YATYYADSVK  300
GRFTISRDDS KNTLYLQMNS LRAEDTAVYY CVRHGNFGDS YVSWFAYWGQ GTLVTVSSGK  360
PGSGKPGSGK PGSGKPGSQA VVTQEPSLTV SPGGTVTLTC GSSTGAVTTS NYANWVQQKP  420
GKSPRGLIGG TNKRAPGVPA RFSGSLLGGK AALTISGAQP EDEADYYCAL WYSNHWVFGG  480
GTKLTVLGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                                722

SEQ ID NO: 446           moltype = AA  length = 214
FEATURE                  Location/Qualifiers
REGION                   1..214
                         note = Description of Artificial Sequence: Synthetic
                          polypeptide
REGION                   1..214
                         note = XENP31709 Chain 3 - MESO-C[MSLN]_L1 Light Chain
source                   1..214
                         mol_type = protein
                         organism = synthetic construct
SEQUENCE: 446
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 447           moltype = AA  length = 449
FEATURE                  Location/Qualifiers
REGION                   1..449
                         note = Description of Artificial Sequence: Synthetic
                          polypeptide
REGION                   1..449
                         note = XENP32744 Chain 1 -
                          MESO-C[MSLN]_H1_IgG1_pI(-)_Isosteric_A_
                          /PVA_/S267K/L368D/K370S
source                   1..449
                         mol_type = protein
                         organism = synthetic construct
SEQUENCE: 447
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
```

```
TYRVVSVLTV LHQDWLNGKE YKCKVSNKAL PAPIEKTISK AKGQPREPQV YTLPPSREEM 360
TKNQVSLTCD VSGFYPSDIA VEWESDGQPE NNYKTTPPVL DSDGSFFLYS KLTVDKSRWE 420
QGDVFSCSVM HEALHNHYTQ KSLSLSPGK                                     449

SEQ ID NO: 448           moltype = AA  length = 722
FEATURE                  Location/Qualifiers
REGION                   1..722
                         note = Description of Artificial Sequence: Synthetic
                          polypeptide
REGION                   1..722
                         note = XENP32744 Chain 2 -
                          MESO-C[MSLN]_H1_(G4S)2_[CD3]_H1.32_L1.4
                          7_scFv(GKPGS)4_Fc(216)_IgG1_C220S/PVA_/S267K/S364K/E357Q
source                   1..722
                         mol_type = protein
                         organism = synthetic construct
SEQUENCE: 448
QVQLVQSGAE VKKPGASVKV SCKASGYTFT SYWMHWVRQA PGQGLEWMGM IHPNSDNTIY 60
YEKFQGRVTM TVDKSISTAY MELSRLRSDD TAVYYCAIII TPVVPKFDYW GQGTLVTVSS 120
ASTKGPSVFP LAPSSKSTSG GTAALGCLVK DYFPEPVTVS WNSGALTSGV HTFPAVLQSS 180
GLYSLSSVVT VPSSSLGTQT YICNVNHKPS NTKVDKKVEP KSCGGGGSGG GGSEVQLVES 240
GGGLVQPGGS LRLSCAASGF TFSTYAMNWV RQAPGKGLEW VGRIRSKANN YATYYADSVK 300
GRFTISRDDS KNTLYLQMNS LRAEDTAVYY CVRHGNFGDS YVSWFAYWGQ GTLVTVSSGK 360
PGSGKPGSGK PGSGKPGSQA VVTQEPSLTV SPGGTVTLTC GSSTGAVTTS NYANWVQQKP 420
GKSPRGLIGG TNKRAPGVPA RFSGSLLGGK AALTISGAQP EDEADYYCAL WYSNHWVFGG 480
GTKLTVLGGG GSGGGGSKTH TCPPCPAPPV AGPSVFLFPP KPKDTLMISR TPEVTCVVVD 540
VKHEDPEVKF NWYVDGVEVH NAKTKPREEQ YNSTYRVVSV LTVLHQDWLN GKEYKCKVSN 600
KALPAPIEKT ISKAKGQPRE PQVYTLPPSR EQMTKNQVKL TCLVKGFYPS DIAVEWESNG 660
QPENNYKTTP PVLDSDGSFF LYSKLTVDKS RWQQGNVFSC SVMHEALHNH YTQKSLSLSP 720
GK                                                                722

SEQ ID NO: 449           moltype = AA  length = 214
FEATURE                  Location/Qualifiers
REGION                   1..214
                         note = Description of Artificial Sequence: Synthetic
                          polypeptide
REGION                   1..214
                         note = XENP32744 Chain 3 - MESO-C[MSLN]_L1.3 Light Chain
source                   1..214
                         mol_type = protein
                         organism = synthetic construct
SEQUENCE: 449
DIVMTQSPDS LAVSLGERAT INCKASHSVG TSVAWYQQKP GQSPKLLIYW ASTRHTGVPD 60
RFTGSGSGTD FTLTISSLQA EDVAVYFCQQ YSSYPLTFGA GTKLEIKRTV AAPSVFIFPP 120
SDEQLKSGTA SVVCLLNNFY PREAKVQWKV DNALQSGNSQ ESVTEQDSKD STYSLSSTLT 180
LSKADYEKHK VYACEVTHQG LSSPVTKSFN RGEC                              214

SEQ ID NO: 450           moltype = AA  length = 449
FEATURE                  Location/Qualifiers
REGION                   1..449
                         note = Description of Artificial Sequence: Synthetic
                          polypeptide
REGION                   1..449
                         note = XENP32747 Chain 1 -
                          MESO-C[MSLN]_H1_IgG1_pI(-)_Isosteric_A_
                          /PVA_/S267K/L368D/K370S
source                   1..449
                         mol_type = protein
                         organism = synthetic construct
SEQUENCE: 450
QVQLVQSGAE VKKPGASVKV SCKASGYTFT SYWMHWVRQA PGQGLEWMGM IHPNSDNTIY 60
YEKFQGRVTM TVDKSISTAY MELSRLRSDD TAVYYCAIII TPVVPKFDYW GQGTLVTVSS 120
ASTKGPSVFP LAPSSKSTSG GTAALGCLVK DYFPEPVTVS WNSGALTSGV HTFPAVLQSS 180
GLYSLSSVVT VPSSSLGTQT YICNVNHKPS DTKVDKKVEP KSCDKTHTCP PCPAPPVAGP 240
SVFLFPPKPK DTLMISRTPE VTCVVVDVKH EDPEVKFNWY VDGVEVHNAK TKPREEEYNS 300
TYRVVSVLTV LHQDWLNGKE YKCKVSNKAL PAPIEKTISK AKGQPREPQV YTLPPSREEM 360
TKNQVSLTCD VSGFYPSDIA VEWESDGQPE NNYKTTPPVL DSDGSFFLYS KLTVDKSRWE 420
QGDVFSCSVM HEALHNHYTQ KSLSLSPGK                                    449

SEQ ID NO: 451           moltype = AA  length = 722
FEATURE                  Location/Qualifiers
REGION                   1..722
                         note = Description of Artificial Sequence: Synthetic
                          polypeptide
REGION                   1..722
                         note = XENP32747 Chain 2 -
                          MESO-C[MSLN]_H1_(G4S)2_[CD3]_H1.32_L1.4
                          7_scFv(GKPGS)4_Fc(216)_IgG1_C220S/PVA_/S267K/S364K/E357Q
source                   1..722
```

```
                        mol_type = protein
                        organism = synthetic construct
SEQUENCE: 451
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSEVQLVES  240
GGGLVQPGGS LRLSCAASGF TFSTYAMNWV RQAPGKGLEW VGRIRSKANN YATYYADSVK  300
GRFTISRDDS KNTLYLQMNS LRAEDTAVYY CVRHGNFGDS YVSWFAYWGQ GTLVTVSSGK  360
PGSGKPGSGK PGSGKPGSQA VVTQEPSLTV SPGGTVTLTC GSSTGAVTTS NYANWVQQKP  420
GKSPRGLIGG TNKRAPGVPA RFSGSLLGGK AALTISGAQP EDEADYYCAL WYSNHWVFGG  480
GTKLTVLGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                                722

SEQ ID NO: 452         moltype = AA  length = 214
FEATURE                Location/Qualifiers
REGION                 1..214
                       note = Description of Artificial Sequence: Synthetic
                        polypeptide
REGION                 1..214
                       note = XENP32747 Chain 3 - MESO-C[MSLN]_L1.4 Light Chain
source                 1..214
                       mol_type = protein
                       organism = synthetic construct
SEQUENCE: 452
DIVMTQSPDS LAVSLGERAT INCKASHDVL TSVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 453         moltype = AA  length = 449
FEATURE                Location/Qualifiers
REGION                 1..449
                       note = Description of Artificial Sequence: Synthetic
                        polypeptide
REGION                 1..449
                       note = XENP32750 Chain 1 -
                        MESO-C[MSLN]_H1_IgG1_pI(-)_Isosteric_A_
                        /PVA_/S267K/L368D/K370S
source                 1..449
                       mol_type = protein
                       organism = synthetic construct
SEQUENCE: 453
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                   449

SEQ ID NO: 454         moltype = AA  length = 722
FEATURE                Location/Qualifiers
REGION                 1..722
                       note = Description of Artificial Sequence: Synthetic
                        polypeptide
REGION                 1..722
                       note = XENP32750 Chain 2 -
                        MESO-C[MSLN]_H1_(G4S)2_[CD3]_H1.32_L1.4
                        7_scFv(GKPGS)4_Fc(216)_IgG1_C220S/PVA_/S267K/S364K/E357Q
source                 1..722
                       mol_type = protein
                       organism = synthetic construct
SEQUENCE: 454
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSEVQLVES  240
GGGLVQPGGS LRLSCAASGF TFSTYAMNWV RQAPGKGLEW VGRIRSKANN YATYYADSVK  300
GRFTISRDDS KNTLYLQMNS LRAEDTAVYY CVRHGNFGDS YVSWFAYWGQ GTLVTVSSGK  360
PGSGKPGSGK PGSGKPGSQA VVTQEPSLTV SPGGTVTLTC GSSTGAVTTS NYANWVQQKP  420
GKSPRGLIGG TNKRAPGVPA RFSGSLLGGK AALTISGAQP EDEADYYCAL WYSNHWVFGG  480
GTKLTVLGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
```

```
QPENNYKTTP PVLDSDGSFF LYSKLTVDKS RWQQGNVFSC SVMHEALHNH YTQKSLSLSP   720
GK                                                                 722

SEQ ID NO: 455          moltype = AA  length = 214
FEATURE                 Location/Qualifiers
REGION                  1..214
                        note = Description of Artificial Sequence: Synthetic
                         polypeptide
REGION                  1..214
                        note = XENP32750 Chain 3 - MESO-C[MSLN]_L1.5 Light Chain
source                  1..214
                        mol_type = protein
                        organism = synthetic construct
SEQUENCE: 455
DIVMTQSPDS LAVSLGERAT INCKASHDVG TYVAWYQQKP GQSPKLLIYW ASTRHTGVPD   60
RFTGSGSGTD FTLTISSLQA EDVAVYFCQQ YSSYPLTFGA GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 456          moltype = AA  length = 449
FEATURE                 Location/Qualifiers
REGION                  1..449
                        note = Description of Artificial Sequence: Synthetic
                         polypeptide
REGION                  1..449
                        note = XENP32851 Chain 1 -
                         MESO-C[MSLN]_H1_IgG1_pI(-)_Isosteric_A_
                         /PVA_/S267K/L368D/K370S
source                  1..449
                        mol_type = protein
                        organism = synthetic construct
SEQUENCE: 456
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                    449

SEQ ID NO: 457          moltype = AA  length = 722
FEATURE                 Location/Qualifiers
REGION                  1..722
                        note = Description of Artificial Sequence: Synthetic
                         polypeptide
REGION                  1..722
                        note = XENP32851 Chain 2 -
                         MESO-C[MSLN]_H1_(G4S)2_[CD3]_H1.32_L1.4
                         7_scFv(GKPGS)4_Fc(216)_IgG1_C220S/PVA_/S267K/S364K/E357Q
source                  1..722
                        mol_type = protein
                        organism = synthetic construct
SEQUENCE: 457
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCGGGGSGG GGSEVQLVES   240
GGGLVQPGGS LRLSCAASGF TFSTYAMNWV RQAPGKGLEW VGRIRSKANN YATYYADSVK   300
GRFTISRDDS KNTLYLQMNS LRAEDTAVYY CVRHGNFGDS YVSWFAYWGQ GTLVTVSSGK   360
PGSGKPGSGK PGSGKPGSQA VVTQEPSLTV SPGGTVTLTC GSSTGAVTTS NYANWVQQKP   420
GKSPRGLIGG TNKRAPGVPA RFSGSLLGGK AALTISGAQP EDEADYYCAL WYSNHWVFGG   480
GTKLTVLGGG GSGGGGSKTH TCPPCPAPPV AGPSVFLFPP KPKDTLMISR TPEVTCVVVD   540
VKHEDPEVKF NWYVDGVEVH NAKTKPREEQ YNSTYRVVSV LTVLHQDWLN GKEYKCKVSN   600
KALPAPIEKT ISKAKGQPRE PQVYTLPPSR EQMTKNQVKL TCLVKGFYPS DIAVEWESNG   660
QPENNYKTTP PVLDSDGSFF LYSKLTVDKS RWQQGNVFSC SVMHEALHNH YTQKSLSLSP   720
GK                                                                 722

SEQ ID NO: 458          moltype = AA  length = 214
FEATURE                 Location/Qualifiers
REGION                  1..214
                        note = Description of Artificial Sequence: Synthetic
                         polypeptide
REGION                  1..214
                        note = XENP32851 Chain 3 - MESO-C[MSLN]_L1.9 Light Chain
source                  1..214
                        mol_type = protein
                        organism = synthetic construct
SEQUENCE: 458
```

```
DIVMTQSPDS LAVSLGERAT INCKASHDVG TSVAWYQQKP GQSPKLLIYW ASTRHTGVPD    60
RFTGSGSGTD FTLTISSLQA EDVAVYFCQQ YYSYPLTFGA GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 459            moltype = AA  length = 453
FEATURE                   Location/Qualifiers
REGION                    1..453
                          note = Description of Artificial Sequence: Synthetic
                           polypeptide
REGION                    1..453
                          note = XENP31453 Chain 1 -
                           MESO-A[MSLN]_H1.1_IgG1_pI(-)_Isosteric_
                           A_/PVA_/S267K/L368D/K370S
source                    1..453
                          mol_type = protein
                          organism = synthetic construct
SEQUENCE: 459
EVQLVESGGG LVQPGGSLKL SCAASGFDFS RYWMSWVRQA PGKGLEWVSE INPDSSTIVY    60
TPSVKGRFTI SRDNAKNSLY LQMNSLRAED TAVYYCARRG SHYYGYRTGY FDVWGAGTTV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSDTKVDK KVEPPKSCDKT HTCPPCPAPP  240
VAGPSVFLFP PKPKDTLMIS RTPEVTCVVV DVKHEDPEVK FNWYVDGVEV HNAKTKPREE   300
EYNSTYRVVS VLTVLHQDWL NGKEYKCKVS NKALPAPIEK TISKAKGQPR EPQVYTLPPS   360
REEMTKNQVS LTCDVSGFYP SDIAVEWESD GQPENNYKTT PPVLDSDGSF FLYSKLTVDK   420
SRWEQGDVFS CSVMHEALHN HYTQKSLSLS PGK                                453

SEQ ID NO: 460            moltype = AA  length = 726
FEATURE                   Location/Qualifiers
REGION                    1..726
                          note = Description of Artificial Sequence: Synthetic
                           polypeptide
REGION                    1..726
                          note = XENP31453 Chain 2 -
                           MESO-A[MSLN]_H1.1_(G4S)2_[CD3]_L1.47_H1
                           .32_scFv(GKPGS)4_Fc(216)_IgG1_C220S/PVA_/S267K/S364K/E357Q
source                    1..726
                          mol_type = protein
                          organism = synthetic construct
SEQUENCE: 460
EVQLVESGGG LVQPGGSLKL SCAASGFDFS RYWMSWVRQA PGKGLEWVSE INPDSSTIVY    60
TPSVKGRFTI SRDNAKNSLY LQMNSLRAED TAVYYCARRG SHYYGYRTGY FDVWGAGTTV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK KVEPKSCGGG GSGGGGSQAV   240
VTQEPSLTVS PGGTVTLTCG SSTGAVTTSN YANWVQQKPG KSPRGLIGGT NKRAPGVPAR   300
FSGSLLGGKA ALTISGAQPE DEADYYCALW YSNHWVFGGG TKLTVLGKPG SGKPGSGKPG   360
SGKPGSEVQL VESGGGLVQP GGSLRLSCAA SGFTFSTYAM NWVRQAPGKG LEWVGRIRSK   420
ANNYATYYAD SVKGRFTISR DDSKNTLYLQ MNSLRAEDTA VYYCVRHGNF GDSYVSWFAY   480
WGQGTLVTVS SGGGGSGGGG SKTHTCPPCP APPVAGPSVF LFPPKPKDTL MISRTPEVTC   540
VVVDVKHEDP EVKFNWYVDG VEVHNAKTKP REEQYNSTYR VVSVLTVLHQ DWLNGKEYKC   600
KVSNKALPAP IEKTISKAKG QPREPQVYTL PPSREQMTKN QVKLTCLVKG FYPSDIAVEW   660
ESNGQPENNY KTTPPVLDSD GSFFLYSKLT VDKSRWQQGN VFSCSVMHEA LHNHYTQKSL   720
SLSPGK                                                             726

SEQ ID NO: 461            moltype = AA  length = 213
FEATURE                   Location/Qualifiers
REGION                    1..213
                          note = Description of Artificial Sequence: Synthetic
                           polypeptide
REGION                    1..213
                          note = XENP31453 Chain 3 - MESO-A[MSLN]_L1 Light Chain
source                    1..213
                          mol_type = protein
                          organism = synthetic construct
SEQUENCE: 461
DVVLTQSPAT LSLSPGERAT LSCRASSSVS YMYWHQQKPD QSPKLLIYDT SNLASGVPVR    60
FSGSGSGTDY TLTISSLEPE DFAVYYCQQW SSYPPTFGGG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 462            moltype = AA  length = 452
FEATURE                   Location/Qualifiers
REGION                    1..452
                          note = Description of Artificial Sequence: Synthetic
                           polypeptide
REGION                    1..452
                          note = XENP31454 Chain 1 -
                           MESO-B[MSLN]_H0_IgG1_pI(-)_Isosteric_A_
                           /PVA_/S267K/L368D/K370S
```

-continued

```
source                    1..452
                          mol_type = protein
                          organism = synthetic construct
SEQUENCE: 462
QVQLQQSGPG LVTPSQTLSL TCAISGDSVS SNSATWNWIR QSPSRGLEWL GRTYYRSKWY   60
NDYAVSVKSR MSINPDTSKN QFSLQLNSVT PEDTAVYYCA RGMMTYYYGM DVWGQGTTVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSDTKVDKK VEPKSCDKTH TCPPCPAPPV  240
AGPSVFLFPP KPKDTLMISR TPEVTCVVVD VKHEDPEVKF NWYVDGVEVH NAKTKPREEE  300
YNSTYRVVSV LTVLHQDWLN GKEYKCKVSN KALPAPIEKT ISKAKGQPRE PQVYTLPPSR  360
EEMTKNQVSL TCDVSGFYPS DIAVEWESDG QPENNYKTTP PVLDSDGSFF LYSKLTVDKS  420
RWEQGDVFSC SVMHEALHNH YTQKSLSLSP GK                                452

SEQ ID NO: 463           moltype = AA  length = 725
FEATURE                  Location/Qualifiers
REGION                   1..725
                         note = Description of Artificial Sequence: Synthetic
                          polypeptide
REGION                   1..725
                         note = XENP31454 Chain 2 -
                          MESO-B[MSLN]_H0_(G4S)2_[CD3]_L1.47_H1.3
                          2_scFv(GKPGS)4_Fc(216)_IgG1_C220S/PVA_/S267K/S364K/E357Q
source                   1..725
                         mol_type = protein
                         organism = synthetic construct
SEQUENCE: 463
QVQLQQSGPG LVTPSQTLSL TCAISGDSVS SNSATWNWIR QSPSRGLEWL GRTYYRSKWY   60
NDYAVSVKSR MSINPDTSKN QFSLQLNSVT PEDTAVYYCA RGMMTYYYGM DVWGQGTTVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCGGGG SGGGGSQAVV  240
TQEPSLTVSP GGTVTLTCGS STGAVTTSNY ANWVQQKPGK SPRGLIGGTN KRAPGVPARF  300
SGSLLGGKAA LTISGAQPED EADYYCALWY SNHWVFGGGT KLTVLGKPGS GKPGSGKPGS  360
GKPGSEVQLV ESGGGLVQPG GSLRLSCAAS GFTFSTYAMN WVRQAPGKGL EWVGRIRSKA  420
NNYATYYADS VKGRFTISRD DSKNTLYLQM NSLRAEDTAV YCVRHGNFG DSYVSWFAYW  480
GQGTLVTVSS GGGGSGGGGS KTHTCPPCPA PPVAGPSVFL FPPKPKDTLM ISRTPEVTCV  540
VVDVKHEDPE VKFNWYVDGV EVHNAKTKPR EEQYNSTYRV VSVLTVLHQD WLNGKEYKCK  600
VSNKALPAPI EKTISKAKGQ PREPQVYTLP PSREQMTKNQ VKLTCLVKGF YPSDIAVEWE  660
SNGQPENNYK TTPPVLDSDG SFFLYSKLTV DKSRWQQGNV FSCSVMHEAL HNHYTQKSLS  720
LSPGK                                                             725

SEQ ID NO: 464           moltype = AA  length = 221
FEATURE                  Location/Qualifiers
REGION                   1..221
                         note = Description of Artificial Sequence: Synthetic
                          polypeptide
REGION                   1..221
                         note = XENP31454 Chain 3 - MESO-B[MSLN]_L0 Light Chain
source                   1..221
                         mol_type = protein
                         organism = synthetic construct
SEQUENCE: 464
QPVLTQSSSL SASPGASASL TCTLRSGINV GPYRIYWYQQ KPGSPPQYLL NYKSDSDKQQ   60
GSGVPSRFSG SKDASANAGV LLISGLRSED EADYYCMIWH SSAAVFGGGT QLTVLGQPKA  120
APSVTLFPPS SEELQANKAT LVCLISDFYP GAVTVAWKAD SSPVKAGVET TTPSKQSNNK  180
YAASSYLSLT PEQWKSHRSY SCQVTHEGST VEKTVAPTEC S                     221

SEQ ID NO: 465           moltype = AA  length = 449
FEATURE                  Location/Qualifiers
REGION                   1..449
                         note = Description of Artificial Sequence: Synthetic
                          polypeptide
REGION                   1..449
                         note = XENP31717 Chain 1 -
                          MESO-C[MSLN]_H1_IgG1_pI(-)_Isosteric_A_
                          /PVA_/S267K/L368D/K370S
source                   1..449
                         mol_type = protein
                         organism = synthetic construct
SEQUENCE: 465
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 466           moltype = AA  length = 722
```

```
FEATURE           Location/Qualifiers
REGION            1..722
                  note = Description of Artificial Sequence: Synthetic
                   polypeptide
REGION            1..722
                  note = XENP31717 Chain 2 -
                   MESO-C[MSLN]_H1_[CD3]_L1.47_H1.32_scFv(
                   GKPGS)4_Fc(216)_IgG1_C220S/PVA_/S267K/S364K/E357Q
source            1..722
                  mol_type = protein
                  organism = synthetic construct
SEQUENCE: 466
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS 120
ASTKGPSVFP LAPSSKSTSG GTAALGCLVK DYFPEPVTVS WNSGALTSGV HTFPAVLQSS 180
GLYSLSSVVT VPSSSLGTQT YICNVNHKPS NTKVDKKVEP KSCGGGGSGG GGSQAVVTQE 240
PSLTVSPGGT VTLTCGSSTG AVTTSNYANW VQQKPGKSPR GLIGGTNKRA PGVPARFSGS 300
LLGGKAALTI SGAQPEDEAD YYCALWYSNH WVFGGGTKLT VLGKPGSGKP GSGKPGSGKP 360
GSEVQLVESG GGLVQPGGSL RLSCAASGFT FSTYAMNWVR QAPGKGLEWV GRIRSKANNY 420
ATYYADSVKG RFTISRDDSK NTLYLQMNSL RAEDTAVYYC VRHGNFGDSY VSWFAYWGQG 480
TLVTVSSGGG GSGGGGSKTH TCPPCPAPPV AGPSVFLFPP KPKDTLMISR TPEVTCVVVD 540
VKHEDPEVKF NWYVDGVEVH NAKTKPREEQ YNSTYRVVSV LTVLHQDWLN GKEYKCKVSN 600
KALPAPIEKT ISKAKGQPRE PQVYTLPPSR EQMTKNQVKL TCLVKGFYPS DIAVEWESNG 660
QPENNYKTTP PVLDSDGSFF LYSKLTVDKS RWQQGNVFSC SVMHEALHNH YTQKSLSLSP 720
GK                                                                722

SEQ ID NO: 467      moltype = AA   length = 214
FEATURE             Location/Qualifiers
REGION              1..214
                    note = Description of Artificial Sequence: Synthetic
                     polypeptide
REGION              1..214
                    note = XENP31717 Chain 3 - MESO-C[MSLN]_L1 Light Chain
source              1..214
                    mol_type = protein
                    organism = synthetic construct
SEQUENCE: 467
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP 120
SDEQLKSGTA SVVCLLNNFY PREAKVQWKV DNALQSGNSQ ESVTEQDSKD STYSLSSTLT 180
LSKADYEKHK VYACEVTHQG LSSPVTKSFN RGEC                              214

SEQ ID NO: 468      moltype = AA   length = 449
FEATURE             Location/Qualifiers
REGION              1..449
                    note = Description of Artificial Sequence: Synthetic
                     polypeptide
REGION              1..449
                    note = XENP32745 Chain 1 -
                     MESO-C[MSLN]_H1_IgG1_pI(-)_Isosteric_A_
                     /PVA_/S267K/L368D/K370S
source              1..449
                    mol_type = protein
                    organism = synthetic construct
SEQUENCE: 468
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS 120
ASTKGPSVFP LAPSSKSTSG GTAALGCLVK DYFPEPVTVS WNSGALTSGV HTFPAVLQSS 180
GLYSLSSVVT VPSSSLGTQT YICNVNHKPS DTKVDKKVEP KSCDKTHTCP PCPAPPVAGP 240
SVFLFPPKPK DTLMISRTPE VTCVVVDVKH EDPEVKFNWY VDGVEVHNAK TKPREEYNS 300
TYRVVSVLTV LHQDWLNGKE YKCKVSNKAL PAPIEKTISK AKGQPREPQV YTLPPSREEM 360
TKNQVSLTCD VSGFYPSDIA VEWESDGQPE NNYKTTPPVL DSDGSFFLYS KLTVDKSRWE 420
QGDVFSCSVM HEALHNHYTQ KSLSLSPGK                                    449

SEQ ID NO: 469      moltype = AA   length = 722
FEATURE             Location/Qualifiers
REGION              1..722
                    note = Description of Artificial Sequence: Synthetic
                     polypeptide
REGION              1..722
                    note = XENP32745 Chain 2 -
                     MESO-C[MSLN]_H1_(G4S)2_[CD3]_L1.47_H1.3
                     2_scFv(GKPGS)4_Fc(216)_IgG1_C220S/PVA_/S267K/S364K/E357Q
source              1..722
                    mol_type = protein
                    organism = synthetic construct
SEQUENCE: 469
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS 120
```

-continued

```
ASTKGPSVFP LAPSSKSTSG GTAALGCLVK DYFPPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKANNY  420
ATYYADSVKG RFTISRDDSK NTLYLQMNSL RAEDTAVYYC VRHGNFGDSY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                                          722
```

```
SEQ ID NO: 470          moltype = AA  length = 214
FEATURE                 Location/Qualifiers
REGION                  1..214
                        note = Description of Artificial Sequence: Synthetic
                         polypeptide
REGION                  1..214
                        note = XENP32745 Chain 3 - MESO-C[MSLN]_L1.3 Light Chain
source                  1..214
                        mol_type = protein
                        organism = synthetic construct
SEQUENCE: 470
DIVMTQSPDS LAVSLGERAT INCKASHSVG TSVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214
```

```
SEQ ID NO: 471          moltype = AA  length = 449
FEATURE                 Location/Qualifiers
REGION                  1..449
                        note = Description of Artificial Sequence: Synthetic
                         polypeptide
REGION                  1..449
                        note = XENP32748 Chain 1 -
                         MESO-C[MSLN]_H1_IgG1_pI(-)_Isosteric_A_
                         /PVA_/S267K/L368D/K370S
source                  1..449
                        mol_type = protein
                        organism = synthetic construct
SEQUENCE: 471
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                     449
```

```
SEQ ID NO: 472          moltype = AA  length = 722
FEATURE                 Location/Qualifiers
REGION                  1..722
                        note = Description of Artificial Sequence: Synthetic
                         polypeptide
REGION                  1..722
                        note = XENP32748 Chain 2 -
                         MESO-C[MSLN]_H1_(G4S)2_[CD3]_L1.47_H1.3
                         2_scFv(GKPGS)4_Fc(216)_IgG1_C220S/PVA_/S267K/S364K/E357Q
source                  1..722
                        mol_type = protein
                        organism = synthetic construct
SEQUENCE: 472
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKANNY  420
ATYYADSVKG RFTISRDDSK NTLYLQMNSL RAEDTAVYYC VRHGNFGDSY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                                          722
```

```
SEQ ID NO: 473          moltype = AA  length = 214
FEATURE                 Location/Qualifiers
```

-continued

```
REGION                    1..214
                          note = Description of Artificial Sequence: Synthetic
                           polypeptide
REGION                    1..214
                          note = XENP32748 Chain 3 - MESO-C[MSLN]_L1.4 Light Chain
source                    1..214
                          mol_type = protein
                          organism = synthetic construct
SEQUENCE: 473
DIVMTQSPDS LAVSLGERAT INCKASHDVL TSVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 474            moltype = AA   length = 449
FEATURE                   Location/Qualifiers
REGION                    1..449
                          note = Description of Artificial Sequence: Synthetic
                           polypeptide
REGION                    1..449
                          note = XENP32751 Chain 1 -
                           MESO-C[MSLN]_H1_IgG1_pI(-)_Isosteric_A_
                           /PVA_/S267K/L368D/K370S
source                    1..449
                          mol_type = protein
                          organism = synthetic construct
SEQUENCE: 474
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                   449

SEQ ID NO: 475            moltype = AA   length = 722
FEATURE                   Location/Qualifiers
REGION                    1..722
                          note = Description of Artificial Sequence: Synthetic
                           polypeptide
REGION                    1..722
                          note = XENP32751 Chain 2 -
                           MESO-C[MSLN]_H1_(G4S)2_[CD3]_L1.47_H1.3
                           2_scFv(GKPGS)4_Fc(216)_IgG1_C220S/PVA_/S267K/S364K/E357Q
source                    1..722
                          mol_type = protein
                          organism = synthetic construct
SEQUENCE: 475
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKANNY  420
ATYYADSVKG RFTISRDDSK NTLYLQMNSL RAEDTAVYYC VRHGNFGDSY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                              722

SEQ ID NO: 476            moltype = AA   length = 213
FEATURE                   Location/Qualifiers
REGION                    1..213
                          note = Description of Artificial Sequence: Synthetic
                           polypeptide
REGION                    1..213
                          note = XENP32751 Chain 3 - MESO-C[MSLN]_L1.5 Light Chain
source                    1..213
                          mol_type = protein
                          organism = synthetic construct
SEQUENCE: 476
DIVMTQSPDS LAVSLGERAT INCKASHDVG TYVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGE                             213
```

```
SEQ ID NO: 477         moltype = AA   length = 449
FEATURE                Location/Qualifiers
REGION                 1..449
                       note = Description of Artificial Sequence: Synthetic
                       polypeptide
REGION                 1..449
                       note = XENP32852 Chain 1 -
                       MESO-C[MSLN]_H1_IgG1_pI(-)_Isosteric_A_
                       /PVA_/S267K/L368D/K370S
source                 1..449
                       mol_type = protein
                       organism = synthetic construct
SEQUENCE: 477
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 478         moltype = AA   length = 722
FEATURE                Location/Qualifiers
REGION                 1..722
                       note = Description of Artificial Sequence: Synthetic
                       polypeptide
REGION                 1..722
                       note = XENP32852 Chain 2 -
                       MESO-C[MSLN]_H1_(G4S)2_[CD3]_L1.47_H1.3
                       2_scFv(GKPGS)4_Fc(216)_IgG1_C220S/PVA_/S267K/S364K/E357Q
source                 1..722
                       mol_type = protein
                       organism = synthetic construct
SEQUENCE: 478
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKANNY  420
ATYYADSVKG RFTISRDDSK NTLYLQMNSL RAEDTAVYYC VRHGNFGDSY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                                722

SEQ ID NO: 479         moltype = AA   length = 214
FEATURE                Location/Qualifiers
REGION                 1..214
                       note = Description of Artificial Sequence: Synthetic
                       polypeptide
REGION                 1..214
                       note = XENP32852 Chain 3 - MESO-C[MSLN]_L1.9 Light Chain
source                 1..214
                       mol_type = protein
                       organism = synthetic construct
SEQUENCE: 479
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YYSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 480         moltype = AA   length = 449
FEATURE                Location/Qualifiers
REGION                 1..449
                       note = Description of Artificial Sequence: Synthetic
                       polypeptide
REGION                 1..449
                       note = XENP32947 Chain 1 -
                       MESO-C[MSLN]_H1.3_IgG1_pI(-)_Isosteric_
                       A_/PVA_/S267K/L368D/K370S
source                 1..449
                       mol_type = protein
                       organism = synthetic construct
SEQUENCE: 480
QVQLVQSGAE VKKPGASVKV SCKASGYTFT SYWMHWVRQA PGQGLEWMGW IHPNSDNTIY   60
```

```
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                     449

SEQ ID NO: 481          moltype = AA  length = 722
FEATURE                 Location/Qualifiers
REGION                  1..722
                        note = Description of Artificial Sequence: Synthetic
                         polypeptide
REGION                  1..722
                        note = XENP32947 Chain 2 -
                         MESO-C[MSLN]_H1.3_(G4S)2_[CD3]_L1.47_H1
                         .32_scFv(GKPGS)4_Fc(216)_IgG1_C220S/PVA_/S267K/S364K/E357Q
source                  1..722
                        mol_type = protein
                        organism = synthetic construct
SEQUENCE: 481
QVQLVQSGAE VKKPGASVKV SCKASGYTFT SYWMHWVRQA PGQGLEWMGW IHPNSDNTIY   60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCGGGGSGG GGSQAVVTQE   240
PSLTVSPGGT VTLTCGSSTG AVTTSNYANW VQQKPGKSPR GLIGGTNKRA PGVPARFSGS   300
LLGGKAALTI SGAQPEDEAD YYCALWYSNH WVFGGGTKLT VLGKPGSGKP GSGKPGSGKP   360
GSEVQLVESG GGLVQPGGSL RLSCAASGFT FSTYAMNWVR QAPGKGLEWV GRIRSKANNY   420
ATYYADSVKG RFTISRDDSK NTLYLQMNSL RAEDTAVYYC VRHGNFGDSY VSWFAYWGQG   480
TLVTVSSGGG GSGGGGSKTH TCPPCPAPPV AGPSVFLFPP KPKDTLMISR TPEVTCVVVD   540
VKHEDPEVKF NWYVDGVEVH NAKTKPREEQ YNSTYRVVSV LTVLHQDWLN GKEYKCKVSN   600
KALPAPIEKT ISKAKGQPRE PQVYTLPPSR EQMTKNQVKL TCLVKGFYPS DIAVEWESNG   660
QPENNYKTTP PVLDSDGSFF LYSKLTVDKS RWQQGNVFSC SVMHEALHNH YTQKSLSLSP   720
GK                                                                 722

SEQ ID NO: 482          moltype = AA  length = 214
FEATURE                 Location/Qualifiers
REGION                  1..214
                        note = Description of Artificial Sequence: Synthetic
                         polypeptide
REGION                  1..214
                        note = XENP32947 Chain 3 - MESO-C[MSLN]_L1 Light Chain
source                  1..214
                        mol_type = protein
                        organism = synthetic construct
SEQUENCE: 482
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YSSYPLTFGA GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 483          moltype = AA  length = 449
FEATURE                 Location/Qualifiers
REGION                  1..449
                        note = Description of Artificial Sequence: Synthetic
                         polypeptide
REGION                  1..449
                        note = XENP32948 Chain 1 -
                         MESO-C[MSLN]_H1.12_IgG1_pI(-)_Isosteric
                         _A_/PVA_/S267K/L368D/K370S
source                  1..449
                        mol_type = protein
                        organism = synthetic construct
SEQUENCE: 483
QVQLVQSGAE VKKPGASVKV SCKASGYTFT SYWMHWVRQA PGQGLEWMGM IHPNSDNTIY   60
YQKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                     449

SEQ ID NO: 484          moltype = AA  length = 722
FEATURE                 Location/Qualifiers
REGION                  1..722
                        note = Description of Artificial Sequence: Synthetic
                         polypeptide
REGION                  1..722
```

-continued

```
                        note = XENP32948 Chain 2 -
                          MESO-C[MSLN]_H1.12_(G4S)2_[CD3]_L1.47_H
                          1.32_scFv(GKPGS)4_Fc(216)_IgG1_C220S/PVA_/S267K/S364K/E357Q
source                  1..722
                        mol_type = protein
                        organism = synthetic construct
SEQUENCE: 484
QVQLVQSGAE VKKPGASVKV SCKASGYTFT SYWMHWVRQA PGQGLEWMGM IHPNSDNTIY  60
YQKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKANNY  420
ATYYADSVKG RFTISRDDSK NTLYLQMNSL RAEDTAVYYC VRHGNFGDSY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                                722

SEQ ID NO: 485          moltype = AA  length = 214
FEATURE                 Location/Qualifiers
REGION                  1..214
                        note = Description of Artificial Sequence: Synthetic
                         polypeptide
REGION                  1..214
                        note = XENP32948 Chain 3 - MESO-C[MSLN]_L1.9 Light Chain
source                  1..214
                        mol_type = protein
                        organism = synthetic construct
SEQUENCE: 485
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YYSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 486          moltype = AA  length = 449
FEATURE                 Location/Qualifiers
REGION                  1..449
                        note = Description of Artificial Sequence: Synthetic
                         polypeptide
REGION                  1..449
                        note = XENP32949 Chain 1 -
                          MESO-C[MSLN]_H1.13_IgG1_pI(-)_Isosteric
                          _A_/PVA_/S267K/L368D/K370S
source                  1..449
                        mol_type = protein
                        organism = synthetic construct
SEQUENCE: 486
QVQLVQSGAE VKKPGASVKV SCKASGYTFT SYWMHWVRQA PGQGLEWMGM IHPNSDNTIY  60
YYKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 487          moltype = AA  length = 722
FEATURE                 Location/Qualifiers
REGION                  1..722
                        note = Description of Artificial Sequence: Synthetic
                         polypeptide
REGION                  1..722
                        note = XENP32949 Chain 2 -
                          MESO-C[MSLN]_H1.13_(G4S)2_[CD3]_L1.47_H
                          1.32_scFv(GKPGS)4_Fc(216)_IgG1_C220S/PVA_/S267K/S364K/E357Q
source                  1..722
                        mol_type = protein
                        organism = synthetic construct
SEQUENCE: 487
QVQLVQSGAE VKKPGASVKV SCKASGYTFT SYWMHWVRQA PGQGLEWMGM IHPNSDNTIY  60
YYKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKANNY  420
```

```
ATYYADSVKG RFTISRDDSK NTLYLQMNSL RAEDTAVYYC VRHGNFGDSY VSWFAYWGQG   480
TLVTVSSGGG GSGGGGSKTH TCPPCPAPPV AGPSVFLFPP KPKDTLMISR TPEVTCVVVD   540
VKHEDPEVKF NWYVDGVEVH NAKTKPREEQ YNSTYRVVSV LTVLHQDWLN GKEYKCKVSN   600
KALPAPIEKT ISKAKGQPRE PQVYTLPPSR EQMTKNQVKL TCLVKGFYPS DIAVEWESNG   660
QPENNYKTTP PVLDSDGSFF LYSKLTVDKS RWQQGNVFSC SVMHEALHNH YTQKSLSLSP   720
GK                                                                 722

SEQ ID NO: 488          moltype = AA  length = 214
FEATURE                 Location/Qualifiers
REGION                  1..214
                        note = Description of Artificial Sequence: Synthetic
                         polypeptide
REGION                  1..214
                        note = XENP32949 Chain 3 - MESO-C[MSLN]_L1.9 Light Chain
source                  1..214
                        mol_type = protein
                        organism = synthetic construct
SEQUENCE: 488
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YYSYPLTFGA GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 489          moltype = AA  length = 449
FEATURE                 Location/Qualifiers
REGION                  1..449
                        note = Description of Artificial Sequence: Synthetic
                         polypeptide
REGION                  1..449
                        note = XENP32950 Chain 1 -
                         MESO-C[MSLN]_H1.3_IgG1_pI(-)_Isosteric_
                         A_/PVA_/S267K/L368D/K370S
source                  1..449
                        mol_type = protein
                        organism = synthetic construct
SEQUENCE: 489
QVQLVQSGAE VKKPGASVKV SCKASGYTFT SYWMHWVRQA PGQGLEWMGW IHPNSDNTIY   60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                     449

SEQ ID NO: 490          moltype = AA  length = 722
FEATURE                 Location/Qualifiers
REGION                  1..722
                        note = Description of Artificial Sequence: Synthetic
                         polypeptide
REGION                  1..722
                        note = XENP32950 Chain 2 -
                         MESO-C[MSLN]_H1.3_(G4S)2_[CD3]_L1.47_H1
                         .32_scFv(GKPGS)4_Fc(216)_IgG1_C220S/PVA_/S267K/S364K/E357Q
source                  1..722
                        mol_type = protein
                        organism = synthetic construct
SEQUENCE: 490
QVQLVQSGAE VKKPGASVKV SCKASGYTFT SYWMHWVRQA PGQGLEWMGW IHPNSDNTIY   60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCGGGGSGG GGSQAVVTQE   240
PSLTVSPGGT VTLTCGSSTG AVTTSNYANW VQQKPGKSPR GLIGGTNKRA PGVPARFSGS   300
LLGGKAALTI SGAQPEDEAD YYCALWYSNH WVFGGGTKLT VLGKPGSGKP GSGKPGSGKP   360
GSEVQLVESG GGLVQPGGSL RLSCAASGFT FSTYAMNWVR QAPGKGLEWV GRIRSKANNY   420
ATYYADSVKG RFTISRDDSK NTLYLQMNSL RAEDTAVYYC VRHGNFGDSY VSWFAYWGQG   480
TLVTVSSGGG GSGGGGSKTH TCPPCPAPPV AGPSVFLFPP KPKDTLMISR TPEVTCVVVD   540
VKHEDPEVKF NWYVDGVEVH NAKTKPREEQ YNSTYRVVSV LTVLHQDWLN GKEYKCKVSN   600
KALPAPIEKT ISKAKGQPRE PQVYTLPPSR EQMTKNQVKL TCLVKGFYPS DIAVEWESNG   660
QPENNYKTTP PVLDSDGSFF LYSKLTVDKS RWQQGNVFSC SVMHEALHNH YTQKSLSLSP   720
GK                                                                 722

SEQ ID NO: 491          moltype = AA  length = 214
FEATURE                 Location/Qualifiers
REGION                  1..214
                        note = Description of Artificial Sequence: Synthetic
                         polypeptide
REGION                  1..214
                        note = XENP32950 Chain 3 - MESO-C[MSLN]_L1.9 Light Chain
```

-continued

```
source                      1..214
                            mol_type = protein
                            organism = synthetic construct
SEQUENCE: 491
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YYSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 492            moltype = AA  length = 449
FEATURE                   Location/Qualifiers
REGION                    1..449
                          note = Description of Artificial Sequence: Synthetic
                           polypeptide
REGION                    1..449
                          note = XENP32951 Chain 1 -
                           MESO-C[MSLN]_H1.3_IgG1_pI(-)_Isosteric_
                           A_/PVA_/S267K/L368D/K370S
source                    1..449
                          mol_type = protein
                          organism = synthetic construct
SEQUENCE: 492
QVQLVQSGAE VKKPGASVKV SCKASGYTFT SYWMHWVRQA PGQGLEWMGW IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP PCPAPPVAGP           240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                   449

SEQ ID NO: 493            moltype = AA  length = 722
FEATURE                   Location/Qualifiers
REGION                    1..722
                          note = Description of Artificial Sequence: Synthetic
                           polypeptide
REGION                    1..722
                          note = XENP32951 Chain 2 -
                           MESO-C[MSLN]_H1.3_(G4S)2_[CD3]_L1.47_H1
                           .32_scFv(GKPGS)4_Fc(216)_IgG1_C220S/PVA_/S267K/S364K/E357Q
source                    1..722
                          mol_type = protein
                          organism = synthetic construct
SEQUENCE: 493
QVQLVQSGAE VKKPGASVKV SCKASGYTFT SYWMHWVRQA PGQGLEWMGW IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKANNY  420
ATYYADSVKG RFTISRDDSK NTLYLQMNSL RAEDTAVYYC VRHGNFGDSY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                               722

SEQ ID NO: 494            moltype = AA  length = 214
FEATURE                   Location/Qualifiers
REGION                    1..214
                          note = Description of Artificial Sequence: Synthetic
                           polypeptide
REGION                    1..214
                          note = XENP32951 Chain 3 - MESO-C[MSLN]_L1.5 Light Chain
source                    1..214
                          mol_type = protein
                          organism = synthetic construct
SEQUENCE: 494
DIVMTQSPDS LAVSLGERAT INCKASHDVG TYVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 495            moltype = AA  length = 449
FEATURE                   Location/Qualifiers
REGION                    1..449
                          note = Description of Artificial Sequence: Synthetic
                           polypeptide
```

-continued

```
REGION                    1..449
                          note = XENP33366 Chain 1 -
                           MESO-C[MSLN]_H1.3_IgG1_pI(-)_Isosteric_
                           A_/PVA_/S267K/L368D/K370S
source                    1..449
                          mol_type = protein
                          organism = synthetic construct
SEQUENCE: 495
QVQLVQSGAE VKKPGASVKV SCKASGYTFT SYWMHWVRQA PGQGLEWMGW IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 496           moltype = AA  length = 722
FEATURE                  Location/Qualifiers
REGION                   1..722
                         note = Description of Artificial Sequence: Synthetic
                          polypeptide
REGION                   1..722
                         note = XENP33366 Chain 2 -
                          MESO-C[MSLN]_H1.3_(G4S)2_[CD3]_L1.47_H1
                          .32_scFv(GKPGS)4_Fc(216)_IgG1_C220S/PVA_/S267K/S364K/E357Q
source                   1..722
                         mol_type = protein
                         organism = synthetic construct
SEQUENCE: 496
QVQLVQSGAE VKKPGASVKV SCKASGYTFT SYWMHWVRQA PGQGLEWMGW IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKANNY  420
ATYYADSVKG RFTISRDDSK NTLYLQMNSL RAEDTAVYYC VRHGNFGDSY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                                722

SEQ ID NO: 497           moltype = AA  length = 214
FEATURE                  Location/Qualifiers
REGION                   1..214
                         note = Description of Artificial Sequence: Synthetic
                          polypeptide
REGION                   1..214
                         note = XENP33366 Chain 3 - MESO-C[MSLN]_L1.13 Light Chain
source                   1..214
                         mol_type = protein
                         organism = synthetic construct
SEQUENCE: 497
DIVMTQSPDS LAVSLGERAT INCKASHDVG QSVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 498           moltype = AA  length = 449
FEATURE                  Location/Qualifiers
REGION                   1..449
                         note = Description of Artificial Sequence: Synthetic
                          polypeptide
REGION                   1..449
                         note = XENP33367 Chain 1 -
                          MESO-C[MSLN]_H1.3_IgG1_pI(-)_Isosteric_
                          A_/PVA_/S267K/L368D/K370S
source                   1..449
                         mol_type = protein
                         organism = synthetic construct
SEQUENCE: 498
QVQLVQSGAE VKKPGASVKV SCKASGYTFT SYWMHWVRQA PGQGLEWMGW IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
```

```
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                     449

SEQ ID NO: 499        moltype = AA  length = 722
FEATURE               Location/Qualifiers
REGION                1..722
                      note = Description of Artificial Sequence: Synthetic
                       polypeptide
REGION                1..722
                      note = XENP33367 Chain 2 -
                       MESO-C[MSLN]_H1.3_(G4S)2_[CD3]_L1.47_H1
                       .32_scFv(GKPGS)4_Fc(216)_IgG1_C220S/PVA_/S267K/S364K/E357Q
source                1..722
                      mol_type = protein
                      organism = synthetic construct
SEQUENCE: 499
QVQLVQSGAE VKKPGASVKV SCKASGYTFT SYWMHWVRQA PGQGLEWMGW IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKANNY  420
ATYYADSVKG RFTISRDDSK NTLYLQMNSL RAEDTAVYYC VRHGNFGDSY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                                 722

SEQ ID NO: 500        moltype = AA  length = 214
FEATURE               Location/Qualifiers
REGION                1..214
                      note = Description of Artificial Sequence: Synthetic
                       polypeptide
REGION                1..214
                      note = XENP33367 Chain 3 - MESO-C[MSLN]_L1.14 Light Chain
source                1..214
                      mol_type = protein
                      organism = synthetic construct
SEQUENCE: 500
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSFPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 501        moltype = AA  length = 449
FEATURE               Location/Qualifiers
REGION                1..449
                      note = Description of Artificial Sequence: Synthetic
                       polypeptide
REGION                1..449
                      note = XENP33460 Chain 1 -
                       MESO-C[MSLN]_H1_IgG1_pI(-)_Isosteric_A_
                       /PVA_/S267K/L368D/K370S
source                1..449
                      mol_type = protein
                      organism = synthetic construct
SEQUENCE: 501
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                     449

SEQ ID NO: 502        moltype = AA  length = 722
FEATURE               Location/Qualifiers
REGION                1..722
                      note = Description of Artificial Sequence: Synthetic
                       polypeptide
REGION                1..722
                      note = XENP33460 Chain 2 -
                       MESO-C[MSLN]_H1_(G4S)2_[CD3]_L1.47_H1.3
                       2_scFv(GKPGS)4_Fc(216)_IgG1_C220S/PVA_/S267K/S364K/E357Q
source                1..722
                      mol_type = protein
```

-continued

```
                          organism = synthetic construct
SEQUENCE: 502
QVQLVQSGAE VKKPGASVKV SCKASGYTFT SYWMHWVRQA PGQGLEWMGM IHPNSDNTIY    60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCGGGGSGG GGSQAVVTQE   240
PSLTVSPGGT VTLTCGSSTG AVTTSNYANW VQQKPGKSPR GLIGGTNKRA PGVPARFSGS   300
LLGGKAALTI SGAQPEDEAD YYCALWYSNH WVFGGGTKLT VLGKPGSGKP GSGKPGSGKP   360
GSEVQLVESG GGLVQPGGSL RLSCAASGFT FSTYAMNWVR QAPGKGLEWV GRIRSKANNY   420
ATYYADSVKG RFTISRDDSK NTLYLQMNSL RAEDTAVYYC VRHGNFGDSY VSWFAYWGQG   480
TLVTVSSGGG GSGGGGSKTH TCPPCPAPPV AGPSVFLPP PKPKDTLMISR TPEVTCVVVD   540
VKHEDPEVKF NWYVDGVEVH NAKTKPREEQ YNSTYRVVSV LTVLHQDWLN GKEYKCKVSN   600
KALPAPIEKT ISKAKGQPRE PQVYTLPPSR EQMTKNQVKL TCLVKGFYPS DIAVEWESNG   660
QPENNYKTTP PVLDSDGSFF LYSKLTVDKS RWQQGNVFSC SVMHEALHNH YTQKSLSLSP   720
GK                                                                 722

SEQ ID NO: 503           moltype = AA   length = 214
FEATURE                  Location/Qualifiers
REGION                   1..214
                         note = Description of Artificial Sequence: Synthetic
                          polypeptide
REGION                   1..214
                         note = XENP33460 Chain 3 - MESO-C[MSLN]_L1.19 Light Chain
source                   1..214
                         mol_type = protein
                         organism = synthetic construct
SEQUENCE: 503
DIVMTQSPDS LAVSLGERAT INCKASHDVG TYVAWYQQKP GQSPKLLIYW ASTRHTGVPD    60
RFTGSGSGTD FTLTISSLQA EDVAVYFCQQ YYSYPLTFGA GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 504           moltype = AA   length = 449
FEATURE                  Location/Qualifiers
REGION                   1..449
                         note = Description of Artificial Sequence: Synthetic
                          polypeptide
REGION                   1..449
                         note = XENP33461 Chain 1 -
                          MESO-C[MSLN]_H1_IgG1_pI(-)_Isosteric_A_
                          /PVA_/S267K/L368D/K370S
source                   1..449
                         mol_type = protein
                         organism = synthetic construct
SEQUENCE: 504
QVQLVQSGAE VKKPGASVKV SCKASGYTFT SYWMHWVRQA PGQGLEWMGM IHPNSDNTIY    60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                     449

SEQ ID NO: 505           moltype = AA   length = 722
FEATURE                  Location/Qualifiers
REGION                   1..722
                         note = Description of Artificial Sequence: Synthetic
                          polypeptide
REGION                   1..722
                         note = XENP33461 Chain 2 -
                          MESO-C[MSLN]_H1_(G4S)2_[CD3]_L1.47_H1.3
                          2_scFv(GKPGS)4_Fc(216)_IgG1_C220S/PVA_/S267K/S364K/E357Q
source                   1..722
                         mol_type = protein
                         organism = synthetic construct
SEQUENCE: 505
QVQLVQSGAE VKKPGASVKV SCKASGYTFT SYWMHWVRQA PGQGLEWMGM IHPNSDNTIY    60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCGGGGSGG GGSQAVVTQE   240
PSLTVSPGGT VTLTCGSSTG AVTTSNYANW VQQKPGKSPR GLIGGTNKRA PGVPARFSGS   300
LLGGKAALTI SGAQPEDEAD YYCALWYSNH WVFGGGTKLT VLGKPGSGKP GSGKPGSGKP   360
GSEVQLVESG GGLVQPGGSL RLSCAASGFT FSTYAMNWVR QAPGKGLEWV GRIRSKANNY   420
ATYYADSVKG RFTISRDDSK NTLYLQMNSL RAEDTAVYYC VRHGNFGDSY VSWFAYWGQG   480
TLVTVSSGGG GSGGGGSKTH TCPPCPAPPV AGPSVFLPP PKPKDTLMISR TPEVTCVVVD   540
VKHEDPEVKF NWYVDGVEVH NAKTKPREEQ YNSTYRVVSV LTVLHQDWLN GKEYKCKVSN   600
KALPAPIEKT ISKAKGQPRE PQVYTLPPSR EQMTKNQVKL TCLVKGFYPS DIAVEWESNG   660
QPENNYKTTP PVLDSDGSFF LYSKLTVDKS RWQQGNVFSC SVMHEALHNH YTQKSLSLSP   720
```

-continued

```
GK                                                                       722

SEQ ID NO: 506          moltype = AA  length = 214
FEATURE                 Location/Qualifiers
REGION                  1..214
                        note = Description of Artificial Sequence: Synthetic
                         polypeptide
REGION                  1..214
                        note = XENP33461 Chain 3 - MESO-C[MSLN]_L1.20 Light Chain
source                  1..214
                        mol_type = protein
                        organism = synthetic construct
SEQUENCE: 506
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YYSFPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                                214

SEQ ID NO: 507          moltype = AA  length = 449
FEATURE                 Location/Qualifiers
REGION                  1..449
                        note = Description of Artificial Sequence: Synthetic
                         polypeptide
REGION                  1..449
                        note = XENP33462 Chain 1 -
                         MESO-C[MSLN]_H1_IgG1_pI(-)_Isosteric_A_
                         /PVA_/S267K/L368D/K370S
source                  1..449
                        mol_type = protein
                        organism = synthetic construct
SEQUENCE: 507
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEHNAK  TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                     449

SEQ ID NO: 508          moltype = AA  length = 722
FEATURE                 Location/Qualifiers
REGION                  1..722
                        note = Description of Artificial Sequence: Synthetic
                         polypeptide
REGION                  1..722
                        note = XENP33462 Chain 2 -
                         MESO-C[MSLN]_H1_(G4S)2_[CD3]_L1.47_H1.3
                         2_scFv(GKPGS)4_Fc(216)_IgG1_C220S/PVA_/S267K/S364K/E357Q
source                  1..722
                        mol_type = protein
                        organism = synthetic construct
SEQUENCE: 508
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKANNY  420
ATYYADSVKG RFTISRDDSK NTLYLQMNSL RAEDTAVYYC VRHGNFGDSY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                                  722

SEQ ID NO: 509          moltype = AA  length = 214
FEATURE                 Location/Qualifiers
REGION                  1..214
                        note = Description of Artificial Sequence: Synthetic
                         polypeptide
REGION                  1..214
                        note = XENP33462 Chain 3 - MESO-C[MSLN]_L1.21 Light Chain
source                  1..214
                        mol_type = protein
                        organism = synthetic construct
SEQUENCE: 509
DIVMTQSPDS LAVSLGERAT INCKASHDVG TSVAWYQQKP GQSPKLLIYW ASTRHTGVPD  60
```

```
RFTGSGSGTD FTLTISSLQA EDVAVYFCQQ YYSVPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 510          moltype = AA  length = 449
FEATURE                 Location/Qualifiers
REGION                  1..449
                        note = Description of Artificial Sequence: Synthetic
                         polypeptide
REGION                  1..449
                        note = XENP33463 Chain 1 -
                         MESO-C[MSLN]_H1_IgG1_pI(-)_Isosteric_A_
                         /PVA_/S267K/L368D/K370S
source                  1..449
                        mol_type = protein
                        organism = synthetic construct
SEQUENCE: 510
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 511          moltype = AA  length = 722
FEATURE                 Location/Qualifiers
REGION                  1..722
                        note = Description of Artificial Sequence: Synthetic
                         polypeptide
REGION                  1..722
                        note = XENP33463 Chain 2 -
                         MESO-C[MSLN]_H1_(G4S)2_[CD3]_L1.47_H1.3
                         2_scFv(GKPGS)4_Fc(216)_IgG1_C220S/PVA_/S267K/S364K/E357Q
source                  1..722
                        mol_type = protein
                        organism = synthetic construct
SEQUENCE: 511
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKANNY  420
ATYYADSVKG RFTISRDDSK NTLYLQMNSL RAEDTAVYYC VRHGNFGDSY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                                722

SEQ ID NO: 512          moltype = AA  length = 214
FEATURE                 Location/Qualifiers
REGION                  1..214
                        note = Description of Artificial Sequence: Synthetic
                         polypeptide
REGION                  1..214
                        note = XENP33463 Chain 3 - MESO-C[MSLN]_L1.22 Light Chain
source                  1..214
                        mol_type = protein
                        organism = synthetic construct
SEQUENCE: 512
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YYSIPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 513          moltype = AA  length = 449
FEATURE                 Location/Qualifiers
REGION                  1..449
                        note = Description of Artificial Sequence: Synthetic
                         polypeptide
REGION                  1..449
                        note = XENP33464 Chain 1 -
                         MESO-C[MSLN]_H1.12_IgG1_pI(-)_Isosteric
                         _A_/PVA_/S267K/L368D/K370S
source                  1..449
```

```
                              mol_type = protein
                              organism = synthetic construct
SEQUENCE: 513
QVQLVQSGAE VKKPGASVKV SCKASGYTFT SYWMHWVRQA PGQGLEWMGM IHPNSDNTIY   60
YQKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 514            moltype = AA  length = 722
FEATURE                   Location/Qualifiers
REGION                    1..722
                          note = Description of Artificial Sequence: Synthetic
                           polypeptide
REGION                    1..722
                          note = XENP33464 Chain 2 -
                           MESO-C[MSLN]_H1.12_(G4S)2_[CD3]_L1.47_H
                           1.32_scFv(GKPGS)4_Fc(216)_IgG1_C220S/PVA_/S267K/S364K/E357Q
source                    1..722
                          mol_type = protein
                          organism = synthetic construct
SEQUENCE: 514
QVQLVQSGAE VKKPGASVKV SCKASGYTFT SYWMHWVRQA PGQGLEWMGM IHPNSDNTIY   60
YQKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGQSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKANNY  420
ATYYADSVKG RFTISRDDSK NTLYLQMNSL RAEDTAVYYC VRHGNFGDSY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                                722

SEQ ID NO: 515            moltype = AA  length = 214
FEATURE                   Location/Qualifiers
REGION                    1..214
                          note = Description of Artificial Sequence: Synthetic
                           polypeptide
REGION                    1..214
                          note = XENP33464 Chain 3 - MESO-C[MSLN]_L1.19 Light Chain
source                    1..214
                          mol_type = protein
                          organism = synthetic construct
SEQUENCE: 515
DIVMTQSPDS LAVSLGERAT INCKASHDVG TYVAWYQQKP GQSPKLLIYW ASTRHTGVPD   60
RFTGSGSGTD FTLTISSLQA EDVAVYFCQQ YYSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 516            moltype = AA  length = 449
FEATURE                   Location/Qualifiers
REGION                    1..449
                          note = Description of Artificial Sequence: Synthetic
                           polypeptide
REGION                    1..449
                          note = XENP33465 Chain 1 -
                           MESO-C[MSLN]_H1.12_IgG1_pI(-)_Isosteric
                           _A_/PVA_/S267K/L368D/K370S
source                    1..449
                          mol_type = protein
                          organism = synthetic construct
SEQUENCE: 516
QVQLVQSGAE VKKPGASVKV SCKASGYTFT SYWMHWVRQA PGQGLEWMGM IHPNSDNTIY   60
YQKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 517            moltype = AA  length = 722
FEATURE                   Location/Qualifiers
```

```
REGION                   1..722
                         note = Description of Artificial Sequence: Synthetic
                         polypeptide
REGION                   1..722
                         note = XENP33465 Chain 2 -
                         MESO-C[MSLN]_H1.12_(G4S)2_[CD3]_L1.47_H
                         1.32_scFv(GKPGS)4_Fc(216)_IgG1_C220S/PVA_/S267K/S364K/E357Q
source                   1..722
                         mol_type = protein
                         organism = synthetic construct
SEQUENCE: 517
QVQLVQSGAE VKKPGASVKV SCKASGYTFT SYWMHWVRQA PGQGLEWMGM IHPNSDNTIY   60
YQKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKANY   420
ATYYADSVKG RFTISRDDSK NTLYLQMNSL RAEDTAVYYC VRHGNFGDSY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                                722

SEQ ID NO: 518          moltype = AA  length = 214
FEATURE                 Location/Qualifiers
REGION                  1..214
                        note = Description of Artificial Sequence: Synthetic
                        polypeptide
REGION                  1..214
                        note = XENP33465 Chain 3 - MESO-C[MSLN]_L1.20 Light Chain
source                  1..214
                        mol_type = protein
                        organism = synthetic construct
SEQUENCE: 518
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YYSFPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 519          moltype = AA  length = 449
FEATURE                 Location/Qualifiers
REGION                  1..449
                        note = Description of Artificial Sequence: Synthetic
                        polypeptide
REGION                  1..449
                        note = XENP33466 Chain 1 -
                        MESO-C[MSLN]_H1.12_IgG1_pI(-)_Isosteric
                        _A_/PVA_/S267K/L368D/K370S
source                  1..449
                        mol_type = protein
                        organism = synthetic construct
SEQUENCE: 519
QVQLVQSGAE VKKPGASVKV SCKASGYTFT SYWMHWVRQA PGQGLEWMGM IHPNSDNTIY   60
YQKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                   449

SEQ ID NO: 520          moltype = AA  length = 722
FEATURE                 Location/Qualifiers
REGION                  1..722
                        note = Description of Artificial Sequence: Synthetic
                        polypeptide
REGION                  1..722
                        note = XENP33466 Chain 2 -
                        MESO-C[MSLN]_H1.12_(G4S)2_[CD3]_L1.47_H
                        1.32_scFv(GKPGS)4_Fc(216)_IgG1_C220S/PVA_/S267K/S364K/E357Q
source                  1..722
                        mol_type = protein
                        organism = synthetic construct
SEQUENCE: 520
QVQLVQSGAE VKKPGASVKV SCKASGYTFT SYWMHWVRQA PGQGLEWMGM IHPNSDNTIY   60
YQKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
```

```
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKANNY  420
ATYYADSVKG RFTISRDDSK NTLYLQMNSL RAEDTAVYYC VRHGNFGDSY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                                722
```

SEQ ID NO: 521          moltype = AA  length = 214
FEATURE                 Location/Qualifiers
REGION                  1..214
                        note = Description of Artificial Sequence: Synthetic
                        polypeptide
REGION                  1..214
                        note = XENP33466 Chain 3 - MESO-C[MSLN]_L1.21 Light Chain
source                  1..214
                        mol_type = protein
                        organism = synthetic construct
SEQUENCE: 521
```
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YYSVPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

SEQ ID NO: 522          moltype = AA  length = 449
FEATURE                 Location/Qualifiers
REGION                  1..449
                        note = Description of Artificial Sequence: Synthetic
                        polypeptide
REGION                  1..449
                        note = XENP33467 Chain 1 -
                        MESO-C[MSLN]_H1.12_IgG1_pI(-)_Isosteric
                        _A_/PVA_/S267K/L368D/K370S
source                  1..449
                        mol_type = protein
                        organism = synthetic construct
SEQUENCE: 522
```
QVQLVQSGAE VKKPGASVKV SCKASGYTFT SYWMHWVRQA PGQGLEWMGM IHPNSDNTIY  60
YQKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449
```

SEQ ID NO: 523          moltype = AA  length = 722
FEATURE                 Location/Qualifiers
REGION                  1..722
                        note = Description of Artificial Sequence: Synthetic
                        polypeptide
REGION                  1..722
                        note = XENP33467 Chain 2 -
                        MESO-C[MSLN]_H1.12_(G4S)2_[CD3]_L1.47_H
                        1.32_scFv(GKPGS)4_Fc(216)_IgG1_C220S/PVA_/S267K/S364K/E357Q
source                  1..722
                        mol_type = protein
                        organism = synthetic construct
SEQUENCE: 523
```
QVQLVQSGAE VKKPGASVKV SCKASGYTFT SYWMHWVRQA PGQGLEWMGM IHPNSDNTIY  60
YQKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKANNY  420
ATYYADSVKG RFTISRDDSK NTLYLQMNSL RAEDTAVYYC VRHGNFGDSY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                                722
```

SEQ ID NO: 524          moltype = AA  length = 214
FEATURE                 Location/Qualifiers
REGION                  1..214

-continued

```
                        note = Description of Artificial Sequence: Synthetic
                         polypeptide
REGION                  1..214
                        note = XENP33467 Chain 3 - MESO-C[MSLN]_L1.22 Light Chain
source                  1..214
                        mol_type = protein
                        organism = synthetic construct
SEQUENCE: 524
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YYSIPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 525          moltype = AA  length = 449
FEATURE                 Location/Qualifiers
REGION                  1..449
                        note = Description of Artificial Sequence: Synthetic
                         polypeptide
REGION                  1..449
                        note = XENP3396 Chain 1 -
                         MESO-C[MSLN]_H1.14_IgG1_pI(-)_Isosteric_
                         A_PVA_/S267K/L368D/K370S-(G4S)2_IgG1_PVA_/S267K/S364K/E357Q
source                  1..449
                        mol_type = protein
                        organism = synthetic construct
SEQUENCE: 525
QVQLVQSGAE VKKPGASVKV SCKASGYTFT SYWMHWVRQA PGQGLEWMGW IHPQSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                   449

SEQ ID NO: 526          moltype = AA  length = 722
FEATURE                 Location/Qualifiers
REGION                  1..722
                        note = Description of Artificial Sequence: Synthetic
                         polypeptide
REGION                  1..722
                        note = XENP3396 Chain 2 -
                         MESO-C[MSLN]_H1.14_(G4S)2_[CD3]_(G4S)2_I
                         gG1_PVA_/S267K/S364K/E357Q
source                  1..722
                        mol_type = protein
                        organism = synthetic construct
SEQUENCE: 526
QVQLVQSGAE VKKPGASVKV SCKASGYTFT SYWMHWVRQA PGQGLEWMGW IHPQSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKANNY  420
ATYYADSVKG RFTISRDDSK NTLYLQMNSL RAEDTAVYYC VRHGNFGDSY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                               722

SEQ ID NO: 527          moltype = AA  length = 214
FEATURE                 Location/Qualifiers
REGION                  1..214
                        note = Description of Artificial Sequence: Synthetic
                         polypeptide
REGION                  1..214
                        note = XENP3396 Chain 3 - MESO-C[MSLN]_L1.14 Light Chain
source                  1..214
                        mol_type = protein
                        organism = synthetic construct
SEQUENCE: 527
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSFPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 528          moltype = AA  length = 449
```

-continued

```
FEATURE              Location/Qualifiers
REGION               1..449
                     note = Description of Artificial Sequence: Synthetic
                      polypeptide
REGION               1..449
                     note = XENP33970 Chain 1 -
                      MESO-C[MSLN]_H1.15_IgG1_pI(-)_Isosteric
                      _A_PVA_/S267K/L368D/K370S-(G4S)2_IgG1_PVA_/S267K/S364K/E357
                      Q
source               1..449
                     mol_type = protein
                     organism = synthetic construct
SEQUENCE: 528
QVQLVQSGAE VKKPGASVKV SCKASGYTFT SYWMHWVRQA PGQGLEWMGW IHPNSDNTIY   60
YEKFQGRVTM TVDKSISTAY MELSRLRSDD TAVYYCARII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 529       moltype = AA  length = 722
FEATURE              Location/Qualifiers
REGION               1..722
                     note = Description of Artificial Sequence: Synthetic
                      polypeptide
REGION               1..722
                     note = XENP33970 Chain 2 -
                      MESO-C[MSLN]_H1.15_(G4S)2_[CD3]_(G4S)2_
                      IgG1_PVA_/S267K/S364K/E357Q
source               1..722
                     mol_type = protein
                     organism = synthetic construct
SEQUENCE: 529
QVQLVQSGAE VKKPGASVKV SCKASGYTFT SYWMHWVRQA PGQGLEWMGW IHPNSDNTIY   60
YEKFQGRVTM TVDKSISTAY MELSRLRSDD TAVYYCARII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKANNY  420
ATYYADSVKG RFTISRDDSK NTLYLQMNSL RAEDTAVYYC VRHGNFGDSY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                                722

SEQ ID NO: 530       moltype = AA  length = 214
FEATURE              Location/Qualifiers
REGION               1..214
                     note = Description of Artificial Sequence: Synthetic
                      polypeptide
REGION               1..214
                     note = XENP33970 Chain 3 - MESO-C[MSLN]_L1.14 Light Chain
source               1..214
                     mol_type = protein
                     organism = synthetic construct
SEQUENCE: 530
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YSSFPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 531       moltype = AA  length = 449
FEATURE              Location/Qualifiers
REGION               1..449
                     note = Description of Artificial Sequence: Synthetic
                      polypeptide
REGION               1..449
                     note = XENP33972 Chain 1 -
                      MESO-C[MSLN]_H1.16_IgG1_pI(-)_Isosteric
                      _A_PVA_/S267K/L368D/K370S-(G4S)2_IgG1_PVA_/S267K/S364K/E357
                      Q
source               1..449
                     mol_type = protein
                     organism = synthetic construct
SEQUENCE: 531
```

```
QVQLVQSGAE VKKPGASVKV SCKASGYTFT SYWMHWVRQA PGQGLEWMGW IHPQSDNTIY  60
YEKFQGRVTM TVDKSISTAY MELSRLRSDD TAVYYCARII TPVVPKFDYW GQGTLVTVSS 120
ASTKGPSVFP LAPSSKSTSG GTAALGCLVK DYFPEPVTVS WNSGALTSGV HTFPAVLQSS 180
GLYSLSSVVT VPSSSLGTQT YICNVNHKPS DTKVDKKVEP KSCDKTHTCP PCPAPPVAGP 240
SVFLFPPKPK DTLMISRTPE VTCVVVDVKH EDPEVKFNWY VDGVEVHNAK TKPREEEYNS 300
TYRVVSVLTV LHQDWLNGKE YKCKVSNKAL PAPIEKTISK AKGQPREPQV YTLPPSREEM 360
TKNQVSLTCD VSGFYPSDIA VEWESDGQPE NNYKTTPPVL DSDGSFFLYS KLTVDKSRWE 420
QGDVFSCSVM HEALHNHYTQ KSLSLSPGK                                    449

SEQ ID NO: 532          moltype = AA  length = 722
FEATURE                 Location/Qualifiers
REGION                  1..722
                        note = Description of Artificial Sequence: Synthetic
                         polypeptide
REGION                  1..722
                        note = XENP33972 Chain 2 -
                         MESO-C[MSLN]_H1.16_(G4S)2_[CD3]_(G4S)2_
                         IgG1_PVA_/S267K/S364K/E357Q
source                  1..722
                        mol_type = protein
                        organism = synthetic construct
SEQUENCE: 532
QVQLVQSGAE VKKPGASVKV SCKASGYTFT SYWMHWVRQA PGQGLEWMGW IHPQSDNTIY  60
YEKFQGRVTM TVDKSISTAY MELSRLRSDD TAVYYCARII TPVVPKFDYW GQGTLVTVSS 120
ASTKGPSVFP LAPSSKSTSG GTAALGCLVK DYFPEPVTVS WNSGALTSGV HTFPAVLQSS 180
GLYSLSSVVT VPSSSLGTQT YICNVNHKPS NTKVDKKVEP KSCGGGGSGG GGSQAVVTQE 240
PSLTVSPGGT VTLTCGSSTG AVTTSNYANW VQQKPGKSPR GLIGGTNKRA PGVPARFSGS 300
LLGGKAALTI SGAQPEDEAD YYCALWYSNH WVFGGGTKLT VLGKPGSGKP GSGKPGSGKP 360
GSEVQLVESG GGLVQPGGSL RLSCAASGFT FSTYAMNWVR QAPGKGLEWV GRIRSKANNY 420
ATYYADSVKG RFTISRDDSK NTLYLQMNSL RAEDTAVYYC VRHGNFGDSY VSWFAYWGQG 480
TLVTVSSGGG GSGGGGSKTH TCPPCPAPPV AGPSVFLFPP KPKDTLMISR TPEVTCVVVD 540
VKHEDPEVKF NWYVDGVEVH NAKTKPREEQ YNSTYRVVSV LTVLHQDWLN GKEYKCKVSN 600
KALPAPIEKT ISKAKGQPRE PQVYTLPPSR EQMTKNQVKL TCLVKGFYPS DIAVEWESNG 660
QPENNYKTTP PVLDSDGSFF LYSKLTVDKS RWQQGNVFSC SVMHEALHNH YTQKSLSLSP 720
GK                                                                722

SEQ ID NO: 533          moltype = AA  length = 214
FEATURE                 Location/Qualifiers
REGION                  1..214
                        note = Description of Artificial Sequence: Synthetic
                         polypeptide
REGION                  1..214
                        note = XENP33972 Chain 3 - MESO-C[MSLN]_L1.14 Light Chain
source                  1..214
                        mol_type = protein
                        organism = synthetic construct
SEQUENCE: 533
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSFPLTFGA GTKLEIKRTV AAPSVFIFPP 120
SDEQLKSGTA SVVCLLNNFY PREAKVQWKV DNALQSGNSQ ESVTEQDSKD STYSLSSTLT 180
LSKADYEKHK VYACEVTHQG LSSPVTKSFN RGEC                              214

SEQ ID NO: 534          moltype = AA  length = 449
FEATURE                 Location/Qualifiers
REGION                  1..449
                        note = Description of Artificial Sequence: Synthetic
                         polypeptide
REGION                  1..449
                        note = XENP34155 Chain 1 -
                         MESO-C[MSLN]_H1.3_IgG1_pI(-)_Isosteric_
                         A_/PVA_/S267K/L368D/K370S/M248L/N434S
source                  1..449
                        mol_type = protein
                        organism = synthetic construct
SEQUENCE: 534
QVQLVQSGAE VKKPGASVKV SCKASGYTFT SYWMHWVRQA PGQGLEWMGW IHPNSDNTIY  60
YEKFQGRVTM TVDKSISTAY MELSRLRSDD TAVYYCAIII TPVVPKFDYW GQGTLVTVSS 120
ASTKGPSVFP LAPSSKSTSG GTAALGCLVK DYFPEPVTVS WNSGALTSGV HTFPAVLQSS 180
GLYSLSSVVT VPSSSLGTQT YICNVNHKPS DTKVDKKVEP KSCDKTHTCP PCPAPPVAGP 240
SVFLFPPKPK DTLMISRTPE VTCVVVDVKH EDPEVKFNWY VDGVEVHNAK TKPREEEYNS 300
TYRVVSVLTV LHQDWLNGKE YKCKVSNKAL PAPIEKTISK AKGQPREPQV YTLPPSREEM 360
TKNQVSLTCD VSGFYPSDIA VEWESDGQPE NNYKTTPPVL DSDGSFFLYS KLTVDKSRWE 420
QGDVFSCSVL HEALHSHYTQ KSLSLSPGK                                    449

SEQ ID NO: 535          moltype = AA  length = 722
FEATURE                 Location/Qualifiers
REGION                  1..722
                        note = Description of Artificial Sequence: Synthetic
                         polypeptide
```

```
REGION                     1..722
                           note = XENP34155 Chain 2 -
                            MESO-C[MSLN]_H1.3_(G4S)2_[CD3]_L1.47_H1
                            .32_scFv(GKPGS)4_Fc(216)_IgG1_C220S/PVA_/S267K/S364K/E357Q/
                            M248L/N434S
source                     1..722
                           mol_type = protein
                           organism = synthetic construct
SEQUENCE: 535
QVQLVQSGAE VKKPGASVKV SCKASGYTFT SYWMHWVRQA PGQGLEWMGW IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKANNY  420
ATYYADSVKG RFTISRDDSK NTLYLQMNSL RAEDTAVYYC VRHGNFGDSY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVLHEALHSH YTQKSLSLSP  720
GK                                                                722

SEQ ID NO: 536             moltype = AA  length = 214
FEATURE                    Location/Qualifiers
REGION                     1..214
                           note = Description of Artificial Sequence: Synthetic
                            polypeptide
REGION                     1..214
                           note = XENP34155 Chain 3 - MESO-C[MSLN]_L1.14 Light Chain
source                     1..214
                           mol_type = protein
                           organism = synthetic construct
SEQUENCE: 536
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YSSFPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 537             moltype = AA  length = 449
FEATURE                    Location/Qualifiers
REGION                     1..449
                           note = Description of Artificial Sequence: Synthetic
                            polypeptide
REGION                     1..449
                           note = XENP34156 Chain 1 -
                            MESO-C[MSLN]_H1.3_IgG1_pI(-)_Isosteric_
                            A_/PVA_/S267K/L368D/K370S/M248L/N434S
source                     1..449
                           mol_type = protein
                           organism = synthetic construct
SEQUENCE: 537
QVQLVQSGAE VKKPGASVKV SCKASGYTFT SYWMHWVRQA PGQGLEWMGW IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVL HEALHSHYTQ KSLSLSPGK                                   449

SEQ ID NO: 538             moltype = AA  length = 722
FEATURE                    Location/Qualifiers
REGION                     1..722
                           note = Description of Artificial Sequence: Synthetic
                            polypeptide
REGION                     1..722
                           note = XENP34156 Chain 2 -
                            MESO-C[MSLN]_H1.3_(G4S)2_[CD3]_L1.47_H1
                            .32_scFv(GKPGS)4_Fc(216)_IgG1_C220S/PVA_/S267K/S364K/E357Q/
                            M248L/N434S
source                     1..722
                           mol_type = protein
                           organism = synthetic construct
SEQUENCE: 538
QVQLVQSGAE VKKPGASVKV SCKASGYTFT SYWMHWVRQA PGQGLEWMGW IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
```

```
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKANNY  420
ATYYADSVKG RFTISRDDSK NTLYLQMNSL RAEDTAVYYC VRHGNFGDSY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVLHEALHSH YTQKSLSLSP  720
GK                                                                722

SEQ ID NO: 539          moltype = AA  length = 214
FEATURE                 Location/Qualifiers
REGION                  1..214
                        note = Description of Artificial Sequence: Synthetic
                         polypeptide
REGION                  1..214
                        note = XENP34156 Chain 3 - MESO-C[MSLN]_L1.13 Light Chain
source                  1..214
                        mol_type = protein
                        organism = synthetic construct
SEQUENCE: 539
DIVMTQSPDS LAVSLGERAT INCKASHDVG QSVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 540          moltype = AA  length = 449
FEATURE                 Location/Qualifiers
REGION                  1..449
                        note = Description of Artificial Sequence: Synthetic
                         polypeptide
REGION                  1..449
                        note = XENP34157 Chain 1 -
                         MESO-C[MSLN]_H1.3_IgG1_pI(-)_Isosteric_
                         A_/PVA_/S267K/L368D/K370S/M248L/N434S
source                  1..449
                        mol_type = protein
                        organism = synthetic construct
SEQUENCE: 540
QVQLVQSGAE VKKPGASVKV SCKASGYTFT SYWMHWVRQA PGQGLEWMGW IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVL HEALHSHYTQ KSLSLSPGK                                    449

SEQ ID NO: 541          moltype = AA  length = 722
FEATURE                 Location/Qualifiers
REGION                  1..722
                        note = Description of Artificial Sequence: Synthetic
                         polypeptide
REGION                  1..722
                        note = XENP34157 Chain 2 -
                         MESO-C[MSLN]_H1.3_(G4S)2_[CD3]_L1.47_H1
                         .32_scFv(GKPGS)4_Fc(216)_IgG1_C220S/PVA_/S267K/S364K/E357Q/
                         M248L/N434S
source                  1..722
                        mol_type = protein
                        organism = synthetic construct
SEQUENCE: 541
QVQLVQSGAE VKKPGASVKV SCKASGYTFT SYWMHWVRQA PGQGLEWMGW IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKANNY  420
ATYYADSVKG RFTISRDDSK NTLYLQMNSL RAEDTAVYYC VRHGNFGDSY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVLHEALHSH YTQKSLSLSP  720
GK                                                                722

SEQ ID NO: 542          moltype = AA  length = 214
FEATURE                 Location/Qualifiers
REGION                  1..214
```

```
                        note = Description of Artificial Sequence: Synthetic
                         polypeptide
REGION                  1..214
                        note = XENP34157 Chain 3 - MESO-C[MSLN]_L1 Light Chain
source                  1..214
                        mol_type = protein
                        organism = synthetic construct
SEQUENCE: 542
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 543          moltype = AA   length = 449
FEATURE                 Location/Qualifiers
REGION                  1..449
                        note = Description of Artificial Sequence: Synthetic
                         polypeptide
REGION                  1..449
                        note = XENP34158 Chain 1 -
                         MESO-C[MSLN]_H1.12_IgG1_pI(-)_Isosteric
                         _A_/PVA_/S267K/L368D/K370S/M248L/N434S
source                  1..449
                        mol_type = protein
                        organism = synthetic construct
SEQUENCE: 543
QVQLVQSGAE VKKPGASVKV SCKASGYTFT SYWMHWVRQA PGQGLEWMGM IHPNSDNTIY  60
YQKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVL HEALHSHYTQ KSLSLSPGK                                    449

SEQ ID NO: 544          moltype = AA   length = 722
FEATURE                 Location/Qualifiers
REGION                  1..722
                        note = Description of Artificial Sequence: Synthetic
                         polypeptide
REGION                  1..722
                        note = XENP34158 Chain 2 -
                         MESO-C[MSLN]_H1.12_(G4S)2_[CD3]_L1.47_H
                         1.32_scFv(GKPGS)4_Fc(216)_IgG1_C220S/PVA_/S267K/S364K/E357Q
                         /M248L/N434S
source                  1..722
                        mol_type = protein
                        organism = synthetic construct
SEQUENCE: 544
QVQLVQSGAE VKKPGASVKV SCKASGYTFT SYWMHWVRQA PGQGLEWMGM IHPNSDNTIY  60
YQKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKANNY  420
ATYYADSVKG RFTISRDDSK NTLYLQMNSL RAEDTAVYYC VRHGNFGDSY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVLHEALHSH YTQKSLSLSP  720
GK                                                                722

SEQ ID NO: 545          moltype = AA   length = 214
FEATURE                 Location/Qualifiers
REGION                  1..214
                        note = Description of Artificial Sequence: Synthetic
                         polypeptide
REGION                  1..214
                        note = XENP34158 Chain 3 - MESO-C[MSLN]_L1.9 Light Chain
source                  1..214
                        mol_type = protein
                        organism = synthetic construct
SEQUENCE: 545
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

```
SEQ ID NO: 546          moltype = AA   length = 453
FEATURE                 Location/Qualifiers
REGION                  1..453
                        note = Description of Artificial Sequence: Synthetic
                        polypeptide
REGION                  1..453
                        note = XENP31455 Chain 1 -
                        MESO-A[MSLN]_H1.1_IgG1_pI(-)_Isosteric_
                        A_/PVA_/S267K/L368D/K370S
source                  1..453
                        mol_type = protein
                        organism = synthetic construct
SEQUENCE: 546
EVQLVESGGG LVQPGGSLKL SCAASGFDFS RYWMSWVRQA PGKGLEWVSE INPDSSTIVY   60
TPSVKGRFTI SRDNAKNSLY LQMNSLRAED TAVYYCARRG SHYYGYRTGY FDVWGAGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSDTKVDK KVEPKSCDKT HTCPPCPAPP  240
VAGPSVFLFP PKPKDTLMIS RTPEVTCVVV DVKHEDPEVK FNWYVDGVEV HNAKTKPREE  300
EYNSTYRVVS VLTVLHQDWL NGKEYKCKVS NKALPAPIEK TISKAKGQPR EPQVYTLPPS  360
REEMTKNQVS LTCDVSGFYP SDIAVEWESD GQPENNYKTT PPVLDSDGSF FLYSKLTVDK  420
SRWEQGDVFS CSVMHEALHN HYTQKSLSLS PGK                                453

SEQ ID NO: 547          moltype = AA   length = 726
FEATURE                 Location/Qualifiers
REGION                  1..726
                        note = Description of Artificial Sequence: Synthetic
                        polypeptide
REGION                  1..726
                        note = XENP31455 Chain 2 -
                        MESO-A[MSLN]_H1.1_(G4S)2_[CD3]_(G4S)2_I
                        gG1_C220S/PVA_/S267K/S364K/E357Q
source                  1..726
                        mol_type = protein
                        organism = synthetic construct
SEQUENCE: 547
EVQLVESGGG LVQPGGSLKL SCAASGFDFS RYWMSWVRQA PGKGLEWVSE INPDSSTIVY   60
TPSVKGRFTI SRDNAKNSLY LQMNSLRAED TAVYYCARRG SHYYGYRTGY FDVWGAGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCGGG GSGGGGSQAV  240
VTQEPSLTVS PGGTVTLTCG SSTGAVTTSN YANWVQQKPG KSPRGLIGGT NKRAPGVPAR  300
FSGSLLGGKA ALTISGAQPE DEADYYCALW YSNHWVFGGG TKLTVLGKPG SGKPGSGKPG  360
SGKPGSEVQL VESGGGLVQP GGSLRLSCAA SGFTFSTYAM NWVRQAPGKG LEWVGRIRSK  420
YNNYATYYAD SVKGRFTISR DDSKNTLYLQ MNSLRAEDTA VYYCVRHGNF GDEYVSWFAY  480
WGQGTLVTVS SGGGGSGGGG SKTHTCPPCP APPVAGPSVF LFPPKPKDTL MISRTPEVTC  540
VVVDVKHEDP EVKFNWYVDG VEVHNAKTKP REEQYNSTYR VVSVLTVLHQ DWLNGKEYKC  600
KVSNKALPAP IEKTISKAKG QPREPQVYTL PPSREQMTKN QVKLTCLVKG FYPSDIAVEW  660
ESNGQPENNY KTTPPVLDSD GSFFLYSKLT VDKSRWQQGN VFSCSVMHEA LHNHYTQKSL  720
SLSPGK                                                             726

SEQ ID NO: 548          moltype = AA   length = 213
FEATURE                 Location/Qualifiers
REGION                  1..213
                        note = Description of Artificial Sequence: Synthetic
                        polypeptide
REGION                  1..213
                        note = XENP31455 Chain 3 - MESO-A[MSLN]_L1 Light Chain
source                  1..213
                        mol_type = protein
                        organism = synthetic construct
SEQUENCE: 548
DVVLTQSPAT LSLSPGERAT LSCRASSSVS YMYWHQQKPD QSPKLLIYDT SNLASGVPVR   60
FSGSGSGTDY TLTISSLEPE DFAVYYCQQW SSYPPTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                                213

SEQ ID NO: 549          moltype = AA   length = 452
FEATURE                 Location/Qualifiers
REGION                  1..452
                        note = Description of Artificial Sequence: Synthetic
                        polypeptide
REGION                  1..452
                        note = XENP31456 Chain 1 -
                        MESO-B[MSLN]_H0_IgG1_pI(-)_Isosteric_A_
                        /PVA_/S267K/L368D/K370S
source                  1..452
                        mol_type = protein
                        organism = synthetic construct
SEQUENCE: 549
QVQLQQSGPG LVTPSQTLSL TCAISGDSVS SNSATWNWIR QSPSRGLEWL GRTYYRSKWY   60
```

```
NDYAVSVKSR MSINPDTSKN QFSLQLNSVT PEDTAVYYCA RGMMTYYYGM DVWGQGTTVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSDTKVDKK VEPKSCDKTH TCPPCPAPPV   240
AGPSVFLFPP KPKDTLMISR TPEVTCVVVD VKHEDPEVKF NWYVDGVEVH NAKTKPREEE   300
YNSTYRVVSV LTVLHQDWLN GKEYKCKVSN KALPAPIEKT ISKAKGQPRE PQVYTLPPSR   360
EEMTKNQVSL TCDVSGFYPS DIAVEWESDG QPENNYKTTP PVLDSDGSFF LYSKLTVDKS   420
RWEQGDVFSC SVMHEALHNH YTQKSLSLSP GK                                 452

SEQ ID NO: 550          moltype = AA  length = 725
FEATURE                 Location/Qualifiers
REGION                  1..725
                        note = Description of Artificial Sequence: Synthetic
                         polypeptide
REGION                  1..725
                        note = XENP31456 Chain 2 -
                         MESO-B[MSLN]_H0_(G4S)2_[CD3]_(G4S)2_IgG
                         1_C220S/PVA_/S267K/S364K/E357Q
source                  1..725
                        mol_type = protein
                        organism = synthetic construct
SEQUENCE: 550
QVQLQQSGPG LVTPSQTLSL TCAISGDSVS SNSATWNWIR QSPSRGLEWL GRTYYRSKWY   60
NDYAVSVKSR MSINPDTSKN QFSLQLNSVT PEDTAVYYCA RGMMTYYYGM DVWGQGTTVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCGGGG SGGGGSQAVV   240
TQEPSLTVSP GGTVTLTCGS STGAVTTSNY ANWVQQKPGQ SPRGLIGGTN KRAPGVPARF   300
SGSLLGGKAA LTISGAQPED EADYYCALWY SNHWVFGGGT KLTVLGKPGS GKPGSGKPGS   360
GKPGSEVQLV ESGGGLVQPG GSLRLSCAAS GFTFSTYAMN WVRQAPGKGL EWVGRIRSKY   420
NNYATYYADS VKGRFTISRD DSKNTLYLQM NSLRAEDTAV YYCVRHGNFG DEYVSWFAYW   480
GQGTLVTVSS GGGGSGGGGS KTHTCPPCPA PPVAGPSVFL FPPKPKDTLM ISRTPEVTCV   540
VVDVKHEDPE VKFNWYVDGV EVHNAKTKPR EEQYNSTYRV VSVLTVLHQD WLNGKEYKCK   600
VSNKALPAPI EKTISKAKGQ PREPQVYTLP PSREQMTKNQ VKLTCLVGKF YPSDIAVEWE   660
SNGQPENNYK TTPPVLDSDG SFFLYSKLTV DKSRWQQGNV FSCSVMHEAL HNHYTQKSLS   720
LSPGK                                                              725

SEQ ID NO: 551          moltype = AA  length = 221
FEATURE                 Location/Qualifiers
REGION                  1..221
                        note = Description of Artificial Sequence: Synthetic
                         polypeptide
REGION                  1..221
                        note = XENP31456 Chain 3 - MESO-B[MSLN]_L0 Light Chain
source                  1..221
                        mol_type = protein
                        organism = synthetic construct
SEQUENCE: 551
QPVLTQSSSL SASPGASASL TCTLRSGINV GPYRIYWYQQ KPGSPPQYLL NYKSDSDKQQ   60
GSGVPSRFSG SKDASANAGV LLISGLRSED EADYYCMIWH SSAAVFGGGT QLTVLGQPKA   120
APSVTLFPPS SEELQANKAT LVCLISDFYP GAVTVAWKAD SSPVKAGVET TTPSKQSNNK   180
YAASSYLSLT PEQWKSHRSY SCQVTHEGST VEKTVAPTEC S                       221

SEQ ID NO: 552          moltype = AA  length = 453
FEATURE                 Location/Qualifiers
REGION                  1..453
                        note = Description of Artificial Sequence: Synthetic
                         polypeptide
REGION                  1..453
                        note = XENP32249 Chain 1 -
                         MESO-A[MSLN]_H1.1_IgG1_pI(-)_Isosteric_
                         A_/PVA_/S267K/L368D/K370S
source                  1..453
                        mol_type = protein
                        organism = synthetic construct
SEQUENCE: 552
EVQLVESGGG LVQPGGSLKL SCAASGFDFS RYWMSWVRQA PGKGLEWVSE INPDSSTIVY   60
TPSVKGRFTI SRDNAKNSLY LQMNSLRAED TAVYYCARRG SHYYGYRTGY FDVWGAGTTV   120
TVSSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSDTKVDK KVEPKSCDKT HTCPPCPAPP   240
VAGPSVFLFP PKPKDTLMIS RTPEVTCVVV DVKHEDPEVK FNWYVDGVEV HNAKTKPREE   300
EYNSTYRVVS VLTVLHQDWL NGKEYKCKVS NKALPAPIEK TISKAKGQPR EPQVYTLPPS   360
REEMTKNQVS LTCDVSGFYP SDIAVEWESD GQPENNYKTT PPVLDSDGSF FLYSKLTVDK   420
SRWEQGDVFS CSVMHEALHN HYTQKSLSLS PGK                                453

SEQ ID NO: 553          moltype = AA  length = 722
FEATURE                 Location/Qualifiers
REGION                  1..722
                        note = Description of Artificial Sequence: Synthetic
                         polypeptide
REGION                  1..722
```

```
                        note = XENP32249 Chain 2 -
                        MESO-A[MSLN]_H1.1_(G4S)2_[CD3]_L1.47_H1
                        .89_scFv(GKPGS)4_Fc(216)_IgG1_C220S/PVA_/S267K/S364K/E357Q
source                  1..722
                        mol_type = protein
                        organism = synthetic construct
SEQUENCE: 553
EVQLVESGGG LVQPGGSLKL SCAASGFDFS RYWMSWVRQA PGKGLEWVSE INPDSSTIVY  60
TPSVKGRFTI SRDNAKNSLY LQMNSLRAED TAVYYCARRG SHYYGYRTGY FDVWGAGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCGGG GSGGGGSQAV  240
VTQEPSLTVS PGGTVTLTCG SSTGAVTTSN YANWVQQKPG KSPRGLIGGT NKRAPGVPAR  300
FSGSLLGGKA ALTISGAQPE DEADYYCALW YSNHWVFGGG TKLTVLGKPG SGKPGSGKPG  360
SGKPGSEVQL VESGGGLVQP GGSLRLSCAA SGFTFSTYAM NWVRQAPGKG LEWVGRIRSK  420
YNNYATYYAD SVKGRFTISR DDSKNTLYLQ MNSLRAEDTA VYYCVRHGNF GDEYVSWFAY  480
WGQGTLVTVS SEPKSSDKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                                722

SEQ ID NO: 554          moltype = AA  length = 213
FEATURE                 Location/Qualifiers
REGION                  1..213
                        note = Description of Artificial Sequence: Synthetic
                        polypeptide
REGION                  1..213
                        note = XENP32249 Chain 3 - MESO-A[MSLN]_L1 Light Chain
source                  1..213
                        mol_type = protein
                        organism = synthetic construct
SEQUENCE: 554
DVVLTQSPAT LSLSPGERAT LSCRASSSVS YMYWHQQKPD QSPKLLIYDT SNLASGVPVR  60
FSGSGSGTDY TLTISSLEPE DFAVYYCQQW SSYPPTGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 555          moltype = AA  length = 452
FEATURE                 Location/Qualifiers
REGION                  1..452
                        note = Description of Artificial Sequence: Synthetic
                        polypeptide
REGION                  1..452
                        note = XENP32250 Chain 1 -
                        MESO-B[MSLN]_H0_IgG1_pI(-)_Isosteric_A_
                        /PVA_/S267K/L368D/K370S
source                  1..452
                        mol_type = protein
                        organism = synthetic construct
SEQUENCE: 555
QVQLQQSGPG LVTPSQTLSL TCAISGDSVS SNSATWNWIR QSPSRGLEWL GRTYYRSKWY  60
NDYAVSVKSR MSINPDTSKN QFSLQLNSVT PEDTAVYYCA RGMMTYYYGM DVWGQGTTVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSDTKVDKK VEPKSCDKTH TCPPCPAPPV  240
AGPSVFLFPP KPKDTLMISR TPEVTCVVVD VKHEDPEVKF NWYVDGVEVH NAKTKPREEE  300
YNSTYRVVSV LTVLHQDWLN GKEYKCKVSN KALPAPIEKT ISKAKGQPRE PQVYTLPPSR  360
EEMTKNQVSL TCDVSGFYPS DIAVEWESDG QPENNYKTTP PVLDSDGSFF LYSKLTVDKS  420
RWEQGDVFSC SVMHEALHNH YTQKSLSLSP GK                                452

SEQ ID NO: 556          moltype = AA  length = 721
FEATURE                 Location/Qualifiers
REGION                  1..721
                        note = Description of Artificial Sequence: Synthetic
                        polypeptide
REGION                  1..721
                        note = XENP32250 Chain 2 -
                        MESO-B[MSLN]_H0_(G4S)2_[CD3]_L1.47_H1.8
                        9_scFv(GKPGS)4_Fc(216)_IgG1_C220S/PVA_/S267K/S364K/E357Q
source                  1..721
                        mol_type = protein
                        organism = synthetic construct
SEQUENCE: 556
QVQLQQSGPG LVTPSQTLSL TCAISGDSVS SNSATWNWIR QSPSRGLEWL GRTYYRSKWY  60
NDYAVSVKSR MSINPDTSKN QFSLQLNSVT PEDTAVYYCA RGMMTYYYGM DVWGQGTTVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCGGGG SGGGGSQAVV  240
TQEPSLTVSP GGTVTLTCGS STGAVTTSNY ANWVQQKPGK SPRGLIGGTN KRAPGVPARF  300
SGSLLGGKAA LTISGAQPED EADYCALWY SNHWVFGGGT KLTVLGKPGS GKPGSGKPGS  360
GKPGSEVQLV ESGGGLVQPG GSLRLSCAAS GFTFSTYAMN WVRQAPGKGL EWVGRIRSKY  420
```

-continued

```
NNYATYYADS VKGRFTISRD DSKNTLYLQM NSLRAEDTAV YYCVRHGNFG DEYVSWFAYW   480
GQGTLVTVSS EPKSSDKTHT CPPCPAPPVA GPSVFLFPPK PKDTLMISRT PEVTCVVVDV   540
KHEDPEVKFN WYVDGVEVHN AKTKPREEQY NSTYRVVSVL TVLHQDWLNG KEYKCKVSNK   600
ALPAPIEKTI SKAKGQPREP QVYTLPPSRE QMTKNQVKLT CLVKGFYPSD IAVEWESNGQ   660
PENNYKTTPP VLDSDGSFFL YSKLTVDKSR WQQGNVFSCS VMHEALHNHY TQKSLSLSPG   720
K                                                                  721

SEQ ID NO: 557          moltype = AA  length = 221
FEATURE                 Location/Qualifiers
REGION                  1..221
                        note = Description of Artificial Sequence: Synthetic
                         polypeptide
REGION                  1..221
                        note = XENP32250 Chain 3 - MESO-B[MSLN]_L0 Light Chain
source                  1..221
                        mol_type = protein
                        organism = synthetic construct
SEQUENCE: 557
QPVLTQSSSL SASPGASASL TCTLRSGINV GPYRIYWYQQ KPGSPPQYLL NYKSDSDKQQ   60
GSGVPSRFSG SKDASANAGV LLISGLRSED EADYYCMIWH SSAAVFGGGT QLTVLGQPKA   120
APSVTLFPPS SEELQANKAT LVCLISDFYP GAVTVAWKAD SSPVKAGVET TTPSKQSNNK   180
YAASSYLSLT PEQWKSHRSY SCQVTHEGST VEKTVAPTEC S                      221

SEQ ID NO: 558          moltype = AA  length = 449
FEATURE                 Location/Qualifiers
REGION                  1..449
                        note = Description of Artificial Sequence: Synthetic
                         polypeptide
REGION                  1..449
                        note = XENP32251 Chain 1 -
                         MESO-C[MSLN]_H1_IgG1_pI(-)_Isosteric_A_
                         /PVA_/S267K/L368D/K370S
source                  1..449
                        mol_type = protein
                        organism = synthetic construct
SEQUENCE: 558
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                    449

SEQ ID NO: 559          moltype = AA  length = 718
FEATURE                 Location/Qualifiers
REGION                  1..718
                        note = Description of Artificial Sequence: Synthetic
                         polypeptide
REGION                  1..718
                        note = XENP32251 Chain 2 -
                         MESO-C[MSLN]_H1_[CD3]_L1.47_H1.89_scFv(
                         GKPGS)4_Fc(216)_IgG1_C220S/PVA_/S267K/S364K/E357Q
source                  1..718
                        mol_type = protein
                        organism = synthetic construct
SEQUENCE: 559
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCGGGGSGG GGSQAVVTQE   240
PSLTVSPGGT VTLTCGSSTG AVTTSNYANW VQQKPGSPGR GLIGGTNKRA PGVPARFSGS   300
LLGGKAALTI SGAQPEDEAD YYCALWYSNH WVFGGGTKLT VLGKPGSGKP GSGKPGSGKP   360
GSEVQLVESG GGLVQPGGSL RLSCAASGFT FSTYAMNWVR QAPGKGLEWV GRIRSKYNNY   420
ATYYADSVKG RFTISRDDSK NTLYLQMNSL RAEDTAVYYC VRHGNFGDEY VSWFAYWGQG   480
TLVTVSSEPK SSDKTHTCPP CPAPPVAGPS VFLFPPKPKD TLMISRTPEV TCVVVDVKHE   540
DPEVKFNWYV DGVEVHNAKT KPREEQYNST YRVVSVLTVL HQDWLNGKEY KCKVSNKALP   600
APIEKTISKA KGQPREPQVY TLPPSREQMT KNQVKLTCLV KGFYPSDIAV EWESNGQPEN   660
NYKTTPPVLD SDGSFFLYSK LTVDKSRWQQ GNVFSCSVMH EALHNHYTQK SLSLSPGK    718

SEQ ID NO: 560          moltype = AA  length = 214
FEATURE                 Location/Qualifiers
REGION                  1..214
                        note = Description of Artificial Sequence: Synthetic
                         polypeptide
REGION                  1..214
                        note = XENP32251 Chain 3 - MESO-C[MSLN]_L1 Light Chain
source                  1..214
```

-continued

```
                         mol_type = protein
                         organism = synthetic construct
SEQUENCE: 560
DIVMTQSPDS LAVSLGERAT INCKASHDVG TSVAWYQQKP GQSPKLLIYW ASTRHTGVPD    60
RFTGSGSGTD FTLTISSLQA EDVAVYFCQQ YSSYPLTFGA GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 561         moltype = AA  length = 449
FEATURE                Location/Qualifiers
REGION                 1..449
                       note = Description of Artificial Sequence: Synthetic
                        polypeptide
REGION                 1..449
                       note = XENP32746 Chain 1 -
                        MESO-C[MSLN]_H1_IgG1_pI(-)_Isosteric_A_
                        /PVA_/S267K/L368D/K370S
source                 1..449
                       mol_type = protein
                       organism = synthetic construct
SEQUENCE: 561
QVQLVQSGAE VKKPGASVKV SCKASGYTFT SYWMHWVRQA PGQGLEWMGM IHPNSDNTIY    60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                     449

SEQ ID NO: 562         moltype = AA  length = 718
FEATURE                Location/Qualifiers
REGION                 1..718
                       note = Description of Artificial Sequence: Synthetic
                        polypeptide
REGION                 1..718
                       note = XENP32746 Chain 2 -
                        MESO-C[MSLN]_H1_(G4S)2_[CD3]_L1.47_H1.8
                        9_scFv(GKPGS)4_Fc(216)_IgG1_C220S/PVA_/S267K/S364K/E357Q
source                 1..718
                       mol_type = protein
                       organism = synthetic construct
SEQUENCE: 562
QVQLVQSGAE VKKPGASVKV SCKASGYTFT SYWMHWVRQA PGQGLEWMGM IHPNSDNTIY    60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCGGGGSGG GGSQAVVTQE   240
PSLTVSPGGT VTLTCGSSTG AVTTSNYANW VQQKPGKSPR GLIGGTNKRA PGVPARFSGS   300
LLGGKAALTI SGAQPEDEAD YYCALWYSNH WVFGGGTKLT VLGKPGSGKP GSGKPGSGKP   360
GSEVQLVESG GGLVQPGGSL RLSCAASGFT FSTYAMNWVR QAPGKGLEWV GRIRSKYNNY   420
ATYYADSVKG RFTISRDDSK NTLYLQMNSL RAEDTAVYYC VRHGNFGDEY VSWFAYWGQG   480
TLVTVSSEPK SSDKTHTCPP CPAPPVAGPS VFLFPPKPKD TLMISRTPEV TCVVVDVKHE   540
DPEVKFNWYV DGVEVHNAKT KPREEQYNST YRVVSVLTVL HQDWLNGKEY KCKVSNKALP   600
APIEKTISKA KGQPREPQVY TLPPSREQMT KNQVKLTCLV KGFYPSDIAV EWESNGQPEN   660
NYKTTPPVLD SDGSFFLYSK LTVDKSRWQQ GNVFSCSVMH EALHNHYTQK SLSLSPGK    718

SEQ ID NO: 563         moltype = AA  length = 214
FEATURE                Location/Qualifiers
REGION                 1..214
                       note = Description of Artificial Sequence: Synthetic
                        polypeptide
REGION                 1..214
                       note = XENP32746 Chain 3 - MESO-C[MSLN]_L1.3 Light Chain
source                 1..214
                       mol_type = protein
                       organism = synthetic construct
SEQUENCE: 563
DIVMTQSPDS LAVSLGERAT INCKASHSVG TSVAWYQQKP GQSPKLLIYW ASTRHTGVPD    60
RFTGSGSGTD FTLTISSLQA EDVAVYFCQQ YSSYPLTFGA GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 564         moltype = AA  length = 449
FEATURE                Location/Qualifiers
REGION                 1..449
                       note = Description of Artificial Sequence: Synthetic
                        polypeptide
REGION                 1..449
                       note = XENP32749 Chain 1 -
```

```
                          MESO-C[MSLN]_H1_IgG1_pI(-)_Isosteric_A_
                          /PVA_/S267K/L368D/K370S
source                    1..449
                          mol_type = protein
                          organism = synthetic construct
SEQUENCE: 564
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 565            moltype = AA  length = 718
FEATURE                   Location/Qualifiers
REGION                    1..718
                          note = Description of Artificial Sequence: Synthetic
                          polypeptide
REGION                    1..718
                          note = XENP32749 Chain 2 - MESO
                          C[MSLN]_H1_(G4S)2_[CD3]_L1.47_H1.8
                          9_scFv(GKPGS)4_Fc(216)_IgG1_C220S/PVA_/S267K/S364K/E357Q
source                    1..718
                          mol_type = protein
                          organism = synthetic construct
SEQUENCE: 565
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKYNNY  420
ATYYADSVKG RFTISRDDSK NTLYLQMNSL RAEDTAVYYC VRHGNFGDEY VSWFAYWGQG  480
TLVTVSSEPK SSDKTHTCPP CPAPPVAGPS VFLFPPKPKD TLMISRTPEV TCVVVDVKHE  540
DPEVKFNWYV DGVEVHNAKT KPREEQYNST YRVVSVLTVL HQDWLNGKEY KCKVSNKALP  600
APIEKTISKA KGQPREPQVY TLPPSREQMT KNQVKLTCLV KGFYPSDIAV EWESNGQPEN  660
NYKTTPPVLD SDGSFFLYSK LTVDKSRWQQ GNVFSCSVMH EALHNHYTQK SLSLSPGK    718

SEQ ID NO: 566            moltype = AA  length = 214
FEATURE                   Location/Qualifiers
REGION                    1..214
                          note = Description of Artificial Sequence: Synthetic
                          polypeptide
REGION                    1..214
                          note = XENP32749 Chain 3 - MESO-C[MSLN]_L1.4 Light Chain
source                    1..214
                          mol_type = protein
                          organism = synthetic construct
SEQUENCE: 566
DIVMTQSPDS LAVSLGERAT INCKASHDVL TSVAWYQQKP GQSPKLLIYW ASTRHTGVPD   60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 567            moltype = AA  length = 449
FEATURE                   Location/Qualifiers
REGION                    1..449
                          note = Description of Artificial Sequence: Synthetic
                          polypeptide
REGION                    1..449
                          note = XENP32752 Chain 1 -
                          MESO-C[MSLN]_H1_IgG1_pI(-)_Isosteric_A_
                          /PVA_/S267K/L368D/K370S
source                    1..449
                          mol_type = protein
                          organism = synthetic construct
SEQUENCE: 567
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449
```

```
SEQ ID NO: 568          moltype = AA  length = 718
FEATURE                 Location/Qualifiers
REGION                  1..718
                        note = Description of Artificial Sequence: Synthetic
                         polypeptide
REGION                  1..718
                        note = XENP32752 Chain 2 -
                         MESO-C[MSLN]_H1_(G4S)2_[CD3]_L1.47_H1.8
                         9_scFv(GKPGS)4_Fc(216)_IgG1_C220S/PVA_/S267K/S364K/E357Q
source                  1..718
                        mol_type = protein
                        organism = synthetic construct
SEQUENCE: 568
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKYNNY  420
ATYYADSVKG RFTISRDDSK NTLYLQMNSL RAEDTAVYYC VRHGNFGDEY VSWFAYWGQG  480
TLVTVSSEPK SSDKTHTCPP CPAPPVAGPS VFLFPPKPKD TLMISRTPEV TCVVVDVKHE  540
DPEVKFNWYV DGVEVHNAKT KPREEQYNST YRVVSVLTVL HQDWLNGKEY KCKVSNKALP  600
APIEKTISKA KGQPREPQVY TLPPSREQMT KNQVKLTCLV KGFYPSDIAV EWESNGQPEN  660
NYKTTPPVLD SDGSFFLYSK LTVDKSRWQQ GNVFSCSVMH EALHNHYTQK SLSLSPGK    718

SEQ ID NO: 569          moltype = AA  length = 214
FEATURE                 Location/Qualifiers
REGION                  1..214
                        note = Description of Artificial Sequence: Synthetic
                         polypeptide
REGION                  1..214
                        note = XENP32752 Chain 3 - MESO-C[MSLN]_L1.5 Light Chain
source                  1..214
                        mol_type = protein
                        organism = synthetic construct
SEQUENCE: 569
DIVMTQSPDS LAVSLGERAT INCKASHDVG TYVAWYQQKP GQSPKLLIYW ASTRHTGVPD   60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 570          moltype = AA  length = 449
FEATURE                 Location/Qualifiers
REGION                  1..449
                        note = Description of Artificial Sequence: Synthetic
                         polypeptide
REGION                  1..449
                        note = XENP32853 Chain 1 -
                         MESO-C[MSLN]_H1_IgG1_pI(-)_Isosteric_A_
                         /PVA_/S267K/L368D/K370S
source                  1..449
                        mol_type = protein
                        organism = synthetic construct
SEQUENCE: 570
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                     449

SEQ ID NO: 571          moltype = AA  length = 718
FEATURE                 Location/Qualifiers
REGION                  1..718
                        note = Description of Artificial Sequence: Synthetic
                         polypeptide
REGION                  1..718
                        note = XENP32853 Chain 2 -
                         MESO-C[MSLN]_H1_(G4S)2_[CD3]_L1.47_H1.8
                         9_scFv(GKPGS)4_Fc(216)_IgG1_C220S/PVA_/S267K/S364K/E357Q
source                  1..718
                        mol_type = protein
                        organism = synthetic construct
SEQUENCE: 571
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS  120
```

```
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCGGGGSGG GGSQAVVTQE   240
PSLTVSPGGT VTLTCGSSTG AVTTSNYANW VQQKPGKSPR GLIGGTNKRA PGVPARFSGS   300
LLGGKAALTI SGAQPEDEAD YYCALWYSNH WVFGGGTKLT VLGKPGSGKP GSGKPGSGKP   360
GSEVQLVESG GGLVQPGGSL RLSCAASGFT FSTYAMNWVR QAPGKGLEWV GRIRSKYNNY   420
ATYYADSVKG RFTISRDDSK NTLYLQMNSL RAEDTAVYYC VRHGNFGDEY VSWFAYWGQG   480
TLVTVSSEPK SSDKTHTCPP CPAPPVAGPS VFLFPPKPKD TLMISRTPEV TCVVVDVKHE   540
DPEVKFNWYV DGVEVHNAKT KPREEQYNST YRVVSVLTVL HQDWLNGKEY KCKVSNKALP   600
APIEKTISKA KGQPREPQVY TLPPSREQMT KNQVKLTCLV KGFYPSDIAV EWESNGQPEN   660
NYKTTPPVLD SDGSFFLYSK LTVDKSRWQQ GNVFSCSVMH EALHNHYTQK SLSLSPGK    718

SEQ ID NO: 572              moltype = AA  length = 214
FEATURE                    Location/Qualifiers
REGION                     1..214
                           note = Description of Artificial Sequence: Synthetic
                            polypeptide
REGION                     1..214
                           note = XENP32853 Chain 3 - MESO-C[MSLN]_L1.9 Light Chain
source                     1..214
                           mol_type = protein
                           organism = synthetic construct
SEQUENCE: 572
DIVMTQSPDS LAVSLGERAT INCKASHDVG TSVAWYQQKP GQSPKLLIYW ASTRHTGVPD    60
RFTGSGSGTD FTLTISSLQA EDVAVYFCQQ YYSYPLTFGA GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                                214

SEQ ID NO: 573              moltype = AA  length = 718
FEATURE                    Location/Qualifiers
REGION                     1..718
                           note = Description of Artificial Sequence: Synthetic
                            polypeptide
REGION                     1..718
                           note = XENP33974 Chain 1 -
                            MESO-C[MSLN]_H1.3_IgG1_pI(-)_Isosteric_
                            A_PVA_/S267K/L368D/K370S
source                     1..718
                           mol_type = protein
                           organism = synthetic construct
SEQUENCE: 573
QVQLVQSGAE VKKPGASVKV SCKASGYTFT SYWMHWVRQA PGQGLEWMGW IHPNSDNTIY    60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCGGGGSGG GGSQAVVTQE   240
PSLTVSPGGT VTLTCGSSTG AVTTSNYANW VQQKPGKSPR GLIGGTNKRA PGVPARFSGS   300
LLGGKAALTI SGAQPEDEAD YYCALWYSNH WVFGGGTKLT VLGKPGSGKP GSGKPGSGKP   360
GSEVQLVESG GGLVQPGGSL RLSCAASGFT FSTYAMNWVR QAPGKGLEWV GRIRSKYNNY   420
ATYYADSVKG RFTISRDDSK NTLYLQMNSL RAEDTAVYYC VRHGNFGDEY VSWFAYWGQG   480
TLVTVSSEPK SSDKTHTCPP CPAPPVAGPS VFLFPPKPKD TLMISRTPEV TCVVVDVKHE   540
DPEVKFNWYV DGVEVHNAKT KPREEQYNST YRVVSVLTVL HQDWLNGKEY KCKVSNKALP   600
APIEKTISKA KGQPREPQVY TLPPSREQMT KNQVKLTCLV KGFYPSDIAV EWESNGQPEN   660
NYKTTPPVLD SDGSFFLYSK LTVDKSRWQQ GNVFSCSVMH EALHNHYTQK SLSLSPGK    718

SEQ ID NO: 574              moltype = AA  length = 449
FEATURE                    Location/Qualifiers
REGION                     1..449
                           note = Description of Artificial Sequence: Synthetic
                            polypeptide
REGION                     1..449
                           note = XENP33974 Chain 2 -
                            MESO-C[MSLN]_H1.3_(G4S)2_[CD3]_L1.47_H1
                            .89_scFv(GKPGS)4_Fc(216)_IgG1_PVA_/S267K/S364K/E357Q
source                     1..449
                           mol_type = protein
                           organism = synthetic construct
SEQUENCE: 574
QVQLVQSGAE VKKPGASVKV SCKASGYTFT SYWMHWVRQA PGQGLEWMGW IHPNSDNTIY    60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                     449

SEQ ID NO: 575              moltype = AA  length = 214
FEATURE                    Location/Qualifiers
REGION                     1..214
                           note = Description of Artificial Sequence: Synthetic
```

-continued

```
                            polypeptide
REGION                      1..214
                            note = XENP33974 Chain 3 - MESO-C[MSLN]_L1.14 Light Chain
source                      1..214
                            mol_type = protein
                            organism = synthetic construct
SEQUENCE: 575
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSFPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 576              moltype = AA  length = 718
FEATURE                     Location/Qualifiers
REGION                      1..718
                            note = Description of Artificial Sequence: Synthetic
                             polypeptide
REGION                      1..718
                            note = XENP33975 Chain 1 -
                             MESO-C[MSLN]_H1_IgG1_pI(-)_Isosteric_A_
                             PVA_/S267K/L368D/K370S
source                      1..718
                            mol_type = protein
                            organism = synthetic construct
SEQUENCE: 576
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKYNNY  420
ATYYADSVKG RFTISRDDSK NTLYLQMNSL RAEDTAVYYC VRHGNFGDEY VSWFAYWGQG  480
TLVTVSSEPK SSDKTHTCPP CPAPPVAGPS VFLFPPKPKD TLMISRTPEV TCVVVDVKHE  540
DPEVKFNWYV DGVEVHNAKT KPREEQYNST YRVVSVLTVL HQDWLNGKEY KCKVSNKALP  600
APIEKTISKA KGQPREPQVY TLPPSREQMT KNQVKLTCLV KGFYPSDIAV EWESNGQPEN  660
NYKTTPPVLD SDGSFFLYSK LTVDKSRWQQ GNVFSCSVMH EALHNHYTQK SLSLSPGK    718

SEQ ID NO: 577              moltype = AA  length = 449
FEATURE                     Location/Qualifiers
REGION                      1..449
                            note = Description of Artificial Sequence: Synthetic
                             polypeptide
REGION                      1..449
                            note = XENP33975 Chain 2 -
                             MESO-C[MSLN]_H1_(G4S)2_[CD3]_L1.47_H1.8
                             9_scFv(GKPGS)4_Fc(216)_IgG1_PVA_/S267K/S364K/E357Q
source                      1..449
                            mol_type = protein
                            organism = synthetic construct
SEQUENCE: 577
QVQLVQSGAE VKKPGASVKV SCKASGYTFT SYWMHWVRQA PGQGLEWMGM IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                   449

SEQ ID NO: 578              moltype = AA  length = 214
FEATURE                     Location/Qualifiers
REGION                      1..214
                            note = Description of Artificial Sequence: Synthetic
                             polypeptide
REGION                      1..214
                            note = XENP33975 Chain 3 - MESO-C[MSLN]_L1.20 Light Chain
source                      1..214
                            mol_type = protein
                            organism = synthetic construct
SEQUENCE: 578
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YYSFPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 579              moltype = AA  length = 718
FEATURE                     Location/Qualifiers
REGION                      1..718
```

-continued

```
                              note = Description of Artificial Sequence: Synthetic
                               polypeptide
REGION                        1..718
                              note = XENP33976 Chain 1 -
                               MESO-C[MSLN]_H1.12_IgG1_pI(-)_Isosteric
                               _A_PVA_/S267K/L368D/K370S
source                        1..718
                              mol_type = protein
                              organism = synthetic construct
SEQUENCE: 579
QVQLVQSGAE VKKPGASVKV SCKASGYTFT SYWMHWVRQA PGQGLEWMGM IHPNSDNTIY  60
YQKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKYNNY  420
ATYYADSVKG RFTISRDDSK NTLYLQMNSL RAEDTAVYYC VRHGNFGDEY VSWFAYWGQG  480
TLVTVSSEPK SSDKTHTCPP CPAPPVAGPS VFLFPPKPKD TLMISRTPEV TCVVVDVKHE  540
DPEVKFNWYV DGVEVHNAKT KPREEQYNST YRVVSVLTVL HQDWLNGKEY KCKVSNKALP  600
APIEKTISKA KGQPREPQVY TLPPSREQMT KNQVKLTCLV KGFYPSDIAV EWESNGQPEN  660
NYKTTPPVLD SDGSFFLYSK LTVDKSRWQQ GNVFSCSVMH EALHNHYTQK SLSLSPGK    718
```

```
SEQ ID NO: 580              moltype = AA  length = 449
FEATURE                     Location/Qualifiers
REGION                      1..449
                            note = Description of Artificial Sequence: Synthetic
                             polypeptide
REGION                      1..449
                            note = XENP33976 Chain 2 -
                             MESO-C[MSLN]_H1.12_(G4S)2_[CD3]_L1.47_H
                             1.89_scFv(GKPGS)4_Fc(216)_IgG1_PVA_/S267K/S364K/E357Q
source                      1..449
                            mol_type = protein
                            organism = synthetic construct
SEQUENCE: 580
QVQLVQSGAE VKKPGASVKV SCKASGYTFT SYWMHWVRQA PGQGLEWMGM IHPNSDNTIY  60
YQKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                     449
```

```
SEQ ID NO: 581              moltype = AA  length = 214
FEATURE                     Location/Qualifiers
REGION                      1..214
                            note = Description of Artificial Sequence: Synthetic
                             polypeptide
REGION                      1..214
                            note = XENP33976 Chain 3 - MESO-C[MSLN]_L1.20 Light Chain
source                      1..214
                            mol_type = protein
                            organism = synthetic construct
SEQUENCE: 581
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YYSFPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

```
SEQ ID NO: 582              moltype = AA  length = 718
FEATURE                     Location/Qualifiers
REGION                      1..718
                            note = Description of Artificial Sequence: Synthetic
                             polypeptide
REGION                      1..718
                            note = XENP33977 Chain 1 -
                             MESO-C[MSLN]_H1.3_IgG1_pI(-)_Isosteric_
                             A_PVA_/S267K/L368D/K370S
source                      1..718
                            mol_type = protein
                            organism = synthetic construct
SEQUENCE: 582
QVQLVQSGAE VKKPGASVKV SCKASGYTFT SYWMHWVRQA PGQGLEWMGW IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
```

-continued

```
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKYNNY  420
ATYYADSVKG RFTISRDDSK NTLYLQMNSL RAEDTAVYYC VRHGNFGDEY VSWFAYWGQG  480
TLVTVSSEPK SSDKTHTCPP CPAPPVAGPS VFLFPPKPKD TLMISRTPEV TCVVVDVKHE  540
DPEVKFNWYV DGVEVHNAKT KPREEQYNST YRVVSVLTVL HQDWLNGKEY KCKVSNKALP  600
APIEKTISKA KGQPREPQVY TLPPSREQMT KNQVKLTCLV KGFYPSDIAV EWESNGQPEN  660
NYKTTPPVLD SDGSFFLYSK LTVDKSRWQQ GNVFSCSVMH EALHNHYTQK SLSLSPGK    718
```

```
SEQ ID NO: 583             moltype = AA  length = 449
FEATURE                    Location/Qualifiers
REGION                     1..449
                           note = Description of Artificial Sequence: Synthetic
                            polypeptide
REGION                     1..449
                           note = XENP33977 Chain 2 -
                            MESO-C[MSLN]_H1.3_(G4S)2_[CD3]_L1.47_H1
                            .89_scFv(GKPGS)4_Fc(216)_IgG1_PVA_/S267K/S364K/E357Q
source                     1..449
                           mol_type = protein
                           organism = synthetic construct
SEQUENCE: 583
QVQLVQSGAE VKKPGASVKV SCKASGYTFT SYWMHWVRQA PGQGLEWMGW IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY DGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449
```

```
SEQ ID NO: 584             moltype = AA  length = 214
FEATURE                    Location/Qualifiers
REGION                     1..214
                           note = Description of Artificial Sequence: Synthetic
                            polypeptide
REGION                     1..214
                           note = XENP33977 Chain 3 - MESO-C[MSLN]_L1.13 Light Chain
source                     1..214
                           mol_type = protein
                           organism = synthetic construct
SEQUENCE: 584
DIVMTQSPDS LAVSLGERAT INCKASHDVG QSVAWYQQKP GQSPKLLIYW ASTRHTGVPD  60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

```
SEQ ID NO: 585             moltype = AA  length = 718
FEATURE                    Location/Qualifiers
REGION                     1..718
                           note = Description of Artificial Sequence: Synthetic
                            polypeptide
REGION                     1..718
                           note = XENP33978 Chain 1 -
                            MESO-C[MSLN]_H1.3_IgG1_pI(-)_Isosteric_
                            A_PVA_/S267K/L368D/K370S
source                     1..718
                           mol_type = protein
                           organism = synthetic construct
SEQUENCE: 585
QVQLVQSGAE VKKPGASVKV SCKASGYTFT SYWMHWVRQA PGQGLEWMGW IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKYNNY  420
ATYYADSVKG RFTISRDDSK NTLYLQMNSL RAEDTAVYYC VRHGNFGDEY VSWFAYWGQG  480
TLVTVSSEPK SSDKTHTCPP CPAPPVAGPS VFLFPPKPKD TLMISRTPEV TCVVVDVKHE  540
DPEVKFNWYV DGVEVHNAKT KPREEQYNST YRVVSVLTVL HQDWLNGKEY KCKVSNKALP  600
APIEKTISKA KGQPREPQVY TLPPSREQMT KNQVKLTCLV KGFYPSDIAV EWESNGQPEN  660
NYKTTPPVLD SDGSFFLYSK LTVDKSRWQQ GNVFSCSVMH EALHNHYTQK SLSLSPGK    718
```

```
SEQ ID NO: 586             moltype = AA  length = 449
FEATURE                    Location/Qualifiers
REGION                     1..449
                           note = Description of Artificial Sequence: Synthetic
                            polypeptide
REGION                     1..449
                           note = XENP33978 Chain 2 -
```

-continued

```
                          MESO-C[MSLN]_H1.3_(G4S)2_[CD3]_L1.47_H1
                          .89_scFv(GKPGS)4_Fc(216)_IgG1_PVA_/S267K/S364K/E357Q
source                    1..449
                          mol_type = protein
                          organism = synthetic construct
SEQUENCE: 586
QVQLVQSGAE VKKPGASVKV SCKASGYTFT SYWMHWVRQA PGQGLEWMGW IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                     449

SEQ ID NO: 587           moltype = AA   length = 214
FEATURE                  Location/Qualifiers
REGION                   1..214
                         note = Description of Artificial Sequence: Synthetic
                          polypeptide
REGION                   1..214
                         note = XENP33978 Chain 3 - MESO-C[MSLN]_L1 Light Chain
source                   1..214
                         mol_type = protein
                         organism = synthetic construct
SEQUENCE: 587
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 588           moltype = AA   length = 718
FEATURE                  Location/Qualifiers
REGION                   1..718
                         note = Description of Artificial Sequence: Synthetic
                          polypeptide
REGION                   1..718
                         note = XENP33979 Chain 1 -
                          MESO-C[MSLN]_H1_IgG1_pI(-)_Isosteric_A_
                          PVA_/S267K/L368D/K370S
source                   1..718
                         mol_type = protein
                         organism = synthetic construct
SEQUENCE: 588
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKYNNY  420
ATYYADSVKG RFTISRDDSK NTLYLQMNSL RAEDTAVYYC VRHGNFGDEY VSWFAYWGQG  480
TLVTVSSEPK SSDKTHTCPP CPAPPVAGPS VFLFPPKPKD TLMISRTPEV TCVVVDVKHE  540
DPEVKFNWYV DGVEVHNAKT KPREEQYNST YRVVSVLTVL HQDWLNGKEY KCKVSNKALP  600
APIEKTISKA KGQPREPQVY TLPPSREQMT KNQVKLTCLV KGFYPSDIAV EWESNGQPEN  660
NYKTTPPVLD SDGSFFLYSK LTVDKSRWQQ GNVFSCSVMH EALHNHYTQK SLSLSPGK    718

SEQ ID NO: 589           moltype = AA   length = 449
FEATURE                  Location/Qualifiers
REGION                   1..449
                         note = Description of Artificial Sequence: Synthetic
                          polypeptide
REGION                   1..449
                         note = XENP33979 Chain 2 -
                          MESO-C[MSLN]_H1_(G4S)2_[CD3]_L1.47_H1.8
                          9_scFv(GKPGS)4_Fc(216)_IgG1_PVA_/S267K/S364K/E357Q
source                   1..449
                         mol_type = protein
                         organism = synthetic construct
SEQUENCE: 589
QVQLVQSGAE VKKPGASVKV SCKASGYTFT SYWMHWVRQA PGQGLEWMGM IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                     449
```

```
SEQ ID NO: 590          moltype = AA   length = 214
FEATURE                 Location/Qualifiers
REGION                  1..214
                        note = Description of Artificial Sequence: Synthetic
                        polypeptide
REGION                  1..214
                        note = XENP33979 Chain 3 - MESO-C[MSLN]_L1.9 Light Chain
source                  1..214
                        mol_type = protein
                        organism = synthetic construct
SEQUENCE: 590
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YYSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 591          moltype = AA   length = 718
FEATURE                 Location/Qualifiers
REGION                  1..718
                        note = Description of Artificial Sequence: Synthetic
                        polypeptide
REGION                  1..718
                        note = XENP33980 Chain 1 -
                        MESO-C[MSLN]_H1.12_IgG1_pI(-)_Isosteric
                        _A_PVA_/S267K/L368D/K370S
source                  1..718
                        mol_type = protein
                        organism = synthetic construct
SEQUENCE: 591
QVQLVQSGAE VKKPGASVKV SCKASGYTFT SYWMHWVRQA PGQGLEWMGM IHPNSDNTIY   60
YQKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGQSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKYNNY  420
ATYYADSVKG RFTISRDDSK NTLYLQMNSL RAEDTAVYYC VRHGNFGDEY VSWFAYWGQG  480
TLVTVSSEPK SSDKTHTCPP CPAPPVAGPS VFLFPPKPKD TLMISRTPEV TCVVVDVKHE  540
DPEVKFNWYV DGVEVHNAKT KPREEQYNST YRVVSVLTVL HQDWLNGKEY KCKVSNKALP  600
APIEKTISKA KGQPREPQVY TLPPSREQMT KNQVKLTCLV KGFYPSDIAV EWESNGQPEN  660
NYKTTPPVLD SDGSFFLYSK LTVDKSRWQQ GNVFSCSVMH EALHNHYTQK SLSLSPGK    718

SEQ ID NO: 592          moltype = AA   length = 449
FEATURE                 Location/Qualifiers
REGION                  1..449
                        note = Description of Artificial Sequence: Synthetic
                        polypeptide
REGION                  1..449
                        note = XENP33980 Chain 2 -
                        MESO-C[MSLN]_H1.12_(G4S)2_[CD3]_L1.47_H
                        1.89_scFv(GKPGS)4_Fc(216)_IgG1_PVA_/S267K/S364K/E357Q
source                  1..449
                        mol_type = protein
                        organism = synthetic construct
SEQUENCE: 592
QVQLVQSGAE VKKPGASVKV SCKASGYTFT SYWMHWVRQA PGQGLEWMGM IHPNSDNTIY   60
YQKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 593          moltype = AA   length = 214
FEATURE                 Location/Qualifiers
REGION                  1..214
                        note = Description of Artificial Sequence: Synthetic
                        polypeptide
REGION                  1..214
                        note = XENP33980 Chain 3 - MESO-C[MSLN]_L1.9 Light Chain
source                  1..214
                        mol_type = protein
                        organism = synthetic construct
SEQUENCE: 593
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YYSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

```
SEQ ID NO: 594          moltype = AA  length = 449
FEATURE                 Location/Qualifiers
REGION                  1..449
                        note = Description of Artificial Sequence: Synthetic
                        polypeptide
REGION                  1..449
                        note = XENP34151 Chain 1 -
                        MESO-C[MSLN]_H1.3_IgG1_pI(-)_Isosteric_
                        A_/PVA_/S267K/L368D/K370S
source                  1..449
                        mol_type = protein
                        organism = synthetic construct
SEQUENCE: 594
QVQLVQSGAE VKKPGASVKV SCKASGYTFT SYWMHWVRQA PGQGLEWMGW IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 595          moltype = AA  length = 722
FEATURE                 Location/Qualifiers
REGION                  1..722
                        note = Description of Artificial Sequence: Synthetic
                        polypeptide
REGION                  1..722
                        note = XENP34151 Chain 2 -
                        MESO-C[MSLN]_H1.3_(G4S)2_[CD3]_L1.47_H1
                        .89_scFv(GKPGS)4_Fc(216)_IgG1_C220S/PVA_/S267K/S364K/E357Q
source                  1..722
                        mol_type = protein
                        organism = synthetic construct
SEQUENCE: 595
QVQLVQSGAE VKKPGASVKV SCKASGYTFT SYWMHWVRQA PGQGLEWMGW IHPNSDNTIY  60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKYNNY  420
ATYYADSVKG RFTISRDDSK NTLYLQMNSL RAEDTAVYYC VRHGNFGDEY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                                722

SEQ ID NO: 596          moltype = AA  length = 214
FEATURE                 Location/Qualifiers
REGION                  1..214
                        note = Description of Artificial Sequence: Synthetic
                        polypeptide
REGION                  1..214
                        note = XENP34151 Chain 3 - MESO-C[MSLN]_L1.14 Light Chain
source                  1..214
                        mol_type = protein
                        organism = synthetic construct
SEQUENCE: 596
DIVMTQSPDS LAVSLGERAT INCKASHDVG TSVAWYQQKP GQSPKLLIYW ASTRHTGVPD  60
RFTGSGSGTD FTLTISSLQA EDVAVYFCQQ YSSFPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 597          moltype = AA  length = 449
FEATURE                 Location/Qualifiers
REGION                  1..449
                        note = Description of Artificial Sequence: Synthetic
                        polypeptide
REGION                  1..449
                        note = XENP34152 Chain 1 -
                        MESO-C[MSLN]_H1.3_IgG1_pI(-)_Isosteric_
                        A_/PVA_/S267K/L368D/K370S
source                  1..449
                        mol_type = protein
                        organism = synthetic construct
SEQUENCE: 597
```

```
QVQLVQSGAE VKKPGASVKV SCKASGYTFT SYWMHWVRQA PGQGLEWMGW IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 598          moltype = AA  length = 722
FEATURE                 Location/Qualifiers
REGION                  1..722
                        note = Description of Artificial Sequence: Synthetic
                         polypeptide
REGION                  1..722
                        note = XENP34152 Chain 2 -
                         MESO-C[MSLN]_H1.3_(G4S)2_[CD3]_L1.47_H1
                         .89_scFv(GKPGS)4_Fc(216)_IgG1_C220S/PVA_/S267K/S364K/E357Q
source                  1..722
                        mol_type = protein
                        organism = synthetic construct
SEQUENCE: 598
QVQLVQSGAE VKKPGASVKV SCKASGYTFT SYWMHWVRQA PGQGLEWMGW IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKYNNY  420
ATYYADSVKG RFTISRDDSK NTLYLQMNSL RAEDTAVYYC VRHGNFGDEY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVMHEALHNH YTQKSLSLSP  720
GK                                                                722

SEQ ID NO: 599          moltype = AA  length = 214
FEATURE                 Location/Qualifiers
REGION                  1..214
                        note = Description of Artificial Sequence: Synthetic
                         polypeptide
REGION                  1..214
                        note = XENP34152 Chain 3 - MESO-C[MSLN]_L1.13 Light Chain
source                  1..214
                        mol_type = protein
                        organism = synthetic construct
SEQUENCE: 599
DIVMTQSPDS LAVSLGERAT INCKASHDVG QSVAWYQQKP GQSPKLLIYW ASTRHTGVPD   60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 600          moltype = AA  length = 449
FEATURE                 Location/Qualifiers
REGION                  1..449
                        note = Description of Artificial Sequence: Synthetic
                         polypeptide
REGION                  1..449
                        note = XENP34153 Chain 1 -
                         MESO-C[MSLN]_H1.3_IgG1_pI(-)_Isosteric_
                         A_/PVA_/S267K/L368D/K370S
source                  1..449
                        mol_type = protein
                        organism = synthetic construct
SEQUENCE: 600
QVQLVQSGAE VKKPGASVKV SCKASGYTFT SYWMHWVRQA PGQGLEWMGW IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVM HEALHNHYTQ KSLSLSPGK                                    449

SEQ ID NO: 601          moltype = AA  length = 722
FEATURE                 Location/Qualifiers
REGION                  1..722
                        note = Description of Artificial Sequence: Synthetic
                         polypeptide
```

-continued

```
REGION                    1..722
                          note = XENP34153 Chain 2 -
                           MESO-C[MSLN]_H1.3_(G4S)2_[CD3]_L1.47_H1
                           .89_scFv(GKPGS)4_Fc(216)_IgG1_C220S/PVA_/S267K/S364K/E357Q
source                    1..722
                          mol_type = protein
                          organism = synthetic construct
SEQUENCE: 601
QVQLVQSGAE VKKPGASVKV SCKASGYTFT SYWMHWVRQA PGQGLEWMGW IHPNSDNTIY    60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCGGGGSGG GGSQAVVTQE   240
PSLTVSPGGT VTLTCGSSTG AVTTSNYANW VQQKPGKSPR GLIGGTNKRA PGVPARFSGS   300
LLGGKAALTI SGAQPEDEAD YYCALWYSNH WVFGGGTKLT VLGKPGSGKP GSGKPGSGKP   360
GSEVQLVESG GGLVQPGGSL RLSCAASGFT FSTYAMNWVR QAPGKGLEWV GRIRSKYNNY   420
ATYYADSVKG RFTISRDDSK NTLYLQMNSL RAEDTAVYYC VRHGNFGDEY VSWFAYWGQG   480
TLVTVSSGGG GSGGGGSKTH TCPPCPAPPV AGPSVFLFPP KPKDTLMISR TPEVTCVVVD   540
VKHEDPEVKF NWYVDGVEVH NAKTKPREEQ YNSTYRVVSV LTVLHQDWLN GKEYKCKVSN   600
KALPAPIEKT ISKAKGQPRE PQVYTLPPSR EQMTKNQVKL TCLVKGFYPS DIAVEWESNG   660
QPENNYKTTP PVLDSDGSFF LYSKLTVDKS RWQQGNVFSC SVMHEALHNH YTQKSLSLSP   720
GK                                                                  722

SEQ ID NO: 602            moltype = AA  length = 214
FEATURE                   Location/Qualifiers
REGION                    1..214
                          note = Description of Artificial Sequence: Synthetic
                           polypeptide
REGION                    1..214
                          note = XENP34153 Chain 3 - MESO-C[MSLN]_L1 Light Chain
source                    1..214
                          mol_type = protein
                          organism = synthetic construct
SEQUENCE: 602
DIVMTQSPDS LAVSLGERAT INCKASHDVG TSVAWYQQKP GQSPKLLIYW ASTRHTGVPD    60
RFTGSGSGTD FTLTISSLQA EDVAVYFCQQ YSSYPLTFGA GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 603            moltype = AA  length = 449
FEATURE                   Location/Qualifiers
REGION                    1..449
                          note = Description of Artificial Sequence: Synthetic
                           polypeptide
REGION                    1..449
                          note = XENP34154 Chain 1 -
                           MESO-C[MSLN]_H1.12_IgG1_pI(-)_Isosteric
                           _A_/PVA_/S267K/L368D/K370S
source                    1..449
                          mol_type = protein
                          organism = synthetic construct
SEQUENCE: 603
QVQLVQSGAE VKKPGASVKV SCKASGYTFT SYWMHWVRQA PGQGLEWMGM IHPNSDNTIY    60
YQKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVM HEALHNHYTQ KSLSLSPGK                                     449

SEQ ID NO: 604            moltype = AA  length = 722
FEATURE                   Location/Qualifiers
REGION                    1..722
                          note = Description of Artificial Sequence: Synthetic
                           polypeptide
REGION                    1..722
                          note = XENP34154 Chain 2 -
                           MESO-C[MSLN]_H1.12_(G4S)2_[CD3]_L1.47_H
                           1.89_scFv(GKPGS)4_Fc(216)_IgG1_C220S/PVA_/S267K/S364K/E357Q
source                    1..722
                          mol_type = protein
                          organism = synthetic construct
SEQUENCE: 604
QVQLVQSGAE VKKPGASVKV SCKASGYTFT SYWMHWVRQA PGQGLEWMGM IHPNSDNTIY    60
YQKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCGGGGSGG GGSQAVVTQE   240
PSLTVSPGGT VTLTCGSSTG AVTTSNYANW VQQKPGKSPR GLIGGTNKRA PGVPARFSGS   300
LLGGKAALTI SGAQPEDEAD YYCALWYSNH WVFGGGTKLT VLGKPGSGKP GSGKPGSGKP   360
```

```
GSEVQLVESG GGLVQPGGSL RLSCAASGFT FSTYAMNWVR QAPGKGLEWV GRIRSKYNNY   420
ATYYADSVKG RFTISRDDSK NTLYLQMNSL RAEDTAVYYC VRHGNFGDEY VSWFAYWGQG   480
TLVTVSSGGG GSGGGGSKTH TCPPCPAPPV AGPSVFLFPP KPKDTLMISR TPEVTCVVVD   540
VKHEDPEVKF NWYVDGVEVH NAKTKPREEQ YNSTYRVVSV LTVLHQDWLN GKEYKCKVSN   600
KALPAPIEKT ISKAKGQPRE PQVYTLPPSR EQMTKNQVKL TCLVKGFYPS DIAVEWESNG   660
QPENNYKTTP PVLDSDGSFF LYSKLTVDKS RWQQGNVFSC SVMHEALHNH YTQKSLSLSP   720
GK                                                                 722

SEQ ID NO: 605          moltype = AA  length = 214
FEATURE                 Location/Qualifiers
REGION                  1..214
                        note = Description of Artificial Sequence: Synthetic
                         polypeptide
REGION                  1..214
                        note = XENP34154 Chain 3 - MESO-C[MSLN]_L1.9 Light Chain
source                  1..214
                        mol_type = protein
                        organism = synthetic construct
SEQUENCE: 605
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YYSYPLTFGA GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 606          moltype = AA  length = 449
FEATURE                 Location/Qualifiers
REGION                  1..449
                        note = Description of Artificial Sequence: Synthetic
                         polypeptide
REGION                  1..449
                        note = XENP34159 Chain 1 -
                         MESO-C[MSLN]_H1.3_IgG1_pI(-)_Isosteric_
                         A_/PVA_/S267K/L368D/K370S/M248L/N434S
source                  1..449
                        mol_type = protein
                        organism = synthetic construct
SEQUENCE: 606
QVQLVQSGAE VKKPGASVKV SCKASGYTFT SYWMHWVRQA PGQGLEWMGW IHPNSDNTIY   60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS DTKVDKKVEP KSCDKTHTCP PCPAPPVAGP   240
SVFLFPPKPK DTLMISRTPE VTCVVVDVKH EDPEVKFNWY VDGVEVHNAK TKPREEEYNS   300
TYRVVSVLTV LHQDWLNGKE YKCKVSNKAL PAPIEKTISK AKGQPREPQV YTLPPSREEM   360
TKNQVSLTCD VSGFYPSDIA VEWESDGQPE NNYKTTPPVL DSDGSFFLYS KLTVDKSRWE   420
QGDVFSCSVL HEALHSHYTQ KSLSLSPGK                                     449

SEQ ID NO: 607          moltype = AA  length = 722
FEATURE                 Location/Qualifiers
REGION                  1..722
                        note = Description of Artificial Sequence: Synthetic
                         polypeptide
REGION                  1..722
                        note = XENP34159 Chain 2 -
                         MESO-C[MSLN]_H1.3_(G4S)2_[CD3]_L1.47_H1
                         .89_scFv(GKPGS)4_Fc(216)_IgG1_C220S/PVA_/S267K/S364K/E357Q/
                         M248L/N434S
source                  1..722
                        mol_type = protein
                        organism = synthetic construct
SEQUENCE: 607
QVQLVQSGAE VKKPGASVKV SCKASGYTFT SYWMHWVRQA PGQGLEWMGW IHPNSDNTIY   60
YEKFQGRVTM TVDKSISTAY MELSRLRSDD TAVYYCAIII TPVVPKFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCGGGGSGG GGSQAVVTQE   240
PSLTVSPGGT VTLTCGSSTG AVTTSNYANW VQQKPGKSPR GLIGGTNKRA PGVPARFSGS   300
LLGGKAALTI SGAQPEDEAD YYCALWYSNH WVFGGGTKLT VLGKPGSGKP GSGKPGSGKP   360
GSEVQLVESG GGLVQPGGSL RLSCAASGFT FSTYAMNWVR QAPGKGLEWV GRIRSKYNNY   420
ATYYADSVKG RFTISRDDSK NTLYLQMNSL RAEDTAVYYC VRHGNFGDEY VSWFAYWGQG   480
TLVTVSSGGG GSGGGGSKTH TCPPCPAPPV AGPSVFLFPP KPKDTLMISR TPEVTCVVVD   540
VKHEDPEVKF NWYVDGVEVH NAKTKPREEQ YNSTYRVVSV LTVLHQDWLN GKEYKCKVSN   600
KALPAPIEKT ISKAKGQPRE PQVYTLPPSR EQMTKNQVKL TCLVKGFYPS DIAVEWESNG   660
QPENNYKTTP PVLDSDGSFF LYSKLTVDKS RWQQGNVFSC SVLHEALHSH YTQKSLSLSP   720
GK                                                                 722

SEQ ID NO: 608          moltype = AA  length = 214
FEATURE                 Location/Qualifiers
REGION                  1..214
                        note = Description of Artificial Sequence: Synthetic
                         polypeptide
```

-continued

```
REGION                  1..214
                        note = XENP34159 Chain 3 - MESO-C[MSLN]_L1.14 Light Chain
source                  1..214
                        mol_type = protein
                        organism = synthetic construct
SEQUENCE: 608
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YSSFPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 609          moltype = AA  length = 449
FEATURE                 Location/Qualifiers
REGION                  1..449
                        note = Description of Artificial Sequence: Synthetic
                         polypeptide
REGION                  1..449
                        note = XENP34160 Chain 1 -
                         MESO-C[MSLN]_H1.3_IgG1_pI(-)_Isosteric_
                         A_/PVA_/S267K/L368D/K370S/M248L/N434S
source                  1..449
                        mol_type = protein
                        organism = synthetic construct
SEQUENCE: 609
QVQLVQSGAE VKKPGASVKV SCKASGYTFT SYWMHWVRQA PGQGLEWMGW IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVL HEALHSHYTQ KSLSLSPGK                                    449

SEQ ID NO: 610          moltype = AA  length = 722
FEATURE                 Location/Qualifiers
REGION                  1..722
                        note = Description of Artificial Sequence: Synthetic
                         polypeptide
REGION                  1..722
                        note = XENP34160 Chain 2 -
                         MESO-C[MSLN]_H1.3_(G4S)2_[CD3]_L1.47_H1
                         .89_scFv(GKPGS)4_Fc(216)_IgG1_C220S/PVA_/S267K/S364K/E357Q/
                         M248L/N434S
source                  1..722
                        mol_type = protein
                        organism = synthetic construct
SEQUENCE: 610
QVQLVQSGAE VKKPGASVKV SCKASGYTFT SYWMHWVRQA PGQGLEWMGW IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKYNNY  420
ATYYADSVKG RFTISRDDSK NTLYLQMNSL RAEDTAVYYC VRHGNFGDEY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVLHEALHSH YTQKSLSLSP  720
GK                                                                722

SEQ ID NO: 611          moltype = AA  length = 214
FEATURE                 Location/Qualifiers
REGION                  1..214
                        note = Description of Artificial Sequence: Synthetic
                         polypeptide
REGION                  1..214
                        note = XENP34160 Chain 3 - MESO-C[MSLN]_L1.13 Light Chain
source                  1..214
                        mol_type = protein
                        organism = synthetic construct
SEQUENCE: 611
DIVMTQSPDS LAVSLGERAT INCKASHDVG QSVAWYQQKP GQSPKLLIYW ASTRHTGVPD   60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 612          moltype = AA  length = 449
FEATURE                 Location/Qualifiers
```

-continued

```
REGION                    1..449
                          note = Description of Artificial Sequence: Synthetic
                           polypeptide
REGION                    1..449
                          note = XENP34161 Chain 1 -
                           MESO-C[MSLN]_H1.3_IgG1_pI(-)_Isosteric_
                           A_/PVA_/S267K/L368D/K370S/M248L/N434S
source                    1..449
                          mol_type = protein
                          organism = synthetic construct
SEQUENCE: 612
QVQLVQSGAE VKKPGASVKV SCKASGYTFT SYWMHWVRQA PGQGLEWMGW IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVL HEALHSHYTQ KSLSLSPGK                                    449

SEQ ID NO: 613            moltype = AA  length = 722
FEATURE                   Location/Qualifiers
REGION                    1..722
                          note = Description of Artificial Sequence: Synthetic
                           polypeptide
REGION                    1..722
                          note = XENP34161 Chain 2 -
                           MESO-C[MSLN]_H1.3_(G4S)2_[CD3]_L1.47_H1
                            .89_scFv(GKPGS)4_Fc(216)_IgG1_C220S/PVA_/S267K/S364K/E357Q/
                            M248L/N434S
source                    1..722
                          mol_type = protein
                          organism = synthetic construct
SEQUENCE: 613
QVQLVQSGAE VKKPGASVKV SCKASGYTFT SYWMHWVRQA PGQGLEWMGW IHPNSDNTIY   60
YEKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKYNNY  420
ATYYADSVKG RFTISRDDSK NTLYLQMNSL RAEDTAVYYC VRHGNFGDEY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVLHEALHSH YTQKSLSLSP  720
GK                                                                722

SEQ ID NO: 614            moltype = AA  length = 214
FEATURE                   Location/Qualifiers
REGION                    1..214
                          note = Description of Artificial Sequence: Synthetic
                           polypeptide
REGION                    1..214
                          note = XENP34161 Chain 3 - MESO-C[MSLN]_L1 Light Chain
source                    1..214
                          mol_type = protein
                          organism = synthetic construct
SEQUENCE: 614
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YSSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 615            moltype = AA  length = 449
FEATURE                   Location/Qualifiers
REGION                    1..449
                          note = Description of Artificial Sequence: Synthetic
                           polypeptide
REGION                    1..449
                          note = XENP34162 Chain 1 -
                           MESO-C[MSLN]_H1.12_IgG1_pI(-)_Isosteric
                           _A_/PVA_/S267K/L368D/K370S/M248L/N434S
source                    1..449
                          mol_type = protein
                          organism = synthetic construct
SEQUENCE: 615
QVQLVQSGAE VKKPGASVKV SCKASGYTFT SYWMHWVRQA PGQGLEWMGM IHPNSDNTIY   60
YQKFQGRVTM TVDKSISTAY MELSRLRSDD TAVYYCAIII TPVVPKFDYW GQGTLVTVSS  120
```

-continued

```
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS DTKVDKKVEP KSCDKTHTCP PCPAPPVAGP  240
SVFLFPPKPK DTLMISRTPE VTCVVVDVKH EDPEVKFNWY VDGVEVHNAK TKPREEEYNS  300
TYRVVSVLTV LHQDWLNGKE YKCKVSNKAL PAPIEKTISK AKGQPREPQV YTLPPSREEM  360
TKNQVSLTCD VSGFYPSDIA VEWESDGQPE NNYKTTPPVL DSDGSFFLYS KLTVDKSRWE  420
QGDVFSCSVL HEALHSHYTQ KSLSLSPGK                                    449

SEQ ID NO: 616         moltype = AA  length = 722
FEATURE                Location/Qualifiers
REGION                 1..722
                       note = Description of Artificial Sequence: Synthetic
                        polypeptide
REGION                 1..722
                       note = XENP34162 Chain 2 -
                        MESO-C[MSLN]_H1.12_(G4S)2_[CD3]_L1.47_H
                        1.89_scFv(GKPGS)4_Fc(216)_IgG1_C220S/PVA_/S267K/S364K/E357Q
                        /M248L/N434S
source                 1..722
                       mol_type = protein
                       organism = synthetic construct
SEQUENCE: 616
QVQLVQSGAE VKKPGASVKV SCKASGYTFT SYWMHWVRQA PGQGLEWMGM IHPNSDNTIY   60
YQKFQGRVTM TVDKSISTAY MELSRLRSDD TAVYYCAIII TPVVPKFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCGGGGSGG GGSQAVVTQE  240
PSLTVSPGGT VTLTCGSSTG AVTTSNYANW VQQKPGKSPR GLIGGTNKRA PGVPARFSGS  300
LLGGKAALTI SGAQPEDEAD YYCALWYSNH WVFGGGTKLT VLGKPGSGKP GSGKPGSGKP  360
GSEVQLVESG GGLVQPGGSL RLSCAASGFT FSTYAMNWVR QAPGKGLEWV GRIRSKYNNY  420
ATYYADSVKG RFTISRDDSK NTLYLQMNSL RAEDTAVYYC VRHGNFGDEY VSWFAYWGQG  480
TLVTVSSGGG GSGGGGSKTH TCPPCPAPPV AGPSVFLFPP KPKDTLMISR TPEVTCVVVD  540
VKHEDPEVKF NWYVDGVEVH NAKTKPREEQ YNSTYRVVSV LTVLHQDWLN GKEYKCKVSN  600
KALPAPIEKT ISKAKGQPRE PQVYTLPPSR EQMTKNQVKL TCLVKGFYPS DIAVEWESNG  660
QPENNYKTTP PVLDSDGSFF LYSKLTVDKS RWQQGNVFSC SVLHEALHSH YTQKSLSLSP  720
GK                                                                722

SEQ ID NO: 617         moltype = AA  length = 214
FEATURE                Location/Qualifiers
REGION                 1..214
                       note = Description of Artificial Sequence: Synthetic
                        polypeptide
REGION                 1..214
                       note = XENP34162 Chain 3 - MESO-C[MSLN]_L1.9 Light Chain
source                 1..214
                       mol_type = protein
                       organism = synthetic construct
SEQUENCE: 617
DIVMTQSPDS LAVSLGERAT INCKASHDVG TSVAWYQQKP GQSPKLLIYW ASTRHTGVPD   60
RFTGSGSGTD FTLTISSLQA EDVAVYFCQQ YYSYPLTFGA GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 618         moltype = AA  length = 5
FEATURE                Location/Qualifiers
REGION                 1..5
                       note = Description of Artificial Sequence: Synthetic peptide
REGION                 1..5
                       note = See specification as filed for detailed description
                        of substitutions and preferred embodiments
source                 1..5
                       mol_type = protein
                       organism = synthetic construct
SEQUENCE: 618
GGGGS                                                                5
```

What is claimed is:

1. A mesothelin (MSLN) antigen binding domain comprising a variable heavy domain having at least 90% identity to the amino acid sequence of SEQ ID NO: 241 and a variable light domain having at least 90% identity to the amino acid sequence of SEQ ID NO: 245.

2. The MSLN antigen binding domain according to claim 1, wherein said variable heavy domain has at least 95% identity to the amino acid sequence of SEQ ID NO: 241 and said variable light domain has at least 95% identity to the amino acid sequence of SEQ ID NO: 245.

3. The MSLN antigen binding domain according to claim 1, wherein said variable heavy domain has the amino acid sequence of SEQ ID NO: 241, and said variable light domain has the amino acid sequence of SEQ ID NO: 245.

4. An antibody comprising a mesothelin (MSLN) antigen binding domain comprising a variable heavy domain having at least 90% identity to the amino acid sequence of SEQ ID NO: 241 and a variable light domain having at least 90% identity to the amino acid sequence of SEQ ID NO: 245.

5. The antibody comprising the MSLN antigen binding domain according to claim 4 wherein said variable heavy domain has at least 95% identity to the amino acid sequence of SEQ ID NO: 241 and said variable light domain has at least 95% identity to the amino acid sequence of SEQ ID NO: 245.

6. The antibody comprising the MSLN antigen binding domain according to claim 4, wherein said variable heavy domain has the amino acid sequence of SEQ ID NO: 241, and said variable light domain has the amino acid sequence of SEQ ID NO: 245.

* * * * *